United States Patent
Shelton, IV et al.

(10) Patent No.: US 10,245,028 B2
(45) Date of Patent: Apr. 2, 2019

(54) POWER ADAPTER FOR A SURGICAL INSTRUMENT

(71) Applicant: Ethicon Endo-Surgery, LLC, Guaynabo, PR (US)

(72) Inventors: Frederick E. Shelton, IV, Hillsboro, OH (US); Jerome R. Morgan, Cincinnati, OH (US); Jason L. Harris, Lebanon, OH (US); Andrew T. Beckman, Cincinnati, OH (US); Chester O. Baxter, III, Loveland, OH (US)

(73) Assignee: ETHICON LLC, Guaynabo, PR (US)

( * ) Notice: Subject to any disclaimer, the term of this patent is extended or adjusted under 35 U.S.C. 154(b) by 807 days.

(21) Appl. No.: 14/633,548

(22) Filed: Feb. 27, 2015

(65) Prior Publication Data
US 2016/0249909 A1 Sep. 1, 2016

(51) Int. Cl.
*H02J 7/00* (2006.01)
*A61B 17/068* (2006.01)
(Continued)

(52) U.S. Cl.
CPC .......... *A61B 17/068* (2013.01); *A61B 17/072* (2013.01); *A61B 17/07207* (2013.01);
(Continued)

(58) Field of Classification Search
CPC ................ A61B 17/068; A61B 17/072; A61B 17/07207; A61B 2017/00734; H02J 7/00;
(Continued)

(56) References Cited

U.S. PATENT DOCUMENTS

| 66,052 A | 6/1867 | Smith |
|---|---|---|
| 662,587 A | 11/1900 | Blake |

(Continued)

FOREIGN PATENT DOCUMENTS

| AU | 2008207624 A1 | 3/2009 |
|---|---|---|
| AU | 2010214687 A1 | 9/2010 |

(Continued)

OTHER PUBLICATIONS

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

(Continued)

*Primary Examiner* — Gloria R Weeks

(57) ABSTRACT

A surgical instrument system is disclosed which comprises a handle and a battery positioned in the handle. The system can further include a power adapter which can be exchanged for the battery and can supply power from an alternate power source. In other instances, the system can include a power adapter which is engageable with the battery to supply power from an alternate power source. The power adapter can be placed in series with the battery. Alternatively, the engagement of the power adapter with the handle can electrically decouple the battery from the handle. Also disclosed herein is a supplemental battery which can be attached to the handle to provide additional power to the handle.

15 Claims, 79 Drawing Sheets

(51) Int. Cl.
    *A61B 17/072* (2006.01)
    *H01M 2/10* (2006.01)
    *H01M 10/04* (2006.01)
    *A61B 17/10* (2006.01)
    *A61B 17/115* (2006.01)
    *A61B 90/70* (2016.01)
    *A61B 90/98* (2016.01)
    *A61B 17/00* (2006.01)
    *A61B 90/00* (2016.01)
    *H01M 10/42* (2006.01)

(52) U.S. Cl.
    CPC ........ *A61B 17/105* (2013.01); *A61B 17/1155* (2013.01); *A61B 90/70* (2016.02); *A61B 90/98* (2016.02); *H01M 2/1022* (2013.01); *H01M 10/0445* (2013.01); *H02J 7/0042* (2013.01); *H02J 7/0045* (2013.01); *A61B 2017/0003* (2013.01); *A61B 2017/0046* (2013.01); *A61B 2017/00084* (2013.01); *A61B 2017/00115* (2013.01); *A61B 2017/00199* (2013.01); *A61B 2017/00221* (2013.01); *A61B 2017/00398* (2013.01); *A61B 2017/00464* (2013.01); *A61B 2017/00716* (2013.01); *A61B 2017/00725* (2013.01); *A61B 2017/00734* (2013.01); *A61B 2090/0803* (2016.02); *A61B 2090/0809* (2016.02); *A61B 2090/0812* (2016.02); *A61B 2090/0813* (2016.02); *A61B 2090/0814* (2016.02); *H01M 2/1027* (2013.01); *H01M 2/1066* (2013.01); *H01M 10/4257* (2013.01); *H01M 2220/30* (2013.01); *H02J 7/0027* (2013.01); *H02J 2007/005* (2013.01)

(58) Field of Classification Search
    CPC ...... H02J 7/34; H01M 2/1016; H01M 2/1022; H01M 2/1027; H01M 2/1066; H01M 10/4257; H01M 2220/30
    USPC .... 227/175.1, 176.1; 307/43, 46, 48, 52, 64, 307/66, 150; 320/107
    See application file for complete search history.

(56) References Cited

U.S. PATENT DOCUMENTS

| | | |
|---|---|---|
| 670,748 A | 3/1901 | Weddeler |
| 719,487 A | 2/1903 | Minor |
| 804,229 A | 11/1905 | Hutchinson |
| 951,393 A | 3/1910 | Hahn |
| 1,306,107 A | 6/1919 | Elliott |
| 1,314,601 A | 9/1919 | McCaskey |
| 1,677,337 A | 7/1928 | Grove |
| 1,794,907 A | 3/1931 | Kelly |
| 1,849,427 A | 3/1932 | Hook |
| 1,944,116 A | 1/1934 | Stratman |
| 1,954,048 A | 4/1934 | Jeffrey et al. |
| 2,037,727 A | 4/1936 | La Chapelle |
| 2,132,295 A | 10/1938 | Hawkins |
| 2,161,632 A | 6/1939 | Nattenheimer |
| 2,211,117 A | 8/1940 | Hess |
| 2,214,870 A | 9/1940 | West |
| 2,224,882 A | 12/1940 | Peck |
| 2,318,379 A | 5/1943 | Davis et al. |
| 2,329,440 A | 9/1943 | La Place |
| 2,441,096 A | 5/1948 | Happe |
| 2,448,741 A | 9/1948 | Scott et al. |
| 2,450,527 A | 10/1948 | Smith |
| 2,526,902 A | 10/1950 | Rublee |
| 2,527,256 A | 10/1950 | Jackson |
| 2,578,686 A | 12/1951 | Fish |
| 2,638,901 A | 5/1953 | Sugarbaker |
| 2,674,149 A | 4/1954 | Benson |
| 2,711,461 A | 6/1955 | Happe |
| 2,742,955 A | 4/1956 | Dominguez |
| 2,804,848 A | 9/1957 | O'Farrell et al. |
| 2,808,482 A | 10/1957 | Zanichkowsky et al. |
| 2,853,074 A | 9/1958 | Olson |
| 2,887,004 A | 5/1959 | Stewart |
| 2,957,353 A | 10/1960 | Lewis |
| 2,959,974 A | 11/1960 | Emrick |
| 3,032,769 A | 5/1962 | Palmer |
| 3,060,972 A | 10/1962 | Sheldon |
| 3,075,062 A | 1/1963 | Iaccarino |
| 3,078,465 A | 2/1963 | Bobrov |
| 3,079,606 A | 3/1963 | Bobrov et al. |
| 3,080,564 A | 3/1963 | Strekopitov et al. |
| 3,166,072 A | 1/1965 | Sullivan, Jr. |
| 3,180,236 A | 4/1965 | Beckett |
| 3,196,869 A | 7/1965 | Scholl |
| 3,204,731 A | 9/1965 | Bent et al. |
| 3,266,494 A | 8/1966 | Brownrigg et al. |
| 3,269,630 A | 8/1966 | Fleischer |
| 3,269,631 A | 8/1966 | Takaro |
| 3,275,211 A | 9/1966 | Hirsch et al. |
| 3,317,103 A | 5/1967 | Cullen et al. |
| 3,317,105 A | 5/1967 | Astafjev et al. |
| 3,357,296 A | 12/1967 | Lefever |
| 3,359,978 A | 12/1967 | Smith, Jr. |
| 3,480,193 A | 11/1969 | Ralston |
| 3,490,675 A | 1/1970 | Green et al. |
| 3,494,533 A | 2/1970 | Green et al. |
| 3,499,591 A | 3/1970 | Green |
| 3,503,396 A | 3/1970 | Pierie et al. |
| 3,509,629 A | 5/1970 | Kidokoro |
| 3,551,987 A | 1/1971 | Wilkinson |
| 3,568,675 A | 3/1971 | Harvey |
| 3,572,159 A | 3/1971 | Tschanz |
| 3,583,393 A | 6/1971 | Takahashi |
| 3,589,589 A | 6/1971 | Akopov |
| 3,598,943 A | 8/1971 | Barrett |
| 3,608,549 A | 9/1971 | Merrill |
| 3,618,842 A | 11/1971 | Bryan |
| 3,638,652 A | 2/1972 | Kelley |
| 3,640,317 A | 2/1972 | Panfili |
| 3,643,851 A | 2/1972 | Green et al. |
| 3,650,453 A | 3/1972 | Smith, Jr. |
| 3,661,666 A | 5/1972 | Foster et al. |
| 3,662,939 A | 5/1972 | Bryan |
| 3,688,966 A | 9/1972 | Perkins et al. |
| 3,695,646 A | 10/1972 | Mommsen |
| 3,709,221 A | 1/1973 | Riely |
| 3,717,294 A | 2/1973 | Green |
| 3,734,207 A | 5/1973 | Fishbein |
| 3,740,994 A | 6/1973 | De Carlo, Jr. |
| 3,744,495 A | 7/1973 | Johnson |
| 3,746,002 A | 7/1973 | Haller |
| 3,747,603 A | 7/1973 | Adler |
| 3,751,902 A | 8/1973 | Kingsbury et al. |
| 3,752,161 A | 8/1973 | Bent |
| 3,799,151 A | 3/1974 | Fukaumi et al. |
| 3,808,452 A | 4/1974 | Hutchinson |
| 3,815,476 A | 6/1974 | Green et al. |
| 3,819,100 A | 6/1974 | Noiles et al. |
| 3,821,919 A | 7/1974 | Knohl |
| 3,836,171 A | 9/1974 | Hayashi et al. |
| 3,837,555 A | 9/1974 | Green |
| 3,841,474 A | 10/1974 | Maier |
| 3,851,196 A | 11/1974 | Hinds |
| 3,863,639 A | 2/1975 | Kleaveland |
| 3,883,624 A | 5/1975 | McKenzie et al. |
| 3,885,491 A | 5/1975 | Curtis |
| 3,892,228 A | 7/1975 | Mitsui |
| 3,894,174 A | 7/1975 | Cartun |
| 3,902,247 A | 9/1975 | Fleer et al. |
| 3,940,844 A | 3/1976 | Colby et al. |
| 3,944,163 A | 3/1976 | Hayashi et al. |
| 3,950,686 A | 4/1976 | Randall |
| 3,952,747 A | 4/1976 | Kimmell, Jr. |
| 3,955,581 A | 5/1976 | Spasiano et al. |
| 3,959,879 A | 6/1976 | Sellers |
| RE28,932 E | 8/1976 | Noiles et al. |
| 3,972,734 A | 8/1976 | King |

(56) References Cited

U.S. PATENT DOCUMENTS

| | | |
|---|---|---|
| 3,981,051 A | 9/1976 | Brumlik |
| 4,025,216 A | 5/1977 | Hives |
| 4,027,746 A | 6/1977 | Kine |
| 4,034,143 A | 7/1977 | Sweet |
| 4,054,108 A | 10/1977 | Gill |
| 4,060,089 A | 11/1977 | Noiles |
| 4,066,133 A | 1/1978 | Voss |
| 4,100,820 A | 7/1978 | Evett |
| 4,106,446 A | 8/1978 | Yamada et al. |
| 4,108,211 A | 8/1978 | Tanaka |
| 4,111,206 A | 9/1978 | Vishnevsky et al. |
| 4,127,227 A | 11/1978 | Green |
| 4,129,059 A | 12/1978 | Van Eck |
| 4,135,517 A | 1/1979 | Reale |
| 4,154,122 A | 5/1979 | Severin |
| 4,169,990 A | 10/1979 | Lerdman |
| 4,180,285 A | 12/1979 | Reneau |
| 4,185,701 A | 1/1980 | Boys |
| 4,190,042 A | 2/1980 | Sinnreich |
| 4,198,734 A | 4/1980 | Brumlik |
| 4,198,982 A | 4/1980 | Fortner et al. |
| 4,207,898 A | 6/1980 | Becht |
| 4,213,562 A | 7/1980 | Garrett et al. |
| 4,226,242 A | 10/1980 | Jarvik |
| 4,239,431 A | 12/1980 | Davini |
| 4,241,861 A | 12/1980 | Fleischer |
| 4,244,372 A | 1/1981 | Kapitanov et al. |
| 4,250,436 A | 2/1981 | Weissman |
| 4,261,244 A | 4/1981 | Becht et al. |
| 4,272,002 A | 6/1981 | Moshofsky |
| 4,272,662 A | 6/1981 | Simpson |
| 4,274,304 A | 6/1981 | Curtiss |
| 4,274,398 A | 6/1981 | Scott, Jr. |
| 4,275,813 A | 6/1981 | Noiles |
| 4,278,091 A | 7/1981 | Borzone |
| 4,289,131 A | 9/1981 | Mueller |
| 4,289,133 A | 9/1981 | Rothfuss |
| 4,290,542 A | 9/1981 | Fedotov et al. |
| D261,356 S | 10/1981 | Robinson |
| 4,296,654 A | 10/1981 | Mercer |
| 4,296,881 A | 10/1981 | Lee |
| 4,304,236 A | 12/1981 | Conta et al. |
| 4,305,539 A | 12/1981 | Korolkov et al. |
| 4,312,363 A | 1/1982 | Rothfuss et al. |
| 4,312,685 A | 1/1982 | Riedl |
| 4,317,451 A | 3/1982 | Cerwin et al. |
| 4,319,576 A | 3/1982 | Rothfuss |
| 4,321,002 A | 3/1982 | Froehlich |
| 4,321,746 A | 3/1982 | Grinage |
| 4,328,839 A | 5/1982 | Lyons et al. |
| 4,331,277 A | 5/1982 | Green |
| 4,340,331 A | 7/1982 | Savino |
| 4,347,450 A | 8/1982 | Colligan |
| 4,349,028 A | 9/1982 | Green |
| 4,350,151 A | 9/1982 | Scott |
| 4,353,371 A | 10/1982 | Cosman |
| 4,357,940 A | 11/1982 | Muller |
| 4,361,057 A | 11/1982 | Kochera |
| 4,366,544 A | 12/1982 | Shima et al. |
| 4,373,147 A | 2/1983 | Carlson, Jr. |
| 4,376,380 A | 3/1983 | Burgess |
| 4,379,457 A | 4/1983 | Gravener et al. |
| 4,380,312 A | 4/1983 | Landrus |
| 4,382,326 A | 5/1983 | Rabuse |
| 4,383,634 A | 5/1983 | Green |
| 4,393,728 A | 7/1983 | Larson et al. |
| 4,396,139 A | 8/1983 | Hall et al. |
| 4,397,311 A | 8/1983 | Kanshin et al. |
| 4,402,445 A | 9/1983 | Green |
| 4,406,621 A | 9/1983 | Bailey |
| 4,408,692 A | 10/1983 | Sigel et al. |
| 4,409,057 A | 10/1983 | Molenda et al. |
| 4,415,112 A | 11/1983 | Green |
| 4,416,276 A | 11/1983 | Newton et al. |
| 4,417,890 A | 11/1983 | Dennehey et al. |
| 4,423,456 A | 12/1983 | Zaidenweber |
| 4,428,376 A | 1/1984 | Mericle |
| 4,429,695 A | 2/1984 | Green |
| 4,430,997 A | 2/1984 | DiGiovanni et al. |
| 4,434,796 A | 3/1984 | Karapetian et al. |
| 4,438,659 A | 3/1984 | Desplats |
| 4,442,964 A | 4/1984 | Becht |
| 4,448,194 A | 5/1984 | DiGiovanni et al. |
| 4,451,743 A | 5/1984 | Suzuki et al. |
| 4,452,376 A | 6/1984 | Klieman et al. |
| 4,454,887 A | 6/1984 | Kruger |
| 4,461,305 A | 7/1984 | Cibley |
| 4,467,805 A | 8/1984 | Fukuda |
| 4,469,481 A | 9/1984 | Kobayashi |
| 4,470,414 A | 9/1984 | Imagawa et al. |
| 4,471,780 A | 9/1984 | Menges et al. |
| 4,471,781 A | 9/1984 | Di Giovanni et al. |
| 4,473,077 A | 9/1984 | Noiles et al. |
| 4,475,679 A | 10/1984 | Fleury, Jr. |
| 4,478,220 A | 10/1984 | Di Giovanni et al. |
| 4,480,641 A | 11/1984 | Failla et al. |
| 4,485,816 A | 12/1984 | Krumme |
| 4,485,817 A | 12/1984 | Swiggett |
| 4,486,928 A | 12/1984 | Tucker et al. |
| 4,488,523 A | 12/1984 | Shichman |
| 4,489,875 A | 12/1984 | Crawford et al. |
| 4,493,983 A | 1/1985 | Taggert |
| 4,499,895 A | 2/1985 | Takayama |
| 4,500,024 A | 2/1985 | DiGiovanni et al. |
| 4,503,842 A | 3/1985 | Takayama |
| 4,505,272 A | 3/1985 | Utyamyshev et al. |
| 4,505,273 A | 3/1985 | Braun et al. |
| 4,505,414 A | 3/1985 | Filipi |
| 4,506,671 A | 3/1985 | Green |
| 4,512,038 A | 4/1985 | Alexander et al. |
| 4,520,817 A | 6/1985 | Green |
| 4,522,327 A | 6/1985 | Korthoff et al. |
| 4,526,174 A | 7/1985 | Froehlich |
| 4,527,724 A | 7/1985 | Chow et al. |
| 4,530,357 A | 7/1985 | Pawloski et al. |
| 4,530,453 A | 7/1985 | Green |
| 4,531,522 A | 7/1985 | Bedi et al. |
| 4,532,927 A | 8/1985 | Miksza, Jr. |
| 4,540,202 A | 9/1985 | Amphoux et al. |
| 4,548,202 A | 10/1985 | Duncan |
| 4,556,058 A | 12/1985 | Green |
| 4,560,915 A | 12/1985 | Soultanian |
| 4,565,109 A | 1/1986 | Tsay |
| 4,565,189 A | 1/1986 | Mabuchi |
| 4,566,620 A | 1/1986 | Green et al. |
| 4,569,346 A | 2/1986 | Poirier |
| 4,569,469 A | 2/1986 | Mongeon et al. |
| 4,571,213 A | 2/1986 | Ishimoto |
| 4,573,468 A | 3/1986 | Conta et al. |
| 4,573,469 A | 3/1986 | Golden et al. |
| 4,573,622 A | 3/1986 | Green et al. |
| 4,576,165 A | 3/1986 | Green et al. |
| 4,576,167 A | 3/1986 | Noiles |
| 4,580,712 A | 4/1986 | Green |
| 4,585,153 A | 4/1986 | Failla et al. |
| 4,586,501 A | 5/1986 | Claracq |
| 4,586,502 A | 5/1986 | Bedi et al. |
| 4,589,416 A | 5/1986 | Green |
| 4,589,870 A | 5/1986 | Citrin et al. |
| 4,591,085 A | 5/1986 | Di Giovanni |
| RE32,214 E | 7/1986 | Schramm |
| 4,597,753 A | 7/1986 | Turley |
| 4,600,037 A | 7/1986 | Hatten |
| 4,604,786 A | 8/1986 | Howie, Jr. |
| 4,605,001 A | 8/1986 | Rothfuss et al. |
| 4,605,004 A | 8/1986 | Di Giovanni et al. |
| 4,606,343 A | 8/1986 | Conta et al. |
| 4,607,638 A | 8/1986 | Crainich |
| 4,608,981 A | 9/1986 | Rothfuss et al. |
| 4,610,250 A | 9/1986 | Green |
| 4,610,383 A | 9/1986 | Rothfuss et al. |
| 4,612,933 A | 9/1986 | Brinkerhoff et al. |
| D286,180 S | 10/1986 | Korthoff |
| D286,442 S | 10/1986 | Korthoff et al. |

(56) References Cited

U.S. PATENT DOCUMENTS

| | | |
|---|---|---|
| 4,617,914 A | 10/1986 | Ueda |
| 4,619,262 A | 10/1986 | Taylor |
| 4,619,391 A | 10/1986 | Sharkany et al. |
| D287,278 S | 12/1986 | Spreckelmeier |
| 4,628,459 A | 12/1986 | Shinohara et al. |
| 4,629,107 A | 12/1986 | Fedotov et al. |
| 4,632,290 A | 12/1986 | Green et al. |
| 4,633,861 A | 1/1987 | Chow et al. |
| 4,633,874 A | 1/1987 | Chow et al. |
| 4,634,419 A | 1/1987 | Kreizman et al. |
| 4,635,638 A | 1/1987 | Weintraub et al. |
| 4,641,076 A | 2/1987 | Linden |
| 4,642,618 A | 2/1987 | Johnson et al. |
| 4,643,173 A | 2/1987 | Bell et al. |
| 4,643,731 A | 2/1987 | Eckenhoff |
| 4,646,722 A | 3/1987 | Silverstein et al. |
| 4,646,745 A | 3/1987 | Noiles |
| 4,652,820 A | 3/1987 | Maresca |
| 4,654,028 A | 3/1987 | Suma |
| 4,655,222 A | 4/1987 | Florez et al. |
| 4,662,555 A | 5/1987 | Thornton |
| 4,663,874 A | 5/1987 | Sano et al. |
| 4,664,305 A | 5/1987 | Blake, III et al. |
| 4,665,916 A | 5/1987 | Green |
| 4,667,674 A | 5/1987 | Korthoff et al. |
| 4,669,647 A | 6/1987 | Storace |
| 4,671,278 A | 6/1987 | Chin |
| 4,671,280 A | 6/1987 | Dorband et al. |
| 4,671,445 A | 6/1987 | Barker et al. |
| 4,672,964 A | 6/1987 | Dee et al. |
| 4,675,944 A | 6/1987 | Wells |
| 4,676,245 A | 6/1987 | Fukuda |
| 4,679,460 A | 7/1987 | Yoshigai |
| 4,679,719 A | 7/1987 | Kramer |
| 4,684,051 A | 8/1987 | Akopov et al. |
| 4,688,555 A | 8/1987 | Wardle |
| 4,691,703 A | 9/1987 | Auth et al. |
| 4,693,248 A | 9/1987 | Failla |
| 4,698,579 A | 10/1987 | Richter et al. |
| 4,700,703 A | 10/1987 | Resnick et al. |
| 4,705,038 A | 11/1987 | Sjostrom et al. |
| 4,708,141 A | 11/1987 | Inoue et al. |
| 4,709,120 A | 11/1987 | Pearson |
| 4,715,520 A | 12/1987 | Roehr, Jr. et al. |
| 4,719,917 A | 1/1988 | Barrows et al. |
| 4,721,099 A | 1/1988 | Chikama |
| 4,724,840 A | 2/1988 | McVay et al. |
| 4,727,308 A | 2/1988 | Huljak et al. |
| 4,728,020 A | 3/1988 | Green et al. |
| 4,728,876 A | 3/1988 | Mongeon et al. |
| 4,729,260 A | 3/1988 | Dudden |
| 4,730,726 A | 3/1988 | Holzwarth |
| 4,741,336 A | 5/1988 | Failla et al. |
| 4,743,214 A | 5/1988 | Tai-Cheng |
| 4,744,363 A | 5/1988 | Hasson |
| 4,747,820 A | 5/1988 | Hornlein et al. |
| 4,750,902 A | 6/1988 | Wuchinich et al. |
| 4,752,024 A | 6/1988 | Green et al. |
| 4,754,909 A | 7/1988 | Barker et al. |
| 4,763,669 A | 8/1988 | Jaeger |
| 4,767,044 A | 8/1988 | Green |
| 4,773,420 A | 9/1988 | Green |
| 4,777,780 A | 10/1988 | Holzwarth |
| 4,781,186 A | 11/1988 | Simpson et al. |
| 4,784,137 A | 11/1988 | Kulik et al. |
| 4,787,387 A | 11/1988 | Burbank, III et al. |
| 4,790,225 A | 12/1988 | Moody et al. |
| 4,790,314 A | 12/1988 | Weaver |
| 4,805,617 A | 2/1989 | Bedi et al. |
| 4,805,823 A | 2/1989 | Rothfuss |
| 4,807,628 A | 2/1989 | Peters et al. |
| 4,809,695 A | 3/1989 | Gwathmey et al. |
| 4,815,460 A | 3/1989 | Porat et al. |
| 4,817,643 A | 4/1989 | Olson |
| 4,817,847 A | 4/1989 | Redtenbacher et al. |
| 4,819,853 A | 4/1989 | Green |
| 4,821,939 A | 4/1989 | Green |
| 4,827,911 A | 5/1989 | Broadwin et al. |
| 4,828,542 A | 5/1989 | Hermann |
| 4,828,944 A | 5/1989 | Yabe et al. |
| 4,830,855 A | 5/1989 | Stewart |
| 4,833,937 A | 5/1989 | Nagano |
| 4,834,720 A | 5/1989 | Blinkhorn |
| 4,838,859 A | 6/1989 | Strassmann |
| 4,844,068 A | 7/1989 | Arata et al. |
| 4,848,637 A | 7/1989 | Pruitt |
| 4,856,078 A | 8/1989 | Konopka |
| 4,860,644 A | 8/1989 | Kohl et al. |
| 4,862,891 A | 9/1989 | Smith |
| 4,863,423 A | 9/1989 | Wallace |
| 4,865,030 A | 9/1989 | Polyak |
| 4,868,530 A | 9/1989 | Ahs |
| 4,869,414 A | 9/1989 | Green et al. |
| 4,869,415 A | 9/1989 | Fox |
| 4,873,977 A | 10/1989 | Avant et al. |
| 4,875,486 A | 10/1989 | Rapoport et al. |
| 4,880,015 A | 11/1989 | Nierman |
| 4,890,613 A | 1/1990 | Golden et al. |
| 4,892,244 A | 1/1990 | Fox et al. |
| 4,893,622 A | 1/1990 | Green et al. |
| 4,894,051 A | 1/1990 | Shiber |
| 4,896,584 A | 1/1990 | Stoll et al. |
| 4,896,678 A | 1/1990 | Ogawa |
| 4,900,303 A | 2/1990 | Lemelson |
| 4,903,697 A | 2/1990 | Resnick et al. |
| 4,909,789 A | 3/1990 | Taguchi et al. |
| 4,915,100 A | 4/1990 | Green |
| 4,919,679 A | 4/1990 | Averill et al. |
| 4,921,479 A | 5/1990 | Grayzel |
| 4,925,082 A | 5/1990 | Kim |
| 4,928,699 A | 5/1990 | Sasai |
| 4,930,503 A | 6/1990 | Pruitt |
| 4,930,674 A | 6/1990 | Barak |
| 4,931,047 A | 6/1990 | Broadwin et al. |
| 4,931,737 A | 6/1990 | Hishiki |
| 4,932,960 A | 6/1990 | Green et al. |
| 4,933,843 A | 6/1990 | Scheller et al. |
| D309,350 S | 7/1990 | Sutherland et al. |
| 4,938,408 A | 7/1990 | Bedi et al. |
| 4,941,623 A | 7/1990 | Pruitt |
| 4,943,182 A | 7/1990 | Hoblingre |
| 4,944,443 A | 7/1990 | Oddsen et al. |
| 4,946,067 A | 8/1990 | Kelsall |
| 4,948,327 A | 8/1990 | Crupi, Jr. |
| 4,949,707 A | 8/1990 | LeVahn et al. |
| 4,951,860 A | 8/1990 | Peters et al. |
| 4,951,861 A | 8/1990 | Schulze et al. |
| 4,955,959 A | 9/1990 | Tompkins et al. |
| 4,957,212 A | 9/1990 | Duck et al. |
| 4,962,877 A | 10/1990 | Hervas |
| 4,964,559 A | 10/1990 | Deniega et al. |
| 4,964,863 A | 10/1990 | Kanshin et al. |
| 4,965,709 A | 10/1990 | Ngo |
| 4,973,274 A | 11/1990 | Hirukawa |
| 4,973,302 A | 11/1990 | Armour et al. |
| 4,978,049 A | 12/1990 | Green |
| 4,978,333 A | 12/1990 | Broadwin et al. |
| 4,979,952 A | 12/1990 | Kubota et al. |
| 4,984,564 A | 1/1991 | Yuen |
| 4,986,808 A | 1/1991 | Broadwin et al. |
| 4,987,049 A | 1/1991 | Komamura et al. |
| 4,988,334 A | 1/1991 | Hornlein et al. |
| 4,995,877 A | 2/1991 | Ams et al. |
| 4,995,959 A | 2/1991 | Metzner |
| 4,996,975 A | 3/1991 | Nakamura |
| 5,002,543 A | 3/1991 | Bradshaw et al. |
| 5,002,553 A | 3/1991 | Shiber |
| 5,005,754 A | 4/1991 | Van Overloop |
| 5,009,661 A | 4/1991 | Michelson |
| 5,012,411 A | 4/1991 | Policastro et al. |
| 5,014,898 A | 5/1991 | Heidrich |
| 5,014,899 A | 5/1991 | Presty et al. |
| 5,015,227 A | 5/1991 | Broadwin et al. |
| 5,018,515 A | 5/1991 | Gilman |

(56) References Cited

U.S. PATENT DOCUMENTS

| | | |
|---|---|---|
| 5,018,657 A | 5/1991 | Pedlick et al. |
| 5,024,652 A | 6/1991 | Dumenek et al. |
| 5,024,671 A | 6/1991 | Tu et al. |
| 5,027,834 A | 7/1991 | Pruitt |
| 5,030,226 A | 7/1991 | Green et al. |
| 5,031,814 A | 7/1991 | Tompkins et al. |
| 5,035,040 A | 7/1991 | Kerrigan et al. |
| 5,038,109 A | 8/1991 | Goble et al. |
| 5,038,247 A | 8/1991 | Kelley et al. |
| 5,040,715 A | 8/1991 | Green et al. |
| 5,042,707 A | 8/1991 | Taheri |
| 5,061,269 A | 10/1991 | Muller |
| 5,062,491 A | 11/1991 | Takeshima et al. |
| 5,062,563 A | 11/1991 | Green et al. |
| 5,065,929 A | 11/1991 | Schulze et al. |
| 5,071,052 A | 12/1991 | Rodak et al. |
| 5,071,430 A | 12/1991 | de Salis et al. |
| 5,074,454 A | 12/1991 | Peters |
| 5,077,506 A | 12/1991 | Krause |
| 5,079,006 A | 1/1992 | Urquhart |
| 5,080,556 A | 1/1992 | Carreno |
| 5,083,695 A | 1/1992 | Foslien et al. |
| 5,084,057 A | 1/1992 | Green et al. |
| 5,088,979 A | 2/1992 | Filipi et al. |
| 5,088,997 A | 2/1992 | Delahuerga et al. |
| 5,089,606 A | 2/1992 | Cole et al. |
| 5,094,247 A | 3/1992 | Hernandez et al. |
| 5,098,004 A | 3/1992 | Kerrigan |
| 5,098,360 A | 3/1992 | Hirota |
| 5,100,042 A | 3/1992 | Gravener et al. |
| 5,100,420 A | 3/1992 | Green et al. |
| 5,104,025 A | 4/1992 | Main et al. |
| 5,104,397 A | 4/1992 | Vasconcelos et al. |
| 5,104,400 A | 4/1992 | Berguer et al. |
| 5,106,008 A | 4/1992 | Tompkins et al. |
| 5,108,368 A | 4/1992 | Hammerslag et al. |
| 5,109,722 A | 5/1992 | Hufnagle et al. |
| 5,111,987 A | 5/1992 | Moeinzadeh et al. |
| 5,116,349 A | 5/1992 | Aranyi |
| D327,323 S | 6/1992 | Hunt |
| 5,119,009 A | 6/1992 | McCaleb et al. |
| 5,122,156 A | 6/1992 | Granger et al. |
| 5,124,990 A | 6/1992 | Williamson |
| 5,129,570 A | 7/1992 | Schulze et al. |
| 5,137,198 A | 8/1992 | Nobis et al. |
| 5,139,513 A | 8/1992 | Segato |
| 5,141,144 A | 8/1992 | Foslien et al. |
| 5,142,932 A | 9/1992 | Moya et al. |
| 5,155,941 A | 10/1992 | Takahashi et al. |
| 5,156,315 A | 10/1992 | Green et al. |
| 5,156,609 A | 10/1992 | Nakao et al. |
| 5,156,614 A | 10/1992 | Green et al. |
| 5,158,567 A | 10/1992 | Green |
| D330,699 S | 11/1992 | Gill |
| 5,163,598 A | 11/1992 | Peters et al. |
| 5,168,605 A | 12/1992 | Bartlett |
| 5,170,925 A | 12/1992 | Madden et al. |
| 5,171,247 A | 12/1992 | Hughett et al. |
| 5,171,249 A | 12/1992 | Stefanchik et al. |
| 5,171,253 A | 12/1992 | Klieman |
| 5,173,133 A | 12/1992 | Morin et al. |
| 5,176,677 A | 1/1993 | Wuchinich |
| 5,176,688 A | 1/1993 | Narayan et al. |
| 5,187,422 A | 2/1993 | Izenbaard et al. |
| 5,188,102 A | 2/1993 | Idemoto et al. |
| 5,188,111 A | 2/1993 | Yates et al. |
| 5,190,517 A | 3/1993 | Zieve et al. |
| 5,190,544 A | 3/1993 | Chapman et al. |
| 5,190,560 A | 3/1993 | Woods et al. |
| 5,192,288 A | 3/1993 | Thompson et al. |
| 5,195,505 A | 3/1993 | Josefsen |
| 5,195,968 A | 3/1993 | Lundquist et al. |
| 5,197,648 A | 3/1993 | Gingold |
| 5,197,649 A | 3/1993 | Bessler et al. |
| 5,197,966 A | 3/1993 | Sommerkamp |
| 5,197,970 A | 3/1993 | Green et al. |
| 5,200,280 A | 4/1993 | Karasa |
| 5,201,750 A | 4/1993 | Hocherl et al. |
| 5,205,459 A | 4/1993 | Brinkerhoff et al. |
| 5,207,697 A | 5/1993 | Carusillo et al. |
| 5,209,747 A | 5/1993 | Knoepfler |
| 5,209,756 A | 5/1993 | Seedhom et al. |
| 5,211,649 A | 5/1993 | Kohler et al. |
| 5,211,655 A | 5/1993 | Hasson |
| 5,217,457 A | 6/1993 | Delahuerga et al. |
| 5,217,478 A | 6/1993 | Rexroth |
| 5,219,111 A | 6/1993 | Bilotti et al. |
| 5,220,269 A * | 6/1993 | Chen ................. H02J 7/0042 224/902 |
| 5,221,036 A | 6/1993 | Takase |
| 5,221,281 A | 6/1993 | Klicek |
| 5,222,945 A | 6/1993 | Basnight |
| 5,222,963 A | 6/1993 | Brinkerhoff et al. |
| 5,222,975 A | 6/1993 | Crainich |
| 5,222,976 A | 6/1993 | Yoon |
| 5,223,675 A | 6/1993 | Taft |
| D338,729 S | 8/1993 | Sprecklemeier et al. |
| 5,234,447 A | 8/1993 | Kaster et al. |
| 5,236,424 A | 8/1993 | Imran |
| 5,236,440 A | 8/1993 | Hlavacek |
| 5,239,981 A | 8/1993 | Anapliotis |
| 5,240,163 A | 8/1993 | Stein et al. |
| 5,242,457 A | 9/1993 | Akopov et al. |
| 5,244,462 A | 9/1993 | Delahuerga et al. |
| 5,246,156 A | 9/1993 | Rothfuss et al. |
| 5,246,443 A | 9/1993 | Mai |
| 5,253,793 A | 10/1993 | Green et al. |
| 5,258,007 A | 11/1993 | Spetzler et al. |
| 5,258,008 A | 11/1993 | Wilk |
| 5,258,009 A | 11/1993 | Conners |
| 5,258,010 A | 11/1993 | Green et al. |
| 5,258,012 A | 11/1993 | Luscombe et al. |
| 5,259,366 A | 11/1993 | Reydel et al. |
| 5,259,835 A | 11/1993 | Clark et al. |
| 5,260,637 A | 11/1993 | Pizzi |
| 5,261,877 A | 11/1993 | Fine et al. |
| 5,261,922 A | 11/1993 | Hood |
| 5,263,629 A | 11/1993 | Trumbull et al. |
| 5,263,937 A | 11/1993 | Shipp |
| 5,263,973 A | 11/1993 | Cook |
| 5,264,218 A | 11/1993 | Rogozinski |
| 5,268,622 A | 12/1993 | Philipp |
| 5,271,543 A | 12/1993 | Grant et al. |
| 5,271,544 A | 12/1993 | Fox et al. |
| RE34,519 E | 1/1994 | Fox et al. |
| 5,275,322 A | 1/1994 | Brinkerhoff et al. |
| 5,275,323 A | 1/1994 | Schulze et al. |
| 5,275,608 A | 1/1994 | Forman et al. |
| 5,279,416 A | 1/1994 | Malec et al. |
| 5,281,216 A | 1/1994 | Klicek |
| 5,282,806 A | 2/1994 | Haber et al. |
| 5,282,829 A | 2/1994 | Hermes |
| 5,284,128 A | 2/1994 | Hart |
| 5,285,381 A | 2/1994 | Iskarous et al. |
| 5,285,945 A | 2/1994 | Brinkerhoff et al. |
| 5,286,253 A | 2/1994 | Fucci |
| 5,289,963 A | 3/1994 | McGarry et al. |
| 5,290,271 A | 3/1994 | Jernberg |
| 5,290,310 A | 3/1994 | Makower et al. |
| 5,292,053 A | 3/1994 | Bilotti et al. |
| 5,297,714 A | 3/1994 | Kramer |
| 5,304,204 A | 4/1994 | Bregen |
| D347,474 S | 5/1994 | Olson |
| 5,307,976 A | 5/1994 | Olson et al. |
| 5,308,576 A | 5/1994 | Green et al. |
| 5,309,387 A | 5/1994 | Mori et al. |
| 5,309,927 A | 5/1994 | Welch |
| 5,312,023 A | 5/1994 | Green et al. |
| 5,312,024 A | 5/1994 | Grant et al. |
| 5,312,329 A | 5/1994 | Beaty et al. |
| 5,313,935 A | 5/1994 | Kortenbach et al. |
| 5,313,967 A | 5/1994 | Lieber et al. |
| 5,314,424 A | 5/1994 | Nicholas |
| 5,314,445 A | 5/1994 | Heidmueller et al. |

(56) References Cited

U.S. PATENT DOCUMENTS

| | | |
|---|---|---|
| 5,314,466 A | 5/1994 | Stern et al. |
| 5,318,221 A | 6/1994 | Green et al. |
| 5,320,627 A | 6/1994 | Sorensen et al. |
| D348,930 S | 7/1994 | Olson |
| 5,326,013 A | 7/1994 | Green et al. |
| 5,329,923 A | 7/1994 | Lundquist |
| 5,330,487 A | 7/1994 | Thornton et al. |
| 5,330,502 A | 7/1994 | Hassler et al. |
| 5,331,971 A | 7/1994 | Bales et al. |
| 5,332,142 A | 7/1994 | Robinson et al. |
| 5,333,422 A | 8/1994 | Warren et al. |
| 5,333,772 A | 8/1994 | Rothfuss et al. |
| 5,333,773 A | 8/1994 | Main et al. |
| 5,334,183 A | 8/1994 | Wuchinich |
| 5,336,130 A | 8/1994 | Ray |
| 5,336,229 A | 8/1994 | Noda |
| 5,336,232 A | 8/1994 | Green et al. |
| 5,339,799 A | 8/1994 | Kami et al. |
| 5,341,724 A | 8/1994 | Vatel |
| 5,341,807 A | 8/1994 | Nardella |
| 5,341,810 A | 8/1994 | Dardel |
| 5,342,380 A | 8/1994 | Hood |
| 5,342,381 A | 8/1994 | Tidemand |
| 5,342,385 A | 8/1994 | Norelli et al. |
| 5,342,395 A | 8/1994 | Jarrett et al. |
| 5,342,396 A | 8/1994 | Cook |
| 5,343,382 A | 8/1994 | Hale et al. |
| 5,343,391 A | 8/1994 | Mushabac |
| 5,344,059 A | 9/1994 | Green et al. |
| 5,344,060 A | 9/1994 | Gravener et al. |
| 5,344,454 A | 9/1994 | Clarke et al. |
| 5,346,504 A | 9/1994 | Ortiz et al. |
| 5,348,259 A | 9/1994 | Blanco et al. |
| 5,350,355 A | 9/1994 | Sklar |
| 5,350,388 A | 9/1994 | Epstein |
| 5,350,391 A | 9/1994 | Iacovelli |
| 5,350,400 A | 9/1994 | Esposito et al. |
| 5,352,229 A | 10/1994 | Goble et al. |
| 5,352,235 A | 10/1994 | Koros et al. |
| 5,352,238 A | 10/1994 | Green et al. |
| 5,354,250 A | 10/1994 | Christensen |
| 5,354,303 A | 10/1994 | Spaeth et al. |
| 5,356,006 A | 10/1994 | Alpern et al. |
| 5,356,064 A | 10/1994 | Green et al. |
| 5,358,506 A | 10/1994 | Green et al. |
| 5,358,510 A | 10/1994 | Luscombe et al. |
| 5,359,231 A | 10/1994 | Flowers et al. |
| D352,780 S | 11/1994 | Glaeser et al. |
| 5,359,993 A | 11/1994 | Slater et al. |
| 5,360,305 A | 11/1994 | Kerrigan |
| 5,360,428 A | 11/1994 | Hutchinson, Jr. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,366,134 A | 11/1994 | Green et al. |
| 5,366,479 A | 11/1994 | McGarry et al. |
| 5,368,015 A | 11/1994 | Wilk |
| 5,368,592 A | 11/1994 | Stern et al. |
| 5,369,565 A * | 11/1994 | Chen .................... H02J 7/0042 224/902 |
| 5,370,645 A | 12/1994 | Klicek et al. |
| 5,372,124 A | 12/1994 | Takayama et al. |
| 5,372,596 A | 12/1994 | Klicek et al. |
| 5,372,602 A | 12/1994 | Burke |
| 5,374,277 A | 12/1994 | Hassler |
| 5,375,588 A | 12/1994 | Yoon |
| 5,376,095 A | 12/1994 | Ortiz |
| 5,379,933 A | 1/1995 | Green et al. |
| 5,381,649 A | 1/1995 | Webb |
| 5,381,782 A | 1/1995 | DeLaRama et al. |
| 5,381,943 A | 1/1995 | Allen et al. |
| 5,382,247 A | 1/1995 | Cimino et al. |
| 5,383,880 A | 1/1995 | Hooven |
| 5,383,881 A | 1/1995 | Green et al. |
| 5,383,882 A | 1/1995 | Buess et al. |
| 5,383,888 A | 1/1995 | Zvenyatsky et al. |
| 5,383,895 A | 1/1995 | Holmes et al. |
| 5,388,568 A | 2/1995 | van der Heide |
| 5,389,098 A | 2/1995 | Tsuruta et al. |
| 5,389,102 A | 2/1995 | Green et al. |
| 5,389,104 A | 2/1995 | Hahnen et al. |
| 5,391,180 A | 2/1995 | Tovey et al. |
| 5,392,979 A | 2/1995 | Green et al. |
| 5,395,030 A | 3/1995 | Kuramoto et al. |
| 5,395,033 A | 3/1995 | Byrne et al. |
| 5,395,034 A | 3/1995 | Allen et al. |
| 5,395,312 A | 3/1995 | Desai |
| 5,395,384 A | 3/1995 | Duthoit et al. |
| 5,397,046 A | 3/1995 | Savage et al. |
| 5,397,324 A | 3/1995 | Carroll et al. |
| 5,400,267 A | 3/1995 | Denen et al. |
| 5,403,276 A | 4/1995 | Schechter et al. |
| 5,403,312 A | 4/1995 | Yates et al. |
| 5,404,106 A | 4/1995 | Matsuda |
| 5,404,870 A | 4/1995 | Brinkerhoff et al. |
| 5,404,960 A | 4/1995 | Wada et al. |
| 5,405,072 A | 4/1995 | Zlock et al. |
| 5,405,073 A | 4/1995 | Porter |
| 5,405,344 A | 4/1995 | Williamson et al. |
| 5,405,360 A | 4/1995 | Tovey |
| 5,407,293 A | 4/1995 | Crainich |
| 5,408,409 A | 4/1995 | Glassman et al. |
| 5,409,498 A | 4/1995 | Braddock et al. |
| 5,409,703 A | 4/1995 | McAnalley et al. |
| D357,981 S | 5/1995 | Green et al. |
| 5,411,481 A | 5/1995 | Allen et al. |
| 5,411,508 A | 5/1995 | Bessler et al. |
| 5,413,107 A | 5/1995 | Oakley et al. |
| 5,413,267 A | 5/1995 | Solyntjes et al. |
| 5,413,268 A | 5/1995 | Green et al. |
| 5,413,272 A | 5/1995 | Green et al. |
| 5,413,573 A | 5/1995 | Koivukangas |
| 5,415,334 A | 5/1995 | Williamson et al. |
| 5,415,335 A | 5/1995 | Knodell, Jr. |
| 5,417,203 A | 5/1995 | Tovey et al. |
| 5,417,361 A | 5/1995 | Williamson, IV |
| 5,419,766 A | 5/1995 | Chang et al. |
| 5,421,829 A | 6/1995 | Olichney et al. |
| 5,422,567 A | 6/1995 | Matsunaga |
| 5,423,471 A | 6/1995 | Mastri et al. |
| 5,423,809 A | 6/1995 | Klicek |
| 5,423,835 A | 6/1995 | Green et al. |
| 5,425,745 A | 6/1995 | Green et al. |
| 5,427,298 A | 6/1995 | Tegtmeier |
| 5,431,322 A | 7/1995 | Green et al. |
| 5,431,323 A | 7/1995 | Smith et al. |
| 5,431,654 A | 7/1995 | Nic |
| 5,431,668 A | 7/1995 | Burbank, III et al. |
| 5,433,721 A | 7/1995 | Hooven et al. |
| 5,437,681 A | 8/1995 | Meade et al. |
| 5,438,302 A | 8/1995 | Goble |
| 5,439,155 A | 8/1995 | Viola |
| 5,439,156 A | 8/1995 | Grant et al. |
| 5,439,479 A | 8/1995 | Shichman et al. |
| 5,441,191 A | 8/1995 | Linden |
| 5,441,193 A | 8/1995 | Gravener |
| 5,441,483 A | 8/1995 | Avitall |
| 5,441,494 A | 8/1995 | Ortiz |
| 5,443,197 A | 8/1995 | Malis et al. |
| 5,443,463 A | 8/1995 | Stern et al. |
| 5,444,113 A | 8/1995 | Sinclair et al. |
| 5,445,155 A | 8/1995 | Sieben |
| 5,445,304 A | 8/1995 | Plyley et al. |
| 5,445,604 A | 8/1995 | Lang |
| 5,445,644 A | 8/1995 | Pietrafitta et al. |
| 5,447,265 A | 9/1995 | Vidal et al. |
| 5,447,417 A | 9/1995 | Kuhl et al. |
| 5,447,513 A | 9/1995 | Davison et al. |
| 5,449,355 A | 9/1995 | Rhum et al. |
| 5,449,365 A | 9/1995 | Green et al. |
| 5,449,370 A | 9/1995 | Vaitekunas |
| 5,452,836 A | 9/1995 | Huitema et al. |
| 5,452,837 A | 9/1995 | Williamson, IV et al. |

(56) References Cited

U.S. PATENT DOCUMENTS

| | | |
|---|---|---|
| 5,454,378 A | 10/1995 | Palmer et al. |
| 5,454,822 A | 10/1995 | Schob et al. |
| 5,454,827 A | 10/1995 | Aust et al. |
| 5,456,401 A | 10/1995 | Green et al. |
| 5,456,917 A | 10/1995 | Wise et al. |
| 5,458,279 A | 10/1995 | Plyley |
| 5,458,579 A | 10/1995 | Chodorow et al. |
| 5,462,215 A | 10/1995 | Viola et al. |
| 5,464,013 A | 11/1995 | Lemelson |
| 5,464,144 A | 11/1995 | Guy et al. |
| 5,464,300 A | 11/1995 | Crainich |
| 5,465,819 A | 11/1995 | Weilant et al. |
| 5,465,894 A | 11/1995 | Clark et al. |
| 5,465,895 A | 11/1995 | Knodel et al. |
| 5,465,896 A | 11/1995 | Allen et al. |
| 5,466,020 A | 11/1995 | Page et al. |
| 5,467,911 A | 11/1995 | Tsuruta et al. |
| 5,468,253 A | 11/1995 | Bezwada et al. |
| 5,470,006 A | 11/1995 | Rodak |
| 5,470,007 A | 11/1995 | Plyley et al. |
| 5,470,008 A | 11/1995 | Rodak |
| 5,470,009 A | 11/1995 | Rodak |
| 5,470,010 A | 11/1995 | Rothfuss et al. |
| 5,471,129 A | 11/1995 | Mann |
| 5,472,132 A | 12/1995 | Savage et al. |
| 5,472,442 A | 12/1995 | Klicek |
| 5,473,204 A | 12/1995 | Temple |
| 5,474,057 A | 12/1995 | Makower et al. |
| 5,474,223 A | 12/1995 | Viola et al. |
| 5,474,566 A | 12/1995 | Alesi et al. |
| 5,476,206 A | 12/1995 | Green et al. |
| 5,476,479 A | 12/1995 | Green et al. |
| 5,476,481 A | 12/1995 | Schondorf |
| 5,478,003 A | 12/1995 | Green et al. |
| 5,478,354 A | 12/1995 | Tovey et al. |
| 5,480,089 A | 1/1996 | Blewett |
| 5,480,409 A | 1/1996 | Riza |
| 5,482,197 A | 1/1996 | Green et al. |
| 5,483,952 A | 1/1996 | Aranyi |
| 5,484,095 A | 1/1996 | Green et al. |
| 5,484,398 A | 1/1996 | Stoddard |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,489,256 A | 2/1996 | Adair |
| 5,489,290 A | 2/1996 | Furnish |
| 5,490,819 A | 2/1996 | Nicholas et al. |
| 5,492,671 A | 2/1996 | Krafft |
| 5,496,312 A | 3/1996 | Klicek |
| 5,496,317 A | 3/1996 | Goble et al. |
| 5,497,933 A | 3/1996 | DeFonzo et al. |
| 5,501,654 A | 3/1996 | Failla et al. |
| 5,503,320 A | 4/1996 | Webster et al. |
| 5,503,635 A | 4/1996 | Sauer et al. |
| 5,503,638 A | 4/1996 | Cooper et al. |
| 5,505,363 A | 4/1996 | Green et al. |
| 5,507,426 A | 4/1996 | Young et al. |
| 5,509,596 A | 4/1996 | Green et al. |
| 5,509,916 A | 4/1996 | Taylor |
| 5,511,564 A | 4/1996 | Wilk |
| 5,514,129 A | 5/1996 | Smith |
| 5,514,149 A | 5/1996 | Green et al. |
| 5,514,157 A | 5/1996 | Nicholas et al. |
| 5,518,163 A | 5/1996 | Hooven |
| 5,518,164 A | 5/1996 | Hooven |
| 5,520,609 A | 5/1996 | Moll et al. |
| 5,520,634 A | 5/1996 | Fox et al. |
| 5,520,678 A | 5/1996 | Heckele et al. |
| 5,520,700 A | 5/1996 | Beyar et al. |
| 5,522,817 A | 6/1996 | Sander et al. |
| 5,522,831 A | 6/1996 | Sleister et al. |
| 5,527,264 A | 6/1996 | Moll et al. |
| 5,527,320 A | 6/1996 | Carruthers et al. |
| 5,529,235 A | 6/1996 | Boiarski et al. |
| D372,086 S | 7/1996 | Grasso et al. |
| 5,531,305 A | 7/1996 | Roberts et al. |
| 5,531,744 A | 7/1996 | Nardella et al. |
| 5,531,856 A | 7/1996 | Moll et al. |
| 5,533,521 A | 7/1996 | Granger |
| 5,533,581 A | 7/1996 | Barth et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,540,705 A | 7/1996 | Meade et al. |
| 5,541,376 A | 7/1996 | Ladtkow et al. |
| 5,541,489 A | 7/1996 | Dunstan |
| 5,542,594 A | 8/1996 | McKean et al. |
| 5,542,949 A | 8/1996 | Yoon |
| 5,543,119 A | 8/1996 | Sutter et al. |
| 5,543,695 A | 8/1996 | Culp et al. |
| 5,544,802 A | 8/1996 | Crainich |
| 5,547,117 A | 8/1996 | Hamblin et al. |
| 5,549,583 A | 8/1996 | Sanford et al. |
| 5,549,621 A | 8/1996 | Bessler et al. |
| 5,549,627 A | 8/1996 | Kieturakis |
| 5,549,628 A | 8/1996 | Cooper et al. |
| 5,549,637 A | 8/1996 | Crainich |
| 5,551,622 A | 9/1996 | Yoon |
| 5,553,624 A | 9/1996 | Francese et al. |
| 5,553,675 A | 9/1996 | Pitzen et al. |
| 5,553,765 A | 9/1996 | Knodel et al. |
| 5,554,148 A | 9/1996 | Aebischer et al. |
| 5,554,169 A | 9/1996 | Green et al. |
| 5,556,020 A | 9/1996 | Hou |
| 5,556,416 A | 9/1996 | Clark et al. |
| 5,558,533 A | 9/1996 | Hashizawa et al. |
| 5,558,665 A | 9/1996 | Kieturakis |
| 5,558,671 A | 9/1996 | Yates |
| 5,560,530 A | 10/1996 | Bolanos et al. |
| 5,560,532 A | 10/1996 | DeFonzo et al. |
| 5,561,881 A | 10/1996 | Klinger et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,690 A | 10/1996 | Green et al. |
| 5,562,701 A | 10/1996 | Huitema et al. |
| 5,562,702 A | 10/1996 | Huitema et al. |
| 5,563,481 A | 10/1996 | Krause |
| 5,564,615 A | 10/1996 | Bishop et al. |
| 5,569,161 A | 10/1996 | Ebling et al. |
| 5,569,270 A | 10/1996 | Weng |
| 5,569,284 A | 10/1996 | Young et al. |
| 5,571,090 A | 11/1996 | Sherts |
| 5,571,100 A | 11/1996 | Goble et al. |
| 5,571,116 A | 11/1996 | Bolanos et al. |
| 5,571,285 A | 11/1996 | Chow et al. |
| 5,571,488 A | 11/1996 | Beerstecher et al. |
| 5,573,169 A | 11/1996 | Green et al. |
| 5,573,543 A | 11/1996 | Akopov et al. |
| 5,574,431 A | 11/1996 | McKeown et al. |
| 5,575,054 A | 11/1996 | Klinzing et al. |
| 5,575,789 A | 11/1996 | Bell et al. |
| 5,575,799 A | 11/1996 | Bolanos et al. |
| 5,575,803 A | 11/1996 | Cooper et al. |
| 5,575,805 A | 11/1996 | Li |
| 5,577,654 A | 11/1996 | Bishop |
| 5,578,052 A | 11/1996 | Koros et al. |
| 5,579,978 A | 12/1996 | Green et al. |
| 5,580,067 A | 12/1996 | Hamblin et al. |
| 5,582,611 A | 12/1996 | Tsuruta et al. |
| 5,582,617 A | 12/1996 | Klieman et al. |
| 5,583,114 A | 12/1996 | Barrows et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,591,170 A | 1/1997 | Spievack et al. |
| 5,591,187 A | 1/1997 | Dekel |

(56) References Cited

U.S. PATENT DOCUMENTS

| | | |
|---|---|---|
| 5,597,107 A | 1/1997 | Knodel et al. |
| 5,599,151 A | 2/1997 | Daum et al. |
| 5,599,279 A | 2/1997 | Slotman et al. |
| 5,599,344 A | 2/1997 | Paterson |
| 5,599,350 A | 2/1997 | Schulze et al. |
| 5,599,852 A | 2/1997 | Scopelianos et al. |
| 5,601,224 A | 2/1997 | Bishop et al. |
| 5,601,573 A | 2/1997 | Fogelberg et al. |
| 5,601,604 A | 2/1997 | Vincent |
| 5,602,449 A | 2/1997 | Krause et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,607,433 A | 3/1997 | Polla et al. |
| 5,607,450 A | 3/1997 | Zvenyatsky et al. |
| 5,607,474 A | 3/1997 | Athanasiou et al. |
| 5,609,285 A | 3/1997 | Grant et al. |
| 5,609,601 A | 3/1997 | Kolesa et al. |
| 5,611,709 A | 3/1997 | McAnulty |
| 5,613,499 A | 3/1997 | Palmer et al. |
| 5,613,937 A | 3/1997 | Garrison et al. |
| 5,613,966 A | 3/1997 | Makower et al. |
| 5,614,887 A | 3/1997 | Buchbinder |
| 5,615,820 A | 4/1997 | Viola |
| 5,618,294 A | 4/1997 | Aust et al. |
| 5,618,303 A | 4/1997 | Marlow et al. |
| 5,618,307 A | 4/1997 | Donlon et al. |
| 5,619,992 A | 4/1997 | Guthrie et al. |
| 5,620,289 A | 4/1997 | Curry |
| 5,620,326 A | 4/1997 | Younker |
| 5,620,452 A | 4/1997 | Yoon |
| 5,624,398 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,628,446 A | 5/1997 | Geiste et al. |
| 5,628,743 A | 5/1997 | Cimino |
| 5,628,745 A | 5/1997 | Bek |
| 5,630,539 A | 5/1997 | Plyley et al. |
| 5,630,540 A | 5/1997 | Blewett |
| 5,630,541 A | 5/1997 | Williamson, IV et al. |
| 5,630,782 A | 5/1997 | Adair |
| 5,632,432 A | 5/1997 | Schulze et al. |
| 5,632,433 A | 5/1997 | Grant et al. |
| 5,633,374 A | 5/1997 | Humphrey et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| D381,077 S | 7/1997 | Hunt |
| 5,643,291 A | 7/1997 | Pier et al. |
| 5,643,294 A | 7/1997 | Tovey et al. |
| 5,643,319 A | 7/1997 | Green et al. |
| 5,645,209 A | 7/1997 | Green et al. |
| 5,647,526 A | 7/1997 | Green et al. |
| 5,647,869 A | 7/1997 | Goble et al. |
| 5,649,937 A | 7/1997 | Bito et al. |
| 5,649,956 A | 7/1997 | Jensen et al. |
| 5,651,491 A | 7/1997 | Heaton et al. |
| 5,651,762 A | 7/1997 | Bridges |
| 5,651,821 A | 7/1997 | Uchida |
| 5,653,373 A | 8/1997 | Green et al. |
| 5,653,374 A | 8/1997 | Young et al. |
| 5,653,677 A | 8/1997 | Okada et al. |
| 5,653,721 A | 8/1997 | Knodel et al. |
| 5,655,698 A | 8/1997 | Yoon |
| 5,657,417 A | 8/1997 | Di Troia |
| 5,657,429 A | 8/1997 | Wang et al. |
| 5,657,921 A | 8/1997 | Young et al. |
| 5,658,238 A | 8/1997 | Suzuki et al. |
| 5,658,281 A | 8/1997 | Heard |
| 5,658,298 A | 8/1997 | Vincent et al. |
| 5,658,300 A | 8/1997 | Bito et al. |
| 5,658,307 A | 8/1997 | Exconde |
| 5,662,258 A | 9/1997 | Knodel et al. |
| 5,662,260 A | 9/1997 | Yoon |
| 5,662,662 A | 9/1997 | Bishop et al. |
| 5,662,667 A | 9/1997 | Knodel |
| 5,665,085 A | 9/1997 | Nardella |
| 5,667,517 A | 9/1997 | Hooven |
| 5,667,526 A | 9/1997 | Levin |
| 5,667,527 A | 9/1997 | Cook |
| 5,669,544 A | 9/1997 | Schulze et al. |
| 5,669,904 A | 9/1997 | Platt, Jr. et al. |
| 5,669,907 A | 9/1997 | Platt, Jr. et al. |
| 5,669,918 A | 9/1997 | Balazs et al. |
| 5,673,840 A | 10/1997 | Schulze et al. |
| 5,673,841 A | 10/1997 | Schulze et al. |
| 5,673,842 A | 10/1997 | Bittner et al. |
| 5,674,286 A | 10/1997 | D'Alessio et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,681,341 A | 10/1997 | Lunsford et al. |
| 5,683,349 A | 11/1997 | Makower et al. |
| 5,685,474 A | 11/1997 | Seeber |
| 5,686,090 A | 11/1997 | Schilder et al. |
| 5,688,270 A | 11/1997 | Yates et al. |
| 5,690,269 A | 11/1997 | Bolanos et al. |
| 5,692,668 A | 12/1997 | Schulze et al. |
| 5,693,020 A | 12/1997 | Rauh |
| 5,693,042 A | 12/1997 | Boiarski et al. |
| 5,693,051 A | 12/1997 | Schulze et al. |
| 5,695,494 A | 12/1997 | Becker |
| 5,695,502 A | 12/1997 | Pier et al. |
| 5,695,504 A | 12/1997 | Gifford, III et al. |
| 5,695,524 A | 12/1997 | Kelley et al. |
| 5,697,542 A | 12/1997 | Knodel et al. |
| 5,697,543 A | 12/1997 | Burdorff |
| 5,697,909 A | 12/1997 | Eggers et al. |
| 5,697,943 A | 12/1997 | Sauer et al. |
| 5,700,270 A | 12/1997 | Peyser et al. |
| 5,700,276 A | 12/1997 | Benecke |
| 5,702,387 A | 12/1997 | Arts et al. |
| 5,702,408 A | 12/1997 | Wales et al. |
| 5,702,409 A | 12/1997 | Rayburn et al. |
| 5,704,087 A | 1/1998 | Strub |
| 5,704,534 A | 1/1998 | Huitema et al. |
| 5,706,997 A | 1/1998 | Green et al. |
| 5,706,998 A | 1/1998 | Plyley et al. |
| 5,707,392 A | 1/1998 | Kortenbach |
| 5,709,334 A | 1/1998 | Sorrentino et al. |
| 5,709,335 A | 1/1998 | Heck |
| 5,709,680 A | 1/1998 | Yates et al. |
| 5,709,706 A | 1/1998 | Kienzle et al. |
| 5,711,472 A | 1/1998 | Bryan |
| 5,712,460 A | 1/1998 | Carr et al. |
| 5,713,128 A | 2/1998 | Schrenk et al. |
| 5,713,505 A | 2/1998 | Huitema |
| 5,713,895 A | 2/1998 | Lontine et al. |
| 5,713,896 A | 2/1998 | Nardella |
| 5,713,920 A | 2/1998 | Bezwada et al. |
| 5,715,604 A | 2/1998 | Lanzoni |
| 5,715,987 A | 2/1998 | Kelley et al. |
| 5,715,988 A | 2/1998 | Palmer |
| 5,716,366 A | 2/1998 | Yates |
| 5,718,359 A | 2/1998 | Palmer et al. |
| 5,718,360 A | 2/1998 | Green et al. |
| 5,718,548 A | 2/1998 | Cotellessa |
| 5,718,714 A | 2/1998 | Livneh |
| 5,720,744 A | 2/1998 | Eggleston et al. |
| D393,067 S | 3/1998 | Geary et al. |
| 5,724,025 A | 3/1998 | Tavori |
| 5,725,536 A | 3/1998 | Oberlin et al. |
| 5,725,554 A | 3/1998 | Simon et al. |
| 5,728,110 A | 3/1998 | Vidal et al. |
| 5,728,113 A | 3/1998 | Sherts |
| 5,728,121 A | 3/1998 | Bimbo et al. |
| 5,730,758 A | 3/1998 | Allgeyer |
| 5,732,821 A | 3/1998 | Stone et al. |
| 5,732,871 A | 3/1998 | Clark et al. |

(56) References Cited

U.S. PATENT DOCUMENTS

| | | |
|---|---|---|
| 5,732,872 A | 3/1998 | Bolduc et al. |
| 5,733,308 A | 3/1998 | Daugherty et al. |
| 5,735,445 A | 4/1998 | Vidal et al. |
| 5,735,848 A | 4/1998 | Yates et al. |
| 5,735,874 A | 4/1998 | Measamer et al. |
| 5,738,474 A | 4/1998 | Blewett |
| 5,738,629 A | 4/1998 | Moll et al. |
| 5,738,648 A | 4/1998 | Lands et al. |
| 5,741,271 A | 4/1998 | Nakao et al. |
| 5,743,456 A | 4/1998 | Jones et al. |
| 5,747,953 A | 5/1998 | Philipp |
| 5,749,889 A | 5/1998 | Bacich et al. |
| 5,749,893 A | 5/1998 | Vidal et al. |
| 5,749,968 A | 5/1998 | Melanson et al. |
| 5,752,644 A | 5/1998 | Bolanos et al. |
| 5,752,965 A | 5/1998 | Francis et al. |
| 5,752,970 A | 5/1998 | Yoon |
| 5,755,717 A | 5/1998 | Yates et al. |
| 5,758,814 A | 6/1998 | Gallagher et al. |
| 5,762,255 A | 6/1998 | Chrisman et al. |
| 5,762,256 A | 6/1998 | Mastri et al. |
| 5,766,188 A | 6/1998 | Igaki |
| 5,766,205 A | 6/1998 | Zvenyatsky et al. |
| 5,769,303 A | 6/1998 | Knodel et al. |
| 5,769,748 A | 6/1998 | Eyerly et al. |
| 5,769,791 A | 6/1998 | Benaron et al. |
| 5,769,892 A | 6/1998 | Kingwell |
| 5,772,379 A | 6/1998 | Evensen |
| 5,772,578 A | 6/1998 | Heimberger et al. |
| 5,772,659 A | 6/1998 | Becker et al. |
| 5,776,130 A | 7/1998 | Buysse et al. |
| 5,778,939 A | 7/1998 | Hok-Yin |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,748 A | 7/1998 | Palmer et al. |
| 5,782,749 A | 7/1998 | Riza |
| 5,782,859 A | 7/1998 | Nicholas et al. |
| 5,784,934 A | 7/1998 | Izumisawa |
| 5,785,232 A | 7/1998 | Vidal et al. |
| 5,785,647 A | 7/1998 | Tompkins et al. |
| 5,787,897 A | 8/1998 | Kieturakis |
| 5,791,231 A | 8/1998 | Cohn et al. |
| 5,792,135 A | 8/1998 | Madhani et al. |
| 5,792,162 A | 8/1998 | Jolly et al. |
| 5,792,165 A | 8/1998 | Klieman et al. |
| 5,794,834 A | 8/1998 | Hamblin et al. |
| 5,796,188 A | 8/1998 | Bays |
| 5,797,536 A | 8/1998 | Smith et al. |
| 5,797,537 A | 8/1998 | Oberlin et al. |
| 5,797,538 A | 8/1998 | Heaton et al. |
| 5,797,637 A | 8/1998 | Ervin |
| 5,797,906 A | 8/1998 | Rhum et al. |
| 5,797,927 A | 8/1998 | Yoon |
| 5,797,941 A | 8/1998 | Schulze et al. |
| 5,797,959 A | 8/1998 | Castro et al. |
| 5,799,857 A | 9/1998 | Robertson et al. |
| 5,800,379 A | 9/1998 | Edwards |
| 5,800,423 A | 9/1998 | Jensen |
| 5,804,726 A | 9/1998 | Geib et al. |
| 5,804,936 A | 9/1998 | Brodsky et al. |
| 5,806,676 A | 9/1998 | Wasgien |
| 5,807,376 A | 9/1998 | Viola et al. |
| 5,807,378 A | 9/1998 | Jensen et al. |
| 5,807,393 A | 9/1998 | Williamson, IV et al. |
| 5,809,441 A | 9/1998 | McKee |
| 5,810,721 A | 9/1998 | Mueller et al. |
| 5,810,811 A | 9/1998 | Yates et al. |
| 5,810,846 A | 9/1998 | Virnich et al. |
| 5,810,855 A | 9/1998 | Rayburn et al. |
| 5,813,813 A | 9/1998 | Daum et al. |
| 5,814,055 A | 9/1998 | Knodel et al. |
| 5,814,057 A | 9/1998 | Oi et al. |
| 5,816,471 A | 10/1998 | Plyley et al. |
| 5,817,084 A | 10/1998 | Jensen |
| 5,817,091 A | 10/1998 | Nardella et al. |
| 5,817,093 A | 10/1998 | Williamson, IV et al. |
| 5,817,109 A | 10/1998 | McGarry et al. |
| 5,817,119 A | 10/1998 | Klieman et al. |
| 5,820,009 A | 10/1998 | Melling et al. |
| 5,823,066 A | 10/1998 | Huitema et al. |
| 5,824,333 A | 10/1998 | Scopelianos et al. |
| 5,826,776 A | 10/1998 | Schulze et al. |
| 5,827,271 A | 10/1998 | Buysse et al. |
| 5,827,298 A | 10/1998 | Hart et al. |
| 5,829,662 A | 11/1998 | Allen et al. |
| 5,830,598 A | 11/1998 | Patterson |
| 5,833,690 A | 11/1998 | Yates et al. |
| 5,833,695 A | 11/1998 | Yoon |
| 5,833,696 A | 11/1998 | Whitfield et al. |
| 5,836,503 A | 11/1998 | Ehrenfels et al. |
| 5,836,960 A | 11/1998 | Kolesa et al. |
| 5,839,369 A | 11/1998 | Chatterjee et al. |
| 5,839,639 A | 11/1998 | Sauer et al. |
| 5,843,021 A | 12/1998 | Edwards et al. |
| 5,843,096 A | 12/1998 | Igaki et al. |
| 5,843,097 A | 12/1998 | Mayenberger et al. |
| 5,843,122 A | 12/1998 | Riza |
| 5,843,132 A | 12/1998 | Ilvento |
| 5,843,169 A | 12/1998 | Taheri |
| 5,846,254 A | 12/1998 | Schulze et al. |
| 5,847,566 A | 12/1998 | Marritt et al. |
| 5,849,011 A | 12/1998 | Jones et al. |
| 5,849,020 A | 12/1998 | Long et al. |
| 5,849,023 A | 12/1998 | Mericle |
| 5,851,179 A | 12/1998 | Ritson et al. |
| 5,853,366 A | 12/1998 | Dowlatshahi |
| 5,855,311 A | 1/1999 | Hamblin et al. |
| 5,855,583 A | 1/1999 | Wang et al. |
| 5,860,581 A | 1/1999 | Robertson et al. |
| 5,860,975 A | 1/1999 | Goble et al. |
| 5,865,361 A | 2/1999 | Milliman et al. |
| 5,865,638 A | 2/1999 | Trafton |
| 5,868,361 A | 2/1999 | Rinderer |
| 5,868,760 A | 2/1999 | McGuckin, Jr. |
| 5,868,790 A | 2/1999 | Vincent et al. |
| 5,871,135 A | 2/1999 | Williamson, IV et al. |
| 5,873,885 A | 2/1999 | Weidenbenner |
| 5,876,401 A | 3/1999 | Schulze et al. |
| 5,878,193 A | 3/1999 | Wang et al. |
| 5,878,607 A | 3/1999 | Nunes et al. |
| 5,878,937 A | 3/1999 | Green et al. |
| 5,878,938 A | 3/1999 | Bittner et al. |
| 5,881,777 A | 3/1999 | Bassi et al. |
| 5,891,094 A | 4/1999 | Masterson et al. |
| 5,891,160 A | 4/1999 | Williamson, IV et al. |
| 5,891,558 A | 4/1999 | Bell et al. |
| 5,893,506 A | 4/1999 | Powell |
| 5,893,835 A | 4/1999 | Witt et al. |
| 5,893,878 A | 4/1999 | Pierce |
| 5,894,979 A | 4/1999 | Powell |
| 5,897,552 A | 4/1999 | Edwards et al. |
| 5,897,562 A | 4/1999 | Bolanos et al. |
| 5,899,824 A | 5/1999 | Kurtz et al. |
| 5,899,914 A | 5/1999 | Zirps et al. |
| 5,901,895 A | 5/1999 | Heaton et al. |
| 5,902,312 A | 5/1999 | Frater et al. |
| 5,903,117 A | 5/1999 | Gregory |
| 5,904,647 A | 5/1999 | Ouchi |
| 5,904,693 A | 5/1999 | Dicesare et al. |
| 5,904,702 A | 5/1999 | Ek et al. |
| 5,906,577 A | 5/1999 | Beane et al. |
| 5,906,625 A | 5/1999 | Bito et al. |
| 5,907,211 A | 5/1999 | Hall et al. |
| 5,908,402 A | 6/1999 | Blythe |
| 5,908,427 A | 6/1999 | McKean et al. |
| 5,909,062 A * | 6/1999 | Krietzman ............ H02J 9/061 307/150 |
| 5,911,353 A | 6/1999 | Bolanos et al. |
| 5,915,616 A | 6/1999 | Viola et al. |
| 5,916,225 A | 6/1999 | Kugel |
| 5,918,791 A | 7/1999 | Sorrentino et al. |

(56) References Cited

U.S. PATENT DOCUMENTS

| | | |
|---|---|---|
| 5,919,198 A | 7/1999 | Graves, Jr. et al. |
| 5,921,956 A | 7/1999 | Grinberg et al. |
| 5,924,864 A | 7/1999 | Loge et al. |
| 5,928,137 A | 7/1999 | Green |
| 5,928,256 A | 7/1999 | Riza |
| 5,931,847 A | 8/1999 | Bittner et al. |
| 5,931,853 A | 8/1999 | McEwen et al. |
| 5,937,951 A | 8/1999 | Izuchukwu et al. |
| 5,938,667 A | 8/1999 | Peyser et al. |
| 5,941,442 A | 8/1999 | Geiste et al. |
| 5,941,890 A | 8/1999 | Voegele et al. |
| 5,944,172 A | 8/1999 | Hannula |
| 5,944,715 A | 8/1999 | Goble et al. |
| 5,946,978 A | 9/1999 | Yamashita |
| 5,947,984 A | 9/1999 | Whipple |
| 5,947,996 A | 9/1999 | Logeman |
| 5,948,030 A | 9/1999 | Miller et al. |
| 5,948,429 A | 9/1999 | Bell et al. |
| 5,951,301 A | 9/1999 | Younker |
| 5,951,516 A | 9/1999 | Bunyan |
| 5,951,552 A | 9/1999 | Long et al. |
| 5,951,574 A | 9/1999 | Stefanchik et al. |
| 5,951,581 A | 9/1999 | Saadat et al. |
| 5,954,259 A | 9/1999 | Viola et al. |
| 5,964,394 A | 10/1999 | Robertson |
| 5,964,774 A | 10/1999 | McKean et al. |
| 5,971,916 A | 10/1999 | Koren |
| 5,973,221 A | 10/1999 | Collyer et al. |
| D416,089 S | 11/1999 | Barton et al. |
| 5,976,122 A | 11/1999 | Madhani et al. |
| 5,977,746 A | 11/1999 | Hershberger et al. |
| 5,984,949 A | 11/1999 | Levin |
| 5,988,479 A | 11/1999 | Palmer |
| 5,990,379 A | 11/1999 | Gregory |
| 5,993,466 A | 11/1999 | Yoon |
| 5,997,528 A | 12/1999 | Bisch et al. |
| 5,997,552 A | 12/1999 | Person et al. |
| 6,001,108 A | 12/1999 | Wang et al. |
| 6,003,517 A | 12/1999 | Sheffield et al. |
| 6,004,319 A | 12/1999 | Goble et al. |
| 6,004,335 A | 12/1999 | Vaitekunas et al. |
| 6,007,521 A | 12/1999 | Bidwell et al. |
| 6,010,054 A | 1/2000 | Johnson et al. |
| 6,010,513 A | 1/2000 | Tormala et al. |
| 6,010,520 A | 1/2000 | Pattison |
| 6,012,494 A | 1/2000 | Balazs |
| 6,013,076 A | 1/2000 | Goble et al. |
| 6,015,406 A | 1/2000 | Goble et al. |
| 6,015,417 A | 1/2000 | Reynolds, Jr. |
| 6,017,322 A | 1/2000 | Snoke et al. |
| 6,017,354 A | 1/2000 | Culp et al. |
| 6,017,356 A | 1/2000 | Frederick et al. |
| 6,018,227 A | 1/2000 | Kumar et al. |
| 6,019,745 A | 2/2000 | Gray |
| 6,022,352 A | 2/2000 | Vandewalle |
| 6,023,641 A | 2/2000 | Thompson |
| 6,024,708 A | 2/2000 | Bales et al. |
| 6,024,741 A | 2/2000 | Williamson, IV et al. |
| 6,024,748 A | 2/2000 | Manzo et al. |
| 6,024,750 A | 2/2000 | Mastri et al. |
| 6,024,764 A | 2/2000 | Schroeppel |
| 6,027,501 A | 2/2000 | Goble et al. |
| 6,030,384 A | 2/2000 | Nezhat |
| 6,032,849 A | 3/2000 | Mastri et al. |
| 6,033,105 A | 3/2000 | Barker et al. |
| 6,033,378 A | 3/2000 | Lundquist et al. |
| 6,033,399 A | 3/2000 | Gines |
| 6,033,427 A | 3/2000 | Lee |
| 6,036,667 A | 3/2000 | Manna et al. |
| 6,037,724 A | 3/2000 | Buss et al. |
| 6,037,927 A | 3/2000 | Rosenberg |
| 6,039,733 A | 3/2000 | Buysse et al. |
| 6,039,734 A | 3/2000 | Goble |
| 6,042,601 A | 3/2000 | Smith |
| 6,042,607 A | 3/2000 | Williamson, IV et al. |
| 6,043,626 A * | 3/2000 | Snyder ............... A45F 5/02 320/107 |
| 6,045,560 A | 4/2000 | McKean et al. |
| 6,047,861 A | 4/2000 | Vidal et al. |
| 6,049,145 A | 4/2000 | Austin et al. |
| 6,050,172 A | 4/2000 | Corves et al. |
| 6,050,472 A | 4/2000 | Shibata |
| 6,050,989 A | 4/2000 | Fox et al. |
| 6,050,990 A | 4/2000 | Tankovich et al. |
| 6,050,996 A | 4/2000 | Schmaltz et al. |
| 6,053,390 A | 4/2000 | Green et al. |
| 6,053,899 A | 4/2000 | Slanda et al. |
| 6,053,922 A | 4/2000 | Krause et al. |
| RE36,720 E | 5/2000 | Green et al. |
| 6,056,735 A | 5/2000 | Okada et al. |
| 6,056,746 A | 5/2000 | Goble et al. |
| 6,059,806 A | 5/2000 | Hoegerle |
| 6,062,360 A | 5/2000 | Shields |
| 6,063,025 A | 5/2000 | Bridges et al. |
| 6,063,050 A | 5/2000 | Manna et al. |
| 6,063,095 A | 5/2000 | Wang et al. |
| 6,063,097 A | 5/2000 | Oi et al. |
| 6,063,098 A | 5/2000 | Houser et al. |
| 6,065,679 A | 5/2000 | Levie et al. |
| 6,065,919 A | 5/2000 | Peck |
| 6,066,132 A | 5/2000 | Chen et al. |
| 6,066,151 A | 5/2000 | Miyawaki et al. |
| 6,068,627 A | 5/2000 | Orszulak et al. |
| 6,071,233 A | 6/2000 | Ishikawa et al. |
| 6,074,386 A | 6/2000 | Goble et al. |
| 6,074,401 A | 6/2000 | Gardiner et al. |
| 6,077,280 A | 6/2000 | Fossum |
| 6,077,286 A | 6/2000 | Cuschieri et al. |
| 6,077,290 A | 6/2000 | Marini |
| 6,079,606 A | 6/2000 | Milliman et al. |
| 6,080,181 A | 6/2000 | Jensen et al. |
| 6,082,577 A | 7/2000 | Coates et al. |
| 6,083,191 A | 7/2000 | Rose |
| 6,083,223 A | 7/2000 | Baker |
| 6,083,234 A | 7/2000 | Nicholas et al. |
| 6,083,242 A | 7/2000 | Cook |
| 6,086,544 A | 7/2000 | Hibner et al. |
| 6,086,600 A | 7/2000 | Kortenbach |
| 6,090,106 A | 7/2000 | Goble et al. |
| 6,093,186 A | 7/2000 | Goble |
| 6,099,537 A | 8/2000 | Sugai et al. |
| 6,099,551 A | 8/2000 | Gabbay |
| 6,102,271 A | 8/2000 | Longo et al. |
| 6,104,162 A | 8/2000 | Sainsbury et al. |
| 6,104,304 A | 8/2000 | Clark et al. |
| 6,106,511 A | 8/2000 | Jensen |
| 6,109,500 A | 8/2000 | Alli et al. |
| 6,110,187 A | 8/2000 | Donlon |
| 6,113,618 A | 9/2000 | Nic |
| 6,117,148 A | 9/2000 | Ravo et al. |
| 6,117,158 A | 9/2000 | Measamer et al. |
| 6,119,913 A | 9/2000 | Adams et al. |
| 6,120,433 A | 9/2000 | Mizuno et al. |
| 6,120,462 A | 9/2000 | Hibner et al. |
| 6,123,241 A | 9/2000 | Walter et al. |
| 6,123,701 A | 9/2000 | Nezhat |
| H001904 H | 10/2000 | Yates et al. |
| 6,126,058 A | 10/2000 | Adams et al. |
| 6,126,359 A | 10/2000 | Dittrich et al. |
| 6,126,670 A | 10/2000 | Walker et al. |
| 6,131,789 A | 10/2000 | Schulze et al. |
| 6,131,790 A | 10/2000 | Piraka |
| 6,132,368 A | 10/2000 | Cooper |
| 6,139,546 A | 10/2000 | Koenig et al. |
| 6,142,149 A | 11/2000 | Steen |
| 6,142,933 A | 11/2000 | Longo et al. |
| 6,147,135 A | 11/2000 | Yuan et al. |
| 6,149,660 A | 11/2000 | Laufer et al. |
| 6,151,323 A | 11/2000 | O'Connell et al. |
| 6,152,935 A | 11/2000 | Kammerer et al. |
| 6,155,473 A | 12/2000 | Tompkins et al. |
| 6,156,056 A | 12/2000 | Kearns et al. |
| 6,157,169 A | 12/2000 | Lee |
| 6,159,146 A | 12/2000 | El Gazayerli |

(56) References Cited

U.S. PATENT DOCUMENTS

| | | |
|---|---|---|
| 6,159,200 A | 12/2000 | Verdura et al. |
| 6,159,224 A | 12/2000 | Yoon |
| 6,162,208 A | 12/2000 | Hipps |
| 6,162,220 A | 12/2000 | Nezhat |
| 6,162,537 A | 12/2000 | Martin et al. |
| 6,165,175 A | 12/2000 | Wampler et al. |
| 6,165,184 A | 12/2000 | Verdura et al. |
| 6,165,188 A | 12/2000 | Saadat et al. |
| 6,167,185 A | 12/2000 | Smiley et al. |
| 6,168,605 B1 | 1/2001 | Measamer et al. |
| 6,171,305 B1 | 1/2001 | Sherman |
| 6,171,316 B1 | 1/2001 | Kovac et al. |
| 6,171,330 B1 | 1/2001 | Benchetrit |
| 6,173,074 B1 | 1/2001 | Russo |
| 6,174,308 B1 | 1/2001 | Goble et al. |
| 6,174,309 B1 | 1/2001 | Wrublewski et al. |
| 6,174,318 B1 | 1/2001 | Bates et al. |
| 6,175,290 B1 | 1/2001 | Forsythe et al. |
| 6,179,195 B1 | 1/2001 | Adams et al. |
| 6,179,776 B1 | 1/2001 | Adams et al. |
| 6,181,105 B1 | 1/2001 | Cutolo et al. |
| 6,182,673 B1 | 2/2001 | Kindermann et al. |
| 6,185,356 B1 | 2/2001 | Parker et al. |
| 6,186,142 B1 | 2/2001 | Schmidt et al. |
| 6,187,003 B1 | 2/2001 | Buysse et al. |
| 6,190,386 B1 | 2/2001 | Rydell |
| 6,193,129 B1 | 2/2001 | Bittner et al. |
| 6,197,042 B1 | 3/2001 | Ginn et al. |
| 6,200,330 B1 | 3/2001 | Benderev et al. |
| 6,202,914 B1 | 3/2001 | Geiste et al. |
| 6,206,894 B1 | 3/2001 | Thompson et al. |
| 6,206,897 B1 | 3/2001 | Jamiolkowski et al. |
| 6,206,904 B1 | 3/2001 | Ouchi |
| 6,209,414 B1 | 4/2001 | Uneme |
| 6,210,403 B1 | 4/2001 | Klicek |
| 6,213,999 B1 | 4/2001 | Platt, Jr. et al. |
| 6,214,028 B1 | 4/2001 | Yoon et al. |
| 6,220,368 B1 | 4/2001 | Ark et al. |
| 6,221,007 B1 | 4/2001 | Green |
| 6,221,023 B1 | 4/2001 | Matsuba et al. |
| 6,223,100 B1 | 4/2001 | Green |
| 6,223,835 B1 | 5/2001 | Habedank et al. |
| 6,224,617 B1 | 5/2001 | Saadat et al. |
| 6,228,080 B1 | 5/2001 | Gines |
| 6,228,081 B1 | 5/2001 | Goble |
| 6,228,083 B1 | 5/2001 | Lands et al. |
| 6,228,084 B1 | 5/2001 | Kirwan, Jr. |
| 6,228,089 B1 | 5/2001 | Wahrburg |
| 6,228,098 B1 | 5/2001 | Kayan et al. |
| 6,231,565 B1 | 5/2001 | Tovey et al. |
| 6,234,178 B1 | 5/2001 | Goble et al. |
| 6,237,604 B1 | 5/2001 | Burnside et al. |
| 6,238,384 B1 | 5/2001 | Peer |
| 6,241,139 B1 | 6/2001 | Milliman et al. |
| 6,241,140 B1 | 6/2001 | Adams et al. |
| 6,241,723 B1 | 6/2001 | Heim et al. |
| 6,245,084 B1 | 6/2001 | Mark et al. |
| 6,248,116 B1 | 6/2001 | Chevillon et al. |
| 6,248,117 B1 | 6/2001 | Blatter |
| 6,249,076 B1 | 6/2001 | Madden et al. |
| 6,249,105 B1 | 6/2001 | Andrews et al. |
| 6,250,532 B1 | 6/2001 | Green et al. |
| 6,251,485 B1 | 6/2001 | Harris et al. |
| 6,254,534 B1 | 7/2001 | Butler et al. |
| 6,254,619 B1 | 7/2001 | Garabet et al. |
| 6,254,642 B1 | 7/2001 | Taylor |
| 6,258,107 B1 | 7/2001 | Balazs et al. |
| 6,261,286 B1 | 7/2001 | Goble et al. |
| 6,261,679 B1 | 7/2001 | Chen et al. |
| 6,264,086 B1 | 7/2001 | McGuckin, Jr. |
| 6,264,087 B1 | 7/2001 | Whitman |
| 6,264,617 B1 | 7/2001 | Bales et al. |
| 6,270,508 B1 | 8/2001 | Klieman et al. |
| 6,270,916 B1 | 8/2001 | Sink et al. |
| 6,273,876 B1 | 8/2001 | Klima et al. |
| 6,273,897 B1 | 8/2001 | Dalessandro et al. |
| 6,277,114 B1 | 8/2001 | Bullivant et al. |
| 6,280,407 B1 | 8/2001 | Manna et al. |
| 6,293,927 B1 | 9/2001 | McGuckin, Jr. |
| 6,293,942 B1 | 9/2001 | Goble et al. |
| 6,296,640 B1 | 10/2001 | Wampler et al. |
| 6,302,311 B1 | 10/2001 | Adams et al. |
| 6,302,743 B1 | 10/2001 | Chiu et al. |
| 6,305,891 B1 | 10/2001 | Burlingame |
| 6,306,134 B1 | 10/2001 | Goble et al. |
| 6,306,149 B1 | 10/2001 | Meade |
| 6,306,424 B1 | 10/2001 | Vyakarnam et al. |
| 6,309,397 B1 | 10/2001 | Julian et al. |
| 6,309,403 B1 | 10/2001 | Minor et al. |
| 6,312,435 B1 | 11/2001 | Wallace et al. |
| 6,315,184 B1 | 11/2001 | Whitman |
| 6,319,510 B1 | 11/2001 | Yates |
| 6,320,123 B1 | 11/2001 | Reimers |
| 6,322,494 B1 | 11/2001 | Bullivant et al. |
| 6,324,339 B1 | 11/2001 | Hudson et al. |
| 6,325,799 B1 | 12/2001 | Goble |
| 6,325,805 B1 | 12/2001 | Ogilvie et al. |
| 6,325,810 B1 | 12/2001 | Hamilton et al. |
| 6,328,498 B1 | 12/2001 | Mersch |
| 6,330,965 B1 | 12/2001 | Milliman et al. |
| 6,331,181 B1 | 12/2001 | Tierney et al. |
| 6,331,761 B1 | 12/2001 | Kumar et al. |
| 6,333,029 B1 | 12/2001 | Vyakarnam et al. |
| 6,334,860 B1 | 1/2002 | Dorn |
| 6,334,861 B1 | 1/2002 | Chandler et al. |
| 6,336,926 B1 | 1/2002 | Goble |
| 6,338,737 B1 | 1/2002 | Toledano |
| 6,343,731 B1 | 2/2002 | Adams et al. |
| 6,346,077 B1 | 2/2002 | Taylor et al. |
| 6,348,061 B1 | 2/2002 | Whitman |
| D454,951 S | 3/2002 | Bon |
| 6,352,503 B1 | 3/2002 | Matsui et al. |
| 6,352,532 B1 | 3/2002 | Kramer et al. |
| 6,355,699 B1 | 3/2002 | Vyakarnam et al. |
| 6,356,072 B1 | 3/2002 | Chass |
| 6,358,224 B1 | 3/2002 | Tims et al. |
| 6,358,263 B2 | 3/2002 | Mark et al. |
| 6,364,877 B1 | 4/2002 | Goble et al. |
| 6,364,888 B1 | 4/2002 | Niemeyer et al. |
| 6,370,981 B2 | 4/2002 | Watarai |
| 6,371,114 B1 | 4/2002 | Schmidt et al. |
| 6,373,152 B1 | 4/2002 | Wang et al. |
| 6,377,011 B1 | 4/2002 | Ben-Ur |
| 6,383,201 B1 | 5/2002 | Dong |
| 6,387,092 B1 | 5/2002 | Burnside et al. |
| 6,387,113 B1 | 5/2002 | Hawkins et al. |
| 6,387,114 B2 | 5/2002 | Adams |
| 6,391,038 B2 | 5/2002 | Vargas et al. |
| 6,392,854 B1 | 5/2002 | O'Gorman |
| 6,398,779 B1 | 6/2002 | Buysse et al. |
| 6,398,781 B1 | 6/2002 | Goble et al. |
| 6,398,797 B2 | 6/2002 | Bombard et al. |
| 6,402,766 B2 | 6/2002 | Bowman et al. |
| 6,406,440 B1 | 6/2002 | Stefanchik |
| 6,406,472 B1 | 6/2002 | Jensen |
| 6,409,724 B1 | 6/2002 | Penny et al. |
| H002037 H | 7/2002 | Yates et al. |
| 6,412,639 B1 | 7/2002 | Hickey |
| 6,413,274 B1 | 7/2002 | Pedros |
| 6,416,486 B1 | 7/2002 | Wampler |
| 6,416,509 B1 | 7/2002 | Goble et al. |
| 6,419,695 B1 | 7/2002 | Gabbay |
| 6,423,079 B1 | 7/2002 | Blake, III |
| RE37,814 E | 8/2002 | Allgeyer |
| 6,428,070 B1 | 8/2002 | Takanashi et al. |
| 6,428,487 B1 | 8/2002 | Burdorff et al. |
| 6,429,611 B1 | 8/2002 | Li |
| 6,430,298 B1 | 8/2002 | Kettl et al. |
| 6,432,065 B1 | 8/2002 | Burdorff et al. |
| 6,436,097 B1 | 8/2002 | Nardella |
| 6,436,107 B1 | 8/2002 | Wang et al. |
| 6,436,110 B2 | 8/2002 | Bowman et al. |
| 6,436,122 B1 | 8/2002 | Frank et al. |
| 6,439,439 B1 | 8/2002 | Rickard et al. |

(56) References Cited

U.S. PATENT DOCUMENTS

| | | |
|---|---|---|
| 6,439,446 B1 | 8/2002 | Perry et al. |
| 6,440,146 B2 | 8/2002 | Nicholas et al. |
| 6,441,577 B2 | 8/2002 | Blumenkranz et al. |
| D462,758 S | 9/2002 | Epstein et al. |
| 6,443,973 B1 | 9/2002 | Whitman |
| 6,445,530 B1 | 9/2002 | Baker |
| 6,447,518 B1 | 9/2002 | Krause et al. |
| 6,447,523 B1 | 9/2002 | Middleman et al. |
| 6,447,799 B1 | 9/2002 | Ullman |
| 6,447,864 B2 | 9/2002 | Johnson et al. |
| 6,450,391 B1 | 9/2002 | Kayan et al. |
| 6,450,989 B2 | 9/2002 | Dubrul et al. |
| 6,454,781 B1 | 9/2002 | Witt et al. |
| 6,458,077 B1 | 10/2002 | Boebel et al. |
| 6,458,147 B1 | 10/2002 | Cruise et al. |
| 6,460,627 B1 | 10/2002 | Below et al. |
| 6,468,275 B1 | 10/2002 | Wampler et al. |
| 6,468,286 B2 | 10/2002 | Mastri et al. |
| 6,471,106 B1 | 10/2002 | Reining |
| 6,471,659 B2 | 10/2002 | Eggers et al. |
| 6,478,210 B2 | 11/2002 | Adams et al. |
| 6,482,200 B2 | 11/2002 | Shippert |
| 6,482,217 B1 | 11/2002 | Pintor et al. |
| 6,485,490 B2 | 11/2002 | Wampler et al. |
| 6,485,503 B2 | 11/2002 | Jacobs et al. |
| 6,485,667 B1 | 11/2002 | Tan |
| 6,486,286 B1 | 11/2002 | McGall et al. |
| 6,488,196 B1 | 12/2002 | Fenton, Jr. |
| 6,488,197 B1 | 12/2002 | Whitman |
| 6,488,659 B1 | 12/2002 | Rosenman |
| 6,491,201 B1 | 12/2002 | Whitman |
| 6,491,690 B1 | 12/2002 | Goble et al. |
| 6,491,701 B2 | 12/2002 | Tierney et al. |
| 6,492,785 B1 | 12/2002 | Kasten et al. |
| 6,494,885 B1 | 12/2002 | Dhindsa |
| 6,494,896 B1 | 12/2002 | D'Alessio et al. |
| 6,498,480 B1 | 12/2002 | Manara |
| 6,500,176 B1 | 12/2002 | Truckai et al. |
| 6,500,194 B2 | 12/2002 | Benderev et al. |
| 6,503,139 B2 | 1/2003 | Coral |
| 6,503,257 B2 | 1/2003 | Grant et al. |
| 6,503,259 B2 | 1/2003 | Huxel et al. |
| 6,505,768 B2 | 1/2003 | Whitman |
| 6,506,197 B1 | 1/2003 | Rollero et al. |
| 6,510,854 B2 | 1/2003 | Goble |
| 6,511,468 B1 | 1/2003 | Cragg et al. |
| 6,512,360 B1 | 1/2003 | Goto et al. |
| 6,514,252 B2 | 2/2003 | Nezhat et al. |
| 6,516,073 B1 | 2/2003 | Schulz et al. |
| 6,517,528 B1 | 2/2003 | Pantages et al. |
| 6,517,535 B2 | 2/2003 | Edwards |
| 6,517,565 B1 | 2/2003 | Whitman et al. |
| 6,517,566 B1 | 2/2003 | Hovland et al. |
| 6,520,971 B1 | 2/2003 | Perry et al. |
| 6,520,972 B2 | 2/2003 | Peters |
| 6,522,101 B2 | 2/2003 | Malackowski |
| 6,524,180 B1 | 2/2003 | Simms et al. |
| 6,527,782 B2 | 3/2003 | Hogg et al. |
| 6,527,785 B2 | 3/2003 | Sancoff et al. |
| 6,532,958 B1 | 3/2003 | Buan et al. |
| 6,533,157 B1 | 3/2003 | Whitman |
| 6,533,723 B1 | 3/2003 | Lockery et al. |
| 6,533,784 B2 | 3/2003 | Truckai et al. |
| 6,535,764 B2 | 3/2003 | Imran et al. |
| 6,539,816 B2 | 4/2003 | Kogiso et al. |
| 6,543,456 B1 | 4/2003 | Freeman |
| 6,545,384 B1 | 4/2003 | Pelrine et al. |
| 6,547,786 B1 | 4/2003 | Goble |
| 6,550,546 B2 | 4/2003 | Thurler et al. |
| 6,551,333 B2 | 4/2003 | Kuhns et al. |
| 6,554,861 B2 | 4/2003 | Knox et al. |
| 6,555,770 B2 | 4/2003 | Kawase |
| 6,558,378 B2 | 5/2003 | Sherman et al. |
| 6,558,379 B1 | 5/2003 | Batchelor et al. |
| 6,558,429 B2 | 5/2003 | Taylor |
| 6,561,187 B2 | 5/2003 | Schmidt et al. |
| 6,565,560 B1 | 5/2003 | Goble et al. |
| 6,566,619 B2 | 5/2003 | Gillman et al. |
| 6,569,085 B2 | 5/2003 | Kortenbach et al. |
| 6,569,171 B2 | 5/2003 | DeGuillebon et al. |
| 6,578,751 B2 | 6/2003 | Hartwick |
| 6,582,364 B2 | 6/2003 | Butler et al. |
| 6,582,427 B1 | 6/2003 | Goble et al. |
| 6,582,441 B1 | 6/2003 | He et al. |
| 6,583,533 B2 | 6/2003 | Pelrine et al. |
| 6,585,144 B2 | 7/2003 | Adams et al. |
| 6,585,664 B2 | 7/2003 | Burdorff et al. |
| 6,587,750 B2 | 7/2003 | Gerbi et al. |
| 6,588,643 B2 | 7/2003 | Bolduc et al. |
| 6,588,931 B2 | 7/2003 | Betzner et al. |
| 6,589,118 B1 | 7/2003 | Soma et al. |
| 6,589,164 B1 | 7/2003 | Flaherty |
| 6,592,538 B1 | 7/2003 | Hotchkiss et al. |
| 6,592,597 B2 | 7/2003 | Grant et al. |
| 6,594,552 B1 | 7/2003 | Nowlin et al. |
| 6,596,296 B1 | 7/2003 | Nelson et al. |
| 6,596,304 B1 | 7/2003 | Bayon et al. |
| 6,596,432 B2 | 7/2003 | Kawakami et al. |
| 6,599,323 B2 | 7/2003 | Melican et al. |
| D478,665 S | 8/2003 | Isaacs et al. |
| D478,986 S | 8/2003 | Johnston et al. |
| 6,601,749 B2 | 8/2003 | Sullivan et al. |
| 6,602,252 B2 | 8/2003 | Mollenauer |
| 6,602,262 B2 | 8/2003 | Griego et al. |
| 6,603,050 B2 | 8/2003 | Heaton |
| 6,605,078 B2 | 8/2003 | Adams |
| 6,605,669 B2 | 8/2003 | Awokola et al. |
| 6,605,911 B1 | 8/2003 | Klesing |
| 6,607,475 B2 | 8/2003 | Doyle et al. |
| 6,611,793 B1 | 8/2003 | Burnside et al. |
| 6,613,069 B2 | 9/2003 | Boyd et al. |
| 6,616,686 B2 | 9/2003 | Coleman et al. |
| 6,619,529 B2 | 9/2003 | Green et al. |
| 6,620,111 B2 | 9/2003 | Stephens et al. |
| 6,620,166 B1 | 9/2003 | Wenstrom, Jr. et al. |
| 6,625,517 B1 | 9/2003 | Bogdanov et al. |
| 6,626,834 B2 | 9/2003 | Dunne et al. |
| 6,629,630 B2 | 10/2003 | Adams |
| 6,629,974 B2 | 10/2003 | Penny et al. |
| 6,629,988 B2 | 10/2003 | Weadock |
| 6,635,838 B1 | 10/2003 | Kornelson |
| 6,636,412 B2 | 10/2003 | Smith |
| 6,638,108 B2 | 10/2003 | Tachi |
| 6,638,285 B2 | 10/2003 | Gabbay |
| 6,638,297 B1 | 10/2003 | Huitema |
| RE38,335 E | 11/2003 | Aust et al. |
| 6,641,528 B2 | 11/2003 | Torii |
| 6,644,532 B2 | 11/2003 | Green et al. |
| 6,645,201 B1 | 11/2003 | Utley et al. |
| 6,646,307 B1 | 11/2003 | Yu et al. |
| 6,648,816 B2 | 11/2003 | Irion et al. |
| 6,648,901 B2 | 11/2003 | Fleischman et al. |
| 6,652,595 B1 | 11/2003 | Nicolo |
| D484,243 S | 12/2003 | Ryan et al. |
| D484,595 S | 12/2003 | Ryan et al. |
| D484,596 S | 12/2003 | Ryan et al. |
| 6,656,177 B2 | 12/2003 | Truckai et al. |
| 6,656,193 B2 | 12/2003 | Grant et al. |
| 6,659,940 B2 | 12/2003 | Adler |
| 6,663,623 B1 | 12/2003 | Oyama et al. |
| 6,663,641 B1 | 12/2003 | Kovac et al. |
| 6,666,854 B1 | 12/2003 | Lange |
| 6,666,875 B1 | 12/2003 | Sakurai et al. |
| 6,667,825 B2 | 12/2003 | Lu et al. |
| 6,669,073 B2 | 12/2003 | Milliman et al. |
| 6,670,806 B2 | 12/2003 | Wendt et al. |
| 6,671,185 B2 | 12/2003 | Duval |
| D484,977 S | 1/2004 | Ryan et al. |
| 6,676,660 B2 | 1/2004 | Wampler et al. |
| 6,677,687 B2 | 1/2004 | Ho et al. |
| 6,679,269 B2 | 1/2004 | Swanson |
| 6,679,410 B2 | 1/2004 | Wursch et al. |
| 6,681,978 B2 | 1/2004 | Geiste et al. |
| 6,681,979 B2 | 1/2004 | Whitman |

(56) References Cited

U.S. PATENT DOCUMENTS

| | | |
|---|---|---|
| 6,682,527 B2 | 1/2004 | Strul |
| 6,682,528 B2 | 1/2004 | Frazier et al. |
| 6,682,544 B2 | 1/2004 | Mastri et al. |
| 6,685,698 B2 | 2/2004 | Morley et al. |
| 6,685,727 B2 | 2/2004 | Fisher et al. |
| 6,689,153 B1 | 2/2004 | Skiba |
| 6,692,507 B2 | 2/2004 | Pugsley et al. |
| 6,692,692 B2 | 2/2004 | Stetzel |
| 6,695,198 B2 | 2/2004 | Adams et al. |
| 6,695,199 B2 | 2/2004 | Whitman |
| 6,695,774 B2 | 2/2004 | Hale et al. |
| 6,696,814 B2 | 2/2004 | Henderson et al. |
| 6,697,048 B2 | 2/2004 | Rosenberg et al. |
| 6,698,643 B2 | 3/2004 | Whitman |
| 6,699,177 B1 | 3/2004 | Wang et al. |
| 6,699,214 B2 | 3/2004 | Gellman |
| 6,699,235 B2 | 3/2004 | Wallace et al. |
| 6,704,210 B1 | 3/2004 | Myers |
| 6,705,503 B1 | 3/2004 | Pedicini et al. |
| 6,709,445 B2 | 3/2004 | Boebel et al. |
| 6,712,773 B1 | 3/2004 | Viola |
| 6,716,223 B2 | 4/2004 | Leopold et al. |
| 6,716,232 B1 | 4/2004 | Vidal et al. |
| 6,716,233 B1 | 4/2004 | Whitman |
| 6,720,734 B2 | 4/2004 | Norris |
| 6,722,550 B1 | 4/2004 | Ricordi et al. |
| 6,722,552 B2 | 4/2004 | Fenton, Jr. |
| 6,723,087 B2 | 4/2004 | O'Neill et al. |
| 6,723,091 B2 | 4/2004 | Goble et al. |
| 6,723,109 B2 | 4/2004 | Solingen |
| 6,726,697 B2 | 4/2004 | Nicholas et al. |
| 6,726,706 B2 | 4/2004 | Dominguez |
| 6,729,119 B2 | 5/2004 | Schnipke et al. |
| 6,736,825 B2 | 5/2004 | Blatter et al. |
| 6,736,854 B2 | 5/2004 | Vadurro et al. |
| 6,740,030 B2 | 5/2004 | Martone et al. |
| 6,743,230 B2 | 6/2004 | Lutze et al. |
| 6,744,385 B2 | 6/2004 | Kazuya et al. |
| 6,747,121 B2 | 6/2004 | Gogolewski |
| 6,747,300 B2 | 6/2004 | Nadd et al. |
| 6,749,560 B1 | 6/2004 | Konstorum et al. |
| 6,749,600 B1 | 6/2004 | Levy |
| 6,752,768 B2 | 6/2004 | Burdorff et al. |
| 6,752,816 B2 | 6/2004 | Culp et al. |
| 6,754,959 B1 | 6/2004 | Guiette, III et al. |
| 6,755,195 B1 | 6/2004 | Lemke et al. |
| 6,755,338 B2 | 6/2004 | Hahnen et al. |
| 6,755,843 B2 | 6/2004 | Chung et al. |
| 6,756,705 B2 | 6/2004 | Pulford, Jr. |
| 6,758,846 B2 | 7/2004 | Goble et al. |
| 6,761,685 B2 | 7/2004 | Adams et al. |
| 6,762,339 B1 | 7/2004 | Klun et al. |
| 6,764,445 B2 | 7/2004 | Ramans et al. |
| 6,766,957 B2 | 7/2004 | Matsuura et al. |
| 6,767,352 B2 | 7/2004 | Field et al. |
| 6,767,356 B2 | 7/2004 | Kanner et al. |
| 6,769,590 B2 | 8/2004 | Vresh et al. |
| 6,769,594 B2 | 8/2004 | Orban, III |
| 6,770,027 B2 | 8/2004 | Banik et al. |
| 6,770,070 B1 | 8/2004 | Balbierz |
| 6,770,072 B1 | 8/2004 | Truckai et al. |
| 6,773,409 B2 | 8/2004 | Truckai et al. |
| 6,773,438 B1 | 8/2004 | Knodel et al. |
| 6,775,575 B2 | 8/2004 | Bommannan et al. |
| 6,777,838 B2 | 8/2004 | Miekka et al. |
| 6,780,151 B2 | 8/2004 | Grabover et al. |
| 6,780,180 B1 | 8/2004 | Goble et al. |
| 6,783,524 B2 | 8/2004 | Anderson et al. |
| 6,786,382 B1 | 9/2004 | Hoffman |
| 6,786,864 B2 | 9/2004 | Matsuura et al. |
| 6,786,896 B1 | 9/2004 | Madhani et al. |
| 6,788,018 B1 | 9/2004 | Blumenkranz |
| 6,790,173 B2 | 9/2004 | Saadat et al. |
| 6,793,652 B1 | 9/2004 | Whitman et al. |
| 6,793,661 B2 | 9/2004 | Hamilton et al. |
| 6,793,663 B2 | 9/2004 | Kneifel et al. |
| 6,793,669 B2 | 9/2004 | Nakamura et al. |
| 6,796,921 B1 | 9/2004 | Buck et al. |
| 6,802,822 B1 | 10/2004 | Dodge |
| 6,802,843 B2 | 10/2004 | Truckai et al. |
| 6,802,844 B2 | 10/2004 | Ferree |
| 6,805,273 B2 | 10/2004 | Bilotti et al. |
| 6,806,808 B1 | 10/2004 | Watters et al. |
| 6,808,525 B2 | 10/2004 | Latterell et al. |
| 6,810,359 B2 | 10/2004 | Sakaguchi |
| 6,814,741 B2 | 11/2004 | Bowman et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,818,018 B1 | 11/2004 | Sawhney |
| 6,820,791 B2 | 11/2004 | Adams |
| 6,821,273 B2 | 11/2004 | Mollenauer |
| 6,821,282 B2 | 11/2004 | Perry et al. |
| 6,821,284 B2 | 11/2004 | Sturtz et al. |
| 6,827,246 B2 | 12/2004 | Sullivan et al. |
| 6,827,712 B2 | 12/2004 | Tovey et al. |
| 6,827,725 B2 | 12/2004 | Batchelor et al. |
| 6,828,902 B2 | 12/2004 | Casden |
| 6,830,174 B2 | 12/2004 | Hillstead et al. |
| 6,831,629 B2 | 12/2004 | Nishino et al. |
| 6,832,998 B2 | 12/2004 | Goble |
| 6,834,001 B2 | 12/2004 | Myono |
| 6,835,173 B2 | 12/2004 | Couvillon, Jr. |
| 6,835,199 B2 | 12/2004 | McGuckin, Jr. et al. |
| 6,835,336 B2 | 12/2004 | Watt |
| 6,836,611 B2 | 12/2004 | Popovic et al. |
| 6,837,846 B2 | 1/2005 | Jaffe et al. |
| 6,837,883 B2 | 1/2005 | Moll et al. |
| 6,838,493 B2 | 1/2005 | Williams et al. |
| 6,840,423 B2 | 1/2005 | Adams et al. |
| 6,841,967 B2 | 1/2005 | Kim et al. |
| 6,843,403 B2 | 1/2005 | Whitman |
| 6,843,789 B2 | 1/2005 | Goble |
| 6,843,793 B2 | 1/2005 | Brock et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,847,190 B2 | 1/2005 | Schaefer et al. |
| 6,849,071 B2 | 2/2005 | Whitman et al. |
| 6,850,817 B1 | 2/2005 | Green |
| 6,852,122 B2 | 2/2005 | Rush |
| 6,852,330 B2 | 2/2005 | Bowman et al. |
| 6,853,879 B2 | 2/2005 | Sunaoshi |
| 6,858,005 B2 | 2/2005 | Ohline et al. |
| 6,859,882 B2 | 2/2005 | Fung |
| RE38,708 E | 3/2005 | Bolanos et al. |
| D502,994 S | 3/2005 | Blake, III |
| 6,861,142 B1 | 3/2005 | Wilkie et al. |
| 6,861,954 B2 | 3/2005 | Levin |
| 6,863,668 B2 | 3/2005 | Gillespie et al. |
| 6,863,694 B1 | 3/2005 | Boyce et al. |
| 6,866,178 B2 | 3/2005 | Adams et al. |
| 6,866,671 B2 | 3/2005 | Tierney et al. |
| 6,867,248 B1 | 3/2005 | Martin et al. |
| 6,869,430 B2 | 3/2005 | Balbierz et al. |
| 6,869,435 B2 | 3/2005 | Blake, III |
| 6,872,214 B2 | 3/2005 | Sonnenschein et al. |
| 6,874,669 B2 | 4/2005 | Adams et al. |
| 6,877,647 B2 | 4/2005 | Green et al. |
| 6,878,106 B1 | 4/2005 | Herrmann |
| 6,884,392 B2 | 4/2005 | Malkin et al. |
| 6,884,428 B2 | 4/2005 | Binette et al. |
| 6,887,710 B2 | 5/2005 | Call et al. |
| 6,889,116 B2 | 5/2005 | Jinno |
| 6,893,435 B2 | 5/2005 | Goble |
| 6,894,140 B2 | 5/2005 | Roby |
| 6,899,538 B2 | 5/2005 | Matoba |
| 6,899,593 B1 | 5/2005 | Moeller et al. |
| 6,905,057 B2 | 6/2005 | Swayze et al. |
| 6,905,497 B2 | 6/2005 | Truckai et al. |
| 6,905,498 B2 | 6/2005 | Hooven |
| 6,908,472 B2 | 6/2005 | Wiener et al. |
| 6,911,033 B2 | 6/2005 | de Guillebon et al. |
| 6,911,916 B1 | 6/2005 | Wang et al. |

(56) References Cited

U.S. PATENT DOCUMENTS

| | | |
|---|---|---|
| 6,913,579 B2 | 7/2005 | Truckai et al. |
| 6,913,608 B2 | 7/2005 | Liddicoat et al. |
| 6,913,613 B2 | 7/2005 | Schwarz et al. |
| 6,921,397 B2 | 7/2005 | Corcoran et al. |
| 6,921,412 B1 | 7/2005 | Black et al. |
| 6,923,093 B2 | 8/2005 | Ullah |
| 6,923,803 B2 | 8/2005 | Goble |
| 6,923,819 B2 | 8/2005 | Meade et al. |
| 6,926,716 B2 | 8/2005 | Baker et al. |
| 6,928,902 B1 | 8/2005 | Eyssallenne |
| 6,929,641 B2 | 8/2005 | Goble et al. |
| 6,929,644 B2 | 8/2005 | Truckai et al. |
| 6,931,830 B2 | 8/2005 | Liao |
| 6,932,218 B2 | 8/2005 | Kosann et al. |
| 6,932,810 B2 | 8/2005 | Ryan |
| 6,936,042 B2 | 8/2005 | Wallace et al. |
| 6,936,948 B2 | 8/2005 | Bell et al. |
| D509,297 S | 9/2005 | Wells |
| D509,589 S | 9/2005 | Wells |
| 6,939,358 B2 | 9/2005 | Palacios et al. |
| 6,942,662 B2 | 9/2005 | Goble et al. |
| 6,942,674 B2 | 9/2005 | Belef et al. |
| 6,945,444 B2 | 9/2005 | Gresham et al. |
| 6,945,981 B2 | 9/2005 | Donofrio et al. |
| 6,951,562 B2 | 10/2005 | Zwirnmann |
| 6,953,138 B1 | 10/2005 | Dworak et al. |
| 6,953,139 B2 | 10/2005 | Milliman et al. |
| 6,953,461 B2 | 10/2005 | McClurken et al. |
| 6,958,035 B2 | 10/2005 | Friedman et al. |
| 6,959,851 B2 | 11/2005 | Heinrich |
| 6,959,852 B2 | 11/2005 | Shelton, IV et al. |
| 6,960,107 B1 | 11/2005 | Schaub et al. |
| 6,960,163 B2 | 11/2005 | Ewers et al. |
| 6,960,220 B2 | 11/2005 | Marino et al. |
| 6,962,587 B2 | 11/2005 | Johnson et al. |
| 6,963,792 B1 | 11/2005 | Green |
| 6,964,363 B2 | 11/2005 | Wales et al. |
| 6,966,907 B2 | 11/2005 | Goble |
| 6,966,909 B2 | 11/2005 | Marshall et al. |
| 6,968,908 B2 | 11/2005 | Tokunaga et al. |
| 6,969,385 B2 | 11/2005 | Moreyra |
| 6,969,395 B2 | 11/2005 | Eskuri |
| 6,971,988 B2 | 12/2005 | Orban, III |
| 6,972,199 B2 | 12/2005 | Lebouitz et al. |
| 6,974,435 B2 | 12/2005 | Daw et al. |
| 6,974,462 B2 | 12/2005 | Sater |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,941 B2 | 1/2006 | Whitman et al. |
| 6,981,978 B2 | 1/2006 | Gannoe |
| 6,984,203 B2 | 1/2006 | Tartaglia et al. |
| 6,984,231 B2 | 1/2006 | Goble et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,989,034 B2 | 1/2006 | Hammer et al. |
| 6,990,731 B2 | 1/2006 | Haytayan |
| 6,990,796 B2 | 1/2006 | Schnipke et al. |
| 6,993,200 B2 | 1/2006 | Tastl et al. |
| 6,993,413 B2 | 1/2006 | Sunaoshi |
| 6,994,708 B2 | 2/2006 | Manzo |
| 6,995,729 B2 | 2/2006 | Govari et al. |
| 6,996,433 B2 | 2/2006 | Burbank et al. |
| 6,997,931 B2 | 2/2006 | Sauer et al. |
| 6,997,935 B2 | 2/2006 | Anderson et al. |
| 6,998,736 B2 | 2/2006 | Lee et al. |
| 6,998,816 B2 | 2/2006 | Wieck et al. |
| 7,000,818 B2 | 2/2006 | Shelton, IV et al. |
| 7,000,819 B2 | 2/2006 | Swayze et al. |
| 7,000,911 B2 | 2/2006 | McCormick et al. |
| 7,001,380 B2 | 2/2006 | Goble |
| 7,001,408 B2 | 2/2006 | Knodel et al. |
| 7,004,174 B2 | 2/2006 | Eggers et al. |
| 7,007,176 B2 | 2/2006 | Goodfellow et al. |
| 7,008,433 B2 | 3/2006 | Voellmicke et al. |
| 7,008,435 B2 | 3/2006 | Cummins |
| 7,009,039 B2 | 3/2006 | Yayon et al. |
| 7,011,657 B2 | 3/2006 | Truckai et al. |
| 7,014,640 B2 | 3/2006 | Kemppainen et al. |
| 7,018,357 B2 | 3/2006 | Emmons |
| 7,018,390 B2 | 3/2006 | Turovskiy et al. |
| 7,021,669 B1 | 4/2006 | Lindermeir et al. |
| 7,023,159 B2 | 4/2006 | Gorti et al. |
| 7,025,064 B2 | 4/2006 | Wang et al. |
| 7,025,732 B2 | 4/2006 | Thompson et al. |
| 7,025,743 B2 | 4/2006 | Mann et al. |
| 7,025,775 B2 | 4/2006 | Gadberry et al. |
| 7,028,570 B2 | 4/2006 | Ohta et al. |
| 7,029,435 B2 | 4/2006 | Nakao |
| 7,029,439 B2 | 4/2006 | Roberts et al. |
| 7,030,904 B2 | 4/2006 | Adair et al. |
| 7,032,798 B2 | 4/2006 | Whitman et al. |
| 7,032,799 B2 | 4/2006 | Viola et al. |
| 7,033,356 B2 | 4/2006 | Latterell et al. |
| 7,035,716 B2 | 4/2006 | Harris et al. |
| 7,035,762 B2 | 4/2006 | Menard et al. |
| 7,036,680 B1 | 5/2006 | Flannery |
| 7,037,314 B2 | 5/2006 | Armstrong |
| 7,037,344 B2 | 5/2006 | Kagan et al. |
| 7,041,088 B2 | 5/2006 | Nawrocki et al. |
| 7,041,102 B2 | 5/2006 | Truckai et al. |
| 7,041,868 B2 | 5/2006 | Greene et al. |
| 7,043,852 B2 | 5/2006 | Hayashida et al. |
| 7,044,350 B2 | 5/2006 | Kameyama et al. |
| 7,044,352 B2 | 5/2006 | Shelton, IV et al. |
| 7,044,353 B2 | 5/2006 | Mastri et al. |
| 7,046,082 B2 | 5/2006 | Komiya et al. |
| 7,048,687 B1 | 5/2006 | Reuss et al. |
| 7,048,745 B2 | 5/2006 | Tierney et al. |
| 7,052,454 B2 | 5/2006 | Taylor |
| 7,052,494 B2 | 5/2006 | Goble et al. |
| 7,052,499 B2 | 5/2006 | Steger et al. |
| 7,055,730 B2 | 6/2006 | Ehrenfels et al. |
| 7,055,731 B2 | 6/2006 | Shelton, IV et al. |
| 7,056,284 B2 | 6/2006 | Martone et al. |
| 7,056,330 B2 | 6/2006 | Gayton |
| 7,059,331 B2 | 6/2006 | Adams et al. |
| 7,059,508 B2 | 6/2006 | Shelton, IV et al. |
| 7,063,671 B2 | 6/2006 | Couvillon, Jr. |
| 7,063,712 B2 | 6/2006 | Vargas et al. |
| 7,064,509 B1 | 6/2006 | Fu et al. |
| 7,066,879 B2 | 6/2006 | Fowler et al. |
| 7,066,944 B2 | 6/2006 | Laufer et al. |
| 7,067,038 B2 | 6/2006 | Trokhan et al. |
| 7,070,083 B2 | 7/2006 | Jankowski |
| 7,070,559 B2 | 7/2006 | Adams et al. |
| 7,070,597 B2 | 7/2006 | Truckai et al. |
| 7,071,287 B2 | 7/2006 | Rhine et al. |
| 7,075,770 B1 | 7/2006 | Smith |
| 7,077,856 B2 | 7/2006 | Whitman |
| 7,080,769 B2 | 7/2006 | Vresh et al. |
| 7,081,114 B2 | 7/2006 | Rashidi |
| 7,083,073 B2 | 8/2006 | Yoshie et al. |
| 7,083,075 B2 | 8/2006 | Swayze et al. |
| 7,083,571 B2 | 8/2006 | Wang et al. |
| 7,083,615 B2 | 8/2006 | Peterson et al. |
| 7,083,619 B2 | 8/2006 | Truckai et al. |
| 7,083,620 B2 | 8/2006 | Jahns et al. |
| 7,083,626 B2 | 8/2006 | Hart et al. |
| 7,087,049 B2 | 8/2006 | Nowlin et al. |
| 7,087,054 B2 | 8/2006 | Truckai et al. |
| 7,087,071 B2 | 8/2006 | Nicholas et al. |
| 7,090,637 B2 | 8/2006 | Danitz et al. |
| 7,090,673 B2 | 8/2006 | Dycus et al. |
| 7,090,683 B2 | 8/2006 | Brock et al. |
| 7,090,684 B2 | 8/2006 | McGuckin, Jr. et al. |
| 7,091,412 B2 | 8/2006 | Wang et al. |
| 7,094,202 B2 | 8/2006 | Nobis et al. |
| 7,094,247 B2 | 8/2006 | Monassevitch et al. |
| 7,094,916 B2 | 8/2006 | DeLuca et al. |
| 7,096,972 B2 | 8/2006 | Orozco, Jr. |
| 7,097,089 B2 | 8/2006 | Marczyk |
| 7,097,644 B2 | 8/2006 | Long |

(56) References Cited

U.S. PATENT DOCUMENTS

| | | |
|---|---|---|
| 7,097,650 B2 | 8/2006 | Weller et al. |
| 7,098,794 B2 | 8/2006 | Lindsay et al. |
| 7,100,949 B2 | 9/2006 | Williams et al. |
| 7,101,187 B1 | 9/2006 | Deconinck et al. |
| 7,101,394 B2 | 9/2006 | Hamm et al. |
| 7,104,741 B2 | 9/2006 | Krohn |
| 7,108,695 B2 | 9/2006 | Witt et al. |
| 7,108,701 B2 | 9/2006 | Evens et al. |
| 7,108,709 B2 | 9/2006 | Cummins |
| 7,111,768 B2 | 9/2006 | Cummins et al. |
| 7,111,769 B2 | 9/2006 | Wales et al. |
| 7,112,214 B2 | 9/2006 | Peterson et al. |
| RE39,358 E | 10/2006 | Goble |
| 7,114,642 B2 | 10/2006 | Whitman |
| 7,116,100 B1 | 10/2006 | Mock et al. |
| 7,118,020 B2 | 10/2006 | Lee et al. |
| 7,118,528 B1 | 10/2006 | Piskun |
| 7,118,563 B2 | 10/2006 | Weckwerth et al. |
| 7,118,582 B1 | 10/2006 | Wang et al. |
| 7,119,534 B2 | 10/2006 | Butzmann |
| 7,121,446 B2 | 10/2006 | Arad et al. |
| 7,122,028 B2 | 10/2006 | Looper et al. |
| 7,125,403 B2 | 10/2006 | Julian et al. |
| 7,125,409 B2 | 10/2006 | Truckai et al. |
| 7,126,303 B2 | 10/2006 | Farritor et al. |
| 7,126,879 B2 | 10/2006 | Snyder |
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,131,445 B2 | 11/2006 | Amoah |
| 7,133,601 B2 | 11/2006 | Phillips et al. |
| 7,134,587 B2 | 11/2006 | Schwemberger et al. |
| 7,135,027 B2 | 11/2006 | Delmotte |
| 7,137,980 B2 | 11/2006 | Buysse et al. |
| 7,137,981 B2 | 11/2006 | Long |
| 7,139,016 B2 | 11/2006 | Squilla et al. |
| 7,140,527 B2 | 11/2006 | Ehrenfels et al. |
| 7,140,528 B2 | 11/2006 | Shelton, IV |
| 7,141,055 B2 | 11/2006 | Abrams et al. |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,146,191 B2 | 12/2006 | Kerner et al. |
| 7,147,138 B2 | 12/2006 | Shelton, IV |
| 7,147,139 B2 | 12/2006 | Schwemberger et al. |
| 7,147,140 B2 | 12/2006 | Wukusick et al. |
| 7,147,637 B2 | 12/2006 | Goble |
| 7,147,648 B2 | 12/2006 | Lin |
| 7,147,650 B2 | 12/2006 | Lee |
| 7,150,748 B2 | 12/2006 | Ebbutt et al. |
| 7,153,300 B2 | 12/2006 | Goble |
| 7,155,316 B2 | 12/2006 | Sutherland et al. |
| 7,156,863 B2 | 1/2007 | Sonnenschein et al. |
| 7,159,750 B2 | 1/2007 | Racenet et al. |
| 7,160,296 B2 | 1/2007 | Pearson et al. |
| 7,160,299 B2 | 1/2007 | Baily |
| 7,161,036 B2 | 1/2007 | Oikawa et al. |
| 7,161,580 B2 | 1/2007 | Bailey et al. |
| 7,163,563 B2 | 1/2007 | Schwartz et al. |
| 7,166,133 B2 | 1/2007 | Evans et al. |
| 7,168,604 B2 | 1/2007 | Milliman et al. |
| 7,170,910 B2 | 1/2007 | Chen et al. |
| 7,171,279 B2 | 1/2007 | Buckingham et al. |
| 7,172,104 B2 | 2/2007 | Scirica et al. |
| 7,172,593 B2 | 2/2007 | Trieu et al. |
| 7,172,615 B2 | 2/2007 | Morriss et al. |
| 7,174,636 B2 | 2/2007 | Lowe |
| 7,179,223 B2 | 2/2007 | Motoki et al. |
| 7,179,267 B2 | 2/2007 | Nolan et al. |
| 7,182,239 B1 | 2/2007 | Myers |
| 7,182,763 B2 | 2/2007 | Nardella |
| 7,183,737 B2 | 2/2007 | Kitagawa |
| 7,187,960 B2 | 3/2007 | Abreu |
| 7,188,758 B2 | 3/2007 | Viola et al. |
| 7,189,207 B2 | 3/2007 | Viola |
| 7,190,147 B2 | 3/2007 | Gileff et al. |
| 7,195,627 B2 | 3/2007 | Amoah et al. |
| D541,418 S | 4/2007 | Schechter et al. |
| 7,199,537 B2 | 4/2007 | Okamura et al. |
| 7,202,576 B1 * | 4/2007 | Dechene ................ H02J 9/06 307/66 |
| 7,202,653 B2 | 4/2007 | Pai |
| 7,204,404 B2 | 4/2007 | Nguyen et al. |
| 7,204,835 B2 | 4/2007 | Latterell et al. |
| 7,207,233 B2 | 4/2007 | Wadge |
| 7,207,471 B2 | 4/2007 | Heinrich et al. |
| 7,207,472 B2 | 4/2007 | Wukusick et al. |
| 7,207,556 B2 | 4/2007 | Saitoh et al. |
| 7,208,005 B2 | 4/2007 | Frecker et al. |
| 7,210,609 B2 | 5/2007 | Leiboff et al. |
| 7,211,081 B2 | 5/2007 | Goble |
| 7,211,084 B2 | 5/2007 | Goble et al. |
| 7,211,092 B2 | 5/2007 | Hughett |
| 7,211,979 B2 | 5/2007 | Khatib et al. |
| 7,213,736 B2 | 5/2007 | Wales et al. |
| 7,214,224 B2 | 5/2007 | Goble |
| 7,215,517 B2 | 5/2007 | Takamatsu |
| 7,217,285 B2 | 5/2007 | Vargas et al. |
| 7,220,260 B2 | 5/2007 | Fleming et al. |
| 7,220,272 B2 | 5/2007 | Weadock |
| 7,225,959 B2 | 6/2007 | Patton et al. |
| 7,225,963 B2 | 6/2007 | Scirica |
| 7,225,964 B2 | 6/2007 | Mastri et al. |
| 7,226,450 B2 | 6/2007 | Athanasiou et al. |
| 7,229,408 B2 | 6/2007 | Douglas et al. |
| 7,234,624 B2 | 6/2007 | Gresham et al. |
| 7,235,072 B2 | 6/2007 | Sartor et al. |
| 7,235,089 B1 | 6/2007 | McGuckin, Jr. |
| 7,235,302 B2 | 6/2007 | Jing et al. |
| 7,237,708 B1 | 7/2007 | Guy et al. |
| 7,238,195 B2 | 7/2007 | Viola |
| 7,238,901 B2 | 7/2007 | Kim et al. |
| 7,239,657 B1 | 7/2007 | Gunnarsson |
| 7,241,288 B2 | 7/2007 | Braun |
| 7,241,289 B2 | 7/2007 | Braun |
| 7,246,734 B2 | 7/2007 | Shelton, IV |
| 7,247,161 B2 | 7/2007 | Johnston et al. |
| 7,249,267 B2 | 7/2007 | Chapuis |
| 7,252,641 B2 | 8/2007 | Thompson et al. |
| 7,252,660 B2 | 8/2007 | Kunz |
| 7,255,012 B2 | 8/2007 | Hedtke |
| 7,255,696 B2 | 8/2007 | Goble et al. |
| 7,256,695 B2 | 8/2007 | Hamel et al. |
| 7,258,262 B2 | 8/2007 | Mastri et al. |
| 7,258,546 B2 | 8/2007 | Beier et al. |
| 7,260,431 B2 | 8/2007 | Libbus et al. |
| 7,265,374 B2 | 9/2007 | Lee et al. |
| 7,267,677 B2 | 9/2007 | Johnson et al. |
| 7,267,679 B2 | 9/2007 | McGuckin, Jr. et al. |
| 7,272,002 B2 | 9/2007 | Drapeau |
| 7,273,483 B2 | 9/2007 | Wiener et al. |
| 7,275,674 B2 | 10/2007 | Racenet et al. |
| 7,276,044 B2 | 10/2007 | Ferry et al. |
| 7,276,068 B2 | 10/2007 | Johnson et al. |
| 7,278,562 B2 | 10/2007 | Mastri et al. |
| 7,278,563 B1 | 10/2007 | Green |
| 7,278,949 B2 | 10/2007 | Bader |
| 7,278,994 B2 | 10/2007 | Goble |
| 7,282,048 B2 | 10/2007 | Goble et al. |
| 7,286,850 B2 | 10/2007 | Frielink et al. |
| 7,287,682 B1 | 10/2007 | Ezzat et al. |
| 7,289,139 B2 | 10/2007 | Amling et al. |
| 7,293,685 B2 | 11/2007 | Ehrenfels et al. |
| 7,295,893 B2 | 11/2007 | Sunaoshi |
| 7,295,907 B2 | 11/2007 | Lu et al. |
| 7,296,722 B2 | 11/2007 | Ivanko |
| 7,296,724 B2 | 11/2007 | Green et al. |
| 7,297,149 B2 | 11/2007 | Vitali et al. |
| 7,300,373 B2 | 11/2007 | Jinno et al. |
| 7,300,450 B2 | 11/2007 | Vleugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |

(56) References Cited

U.S. PATENT DOCUMENTS

| | | |
|---|---|---|
| 7,303,502 B2 | 12/2007 | Thompson |
| 7,303,556 B2 | 12/2007 | Metzger |
| 7,306,597 B2 | 12/2007 | Manzo |
| 7,308,998 B2 | 12/2007 | Mastri et al. |
| 7,311,238 B2 | 12/2007 | Liu |
| 7,313,430 B2 | 12/2007 | Urquhart et al. |
| 7,314,473 B2 | 1/2008 | Jinno et al. |
| 7,322,859 B2 | 1/2008 | Evans |
| 7,322,975 B2 | 1/2008 | Goble et al. |
| 7,322,994 B2 | 1/2008 | Nicholas et al. |
| 7,324,572 B2 | 1/2008 | Chang |
| 7,326,203 B2 | 2/2008 | Papineau et al. |
| 7,326,213 B2 | 2/2008 | Benderev et al. |
| 7,328,828 B2 | 2/2008 | Ortiz et al. |
| 7,328,829 B2 | 2/2008 | Arad et al. |
| 7,330,004 B2 | 2/2008 | DeJonge et al. |
| 7,331,340 B2 | 2/2008 | Barney |
| 7,331,343 B2 | 2/2008 | Schmidt et al. |
| 7,331,403 B2 | 2/2008 | Berry et al. |
| 7,331,969 B1 | 2/2008 | Inganas et al. |
| 7,334,717 B2 | 2/2008 | Rethy et al. |
| 7,334,718 B2 | 2/2008 | McAlister et al. |
| 7,335,199 B2 | 2/2008 | Goble et al. |
| 7,336,045 B2 | 2/2008 | Clermonts |
| 7,336,048 B2 | 2/2008 | Lohr |
| 7,336,184 B2 | 2/2008 | Smith et al. |
| 7,337,774 B2 | 3/2008 | Webb |
| 7,338,505 B2 | 3/2008 | Belson |
| 7,338,513 B2 | 3/2008 | Lee et al. |
| 7,341,591 B2 | 3/2008 | Grinberg |
| 7,343,920 B2 | 3/2008 | Toby et al. |
| 7,344,532 B2 | 3/2008 | Goble et al. |
| 7,344,533 B2 | 3/2008 | Pearson et al. |
| 7,346,344 B2 | 3/2008 | Fontaine |
| 7,346,406 B2 | 3/2008 | Brotto et al. |
| 7,348,763 B1 | 3/2008 | Reinhart et al. |
| 7,348,875 B2 | 3/2008 | Hughes et al. |
| RE40,237 E | 4/2008 | Bilotti et al. |
| 7,351,258 B2 | 4/2008 | Ricotta et al. |
| 7,354,447 B2 | 4/2008 | Shelton, IV et al. |
| 7,354,502 B2 | 4/2008 | Polat et al. |
| 7,357,287 B2 | 4/2008 | Shelton, IV et al. |
| 7,357,806 B2 | 4/2008 | Rivera et al. |
| 7,361,168 B2 | 4/2008 | Makower et al. |
| 7,361,195 B2 | 4/2008 | Schwartz et al. |
| 7,364,060 B2 | 4/2008 | Milliman |
| 7,364,061 B2 | 4/2008 | Swayze et al. |
| 7,368,124 B2 | 5/2008 | Chun et al. |
| 7,371,210 B2 | 5/2008 | Brock et al. |
| 7,371,403 B2 | 5/2008 | McCarthy et al. |
| 7,377,918 B2 | 5/2008 | Amoah |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,384,403 B2 | 6/2008 | Sherman |
| 7,384,417 B2 | 6/2008 | Cucin |
| 7,386,365 B2 | 6/2008 | Nixon |
| 7,386,730 B2 | 6/2008 | Uchikubo |
| 7,388,217 B2 | 6/2008 | Buschbeck et al. |
| 7,388,484 B2 | 6/2008 | Hsu |
| 7,391,173 B2 | 6/2008 | Schena |
| 7,394,190 B2 | 7/2008 | Huang |
| 7,396,356 B2 | 7/2008 | Mollenauer |
| 7,397,364 B2 | 7/2008 | Govari |
| 7,398,707 B2 | 7/2008 | Morley et al. |
| 7,398,907 B2 | 7/2008 | Racenet et al. |
| 7,398,908 B2 | 7/2008 | Holsten et al. |
| 7,400,107 B2 | 7/2008 | Schneider et al. |
| 7,400,752 B2 | 7/2008 | Zacharias |
| 7,401,000 B2 | 7/2008 | Nakamura |
| 7,401,721 B2 | 7/2008 | Holsten et al. |
| 7,404,449 B2 | 7/2008 | Bermingham et al. |
| 7,404,508 B2 | 7/2008 | Smith et al. |
| 7,404,509 B2 | 7/2008 | Ortiz et al. |
| 7,404,822 B2 | 7/2008 | Viart et al. |
| 7,407,074 B2 | 8/2008 | Ortiz et al. |
| 7,407,075 B2 | 8/2008 | Holsten et al. |
| 7,407,076 B2 | 8/2008 | Racenet et al. |
| 7,407,077 B2 | 8/2008 | Ortiz et al. |
| 7,407,078 B2 | 8/2008 | Shelton, IV et al. |
| 7,408,310 B2 | 8/2008 | Hong et al. |
| 7,410,085 B2 | 8/2008 | Wolf et al. |
| 7,410,086 B2 | 8/2008 | Ortiz et al. |
| 7,410,483 B2 | 8/2008 | Danitz et al. |
| 7,413,563 B2 | 8/2008 | Corcoran et al. |
| 7,418,078 B2 | 8/2008 | Blanz et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,419,321 B2 | 9/2008 | Tereschouk |
| 7,419,495 B2 | 9/2008 | Menn et al. |
| 7,422,136 B1 | 9/2008 | Marczyk |
| 7,422,138 B2 | 9/2008 | Bilotti et al. |
| 7,422,139 B2 | 9/2008 | Shelton, IV et al. |
| 7,424,965 B2 | 9/2008 | Racenet et al. |
| 7,427,607 B2 | 9/2008 | Suzuki |
| D578,644 S | 10/2008 | Shumer et al. |
| 7,431,188 B1 | 10/2008 | Marczyk |
| 7,431,189 B2 | 10/2008 | Shelton, IV et al. |
| 7,431,694 B2 | 10/2008 | Stefanchik et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,435,249 B2 | 10/2008 | Buysse et al. |
| 7,438,209 B1 | 10/2008 | Hess et al. |
| 7,438,718 B2 | 10/2008 | Milliman et al. |
| 7,439,354 B2 | 10/2008 | Lenges et al. |
| 7,441,684 B2 | 10/2008 | Shelton, IV et al. |
| 7,441,685 B1 | 10/2008 | Boudreaux |
| 7,442,201 B2 | 10/2008 | Pugsley et al. |
| 7,443,547 B2 | 10/2008 | Moreno et al. |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,455,682 B2 | 11/2008 | Viola |
| 7,461,767 B2 | 12/2008 | Viola et al. |
| 7,462,187 B2 | 12/2008 | Johnston et al. |
| 7,464,845 B2 | 12/2008 | Chou |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,467,849 B2 | 12/2008 | Silverbrook et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,221 B2 | 1/2009 | Ewers et al. |
| 7,473,253 B2 | 1/2009 | Dycus et al. |
| 7,473,263 B2 | 1/2009 | Johnston et al. |
| 7,476,237 B2 | 1/2009 | Taniguchi et al. |
| 7,479,608 B2 | 1/2009 | Smith |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,485,124 B2 | 2/2009 | Kuhns et al. |
| 7,485,133 B2 | 2/2009 | Cannon et al. |
| 7,485,142 B2 | 2/2009 | Milo |
| 7,487,899 B2 | 2/2009 | Shelton, IV et al. |
| 7,489,055 B2 | 2/2009 | Jeong et al. |
| 7,490,749 B2 | 2/2009 | Schall et al. |
| 7,491,232 B2 | 2/2009 | Bolduc et al. |
| 7,494,039 B2 | 2/2009 | Racenet et al. |
| 7,494,499 B2 | 2/2009 | Nagase et al. |
| 7,494,501 B2 | 2/2009 | Ahlberg et al. |
| 7,500,979 B2 | 3/2009 | Hueil et al. |
| 7,501,198 B2 | 3/2009 | Barlev et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,507,202 B2 | 3/2009 | Schoellhorn |
| 7,510,107 B2 | 3/2009 | Timm et al. |
| 7,510,534 B2 | 3/2009 | Burdorff et al. |

(56) References Cited

U.S. PATENT DOCUMENTS

| | | |
|---|---|---|
| 7,510,566 B2 | 3/2009 | Jacobs et al. |
| 7,513,407 B1 | 4/2009 | Chang |
| 7,513,408 B2 | 4/2009 | Shelton, IV et al. |
| 7,517,356 B2 | 4/2009 | Heinrich |
| 7,524,320 B2 | 4/2009 | Tierney et al. |
| 7,527,632 B2 | 5/2009 | Houghton et al. |
| 7,530,984 B2 | 5/2009 | Sonnenschein et al. |
| 7,530,985 B2 | 5/2009 | Takemoto et al. |
| 7,533,906 B2 | 5/2009 | Luettgen et al. |
| 7,534,259 B2 | 5/2009 | Lashinski et al. |
| 7,540,867 B2 | 6/2009 | Jinno et al. |
| 7,542,807 B2 | 6/2009 | Bertolero et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,549,563 B2 | 6/2009 | Mather et al. |
| 7,549,564 B2 | 6/2009 | Boudreaux |
| 7,549,998 B2 | 6/2009 | Braun |
| 7,552,854 B2 | 6/2009 | Wixey et al. |
| 7,553,173 B2 | 6/2009 | Kowalick |
| 7,553,275 B2 | 6/2009 | Padget et al. |
| 7,554,343 B2 | 6/2009 | Bromfield |
| 7,556,185 B2 | 7/2009 | Viola |
| 7,556,186 B2 | 7/2009 | Milliman |
| 7,556,647 B2 | 7/2009 | Drews et al. |
| 7,559,449 B2 | 7/2009 | Viola |
| 7,559,450 B2 | 7/2009 | Wales et al. |
| 7,559,452 B2 | 7/2009 | Wales et al. |
| 7,559,937 B2 | 7/2009 | de la Torre et al. |
| 7,561,637 B2 | 7/2009 | Jonsson et al. |
| 7,562,910 B2 | 7/2009 | Kertesz et al. |
| 7,563,269 B2 | 7/2009 | Hashiguchi |
| 7,563,862 B2 | 7/2009 | Sieg et al. |
| 7,565,993 B2 | 7/2009 | Milliman et al. |
| 7,566,300 B2 | 7/2009 | Devierre et al. |
| 7,567,045 B2 | 7/2009 | Fristedt |
| 7,568,603 B2 | 8/2009 | Shelton, IV et al. |
| 7,568,604 B2 | 8/2009 | Ehrenfels et al. |
| 7,568,619 B2 | 8/2009 | Todd et al. |
| 7,575,144 B2 | 8/2009 | Ortiz et al. |
| 7,578,825 B2 | 8/2009 | Huebner |
| 7,583,063 B2 | 9/2009 | Dooley |
| 7,586,289 B2 | 9/2009 | Andruk et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,591,783 B2 | 9/2009 | Boulais et al. |
| 7,591,818 B2 | 9/2009 | Bertolero et al. |
| 7,597,229 B2 | 10/2009 | Boudreaux et al. |
| 7,597,230 B2 | 10/2009 | Racenet et al. |
| 7,597,693 B2 | 10/2009 | Garrison |
| 7,597,699 B2 | 10/2009 | Rogers |
| 7,598,972 B2 | 10/2009 | Tomita |
| 7,600,663 B2 | 10/2009 | Green |
| 7,604,150 B2 | 10/2009 | Boudreaux |
| 7,604,151 B2 | 10/2009 | Hess et al. |
| 7,604,668 B2 | 10/2009 | Farnsworth et al. |
| 7,607,557 B2 | 10/2009 | Shelton, IV et al. |
| 7,611,038 B2 | 11/2009 | Racenet et al. |
| 7,611,474 B2 | 11/2009 | Hibner et al. |
| 7,615,003 B2 | 11/2009 | Stefanchik et al. |
| 7,615,067 B2 | 11/2009 | Lee et al. |
| 7,617,961 B2 | 11/2009 | Viola |
| 7,624,902 B2 | 12/2009 | Marczyk et al. |
| 7,624,903 B2 | 12/2009 | Green et al. |
| 7,625,370 B2 | 12/2009 | Hart et al. |
| 7,630,841 B2 | 12/2009 | Comisky et al. |
| 7,631,793 B2 | 12/2009 | Rethy et al. |
| 7,631,794 B2 | 12/2009 | Rethy et al. |
| 7,635,074 B2 | 12/2009 | Olson et al. |
| 7,637,409 B2 | 12/2009 | Marczyk |
| 7,637,410 B2 | 12/2009 | Marczyk |
| 7,638,958 B2 | 12/2009 | Philipp et al. |
| 7,641,091 B2 | 1/2010 | Olson et al. |
| 7,641,092 B2 | 1/2010 | Kruszynski et al. |
| 7,641,093 B2 | 1/2010 | Doll et al. |
| 7,641,095 B2 | 1/2010 | Viola |
| 7,644,783 B2 | 1/2010 | Roberts et al. |
| 7,644,848 B2 | 1/2010 | Swayze et al. |
| 7,645,230 B2 | 1/2010 | Mikkaichi et al. |
| 7,648,457 B2 | 1/2010 | Stefanchik et al. |
| 7,648,519 B2 | 1/2010 | Lee et al. |
| 7,650,185 B2 | 1/2010 | Maile et al. |
| 7,651,017 B2 | 1/2010 | Ortiz et al. |
| 7,651,498 B2 | 1/2010 | Shifrin et al. |
| 7,654,431 B2 | 2/2010 | Hueil et al. |
| 7,655,004 B2 | 2/2010 | Long |
| 7,655,288 B2 | 2/2010 | Bauman et al. |
| 7,655,584 B2 | 2/2010 | Biran et al. |
| 7,656,131 B2 | 2/2010 | Embrey et al. |
| 7,658,311 B2 | 2/2010 | Boudreaux |
| 7,658,312 B2 | 2/2010 | Vidal et al. |
| 7,658,705 B2 | 2/2010 | Melvin et al. |
| 7,659,219 B2 | 2/2010 | Biran et al. |
| 7,662,161 B2 | 2/2010 | Briganti et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,674,253 B2 | 3/2010 | Fisher et al. |
| 7,674,255 B2 | 3/2010 | Braun |
| 7,674,263 B2 | 3/2010 | Ryan |
| 7,674,270 B2 | 3/2010 | Layer |
| 7,682,307 B2 | 3/2010 | Danitz et al. |
| 7,682,367 B2 | 3/2010 | Shah et al. |
| 7,682,686 B2 | 3/2010 | Curro et al. |
| 7,686,201 B2 | 3/2010 | Csiky |
| 7,686,804 B2 | 3/2010 | Johnson et al. |
| 7,686,826 B2 | 3/2010 | Lee et al. |
| 7,688,028 B2 | 3/2010 | Phillips et al. |
| 7,691,098 B2 | 4/2010 | Wallace et al. |
| 7,691,103 B2 | 4/2010 | Fernandez et al. |
| 7,691,106 B2 | 4/2010 | Schenberger et al. |
| 7,694,864 B2 | 4/2010 | Okada et al. |
| 7,694,865 B2 | 4/2010 | Scirica |
| 7,695,485 B2 | 4/2010 | Whitman et al. |
| 7,699,204 B2 | 4/2010 | Viola |
| 7,699,835 B2 | 4/2010 | Lee et al. |
| 7,699,844 B2 | 4/2010 | Utley et al. |
| 7,699,846 B2 | 4/2010 | Ryan |
| 7,699,856 B2 | 4/2010 | Van Wyk et al. |
| 7,699,859 B2 | 4/2010 | Bombard et al. |
| 7,699,860 B2 | 4/2010 | Huitema et al. |
| 7,703,653 B2 | 4/2010 | Shah et al. |
| 7,708,180 B2 | 5/2010 | Murray et al. |
| 7,708,181 B2 | 5/2010 | Cole et al. |
| 7,708,182 B2 | 5/2010 | Viola |
| 7,708,758 B2 | 5/2010 | Lee et al. |
| 7,712,182 B2 | 5/2010 | Zeiler et al. |
| 7,713,190 B2 | 5/2010 | Brock et al. |
| 7,714,239 B2 | 5/2010 | Smith |
| 7,714,334 B2 | 5/2010 | Lin |
| 7,717,312 B2 | 5/2010 | Beetel |
| 7,717,313 B2 | 5/2010 | Criscuolo et al. |
| 7,717,846 B2 | 5/2010 | Zirps et al. |
| 7,717,873 B2 | 5/2010 | Swick |
| 7,717,915 B2 | 5/2010 | Miyazawa |
| 7,718,180 B2 | 5/2010 | Karp |
| 7,718,556 B2 | 5/2010 | Matsuda et al. |
| 7,721,930 B2 | 5/2010 | McKenna et al. |
| 7,721,931 B2 | 5/2010 | Shelton, IV et al. |
| 7,721,933 B2 | 5/2010 | Ehrenfels et al. |
| 7,721,934 B2 | 5/2010 | Shelton, IV et al. |
| 7,721,936 B2 | 5/2010 | Shalton, IV et al. |
| 7,722,527 B2 | 5/2010 | Bouchier et al. |
| 7,722,607 B2 | 5/2010 | Dumbauld et al. |
| 7,722,610 B2 | 5/2010 | Viola et al. |
| 7,725,214 B2 | 5/2010 | Diolaiti |

(56) References Cited

U.S. PATENT DOCUMENTS

| | | |
|---|---|---|
| 7,726,171 B2 | 6/2010 | Langlotz et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,727,954 B2 | 6/2010 | McKay |
| 7,728,553 B2 | 6/2010 | Carrier et al. |
| 7,729,742 B2 | 6/2010 | Govari |
| 7,731,072 B2 | 6/2010 | Timm et al. |
| 7,731,073 B2 | 6/2010 | Wixey et al. |
| 7,731,724 B2 | 6/2010 | Huitema et al. |
| 7,735,703 B2 | 6/2010 | Morgan et al. |
| 7,736,254 B2 | 6/2010 | Schena |
| 7,736,306 B2 | 6/2010 | Brustad et al. |
| 7,736,374 B2 | 6/2010 | Vaughan et al. |
| 7,738,971 B2 | 6/2010 | Swayze et al. |
| 7,740,159 B2 | 6/2010 | Shelton, IV et al. |
| 7,742,036 B2 | 6/2010 | Grant et al. |
| 7,743,960 B2 | 6/2010 | Whitman et al. |
| 7,744,624 B2 | 6/2010 | Bettuchi |
| 7,744,627 B2 | 6/2010 | Orban, III et al. |
| 7,744,628 B2 | 6/2010 | Viola |
| 7,747,146 B2 | 6/2010 | Milano et al. |
| 7,748,587 B2 | 7/2010 | Haramiishi et al. |
| 7,748,632 B2 | 7/2010 | Coleman et al. |
| 7,749,204 B2 | 7/2010 | Dhanaraj et al. |
| 7,751,870 B2 | 7/2010 | Whitman |
| 7,753,245 B2 | 7/2010 | Boudreaux et al. |
| 7,753,246 B2 | 7/2010 | Scirica |
| 7,753,904 B2 | 7/2010 | Shelton, IV et al. |
| 7,757,924 B2 | 7/2010 | Gerbi et al. |
| 7,758,612 B2 | 7/2010 | Shipp |
| 7,762,462 B2 | 7/2010 | Gelbman |
| 7,762,998 B2 | 7/2010 | Birk et al. |
| 7,766,207 B2 | 8/2010 | Mather et al. |
| 7,766,209 B2 | 8/2010 | Baxter, III et al. |
| 7,766,210 B2 | 8/2010 | Shelton, IV et al. |
| 7,766,821 B2 | 8/2010 | Brunnen et al. |
| 7,766,894 B2 | 8/2010 | Weitzner et al. |
| 7,770,658 B2 | 8/2010 | Ito et al. |
| 7,770,773 B2 | 8/2010 | Whitman et al. |
| 7,770,774 B2 | 8/2010 | Mastri et al. |
| 7,770,775 B2 | 8/2010 | Shelton, IV et al. |
| 7,770,776 B2 | 8/2010 | Chen et al. |
| 7,771,396 B2 | 8/2010 | Stefanchik et al. |
| 7,772,720 B2 | 8/2010 | McGee et al. |
| 7,772,725 B2 | 8/2010 | Siman-Tov |
| 7,775,972 B2 | 8/2010 | Brock et al. |
| 7,776,037 B2 | 8/2010 | Odom |
| 7,776,060 B2 | 8/2010 | Mooradian et al. |
| 7,776,065 B2 | 8/2010 | Griffiths et al. |
| 7,778,004 B2 | 8/2010 | Nerheim et al. |
| 7,780,054 B2 | 8/2010 | Wales |
| 7,780,055 B2 | 8/2010 | Scirica et al. |
| 7,780,309 B2 * | 8/2010 | McMillan ............... F21L 4/027 362/202 |
| 7,780,663 B2 | 8/2010 | Yates et al. |
| 7,780,685 B2 | 8/2010 | Hunt et al. |
| 7,784,662 B2 | 8/2010 | Wales et al. |
| 7,784,663 B2 | 8/2010 | Shelton, IV |
| 7,787,256 B2 | 8/2010 | Chan et al. |
| 7,789,283 B2 | 9/2010 | Shah |
| 7,789,875 B2 | 9/2010 | Brock et al. |
| 7,789,883 B2 | 9/2010 | Takashino et al. |
| 7,789,889 B2 | 9/2010 | Zubik et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,799,044 B2 | 9/2010 | Johnston et al. |
| 7,799,965 B2 | 9/2010 | Patel et al. |
| 7,803,151 B2 | 9/2010 | Whitman |
| 7,806,871 B2 | 10/2010 | Li et al. |
| 7,806,891 B2 | 10/2010 | Nowlin et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,811,275 B2 | 10/2010 | Birk et al. |
| 7,814,816 B2 | 10/2010 | Alberti et al. |
| 7,815,092 B2 | 10/2010 | Whitman et al. |
| 7,815,565 B2 | 10/2010 | Stefanchik et al. |
| 7,815,662 B2 | 10/2010 | Spivey et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,799 B2 | 10/2010 | Merril et al. |
| 7,819,884 B2 | 10/2010 | Lee et al. |
| 7,819,886 B2 | 10/2010 | Whitfield et al. |
| 7,823,592 B2 | 11/2010 | Bettuchi et al. |
| 7,823,760 B2 | 11/2010 | Zemlok et al. |
| 7,824,401 B2 | 11/2010 | Manzo et al. |
| 7,824,422 B2 | 11/2010 | Benchetrit |
| 7,824,426 B2 | 11/2010 | Racenet et al. |
| 7,828,189 B2 | 11/2010 | Holsten et al. |
| 7,828,794 B2 | 11/2010 | Sartor |
| 7,828,808 B2 | 11/2010 | Hinman et al. |
| 7,831,292 B2 | 11/2010 | Quaid et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,833,234 B2 | 11/2010 | Bailly et al. |
| 7,835,823 B2 | 11/2010 | Sillman et al. |
| 7,836,400 B2 | 11/2010 | May et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,837,425 B2 | 11/2010 | Saeki et al. |
| 7,837,685 B2 | 11/2010 | Weinberg et al. |
| 7,837,694 B2 | 11/2010 | Tethrake et al. |
| 7,838,789 B2 | 11/2010 | Stoffers et al. |
| 7,839,109 B2 | 11/2010 | Carmen, Jr. et al. |
| 7,841,503 B2 | 11/2010 | Sonnenschein et al. |
| 7,842,025 B2 | 11/2010 | Coleman et al. |
| 7,842,028 B2 | 11/2010 | Lee |
| 7,843,158 B2 | 11/2010 | Prisco |
| 7,845,533 B2 | 12/2010 | Marczyk et al. |
| 7,845,534 B2 | 12/2010 | Viola et al. |
| 7,845,535 B2 | 12/2010 | Scircia |
| 7,845,536 B2 | 12/2010 | Viola et al. |
| 7,845,537 B2 | 12/2010 | Shelton, IV et al. |
| 7,846,085 B2 | 12/2010 | Silverman et al. |
| 7,846,149 B2 | 12/2010 | Jankowski |
| 7,848,066 B2 | 12/2010 | Yanagishima |
| 7,850,623 B2 | 12/2010 | Griffin et al. |
| 7,850,642 B2 | 12/2010 | Moll et al. |
| 7,850,982 B2 | 12/2010 | Stopek et al. |
| 7,854,735 B2 | 12/2010 | Houser et al. |
| 7,854,736 B2 | 12/2010 | Ryan |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,857,813 B2 | 12/2010 | Schmitz et al. |
| 7,861,906 B2 | 1/2011 | Doll et al. |
| 7,862,502 B2 | 1/2011 | Pool et al. |
| 7,862,546 B2 | 1/2011 | Conlon et al. |
| 7,862,579 B2 | 1/2011 | Ortiz et al. |
| 7,866,525 B2 | 1/2011 | Scirica |
| 7,866,527 B2 | 1/2011 | Hall et al. |
| 7,866,528 B2 | 1/2011 | Olson et al. |
| 7,870,989 B2 | 1/2011 | Viola et al. |
| 7,871,418 B2 | 1/2011 | Thompson et al. |
| 7,871,440 B2 | 1/2011 | Schwartz et al. |
| 7,875,055 B2 | 1/2011 | Cichocki, Jr. |
| 7,879,063 B2 | 2/2011 | Khosravi |
| 7,879,070 B2 | 2/2011 | Ortiz et al. |
| 7,883,461 B2 | 2/2011 | Albrecht et al. |
| 7,883,465 B2 | 2/2011 | Donofrio et al. |
| 7,886,951 B2 | 2/2011 | Hessler |
| 7,886,952 B2 | 2/2011 | Scirica et al. |
| 7,887,530 B2 | 2/2011 | Zemlok et al. |
| 7,887,535 B2 | 2/2011 | Lands et al. |
| 7,887,536 B2 | 2/2011 | Johnson et al. |

(56) References Cited

U.S. PATENT DOCUMENTS

| | | |
|---|---|---|
| 7,887,563 B2 | 2/2011 | Cummins |
| 7,891,531 B1 | 2/2011 | Ward |
| 7,891,532 B2 | 2/2011 | Mastri et al. |
| 7,892,200 B2 | 2/2011 | Birk et al. |
| 7,892,245 B2 | 2/2011 | Liddicoat et al. |
| 7,893,586 B2 | 2/2011 | West et al. |
| 7,896,214 B2 | 3/2011 | Farascioni |
| 7,896,215 B2 | 3/2011 | Adams et al. |
| 7,896,869 B2 | 3/2011 | DiSilvestro et al. |
| 7,896,877 B2 | 3/2011 | Hall et al. |
| 7,896,895 B2 | 3/2011 | Boudreaux et al. |
| 7,896,897 B2 | 3/2011 | Gresham et al. |
| 7,898,198 B2 | 3/2011 | Murphree |
| 7,900,805 B2 * | 3/2011 | Shelton, IV ..... A61B 17/07207 206/363 |
| 7,900,806 B2 | 3/2011 | Chen et al. |
| 7,901,381 B2 | 3/2011 | Birk et al. |
| 7,905,380 B2 | 3/2011 | Shelton, IV et al. |
| 7,905,381 B2 | 3/2011 | Baxter, III et al. |
| 7,905,881 B2 | 3/2011 | Masuda et al. |
| 7,905,889 B2 | 3/2011 | Catanese, III et al. |
| 7,905,902 B2 | 3/2011 | Huitema et al. |
| 7,909,039 B2 | 3/2011 | Hur |
| 7,909,191 B2 | 3/2011 | Baker et al. |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,543 B2 | 3/2011 | Roth et al. |
| 7,914,551 B2 | 3/2011 | Ortiz et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,918,845 B2 | 4/2011 | Saadat et al. |
| 7,918,848 B2 | 4/2011 | Lau et al. |
| 7,918,861 B2 | 4/2011 | Brock et al. |
| 7,918,867 B2 | 4/2011 | Dana et al. |
| 7,922,061 B2 | 4/2011 | Shelton, IV et al. |
| 7,922,063 B2 | 4/2011 | Zemlok et al. |
| 7,922,743 B2 | 4/2011 | Heinrich et al. |
| 7,923,144 B2 | 4/2011 | Kohn et al. |
| 7,926,691 B2 | 4/2011 | Viola et al. |
| 7,927,328 B2 | 4/2011 | Orszulak et al. |
| 7,928,281 B2 | 4/2011 | Augustine |
| 7,930,040 B1 | 4/2011 | Kelsch et al. |
| 7,930,065 B2 | 4/2011 | Larkin et al. |
| 7,931,660 B2 | 4/2011 | Aranyi et al. |
| 7,931,695 B2 | 4/2011 | Ringeisen |
| 7,931,877 B2 | 4/2011 | Steffens et al. |
| 7,934,630 B2 | 5/2011 | Shelton, IV et al. |
| 7,934,631 B2 | 5/2011 | Balbierz et al. |
| 7,935,773 B2 | 5/2011 | Hadba et al. |
| 7,938,307 B2 | 5/2011 | Bettuchi |
| 7,941,865 B2 | 5/2011 | Seman, Jr. et al. |
| 7,942,303 B2 | 5/2011 | Shah |
| 7,942,890 B2 | 5/2011 | D'Agostino et al. |
| 7,944,175 B2 | 5/2011 | Mori et al. |
| 7,945,792 B2 | 5/2011 | Cherpantier |
| 7,945,798 B2 | 5/2011 | Carlson et al. |
| 7,946,453 B2 | 5/2011 | Voegele et al. |
| 7,947,011 B2 | 5/2011 | Birk et al. |
| 7,950,560 B2 | 5/2011 | Zemlok et al. |
| 7,950,561 B2 | 5/2011 | Aranyi |
| 7,951,071 B2 | 5/2011 | Whitman et al. |
| 7,951,166 B2 | 5/2011 | Orban, III et al. |
| 7,954,682 B2 | 6/2011 | Giordano et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,955,253 B2 | 6/2011 | Ewers et al. |
| 7,955,257 B2 | 6/2011 | Frasier et al. |
| 7,955,322 B2 | 6/2011 | Devengenzo et al. |
| 7,955,327 B2 | 6/2011 | Sartor et al. |
| 7,955,380 B2 | 6/2011 | Chu et al. |
| 7,959,050 B2 | 6/2011 | Smith et al. |
| 7,959,051 B2 | 6/2011 | Smith et al. |
| 7,959,052 B2 | 6/2011 | Sonnenschein et al. |
| 7,963,432 B2 | 6/2011 | Knodel et al. |
| 7,963,433 B2 | 6/2011 | Whitman et al. |
| 7,963,913 B2 | 6/2011 | Devengenzo et al. |
| 7,963,963 B2 | 6/2011 | Francischelli et al. |
| 7,963,964 B2 | 6/2011 | Santilli et al. |
| 7,964,206 B2 | 6/2011 | Suokas et al. |
| 7,966,236 B2 | 6/2011 | Noriega et al. |
| 7,966,799 B2 | 6/2011 | Morgan et al. |
| 7,967,178 B2 | 6/2011 | Scirica et al. |
| 7,967,179 B2 | 6/2011 | Olson et al. |
| 7,967,180 B2 | 6/2011 | Scirica |
| 7,967,181 B2 | 6/2011 | Viola et al. |
| 7,967,791 B2 | 6/2011 | Franer et al. |
| 7,967,839 B2 | 6/2011 | Flock et al. |
| 7,972,298 B2 | 7/2011 | Wallace et al. |
| 7,972,315 B2 | 7/2011 | Birk et al. |
| 7,976,213 B2 | 7/2011 | Bertolotti et al. |
| 7,976,563 B2 | 7/2011 | Summerer |
| 7,979,137 B2 | 7/2011 | Tracey et al. |
| 7,980,443 B2 | 7/2011 | Scheib et al. |
| 7,981,132 B2 | 7/2011 | Dubrul et al. |
| 7,987,405 B2 | 7/2011 | Turner et al. |
| 7,988,015 B2 | 8/2011 | Mason, II et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,988,779 B2 | 8/2011 | Disalvo et al. |
| 7,992,757 B2 | 8/2011 | Wheeler et al. |
| 7,993,360 B2 | 8/2011 | Hacker et al. |
| 7,994,670 B2 | 8/2011 | Ji |
| 7,997,054 B2 | 8/2011 | Bertsch et al. |
| 7,997,468 B2 | 8/2011 | Farascioni |
| 7,997,469 B2 | 8/2011 | Olson et al. |
| 8,002,696 B2 | 8/2011 | Suzuki |
| 8,002,784 B2 | 8/2011 | Jinno et al. |
| 8,002,785 B2 | 8/2011 | Weiss et al. |
| 8,002,795 B2 | 8/2011 | Beetel |
| 8,006,365 B2 | 8/2011 | Levin et al. |
| 8,006,885 B2 | 8/2011 | Marczyk |
| 8,006,889 B2 | 8/2011 | Adams et al. |
| 8,007,370 B2 | 8/2011 | Hirsch et al. |
| 8,007,465 B2 | 8/2011 | Birk et al. |
| 8,007,479 B2 | 8/2011 | Birk et al. |
| 8,007,511 B2 | 8/2011 | Brock et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,016,176 B2 | 9/2011 | Kasvikis et al. |
| 8,016,177 B2 | 9/2011 | Bettuchi et al. |
| 8,016,178 B2 | 9/2011 | Olson et al. |
| 8,016,849 B2 | 9/2011 | Wenchell |
| 8,016,855 B2 | 9/2011 | Whitman et al. |
| 8,016,858 B2 | 9/2011 | Whitman |
| 8,016,881 B2 | 9/2011 | Furst |
| 8,020,742 B2 | 9/2011 | Marczyk |
| 8,020,743 B2 | 9/2011 | Shelton, IV |
| 8,021,375 B2 | 9/2011 | Aldrich et al. |
| 8,025,199 B2 | 9/2011 | Whitman et al. |
| 8,028,882 B2 | 10/2011 | Viola |
| 8,028,883 B2 | 10/2011 | Stopek |
| 8,028,884 B2 | 10/2011 | Sniffin et al. |
| 8,028,885 B2 | 10/2011 | Smith et al. |
| 8,029,510 B2 | 10/2011 | Hoegerle |
| 8,031,069 B2 | 10/2011 | Cohn et al. |
| 8,033,438 B2 | 10/2011 | Scirica |
| 8,033,439 B2 | 10/2011 | Racenet et al. |
| 8,033,440 B2 | 10/2011 | Wenchell et al. |
| 8,034,077 B2 | 10/2011 | Smith et al. |
| 8,034,337 B2 | 10/2011 | Simard |
| 8,034,363 B2 | 10/2011 | Li et al. |
| 8,035,487 B2 | 10/2011 | Malackowski |
| 8,037,591 B2 | 10/2011 | Spivey et al. |

(56) References Cited

U.S. PATENT DOCUMENTS

| | | |
|---|---|---|
| 8,038,045 B2 | 10/2011 | Bettuchi et al. |
| 8,038,046 B2 | 10/2011 | Smith et al. |
| 8,038,686 B2 | 10/2011 | Huitema et al. |
| 8,043,207 B2 | 10/2011 | Adams |
| 8,043,328 B2 | 10/2011 | Hahnen et al. |
| 8,044,536 B2 | 10/2011 | Nguyen et al. |
| 8,044,604 B2 | 10/2011 | Hagino et al. |
| 8,047,236 B2 | 11/2011 | Perry |
| 8,048,503 B2 | 11/2011 | Farnsworth et al. |
| 8,052,636 B2 | 11/2011 | Moll et al. |
| 8,056,787 B2 | 11/2011 | Boudreaux et al. |
| 8,056,788 B2 | 11/2011 | Mastri et al. |
| 8,056,789 B1 | 11/2011 | White et al. |
| 8,057,508 B2 | 11/2011 | Shelton, IV |
| 8,058,771 B2 | 11/2011 | Giordano et al. |
| 8,060,250 B2 | 11/2011 | Reiland et al. |
| 8,061,014 B2 | 11/2011 | Smith et al. |
| 8,061,576 B2 | 11/2011 | Cappola |
| 8,062,236 B2 | 11/2011 | Soltz |
| 8,062,330 B2 | 11/2011 | Prommersberger et al. |
| 8,063,619 B2 | 11/2011 | Zhu et al. |
| 8,066,158 B2 | 11/2011 | Vogel et al. |
| 8,066,166 B2 | 11/2011 | Demmy et al. |
| 8,066,167 B2 | 11/2011 | Measamer et al. |
| 8,066,168 B2 | 11/2011 | Vidal et al. |
| 8,066,720 B2 | 11/2011 | Knodel et al. |
| D650,074 S | 12/2011 | Hunt et al. |
| 8,070,033 B2 | 12/2011 | Milliman et al. |
| 8,070,035 B2 | 12/2011 | Holsten et al. |
| 8,070,743 B2 | 12/2011 | Kagan et al. |
| 8,074,858 B2 | 12/2011 | Marczyk |
| 8,074,861 B2 | 12/2011 | Ehrenfels et al. |
| 8,075,476 B2 | 12/2011 | Vargas |
| 8,075,571 B2 | 12/2011 | Vitali et al. |
| 8,079,950 B2 | 12/2011 | Stern et al. |
| 8,079,989 B2 | 12/2011 | Birk et al. |
| 8,080,004 B2 | 12/2011 | Downey et al. |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,084,001 B2 | 12/2011 | Burns et al. |
| 8,084,969 B2 | 12/2011 | David et al. |
| 8,085,013 B2 | 12/2011 | Wei et al. |
| 8,087,563 B2 | 1/2012 | Milliman et al. |
| 8,089,509 B2 | 1/2012 | Chatenever et al. |
| 8,091,753 B2 | 1/2012 | Viola |
| 8,091,756 B2 | 1/2012 | Viola |
| 8,092,443 B2 | 1/2012 | Bischoff |
| 8,092,932 B2 | 1/2012 | Phillips et al. |
| 8,093,572 B2 | 1/2012 | Kuduvalli |
| 8,096,458 B2 | 1/2012 | Hessler |
| 8,097,017 B2 | 1/2012 | Viola |
| 8,100,310 B2 | 1/2012 | Zemlok |
| 8,100,824 B2 | 1/2012 | Hegeman et al. |
| 8,100,872 B2 | 1/2012 | Patel |
| 8,102,278 B2 | 1/2012 | Deck et al. |
| 8,105,350 B2 | 1/2012 | Lee et al. |
| 8,107,925 B2 | 1/2012 | Natsuno et al. |
| 8,108,033 B2 | 1/2012 | Drew et al. |
| 8,108,072 B2 | 1/2012 | Zhao et al. |
| 8,109,426 B2 | 2/2012 | Milliman et al. |
| 8,110,208 B1 | 2/2012 | Hen |
| 8,113,405 B2 | 2/2012 | Milliman |
| 8,113,408 B2 | 2/2012 | Wenchell et al. |
| 8,113,410 B2 | 2/2012 | Hall et al. |
| 8,114,100 B2 | 2/2012 | Smith et al. |
| 8,118,206 B2 | 2/2012 | Zand et al. |
| 8,118,207 B2 | 2/2012 | Racenet et al. |
| 8,120,301 B2 | 2/2012 | Goldberg et al. |
| 8,122,128 B2 | 2/2012 | Burke, II et al. |
| 8,123,103 B2 | 2/2012 | Milliman |
| 8,123,523 B2 | 2/2012 | Carron et al. |
| 8,123,766 B2 | 2/2012 | Bauman et al. |
| 8,123,767 B2 | 2/2012 | Bauman et al. |
| 8,125,168 B2 | 2/2012 | Johnson et al. |
| 8,127,975 B2 | 3/2012 | Olson et al. |
| 8,127,976 B2 | 3/2012 | Scirica et al. |
| 8,128,624 B2 | 3/2012 | Couture et al. |
| 8,128,643 B2 | 3/2012 | Aranyi et al. |
| 8,128,645 B2 | 3/2012 | Sonnenschein et al. |
| 8,128,662 B2 | 3/2012 | Altarac et al. |
| 8,132,703 B2 | 3/2012 | Milliman et al. |
| 8,132,706 B2 | 3/2012 | Marczyk et al. |
| 8,134,306 B2 | 3/2012 | Drader et al. |
| 8,136,711 B2 | 3/2012 | Beardsley et al. |
| 8,136,712 B2 | 3/2012 | Zingman |
| 8,136,713 B2 | 3/2012 | Hathaway et al. |
| 8,137,339 B2 | 3/2012 | Jinno et al. |
| 8,140,417 B2 | 3/2012 | Shibata |
| 8,141,762 B2 | 3/2012 | Bedi et al. |
| 8,141,763 B2 | 3/2012 | Milliman |
| 8,142,200 B2 | 3/2012 | Crunkilton et al. |
| 8,142,425 B2 | 3/2012 | Eggers |
| 8,142,461 B2 | 3/2012 | Houser et al. |
| 8,142,515 B2 | 3/2012 | Therin et al. |
| 8,143,520 B2 | 3/2012 | Cutler |
| 8,146,790 B2 | 4/2012 | Milliman |
| 8,147,421 B2 | 4/2012 | Farquhar et al. |
| 8,147,456 B2 | 4/2012 | Fisher et al. |
| 8,147,485 B2 | 4/2012 | Wham et al. |
| 8,152,041 B2 | 4/2012 | Kostrzewski |
| 8,152,756 B2 | 4/2012 | Webster et al. |
| 8,154,239 B2 | 4/2012 | Katsuki et al. |
| 8,157,145 B2 | 4/2012 | Shelton, IV et al. |
| 8,157,148 B2 | 4/2012 | Scirica |
| 8,157,151 B2 | 4/2012 | Ingmanson et al. |
| 8,157,152 B2 | 4/2012 | Holsten et al. |
| 8,157,153 B2 | 4/2012 | Shelton, IV et al. |
| 8,157,793 B2 | 4/2012 | Omori et al. |
| 8,161,977 B2 | 4/2012 | Shelton, IV et al. |
| 8,162,138 B2 | 4/2012 | Bettenhausen et al. |
| 8,162,197 B2 | 4/2012 | Mastri et al. |
| 8,162,668 B2 | 4/2012 | Toly |
| 8,162,933 B2 | 4/2012 | Francischelli et al. |
| 8,162,965 B2 | 4/2012 | Reschke et al. |
| 8,167,185 B2 | 5/2012 | Shelton, IV et al. |
| 8,167,622 B2 | 5/2012 | Zhou |
| 8,167,895 B2 | 5/2012 | D'Agostino et al. |
| 8,167,898 B1 | 5/2012 | Schaller et al. |
| 8,170,241 B2 | 5/2012 | Roe et al. |
| 8,172,004 B2 | 5/2012 | Ho |
| 8,172,120 B2 | 5/2012 | Boyden et al. |
| 8,172,122 B2 | 5/2012 | Kasvikis et al. |
| 8,172,124 B2 | 5/2012 | Shelton, IV et al. |
| 8,177,776 B2 | 5/2012 | Humayun et al. |
| 8,177,797 B2 | 5/2012 | Shimoji et al. |
| 8,179,705 B2 | 5/2012 | Chapuis |
| 8,180,458 B2 | 5/2012 | Kane et al. |
| 8,181,839 B2 | 5/2012 | Beetel |
| 8,181,840 B2 | 5/2012 | Milliman |
| 8,182,422 B2 | 5/2012 | Bayer et al. |
| 8,183,807 B2 | 5/2012 | Tsai et al. |
| 8,186,555 B2 | 5/2012 | Shelton, IV et al. |
| 8,186,556 B2 | 5/2012 | Viola |
| 8,186,558 B2 | 5/2012 | Sapienza |
| 8,186,560 B2 | 5/2012 | Hess et al. |
| 8,191,752 B2 | 6/2012 | Scirica |
| 8,192,460 B2 | 6/2012 | Orban, III et al. |
| 8,192,651 B2 | 6/2012 | Young et al. |
| 8,196,795 B2 | 6/2012 | Moore et al. |
| 8,196,796 B2 | 6/2012 | Shelton, IV et al. |
| 8,197,501 B2 | 6/2012 | Shadeck et al. |
| 8,197,502 B2 | 6/2012 | Smith et al. |
| 8,197,837 B2 | 6/2012 | Jamiolkowski et al. |
| 8,201,720 B2 | 6/2012 | Hessler |
| 8,201,721 B2 | 6/2012 | Zemlok et al. |
| 8,202,549 B2 | 6/2012 | Stucky et al. |
| 8,205,779 B2 | 6/2012 | Ma et al. |
| 8,205,780 B2 | 6/2012 | Sorrentino et al. |
| 8,205,781 B2 | 6/2012 | Baxter, III et al. |
| 8,210,411 B2 | 7/2012 | Yates et al. |
| 8,210,414 B2 | 7/2012 | Bettuchi et al. |
| 8,210,415 B2 | 7/2012 | Ward |
| 8,210,416 B2 | 7/2012 | Milliman et al. |

(56) References Cited

U.S. PATENT DOCUMENTS

| | | |
|---|---|---|
| 8,210,721 B2 | 7/2012 | Chen et al. |
| 8,211,125 B2 | 7/2012 | Spivey |
| 8,214,019 B2 | 7/2012 | Govari et al. |
| 8,215,531 B2 | 7/2012 | Shelton, IV et al. |
| 8,215,532 B2 | 7/2012 | Marczyk |
| 8,215,533 B2 | 7/2012 | Viola et al. |
| 8,220,468 B2 | 7/2012 | Cooper et al. |
| 8,220,688 B2 | 7/2012 | Laurent et al. |
| 8,220,690 B2 | 7/2012 | Hess et al. |
| 8,221,424 B2 | 7/2012 | Cha |
| 8,225,799 B2 | 7/2012 | Bettuchi |
| 8,225,979 B2 | 7/2012 | Farascioni et al. |
| 8,226,553 B2 | 7/2012 | Shelton, IV et al. |
| 8,226,635 B2 | 7/2012 | Petrie et al. |
| 8,226,675 B2 | 7/2012 | Houser et al. |
| 8,226,715 B2 | 7/2012 | Hwang et al. |
| 8,227,946 B2 | 7/2012 | Kim |
| 8,228,048 B2 | 7/2012 | Spencer |
| 8,229,549 B2 | 7/2012 | Whitman et al. |
| 8,231,040 B2 | 7/2012 | Zemlok et al. |
| 8,231,041 B2 | 7/2012 | Marczyk et al. |
| 8,231,042 B2 | 7/2012 | Hessler et al. |
| 8,231,043 B2 | 7/2012 | Tarinelli et al. |
| 8,235,272 B2 | 8/2012 | Nicholas et al. |
| 8,236,010 B2 | 8/2012 | Ortiz et al. |
| 8,236,020 B2 | 8/2012 | Smith et al. |
| 8,237,388 B2 | 8/2012 | Jinno et al. |
| 8,240,537 B2 | 8/2012 | Marczyk |
| 8,241,271 B2 | 8/2012 | Millman et al. |
| 8,241,284 B2 | 8/2012 | Dycus et al. |
| 8,241,308 B2 | 8/2012 | Kortenbach et al. |
| 8,241,322 B2 | 8/2012 | Whitman et al. |
| 8,245,594 B2 | 8/2012 | Rogers et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,245,901 B2 | 8/2012 | Stopek |
| 8,246,608 B2 | 8/2012 | Omori et al. |
| 8,246,637 B2 | 8/2012 | Viola et al. |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,257,251 B2 | 9/2012 | Shelton, IV et al. |
| 8,257,356 B2 | 9/2012 | Bleich et al. |
| 8,257,386 B2 | 9/2012 | Lee et al. |
| 8,257,391 B2 | 9/2012 | Orban, III et al. |
| 8,257,634 B2 | 9/2012 | Scirica |
| 8,258,745 B2 | 9/2012 | Smith et al. |
| 8,262,655 B2 | 9/2012 | Ghabrial et al. |
| 8,267,300 B2 | 9/2012 | Boudreaux |
| 8,267,924 B2 | 9/2012 | Zemlok et al. |
| 8,267,946 B2 | 9/2012 | Whitfield et al. |
| 8,267,951 B2 | 9/2012 | Whayne et al. |
| 8,269,121 B2 | 9/2012 | Smith |
| 8,272,553 B2 | 9/2012 | Mastri et al. |
| 8,272,554 B2 | 9/2012 | Whitman et al. |
| 8,272,918 B2 | 9/2012 | Lam |
| 8,273,404 B2 | 9/2012 | Dave et al. |
| 8,276,801 B2 | 10/2012 | Zemlok et al. |
| 8,276,802 B2 | 10/2012 | Kostrzewski |
| 8,277,473 B2 | 10/2012 | Sunaoshi et al. |
| 8,281,446 B2 | 10/2012 | Moskovich |
| 8,281,973 B2 | 10/2012 | Wenchell et al. |
| 8,281,974 B2 | 10/2012 | Hessler et al. |
| 8,282,654 B2 | 10/2012 | Ferrari et al. |
| 8,285,367 B2 | 10/2012 | Hyde et al. |
| 8,286,723 B2 | 10/2012 | Puzio et al. |
| 8,286,845 B2 | 10/2012 | Perry et al. |
| 8,286,846 B2 | 10/2012 | Smith et al. |
| 8,287,522 B2 | 10/2012 | Moses et al. |
| 8,287,561 B2 | 10/2012 | Nunez et al. |
| 8,292,147 B2 | 10/2012 | Viola |
| 8,292,150 B2 | 10/2012 | Bryant |
| 8,292,151 B2 | 10/2012 | Viola |
| 8,292,152 B2 | 10/2012 | Milliman et al. |
| 8,292,155 B2 | 10/2012 | Shelton, IV et al. |
| 8,292,157 B2 | 10/2012 | Smith et al. |
| 8,292,888 B2 | 10/2012 | Whitman |
| 8,298,161 B2 | 10/2012 | Vargas |
| 8,298,189 B2 | 10/2012 | Fisher et al. |
| 8,298,233 B2 | 10/2012 | Mueller |
| 8,298,677 B2 | 10/2012 | Wiesner et al. |
| 8,302,323 B2 | 11/2012 | Fortier et al. |
| 8,308,040 B2 | 11/2012 | Huang et al. |
| 8,308,042 B2 | 11/2012 | Aranyi |
| 8,308,043 B2 | 11/2012 | Bindra et al. |
| 8,308,046 B2 | 11/2012 | Prommersberger |
| 8,308,659 B2 | 11/2012 | Scheibe et al. |
| 8,308,725 B2 | 11/2012 | Bell et al. |
| 8,310,188 B2 | 11/2012 | Nakai |
| 8,313,496 B2 | 11/2012 | Sauer et al. |
| 8,313,509 B2 | 11/2012 | Kostrzewski |
| 8,317,070 B2 | 11/2012 | Hueil et al. |
| 8,317,071 B1 | 11/2012 | Knodel |
| 8,317,074 B2 | 11/2012 | Ortiz et al. |
| 8,317,744 B2 | 11/2012 | Kirschenman |
| 8,317,790 B2 | 11/2012 | Bell et al. |
| 8,319,002 B2 | 11/2012 | Daniels et al. |
| 8,322,455 B2 | 12/2012 | Shelton, IV et al. |
| 8,322,589 B2 | 12/2012 | Boudreaux |
| 8,322,590 B2 | 12/2012 | Patel et al. |
| 8,322,901 B2 | 12/2012 | Michelotti |
| 8,323,789 B2 | 12/2012 | Rozhin et al. |
| 8,328,061 B2 | 12/2012 | Kasvikis |
| 8,328,062 B2 | 12/2012 | Viola |
| 8,328,063 B2 | 12/2012 | Milliman et al. |
| 8,328,064 B2 | 12/2012 | Racenet et al. |
| 8,328,802 B2 | 12/2012 | Deville et al. |
| 8,328,823 B2 | 12/2012 | Aranyi et al. |
| 8,333,313 B2 | 12/2012 | Boudreaux et al. |
| 8,333,691 B2 | 12/2012 | Schaaf |
| 8,333,764 B2 | 12/2012 | Francischelli et al. |
| 8,333,779 B2 | 12/2012 | Smith et al. |
| 8,334,468 B2 | 12/2012 | Palmer et al. |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,343,150 B2 | 1/2013 | Artale |
| 8,347,978 B2 | 1/2013 | Forster et al. |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,348,837 B2 | 1/2013 | Wenchell |
| 8,348,959 B2 | 1/2013 | Wolford et al. |
| 8,348,972 B2 | 1/2013 | Soltz et al. |
| 8,349,987 B2 | 1/2013 | Kapiamba et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,356,740 B1 | 1/2013 | Knodel |
| 8,357,144 B2 | 1/2013 | Whitman et al. |
| 8,357,161 B2 | 1/2013 | Mueller |
| 8,360,296 B2 | 1/2013 | Zingman |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,361,501 B2 | 1/2013 | DiTizio et al. |
| 8,365,973 B1 | 2/2013 | White et al. |
| 8,365,975 B1 | 2/2013 | Manoux et al. |
| 8,365,976 B2 | 2/2013 | Hess et al. |
| 8,366,559 B2 | 2/2013 | Papenfuss et al. |
| 8,366,787 B2 | 2/2013 | Brown et al. |
| 8,371,393 B2 | 2/2013 | Higuchi et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,371,494 B2 | 2/2013 | Racenet et al. |

(56) References Cited

U.S. PATENT DOCUMENTS

| | | |
|---|---|---|
| 8,372,094 B2 | 2/2013 | Bettuchi et al. |
| 8,376,865 B2 | 2/2013 | Forster et al. |
| 8,377,029 B2 | 2/2013 | Nagao et al. |
| 8,377,044 B2 | 2/2013 | Coe et al. |
| 8,382,773 B2 | 2/2013 | Whitfield et al. |
| 8,382,790 B2 | 2/2013 | Uenohara et al. |
| 8,387,848 B2 | 3/2013 | Johnson et al. |
| 8,388,633 B2 | 3/2013 | Rousseau et al. |
| 8,389,588 B2 | 3/2013 | Ringeisen et al. |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,971 B2 | 3/2013 | Yates et al. |
| 8,397,973 B1 | 3/2013 | Hausen |
| 8,398,633 B2 | 3/2013 | Mueller |
| 8,398,669 B2 | 3/2013 | Kim |
| 8,398,673 B2 | 3/2013 | Hinchliffe et al. |
| 8,400,851 B2 | 3/2013 | Byun |
| 8,403,138 B2 | 3/2013 | Weisshaupt et al. |
| 8,403,198 B2 | 3/2013 | Sorrentino et al. |
| 8,403,832 B2 | 3/2013 | Cunningham et al. |
| 8,403,945 B2 | 3/2013 | Whitfield et al. |
| 8,403,946 B2 | 3/2013 | Whitfield et al. |
| 8,403,950 B2 | 3/2013 | Palmer et al. |
| 8,408,439 B2 | 4/2013 | Huang et al. |
| 8,408,442 B2 | 4/2013 | Racenet et al. |
| 8,409,079 B2 | 4/2013 | Okamoto et al. |
| 8,409,174 B2 | 4/2013 | Omori |
| 8,409,175 B2 | 4/2013 | Lee et al. |
| 8,409,222 B2 | 4/2013 | Whitfield et al. |
| 8,409,223 B2 | 4/2013 | Sorrentino et al. |
| 8,411,500 B2 | 4/2013 | Gapihan et al. |
| 8,413,870 B2 | 4/2013 | Pastorelli et al. |
| 8,413,871 B2 | 4/2013 | Racenet et al. |
| 8,413,872 B2 | 4/2013 | Patel |
| 8,414,577 B2 | 4/2013 | Boudreaux et al. |
| 8,418,073 B2 | 4/2013 | Mohr et al. |
| 8,418,906 B2 | 4/2013 | Farascioni et al. |
| 8,418,908 B1 | 4/2013 | Beardsley |
| 8,418,909 B2 | 4/2013 | Kostrzewski |
| 8,419,717 B2 | 4/2013 | Diolaiti et al. |
| 8,419,747 B2 | 4/2013 | Hinman et al. |
| 8,419,754 B2 | 4/2013 | Laby et al. |
| 8,423,182 B2 | 4/2013 | Robinson et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,424,741 B2 | 4/2013 | McGuckin, Jr. et al. |
| 8,425,600 B2 | 4/2013 | Maxwell |
| 8,427,430 B2 | 4/2013 | Lee et al. |
| 8,430,292 B2 | 4/2013 | Patel et al. |
| 8,430,892 B2 | 4/2013 | Bindra et al. |
| 8,430,898 B2 | 4/2013 | Wiener et al. |
| 8,435,257 B2 | 5/2013 | Smith et al. |
| 8,439,246 B1 | 5/2013 | Knodel |
| 8,444,036 B2 | 5/2013 | Shelton, IV |
| 8,444,037 B2 | 5/2013 | Nicholas et al. |
| 8,444,549 B2 | 5/2013 | Viola et al. |
| 8,453,904 B2 | 6/2013 | Eskaros et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,912 B2 | 6/2013 | Mastri et al. |
| 8,453,914 B2 | 6/2013 | Laurent et al. |
| 8,454,495 B2 | 6/2013 | Kawano et al. |
| 8,454,628 B2 | 6/2013 | Smith et al. |
| 8,454,640 B2 | 6/2013 | Johnston et al. |
| 8,457,757 B2 | 6/2013 | Cauller et al. |
| 8,459,520 B2 | 6/2013 | Giordano et al. |
| 8,459,521 B2 | 6/2013 | Zemlok et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,464,924 B2 | 6/2013 | Gresham et al. |
| 8,464,925 B2 | 6/2013 | Hull et al. |
| 8,465,475 B2 | 6/2013 | Isbell, Jr. |
| 8,465,502 B2 | 6/2013 | Zergiebel |
| 8,465,515 B2 | 6/2013 | Drew et al. |
| 8,469,946 B2 | 6/2013 | Sugita |
| 8,469,973 B2 | 6/2013 | Meade et al. |
| 8,470,355 B2 | 6/2013 | Skalla et al. |
| 8,474,677 B2 | 7/2013 | Woodard, Jr. et al. |
| 8,475,453 B2 | 7/2013 | Marczyk et al. |
| 8,475,454 B1 | 7/2013 | Alshemari |
| 8,475,474 B2 | 7/2013 | Bombard et al. |
| 8,479,968 B2 | 7/2013 | Hodgkinson et al. |
| 8,479,969 B2 | 7/2013 | Shelton, IV |
| 8,480,703 B2 | 7/2013 | Nicholas et al. |
| 8,485,412 B2 | 7/2013 | Shelton, IV et al. |
| 8,485,413 B2 | 7/2013 | Scheib et al. |
| 8,485,970 B2 | 7/2013 | Widenhouse et al. |
| 8,487,199 B2 | 7/2013 | Palmer et al. |
| 8,490,853 B2 | 7/2013 | Criscuolo et al. |
| 8,491,581 B2 | 7/2013 | Deville et al. |
| 8,491,603 B2 | 7/2013 | Yeung et al. |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,499,992 B2 | 8/2013 | Whitman et al. |
| 8,499,993 B2 | 8/2013 | Shelton, IV et al. |
| 8,500,721 B2 | 8/2013 | Jinno |
| 8,500,762 B2 | 8/2013 | Sholev et al. |
| 8,502,091 B2 | 8/2013 | Palmer et al. |
| 8,505,799 B2 | 8/2013 | Viola et al. |
| 8,505,801 B2 | 8/2013 | Ehrenfels et al. |
| 8,506,555 B2 | 8/2013 | Ruiz Morales |
| 8,506,557 B2 | 8/2013 | Zemlok et al. |
| 8,506,580 B2 | 8/2013 | Zergiebel et al. |
| 8,506,581 B2 | 8/2013 | Wingardner, III et al. |
| 8,511,308 B2 | 8/2013 | Hecox et al. |
| 8,512,359 B2 | 8/2013 | Whitman et al. |
| 8,512,402 B2 | 8/2013 | Marczyk et al. |
| 8,517,239 B2 | 8/2013 | Scheib et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,521,273 B2 | 8/2013 | Kliman |
| 8,523,043 B2 | 9/2013 | Ullrich et al. |
| 8,523,881 B2 | 9/2013 | Cabiri et al. |
| 8,523,900 B2 | 9/2013 | Jinno et al. |
| 8,529,588 B2 | 9/2013 | Ahlberg et al. |
| 8,529,600 B2 | 9/2013 | Woodard, Jr. et al. |
| 8,529,819 B2 | 9/2013 | Ostapoff et al. |
| 8,532,747 B2 | 9/2013 | Nock et al. |
| 8,534,528 B2 | 9/2013 | Shelton, IV |
| 8,535,304 B2 | 9/2013 | Sklar et al. |
| 8,535,340 B2 | 9/2013 | Allen |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Bedi et al. |
| 8,540,733 B2 | 9/2013 | Whitman et al. |
| 8,540,735 B2 | 9/2013 | Mitelberg et al. |
| 8,550,984 B2 | 10/2013 | Takemoto |
| 8,551,076 B2 | 10/2013 | Duval et al. |
| 8,555,660 B2 | 10/2013 | Takenaka et al. |
| 8,556,151 B2 | 10/2013 | Viola |
| 8,556,918 B2 | 10/2013 | Bauman et al. |
| 8,556,935 B1 | 10/2013 | Knodel et al. |
| 8,560,147 B2 | 10/2013 | Taylor et al. |
| 8,561,617 B2 | 10/2013 | Lindh et al. |
| 8,561,870 B2 | 10/2013 | Baxter, III et al. |
| 8,561,871 B2 | 10/2013 | Rajappa et al. |
| 8,561,873 B2 | 10/2013 | Ingmanson et al. |
| 8,562,598 B2 | 10/2013 | Falkenstein et al. |
| 8,567,656 B2 | 10/2013 | Shelton, IV et al. |
| 8,568,416 B2 | 10/2013 | Schmitz et al. |
| 8,568,425 B2 | 10/2013 | Ross et al. |
| 8,573,459 B2 | 11/2013 | Smith et al. |
| 8,573,461 B2 | 11/2013 | Shelton, IV et al. |
| 8,573,462 B2 | 11/2013 | Smith et al. |
| 8,573,465 B2 | 11/2013 | Shelton, IV |
| 8,574,199 B2 | 11/2013 | von Bulow et al. |

(56) References Cited

U.S. PATENT DOCUMENTS

| | | |
|---|---|---|
| 8,574,263 B2 | 11/2013 | Mueller |
| 8,575,880 B2 | 11/2013 | Grantz |
| 8,579,176 B2 | 11/2013 | Smith et al. |
| 8,579,178 B2 | 11/2013 | Holsten et al. |
| 8,579,897 B2 | 11/2013 | Vakharia et al. |
| 8,579,937 B2 | 11/2013 | Gresham |
| 8,584,919 B2 | 11/2013 | Hueil et al. |
| 8,584,920 B2 | 11/2013 | Hodgkinson |
| 8,584,921 B2 | 11/2013 | Scirica |
| 8,585,583 B2 | 11/2013 | Sakaguchi et al. |
| 8,585,721 B2 | 11/2013 | Kirsch |
| 8,590,760 B2 | 11/2013 | Cummins et al. |
| 8,590,762 B2 | 11/2013 | Hess et al. |
| 8,590,764 B2 | 11/2013 | Hartwick et al. |
| 8,596,515 B2 | 12/2013 | Okoniewski |
| 8,597,745 B2 | 12/2013 | Farnsworth et al. |
| 8,599,450 B2 | 12/2013 | Kubo et al. |
| 8,602,287 B2 | 12/2013 | Yates et al. |
| 8,602,288 B2 | 12/2013 | Shelton, IV et al. |
| 8,603,077 B2 | 12/2013 | Cooper et al. |
| 8,603,110 B2 | 12/2013 | Maruyama et al. |
| 8,603,135 B2 | 12/2013 | Mueller |
| 8,608,043 B2 | 12/2013 | Scirica |
| 8,608,044 B2 | 12/2013 | Hueil et al. |
| 8,608,045 B2 | 12/2013 | Smith et al. |
| 8,608,046 B2 | 12/2013 | Laurent et al. |
| 8,608,745 B2 | 12/2013 | Guzman et al. |
| 8,613,383 B2 | 12/2013 | Beckman et al. |
| 8,616,427 B2 | 12/2013 | Viola |
| 8,616,431 B2 | 12/2013 | Timm et al. |
| 8,622,275 B2 | 1/2014 | Baxter, III et al. |
| 8,627,993 B2 | 1/2014 | Smith et al. |
| 8,627,995 B2 | 1/2014 | Smith et al. |
| 8,628,518 B2 | 1/2014 | Blumenkranz et al. |
| 8,628,545 B2 | 1/2014 | Cabrera et al. |
| 8,631,987 B2 | 1/2014 | Shelton, IV et al. |
| 8,631,992 B1 | 1/2014 | Hausen et al. |
| 8,631,993 B2 | 1/2014 | Kostrzewski |
| 8,632,462 B2 | 1/2014 | Yoo et al. |
| 8,632,525 B2 | 1/2014 | Kerr et al. |
| 8,632,535 B2 | 1/2014 | Shelton, IV et al. |
| 8,632,563 B2 | 1/2014 | Nagase et al. |
| 8,636,187 B2 | 1/2014 | Hueil et al. |
| 8,636,191 B2 | 1/2014 | Meagher |
| 8,636,193 B2 | 1/2014 | Whitman et al. |
| 8,636,736 B2 | 1/2014 | Yates et al. |
| 8,636,766 B2 | 1/2014 | Milliman et al. |
| 8,639,936 B2 | 1/2014 | Hu et al. |
| 8,640,788 B2 | 2/2014 | Dachs, II et al. |
| 8,646,674 B2 | 2/2014 | Schulte et al. |
| 8,647,258 B2 | 2/2014 | Aranyi et al. |
| 8,652,120 B2 | 2/2014 | Giordano et al. |
| 8,652,151 B2 | 2/2014 | Lehman et al. |
| 8,657,174 B2 | 2/2014 | Yates et al. |
| 8,657,175 B2 | 2/2014 | Sonnenschein et al. |
| 8,657,176 B2 | 2/2014 | Shelton, IV et al. |
| 8,657,177 B2 | 2/2014 | Scirica et al. |
| 8,657,178 B2 | 2/2014 | Hueil et al. |
| 8,657,482 B2 | 2/2014 | Malackowski et al. |
| 8,657,808 B2 | 2/2014 | McPherson et al. |
| 8,657,814 B2 | 2/2014 | Werneth et al. |
| 8,657,821 B2 | 2/2014 | Palermo |
| 8,662,370 B2 | 3/2014 | Takei |
| 8,663,106 B2 | 3/2014 | Stivoric et al. |
| 8,663,192 B2 | 3/2014 | Hester et al. |
| 8,663,245 B2 | 3/2014 | Francischelli et al. |
| 8,663,262 B2 | 3/2014 | Smith et al. |
| 8,663,270 B2 | 3/2014 | Donnigan et al. |
| 8,664,792 B2 | 3/2014 | Rebsdorf |
| 8,668,129 B2 | 3/2014 | Olson |
| 8,668,130 B2 | 3/2014 | Hess et al. |
| 8,672,206 B2 | 3/2014 | Aranyi et al. |
| 8,672,207 B2 | 3/2014 | Shelton, IV et al. |
| 8,672,208 B2 | 3/2014 | Hess et al. |
| 8,672,922 B2 | 3/2014 | Loh et al. |
| 8,672,935 B2 | 3/2014 | Okada et al. |
| 8,672,951 B2 | 3/2014 | Smith et al. |
| 8,673,210 B2 | 3/2014 | Deshays |
| 8,675,820 B2 | 3/2014 | Baic et al. |
| 8,678,263 B2 | 3/2014 | Viola |
| 8,679,093 B2 | 3/2014 | Farra |
| 8,679,098 B2 | 3/2014 | Hart |
| 8,679,137 B2 | 3/2014 | Bauman et al. |
| 8,679,154 B2 | 3/2014 | Smith et al. |
| 8,679,156 B2 | 3/2014 | Smith et al. |
| 8,679,454 B2 | 3/2014 | Guire et al. |
| 8,684,248 B2 | 4/2014 | Milliman |
| 8,684,249 B2 | 4/2014 | Racenet et al. |
| 8,684,250 B2 | 4/2014 | Bettuchi et al. |
| 8,684,253 B2 | 4/2014 | Giordano et al. |
| 8,684,962 B2 | 4/2014 | Kirschenman et al. |
| 8,685,004 B2 | 4/2014 | Zemlock et al. |
| 8,685,020 B2 | 4/2014 | Weizman et al. |
| 8,695,866 B2 | 4/2014 | Leimbach et al. |
| 8,696,665 B2 | 4/2014 | Hunt et al. |
| 8,701,958 B2 | 4/2014 | Shelton, IV et al. |
| 8,701,959 B2 | 4/2014 | Shah |
| 8,708,210 B2 | 4/2014 | Zemlok et al. |
| 8,708,211 B2 | 4/2014 | Zemlok et al. |
| 8,708,213 B2 | 4/2014 | Shelton, IV et al. |
| 8,714,352 B2 | 5/2014 | Farascioni et al. |
| 8,714,429 B2 | 5/2014 | Demmy |
| 8,714,430 B2 | 5/2014 | Natarajan et al. |
| 8,715,256 B2 | 5/2014 | Greener |
| 8,715,302 B2 | 5/2014 | Ibrahim et al. |
| 8,720,766 B2 | 5/2014 | Hess et al. |
| 8,721,630 B2 | 5/2014 | Ortiz et al. |
| 8,721,666 B2 | 5/2014 | Schroeder et al. |
| 8,727,197 B2 | 5/2014 | Hess et al. |
| 8,727,199 B2 | 5/2014 | Wenchell |
| 8,727,200 B2 | 5/2014 | Roy |
| 8,727,961 B2 | 5/2014 | Ziv |
| 8,728,099 B2 | 5/2014 | Cohn et al. |
| 8,728,119 B2 | 5/2014 | Cummins |
| 8,733,612 B2 | 5/2014 | Ma |
| 8,733,613 B2 | 5/2014 | Huitema et al. |
| 8,733,614 B2 | 5/2014 | Ross et al. |
| 8,734,336 B2 | 5/2014 | Bonadio et al. |
| 8,734,359 B2 | 5/2014 | Ibanez et al. |
| 8,734,478 B2 | 5/2014 | Widenhouse et al. |
| 8,739,033 B2 | 5/2014 | Rosenberg |
| 8,739,417 B2 | 6/2014 | Tokunaga et al. |
| 8,740,034 B2 | 6/2014 | Morgan et al. |
| 8,740,037 B2 | 6/2014 | Shelton, IV et al. |
| 8,740,038 B2 | 6/2014 | Shelton, IV et al. |
| 8,740,987 B2 | 6/2014 | Geremakis et al. |
| 8,746,529 B2 | 6/2014 | Shelton, IV et al. |
| 8,746,530 B2 | 6/2014 | Giordano et al. |
| 8,746,533 B2 | 6/2014 | Whitman et al. |
| 8,746,535 B2 | 6/2014 | Shelton, IV et al. |
| 8,747,238 B2 | 6/2014 | Shelton, IV et al. |
| 8,747,441 B2 | 6/2014 | Konieczynski et al. |
| 8,752,264 B2 | 6/2014 | Ackley et al. |
| 8,752,699 B2 | 6/2014 | Morgan et al. |
| 8,752,747 B2 | 6/2014 | Shelton, IV et al. |
| 8,752,748 B2 | 6/2014 | Whitman et al. |
| 8,752,749 B2 | 6/2014 | Moore et al. |
| 8,757,287 B2 | 6/2014 | Mak et al. |
| 8,757,465 B2 | 6/2014 | Woodard, Jr. et al. |
| 8,758,235 B2 | 6/2014 | Jaworek |
| 8,758,366 B2 | 6/2014 | McLean et al. |
| 8,758,391 B2 | 6/2014 | Swayze et al. |
| 8,758,438 B2 | 6/2014 | Boyce et al. |
| 8,763,875 B2 | 7/2014 | Morgan et al. |
| 8,763,877 B2 | 7/2014 | Schall et al. |
| 8,763,879 B2 | 7/2014 | Shelton, IV et al. |
| 8,764,732 B2 | 7/2014 | Hartwell |
| 8,770,458 B2 | 7/2014 | Scirica |
| 8,770,459 B2 | 7/2014 | Racenet et al. |
| 8,770,460 B2 | 7/2014 | Belzer |
| 8,771,169 B2 | 7/2014 | Whitman et al. |
| 8,777,004 B2 | 7/2014 | Shelton, IV et al. |
| 8,777,082 B2 | 7/2014 | Scirica |
| 8,777,083 B2 | 7/2014 | Racenet et al. |

(56) References Cited

U.S. PATENT DOCUMENTS

| | | |
|---|---|---|
| 8,777,898 B2 | 7/2014 | Suon et al. |
| 8,783,541 B2 | 7/2014 | Shelton, IV et al. |
| 8,783,542 B2 | 7/2014 | Riestenberg et al. |
| 8,783,543 B2 | 7/2014 | Shelton, IV et al. |
| 8,784,304 B2 | 7/2014 | Mikkaichi et al. |
| 8,784,404 B2 | 7/2014 | Doyle et al. |
| 8,784,415 B2 | 7/2014 | Malackowski et al. |
| 8,789,737 B2 | 7/2014 | Hodgkinson et al. |
| 8,789,739 B2 | 7/2014 | Swensgard |
| 8,789,740 B2 | 7/2014 | Baxter, III et al. |
| 8,789,741 B2 | 7/2014 | Baxter, III et al. |
| 8,790,658 B2 | 7/2014 | Cigarini et al. |
| 8,790,684 B2 | 7/2014 | Dave et al. |
| 8,794,496 B2 | 8/2014 | Scirica |
| 8,794,497 B2 | 8/2014 | Zingman |
| 8,795,276 B2 | 8/2014 | Dietz et al. |
| 8,795,308 B2 | 8/2014 | Valin |
| 8,795,324 B2 | 8/2014 | Kawai et al. |
| 8,800,681 B2 | 8/2014 | Rousson et al. |
| 8,800,837 B2 | 8/2014 | Zemlok |
| 8,800,838 B2 | 8/2014 | Shelton, IV |
| 8,800,839 B2 | 8/2014 | Beetel |
| 8,800,840 B2 | 8/2014 | Jankowski |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,801,752 B2 | 8/2014 | Fortier et al. |
| 8,806,973 B2 | 8/2014 | Ross et al. |
| 8,807,414 B2 | 8/2014 | Ross et al. |
| 8,808,161 B2 | 8/2014 | Gregg et al. |
| 8,808,274 B2 | 8/2014 | Hartwell |
| 8,808,294 B2 | 8/2014 | Fox et al. |
| 8,808,308 B2 | 8/2014 | Boukhny et al. |
| 8,808,311 B2 | 8/2014 | Heinrich et al. |
| 8,808,325 B2 | 8/2014 | Hess et al. |
| 8,810,197 B2 | 8/2014 | Juergens |
| 8,811,017 B2 | 8/2014 | Fujii et al. |
| 8,813,866 B2 | 8/2014 | Suzuki |
| 8,814,024 B2 | 8/2014 | Woodard, Jr. et al. |
| 8,814,025 B2 | 8/2014 | Miller et al. |
| 8,820,603 B2 | 9/2014 | Shelton, IV et al. |
| 8,820,605 B2 | 9/2014 | Shelton, IV |
| 8,820,606 B2 | 9/2014 | Hodgkinson |
| 8,820,607 B2 | 9/2014 | Marczyk |
| 8,822,934 B2 | 9/2014 | Sayeh et al. |
| 8,825,164 B2 | 9/2014 | Tweden et al. |
| 8,827,133 B2 | 9/2014 | Shelton, IV et al. |
| 8,827,134 B2 | 9/2014 | Viola et al. |
| 8,827,903 B2 | 9/2014 | Shelton, IV et al. |
| 8,833,219 B2 | 9/2014 | Pierce |
| 8,833,630 B2 | 9/2014 | Milliman |
| 8,833,632 B2 | 9/2014 | Swensgard |
| 8,834,498 B2 | 9/2014 | Byrum et al. |
| 8,840,003 B2 | 9/2014 | Morgan et al. |
| 8,840,603 B2 | 9/2014 | Shelton, IV et al. |
| 8,840,609 B2 | 9/2014 | Stuebe |
| 8,844,789 B2 | 9/2014 | Shelton, IV et al. |
| 8,851,354 B2 | 10/2014 | Swensgard et al. |
| 8,852,185 B2 | 10/2014 | Twomey |
| 8,852,199 B2 | 10/2014 | Deslauriers et al. |
| 8,857,693 B2 | 10/2014 | Schuckmann et al. |
| 8,857,694 B2 | 10/2014 | Shelton, IV et al. |
| 8,858,538 B2 | 10/2014 | Belson et al. |
| 8,858,571 B2 | 10/2014 | Shelton, IV et al. |
| 8,858,590 B2 | 10/2014 | Shelton, IV et al. |
| 8,864,007 B2 | 10/2014 | Widenhouse et al. |
| 8,864,009 B2 | 10/2014 | Shelton, IV et al. |
| 8,864,010 B2 | 10/2014 | Williams |
| 8,870,050 B2 | 10/2014 | Hodgkinson |
| 8,870,912 B2 | 10/2014 | Brisson et al. |
| 8,875,971 B2 | 11/2014 | Hall et al. |
| 8,875,972 B2 | 11/2014 | Weisenburgh, II et al. |
| 8,876,857 B2 | 11/2014 | Burbank |
| 8,876,858 B2 | 11/2014 | Braun |
| 8,887,979 B2 | 11/2014 | Mastri et al. |
| 8,888,688 B2 | 11/2014 | Julian et al. |
| 8,888,695 B2 | 11/2014 | Piskun et al. |
| 8,888,792 B2 | 11/2014 | Harris et al. |
| 8,888,809 B2 | 11/2014 | Davison et al. |
| 8,893,946 B2 | 11/2014 | Boudreaux et al. |
| 8,893,949 B2 | 11/2014 | Shelton, IV et al. |
| 8,894,647 B2 | 11/2014 | Beardsley et al. |
| 8,894,654 B2 | 11/2014 | Anderson |
| 8,899,460 B2 | 12/2014 | Wojcicki |
| 8,899,461 B2 | 12/2014 | Farascioni |
| 8,899,463 B2 | 12/2014 | Schall et al. |
| 8,899,464 B2 | 12/2014 | Hueil et al. |
| 8,899,465 B2 | 12/2014 | Shelton, IV et al. |
| 8,899,466 B2 | 12/2014 | Baxter, III et al. |
| 8,905,287 B2 | 12/2014 | Racenet et al. |
| 8,905,977 B2 | 12/2014 | Shelton et al. |
| 8,910,846 B2 | 12/2014 | Viola |
| 8,911,426 B2 | 12/2014 | Coppeta et al. |
| 8,911,448 B2 | 12/2014 | Stein |
| 8,911,460 B2 | 12/2014 | Neurohr et al. |
| 8,911,471 B2 | 12/2014 | Spivey et al. |
| 8,920,433 B2 | 12/2014 | Barrier et al. |
| 8,920,435 B2 | 12/2014 | Smith et al. |
| 8,920,438 B2 | 12/2014 | Aranyi et al. |
| 8,920,443 B2 | 12/2014 | Hiles et al. |
| 8,920,444 B2 | 12/2014 | Hiles et al. |
| 8,922,163 B2 | 12/2014 | Macdonald |
| 8,925,782 B2 | 1/2015 | Shelton, IV |
| 8,925,783 B2 | 1/2015 | Zemlok et al. |
| 8,925,788 B2 | 1/2015 | Hess et al. |
| 8,926,506 B2 | 1/2015 | Widenhouse et al. |
| 8,926,598 B2 | 1/2015 | Mollere et al. |
| 8,931,576 B2 | 1/2015 | Iwata |
| 8,931,679 B2 | 1/2015 | Kostrzewski |
| 8,931,680 B2 | 1/2015 | Milliman |
| 8,931,682 B2 | 1/2015 | Timm et al. |
| 8,936,614 B2 | 1/2015 | Allen, IV |
| 8,939,343 B2 | 1/2015 | Milliman et al. |
| 8,939,344 B2 | 1/2015 | Olson et al. |
| 8,945,163 B2 | 2/2015 | Voegele et al. |
| 8,955,732 B2 | 2/2015 | Zemlok et al. |
| 8,956,342 B1 | 2/2015 | Russo et al. |
| 8,956,390 B2 | 2/2015 | Shah et al. |
| 8,958,860 B2 | 2/2015 | Banerjee et al. |
| 8,960,519 B2 | 2/2015 | Whitman et al. |
| 8,960,520 B2 | 2/2015 | McCuen |
| 8,960,521 B2 | 2/2015 | Kostrzewski |
| 8,961,504 B2 | 2/2015 | Hoarau et al. |
| 8,963,714 B2 | 2/2015 | Medhal et al. |
| 8,967,443 B2 | 3/2015 | McCuen |
| 8,967,444 B2 | 3/2015 | Beetel |
| 8,967,446 B2 | 3/2015 | Beardsley et al. |
| 8,967,448 B2 | 3/2015 | Carter et al. |
| 8,968,276 B2 | 3/2015 | Zemlok et al. |
| 8,968,312 B2 | 3/2015 | Marczyk et al. |
| 8,968,337 B2 | 3/2015 | Whitfield et al. |
| 8,968,340 B2 | 3/2015 | Chowaniec et al. |
| 8,968,355 B2 | 3/2015 | Malkowski et al. |
| 8,968,358 B2 | 3/2015 | Reschke |
| 8,970,507 B2 | 3/2015 | Holbein et al. |
| 8,973,803 B2 | 3/2015 | Hall et al. |
| 8,973,804 B2 | 3/2015 | Hess et al. |
| 8,974,440 B2 | 3/2015 | Farritor et al. |
| 8,978,954 B2 | 3/2015 | Shelton, IV et al. |
| 8,978,955 B2 | 3/2015 | Aronhalt et al. |
| 8,978,956 B2 | 3/2015 | Schall et al. |
| 8,979,843 B2 | 3/2015 | Timm et al. |
| 8,979,890 B2 | 3/2015 | Boudreaux |
| 8,982,195 B2 | 3/2015 | Claus et al. |
| 8,991,676 B2 | 3/2015 | Hess et al. |
| 8,991,677 B2 | 3/2015 | Moore et al. |
| 8,991,678 B2 | 3/2015 | Wellman et al. |
| 8,992,042 B2 | 3/2015 | Eichenholz |
| 8,992,422 B2 | 3/2015 | Spivey et al. |
| 8,992,565 B2 | 3/2015 | Brisson et al. |
| 8,996,165 B2 | 3/2015 | Wang et al. |
| 8,998,058 B2 | 4/2015 | Moore et al. |
| 8,998,059 B2 | 4/2015 | Smith et al. |
| 8,998,061 B2 | 4/2015 | Williams et al. |

(56) References Cited

U.S. PATENT DOCUMENTS

| | | |
|---|---|---|
| 9,002,518 B2 | 4/2015 | Manzo et al. |
| 9,004,339 B1 | 4/2015 | Park |
| 9,005,230 B2 | 4/2015 | Yates et al. |
| 9,005,238 B2 | 4/2015 | DeSantis et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,011,439 B2 | 4/2015 | Shalaby et al. |
| 9,011,471 B2 | 4/2015 | Timm et al. |
| 9,016,539 B2 | 4/2015 | Kostrzewski et al. |
| 9,016,540 B2 | 4/2015 | Whitman et al. |
| 9,016,541 B2 | 4/2015 | Viola et al. |
| 9,016,542 B2 | 4/2015 | Shelton, IV et al. |
| 9,016,545 B2 | 4/2015 | Aranyi et al. |
| 9,017,331 B2 | 4/2015 | Fox |
| 9,017,355 B2 | 4/2015 | Smith et al. |
| 9,017,369 B2 | 4/2015 | Renger et al. |
| 9,017,371 B2 | 4/2015 | Whitman et al. |
| 9,021,684 B2 | 5/2015 | Lenker et al. |
| 9,023,014 B2 | 5/2015 | Chowaniec et al. |
| 9,023,071 B2 | 5/2015 | Miller et al. |
| 9,027,817 B2 | 5/2015 | Milliman et al. |
| 9,028,494 B2 | 5/2015 | Shelton, IV et al. |
| 9,028,495 B2 | 5/2015 | Mueller et al. |
| 9,028,519 B2 | 5/2015 | Yates et al. |
| 9,030,169 B2 | 5/2015 | Christensen et al. |
| 9,033,203 B2 | 5/2015 | Woodard, Jr. et al. |
| 9,033,204 B2 | 5/2015 | Shelton, IV et al. |
| 9,038,881 B1 | 5/2015 | Schaller et al. |
| 9,039,690 B2 | 5/2015 | Kersten et al. |
| 9,039,694 B2 | 5/2015 | Ross et al. |
| 9,039,720 B2 | 5/2015 | Madan |
| 9,043,027 B2 | 5/2015 | Durant et al. |
| 9,044,227 B2 | 6/2015 | Shelton, IV et al. |
| 9,044,228 B2 | 6/2015 | Woodard, Jr. et al. |
| 9,044,229 B2 | 6/2015 | Scheib et al. |
| 9,044,230 B2 | 6/2015 | Morgan et al. |
| 9,050,083 B2 | 6/2015 | Yates et al. |
| 9,050,084 B2 | 6/2015 | Schmid et al. |
| 9,050,100 B2 | 6/2015 | Yates et al. |
| 9,050,120 B2 | 6/2015 | Swarup et al. |
| 9,050,123 B2 | 6/2015 | Krause et al. |
| 9,055,941 B2 | 6/2015 | Schmid et al. |
| 9,055,942 B2 | 6/2015 | Balbierz et al. |
| 9,055,943 B2 | 6/2015 | Zemlok et al. |
| 9,055,944 B2 | 6/2015 | Hodgkinson et al. |
| 9,055,961 B2 | 6/2015 | Manzo et al. |
| 9,060,770 B2 | 6/2015 | Shelton, IV et al. |
| 9,060,776 B2 | 6/2015 | Yates et al. |
| 9,060,794 B2 | 6/2015 | Kang et al. |
| 9,060,894 B2 | 6/2015 | Wubbeling |
| 9,061,392 B2 | 6/2015 | Forgues et al. |
| 9,072,515 B2 | 7/2015 | Hall et al. |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,084,601 B2 | 7/2015 | Moore et al. |
| 9,084,602 B2 | 7/2015 | Gleiman |
| 9,086,875 B2 | 7/2015 | Harrat et al. |
| 9,089,326 B2 | 7/2015 | Krumanaker et al. |
| 9,089,330 B2 | 7/2015 | Widenhouse et al. |
| 9,089,352 B2 | 7/2015 | Jeong |
| 9,091,588 B2 | 7/2015 | Lefler |
| 9,095,339 B2 | 8/2015 | Moore et al. |
| 9,095,346 B2 | 8/2015 | Houser et al. |
| 9,095,362 B2 | 8/2015 | Dachs, II et al. |
| 9,096,033 B2 | 8/2015 | Holop et al. |
| 9,099,863 B2 | 8/2015 | Smith et al. |
| 9,101,358 B2 | 8/2015 | Kerr et al. |
| 9,101,385 B2 | 8/2015 | Shelton, IV et al. |
| 9,101,475 B2 | 8/2015 | Wei et al. |
| 9,107,663 B2 | 8/2015 | Swensgard |
| 9,110,587 B2 | 8/2015 | Kim et al. |
| 9,113,862 B2 | 8/2015 | Morgan et al. |
| 9,113,864 B2 | 8/2015 | Morgan et al. |
| 9,113,865 B2 | 8/2015 | Shelton, IV et al. |
| 9,113,873 B2 | 8/2015 | Marczyk et al. |
| 9,113,874 B2 | 8/2015 | Shelton, IV et al. |
| 9,113,876 B2 | 8/2015 | Zemlok et al. |
| 9,113,881 B2 | 8/2015 | Scirica |
| 9,113,883 B2 | 8/2015 | Aronhalt et al. |
| 9,113,884 B2 | 8/2015 | Shelton, IV et al. |
| 9,113,887 B2 | 8/2015 | Behnke, II et al. |
| 9,119,657 B2 | 9/2015 | Shelton, IV et al. |
| 9,119,898 B2 | 9/2015 | Bayon et al. |
| 9,119,957 B2 | 9/2015 | Gantz et al. |
| 9,123,286 B2 | 9/2015 | Park |
| 9,124,097 B2 | 9/2015 | Cruz |
| 9,125,654 B2 | 9/2015 | Aronhalt et al. |
| 9,125,662 B2 | 9/2015 | Shelton, IV |
| 9,126,317 B2 | 9/2015 | Lawton et al. |
| 9,131,835 B2 | 9/2015 | Widenhouse et al. |
| 9,131,940 B2 | 9/2015 | Huitema et al. |
| 9,131,950 B2 | 9/2015 | Matthew |
| 9,131,957 B2 | 9/2015 | Skarbnik et al. |
| 9,138,225 B2 | 9/2015 | Huang et al. |
| 9,138,226 B2 | 9/2015 | Racenet et al. |
| 9,144,455 B2 | 9/2015 | Kennedy et al. |
| 9,149,274 B2 | 10/2015 | Spivey et al. |
| 9,149,324 B2 | 10/2015 | Huang et al. |
| 9,149,325 B2 | 10/2015 | Worrell et al. |
| 9,153,994 B2 | 10/2015 | Wood et al. |
| 9,161,753 B2 | 10/2015 | Prior |
| 9,161,803 B2 | 10/2015 | Yates et al. |
| 9,168,038 B2 | 10/2015 | Shelton, IV et al. |
| 9,168,039 B1 | 10/2015 | Knodel |
| 9,168,054 B2 | 10/2015 | Turner et al. |
| 9,168,144 B2 | 10/2015 | Rivin et al. |
| 9,179,911 B2 | 11/2015 | Morgan et al. |
| 9,179,912 B2 | 11/2015 | Yates et al. |
| 9,182,244 B2 | 11/2015 | Luke et al. |
| 9,186,046 B2 | 11/2015 | Ramamurthy et al. |
| 9,186,137 B2 | 11/2015 | Farascioni et al. |
| 9,186,140 B2 | 11/2015 | Hiles et al. |
| 9,186,142 B2 | 11/2015 | Fanelli et al. |
| 9,186,143 B2 | 11/2015 | Timm et al. |
| 9,186,148 B2 | 11/2015 | Felder et al. |
| 9,186,221 B2 | 11/2015 | Burbank |
| 9,192,380 B2 | 11/2015 | Racenet et al. |
| 9,192,384 B2 | 11/2015 | Bettuchi |
| 9,192,430 B2 | 11/2015 | Rachlin et al. |
| 9,192,434 B2 | 11/2015 | Twomey et al. |
| 9,193,045 B2 | 11/2015 | Saur et al. |
| 9,198,644 B2 | 12/2015 | Balek et al. |
| 9,198,661 B2 | 12/2015 | Swensgard |
| 9,198,662 B2 | 12/2015 | Barton et al. |
| 9,198,683 B2 | 12/2015 | Friedman et al. |
| 9,204,830 B2 | 12/2015 | Zand et al. |
| 9,204,877 B2 | 12/2015 | Whitman et al. |
| 9,204,878 B2 | 12/2015 | Hall et al. |
| 9,204,879 B2 | 12/2015 | Shelton, IV |
| 9,204,880 B2 | 12/2015 | Baxter, III et al. |
| 9,204,923 B2 | 12/2015 | Manzo et al. |
| 9,204,924 B2 | 12/2015 | Marczyk et al. |
| 9,211,120 B2 | 12/2015 | Scheib et al. |
| 9,211,121 B2 | 12/2015 | Hall et al. |
| 9,211,122 B2 | 12/2015 | Hagerty et al. |
| 9,216,013 B2 | 12/2015 | Scirica et al. |
| 9,216,019 B2 | 12/2015 | Schmid et al. |
| 9,216,020 B2 | 12/2015 | Zhang et al. |
| 9,216,030 B2 | 12/2015 | Fan et al. |
| 9,216,062 B2 | 12/2015 | Duque et al. |
| 9,220,500 B2 | 12/2015 | Swayze et al. |
| 9,220,501 B2 | 12/2015 | Baxter, III et al. |
| 9,220,502 B2 | 12/2015 | Zemlok et al. |
| 9,220,508 B2 | 12/2015 | Dannaher |
| 9,220,559 B2 | 12/2015 | Worrell et al. |
| 9,220,570 B2 | 12/2015 | Kim et al. |
| 9,226,750 B2 | 1/2016 | Weir et al. |
| 9,226,751 B2 | 1/2016 | Shelton, IV et al. |
| 9,226,767 B2 | 1/2016 | Stulen et al. |
| 9,232,941 B2 | 1/2016 | Mandakolathur Vasudevan et al. |
| 9,232,945 B2 | 1/2016 | Zingman |

(56) References Cited

U.S. PATENT DOCUMENTS

| | | |
|---|---|---|
| 9,232,979 B2 | 1/2016 | Parihar et al. |
| 9,233,610 B2 | 1/2016 | Kim et al. |
| 9,237,891 B2 | 1/2016 | Shelton, IV |
| 9,237,892 B2 | 1/2016 | Hodgkinson |
| 9,237,895 B2 | 1/2016 | McCarthy et al. |
| 9,237,921 B2 | 1/2016 | Messerly et al. |
| 9,240,740 B2 | 1/2016 | Zeng et al. |
| 9,241,714 B2 | 1/2016 | Timm et al. |
| 9,241,716 B2 | 1/2016 | Whitman |
| 9,241,731 B2 | 1/2016 | Boudreaux et al. |
| 9,259,274 B2 | 2/2016 | Prisco |
| 9,261,172 B2 | 2/2016 | Solomon et al. |
| 9,265,500 B2 | 2/2016 | Sorrentino et al. |
| 9,265,516 B2 | 2/2016 | Casey et al. |
| 9,265,585 B2 | 2/2016 | Wingardner et al. |
| 9,271,718 B2 | 3/2016 | Milad et al. |
| 9,271,727 B2 | 3/2016 | McGuckin, Jr. et al. |
| 9,271,753 B2 | 3/2016 | Butler et al. |
| 9,271,799 B2 | 3/2016 | Shelton, IV et al. |
| 9,272,406 B2 | 3/2016 | Aronhalt et al. |
| 9,277,919 B2 | 3/2016 | Timmer et al. |
| 9,277,922 B2 | 3/2016 | Carter et al. |
| 9,282,962 B2 | 3/2016 | Schmid et al. |
| 9,282,963 B2 | 3/2016 | Bryant |
| 9,282,966 B2 | 3/2016 | Shelton, IV et al. |
| 9,282,974 B2 | 3/2016 | Shelton, IV |
| 9,283,028 B2 | 3/2016 | Johnson |
| 9,283,045 B2 | 3/2016 | Rhee et al. |
| 9,283,054 B2 | 3/2016 | Morgan et al. |
| 9,289,206 B2 | 3/2016 | Hess et al. |
| 9,289,207 B2 | 3/2016 | Shelton, IV |
| 9,289,210 B2 | 3/2016 | Baxter, III et al. |
| 9,289,211 B2 | 3/2016 | Williams et al. |
| 9,289,212 B2 | 3/2016 | Shelton, IV et al. |
| 9,289,225 B2 | 3/2016 | Shelton, IV et al. |
| 9,289,256 B2 | 3/2016 | Shelton, IV et al. |
| 9,293,757 B2 | 3/2016 | Toussaint et al. |
| 9,295,464 B2 | 3/2016 | Shelton, IV et al. |
| 9,295,465 B2 | 3/2016 | Farascioni |
| 9,295,466 B2 | 3/2016 | Hodgkinson et al. |
| 9,295,468 B2 | 3/2016 | Heinrich et al. |
| 9,295,514 B2 | 3/2016 | Shelton, IV et al. |
| 9,295,522 B2 | 3/2016 | Kostrzewski |
| 9,295,784 B2 | 3/2016 | Eggert et al. |
| 9,301,691 B2 | 4/2016 | Hufnagel et al. |
| 9,301,752 B2 | 4/2016 | Mandakolathur Vasudevan et al. |
| 9,301,753 B2 | 4/2016 | Aldridge et al. |
| 9,301,755 B2 | 4/2016 | Shelton, IV et al. |
| 9,301,759 B2 | 4/2016 | Spivey et al. |
| 9,307,965 B2 | 4/2016 | Ming et al. |
| 9,307,986 B2 | 4/2016 | Hall et al. |
| 9,307,987 B2 | 4/2016 | Swensgard et al. |
| 9,307,988 B2 | 4/2016 | Shelton, IV |
| 9,307,989 B2 | 4/2016 | Shelton, IV et al. |
| 9,307,994 B2 | 4/2016 | Gresham et al. |
| 9,308,009 B2 | 4/2016 | Madan et al. |
| 9,308,011 B2 | 4/2016 | Chao et al. |
| 9,314,246 B2 | 4/2016 | Shelton, IV et al. |
| 9,314,247 B2 | 4/2016 | Shelton, IV et al. |
| 9,314,261 B2 | 4/2016 | Bales, Jr. et al. |
| 9,314,908 B2 | 4/2016 | Tanimoto et al. |
| 9,320,518 B2 | 4/2016 | Henderson et al. |
| 9,320,520 B2 | 4/2016 | Shelton, IV et al. |
| 9,320,521 B2 | 4/2016 | Shelton, IV et al. |
| 9,320,523 B2 | 4/2016 | Shelton, IV et al. |
| 9,326,767 B2 | 5/2016 | Koch, Jr. et al. |
| 9,326,768 B2 | 5/2016 | Shelton, IV |
| 9,326,769 B2 | 5/2016 | Shelton, IV et al. |
| 9,326,770 B2 | 5/2016 | Shelton, IV et al. |
| 9,326,771 B2 | 5/2016 | Baxter, III et al. |
| 9,326,788 B2 | 5/2016 | Batross et al. |
| 9,332,890 B2 | 5/2016 | Ozawa |
| 9,332,974 B2 | 5/2016 | Henderson et al. |
| 9,332,984 B2 | 5/2016 | Weaner et al. |
| 9,332,987 B2 | 5/2016 | Leimbach et al. |
| 9,333,040 B2 | 5/2016 | Shellenberger et al. |
| 9,333,082 B2 | 5/2016 | Wei et al. |
| 9,339,226 B2 | 5/2016 | van der Walt et al. |
| 9,345,477 B2 | 5/2016 | Anim et al. |
| 9,345,480 B2 | 5/2016 | Hessler et al. |
| 9,345,481 B2 | 5/2016 | Hall et al. |
| 9,351,726 B2 | 5/2016 | Leimbach et al. |
| 9,351,727 B2 | 5/2016 | Leimbach et al. |
| 9,351,728 B2 | 5/2016 | Sniffin et al. |
| 9,351,730 B2 | 5/2016 | Schmid et al. |
| 9,351,731 B2 | 5/2016 | Carter et al. |
| 9,351,732 B2 | 5/2016 | Hodgkinson |
| 9,358,003 B2 | 6/2016 | Hall et al. |
| 9,358,005 B2 | 6/2016 | Shelton, IV et al. |
| 9,358,015 B2 | 6/2016 | Sorrentino et al. |
| 9,358,031 B2 | 6/2016 | Manzo |
| 9,364,217 B2 | 6/2016 | Kostrzewski et al. |
| 9,364,219 B2 | 6/2016 | Olson et al. |
| 9,364,220 B2 | 6/2016 | Williams |
| 9,364,226 B2 | 6/2016 | Zemlok et al. |
| 9,364,229 B2 | 6/2016 | D'Agostino et al. |
| 9,364,230 B2 | 6/2016 | Shelton, IV et al. |
| 9,364,231 B2 | 6/2016 | Wenchell |
| 9,364,233 B2 | 6/2016 | Alexander, III et al. |
| 9,364,279 B2 | 6/2016 | Houser et al. |
| 9,368,991 B2 | 6/2016 | Qahouq |
| 9,370,341 B2 | 6/2016 | Ceniccola et al. |
| 9,370,358 B2 | 6/2016 | Shelton, IV et al. |
| 9,370,364 B2 | 6/2016 | Smith et al. |
| 9,375,206 B2 | 6/2016 | Vidal et al. |
| 9,375,255 B2 | 6/2016 | Houser et al. |
| 9,381,058 B2 | 7/2016 | Houser et al. |
| 9,386,983 B2 | 7/2016 | Swensgard et al. |
| 9,386,984 B2 | 7/2016 | Aronhalt et al. |
| 9,386,985 B2 | 7/2016 | Koch, Jr. et al. |
| 9,386,988 B2 | 7/2016 | Baxter, III et al. |
| 9,387,003 B2 | 7/2016 | Kaercher et al. |
| 9,393,015 B2 | 7/2016 | Laurent et al. |
| 9,393,017 B2 | 7/2016 | Flanagan et al. |
| 9,393,018 B2 | 7/2016 | Wang et al. |
| 9,398,911 B2 | 7/2016 | Auld |
| 9,402,604 B2 | 8/2016 | Williams et al. |
| 9,402,626 B2 | 8/2016 | Ortiz et al. |
| 9,402,627 B2 | 8/2016 | Stevenson et al. |
| 9,408,604 B2 | 8/2016 | Shelton, IV et al. |
| 9,408,606 B2 | 8/2016 | Shelton, IV |
| 9,408,622 B2 | 8/2016 | Stulen et al. |
| 9,411,370 B2 | 8/2016 | Benni et al. |
| 9,414,838 B2 | 8/2016 | Shelton, IV et al. |
| 9,414,849 B2 | 8/2016 | Nagashimada |
| 9,414,880 B2 | 8/2016 | Monson et al. |
| 9,420,967 B2 | 8/2016 | Zand et al. |
| 9,421,003 B2 | 8/2016 | Williams et al. |
| 9,421,014 B2 | 8/2016 | Ingmanson et al. |
| 9,421,030 B2 | 8/2016 | Cole et al. |
| 9,421,060 B2 | 8/2016 | Monson et al. |
| 9,427,223 B2 | 8/2016 | Park et al. |
| 9,427,231 B2 | 8/2016 | Racenet et al. |
| 9,433,411 B2 | 9/2016 | Racenet et al. |
| 9,433,419 B2 | 9/2016 | Gonzalez et al. |
| 9,433,420 B2 | 9/2016 | Hodgkinson |
| 9,439,649 B2 | 9/2016 | Shelton, IV et al. |
| 9,439,650 B2 | 9/2016 | McGuckin, Jr. et al. |
| 9,439,651 B2 | 9/2016 | Smith et al. |
| 9,445,808 B2 | 9/2016 | Woodard, Jr. et al. |
| 9,445,813 B2 | 9/2016 | Shelton, IV et al. |
| 9,451,958 B2 | 9/2016 | Shelton, IV et al. |
| 9,461,340 B2 * | 10/2016 | Li .................. H02J 7/0032 |
| 9,463,040 B2 | 10/2016 | Jeong et al. |
| 9,463,260 B2 | 10/2016 | Stopek |
| 9,468,438 B2 | 10/2016 | Baber et al. |
| 9,468,447 B2 | 10/2016 | Aman et al. |
| 9,470,297 B2 | 10/2016 | Aranyi et al. |
| 9,471,969 B2 | 10/2016 | Zeng et al. |
| 9,474,506 B2 | 10/2016 | Magnin et al. |
| 9,474,523 B2 | 10/2016 | Meade et al. |
| 9,474,540 B2 | 10/2016 | Stokes et al. |
| 9,475,180 B2 | 10/2016 | Eshleman et al. |
| 9,480,476 B2 | 11/2016 | Aldridge et al. |

(56) References Cited

U.S. PATENT DOCUMENTS

| | | | |
|---|---|---|---|
| 9,480,492 B2 | 11/2016 | Aranyi et al. |
| 9,483,095 B2 | 11/2016 | Tran et al. |
| 9,486,186 B2 | 11/2016 | Fiebig et al. |
| 9,486,213 B2 | 11/2016 | Altman et al. |
| 9,486,214 B2 | 11/2016 | Shelton, IV |
| 9,486,302 B2 | 11/2016 | Boey et al. |
| 9,488,197 B2 | 11/2016 | Wi |
| 9,492,146 B2 | 11/2016 | Kostrzewski et al. |
| 9,492,167 B2 | 11/2016 | Shelton, IV et al. |
| 9,492,170 B2 | 11/2016 | Bear et al. |
| 9,492,189 B2 | 11/2016 | Williams et al. |
| 9,492,192 B2 | 11/2016 | To et al. |
| 9,498,213 B2 | 11/2016 | Marczyk et al. |
| 9,498,219 B2 | 11/2016 | Moore et al. |
| 9,504,521 B2 | 11/2016 | Deutmeyer et al. |
| D775,336 S | 12/2016 | Shelton, IV et al. |
| 9,510,828 B2 | 12/2016 | Yates et al. |
| 9,510,830 B2 | 12/2016 | Shelton, IV et al. |
| 9,510,846 B2 | 12/2016 | Sholev et al. |
| 9,510,895 B2 | 12/2016 | Houser et al. |
| 9,510,925 B2 | 12/2016 | Hotter et al. |
| 9,517,063 B2 | 12/2016 | Swayze et al. |
| 9,517,068 B2 | 12/2016 | Shelton, IV et al. |
| 9,521,996 B2 | 12/2016 | Armstrong |
| 9,522,029 B2 | 12/2016 | Yates et al. |
| 9,526,481 B2 | 12/2016 | Storz et al. |
| 9,526,499 B2 | 12/2016 | Kostrzewski et al. |
| 9,526,564 B2 | 12/2016 | Rusin |
| 9,532,783 B2 | 1/2017 | Swayze et al. |
| 9,545,258 B2 | 1/2017 | Smith et al. |
| 9,549,732 B2 | 1/2017 | Yates et al. |
| 9,549,735 B2 | 1/2017 | Shelton, IV et al. |
| 9,554,794 B2 | 1/2017 | Baber et al. |
| 9,554,796 B2 | 1/2017 | Kostrzewski |
| 9,554,812 B2 | 1/2017 | Inkpen et al. |
| 9,559,624 B2 | 1/2017 | Philipp |
| 9,561,031 B2 | 2/2017 | Heinrich et al. |
| 9,561,032 B2 | 2/2017 | Shelton, IV et al. |
| 9,561,038 B2 | 2/2017 | Shelton, IV et al. |
| 9,561,045 B2 | 2/2017 | Hinman et al. |
| 9,566,061 B2 | 2/2017 | Aronhalt et al. |
| 9,566,067 B2 | 2/2017 | Milliman et al. |
| 9,572,574 B2 | 2/2017 | Shelton, IV et al. |
| 9,572,577 B2 | 2/2017 | Lloyd et al. |
| 9,572,592 B2 | 2/2017 | Price et al. |
| 9,574,644 B2 | 2/2017 | Parihar |
| 9,585,550 B2 | 3/2017 | Abel et al. |
| 9,585,657 B2 | 3/2017 | Shelton, IV et al. |
| 9,585,658 B2 | 3/2017 | Shelton, IV |
| 9,585,659 B2 | 3/2017 | Viola et al. |
| 9,585,660 B2 | 3/2017 | Laurent et al. |
| 9,585,662 B2 | 3/2017 | Shelton, IV et al. |
| 9,585,663 B2 | 3/2017 | Shelton, IV et al. |
| 9,585,672 B2 | 3/2017 | Bastia |
| 9,592,050 B2 | 3/2017 | Schmid et al. |
| 9,592,052 B2 | 3/2017 | Shelton, IV |
| 9,592,053 B2 | 3/2017 | Shelton, IV et al. |
| 9,592,054 B2 | 3/2017 | Schmid et al. |
| 9,597,073 B2 | 3/2017 | Sorrentino et al. |
| 9,597,075 B2 | 3/2017 | Shelton, IV et al. |
| 9,597,080 B2 | 3/2017 | Milliman et al. |
| 9,597,104 B2 | 3/2017 | Nicholas et al. |
| 9,597,143 B2 | 3/2017 | Madan et al. |
| 9,603,595 B2 | 3/2017 | Shelton, IV et al. |
| 9,603,598 B2 | 3/2017 | Shelton, IV et al. |
| 9,603,991 B2 | 3/2017 | Shelton, IV et al. |
| 9,610,080 B2 | 4/2017 | Whitfield et al. |
| 9,614,258 B2 | 4/2017 | Takahashi et al. |
| 9,615,826 B2 | 4/2017 | Shelton, IV et al. |
| 9,629,623 B2 | 4/2017 | Lytle, IV et al. |
| 9,629,626 B2 | 4/2017 | Soltz et al. |
| 9,629,629 B2 | 4/2017 | Leimbach et al. |
| 9,629,652 B2 | 4/2017 | Mumaw et al. |
| 9,629,814 B2 | 4/2017 | Widenhouse et al. |
| 9,636,850 B2 | 5/2017 | Stopek et al. |
| 9,642,620 B2 | 5/2017 | Baxter, III et al. |
| 9,649,096 B2 | 5/2017 | Sholev |
| 9,649,110 B2 | 5/2017 | Parihar et al. |
| 9,649,111 B2 | 5/2017 | Shelton, IV et al. |
| 9,655,613 B2 | 5/2017 | Schaller |
| 9,655,614 B2 | 5/2017 | Swensgard et al. |
| 9,655,615 B2 | 5/2017 | Knodel et al. |
| 9,655,624 B2 | 5/2017 | Shelton, IV et al. |
| 9,662,108 B2 | 5/2017 | Williams |
| 9,662,110 B2 | 5/2017 | Huang et al. |
| 9,662,116 B2 | 5/2017 | Smith et al. |
| 9,662,131 B2 | 5/2017 | Omori et al. |
| 9,668,729 B2 | 6/2017 | Williams et al. |
| 9,668,732 B2 | 6/2017 | Patel et al. |
| 9,675,344 B2 | 6/2017 | Combrowski et al. |
| 9,675,351 B2 | 6/2017 | Hodgkinson et al. |
| 9,675,355 B2 | 6/2017 | Shelton, IV et al. |
| 9,675,372 B2 | 6/2017 | Laurent et al. |
| 9,675,375 B2 | 6/2017 | Houser et al. |
| 9,675,405 B2 | 6/2017 | Trees et al. |
| 9,681,870 B2 | 6/2017 | Baxter, III et al. |
| 9,681,873 B2 | 6/2017 | Smith et al. |
| 9,681,884 B2 | 6/2017 | Clem et al. |
| 9,687,230 B2 | 6/2017 | Leimbach et al. |
| 9,687,231 B2 | 6/2017 | Baxter, III et al. |
| 9,687,232 B2 | 6/2017 | Shelton, IV et al. |
| 9,687,233 B2 | 6/2017 | Fernandez et al. |
| 9,687,236 B2 | 6/2017 | Leimbach et al. |
| 9,687,237 B2 | 6/2017 | Schmid et al. |
| 9,687,253 B2 * | 6/2017 | Detry ............... A61B 17/1628 |
| 9,689,466 B2 | 6/2017 | Kanai et al. |
| 9,690,362 B2 | 6/2017 | Leimbach et al. |
| 9,693,772 B2 | 7/2017 | Ingmanson et al. |
| 9,693,774 B2 | 7/2017 | Gettinger et al. |
| 9,693,777 B2 | 7/2017 | Schellin et al. |
| 9,700,309 B2 | 7/2017 | Jaworek et al. |
| 9,700,312 B2 | 7/2017 | Kostrzewski et al. |
| 9,700,317 B2 | 7/2017 | Aronhalt et al. |
| 9,700,318 B2 | 7/2017 | Scirica et al. |
| 9,700,319 B2 | 7/2017 | Motooka et al. |
| 9,700,321 B2 | 7/2017 | Shelton, IV et al. |
| 9,706,981 B2 | 7/2017 | Nicholas et al. |
| 9,706,991 B2 | 7/2017 | Hess et al. |
| 9,706,993 B2 | 7/2017 | Hessler et al. |
| 9,707,026 B2 | 7/2017 | Malackowski et al. |
| 9,707,043 B2 | 7/2017 | Bozung |
| 9,707,684 B2 | 7/2017 | Ruiz Morales et al. |
| 9,713,468 B2 | 7/2017 | Harris et al. |
| 9,713,470 B2 | 7/2017 | Scirica et al. |
| 9,724,091 B2 | 8/2017 | Shelton, IV et al. |
| 9,724,092 B2 | 8/2017 | Baxter, III et al. |
| 9,724,094 B2 | 8/2017 | Baber et al. |
| 9,724,096 B2 | 8/2017 | Thompson et al. |
| 9,724,098 B2 | 8/2017 | Baxter, III et al. |
| 9,724,163 B2 | 8/2017 | Orban |
| 9,730,692 B2 | 8/2017 | Shelton, IV et al. |
| 9,730,695 B2 | 8/2017 | Leimbach et al. |
| 9,730,697 B2 | 8/2017 | Morgan et al. |
| 9,730,717 B2 | 8/2017 | Katsuki et al. |
| 9,731,410 B2 | 8/2017 | Hirabayashi et al. |
| 9,733,663 B2 | 8/2017 | Leimbach et al. |
| 9,737,297 B2 | 8/2017 | Racenet et al. |
| 9,737,301 B2 | 8/2017 | Baber et al. |
| 9,737,302 B2 | 8/2017 | Shelton, IV et al. |
| 9,737,303 B2 | 8/2017 | Shelton, IV et al. |
| 9,737,365 B2 | 8/2017 | Hegeman et al. |
| 9,743,927 B2 | 8/2017 | Whitman |
| 9,743,928 B2 | 8/2017 | Shelton, IV et al. |
| 9,743,929 B2 | 8/2017 | Leimbach et al. |
| 9,750,498 B2 | 9/2017 | Timm et al. |
| 9,750,499 B2 | 9/2017 | Leimbach et al. |
| 9,750,501 B2 | 9/2017 | Shelton, IV et al. |
| 9,750,639 B2 | 9/2017 | Barnes et al. |
| 9,757,123 B2 | 9/2017 | Giordano et al. |
| 9,757,124 B2 | 9/2017 | Schellin et al. |
| 9,757,126 B2 | 9/2017 | Cappola |
| 9,757,128 B2 | 9/2017 | Baber et al. |
| 9,757,129 B2 | 9/2017 | Williams |
| 9,757,130 B2 | 9/2017 | Shelton, IV |

(56) References Cited

U.S. PATENT DOCUMENTS

| | | |
|---|---|---|
| 9,763,662 B2 | 9/2017 | Shelton, IV et al. |
| 9,770,245 B2 | 9/2017 | Swayze et al. |
| D800,904 S | 10/2017 | Leimbach et al. |
| 9,775,608 B2 | 10/2017 | Aronhalt et al. |
| 9,775,609 B2 | 10/2017 | Shelton, IV et al. |
| 9,775,610 B2 | 10/2017 | Nicholas et al. |
| 9,775,611 B2 | 10/2017 | Kostrzewski |
| 9,775,613 B2 | 10/2017 | Shelton, IV et al. |
| 9,775,614 B2 | 10/2017 | Shelton, IV et al. |
| 9,782,169 B2 | 10/2017 | Kimsey et al. |
| 9,782,170 B2 | 10/2017 | Zemlok et al. |
| 9,782,214 B2 | 10/2017 | Houser et al. |
| 9,788,834 B2 | 10/2017 | Schmid et al. |
| 9,788,836 B2 | 10/2017 | Overmyer et al. |
| 9,788,847 B2 | 10/2017 | Jinno |
| 9,788,851 B2 | 10/2017 | Dannaher et al. |
| 9,795,379 B2 | 10/2017 | Leimbach et al. |
| 9,795,381 B2 | 10/2017 | Shelton, IV |
| 9,795,382 B2 | 10/2017 | Shelton, IV |
| 9,795,383 B2 | 10/2017 | Aldridge et al. |
| 9,795,384 B2 | 10/2017 | Weaner et al. |
| 9,797,486 B2 | 10/2017 | Zergiebel et al. |
| 9,801,626 B2 | 10/2017 | Parihar et al. |
| 9,801,627 B2 | 10/2017 | Harris et al. |
| 9,801,628 B2 | 10/2017 | Harris et al. |
| 9,801,634 B2 | 10/2017 | Shelton, IV et al. |
| 9,802,033 B2 | 10/2017 | Hibner et al. |
| 9,804,618 B2 | 10/2017 | Leimbach et al. |
| 9,808,244 B2 | 11/2017 | Leimbach et al. |
| 9,808,246 B2 | 11/2017 | Shelton, IV et al. |
| 9,808,247 B2 | 11/2017 | Shelton, IV et al. |
| 9,808,249 B2 | 11/2017 | Shelton, IV |
| 9,814,460 B2 | 11/2017 | Kimsey et al. |
| 9,814,462 B2 | 11/2017 | Woodard, Jr. et al. |
| 9,820,738 B2 | 11/2017 | Lytle, IV et al. |
| 9,820,741 B2 | 11/2017 | Kostrzewski |
| 9,820,768 B2 | 11/2017 | Gee et al. |
| 9,825,455 B2 | 11/2017 | Sandhu et al. |
| 9,826,976 B2 | 11/2017 | Parihar et al. |
| 9,826,977 B2 | 11/2017 | Leimbach et al. |
| 9,826,978 B2 | 11/2017 | Shelton, IV et al. |
| 9,829,698 B2 | 11/2017 | Haraguchi et al. |
| 9,833,236 B2 | 12/2017 | Shelton, IV et al. |
| 9,833,238 B2 | 12/2017 | Baxter, III et al. |
| 9,833,239 B2 | 12/2017 | Yates et al. |
| 9,833,241 B2 | 12/2017 | Huitema et al. |
| 9,833,242 B2 | 12/2017 | Baxter, III et al. |
| 9,839,420 B2 | 12/2017 | Shelton, IV et al. |
| 9,839,421 B2 | 12/2017 | Zerkle et al. |
| 9,839,422 B2 | 12/2017 | Schellin et al. |
| 9,839,423 B2 | 12/2017 | Vendely et al. |
| 9,839,427 B2 | 12/2017 | Swayze et al. |
| 9,839,428 B2 | 12/2017 | Baxter, III et al. |
| 9,839,429 B2 | 12/2017 | Weisenburgh, II et al. |
| 9,839,480 B2 | 12/2017 | Pribanic et al. |
| 9,844,368 B2 | 12/2017 | Boudreaux et al. |
| 9,844,369 B2 | 12/2017 | Huitema et al. |
| 9,844,372 B2 | 12/2017 | Shelton, IV et al. |
| 9,844,373 B2 | 12/2017 | Swayze et al. |
| 9,844,374 B2 | 12/2017 | Lytle, IV et al. |
| 9,844,375 B2 | 12/2017 | Overmyer et al. |
| 9,844,376 B2 | 12/2017 | Baxter, III et al. |
| 9,844,379 B2 | 12/2017 | Shelton, IV et al. |
| 9,848,873 B2 | 12/2017 | Shelton, IV |
| 9,848,875 B2 | 12/2017 | Aronhalt et al. |
| 9,855,662 B2 | 1/2018 | Ruiz Morales et al. |
| 9,861,261 B2 | 1/2018 | Shahinian |
| 9,861,359 B2 | 1/2018 | Shelton, IV et al. |
| 9,861,361 B2 | 1/2018 | Aronhalt et al. |
| 9,861,382 B2 | 1/2018 | Smith et al. |
| 9,867,612 B2 | 1/2018 | Parihar et al. |
| 9,867,618 B2 | 1/2018 | Hall et al. |
| 9,868,198 B2 | 1/2018 | Nicholas et al. |
| 9,872,682 B2 | 1/2018 | Hess et al. |
| 9,872,683 B2 | 1/2018 | Hopkins et al. |
| 9,872,684 B2 | 1/2018 | Hall et al. |
| 9,877,721 B2 | 1/2018 | Schellin et al. |
| 9,877,723 B2 | 1/2018 | Hall et al. |
| 9,883,860 B2 | 2/2018 | Leimbach et al. |
| 9,883,861 B2 | 2/2018 | Shelton, IV et al. |
| 9,884,456 B2 | 2/2018 | Schellin et al. |
| 9,888,919 B2 | 2/2018 | Leimbach et al. |
| 9,888,924 B2 | 2/2018 | Ebersole et al. |
| 9,889,230 B2 | 2/2018 | Bennett et al. |
| 9,895,147 B2 | 2/2018 | Shelton, IV |
| 9,895,148 B2 | 2/2018 | Shelton, IV et al. |
| 9,895,813 B2 | 2/2018 | Blumenkranz et al. |
| 9,901,341 B2 | 2/2018 | Kostrzewski |
| 9,901,342 B2 | 2/2018 | Shelton, IV et al. |
| 9,901,344 B2 | 2/2018 | Moore et al. |
| 9,901,345 B2 | 2/2018 | Moore et al. |
| 9,901,346 B2 | 2/2018 | Moore et al. |
| 9,907,456 B2 | 3/2018 | Miyoshi |
| 9,907,553 B2 | 3/2018 | Cole et al. |
| 9,907,620 B2 | 3/2018 | Shelton, IV et al. |
| 9,913,642 B2 | 3/2018 | Leimbach et al. |
| 9,913,644 B2 | 3/2018 | McCuen |
| 9,913,646 B2 | 3/2018 | Shelton, IV |
| 9,913,647 B2 | 3/2018 | Weisenburgh, II et al. |
| 9,913,648 B2 | 3/2018 | Shelton, IV et al. |
| 9,913,694 B2 | 3/2018 | Brisson |
| 9,918,704 B2 | 3/2018 | Shelton, IV et al. |
| 9,918,715 B2 | 3/2018 | Menn |
| 9,918,716 B2 | 3/2018 | Baxter, III et al. |
| 9,924,944 B2 | 3/2018 | Shelton, IV et al. |
| 9,924,945 B2 | 3/2018 | Zheng et al. |
| 9,924,946 B2 | 3/2018 | Vendely et al. |
| 9,924,947 B2 | 3/2018 | Shelton, IV et al. |
| 9,924,961 B2 | 3/2018 | Shelton, IV et al. |
| 9,931,116 B2 | 4/2018 | Racenet et al. |
| 9,931,118 B2 | 4/2018 | Shelton, IV et al. |
| 9,936,949 B2 | 4/2018 | Measamer et al. |
| 9,936,950 B2 | 4/2018 | Shelton, IV et al. |
| 9,936,951 B2 | 4/2018 | Hufnagel et al. |
| 9,936,954 B2 | 4/2018 | Shelton, IV et al. |
| 9,943,309 B2 | 4/2018 | Shelton, IV et al. |
| 9,943,310 B2 | 4/2018 | Harris et al. |
| 9,943,312 B2 | 4/2018 | Posada et al. |
| 9,955,965 B2 | 5/2018 | Chen et al. |
| 9,955,966 B2 | 5/2018 | Zergiebel |
| 9,962,158 B2 | 5/2018 | Hall et al. |
| 9,962,159 B2 | 5/2018 | Heinrich et al. |
| 9,962,161 B2 | 5/2018 | Scheib et al. |
| 9,968,354 B2 | 5/2018 | Shelton, IV et al. |
| 9,968,355 B2 | 5/2018 | Shelton, IV et al. |
| 9,968,356 B2 | 5/2018 | Shelton, IV et al. |
| 9,968,397 B2 | 5/2018 | Taylor et al. |
| 9,974,529 B2 | 5/2018 | Shelton, IV et al. |
| 9,974,538 B2 | 5/2018 | Baxter, III et al. |
| 9,974,539 B2 | 5/2018 | Yates et al. |
| 9,980,713 B2 | 5/2018 | Aronhalt et al. |
| 9,980,729 B2 | 5/2018 | Moore et al. |
| 9,987,000 B2 | 6/2018 | Shelton, IV et al. |
| 9,987,003 B2 | 6/2018 | Timm et al. |
| 9,993,248 B2 | 6/2018 | Shelton, IV et al. |
| 9,993,258 B2 | 6/2018 | Shelton, IV et al. |
| 9,999,408 B2 | 6/2018 | Boudreaux et al. |
| 9,999,426 B2 | 6/2018 | Moore et al. |
| 9,999,431 B2 | 6/2018 | Shelton, IV et al. |
| 10,004,497 B2 | 6/2018 | Overmyer et al. |
| 10,004,498 B2 | 6/2018 | Morgan et al. |
| 10,004,500 B2 | 6/2018 | Shelton, IV et al. |
| 10,004,501 B2 | 6/2018 | Shelton, IV et al. |
| 10,004,505 B2 | 6/2018 | Moore et al. |
| 10,004,506 B2 | 6/2018 | Shelton, IV et al. |
| 10,010,322 B2 | 7/2018 | Shelton, IV et al. |
| 10,010,324 B2 | 7/2018 | Huitema et al. |
| 10,013,049 B2 | 7/2018 | Leimbach et al. |
| 10,016,199 B2 | 7/2018 | Baber et al. |
| 10,022,125 B2 | 7/2018 | Stopek et al. |
| 10,024,407 B2 | 7/2018 | Aranyi et al. |
| 10,028,742 B2 | 7/2018 | Shelton, IV et al. |
| 10,028,743 B2 | 7/2018 | Shelton, IV et al. |
| 10,028,744 B2 | 7/2018 | Shelton, IV et al. |

(56) References Cited

U.S. PATENT DOCUMENTS

| | | |
|---|---|---|
| 10,028,761 B2 | 7/2018 | Leimbach et al. |
| 10,029,125 B2 | 7/2018 | Shapiro et al. |
| 10,034,668 B2 | 7/2018 | Ebner |
| 10,039,440 B2 | 8/2018 | Fenech et al. |
| 10,039,529 B2 | 8/2018 | Kerr et al. |
| 10,039,545 B2 | 8/2018 | Sadowski et al. |
| 10,041,822 B2 | 8/2018 | Zemlok |
| 10,045,769 B2 | 8/2018 | Aronhalt et al. |
| 10,045,776 B2 | 8/2018 | Shelton, IV et al. |
| 10,045,778 B2 | 8/2018 | Yates et al. |
| 10,045,779 B2 | 8/2018 | Savage et al. |
| 10,045,781 B2 | 8/2018 | Cropper et al. |
| 10,052,044 B2 | 8/2018 | Shelton, IV et al. |
| 10,052,099 B2 | 8/2018 | Morgan et al. |
| 10,052,100 B2 | 8/2018 | Morgan et al. |
| 10,052,102 B2 | 8/2018 | Baxter, III et al. |
| 10,052,104 B2 | 8/2018 | Shelton, IV et al. |
| 10,052,164 B2 | 8/2018 | Overmyer |
| 10,058,317 B2 | 8/2018 | Fan et al. |
| 10,058,327 B2 | 8/2018 | Weisenburgh, II et al. |
| 10,058,963 B2 | 8/2018 | Shelton, IV et al. |
| 10,064,620 B2 | 9/2018 | Gettinger et al. |
| 10,064,621 B2 | 9/2018 | Kerr et al. |
| 10,064,624 B2 | 9/2018 | Shelton, IV et al. |
| 10,064,639 B2 | 9/2018 | Ishida et al. |
| 10,064,649 B2 | 9/2018 | Golebieski et al. |
| 10,064,688 B2 | 9/2018 | Shelton, IV et al. |
| 10,070,861 B2 | 9/2018 | Spivey et al. |
| 10,070,863 B2 | 9/2018 | Swayze et al. |
| 10,071,452 B2 | 9/2018 | Shelton, IV et al. |
| 10,076,325 B2 | 9/2018 | Huang et al. |
| 10,076,326 B2 | 9/2018 | Yates et al. |
| 10,085,624 B2 | 10/2018 | Isoda et al. |
| 10,085,748 B2 | 10/2018 | Morgan et al. |
| 10,085,751 B2 | 10/2018 | Overmyer et al. |
| 10,085,806 B2 | 10/2018 | Hagn et al. |
| 2001/0000531 A1 | 4/2001 | Casscells et al. |
| 2001/0025183 A1 | 9/2001 | Shahidi |
| 2002/0014510 A1 | 2/2002 | Richter et al. |
| 2002/0022810 A1 | 2/2002 | Urich |
| 2002/0022836 A1 | 2/2002 | Goble et al. |
| 2002/0022861 A1 | 2/2002 | Jacobs et al. |
| 2002/0029032 A1 | 3/2002 | Arkin |
| 2002/0029036 A1 | 3/2002 | Goble et al. |
| 2002/0042620 A1 | 4/2002 | Julian et al. |
| 2002/0091374 A1 | 7/2002 | Cooper |
| 2002/0095175 A1 | 7/2002 | Brock et al. |
| 2002/0103494 A1 | 8/2002 | Pacey |
| 2002/0117534 A1 | 8/2002 | Green et al. |
| 2002/0127265 A1 | 9/2002 | Bowman et al. |
| 2002/0128633 A1 | 9/2002 | Brock et al. |
| 2002/0134811 A1 | 9/2002 | Napier et al. |
| 2002/0135474 A1 | 9/2002 | Sylliassen |
| 2002/0143340 A1 | 10/2002 | Kaneko |
| 2002/0158593 A1 | 10/2002 | Henderson et al. |
| 2002/0185514 A1 | 12/2002 | Adams et al. |
| 2002/0188170 A1 | 12/2002 | Santamore et al. |
| 2002/0188287 A1 | 12/2002 | Zvuloni et al. |
| 2003/0009193 A1 | 1/2003 | Corsaro |
| 2003/0011245 A1 | 1/2003 | Fiebig |
| 2003/0066858 A1 | 4/2003 | Holgersson |
| 2003/0078647 A1 | 4/2003 | Vallana et al. |
| 2003/0083648 A1 | 5/2003 | Wang et al. |
| 2003/0084983 A1 | 5/2003 | Rangachari et al. |
| 2003/0093103 A1 | 5/2003 | Malackowski et al. |
| 2003/0094356 A1 | 5/2003 | Waldron |
| 2003/0096158 A1 | 5/2003 | Takano et al. |
| 2003/0114851 A1 | 6/2003 | Truckai et al. |
| 2003/0139741 A1 | 7/2003 | Goble et al. |
| 2003/0153908 A1 | 8/2003 | Goble et al. |
| 2003/0153968 A1 | 8/2003 | Geis et al. |
| 2003/0163085 A1 | 8/2003 | Tanner et al. |
| 2003/0181900 A1 | 9/2003 | Long |
| 2003/0190584 A1 | 10/2003 | Heasley |
| 2003/0195387 A1 | 10/2003 | Kortenbach et al. |
| 2003/0205029 A1 | 11/2003 | Chapolini et al. |
| 2003/0212005 A1 | 11/2003 | Petito et al. |
| 2003/0216732 A1 | 11/2003 | Truckai et al. |
| 2003/0236505 A1 | 12/2003 | Bonadio et al. |
| 2004/0006335 A1 | 1/2004 | Garrison |
| 2004/0006340 A1 | 1/2004 | Latterell et al. |
| 2004/0007608 A1 | 1/2004 | Ehrenfels et al. |
| 2004/0024457 A1 | 2/2004 | Boyce et al. |
| 2004/0028502 A1 | 2/2004 | Cummins |
| 2004/0030333 A1 | 2/2004 | Goble |
| 2004/0034357 A1 | 2/2004 | Beane et al. |
| 2004/0044364 A1 | 3/2004 | DeVries et al. |
| 2004/0049121 A1 | 3/2004 | Yaron |
| 2004/0049172 A1 | 3/2004 | Root et al. |
| 2004/0059362 A1 | 3/2004 | Knodel et al. |
| 2004/0068161 A1 | 4/2004 | Couvillon |
| 2004/0068224 A1 | 4/2004 | Couvillon et al. |
| 2004/0068307 A1 | 4/2004 | Goble |
| 2004/0070369 A1 | 4/2004 | Sakakibara |
| 2004/0073222 A1 | 4/2004 | Koseki |
| 2004/0078037 A1 | 4/2004 | Batchelor et al. |
| 2004/0085180 A1 | 5/2004 | Juang |
| 2004/0093024 A1 | 5/2004 | Lousararian et al. |
| 2004/0098040 A1 | 5/2004 | Taniguchi et al. |
| 2004/0101822 A1 | 5/2004 | Wiesner et al. |
| 2004/0102783 A1 | 5/2004 | Sutterlin et al. |
| 2004/0108357 A1 | 6/2004 | Milliman et al. |
| 2004/0110439 A1 | 6/2004 | Chaikof et al. |
| 2004/0115022 A1 | 6/2004 | Albertson et al. |
| 2004/0116952 A1 | 6/2004 | Sakurai et al. |
| 2004/0122423 A1 | 6/2004 | Dycus et al. |
| 2004/0133095 A1 | 7/2004 | Dunki-Jacobs et al. |
| 2004/0143297 A1 | 7/2004 | Ramsey |
| 2004/0147909 A1 | 7/2004 | Johnston et al. |
| 2004/0153100 A1 | 8/2004 | Ahlberg et al. |
| 2004/0158261 A1 | 8/2004 | Vu |
| 2004/0164123 A1 | 8/2004 | Racenet et al. |
| 2004/0167572 A1 | 8/2004 | Roth et al. |
| 2004/0181219 A1 | 9/2004 | Goble et al. |
| 2004/0193189 A1 | 9/2004 | Kortenbach et al. |
| 2004/0197367 A1 | 10/2004 | Rezania et al. |
| 2004/0199181 A1 | 10/2004 | Knodel et al. |
| 2004/0204735 A1 | 10/2004 | Shiroff et al. |
| 2004/0222268 A1 | 11/2004 | Bilotti et al. |
| 2004/0225186 A1 | 11/2004 | Horne et al. |
| 2004/0232201 A1 | 11/2004 | Wenchell et al. |
| 2004/0236352 A1 | 11/2004 | Wang et al. |
| 2004/0243147 A1 | 12/2004 | Lipow |
| 2004/0243151 A1 | 12/2004 | Demmy et al. |
| 2004/0243163 A1 | 12/2004 | Casiano et al. |
| 2004/0247415 A1 | 12/2004 | Mangone |
| 2004/0249366 A1 | 12/2004 | Kunz |
| 2004/0254455 A1 | 12/2004 | Iddan |
| 2004/0254566 A1 | 12/2004 | Plicchi et al. |
| 2004/0254590 A1 | 12/2004 | Hoffman et al. |
| 2004/0260315 A1 | 12/2004 | Dell et al. |
| 2004/0267310 A1 | 12/2004 | Racenet et al. |
| 2005/0010158 A1 | 1/2005 | Brugger et al. |
| 2005/0010213 A1 | 1/2005 | Stad et al. |
| 2005/0013144 A1 | 1/2005 | Takano et al. |
| 2005/0021078 A1 | 1/2005 | Vleugels et al. |
| 2005/0032511 A1 | 2/2005 | Malone et al. |
| 2005/0033352 A1 | 2/2005 | Zepf et al. |
| 2005/0051163 A1 | 3/2005 | Deem et al. |
| 2005/0054946 A1 | 3/2005 | Krzyzanowski |
| 2005/0057225 A1 | 3/2005 | Marquet |
| 2005/0058890 A1 | 3/2005 | Brazell et al. |
| 2005/0059997 A1 | 3/2005 | Bauman et al. |
| 2005/0070929 A1 | 3/2005 | Dalessandro et al. |
| 2005/0075561 A1 | 4/2005 | Golden |
| 2005/0080342 A1 | 4/2005 | Gilreath et al. |
| 2005/0085693 A1 | 4/2005 | Belson et al. |
| 2005/0090817 A1 | 4/2005 | Phan |
| 2005/0096683 A1 | 5/2005 | Ellins et al. |
| 2005/0116673 A1 | 6/2005 | Carl et al. |
| 2005/0124855 A1 | 6/2005 | Jaffe et al. |
| 2005/0125897 A1 | 6/2005 | Wyslucha et al. |
| 2005/0130682 A1 | 6/2005 | Takara et al. |
| 2005/0131173 A1 | 6/2005 | McDaniel et al. |

(56) References Cited

U.S. PATENT DOCUMENTS

| | | |
|---|---|---|
| 2005/0131211 A1 | 6/2005 | Bayley et al. |
| 2005/0131390 A1 | 6/2005 | Heinrich et al. |
| 2005/0131436 A1 | 6/2005 | Johnston et al. |
| 2005/0131457 A1 | 6/2005 | Douglas et al. |
| 2005/0137454 A1 | 6/2005 | Saadat et al. |
| 2005/0137455 A1 | 6/2005 | Ewers et al. |
| 2005/0139636 A1 | 6/2005 | Schwemberger et al. |
| 2005/0143759 A1 | 6/2005 | Kelly |
| 2005/0143769 A1 | 6/2005 | White et al. |
| 2005/0145671 A1 | 7/2005 | Viola |
| 2005/0150928 A1 | 7/2005 | Kameyama et al. |
| 2005/0154258 A1 | 7/2005 | Tartaglia et al. |
| 2005/0154406 A1 | 7/2005 | Bombard et al. |
| 2005/0159778 A1 | 7/2005 | Heinrich et al. |
| 2005/0165419 A1 | 7/2005 | Sauer et al. |
| 2005/0169974 A1 | 8/2005 | Tenerz et al. |
| 2005/0171522 A1 | 8/2005 | Christopherson |
| 2005/0177181 A1 | 8/2005 | Kagan et al. |
| 2005/0177249 A1 | 8/2005 | Kladakis et al. |
| 2005/0182298 A1 | 8/2005 | Ikeda et al. |
| 2005/0184121 A1 | 8/2005 | Heinrich |
| 2005/0186240 A1 | 8/2005 | Ringeisen et al. |
| 2005/0187545 A1 | 8/2005 | Hooven et al. |
| 2005/0203550 A1 | 9/2005 | Laufer et al. |
| 2005/0209614 A1 | 9/2005 | Fenter et al. |
| 2005/0216055 A1 | 9/2005 | Scirica et al. |
| 2005/0222587 A1 | 10/2005 | Jinno et al. |
| 2005/0222611 A1 | 10/2005 | Weitkamp |
| 2005/0222616 A1 | 10/2005 | Rethy et al. |
| 2005/0222665 A1 | 10/2005 | Aranyi |
| 2005/0228224 A1 | 10/2005 | Okada et al. |
| 2005/0228446 A1 | 10/2005 | Mooradian et al. |
| 2005/0230453 A1 | 10/2005 | Viola |
| 2005/0240178 A1 | 10/2005 | Morley et al. |
| 2005/0245965 A1 | 11/2005 | Orban, III et al. |
| 2005/0251063 A1 | 11/2005 | Basude |
| 2005/0256452 A1 | 11/2005 | DeMarchi et al. |
| 2005/0261676 A1 | 11/2005 | Hall et al. |
| 2005/0263563 A1 | 12/2005 | Racenet et al. |
| 2005/0267455 A1 | 12/2005 | Eggers et al. |
| 2005/0274034 A1 | 12/2005 | Hayashida et al. |
| 2005/0283188 A1 | 12/2005 | Loshakove et al. |
| 2006/0008787 A1 | 1/2006 | Hayman et al. |
| 2006/0015009 A1 | 1/2006 | Jaffe et al. |
| 2006/0020258 A1 | 1/2006 | Strauss et al. |
| 2006/0020336 A1 | 1/2006 | Liddicoat |
| 2006/0025812 A1 | 2/2006 | Shelton |
| 2006/0041188 A1 | 2/2006 | Dirusso et al. |
| 2006/0047275 A1 | 3/2006 | Goble |
| 2006/0049229 A1 | 3/2006 | Milliman et al. |
| 2006/0052824 A1 | 3/2006 | Ransick et al. |
| 2006/0052825 A1 | 3/2006 | Ransick et al. |
| 2006/0064086 A1 | 3/2006 | Odom |
| 2006/0079735 A1 | 4/2006 | Martone et al. |
| 2006/0079879 A1 | 4/2006 | Faller et al. |
| 2006/0086032 A1 | 4/2006 | Valencic et al. |
| 2006/0087746 A1 | 4/2006 | Lipow |
| 2006/0089535 A1 | 4/2006 | Raz et al. |
| 2006/0100643 A1 | 5/2006 | Laufer et al. |
| 2006/0100649 A1 | 5/2006 | Hart |
| 2006/0111711 A1 | 5/2006 | Goble |
| 2006/0111723 A1 | 5/2006 | Chapolini et al. |
| 2006/0116634 A1 | 6/2006 | Shachar |
| 2006/0142772 A1 | 6/2006 | Ralph et al. |
| 2006/0161050 A1 | 7/2006 | Butler et al. |
| 2006/0161185 A1 | 7/2006 | Saadat et al. |
| 2006/0167471 A1 | 7/2006 | Phillips |
| 2006/0173470 A1 | 8/2006 | Oray et al. |
| 2006/0176031 A1 | 8/2006 | Forman et al. |
| 2006/0178556 A1 | 8/2006 | Hasser et al. |
| 2006/0180633 A1 | 8/2006 | Emmons |
| 2006/0180634 A1 | 8/2006 | Shelton et al. |
| 2006/0185682 A1 | 8/2006 | Marczyk |
| 2006/0199999 A1 | 9/2006 | Ikeda et al. |
| 2006/0201989 A1 | 9/2006 | Ojeda |
| 2006/0206100 A1* | 9/2006 | Eskridge ............ A61B 17/1624 606/1 |
| 2006/0217729 A1* | 9/2006 | Eskridge .............. A61B 17/162 606/80 |
| 2006/0235368 A1 | 10/2006 | Oz |
| 2006/0244460 A1 | 11/2006 | Weaver |
| 2006/0252990 A1 | 11/2006 | Kubach |
| 2006/0252993 A1 | 11/2006 | Freed et al. |
| 2006/0258904 A1 | 11/2006 | Stefanchik et al. |
| 2006/0259073 A1 | 11/2006 | Miyamoto et al. |
| 2006/0261763 A1 | 11/2006 | Iott et al. |
| 2006/0264831 A1 | 11/2006 | Skwarek et al. |
| 2006/0264929 A1 | 11/2006 | Goble et al. |
| 2006/0271042 A1 | 11/2006 | Latterell et al. |
| 2006/0271102 A1 | 11/2006 | Bosshard et al. |
| 2006/0282064 A1 | 12/2006 | Shimizu et al. |
| 2006/0284730 A1 | 12/2006 | Schmid et al. |
| 2006/0287576 A1 | 12/2006 | Tsuji et al. |
| 2006/0289602 A1 | 12/2006 | Wales et al. |
| 2006/0291981 A1 | 12/2006 | Viola et al. |
| 2007/0010702 A1 | 1/2007 | Wang et al. |
| 2007/0010838 A1 | 1/2007 | Shelton et al. |
| 2007/0016235 A1 | 1/2007 | Tanaka et al. |
| 2007/0026039 A1 | 2/2007 | Drumheller et al. |
| 2007/0026040 A1 | 2/2007 | Crawley et al. |
| 2007/0027468 A1 | 2/2007 | Wales et al. |
| 2007/0027551 A1 | 2/2007 | Farnsworth et al. |
| 2007/0043387 A1 | 2/2007 | Vargas et al. |
| 2007/0049951 A1 | 3/2007 | Menn |
| 2007/0049966 A1 | 3/2007 | Bonadio et al. |
| 2007/0051375 A1 | 3/2007 | Milliman |
| 2007/0055228 A1 | 3/2007 | Berg et al. |
| 2007/0073341 A1 | 3/2007 | Smith et al. |
| 2007/0073389 A1 | 3/2007 | Bolduc et al. |
| 2007/0078328 A1 | 4/2007 | Ozaki et al. |
| 2007/0078484 A1 | 4/2007 | Talarico et al. |
| 2007/0084897 A1 | 4/2007 | Shelton et al. |
| 2007/0090788 A1 | 4/2007 | Hansford et al. |
| 2007/0093869 A1 | 4/2007 | Bloom et al. |
| 2007/0102472 A1 | 5/2007 | Shelton |
| 2007/0106113 A1 | 5/2007 | Ravo |
| 2007/0106317 A1 | 5/2007 | Shelton et al. |
| 2007/0134251 A1 | 6/2007 | Ashkenazi et al. |
| 2007/0135686 A1 | 6/2007 | Pruitt et al. |
| 2007/0135803 A1 | 6/2007 | Belson |
| 2007/0155010 A1 | 7/2007 | Farnsworth et al. |
| 2007/0170225 A1 | 7/2007 | Shelton et al. |
| 2007/0173687 A1 | 7/2007 | Shima et al. |
| 2007/0173813 A1 | 7/2007 | Odom |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0179477 A1 | 8/2007 | Danger |
| 2007/0185545 A1 | 8/2007 | Duke |
| 2007/0190110 A1 | 8/2007 | Pameijer et al. |
| 2007/0191868 A1 | 8/2007 | Theroux et al. |
| 2007/0194079 A1 | 8/2007 | Hueil et al. |
| 2007/0194082 A1 | 8/2007 | Morgan et al. |
| 2007/0197954 A1 | 8/2007 | Keenan |
| 2007/0198039 A1 | 8/2007 | Jones et al. |
| 2007/0203510 A1 | 8/2007 | Bettuchi |
| 2007/0208375 A1 | 9/2007 | Nishizawa et al. |
| 2007/0213750 A1 | 9/2007 | Weadock |
| 2007/0225562 A1 | 9/2007 | Spivey et al. |
| 2007/0233163 A1 | 10/2007 | Bombard et al. |
| 2007/0243227 A1 | 10/2007 | Gertner |
| 2007/0244471 A1 | 10/2007 | Malackowski |
| 2007/0246505 A1 | 10/2007 | Pace-Floridia et al. |
| 2007/0275035 A1 | 11/2007 | Herman et al. |
| 2007/0276409 A1 | 11/2007 | Ortiz et al. |
| 2007/0279011 A1 | 12/2007 | Jones et al. |
| 2007/0286892 A1 | 12/2007 | Herzberg et al. |
| 2007/0296286 A1 | 12/2007 | Avenell |
| 2008/0003196 A1 | 1/2008 | Jonn et al. |
| 2008/0015598 A1 | 1/2008 | Prommersberger |
| 2008/0021486 A1 | 1/2008 | Oyola et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |

(56) References Cited

U.S. PATENT DOCUMENTS

| | | |
|---|---|---|
| 2008/0029575 A1 | 2/2008 | Shelton et al. |
| 2008/0030170 A1 | 2/2008 | Dacquay et al. |
| 2008/0042861 A1 | 2/2008 | Dacquay et al. |
| 2008/0051833 A1 | 2/2008 | Gramuglia et al. |
| 2008/0064921 A1 | 3/2008 | Larkin et al. |
| 2008/0065153 A1 | 3/2008 | Allard et al. |
| 2008/0071328 A1 | 3/2008 | Haubrich et al. |
| 2008/0078802 A1 | 4/2008 | Hess et al. |
| 2008/0082114 A1 | 4/2008 | McKenna et al. |
| 2008/0082125 A1 | 4/2008 | Murray et al. |
| 2008/0082126 A1 | 4/2008 | Murray et al. |
| 2008/0083807 A1 | 4/2008 | Beardsley et al. |
| 2008/0085296 A1 | 4/2008 | Powell et al. |
| 2008/0086078 A1 | 4/2008 | Powell et al. |
| 2008/0091072 A1 | 4/2008 | Omori et al. |
| 2008/0108443 A1 | 5/2008 | Jinno et al. |
| 2008/0114250 A1 | 5/2008 | Urbano et al. |
| 2008/0125749 A1 | 5/2008 | Olson |
| 2008/0128469 A1 | 6/2008 | Dalessandro et al. |
| 2008/0129253 A1 | 6/2008 | Shiue et al. |
| 2008/0135600 A1 | 6/2008 | Hiranuma et al. |
| 2008/0140115 A1 | 6/2008 | Stopek |
| 2008/0140159 A1 | 6/2008 | Bornhoft et al. |
| 2008/0154299 A1 | 6/2008 | Livneh |
| 2008/0154335 A1 | 6/2008 | Thrope et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0183193 A1 | 7/2008 | Omori et al. |
| 2008/0190989 A1 | 8/2008 | Crews et al. |
| 2008/0196419 A1 | 8/2008 | Dube |
| 2008/0197167 A1 | 8/2008 | Viola et al. |
| 2008/0200755 A1 | 8/2008 | Bakos |
| 2008/0200762 A1 | 8/2008 | Stokes et al. |
| 2008/0200835 A1 | 8/2008 | Monson et al. |
| 2008/0200911 A1 | 8/2008 | Long |
| 2008/0200933 A1 | 8/2008 | Bakos et al. |
| 2008/0200934 A1 | 8/2008 | Fox |
| 2008/0234709 A1 | 9/2008 | Houser |
| 2008/0242939 A1 | 10/2008 | Johnston |
| 2008/0249536 A1 | 10/2008 | Stahler et al. |
| 2008/0249608 A1 | 10/2008 | Dave |
| 2008/0255413 A1 | 10/2008 | Zemlok et al. |
| 2008/0262654 A1 | 10/2008 | Omori et al. |
| 2008/0269596 A1 | 10/2008 | Revie et al. |
| 2008/0281171 A1 | 11/2008 | Fennell et al. |
| 2008/0287944 A1 | 11/2008 | Pearson et al. |
| 2008/0293910 A1 | 11/2008 | Kapiamba et al. |
| 2008/0294179 A1 | 11/2008 | Balbierz et al. |
| 2008/0296346 A1 | 12/2008 | Shelton, IV et al. |
| 2008/0297287 A1 | 12/2008 | Shachar et al. |
| 2008/0308602 A1 | 12/2008 | Timm et al. |
| 2008/0308603 A1 | 12/2008 | Shelton et al. |
| 2008/0312687 A1 | 12/2008 | Blier |
| 2008/0315829 A1 | 12/2008 | Jones et al. |
| 2009/0001121 A1 | 1/2009 | Hess et al. |
| 2009/0001130 A1 | 1/2009 | Hess et al. |
| 2009/0004455 A1 | 1/2009 | Gravagna et al. |
| 2009/0005809 A1 | 1/2009 | Hess et al. |
| 2009/0012534 A1 | 1/2009 | Madhani et al. |
| 2009/0015195 A1 | 1/2009 | Loth-Krausser |
| 2009/0020958 A1 | 1/2009 | Soul |
| 2009/0048583 A1 | 2/2009 | Williams et al. |
| 2009/0048589 A1 | 2/2009 | Takashino et al. |
| 2009/0076506 A1 | 3/2009 | Baker |
| 2009/0078736 A1 | 3/2009 | Van Lue |
| 2009/0081313 A1 | 3/2009 | Aghion et al. |
| 2009/0088659 A1 | 4/2009 | Graham et al. |
| 2009/0090763 A1 | 4/2009 | Zemlok et al. |
| 2009/0092651 A1 | 4/2009 | Shah et al. |
| 2009/0099579 A1 | 4/2009 | Nentwick et al. |
| 2009/0099876 A1 | 4/2009 | Whitman |
| 2009/0119011 A1 | 5/2009 | Kondo et al. |
| 2009/0143855 A1 | 6/2009 | Weber et al. |
| 2009/0149871 A9 | 6/2009 | Kagan et al. |
| 2009/0171147 A1 | 7/2009 | Lee et al. |
| 2009/0177226 A1 | 7/2009 | Reinprecht et al. |
| 2009/0181290 A1 | 7/2009 | Baldwin et al. |
| 2009/0188964 A1 | 7/2009 | Orlov |
| 2009/0198272 A1 | 8/2009 | Kerver et al. |
| 2009/0204108 A1 | 8/2009 | Steffen |
| 2009/0204109 A1 | 8/2009 | Grove et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0209979 A1* | 8/2009 | Yates ............... A61B 17/07207 606/143 |
| 2009/0221993 A1 | 9/2009 | Sohi et al. |
| 2009/0234273 A1 | 9/2009 | Intoccia et al. |
| 2009/0242610 A1 | 10/2009 | Shelton, IV et al. |
| 2009/0247368 A1 | 10/2009 | Chiang |
| 2009/0247901 A1 | 10/2009 | Zimmer |
| 2009/0248041 A1 | 10/2009 | Williams et al. |
| 2009/0253959 A1 | 10/2009 | Yoshie et al. |
| 2009/0255974 A1 | 10/2009 | Viola |
| 2009/0262078 A1 | 10/2009 | Pizzi |
| 2009/0270895 A1 | 10/2009 | Churchill et al. |
| 2009/0290016 A1 | 11/2009 | Suda |
| 2009/0292283 A1 | 11/2009 | Odom |
| 2009/0306639 A1 | 12/2009 | Nevo et al. |
| 2009/0308907 A1 | 12/2009 | Nalagatla et al. |
| 2010/0016888 A1 | 1/2010 | Calabrese et al. |
| 2010/0023024 A1 | 1/2010 | Zeiner et al. |
| 2010/0030233 A1 | 2/2010 | Whitman et al. |
| 2010/0036370 A1 | 2/2010 | Mirel et al. |
| 2010/0065604 A1 | 3/2010 | Weng |
| 2010/0069942 A1 | 3/2010 | Shelton, IV |
| 2010/0076483 A1 | 3/2010 | Imuta |
| 2010/0076489 A1 | 3/2010 | Stopek et al. |
| 2010/0081883 A1 | 4/2010 | Murray et al. |
| 2010/0094340 A1 | 4/2010 | Stopek et al. |
| 2010/0100124 A1 | 4/2010 | Calabrese et al. |
| 2010/0116519 A1 | 5/2010 | Gareis |
| 2010/0122339 A1 | 5/2010 | Boccacci |
| 2010/0133317 A1 | 6/2010 | Shelton, IV et al. |
| 2010/0145146 A1 | 6/2010 | Melder |
| 2010/0147921 A1 | 6/2010 | Olson |
| 2010/0147922 A1 | 6/2010 | Olson |
| 2010/0179022 A1 | 7/2010 | Shirokoshi |
| 2010/0180711 A1 | 7/2010 | Kilibarda et al. |
| 2010/0191262 A1 | 7/2010 | Harris et al. |
| 2010/0191292 A1 | 7/2010 | DeMeo et al. |
| 2010/0193566 A1 | 8/2010 | Scheib et al. |
| 2010/0204717 A1 | 8/2010 | Knodel |
| 2010/0222901 A1 | 9/2010 | Swayze et al. |
| 2010/0249497 A1 | 9/2010 | Peine et al. |
| 2010/0256675 A1 | 10/2010 | Romans |
| 2010/0258327 A1 | 10/2010 | Esenwein et al. |
| 2010/0267662 A1 | 10/2010 | Fielder et al. |
| 2010/0274160 A1 | 10/2010 | Yachi et al. |
| 2010/0292540 A1 | 11/2010 | Hess et al. |
| 2010/0298636 A1 | 11/2010 | Castro et al. |
| 2010/0312261 A1 | 12/2010 | Suzuki et al. |
| 2010/0318085 A1 | 12/2010 | Austin et al. |
| 2010/0331856 A1 | 12/2010 | Carlson et al. |
| 2011/0006101 A1 | 1/2011 | Hall et al. |
| 2011/0011916 A1 | 1/2011 | Levine |
| 2011/0016960 A1 | 1/2011 | Debrailly |
| 2011/0017801 A1* | 1/2011 | Zemlok ............ A61B 17/07207 227/175.1 |
| 2011/0021871 A1 | 1/2011 | Berkelaar |
| 2011/0022032 A1 | 1/2011 | Zemlok et al. |
| 2011/0024477 A1 | 2/2011 | Hall |
| 2011/0024478 A1 | 2/2011 | Shelton, IV |
| 2011/0025311 A1 | 2/2011 | Chauvin et al. |
| 2011/0034910 A1 | 2/2011 | Ross et al. |
| 2011/0036891 A1 | 2/2011 | Zemlok et al. |
| 2011/0046667 A1 | 2/2011 | Culligan et al. |

(56) References Cited

U.S. PATENT DOCUMENTS

| | | | |
|---|---|---|---|
| 2011/0056177 A1* | 3/2011 | Goto | B62M 6/55 56/14.7 |
| 2011/0060363 A1 | 3/2011 | Hess et al. | |
| 2011/0066156 A1 | 3/2011 | McGahan et al. | |
| 2011/0082538 A1 | 4/2011 | Dahlgren et al. | |
| 2011/0087276 A1 | 4/2011 | Bedi et al. | |
| 2011/0087278 A1 | 4/2011 | Viola et al. | |
| 2011/0088921 A1 | 4/2011 | Forgues et al. | |
| 2011/0095064 A1 | 4/2011 | Taylor et al. | |
| 2011/0101069 A1 | 5/2011 | Bombard et al. | |
| 2011/0101794 A1* | 5/2011 | Schroeder | H01M 2/1022 307/150 |
| 2011/0112517 A1 | 5/2011 | Peine et al. | |
| 2011/0112530 A1 | 5/2011 | Keller | |
| 2011/0114697 A1 | 5/2011 | Baxter, III et al. | |
| 2011/0121049 A1 | 5/2011 | Malinouskas et al. | |
| 2011/0125138 A1 | 5/2011 | Malinouskas et al. | |
| 2011/0125176 A1 | 5/2011 | Yates et al. | |
| 2011/0127945 A1 | 6/2011 | Yoneda | |
| 2011/0129706 A1 | 6/2011 | Takahashi et al. | |
| 2011/0144764 A1 | 6/2011 | Bagga et al. | |
| 2011/0147031 A1* | 6/2011 | Matthias | B25F 5/02 173/217 |
| 2011/0147433 A1 | 6/2011 | Shelton, IV et al. | |
| 2011/0163146 A1 | 7/2011 | Ortiz et al. | |
| 2011/0172495 A1 | 7/2011 | Armstrong | |
| 2011/0174861 A1 | 7/2011 | Shelton, IV et al. | |
| 2011/0192882 A1 | 8/2011 | Hess et al. | |
| 2011/0199225 A1 | 8/2011 | Touchberry et al. | |
| 2011/0218400 A1 | 9/2011 | Ma et al. | |
| 2011/0218550 A1 | 9/2011 | Ma | |
| 2011/0230713 A1 | 9/2011 | Kleemann et al. | |
| 2011/0238044 A1 | 9/2011 | Main et al. | |
| 2011/0241597 A1 | 10/2011 | Zhu et al. | |
| 2011/0275901 A1 | 11/2011 | Shelton, IV | |
| 2011/0276083 A1 | 11/2011 | Shelton, IV et al. | |
| 2011/0278343 A1 | 11/2011 | Knodel et al. | |
| 2011/0279268 A1 | 11/2011 | Konishi et al. | |
| 2011/0290856 A1 | 12/2011 | Shelton, IV et al. | |
| 2011/0293690 A1 | 12/2011 | Griffin et al. | |
| 2011/0295295 A1 | 12/2011 | Shelton, IV et al. | |
| 2011/0313894 A1 | 12/2011 | Dye et al. | |
| 2011/0315413 A1 | 12/2011 | Fisher et al. | |
| 2012/0004636 A1 | 1/2012 | Lo | |
| 2012/0016239 A1 | 1/2012 | Barthe et al. | |
| 2012/0016413 A1 | 1/2012 | Timm et al. | |
| 2012/0016467 A1 | 1/2012 | Chen et al. | |
| 2012/0029272 A1 | 2/2012 | Shelton, IV et al. | |
| 2012/0033360 A1 | 2/2012 | Hsu | |
| 2012/0059286 A1 | 3/2012 | Hastings et al. | |
| 2012/0064483 A1 | 3/2012 | Lint et al. | |
| 2012/0074200 A1 | 3/2012 | Schmid et al. | |
| 2012/0078071 A1 | 3/2012 | Bohm et al. | |
| 2012/0078139 A1 | 3/2012 | Aldridge et al. | |
| 2012/0078244 A1 | 3/2012 | Worrell et al. | |
| 2012/0078278 A1* | 3/2012 | Bales, Jr. | A61B 17/320092 606/169 |
| 2012/0080336 A1 | 4/2012 | Shelton, IV et al. | |
| 2012/0080340 A1 | 4/2012 | Shelton, IV et al. | |
| 2012/0080344 A1 | 4/2012 | Shelton, IV | |
| 2012/0080478 A1 | 4/2012 | Morgan et al. | |
| 2012/0080498 A1 | 4/2012 | Shelton, IV et al. | |
| 2012/0086276 A1* | 4/2012 | Sawyers | H02J 1/12 307/66 |
| 2012/0095458 A1 | 4/2012 | Cybulski et al. | |
| 2012/0109186 A1 | 5/2012 | Parrott et al. | |
| 2012/0116261 A1 | 5/2012 | Mumaw et al. | |
| 2012/0116265 A1* | 5/2012 | Houser | A61B 17/00234 601/2 |
| 2012/0116266 A1 | 5/2012 | Houser et al. | |
| 2012/0118595 A1 | 5/2012 | Pellenc | |
| 2012/0123203 A1 | 5/2012 | Riva | |
| 2012/0125792 A1 | 5/2012 | Cassivi | |
| 2012/0132286 A1 | 5/2012 | Lim et al. | |
| 2012/0171539 A1 | 7/2012 | Rejman et al. | |
| 2012/0175398 A1 | 7/2012 | Sandborn et al. | |
| 2012/0184951 A1* | 7/2012 | Viola | A61B 17/00234 606/34 |
| 2012/0197272 A1 | 8/2012 | Oray et al. | |
| 2012/0211542 A1 | 8/2012 | Racenet | |
| 2012/0223121 A1 | 9/2012 | Viola et al. | |
| 2012/0234895 A1 | 9/2012 | O'Connor et al. | |
| 2012/0234897 A1 | 9/2012 | Shelton, IV et al. | |
| 2012/0239068 A1 | 9/2012 | Morris et al. | |
| 2012/0241493 A1 | 9/2012 | Baxter, III et al. | |
| 2012/0248169 A1 | 10/2012 | Widenhouse et al. | |
| 2012/0251861 A1 | 10/2012 | Liang et al. | |
| 2012/0253328 A1* | 10/2012 | Cunningham | A61L 2/00 606/1 |
| 2012/0283707 A1 | 11/2012 | Giordano et al. | |
| 2012/0289979 A1 | 11/2012 | Eskaros et al. | |
| 2012/0292367 A1 | 11/2012 | Morgan et al. | |
| 2012/0298722 A1 | 11/2012 | Hess et al. | |
| 2012/0303002 A1 | 11/2012 | Chowaniec et al. | |
| 2013/0006227 A1 | 1/2013 | Takashino | |
| 2013/0012983 A1 | 1/2013 | Kleyman | |
| 2013/0018400 A1 | 1/2013 | Milton et al. | |
| 2013/0020375 A1 | 1/2013 | Shelton, IV et al. | |
| 2013/0020376 A1 | 1/2013 | Shelton, IV et al. | |
| 2013/0023861 A1 | 1/2013 | Shelton, IV et al. | |
| 2013/0023910 A1 | 1/2013 | Solomon et al. | |
| 2013/0026208 A1 | 1/2013 | Shelton, IV et al. | |
| 2013/0026210 A1 | 1/2013 | Shelton, IV et al. | |
| 2013/0030462 A1 | 1/2013 | Keating et al. | |
| 2013/0068816 A1 | 3/2013 | Mandakolathur Vasudevan et al. | |
| 2013/0072952 A1* | 3/2013 | Storz | A61B 17/1626 606/178 |
| 2013/0087597 A1 | 4/2013 | Shelton, IV et al. | |
| 2013/0090534 A1 | 4/2013 | Burns et al. | |
| 2013/0096568 A1 | 4/2013 | Justis | |
| 2013/0098970 A1 | 4/2013 | Racenet et al. | |
| 2013/0105552 A1 | 5/2013 | Weir et al. | |
| 2013/0116669 A1 | 5/2013 | Shelton, IV et al. | |
| 2013/0123816 A1 | 5/2013 | Hodgkinson et al. | |
| 2013/0126202 A1 | 5/2013 | Oomori et al. | |
| 2013/0131476 A1 | 5/2013 | Siu et al. | |
| 2013/0131651 A1 | 5/2013 | Strobl et al. | |
| 2013/0136969 A1* | 5/2013 | Yasui | H01M 2/0277 429/99 |
| 2013/0153636 A1 | 6/2013 | Shelton, IV et al. | |
| 2013/0153641 A1 | 6/2013 | Shelton, IV et al. | |
| 2013/0158390 A1 | 6/2013 | Tan et al. | |
| 2013/0162198 A1 | 6/2013 | Yokota et al. | |
| 2013/0172929 A1 | 7/2013 | Hess et al. | |
| 2013/0175317 A1 | 7/2013 | Yates et al. | |
| 2013/0181033 A1 | 7/2013 | Shelton, IV et al. | |
| 2013/0181034 A1 | 7/2013 | Shelton, IV et al. | |
| 2013/0190759 A1* | 7/2013 | Waaler | H01M 2/1066 606/52 |
| 2013/0214025 A1 | 8/2013 | Zemlok et al. | |
| 2013/0214030 A1 | 8/2013 | Aronhalt et al. | |
| 2013/0233906 A1 | 9/2013 | Hess et al. | |
| 2013/0238021 A1 | 9/2013 | Gross et al. | |
| 2013/0248578 A1 | 9/2013 | Arteaga Gonzalez | |
| 2013/0253480 A1 | 9/2013 | Kimball et al. | |
| 2013/0256373 A1 | 10/2013 | Schmid et al. | |
| 2013/0256379 A1 | 10/2013 | Schmid et al. | |
| 2013/0256380 A1 | 10/2013 | Schmid et al. | |
| 2013/0270322 A1 | 10/2013 | Scheib et al. | |
| 2013/0277410 A1 | 10/2013 | Fernandez et al. | |
| 2013/0317753 A1 | 11/2013 | Kamen et al. | |
| 2013/0324981 A1 | 12/2013 | Smith et al. | |
| 2013/0324982 A1 | 12/2013 | Smith et al. | |
| 2013/0327552 A1 | 12/2013 | Lovelass et al. | |
| 2013/0330589 A1* | 12/2013 | Detry | A61B 17/1628 429/100 |
| 2013/0333910 A1 | 12/2013 | Tanimoto et al. | |
| 2013/0334280 A1 | 12/2013 | Krehel et al. | |
| 2013/0334283 A1 | 12/2013 | Swayze et al. | |
| 2013/0334284 A1 | 12/2013 | Swayze et al. | |
| 2013/0334285 A1 | 12/2013 | Swayze et al. | |
| 2013/0341374 A1 | 12/2013 | Shelton, IV et al. | |
| 2014/0001231 A1 | 1/2014 | Shelton, IV et al. | |

(56) References Cited

U.S. PATENT DOCUMENTS

| | | |
|---|---|---|
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005702 A1 | 1/2014 | Timm et al. |
| 2014/0005718 A1 | 1/2014 | Shelton, IV et al. |
| 2014/0012289 A1 | 1/2014 | Snow et al. |
| 2014/0012299 A1 | 1/2014 | Stoddard et al. |
| 2014/0014705 A1 | 1/2014 | Baxter, III |
| 2014/0018832 A1 | 1/2014 | Shelton, IV |
| 2014/0039549 A1 | 2/2014 | Belsky et al. |
| 2014/0048580 A1 | 2/2014 | Merchant et al. |
| 2014/0081176 A1 | 3/2014 | Hassan |
| 2014/0100558 A1 | 4/2014 | Schmitz et al. |
| 2014/0107640 A1 | 4/2014 | Yates et al. |
| 2014/0110456 A1 | 4/2014 | Taylor |
| 2014/0114327 A1 | 4/2014 | Boudreaux et al. |
| 2014/0115229 A1 | 4/2014 | Kothamasu et al. |
| 2014/0131418 A1 | 5/2014 | Kostrzewski |
| 2014/0151433 A1 | 6/2014 | Shelton, IV et al. |
| 2014/0158747 A1 | 6/2014 | Measamer et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0171966 A1 | 6/2014 | Giordano et al. |
| 2014/0175147 A1 | 6/2014 | Manoux et al. |
| 2014/0175150 A1 | 6/2014 | Shelton, IV et al. |
| 2014/0175152 A1 | 6/2014 | Hess et al. |
| 2014/0188159 A1 | 7/2014 | Steege |
| 2014/0200561 A1 | 7/2014 | Ingmanson et al. |
| 2014/0207124 A1 | 7/2014 | Aldridge et al. |
| 2014/0207125 A1 | 7/2014 | Applegate et al. |
| 2014/0224857 A1 | 8/2014 | Schmid |
| 2014/0228867 A1 | 8/2014 | Thomas et al. |
| 2014/0230595 A1 | 8/2014 | Butt et al. |
| 2014/0239037 A1 | 8/2014 | Boudreaux et al. |
| 2014/0243865 A1 | 8/2014 | Swayze et al. |
| 2014/0246475 A1 | 9/2014 | Hall et al. |
| 2014/0248167 A1 | 9/2014 | Sugimoto et al. |
| 2014/0249557 A1 | 9/2014 | Koch, Jr. et al. |
| 2014/0249573 A1 | 9/2014 | Arav |
| 2014/0263541 A1 | 9/2014 | Leimbach et al. |
| 2014/0263552 A1 | 9/2014 | Hall et al. |
| 2014/0263554 A1 | 9/2014 | Leimbach et al. |
| 2014/0263558 A1 | 9/2014 | Hausen et al. |
| 2014/0276730 A1 | 9/2014 | Boudreaux et al. |
| 2014/0284371 A1 | 9/2014 | Morgan et al. |
| 2014/0288460 A1 | 9/2014 | Ouyang et al. |
| 2014/0291378 A1 | 10/2014 | Shelton, IV et al. |
| 2014/0291379 A1 | 10/2014 | Schellin et al. |
| 2014/0291383 A1 | 10/2014 | Spivey et al. |
| 2014/0299648 A1 | 10/2014 | Shelton, IV et al. |
| 2014/0303645 A1 | 10/2014 | Morgan et al. |
| 2014/0303660 A1 | 10/2014 | Boyden et al. |
| 2014/0305990 A1 | 10/2014 | Shelton, IV et al. |
| 2014/0305991 A1 | 10/2014 | Parihar et al. |
| 2014/0309666 A1 | 10/2014 | Shelton, IV et al. |
| 2014/0330161 A1 | 11/2014 | Swayze et al. |
| 2014/0367445 A1 | 12/2014 | Ingmanson et al. |
| 2014/0367446 A1 | 12/2014 | Ingmanson et al. |
| 2014/0374130 A1 | 12/2014 | Nakamura et al. |
| 2014/0378950 A1 | 12/2014 | Chiu |
| 2015/0002089 A1 | 1/2015 | Rejman et al. |
| 2015/0008248 A1 | 1/2015 | Giordano et al. |
| 2015/0053737 A1* | 2/2015 | Leimbach .......... A61B 17/07207 227/175.1 |
| 2015/0053739 A1* | 2/2015 | Morgan .............. A61B 17/068 227/175.2 |
| 2015/0053742 A1* | 2/2015 | Shelton, IV ....... A61B 17/07207 227/175.4 |
| 2015/0053743 A1* | 2/2015 | Yates .............. A61B 17/07207 227/175.4 |
| 2015/0053744 A1* | 2/2015 | Swayze ................ A61B 17/072 227/176.1 |
| 2015/0053746 A1 | 2/2015 | Shelton, IV et al. |
| 2015/0053748 A1* | 2/2015 | Yates ..................... G16H 40/63 227/180.1 |
| 2015/0060518 A1 | 3/2015 | Shelton, IV et al. |
| 2015/0060519 A1 | 3/2015 | Shelton, IV et al. |
| 2015/0060520 A1 | 3/2015 | Shelton, IV et al. |
| 2015/0060521 A1 | 3/2015 | Weisenburgh, II et al. |
| 2015/0066000 A1 | 3/2015 | An et al. |
| 2015/0076207 A1 | 3/2015 | Boudreaux et al. |
| 2015/0076208 A1 | 3/2015 | Shelton, IV |
| 2015/0076209 A1 | 3/2015 | Shelton, IV et al. |
| 2015/0076210 A1* | 3/2015 | Shelton, IV ......... A61B 17/072 227/176.1 |
| 2015/0076212 A1 | 3/2015 | Shelton, IV |
| 2015/0080868 A1 | 3/2015 | Kerr |
| 2015/0083781 A1 | 3/2015 | Giordano et al. |
| 2015/0083782 A1 | 3/2015 | Scheib et al. |
| 2015/0090760 A1 | 4/2015 | Giordano et al. |
| 2015/0090761 A1 | 4/2015 | Giordano et al. |
| 2015/0090762 A1 | 4/2015 | Giordano et al. |
| 2015/0090763 A1 | 4/2015 | Murray et al. |
| 2015/0108199 A1 | 4/2015 | Shelton, IV et al. |
| 2015/0122870 A1 | 5/2015 | Zemlok et al. |
| 2015/0148830 A1 | 5/2015 | Stulen et al. |
| 2015/0150554 A1 | 6/2015 | Soltz |
| 2015/0150620 A1 | 6/2015 | Miyamoto et al. |
| 2015/0173744 A1 | 6/2015 | Shelton, IV et al. |
| 2015/0173749 A1 | 6/2015 | Shelton, IV et al. |
| 2015/0173756 A1 | 6/2015 | Baxter, III et al. |
| 2015/0173789 A1 | 6/2015 | Baxter, III et al. |
| 2015/0182220 A1 | 7/2015 | Yates et al. |
| 2015/0196295 A1 | 7/2015 | Shelton, IV et al. |
| 2015/0196296 A1 | 7/2015 | Swayze et al. |
| 2015/0196299 A1 | 7/2015 | Swayze et al. |
| 2015/0196347 A1 | 7/2015 | Yates et al. |
| 2015/0196348 A1 | 7/2015 | Yates et al. |
| 2015/0201932 A1 | 7/2015 | Swayze et al. |
| 2015/0201936 A1 | 7/2015 | Swayze et al. |
| 2015/0201937 A1 | 7/2015 | Swayze et al. |
| 2015/0201938 A1 | 7/2015 | Swayze et al. |
| 2015/0201939 A1 | 7/2015 | Swayze et al. |
| 2015/0201940 A1 | 7/2015 | Swayze et al. |
| 2015/0201941 A1 | 7/2015 | Swayze et al. |
| 2015/0209031 A1 | 7/2015 | Shelton, IV et al. |
| 2015/0222212 A1 | 8/2015 | Iwata |
| 2015/0231409 A1 | 8/2015 | Racenet et al. |
| 2015/0245835 A1 | 9/2015 | Racenet et al. |
| 2015/0265276 A1 | 9/2015 | Huitema et al. |
| 2015/0265357 A1 | 9/2015 | Shelton, IV et al. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0280384 A1 | 10/2015 | Leimbach et al. |
| 2015/0282810 A1 | 10/2015 | Shelton, IV et al. |
| 2015/0289873 A1 | 10/2015 | Shelton, IV et al. |
| 2015/0289874 A1 | 10/2015 | Leimbach et al. |
| 2015/0297200 A1 | 10/2015 | Fitzsimmons et al. |
| 2015/0297210 A1 | 10/2015 | Widenhouse et al. |
| 2015/0297219 A1 | 10/2015 | Shelton, IV et al. |
| 2015/0297222 A1 | 10/2015 | Huitema et al. |
| 2015/0297223 A1 | 10/2015 | Huitema et al. |
| 2015/0297225 A1 | 10/2015 | Huitema et al. |
| 2015/0297228 A1 | 10/2015 | Huitema et al. |
| 2015/0297229 A1 | 10/2015 | Schellin et al. |
| 2015/0297232 A1 | 10/2015 | Huitema et al. |
| 2015/0297233 A1 | 10/2015 | Huitema et al. |
| 2015/0297234 A1 | 10/2015 | Schellin et al. |
| 2015/0297235 A1 | 10/2015 | Harris et al. |
| 2015/0297236 A1 | 10/2015 | Harris et al. |
| 2015/0303417 A1* | 10/2015 | Koeder ................ H01M 2/022 429/164 |
| 2015/0305729 A1 | 10/2015 | Fitzsimmons et al. |
| 2015/0313594 A1 | 11/2015 | Shelton, IV et al. |
| 2015/0324317 A1 | 11/2015 | Collins et al. |
| 2015/0327864 A1 | 11/2015 | Hodgkinson et al. |
| 2015/0335328 A1 | 11/2015 | Shelton, IV et al. |
| 2015/0336249 A1 | 11/2015 | Iwata et al. |
| 2015/0342607 A1 | 12/2015 | Shelton, IV et al. |
| 2015/0351758 A1 | 12/2015 | Shelton, IV et al. |

(56) References Cited

U.S. PATENT DOCUMENTS

| | | |
|---|---|---|
| 2015/0351762 A1 | 12/2015 | Vendely et al. |
| 2015/0352699 A1 | 12/2015 | Sakai et al. |
| 2015/0372265 A1* | 12/2015 | Morisaku ............ H01M 2/204 429/90 |
| 2015/0374360 A1 | 12/2015 | Scheib et al. |
| 2015/0374361 A1 | 12/2015 | Gettinger et al. |
| 2015/0374363 A1 | 12/2015 | Laurent, IV et al. |
| 2015/0374368 A1 | 12/2015 | Swayze et al. |
| 2015/0374369 A1 | 12/2015 | Yates et al. |
| 2015/0374371 A1 | 12/2015 | Richard et al. |
| 2015/0374374 A1 | 12/2015 | Shelton, IV et al. |
| 2015/0374375 A1 | 12/2015 | Shelton, IV et al. |
| 2015/0374376 A1 | 12/2015 | Shelton, IV |
| 2015/0374377 A1 | 12/2015 | Shelton, IV |
| 2015/0374378 A1 | 12/2015 | Giordano et al. |
| 2015/0374379 A1 | 12/2015 | Shelton, IV |
| 2015/0380187 A1 | 12/2015 | Zergiebel et al. |
| 2016/0000430 A1 | 1/2016 | Ming et al. |
| 2016/0000431 A1 | 1/2016 | Giordano et al. |
| 2016/0000437 A1 | 1/2016 | Giordano et al. |
| 2016/0000438 A1 | 1/2016 | Swayze et al. |
| 2016/0000442 A1 | 1/2016 | Shelton, IV |
| 2016/0000452 A1 | 1/2016 | Yates et al. |
| 2016/0000453 A1 | 1/2016 | Yates et al. |
| 2016/0000513 A1 | 1/2016 | Shelton, IV et al. |
| 2016/0007992 A1 | 1/2016 | Yates et al. |
| 2016/0008023 A1 | 1/2016 | Yates et al. |
| 2016/0015391 A1 | 1/2016 | Shelton, IV et al. |
| 2016/0023342 A1 | 1/2016 | Koenig et al. |
| 2016/0030042 A1 | 2/2016 | Heinrich et al. |
| 2016/0030103 A1 | 2/2016 | Manwaring et al. |
| 2016/0051257 A1 | 2/2016 | Shelton, IV et al. |
| 2016/0058443 A1 | 3/2016 | Yates et al. |
| 2016/0066911 A1* | 3/2016 | Baber ................ A61B 5/6847 307/52 |
| 2016/0066912 A1* | 3/2016 | Baber .................. A61B 17/32 307/64 |
| 2016/0066913 A1 | 3/2016 | Swayze et al. |
| 2016/0069449 A1 | 3/2016 | Kanai et al. |
| 2016/0073909 A1 | 3/2016 | Zand et al. |
| 2016/0074040 A1 | 3/2016 | Widenhouse et al. |
| 2016/0082161 A1 | 3/2016 | Zilberman et al. |
| 2016/0089137 A1 | 3/2016 | Hess et al. |
| 2016/0089142 A1 | 3/2016 | Harris et al. |
| 2016/0089146 A1 | 3/2016 | Harris et al. |
| 2016/0089147 A1 | 3/2016 | Harris et al. |
| 2016/0089149 A1 | 3/2016 | Harris et al. |
| 2016/0089198 A1 | 3/2016 | Arya et al. |
| 2016/0095585 A1 | 4/2016 | Zergiebel et al. |
| 2016/0106431 A1 | 4/2016 | Shelton, IV et al. |
| 2016/0113653 A1 | 4/2016 | Zingman |
| 2016/0120544 A1 | 5/2016 | Shelton, IV et al. |
| 2016/0120545 A1 | 5/2016 | Shelton, IV et al. |
| 2016/0166256 A1 | 6/2016 | Baxter, III et al. |
| 2016/0166308 A1 | 6/2016 | Manwaring et al. |
| 2016/0174969 A1 | 6/2016 | Kerr et al. |
| 2016/0174971 A1 | 6/2016 | Baxter, III et al. |
| 2016/0174972 A1 | 6/2016 | Shelton, IV et al. |
| 2016/0174974 A1 | 6/2016 | Schmid et al. |
| 2016/0174984 A1 | 6/2016 | Smith et al. |
| 2016/0174985 A1 | 6/2016 | Baxter, III et al. |
| 2016/0183939 A1 | 6/2016 | Shelton, IV et al. |
| 2016/0183943 A1 | 6/2016 | Shelton, IV |
| 2016/0183944 A1 | 6/2016 | Swensgard et al. |
| 2016/0183945 A1 | 6/2016 | Shelton, IV et al. |
| 2016/0192916 A1 | 7/2016 | Shelton, IV et al. |
| 2016/0192917 A1 | 7/2016 | Shelton, IV et al. |
| 2016/0192918 A1 | 7/2016 | Shelton, IV et al. |
| 2016/0192929 A1 | 7/2016 | Schmid et al. |
| 2016/0192933 A1 | 7/2016 | Shelton, IV |
| 2016/0192936 A1 | 7/2016 | Leimbach et al. |
| 2016/0192977 A1 | 7/2016 | Manwaring et al. |
| 2016/0192996 A1 | 7/2016 | Spivey et al. |
| 2016/0193673 A1 | 7/2016 | Yoshida et al. |
| 2016/0199059 A1 | 7/2016 | Shelton, IV et al. |
| 2016/0199061 A1 | 7/2016 | Shelton, IV et al. |
| 2016/0199063 A1 | 7/2016 | Mandakolathur Vasudevan et al. |
| 2016/0199064 A1 | 7/2016 | Shelton, IV et al. |
| 2016/0199089 A1 | 7/2016 | Hess et al. |
| 2016/0199956 A1 | 7/2016 | Shelton, IV et al. |
| 2016/0206310 A1 | 7/2016 | Shelton, IV |
| 2016/0206314 A1 | 7/2016 | Scheib et al. |
| 2016/0220248 A1 | 8/2016 | Timm et al. |
| 2016/0220249 A1 | 8/2016 | Shelton, IV et al. |
| 2016/0220266 A1 | 8/2016 | Shelton, IV et al. |
| 2016/0220268 A1 | 8/2016 | Shelton, IV et al. |
| 2016/0235403 A1 | 8/2016 | Shelton, IV et al. |
| 2016/0235404 A1 | 8/2016 | Shelton, IV |
| 2016/0235405 A1 | 8/2016 | Shelton, IV et al. |
| 2016/0235406 A1 | 8/2016 | Shelton, IV et al. |
| 2016/0235408 A1 | 8/2016 | Shelton, IV et al. |
| 2016/0235409 A1 | 8/2016 | Shelton, IV et al. |
| 2016/0235494 A1 | 8/2016 | Shelton, IV et al. |
| 2016/0242775 A1 | 8/2016 | Shelton, IV et al. |
| 2016/0242776 A1 | 8/2016 | Shelton, IV et al. |
| 2016/0242777 A1 | 8/2016 | Shelton, IV et al. |
| 2016/0242781 A1 | 8/2016 | Shelton, IV et al. |
| 2016/0242782 A1 | 8/2016 | Shelton, IV et al. |
| 2016/0242783 A1 | 8/2016 | Shelton, IV et al. |
| 2016/0249910 A1 | 9/2016 | Shelton, IV et al. |
| 2016/0249911 A1 | 9/2016 | Timm et al. |
| 2016/0249915 A1 | 9/2016 | Beckman et al. |
| 2016/0249916 A1 | 9/2016 | Shelton, IV et al. |
| 2016/0249917 A1 | 9/2016 | Beckman et al. |
| 2016/0249918 A1 | 9/2016 | Shelton, IV et al. |
| 2016/0249922 A1 | 9/2016 | Morgan et al. |
| 2016/0249927 A1 | 9/2016 | Beckman et al. |
| 2016/0256071 A1 | 9/2016 | Shelton, IV et al. |
| 2016/0256154 A1 | 9/2016 | Shelton, IV et al. |
| 2016/0256156 A1 | 9/2016 | Shelton, IV et al. |
| 2016/0256159 A1 | 9/2016 | Pinjala et al. |
| 2016/0256160 A1 | 9/2016 | Shelton, IV et al. |
| 2016/0256161 A1 | 9/2016 | Overmyer et al. |
| 2016/0256185 A1 | 9/2016 | Shelton, IV et al. |
| 2016/0256229 A1 | 9/2016 | Morgan et al. |
| 2016/0262745 A1 | 9/2016 | Morgan et al. |
| 2016/0262746 A1 | 9/2016 | Shelton, IV et al. |
| 2016/0270780 A1 | 9/2016 | Hall et al. |
| 2016/0278765 A1 | 9/2016 | Shelton, IV et al. |
| 2016/0278775 A1 | 9/2016 | Shelton, IV et al. |
| 2016/0287249 A1 | 10/2016 | Alexander, III et al. |
| 2016/0287250 A1 | 10/2016 | Shelton, IV et al. |
| 2016/0287251 A1 | 10/2016 | Shelton, IV et al. |
| 2016/0287253 A1 | 10/2016 | Shelton, IV et al. |
| 2016/0310143 A1 | 10/2016 | Bettuchi |
| 2016/0331375 A1 | 11/2016 | Shelton, IV et al. |
| 2016/0345976 A1 | 12/2016 | Gonzalez et al. |
| 2016/0346034 A1 | 12/2016 | Arya et al. |
| 2016/0354085 A1 | 12/2016 | Shelton, IV et al. |
| 2016/0367122 A1 | 12/2016 | Ichimura et al. |
| 2016/0367245 A1 | 12/2016 | Wise et al. |
| 2016/0367246 A1 | 12/2016 | Baxter, III et al. |
| 2016/0367247 A1 | 12/2016 | Weaner et al. |
| 2016/0367254 A1 | 12/2016 | Baxter, III et al. |
| 2016/0367255 A1 | 12/2016 | Wise et al. |
| 2016/0367256 A1 | 12/2016 | Hensel et al. |
| 2016/0374675 A1 | 12/2016 | Shelton, IV et al. |
| 2017/0000485 A1 | 1/2017 | Shelton, IV et al. |
| 2017/0007236 A1 | 1/2017 | Shelton, IV et al. |
| 2017/0007237 A1 | 1/2017 | Yates et al. |
| 2017/0007238 A1 | 1/2017 | Yates et al. |
| 2017/0007239 A1 | 1/2017 | Shelton, IV |
| 2017/0007241 A1 | 1/2017 | Shelton, IV et al. |
| 2017/0007242 A1 | 1/2017 | Shelton, IV et al. |
| 2017/0007243 A1 | 1/2017 | Shelton, IV et al. |
| 2017/0007244 A1 | 1/2017 | Shelton, IV et al. |
| 2017/0007245 A1 | 1/2017 | Shelton, IV et al. |
| 2017/0007246 A1 | 1/2017 | Shelton, IV et al. |
| 2017/0007247 A1 | 1/2017 | Shelton, IV et al. |
| 2017/0007248 A1 | 1/2017 | Shelton, IV et al. |
| 2017/0007249 A1 | 1/2017 | Shelton, IV et al. |
| 2017/0007250 A1 | 1/2017 | Shelton, IV et al. |
| 2017/0007251 A1 | 1/2017 | Yates et al. |
| 2017/0007254 A1 | 1/2017 | Jaworek et al. |

(56) References Cited

U.S. PATENT DOCUMENTS

| | | |
|---|---|---|
| 2017/0007255 A1 | 1/2017 | Jaworek et al. |
| 2017/0007338 A1 | 1/2017 | Swensgard et al. |
| 2017/0007340 A1 | 1/2017 | Swensgard et al. |
| 2017/0007341 A1 | 1/2017 | Swensgard et al. |
| 2017/0007347 A1 | 1/2017 | Jaworek et al. |
| 2017/0014125 A1 | 1/2017 | Shelton, IV et al. |
| 2017/0014129 A1 | 1/2017 | Shelton, IV et al. |
| 2017/0049444 A1 | 2/2017 | Schellin et al. |
| 2017/0049447 A1 | 2/2017 | Barton et al. |
| 2017/0049448 A1 | 2/2017 | Widenhouse et al. |
| 2017/0055986 A1 | 3/2017 | Harris et al. |
| 2017/0055989 A1 | 3/2017 | Shelton, IV et al. |
| 2017/0055996 A1 | 3/2017 | Baxter, III et al. |
| 2017/0055997 A1 | 3/2017 | Swayze et al. |
| 2017/0055998 A1 | 3/2017 | Baxter, III et al. |
| 2017/0055999 A1 | 3/2017 | Baxter, III et al. |
| 2017/0056000 A1 | 3/2017 | Nalagatla et al. |
| 2017/0056001 A1 | 3/2017 | Shelton, IV et al. |
| 2017/0056002 A1 | 3/2017 | Nalagatla et al. |
| 2017/0056004 A1 | 3/2017 | Shelton, IV et al. |
| 2017/0056005 A1 | 3/2017 | Shelton, IV et al. |
| 2017/0056006 A1 | 3/2017 | Shelton, IV et al. |
| 2017/0056007 A1 | 3/2017 | Eckert et al. |
| 2017/0079640 A1 | 3/2017 | Overmyer et al. |
| 2017/0079642 A1 | 3/2017 | Overmyer et al. |
| 2017/0079643 A1 | 3/2017 | Yates et al. |
| 2017/0079644 A1 | 3/2017 | Overmyer et al. |
| 2017/0079647 A1 | 3/2017 | Yates et al. |
| 2017/0086823 A1 | 3/2017 | Leimbach et al. |
| 2017/0086827 A1 | 3/2017 | Vendely et al. |
| 2017/0086829 A1 | 3/2017 | Vendely et al. |
| 2017/0086830 A1 | 3/2017 | Yates et al. |
| 2017/0086831 A1 | 3/2017 | Shelton, IV et al. |
| 2017/0086832 A1 | 3/2017 | Harris et al. |
| 2017/0086835 A1 | 3/2017 | Harris et al. |
| 2017/0086836 A1 | 3/2017 | Harris et al. |
| 2017/0086837 A1 | 3/2017 | Vendely et al. |
| 2017/0086838 A1 | 3/2017 | Harris et al. |
| 2017/0086839 A1 | 3/2017 | Vendely et al. |
| 2017/0086840 A1 | 3/2017 | Harris et al. |
| 2017/0086841 A1 | 3/2017 | Vendely et al. |
| 2017/0086842 A1 | 3/2017 | Shelton, IV et al. |
| 2017/0086843 A1 | 3/2017 | Vendely et al. |
| 2017/0086844 A1 | 3/2017 | Vendely et al. |
| 2017/0086845 A1 | 3/2017 | Vendely et al. |
| 2017/0086936 A1 | 3/2017 | Shelton, IV et al. |
| 2017/0119390 A1 | 5/2017 | Schellin et al. |
| 2017/0119397 A1 | 5/2017 | Harris et al. |
| 2017/0128149 A1 | 5/2017 | Heinrich et al. |
| 2017/0135695 A1 | 5/2017 | Shelton, IV et al. |
| 2017/0135697 A1 | 5/2017 | Mozdzierz et al. |
| 2017/0150983 A1 | 6/2017 | Ingmanson et al. |
| 2017/0172672 A1 | 6/2017 | Bailey et al. |
| 2017/0182211 A1 | 6/2017 | Raxworthy et al. |
| 2017/0189018 A1 | 7/2017 | Harris et al. |
| 2017/0189019 A1 | 7/2017 | Harris et al. |
| 2017/0189020 A1 | 7/2017 | Harris et al. |
| 2017/0196558 A1 | 7/2017 | Morgan et al. |
| 2017/0196560 A1 | 7/2017 | Leimbach et al. |
| 2017/0196561 A1 | 7/2017 | Shelton, IV et al. |
| 2017/0196562 A1 | 7/2017 | Shelton, IV et al. |
| 2017/0196637 A1 | 7/2017 | Shelton, IV et al. |
| 2017/0196649 A1 | 7/2017 | Yates et al. |
| 2017/0202596 A1 | 7/2017 | Shelton, IV et al. |
| 2017/0209145 A1 | 7/2017 | Swayze et al. |
| 2017/0209146 A1 | 7/2017 | Yates et al. |
| 2017/0209226 A1 | 7/2017 | Overmyer et al. |
| 2017/0215881 A1 | 8/2017 | Shelton, IV et al. |
| 2017/0224330 A1 | 8/2017 | Worthington et al. |
| 2017/0224331 A1 | 8/2017 | Worthington et al. |
| 2017/0224332 A1 | 8/2017 | Hunter et al. |
| 2017/0224333 A1 | 8/2017 | Hunter et al. |
| 2017/0224334 A1 | 8/2017 | Worthington et al. |
| 2017/0224335 A1 | 8/2017 | Weaner et al. |
| 2017/0224336 A1 | 8/2017 | Hunter et al. |
| 2017/0224339 A1 | 8/2017 | Huang et al. |
| 2017/0224342 A1 | 8/2017 | Worthington et al. |
| 2017/0224343 A1 | 8/2017 | Baxter, III et al. |
| 2017/0231623 A1 | 8/2017 | Shelton, IV et al. |
| 2017/0231626 A1 | 8/2017 | Shelton, IV et al. |
| 2017/0231627 A1 | 8/2017 | Shelton, IV et al. |
| 2017/0231628 A1 | 8/2017 | Shelton, IV et al. |
| 2017/0238928 A1 | 8/2017 | Morgan et al. |
| 2017/0238929 A1 | 8/2017 | Yates et al. |
| 2017/0245952 A1 | 8/2017 | Shelton, IV et al. |
| 2017/0245953 A1 | 8/2017 | Shelton, IV et al. |
| 2017/0249431 A1 | 8/2017 | Shelton, IV et al. |
| 2017/0258469 A1 | 9/2017 | Shelton, IV et al. |
| 2017/0265856 A1 | 9/2017 | Shelton, IV et al. |
| 2017/0281167 A1 | 10/2017 | Shelton, IV et al. |
| 2017/0281180 A1 | 10/2017 | Morgan et al. |
| 2017/0290585 A1 | 10/2017 | Shelton, IV et al. |
| 2017/0296169 A1 | 10/2017 | Yates et al. |
| 2017/0296170 A1 | 10/2017 | Shelton, IV et al. |
| 2017/0296171 A1 | 10/2017 | Shelton, IV et al. |
| 2017/0296172 A1 | 10/2017 | Harris et al. |
| 2017/0296173 A1 | 10/2017 | Shelton, IV et al. |
| 2017/0296177 A1 | 10/2017 | Harris et al. |
| 2017/0296178 A1 | 10/2017 | Miller et al. |
| 2017/0296179 A1 | 10/2017 | Shelton, IV et al. |
| 2017/0296180 A1 | 10/2017 | Harris et al. |
| 2017/0296183 A1 | 10/2017 | Shelton, IV et al. |
| 2017/0296184 A1 | 10/2017 | Harris et al. |
| 2017/0296185 A1 | 10/2017 | Swensgard et al. |
| 2017/0296189 A1 | 10/2017 | Vendely et al. |
| 2017/0296190 A1 | 10/2017 | Aronhalt et al. |
| 2017/0296191 A1 | 10/2017 | Shelton, IV et al. |
| 2017/0296213 A1 | 10/2017 | Swensgard et al. |
| 2017/0311944 A1 | 11/2017 | Morgan et al. |
| 2017/0311949 A1 | 11/2017 | Shelton, IV |
| 2017/0311950 A1 | 11/2017 | Shelton, IV et al. |
| 2017/0312040 A1 | 11/2017 | Giordano et al. |
| 2017/0312041 A1 | 11/2017 | Giordano et al. |
| 2017/0312042 A1 | 11/2017 | Giordano et al. |
| 2017/0319201 A1 | 11/2017 | Morgan et al. |
| 2017/0319207 A1 | 11/2017 | Shelton, IV et al. |
| 2017/0319209 A1 | 11/2017 | Morgan et al. |
| 2017/0319777 A1 | 11/2017 | Shelton, IV et al. |
| 2017/0333034 A1 | 11/2017 | Morgan et al. |
| 2017/0333035 A1 | 11/2017 | Morgan et al. |
| 2017/0333070 A1 | 11/2017 | Laurent et al. |
| 2017/0348043 A1 | 12/2017 | Wang et al. |
| 2017/0354415 A1 | 12/2017 | Casasanta, Jr. et al. |
| 2017/0360442 A1 | 12/2017 | Shelton, IV et al. |
| 2017/0367700 A1 | 12/2017 | Leimbach et al. |
| 2017/0367991 A1 | 12/2017 | Widenhouse et al. |
| 2018/0000483 A1 | 1/2018 | Leimbach et al. |
| 2018/0000545 A1 | 1/2018 | Giordano et al. |
| 2018/0008269 A1 | 1/2018 | Moore et al. |
| 2018/0008270 A1 | 1/2018 | Moore et al. |
| 2018/0008271 A1 | 1/2018 | Moore et al. |
| 2018/0008356 A1 | 1/2018 | Giordano et al. |
| 2018/0008357 A1 | 1/2018 | Giordano et al. |
| 2018/0028184 A1 | 2/2018 | Shelton, IV et al. |
| 2018/0028185 A1 | 2/2018 | Shelton, IV et al. |
| 2018/0042611 A1 | 2/2018 | Swayze et al. |
| 2018/0049824 A1 | 2/2018 | Harris et al. |
| 2018/0049883 A1 | 2/2018 | Moskowitz et al. |
| 2018/0055510 A1 | 3/2018 | Schmid et al. |
| 2018/0055513 A1 | 3/2018 | Shelton, IV et al. |
| 2018/0055524 A1 | 3/2018 | Shelton, IV et al. |
| 2018/0055525 A1 | 3/2018 | Shelton, IV et al. |
| 2018/0055526 A1 | 3/2018 | Shelton, IV et al. |
| 2018/0064437 A1 | 3/2018 | Yates et al. |
| 2018/0064440 A1 | 3/2018 | Shelton, IV et al. |
| 2018/0064441 A1 | 3/2018 | Shelton, IV et al. |
| 2018/0064442 A1 | 3/2018 | Shelton, IV et al. |
| 2018/0064443 A1 | 3/2018 | Shelton, IV et al. |
| 2018/0070939 A1 | 3/2018 | Giordano et al. |
| 2018/0070942 A1 | 3/2018 | Shelton, IV et al. |
| 2018/0070946 A1 | 3/2018 | Shelton, IV et al. |
| 2018/0074535 A1 | 3/2018 | Shelton, IV et al. |
| 2018/0078248 A1 | 3/2018 | Swayze et al. |
| 2018/0085116 A1 | 3/2018 | Yates et al. |

(56) References Cited

U.S. PATENT DOCUMENTS

| | | |
|---|---|---|
| 2018/0085117 A1 | 3/2018 | Shelton, IV et al. |
| 2018/0085123 A1 | 3/2018 | Shelton, IV et al. |
| 2018/0095487 A1 | 4/2018 | Leimbach et al. |
| 2018/0103952 A1 | 4/2018 | Aronhalt et al. |
| 2018/0103953 A1 | 4/2018 | Shelton, IV et al. |
| 2018/0103955 A1 | 4/2018 | Shelton, IV et al. |
| 2018/0110516 A1 | 4/2018 | Baxter, III et al. |
| 2018/0110518 A1 | 4/2018 | Overmyer et al. |
| 2018/0110519 A1 | 4/2018 | Lytle, IV et al. |
| 2018/0110520 A1 | 4/2018 | Shelton, IV et al. |
| 2018/0110521 A1 | 4/2018 | Shelton, IV et al. |
| 2018/0110522 A1 | 4/2018 | Shelton, IV et al. |
| 2018/0110523 A1 | 4/2018 | Shelton, IV |
| 2018/0110574 A1 | 4/2018 | Shelton, IV et al. |
| 2018/0110575 A1 | 4/2018 | Shelton, IV et al. |
| 2018/0116658 A1 | 5/2018 | Aronhalt, IV et al. |
| 2018/0116662 A1 | 5/2018 | Shelton, IV et al. |
| 2018/0116665 A1 | 5/2018 | Hall et al. |
| 2018/0125481 A1 | 5/2018 | Yates et al. |
| 2018/0125488 A1 | 5/2018 | Morgan et al. |
| 2018/0125489 A1 | 5/2018 | Leimbach et al. |
| 2018/0125590 A1 | 5/2018 | Giordano et al. |
| 2018/0126504 A1 | 5/2018 | Shelton, IV et al. |
| 2018/0132845 A1 | 5/2018 | Schmid et al. |
| 2018/0132850 A1 | 5/2018 | Leimbach et al. |
| 2018/0132851 A1 | 5/2018 | Hall et al. |
| 2018/0132952 A1 | 5/2018 | Spivey et al. |
| 2018/0133856 A1 | 5/2018 | Shelton, IV et al. |
| 2018/0140299 A1 | 5/2018 | Weaner et al. |
| 2018/0140368 A1 | 5/2018 | Shelton, IV et al. |
| 2018/0146960 A1 | 5/2018 | Shelton, IV et al. |
| 2018/0153542 A1 | 6/2018 | Shelton, IV et al. |
| 2018/0161034 A1 | 6/2018 | Scheib et al. |
| 2018/0168575 A1 | 6/2018 | Simms et al. |
| 2018/0168576 A1 | 6/2018 | Hunter et al. |
| 2018/0168577 A1 | 6/2018 | Aronhalt et al. |
| 2018/0168578 A1 | 6/2018 | Aronhalt et al. |
| 2018/0168579 A1 | 6/2018 | Aronhalt et al. |
| 2018/0168580 A1 | 6/2018 | Hunter et al. |
| 2018/0168581 A1 | 6/2018 | Hunter et al. |
| 2018/0168582 A1 | 6/2018 | Swayze et al. |
| 2018/0168583 A1 | 6/2018 | Hunter et al. |
| 2018/0168584 A1 | 6/2018 | Harris et al. |
| 2018/0168589 A1 | 6/2018 | Swayze et al. |
| 2018/0168590 A1 | 6/2018 | Overmyer et al. |
| 2018/0168591 A1 | 6/2018 | Swayze et al. |
| 2018/0168592 A1 | 6/2018 | Overmyer et al. |
| 2018/0168593 A1 | 6/2018 | Overmyer et al. |
| 2018/0168594 A1 | 6/2018 | Shelton, IV et al. |
| 2018/0168595 A1 | 6/2018 | Overmyer et al. |
| 2018/0168596 A1 | 6/2018 | Beckman et al. |
| 2018/0168597 A1 | 6/2018 | Fanelli et al. |
| 2018/0168598 A1 | 6/2018 | Shelton, IV et al. |
| 2018/0168599 A1 | 6/2018 | Bakos et al. |
| 2018/0168600 A1 | 6/2018 | Shelton, IV et al. |
| 2018/0168601 A1 | 6/2018 | Bakos et al. |
| 2018/0168602 A1 | 6/2018 | Bakos et al. |
| 2018/0168603 A1 | 6/2018 | Morgan et al. |
| 2018/0168604 A1 | 6/2018 | Shelton, IV et al. |
| 2018/0168605 A1 | 6/2018 | Baber et al. |
| 2018/0168606 A1 | 6/2018 | Shelton, IV et al. |
| 2018/0168607 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168610 A1 | 6/2018 | Shelton, IV et al. |
| 2018/0168611 A1 | 6/2018 | Shelton, IV et al. |
| 2018/0168612 A1 | 6/2018 | Shelton, IV et al. |
| 2018/0168613 A1 | 6/2018 | Shelton, IV et al. |
| 2018/0168614 A1 | 6/2018 | Shelton, IV et al. |
| 2018/0168615 A1 | 6/2018 | Shelton, IV et al. |
| 2018/0168618 A1 | 6/2018 | Scott et al. |
| 2018/0168619 A1 | 6/2018 | Scott et al. |
| 2018/0168620 A1 | 6/2018 | Huang et al. |
| 2018/0168621 A1 | 6/2018 | Shelton, IV et al. |
| 2018/0168622 A1 | 6/2018 | Shelton, IV et al. |
| 2018/0168623 A1 | 6/2018 | Simms et al. |
| 2018/0168624 A1 | 6/2018 | Shelton, IV et al. |
| 2018/0168625 A1 | 6/2018 | Posada et al. |
| 2018/0168626 A1 | 6/2018 | Shelton, IV et al. |
| 2018/0168627 A1 | 6/2018 | Weaner et al. |
| 2018/0168628 A1 | 6/2018 | Hunter et al. |
| 2018/0168629 A1 | 6/2018 | Shelton, IV et al. |
| 2018/0168630 A1 | 6/2018 | Shelton, IV et al. |
| 2018/0168631 A1 | 6/2018 | Harris et al. |
| 2018/0168632 A1 | 6/2018 | Harris et al. |
| 2018/0168633 A1 | 6/2018 | Shelton, IV et al. |
| 2018/0168634 A1 | 6/2018 | Harris et al. |
| 2018/0168635 A1 | 6/2018 | Shelton, IV et al. |
| 2018/0168636 A1 | 6/2018 | Shelton, IV et al. |
| 2018/0168637 A1 | 6/2018 | Harris et al. |
| 2018/0168638 A1 | 6/2018 | Harris et al. |
| 2018/0168639 A1 | 6/2018 | Shelton, IV et al. |
| 2018/0168640 A1 | 6/2018 | Shelton, IV et al. |
| 2018/0168641 A1 | 6/2018 | Harris et al. |
| 2018/0168642 A1 | 6/2018 | Shelton, IV et al. |
| 2018/0168644 A1 | 6/2018 | Shelton, IV et al. |
| 2018/0168645 A1 | 6/2018 | Shelton, IV et al. |
| 2018/0168646 A1 | 6/2018 | Shelton, IV et al. |
| 2018/0168649 A1 | 6/2018 | Shelton, IV et al. |
| 2018/0168651 A1 | 6/2018 | Shelton, IV et al. |
| 2018/0199940 A1 | 7/2018 | Zergiebel et al. |
| 2018/0206843 A1 | 7/2018 | Yates et al. |
| 2018/0206906 A1 | 7/2018 | Moua et al. |
| 2018/0214147 A1 | 8/2018 | Merchant et al. |
| 2018/0221046 A1 | 8/2018 | Demmy et al. |
| 2018/0221050 A1 | 8/2018 | Kostrzewski et al. |
| 2018/0228490 A1 | 8/2018 | Richard et al. |
| 2018/0250001 A1 | 9/2018 | Aronhalt et al. |
| 2018/0256184 A1 | 9/2018 | Shelton, IV et al. |
| 2018/0256185 A1 | 9/2018 | Shelton, IV et al. |
| 2018/0271520 A1 | 9/2018 | Shelton, IV et al. |

FOREIGN PATENT DOCUMENTS

| | | |
|---|---|---|
| AU | 2011218702 B2 | 6/2013 |
| AU | 2012200178 B2 | 7/2013 |
| CA | 1015829 A | 8/1977 |
| CA | 1125615 A | 6/1982 |
| CA | 2458946 A1 | 3/2003 |
| CA | 2477181 A1 | 4/2004 |
| CA | 2512960 A1 | 1/2006 |
| CA | 2514274 A1 | 1/2006 |
| CA | 2639177 A1 | 2/2009 |
| CA | 2576347 C | 8/2015 |
| CN | 86100996 A | 9/1986 |
| CN | 1163558 A | 10/1997 |
| CN | 2488482 Y | 5/2002 |
| CN | 1424891 A | 6/2003 |
| CN | 1523725 A | 8/2004 |
| CN | 1545154 A | 11/2004 |
| CN | 1634601 A | 7/2005 |
| CN | 1636525 A | 7/2005 |
| CN | 1636526 A | 7/2005 |
| CN | 2716900 Y | 8/2005 |
| CN | 2738962 Y | 11/2005 |
| CN | 1726874 A | 2/2006 |
| CN | 1726878 A | 2/2006 |
| CN | 1868411 A | 11/2006 |
| CN | 1915180 A | 2/2007 |
| CN | 2868212 Y | 2/2007 |
| CN | 1960679 A | 5/2007 |
| CN | 101011286 A | 8/2007 |
| CN | 200942099 Y | 9/2007 |
| CN | 200991269 Y | 12/2007 |
| CN | 101095621 A | 1/2008 |
| CN | 101111196 A | 1/2008 |
| CN | 201001747 Y | 1/2008 |
| CN | 101137402 A | 3/2008 |
| CN | 101143105 A | 3/2008 |
| CN | 201029899 Y | 3/2008 |
| CN | 101224122 A | 7/2008 |
| CN | 101224124 A | 7/2008 |
| CN | 101254126 A | 9/2008 |
| CN | 101507620 A | 8/2009 |

(56) References Cited

FOREIGN PATENT DOCUMENTS

| | | |
|---|---|---|
| CN | 101507622 A | 8/2009 |
| CN | 101507623 A | 8/2009 |
| CN | 101507625 A | 8/2009 |
| CN | 101507628 A | 8/2009 |
| CN | 101534724 A | 9/2009 |
| CN | 101626731 A | 1/2010 |
| CN | 101669833 A | 3/2010 |
| CN | 101675898 A | 3/2010 |
| CN | 101683280 A | 3/2010 |
| CN | 101721236 A | 6/2010 |
| CN | 101801284 A | 8/2010 |
| CN | 101828940 A | 9/2010 |
| CN | 101868203 A | 10/2010 |
| CN | 101873834 A | 10/2010 |
| CN | 101073509 B | 12/2010 |
| CN | 101912285 A | 12/2010 |
| CN | 101028205 B | 1/2011 |
| CN | 101933824 A | 1/2011 |
| CN | 101934098 A | 1/2011 |
| CN | 201719298 U | 1/2011 |
| CN | 102038531 A | 5/2011 |
| CN | 102038532 A | 5/2011 |
| CN | 101534722 B | 6/2011 |
| CN | 201879759 U | 6/2011 |
| CN | 101361666 B | 8/2011 |
| CN | 201949071 U | 8/2011 |
| CN | 101224119 B | 9/2011 |
| CN | 101336835 B | 9/2011 |
| CN | 102188270 A | 9/2011 |
| CN | 101779977 B | 12/2011 |
| CN | 101534723 B | 1/2012 |
| CN | 101310680 B | 4/2012 |
| CN | 101912284 B | 7/2012 |
| CN | 202397539 U | 8/2012 |
| CN | 202426586 U | 9/2012 |
| CN | 101317782 B | 10/2012 |
| CN | 202489990 U | 10/2012 |
| CN | 101507639 B | 11/2012 |
| CN | 101541251 A | 11/2012 |
| CN | 102835977 A | 12/2012 |
| CN | 101507633 B | 2/2013 |
| CN | 101023879 B | 3/2013 |
| CN | 101507624 B | 3/2013 |
| CN | 101327137 B | 6/2013 |
| CN | 101401736 B | 6/2013 |
| CN | 101332110 B | 7/2013 |
| CN | 101683281 B | 1/2014 |
| CN | 103648408 A | 3/2014 |
| CN | 203564285 U | 4/2014 |
| CN | 203564287 U | 4/2014 |
| CN | 203597997 U | 5/2014 |
| CN | 103829983 A | 6/2014 |
| CN | 103908313 A | 7/2014 |
| CN | 203736251 U | 7/2014 |
| CN | 102783741 B | 10/2014 |
| CN | 102973300 B | 10/2014 |
| CN | 102793571 B | 12/2014 |
| CN | 104337556 A | 2/2015 |
| CN | 102166129 B | 3/2015 |
| CN | 102469995 B | 3/2015 |
| CN | 102113902 B | 4/2015 |
| CN | 102247177 B | 2/2016 |
| CN | 103750872 B | 5/2016 |
| DE | 273689 C | 5/1914 |
| DE | 1775926 A | 1/1972 |
| DE | 3036217 A1 | 4/1982 |
| DE | 3212828 A1 | 11/1982 |
| DE | 3210466 A1 | 9/1983 |
| DE | 3709067 A1 | 9/1988 |
| DE | 4228909 A1 | 3/1994 |
| DE | 9412228 U1 | 9/1994 |
| DE | 19509116 A1 | 9/1996 |
| DE | 19534043 A1 | 3/1997 |
| DE | 19707373 C1 | 2/1998 |
| DE | 19851291 A1 | 1/2000 |
| DE | 19924311 A1 | 11/2000 |
| DE | 69328576 T2 | 1/2001 |
| DE | 20016423 U1 | 2/2001 |
| DE | 19941859 A1 | 3/2001 |
| DE | 10052679 A1 | 5/2001 |
| DE | 20112837 U1 | 10/2001 |
| DE | 20121753 U1 | 4/2003 |
| DE | 10314827 B3 | 4/2004 |
| DE | 202004012389 U1 | 9/2004 |
| DE | 10314072 A1 | 10/2004 |
| DE | 202007003114 U1 | 6/2007 |
| DE | 102010013150 A1 | 9/2011 |
| EP | 0000756 A1 | 2/1979 |
| EP | 0033633 A2 | 8/1981 |
| EP | 0122046 A1 | 10/1984 |
| EP | 0070230 B1 | 4/1985 |
| EP | 0156774 A2 | 10/1985 |
| EP | 0072754 B1 | 4/1986 |
| EP | 0033548 B1 | 5/1986 |
| EP | 0077262 B1 | 8/1986 |
| EP | 0189807 A2 | 8/1986 |
| EP | 0212278 A2 | 3/1987 |
| EP | 0129442 B1 | 11/1987 |
| EP | 0255631 A1 | 2/1988 |
| EP | 0276104 A2 | 7/1988 |
| EP | 0178940 B1 | 1/1991 |
| EP | 0178941 B1 | 1/1991 |
| EP | 0169044 B1 | 6/1991 |
| EP | 0248844 B1 | 1/1993 |
| EP | 0539762 A1 | 5/1993 |
| EP | 0541950 A1 | 5/1993 |
| EP | 0545029 A1 | 6/1993 |
| EP | 0548998 A1 | 6/1993 |
| EP | 0379721 B1 | 9/1993 |
| EP | 0277959 B1 | 10/1993 |
| EP | 0233940 B1 | 11/1993 |
| EP | 0261230 B1 | 11/1993 |
| EP | 0324636 B1 | 3/1994 |
| EP | 0591946 A1 | 4/1994 |
| EP | 0593920 A1 | 4/1994 |
| EP | 0594148 A1 | 4/1994 |
| EP | 0427949 B1 | 6/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0623311 A2 | 11/1994 |
| EP | 0630612 A1 | 12/1994 |
| EP | 0630614 A1 | 12/1994 |
| EP | 0634144 A1 | 1/1995 |
| EP | 0639349 A2 | 2/1995 |
| EP | 0646356 A2 | 4/1995 |
| EP | 0646357 A1 | 4/1995 |
| EP | 0505036 B1 | 5/1995 |
| EP | 0653189 A2 | 5/1995 |
| EP | 0669104 A1 | 8/1995 |
| EP | 0387980 B1 | 10/1995 |
| EP | 0511470 B1 | 10/1995 |
| EP | 0674876 A2 | 10/1995 |
| EP | 0676173 B1 | 10/1995 |
| EP | 0679367 A2 | 11/1995 |
| EP | 0392547 B1 | 12/1995 |
| EP | 0685204 A1 | 12/1995 |
| EP | 0686374 A2 | 12/1995 |
| EP | 0364216 B1 | 1/1996 |
| EP | 0699418 A1 | 3/1996 |
| EP | 0702937 A1 | 3/1996 |
| EP | 0488768 B1 | 4/1996 |
| EP | 0705571 A1 | 4/1996 |
| EP | 0528478 B1 | 5/1996 |
| EP | 0711611 A2 | 5/1996 |
| EP | 0541987 B1 | 7/1996 |
| EP | 0667119 B1 | 7/1996 |
| EP | 0737446 A1 | 10/1996 |
| EP | 0741996 B1 | 11/1996 |
| EP | 0748614 A1 | 12/1996 |
| EP | 0708618 B1 | 3/1997 |
| EP | 0770355 A1 | 5/1997 |

(56) References Cited

FOREIGN PATENT DOCUMENTS

| | | |
|---|---|---|
| EP | 0503662 B1 | 6/1997 |
| EP | 0447121 B1 | 7/1997 |
| EP | 0621009 B1 | 7/1997 |
| EP | 0625077 B1 | 7/1997 |
| EP | 0633749 B1 | 8/1997 |
| EP | 0710090 B1 | 8/1997 |
| EP | 0578425 B1 | 9/1997 |
| EP | 0623312 B1 | 9/1997 |
| EP | 0621006 B1 | 10/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0649290 B1 | 3/1998 |
| EP | 0598618 B1 | 9/1998 |
| EP | 0678007 B1 | 9/1998 |
| EP | 0869104 A1 | 10/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0695144 B1 | 12/1998 |
| EP | 0722296 B1 | 12/1998 |
| EP | 0760230 B1 | 2/1999 |
| EP | 0623316 B1 | 3/1999 |
| EP | 0650701 B1 | 3/1999 |
| EP | 0537572 B1 | 6/1999 |
| EP | 0923907 A1 | 6/1999 |
| EP | 0640317 B1 | 9/1999 |
| EP | 0843906 B1 | 3/2000 |
| EP | 0552050 B1 | 5/2000 |
| EP | 0833592 B1 | 5/2000 |
| EP | 0832605 B1 | 6/2000 |
| EP | 0484677 B2 | 7/2000 |
| EP | 0830094 B1 | 9/2000 |
| EP | 1034747 A1 | 9/2000 |
| EP | 1034748 A1 | 9/2000 |
| EP | 0726632 B1 | 10/2000 |
| EP | 0694290 B1 | 11/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1058177 A1 | 12/2000 |
| EP | 1080694 A1 | 3/2001 |
| EP | 1090592 A1 | 4/2001 |
| EP | 1095627 A1 | 5/2001 |
| EP | 0806914 B1 | 9/2001 |
| EP | 0768840 B1 | 12/2001 |
| EP | 0908152 B1 | 1/2002 |
| EP | 0717959 B1 | 2/2002 |
| EP | 0872213 B1 | 5/2002 |
| EP | 0862386 B1 | 6/2002 |
| EP | 0949886 B1 | 9/2002 |
| EP | 1238634 A2 | 9/2002 |
| EP | 0858295 B1 | 12/2002 |
| EP | 0656188 B1 | 1/2003 |
| EP | 0717960 B1 | 2/2003 |
| EP | 1284120 A1 | 2/2003 |
| EP | 1287788 A1 | 3/2003 |
| EP | 0717966 B1 | 4/2003 |
| EP | 0717967 B1 | 5/2003 |
| EP | 0869742 B1 | 5/2003 |
| EP | 0829235 B1 | 6/2003 |
| EP | 0887046 B1 | 7/2003 |
| EP | 1323384 A2 | 7/2003 |
| EP | 0852480 B1 | 8/2003 |
| EP | 0891154 B1 | 9/2003 |
| EP | 0813843 B1 | 10/2003 |
| EP | 0873089 B1 | 10/2003 |
| EP | 0856326 B1 | 11/2003 |
| EP | 1374788 A1 | 1/2004 |
| EP | 0814712 B1 | 2/2004 |
| EP | 1402837 A1 | 3/2004 |
| EP | 0705570 B1 | 4/2004 |
| EP | 0959784 B1 | 4/2004 |
| EP | 1407719 A2 | 4/2004 |
| EP | 1411626 A2 | 4/2004 |
| EP | 1086713 B1 | 5/2004 |
| EP | 0996378 B1 | 6/2004 |
| EP | 1426012 A1 | 6/2004 |
| EP | 0833593 B2 | 7/2004 |
| EP | 1442694 A1 | 8/2004 |
| EP | 0888749 B1 | 9/2004 |
| EP | 0959786 B1 | 9/2004 |
| EP | 1453432 A2 | 9/2004 |
| EP | 1459695 A1 | 9/2004 |
| EP | 1254636 B1 | 10/2004 |
| EP | 1473819 A1 | 11/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 0754437 B2 | 12/2004 |
| EP | 1025807 B1 | 12/2004 |
| EP | 1001710 B1 | 1/2005 |
| EP | 1496805 A2 | 1/2005 |
| EP | 1256318 B1 | 2/2005 |
| EP | 1520521 A1 | 4/2005 |
| EP | 1520522 A1 | 4/2005 |
| EP | 1520523 A1 | 4/2005 |
| EP | 1520525 A1 | 4/2005 |
| EP | 1522264 A1 | 4/2005 |
| EP | 1523942 A2 | 4/2005 |
| EP | 1550408 A1 | 7/2005 |
| EP | 1557129 A1 | 7/2005 |
| EP | 1064883 B1 | 8/2005 |
| EP | 1067876 B1 | 8/2005 |
| EP | 0870473 B1 | 9/2005 |
| EP | 1157666 B1 | 9/2005 |
| EP | 0880338 B1 | 10/2005 |
| EP | 1158917 B1 | 11/2005 |
| EP | 1344498 B1 | 11/2005 |
| EP | 0906764 B1 | 12/2005 |
| EP | 1330989 B1 | 12/2005 |
| EP | 0771176 B2 | 1/2006 |
| EP | 1621138 A2 | 2/2006 |
| EP | 1621139 A2 | 2/2006 |
| EP | 1621141 A2 | 2/2006 |
| EP | 1621143 A2 | 2/2006 |
| EP | 1621145 A2 | 2/2006 |
| EP | 1621151 A2 | 2/2006 |
| EP | 1034746 B1 | 3/2006 |
| EP | 1201196 B1 | 3/2006 |
| EP | 1632191 A2 | 3/2006 |
| EP | 1647231 A1 | 4/2006 |
| EP | 1065981 B1 | 5/2006 |
| EP | 1082944 B1 | 5/2006 |
| EP | 1230899 B1 | 5/2006 |
| EP | 1652481 A2 | 5/2006 |
| EP | 1382303 B1 | 6/2006 |
| EP | 1253866 B1 | 7/2006 |
| EP | 1676539 A1 | 7/2006 |
| EP | 1032318 B1 | 8/2006 |
| EP | 1045672 B1 | 8/2006 |
| EP | 1617768 B1 | 8/2006 |
| EP | 1693015 A2 | 8/2006 |
| EP | 1400214 B1 | 9/2006 |
| EP | 1702567 A2 | 9/2006 |
| EP | 1129665 B1 | 11/2006 |
| EP | 1400206 B1 | 11/2006 |
| EP | 1721568 A1 | 11/2006 |
| EP | 1723914 A1 | 11/2006 |
| EP | 1256317 B1 | 12/2006 |
| EP | 1285633 B1 | 12/2006 |
| EP | 1728473 A1 | 12/2006 |
| EP | 1736105 A1 | 12/2006 |
| EP | 1011494 B1 | 1/2007 |
| EP | 1479346 B1 | 1/2007 |
| EP | 1484024 B1 | 1/2007 |
| EP | 1749485 A1 | 2/2007 |
| EP | 1754445 A2 | 2/2007 |
| EP | 1759812 A1 | 3/2007 |

(56) References Cited

FOREIGN PATENT DOCUMENTS

| | | |
|---|---|---|
| EP | 1767157 A1 | 3/2007 |
| EP | 1767163 A1 | 3/2007 |
| EP | 1563792 B1 | 4/2007 |
| EP | 1769756 A1 | 4/2007 |
| EP | 1769758 A1 | 4/2007 |
| EP | 1581128 B1 | 5/2007 |
| EP | 1780825 A1 | 5/2007 |
| EP | 1785097 A2 | 5/2007 |
| EP | 1790293 A2 | 5/2007 |
| EP | 1790294 A1 | 5/2007 |
| EP | 1563793 B1 | 6/2007 |
| EP | 1791473 A2 | 6/2007 |
| EP | 1800610 A1 | 6/2007 |
| EP | 1300117 B1 | 8/2007 |
| EP | 1813199 A1 | 8/2007 |
| EP | 1813200 A2 | 8/2007 |
| EP | 1813201 A1 | 8/2007 |
| EP | 1813202 A1 | 8/2007 |
| EP | 1813203 A2 | 8/2007 |
| EP | 1813207 A1 | 8/2007 |
| EP | 1813209 A1 | 8/2007 |
| EP | 1815950 A1 | 8/2007 |
| EP | 1330991 B1 | 9/2007 |
| EP | 1837041 A1 | 9/2007 |
| EP | 0922435 B1 | 10/2007 |
| EP | 1487359 B1 | 10/2007 |
| EP | 1599146 B1 | 10/2007 |
| EP | 1839596 A1 | 10/2007 |
| EP | 1679096 B1 | 11/2007 |
| EP | 1857057 A2 | 11/2007 |
| EP | 1402821 B1 | 12/2007 |
| EP | 1872727 A1 | 1/2008 |
| EP | 1550410 B1 | 2/2008 |
| EP | 1671593 B1 | 2/2008 |
| EP | 1897502 A1 | 3/2008 |
| EP | 1611856 B1 | 4/2008 |
| EP | 1908417 A2 | 4/2008 |
| EP | 1917929 A1 | 5/2008 |
| EP | 1330201 B1 | 6/2008 |
| EP | 1702568 B1 | 7/2008 |
| EP | 1943955 A2 | 7/2008 |
| EP | 1943957 A2 | 7/2008 |
| EP | 1943959 A1 | 7/2008 |
| EP | 1943962 A2 | 7/2008 |
| EP | 1943964 A1 | 7/2008 |
| EP | 1943976 A2 | 7/2008 |
| EP | 1593337 B1 | 8/2008 |
| EP | 1970014 A1 | 9/2008 |
| EP | 1974678 A2 | 10/2008 |
| EP | 1980213 A2 | 10/2008 |
| EP | 1980214 A2 | 10/2008 |
| EP | 1759645 B1 | 11/2008 |
| EP | 1987780 A2 | 11/2008 |
| EP | 1990014 A2 | 11/2008 |
| EP | 1992296 A1 | 11/2008 |
| EP | 1552795 B1 | 12/2008 |
| EP | 1693008 B1 | 12/2008 |
| EP | 1759640 B1 | 12/2008 |
| EP | 1997439 A2 | 12/2008 |
| EP | 2000101 A2 | 12/2008 |
| EP | 2000102 A2 | 12/2008 |
| EP | 2005894 A2 | 12/2008 |
| EP | 2005897 A2 | 12/2008 |
| EP | 2005901 A1 | 12/2008 |
| EP | 2008595 A2 | 12/2008 |
| EP | 2025293 A1 | 2/2009 |
| EP | 1736104 B1 | 3/2009 |
| EP | 1749486 B1 | 3/2009 |
| EP | 1782743 B1 | 3/2009 |
| EP | 2039302 A2 | 3/2009 |
| EP | 2039308 A2 | 3/2009 |
| EP | 2039316 A2 | 3/2009 |
| EP | 1721576 B1 | 4/2009 |
| EP | 1733686 B1 | 4/2009 |
| EP | 2044890 A1 | 4/2009 |
| EP | 2055243 A2 | 5/2009 |
| EP | 1550409 B1 | 6/2009 |
| EP | 1550413 B1 | 6/2009 |
| EP | 1719461 B1 | 6/2009 |
| EP | 1834594 B1 | 6/2009 |
| EP | 1709911 B1 | 7/2009 |
| EP | 2077093 A2 | 7/2009 |
| EP | 1745748 B1 | 8/2009 |
| EP | 2090231 A1 | 8/2009 |
| EP | 2090237 A1 | 8/2009 |
| EP | 2090241 A1 | 8/2009 |
| EP | 2090245 A1 | 8/2009 |
| EP | 2090254 A1 | 8/2009 |
| EP | 2090256 A2 | 8/2009 |
| EP | 2095777 A2 | 9/2009 |
| EP | 2098170 A2 | 9/2009 |
| EP | 2100562 A2 | 9/2009 |
| EP | 2110082 A1 | 10/2009 |
| EP | 2110083 A2 | 10/2009 |
| EP | 2110084 A2 | 10/2009 |
| EP | 2111803 A2 | 10/2009 |
| EP | 1813208 B1 | 11/2009 |
| EP | 1908426 B1 | 11/2009 |
| EP | 2116195 A1 | 11/2009 |
| EP | 2116197 A2 | 11/2009 |
| EP | 1607050 B1 | 12/2009 |
| EP | 1762190 B8 | 12/2009 |
| EP | 1815804 B1 | 12/2009 |
| EP | 1875870 B1 | 12/2009 |
| EP | 1878395 B1 | 1/2010 |
| EP | 2151204 A1 | 2/2010 |
| EP | 1813211 B1 | 3/2010 |
| EP | 2165654 A1 | 3/2010 |
| EP | 2165656 A2 | 3/2010 |
| EP | 2165660 A2 | 3/2010 |
| EP | 2165663 A2 | 3/2010 |
| EP | 2165664 A2 | 3/2010 |
| EP | 1566150 B1 | 4/2010 |
| EP | 1813206 B1 | 4/2010 |
| EP | 2184014 A2 | 5/2010 |
| EP | 1769754 B1 | 6/2010 |
| EP | 1854416 B1 | 6/2010 |
| EP | 1911408 B1 | 6/2010 |
| EP | 2198787 A1 | 6/2010 |
| EP | 2214610 A1 | 8/2010 |
| EP | 2218409 A1 | 8/2010 |
| EP | 1647286 B1 | 9/2010 |
| EP | 1825821 B1 | 9/2010 |
| EP | 1535565 B1 | 10/2010 |
| EP | 1702570 B1 | 10/2010 |
| EP | 1785098 B1 | 10/2010 |
| EP | 2005896 B1 | 10/2010 |
| EP | 2030578 B1 | 11/2010 |
| EP | 2036505 B1 | 11/2010 |
| EP | 2245993 A2 | 11/2010 |
| EP | 2245994 A1 | 11/2010 |
| EP | 2253280 A1 | 11/2010 |
| EP | 1627605 B1 | 12/2010 |
| EP | 2027811 B1 | 12/2010 |
| EP | 2130498 B1 | 12/2010 |
| EP | 2258282 A2 | 12/2010 |
| EP | 2263568 A2 | 12/2010 |
| EP | 1994890 B1 | 1/2011 |
| EP | 2005900 B1 | 1/2011 |
| EP | 2277667 A1 | 1/2011 |
| EP | 2283780 A2 | 2/2011 |
| EP | 2286738 A2 | 2/2011 |
| EP | 1494595 B1 | 3/2011 |
| EP | 1690502 B1 | 3/2011 |
| EP | 1884201 B1 | 3/2011 |
| EP | 2292153 A1 | 3/2011 |
| EP | 1769755 B1 | 4/2011 |
| EP | 2090240 B1 | 4/2011 |
| EP | 2305135 A1 | 4/2011 |
| EP | 2308388 A1 | 4/2011 |
| EP | 2314254 A2 | 4/2011 |
| EP | 2316345 A1 | 5/2011 |
| EP | 2316366 A2 | 5/2011 |
| EP | 2319443 A1 | 5/2011 |

(56) References Cited

FOREIGN PATENT DOCUMENTS

| | | |
|---|---|---|
| EP | 2324776 A2 | 5/2011 |
| EP | 1813205 B1 | 6/2011 |
| EP | 2042107 B1 | 6/2011 |
| EP | 2090243 B1 | 6/2011 |
| EP | 2329773 A1 | 6/2011 |
| EP | 2090239 B1 | 7/2011 |
| EP | 2340771 A2 | 7/2011 |
| EP | 1728475 B1 | 8/2011 |
| EP | 2353545 A1 | 8/2011 |
| EP | 2361562 A1 | 8/2011 |
| EP | 2377472 A1 | 10/2011 |
| EP | 1836986 B1 | 11/2011 |
| EP | 1908414 B1 | 11/2011 |
| EP | 2153781 B1 | 11/2011 |
| EP | 2387943 A2 | 11/2011 |
| EP | 2389928 A2 | 11/2011 |
| EP | 1847225 B1 | 12/2011 |
| EP | 2397079 A1 | 12/2011 |
| EP | 2399538 A2 | 12/2011 |
| EP | 1785102 B1 | 1/2012 |
| EP | 1316290 B1 | 2/2012 |
| EP | 1962711 B1 | 2/2012 |
| EP | 2415416 A1 | 2/2012 |
| EP | 2090253 B1 | 3/2012 |
| EP | 2430986 A2 | 3/2012 |
| EP | 1347638 B1 | 5/2012 |
| EP | 1943956 B1 | 5/2012 |
| EP | 2446834 A1 | 5/2012 |
| EP | 2455007 A2 | 5/2012 |
| EP | 2457519 A1 | 5/2012 |
| EP | 2462878 A1 | 6/2012 |
| EP | 2462880 A2 | 6/2012 |
| EP | 1813204 B1 | 7/2012 |
| EP | 2189121 B1 | 7/2012 |
| EP | 2248475 B1 | 7/2012 |
| EP | 2478845 A2 | 7/2012 |
| EP | 2005895 B1 | 8/2012 |
| EP | 2090248 B1 | 8/2012 |
| EP | 2481359 A1 | 8/2012 |
| EP | 2484304 A2 | 8/2012 |
| EP | 2486860 A2 | 8/2012 |
| EP | 2486862 A2 | 8/2012 |
| EP | 2486868 A2 | 8/2012 |
| EP | 1908412 B1 | 9/2012 |
| EP | 1935351 B1 | 9/2012 |
| EP | 2497431 A1 | 9/2012 |
| EP | 1550412 B2 | 10/2012 |
| EP | 1616549 B1 | 10/2012 |
| EP | 2030579 B1 | 10/2012 |
| EP | 2090252 B1 | 10/2012 |
| EP | 2517637 A1 | 10/2012 |
| EP | 2517638 A1 | 10/2012 |
| EP | 2517642 A2 | 10/2012 |
| EP | 2517645 A2 | 10/2012 |
| EP | 2517649 A2 | 10/2012 |
| EP | 2517651 A2 | 10/2012 |
| EP | 2526877 A1 | 11/2012 |
| EP | 2526883 A1 | 11/2012 |
| EP | 1884206 B1 | 3/2013 |
| EP | 2286735 B1 | 3/2013 |
| EP | 2090238 B1 | 4/2013 |
| EP | 1806103 B1 | 5/2013 |
| EP | 2586380 A1 | 5/2013 |
| EP | 2586383 A2 | 5/2013 |
| EP | 2606812 A1 | 6/2013 |
| EP | 2606834 A2 | 6/2013 |
| EP | 1982657 B1 | 7/2013 |
| EP | 2614782 A2 | 7/2013 |
| EP | 2617369 A1 | 7/2013 |
| EP | 2620117 A1 | 7/2013 |
| EP | 2090234 B1 | 9/2013 |
| EP | 2633830 A1 | 9/2013 |
| EP | 2090244 B1 | 10/2013 |
| EP | 2644124 A1 | 10/2013 |
| EP | 2644209 A2 | 10/2013 |
| EP | 2649948 A1 | 10/2013 |
| EP | 2649949 A1 | 10/2013 |
| EP | 1997438 B1 | 11/2013 |
| EP | 2684529 A2 | 1/2014 |
| EP | 2687164 A2 | 1/2014 |
| EP | 2700367 A1 | 2/2014 |
| EP | 2713902 A1 | 4/2014 |
| EP | 1772105 B1 | 5/2014 |
| EP | 2743042 A2 | 6/2014 |
| EP | 2759267 A2 | 7/2014 |
| EP | 2764826 A1 | 8/2014 |
| EP | 2764827 A2 | 8/2014 |
| EP | 2767243 A2 | 8/2014 |
| EP | 2772206 A2 | 9/2014 |
| EP | 2772209 A1 | 9/2014 |
| EP | 2777520 A1 | 9/2014 |
| EP | 2777524 A2 | 9/2014 |
| EP | 2777528 A2 | 9/2014 |
| EP | 2777537 A1 | 9/2014 |
| EP | 2777538 A2 | 9/2014 |
| EP | 2786714 A2 | 10/2014 |
| EP | 2792313 A2 | 10/2014 |
| EP | 2803324 A2 | 11/2014 |
| EP | 2815704 A1 | 12/2014 |
| EP | 2446835 B1 | 1/2015 |
| EP | 2842500 A1 | 3/2015 |
| EP | 2845545 A1 | 3/2015 |
| EP | 1943960 B1 | 4/2015 |
| EP | 2090255 B1 | 4/2015 |
| EP | 2853220 A1 | 4/2015 |
| EP | 2923647 A2 | 9/2015 |
| EP | 2923653 A2 | 9/2015 |
| EP | 2923660 A2 | 9/2015 |
| EP | 2932913 A1 | 10/2015 |
| EP | 2944270 A1 | 11/2015 |
| EP | 1774914 B1 | 12/2015 |
| EP | 2090235 B1 | 4/2016 |
| EP | 2823773 B1 | 4/2016 |
| EP | 2131750 B1 | 5/2016 |
| EP | 2298220 B1 | 6/2016 |
| EP | 2510891 B1 | 6/2016 |
| EP | 1915957 B1 | 8/2016 |
| EP | 2296559 B1 | 8/2016 |
| EP | 2586379 B1 | 8/2016 |
| EP | 2777533 B1 | 10/2016 |
| EP | 2364651 B1 | 11/2016 |
| EP | 2747235 B1 | 11/2016 |
| EP | 2116192 B1 | 3/2017 |
| EP | 2789299 B1 | 5/2017 |
| EP | 2311386 B1 | 6/2017 |
| EP | 2839787 B1 | 6/2017 |
| EP | 2745782 B1 | 10/2017 |
| ES | 2396594 T3 | 2/2013 |
| FR | 459743 A | 11/1913 |
| FR | 999646 A | 2/1952 |
| FR | 1112936 A | 3/1956 |
| FR | 2452275 B1 | 4/1983 |
| FR | 2598905 A1 | 11/1987 |
| FR | 2689749 B1 | 7/1994 |
| FR | 2765794 A1 | 1/1999 |
| FR | 2815842 A1 | 5/2002 |
| GB | 939929 A | 10/1963 |
| GB | 1210522 A | 10/1970 |
| GB | 1217159 A | 12/1970 |
| GB | 1339394 A | 12/1973 |
| GB | 2024012 A | 1/1980 |
| GB | 2109241 A | 6/1983 |
| GB | 2090534 B | 6/1984 |
| GB | 2272159 A | 5/1994 |
| GB | 2284242 A | 5/1995 |
| GB | 2286435 A | 8/1995 |
| GB | 2336214 A | 10/1999 |
| GB | 2425903 A | 11/2006 |
| GB | 2426391 A | 11/2006 |
| GB | 2423199 B | 5/2009 |
| GB | 2509523 A | 7/2014 |
| GR | 930100110 A | 11/1993 |
| JP | S4711908 Y1 | 5/1972 |
| JP | S5033988 U | 4/1975 |

(56) References Cited

FOREIGN PATENT DOCUMENTS

| | | |
|---|---|---|
| JP | S56112235 A | 9/1981 |
| JP | S58500053 A | 1/1983 |
| JP | S58501360 A | 8/1983 |
| JP | S59174920 A | 10/1984 |
| JP | S60100955 A | 6/1985 |
| JP | S60212152 A | 10/1985 |
| JP | S6198249 A | 5/1986 |
| JP | S61502036 A | 9/1986 |
| JP | S62170011 U | 10/1987 |
| JP | S6359764 A | 3/1988 |
| JP | S63147449 A | 6/1988 |
| JP | S63203149 A | 8/1988 |
| JP | S63270040 A | 11/1988 |
| JP | H0129503 B2 | 6/1989 |
| JP | H02279149 A | 11/1990 |
| JP | H0312126 A | 1/1991 |
| JP | H0318354 A | 1/1991 |
| JP | H0378514 U | 8/1991 |
| JP | H0385009 U | 8/1991 |
| JP | H04215747 A | 8/1992 |
| JP | H04131860 U | 12/1992 |
| JP | H0584252 A | 4/1993 |
| JP | H05123325 A | 5/1993 |
| JP | H05212039 A | 8/1993 |
| JP | H 05226945 A | 9/1993 |
| JP | H067357 A | 1/1994 |
| JP | H0630945 A | 2/1994 |
| JP | H0654857 A | 3/1994 |
| JP | H0663054 A | 3/1994 |
| JP | H0626812 U | 4/1994 |
| JP | H06121798 A | 5/1994 |
| JP | H06125913 A | 5/1994 |
| JP | H06197901 A | 7/1994 |
| JP | H06237937 A | 8/1994 |
| JP | H06327684 A | 11/1994 |
| JP | H079622 U | 2/1995 |
| JP | H0731623 A | 2/1995 |
| JP | H0747070 A | 2/1995 |
| JP | H0751273 A | 2/1995 |
| JP | H07124166 A | 5/1995 |
| JP | H07163573 A | 6/1995 |
| JP | H07163574 A | 6/1995 |
| JP | H07171163 A | 7/1995 |
| JP | H07255735 A | 10/1995 |
| JP | H07285089 A | 10/1995 |
| JP | H07299074 A | 11/1995 |
| JP | H0833641 A | 2/1996 |
| JP | H0833642 A | 2/1996 |
| JP | H08164141 A | 6/1996 |
| JP | H08173437 A | 7/1996 |
| JP | H08182684 A | 7/1996 |
| JP | H08215201 A | 8/1996 |
| JP | H08507708 A | 8/1996 |
| JP | H08229050 A | 9/1996 |
| JP | H08289895 A | 11/1996 |
| JP | H08336540 A | 12/1996 |
| JP | H08336544 A | 12/1996 |
| JP | H09501081 A | 2/1997 |
| JP | H09501577 A | 2/1997 |
| JP | H09164144 A | 6/1997 |
| JP | H09-323068 A | 12/1997 |
| JP | H10113352 A | 5/1998 |
| JP | H10118090 A | 5/1998 |
| JP | H10-200699 A | 7/1998 |
| JP | H 10296660 A | 11/1998 |
| JP | H10512465 A | 12/1998 |
| JP | H10512469 A | 12/1998 |
| JP | 2000014632 A | 1/2000 |
| JP | 2000033071 A | 2/2000 |
| JP | 2000112002 A | 4/2000 |
| JP | 3056672 B2 | 6/2000 |
| JP | 2000166932 A | 6/2000 |
| JP | 2000171730 A | 6/2000 |
| JP | 2000287987 A | 10/2000 |
| JP | 2000325303 A | 11/2000 |
| JP | 2001037763 A | 2/2001 |
| JP | 2001046384 A | 2/2001 |
| JP | 2001087272 A | 4/2001 |
| JP | 2001514541 A | 9/2001 |
| JP | 2001276091 A | 10/2001 |
| JP | 2001286477 A | 10/2001 |
| JP | 2001517473 A | 10/2001 |
| JP | 2002051974 A | 2/2002 |
| JP | 2002085415 A | 3/2002 |
| JP | 2002143078 A | 5/2002 |
| JP | 2002204801 A | 7/2002 |
| JP | 2002528161 A | 9/2002 |
| JP | 2002314298 A | 10/2002 |
| JP | 2002369820 A | 12/2002 |
| JP | 2002542186 A | 12/2002 |
| JP | 2003000603 A | 1/2003 |
| JP | 2003500153 A | 1/2003 |
| JP | 2003504104 A | 2/2003 |
| JP | 2003135473 A | 5/2003 |
| JP | 2003148903 A | 5/2003 |
| JP | 2003164066 A | 6/2003 |
| JP | 2003521301 A | 7/2003 |
| JP | 2003521304 A | 7/2003 |
| JP | 2003523251 A | 8/2003 |
| JP | 2003523254 A | 8/2003 |
| JP | 2003524431 A | 8/2003 |
| JP | 3442423 B2 | 9/2003 |
| JP | 2003300416 A | 10/2003 |
| JP | 2004147701 A | 5/2004 |
| JP | 2004162035 A | 6/2004 |
| JP | 2004229976 A | 8/2004 |
| JP | 2004524076 A | 8/2004 |
| JP | 2004531280 A | 10/2004 |
| JP | 2004532084 A | 10/2004 |
| JP | 2004532676 A | 10/2004 |
| JP | 2004-535217 A | 11/2004 |
| JP | 2004329624 A | 11/2004 |
| JP | 2004337617 A | 12/2004 |
| JP | 2004344662 A | 12/2004 |
| JP | 2004344663 A | 12/2004 |
| JP | 2005013573 A | 1/2005 |
| JP | 2005028147 A | 2/2005 |
| JP | 2005028148 A | 2/2005 |
| JP | 2005028149 A | 2/2005 |
| JP | 2005505309 A | 2/2005 |
| JP | 2005505322 A | 2/2005 |
| JP | 2005505334 A | 2/2005 |
| JP | 2005080702 A | 3/2005 |
| JP | 2005103280 A | 4/2005 |
| JP | 2005103281 A | 4/2005 |
| JP | 2005103293 A | 4/2005 |
| JP | 2005511131 A | 4/2005 |
| JP | 2005511137 A | 4/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005137423 A | 6/2005 |
| JP | 2005137919 A | 6/2005 |
| JP | 2005144183 A | 6/2005 |
| JP | 2005152416 A | 6/2005 |
| JP | 2005516714 A | 6/2005 |
| JP | 2005187954 A | 7/2005 |
| JP | 2005521109 A | 7/2005 |
| JP | 2005523105 A | 8/2005 |
| JP | 2005524474 A | 8/2005 |
| JP | 2005296412 A | 10/2005 |
| JP | 2005529675 A | 10/2005 |
| JP | 2005529677 A | 10/2005 |
| JP | 2005328882 A | 12/2005 |
| JP | 2005335432 A | 12/2005 |
| JP | 2005342267 A | 12/2005 |
| JP | 2006034975 A | 2/2006 |
| JP | 2006034977 A | 2/2006 |
| JP | 2006034978 A | 2/2006 |
| JP | 2006034980 A | 2/2006 |
| JP | 2006043451 A | 2/2006 |
| JP | 2006506106 A | 2/2006 |

(56) References Cited

FOREIGN PATENT DOCUMENTS

| | | |
|---|---|---|
| JP | 2006510879 A | 3/2006 |
| JP | 3791856 B2 | 6/2006 |
| JP | 2006187649 A | 7/2006 |
| JP | 2006218228 A | 8/2006 |
| JP | 2006218297 A | 8/2006 |
| JP | 2006223872 A | 8/2006 |
| JP | 2006281405 A | 10/2006 |
| JP | 2006289064 A | 10/2006 |
| JP | 2006334412 A | 12/2006 |
| JP | 2006334417 A | 12/2006 |
| JP | 2006346445 A | 12/2006 |
| JP | 2007000634 A | 1/2007 |
| JP | 2007050253 A | 3/2007 |
| JP | 2007061628 A | 3/2007 |
| JP | 3906843 B2 | 4/2007 |
| JP | 2007083051 A | 4/2007 |
| JP | 2007098130 A | 4/2007 |
| JP | 2007105481 A | 4/2007 |
| JP | 2007117725 A | 5/2007 |
| JP | 2007130471 A | 5/2007 |
| JP | 2007130479 A | 5/2007 |
| JP | 3934161 B2 | 6/2007 |
| JP | 2007203047 A | 8/2007 |
| JP | 2007203049 A | 8/2007 |
| JP | 2007203051 A | 8/2007 |
| JP | 2007203055 A | 8/2007 |
| JP | 2007203057 A | 8/2007 |
| JP | 2007524435 A | 8/2007 |
| JP | 2007222615 A | 9/2007 |
| JP | 2007229448 A | 9/2007 |
| JP | 2007526026 A | 9/2007 |
| JP | 4001860 B2 | 10/2007 |
| JP | 2007252916 A | 10/2007 |
| JP | 2007307373 A | 11/2007 |
| JP | 2007325922 A | 12/2007 |
| JP | 2008068073 A | 3/2008 |
| JP | 2008510515 A | 4/2008 |
| JP | 2008516669 A | 5/2008 |
| JP | 2008528203 A | 7/2008 |
| JP | 2008-220032 A | 9/2008 |
| JP | 2008206967 A | 9/2008 |
| JP | 2008212637 A | 9/2008 |
| JP | 2008212638 A | 9/2008 |
| JP | 2008212640 A | 9/2008 |
| JP | 2008220956 A | 9/2008 |
| JP | 2008237881 A | 10/2008 |
| JP | 2008259860 A | 10/2008 |
| JP | 2008264535 A | 11/2008 |
| JP | 2008283459 A | 11/2008 |
| JP | 2008307393 A | 12/2008 |
| JP | 2009000531 A | 1/2009 |
| JP | 2009006137 A | 1/2009 |
| JP | 2009502351 A | 1/2009 |
| JP | 2009502352 A | 1/2009 |
| JP | 2009022742 A | 2/2009 |
| JP | 2009506799 A | 2/2009 |
| JP | 2009507526 A | 2/2009 |
| JP | 2009072595 A | 4/2009 |
| JP | 2009072599 A | 4/2009 |
| JP | 2009090113 A | 4/2009 |
| JP | 2009106752 A | 5/2009 |
| JP | 2009189821 A | 8/2009 |
| JP | 2009189823 A | 8/2009 |
| JP | 2009189836 A | 8/2009 |
| JP | 2009189837 A | 8/2009 |
| JP | 2009189838 A | 8/2009 |
| JP | 2009189846 A | 8/2009 |
| JP | 2009189847 A | 8/2009 |
| JP | 2009201998 A | 9/2009 |
| JP | 2009207260 A | 9/2009 |
| JP | 2009226028 A | 10/2009 |
| JP | 2009536082 A | 10/2009 |
| JP | 2009261944 A | 11/2009 |
| JP | 2009268908 A | 11/2009 |
| JP | 2009538684 A | 11/2009 |
| JP | 2009539420 A | 11/2009 |
| JP | 2009291604 A | 12/2009 |
| JP | 2010504808 A | 2/2010 |
| JP | 2010504809 A | 2/2010 |
| JP | 2010504813 A | 2/2010 |
| JP | 2010504846 A | 2/2010 |
| JP | 2010505524 A | 2/2010 |
| JP | 2010069307 A | 4/2010 |
| JP | 2010069310 A | 4/2010 |
| JP | 2010075694 A | 4/2010 |
| JP | 2010075695 A | 4/2010 |
| JP | 2010088876 A | 4/2010 |
| JP | 2010094514 A | 4/2010 |
| JP | 2010098844 A | 4/2010 |
| JP | 4461008 B2 | 5/2010 |
| JP | 2010-520025 A | 6/2010 |
| JP | 2010-148879 A | 7/2010 |
| JP | 2010142636 A | 7/2010 |
| JP | 4549018 B2 | 9/2010 |
| JP | 2010214166 A | 9/2010 |
| JP | 2010-240429 A | 10/2010 |
| JP | 2010240411 A | 10/2010 |
| JP | 2010246948 A | 11/2010 |
| JP | 2010-540041 A | 12/2010 |
| JP | 2010279690 A | 12/2010 |
| JP | 2010540192 A | 12/2010 |
| JP | 2011005260 A | 1/2011 |
| JP | 2011504391 A | 2/2011 |
| JP | 2011509786 A | 3/2011 |
| JP | 2011072574 A | 4/2011 |
| JP | 2011072797 A | 4/2011 |
| JP | 2011078763 A | 4/2011 |
| JP | 2011-115594 A | 6/2011 |
| JP | 2011-520564 A | 7/2011 |
| JP | 4722849 B2 | 7/2011 |
| JP | 4783373 B2 | 9/2011 |
| JP | 2011524199 A | 9/2011 |
| JP | 2011251156 A | 12/2011 |
| JP | 2012040398 A | 3/2012 |
| JP | 2012507356 A | 3/2012 |
| JP | 2012517289 A | 8/2012 |
| JP | 5140421 B2 | 2/2013 |
| JP | 5162595 B2 | 3/2013 |
| JP | 2013517891 A | 5/2013 |
| JP | 2013526342 A | 6/2013 |
| JP | 2013128791 A | 7/2013 |
| JP | 5333899 B2 | 11/2013 |
| JP | 2016-512057 A | 4/2016 |
| KR | 20100110134 A | 10/2010 |
| KR | 20110003229 A | 1/2011 |
| RU | 1814161 C | 5/1993 |
| RU | 2008830 C1 | 3/1994 |
| RU | 2052979 C1 | 1/1996 |
| RU | 2066128 C1 | 9/1996 |
| RU | 2098025 C1 | 12/1997 |
| RU | 2141279 C1 | 11/1999 |
| RU | 2144791 C1 | 1/2000 |
| RU | 2161450 C1 | 1/2001 |
| RU | 2181566 C2 | 4/2002 |
| RU | 2187249 C2 | 8/2002 |
| RU | 2189091 C2 | 9/2002 |
| RU | 32984 U1 | 10/2003 |
| RU | 2225170 C2 | 3/2004 |
| RU | 42750 U1 | 12/2004 |
| RU | 61114 U1 | 2/2007 |
| RU | 61122 U1 | 2/2007 |
| RU | 2007103563 A | 8/2008 |
| SU | 189517 A | 1/1967 |
| SU | 297156 A | 5/1971 |
| SU | 328636 A | 9/1972 |
| SU | 511939 A1 | 4/1976 |
| SU | 674747 A1 | 7/1979 |
| SU | 728848 A1 | 4/1980 |
| SU | 886900 A1 | 12/1981 |
| SU | 1009439 A | 4/1983 |
| SU | 1022703 A1 | 6/1983 |
| SU | 1271497 A1 | 11/1986 |
| SU | 1333319 A2 | 8/1987 |
| SU | 1377052 A1 | 2/1988 |

(56) References Cited

FOREIGN PATENT DOCUMENTS

| | | |
|---|---|---|
| SU | 1377053 A1 | 2/1988 |
| SU | 1443874 A1 | 12/1988 |
| SU | 1509051 A1 | 9/1989 |
| SU | 1561964 A1 | 5/1990 |
| SU | 1708312 A1 | 1/1992 |
| SU | 1722476 A1 | 3/1992 |
| SU | 1752361 A1 | 8/1992 |
| SU | 1814161 A1 | 5/1993 |
| WO | WO-8202824 A1 | 9/1982 |
| WO | WO-8602254 A1 | 4/1986 |
| WO | WO-9115157 A1 | 10/1991 |
| WO | WO-9220295 A1 | 11/1992 |
| WO | WO-9221300 A1 | 12/1992 |
| WO | WO-9308755 A1 | 5/1993 |
| WO | WO-9313718 A1 | 7/1993 |
| WO | WO-9314690 A1 | 8/1993 |
| WO | WO-9315648 A1 | 8/1993 |
| WO | WO-9315850 A1 | 8/1993 |
| WO | WO-9319681 A1 | 10/1993 |
| WO | WO-9400060 A1 | 1/1994 |
| WO | WO-9411057 A1 | 5/1994 |
| WO | WO-94/14129 A1 | 6/1994 |
| WO | WO-9412108 A1 | 6/1994 |
| WO | WO-9417737 A1 | 8/1994 |
| WO | WO-9418893 A1 | 9/1994 |
| WO | WO-9420030 A1 | 9/1994 |
| WO | WO-9422378 A1 | 10/1994 |
| WO | WO-9423659 A1 | 10/1994 |
| WO | WO-9424943 A1 | 11/1994 |
| WO | WO-9424947 A1 | 11/1994 |
| WO | WO-9502369 A1 | 1/1995 |
| WO | WO-9503743 A1 | 2/1995 |
| WO | WO-9506817 A1 | 3/1995 |
| WO | WO-9509576 A1 | 4/1995 |
| WO | WO-9509577 A1 | 4/1995 |
| WO | WO-9514436 A1 | 6/1995 |
| WO | WO-9517855 A1 | 7/1995 |
| WO | WO-9518383 A1 | 7/1995 |
| WO | WO-9518572 A1 | 7/1995 |
| WO | WO-9519739 A1 | 7/1995 |
| WO | WO-9520360 A1 | 8/1995 |
| WO | WO-9523557 A1 | 9/1995 |
| WO | WO-9524865 A1 | 9/1995 |
| WO | WO-9525471 A3 | 9/1995 |
| WO | WO-9526562 A1 | 10/1995 |
| WO | WO-9529639 A1 | 11/1995 |
| WO | WO-9604858 A1 | 2/1996 |
| WO | WO-9618344 A2 | 6/1996 |
| WO | WO-9619151 A1 | 6/1996 |
| WO | WO-9619152 A1 | 6/1996 |
| WO | WO-9620652 A1 | 7/1996 |
| WO | WO-9621119 A1 | 7/1996 |
| WO | WO-9622055 A1 | 7/1996 |
| WO | WO-9623448 A1 | 8/1996 |
| WO | WO-9624301 A1 | 8/1996 |
| WO | WO-9627337 A1 | 9/1996 |
| WO | WO-9631155 A1 | 10/1996 |
| WO | WO-9635464 A1 | 11/1996 |
| WO | WO-9639085 A1 | 12/1996 |
| WO | WO-9639086 A1 | 12/1996 |
| WO | WO-9639087 A1 | 12/1996 |
| WO | WO-9639088 A1 | 12/1996 |
| WO | WO-9639089 A1 | 12/1996 |
| WO | WO-9700646 A1 | 1/1997 |
| WO | WO-9700647 A1 | 1/1997 |
| WO | WO-9701989 A1 | 1/1997 |
| WO | WO-9706582 A1 | 2/1997 |
| WO | WO-9710763 A1 | 3/1997 |
| WO | WO-9710764 A1 | 3/1997 |
| WO | WO-9711648 A2 | 4/1997 |
| WO | WO-9711649 A1 | 4/1997 |
| WO | WO-9715237 A1 | 5/1997 |
| WO | WO-9724073 A1 | 7/1997 |
| WO | WO-9724993 A1 | 7/1997 |
| WO | WO-9730644 A1 | 8/1997 |
| WO | WO-9730659 A1 | 8/1997 |
| WO | WO-9734533 A1 | 9/1997 |
| WO | WO-9737598 A1 | 10/1997 |
| WO | WO-9739688 A2 | 10/1997 |
| WO | WO-9741767 A2 | 11/1997 |
| WO | WO-9801080 A1 | 1/1998 |
| WO | WO-9817180 A1 | 4/1998 |
| WO | WO-9822154 A2 | 5/1998 |
| WO | WO-9827880 A1 | 7/1998 |
| WO | WO-9830153 A1 | 7/1998 |
| WO | WO-9847436 A1 | 10/1998 |
| WO | WO-9858589 A1 | 12/1998 |
| WO | WO-9902090 A1 | 1/1999 |
| WO | WO-9903407 A1 | 1/1999 |
| WO | WO-9903408 A1 | 1/1999 |
| WO | WO-9903409 A1 | 1/1999 |
| WO | WO-9912483 A1 | 3/1999 |
| WO | WO-9912487 A1 | 3/1999 |
| WO | WO-9912488 A1 | 3/1999 |
| WO | WO-9915086 A1 | 4/1999 |
| WO | WO-9915091 A1 | 4/1999 |
| WO | WO-9923933 A2 | 5/1999 |
| WO | WO-9923959 A1 | 5/1999 |
| WO | WO-9925261 A1 | 5/1999 |
| WO | WO-9929244 A1 | 6/1999 |
| WO | WO-9934744 A1 | 7/1999 |
| WO | WO-9945849 A1 | 9/1999 |
| WO | WO-9948430 A1 | 9/1999 |
| WO | WO-9951158 A1 | 10/1999 |
| WO | WO-0024322 A1 | 5/2000 |
| WO | WO-0024330 A1 | 5/2000 |
| WO | WO-0033755 A1 | 6/2000 |
| WO | WO-0041638 A1 | 7/2000 |
| WO | WO-0048506 A1 | 8/2000 |
| WO | WO-0053112 A2 | 9/2000 |
| WO | WO-0054653 A1 | 9/2000 |
| WO | WO-0057796 A1 | 10/2000 |
| WO | WO-0064365 A1 | 11/2000 |
| WO | WO-0072762 A1 | 12/2000 |
| WO | WO-0072765 A1 | 12/2000 |
| WO | WO-0078222 A1 | 12/2000 |
| WO | WO-0103587 A1 | 1/2001 |
| WO | WO-0105702 A1 | 1/2001 |
| WO | WO-0110482 A1 | 2/2001 |
| WO | WO-0135845 A1 | 5/2001 |
| WO | WO-0154594 A1 | 8/2001 |
| WO | WO-0158371 A1 | 8/2001 |
| WO | WO-0162158 A2 | 8/2001 |
| WO | WO-0162161 A1 | 8/2001 |
| WO | WO-0162162 A1 | 8/2001 |
| WO | WO-0162163 A1 | 8/2001 |
| WO | WO-0162164 A2 | 8/2001 |
| WO | WO-0162169 A2 | 8/2001 |
| WO | WO-0178605 A2 | 10/2001 |
| WO | WO-0180757 A2 | 11/2001 |
| WO | WO-0191646 A1 | 12/2001 |
| WO | WO-0200121 A1 | 1/2002 |
| WO | WO-0207608 A2 | 1/2002 |
| WO | WO-0207618 A1 | 1/2002 |
| WO | WO-0217799 A1 | 3/2002 |
| WO | WO-0219920 A1 | 3/2002 |
| WO | WO-0219932 A1 | 3/2002 |
| WO | WO-0226143 A1 | 4/2002 |
| WO | WO-0230297 A2 | 4/2002 |
| WO | WO-0232322 A2 | 4/2002 |
| WO | WO-0236028 A1 | 5/2002 |
| WO | WO-0243571 A2 | 6/2002 |
| WO | WO-02058568 A1 | 8/2002 |
| WO | WO-02060328 A1 | 8/2002 |
| WO | WO-02065933 A2 | 8/2002 |
| WO | WO-02067785 A2 | 9/2002 |
| WO | WO-02080781 A2 | 10/2002 |
| WO | WO-02085218 A2 | 10/2002 |
| WO | WO-02087586 A1 | 11/2002 |
| WO | WO-02098302 A1 | 12/2002 |
| WO | WO-03000138 A2 | 1/2003 |
| WO | WO-03001329 A2 | 1/2003 |
| WO | WO-03001986 A2 | 1/2003 |
| WO | WO-03013363 A1 | 2/2003 |

(56) References Cited

FOREIGN PATENT DOCUMENTS

| | | |
|---|---|---|
| WO | WO-03013372 A2 | 2/2003 |
| WO | WO-03015604 A2 | 2/2003 |
| WO | WO-03020106 A2 | 3/2003 |
| WO | WO-03020139 A2 | 3/2003 |
| WO | WO-03024339 A1 | 3/2003 |
| WO | WO-03030743 A2 | 4/2003 |
| WO | WO-03037193 A1 | 5/2003 |
| WO | WO-03055402 A1 | 7/2003 |
| WO | WO-03057048 A1 | 7/2003 |
| WO | WO-03057058 A1 | 7/2003 |
| WO | WO-03063694 A1 | 8/2003 |
| WO | WO-03077769 A1 | 9/2003 |
| WO | WO-03079911 A1 | 10/2003 |
| WO | WO-03082126 A1 | 10/2003 |
| WO | WO-03086206 A1 | 10/2003 |
| WO | WO-03088845 A2 | 10/2003 |
| WO | WO-03047436 A3 | 11/2003 |
| WO | WO-03090630 A2 | 11/2003 |
| WO | WO-03094743 A1 | 11/2003 |
| WO | WO-03094745 A1 | 11/2003 |
| WO | WO-03094746 A1 | 11/2003 |
| WO | WO-03094747 A1 | 11/2003 |
| WO | WO-03101313 A1 | 12/2003 |
| WO | WO-03105698 A2 | 12/2003 |
| WO | WO-03105702 A2 | 12/2003 |
| WO | WO-2004004578 A1 | 1/2004 |
| WO | WO-2004006980 A2 | 1/2004 |
| WO | WO-2004011037 A2 | 2/2004 |
| WO | WO-2004014238 A2 | 2/2004 |
| WO | WO-03079909 A3 | 3/2004 |
| WO | WO-2004019769 A1 | 3/2004 |
| WO | WO-2004019803 A1 | 3/2004 |
| WO | WO-2004021868 A2 | 3/2004 |
| WO | WO-2004028585 A2 | 4/2004 |
| WO | WO-2004030554 A1 | 4/2004 |
| WO | WO-2004032754 A2 | 4/2004 |
| WO | WO-2004032760 A2 | 4/2004 |
| WO | WO-2004032762 A1 | 4/2004 |
| WO | WO-2004032763 A2 | 4/2004 |
| WO | WO-2004032783 A1 | 4/2004 |
| WO | WO-2004034875 A2 | 4/2004 |
| WO | WO-2004047626 A1 | 6/2004 |
| WO | WO-2004047653 A2 | 6/2004 |
| WO | WO-2004049956 A2 | 6/2004 |
| WO | WO-2004050971 A2 | 6/2004 |
| WO | WO-2004052426 A2 | 6/2004 |
| WO | WO-2004056276 A1 | 7/2004 |
| WO | WO-2004056277 A1 | 7/2004 |
| WO | WO-2004062516 A1 | 7/2004 |
| WO | WO-2004064600 A2 | 8/2004 |
| WO | WO-2004078050 A2 | 9/2004 |
| WO | WO-2004078051 A2 | 9/2004 |
| WO | WO-2004078236 A2 | 9/2004 |
| WO | WO-2004086987 A1 | 10/2004 |
| WO | WO-2004096015 A2 | 11/2004 |
| WO | WO-2004096057 A2 | 11/2004 |
| WO | WO-2004103157 A2 | 12/2004 |
| WO | WO-2004105593 A1 | 12/2004 |
| WO | WO-2004105621 A1 | 12/2004 |
| WO | WO-2004112618 A2 | 12/2004 |
| WO | WO-2004112652 A2 | 12/2004 |
| WO | WO-2005027983 A2 | 3/2005 |
| WO | WO-2005037329 A2 | 4/2005 |
| WO | WO-2005042041 A1 | 5/2005 |
| WO | WO-2005044078 A2 | 5/2005 |
| WO | WO-2005048809 A1 | 6/2005 |
| WO | WO-2005055846 A1 | 6/2005 |
| WO | WO-2005072634 A2 | 8/2005 |
| WO | WO-2005078892 A1 | 8/2005 |
| WO | WO-2005079675 A2 | 9/2005 |
| WO | WO-2005087128 A1 | 9/2005 |
| WO | WO-2005096954 A2 | 10/2005 |
| WO | WO-2005110243 A2 | 11/2005 |
| WO | WO-2005112806 A2 | 12/2005 |
| WO | WO-2005112808 A1 | 12/2005 |
| WO | WO-2005115251 A1 | 12/2005 |
| WO | WO-2005115253 A2 | 12/2005 |
| WO | WO-2005117735 A1 | 12/2005 |
| WO | WO-2005122936 A1 | 12/2005 |
| WO | WO-2006/026520 A2 | 3/2006 |
| WO | WO-2006023486 A1 | 3/2006 |
| WO | WO-2006023578 A2 | 3/2006 |
| WO | WO-2006027014 A1 | 3/2006 |
| WO | WO-2006028314 A1 | 3/2006 |
| WO | WO-2006044490 A2 | 4/2006 |
| WO | WO-2006044581 A2 | 4/2006 |
| WO | WO-2006044810 A2 | 4/2006 |
| WO | WO-2006049852 A2 | 5/2006 |
| WO | WO-2006050360 A1 | 5/2006 |
| WO | WO-2006051252 A1 | 5/2006 |
| WO | WO-2006/057702 A2 | 6/2006 |
| WO | WO-2006059067 A1 | 6/2006 |
| WO | WO-2006/073581 A2 | 7/2006 |
| WO | WO-2006083748 A1 | 8/2006 |
| WO | WO-2006085389 A1 | 8/2006 |
| WO | WO-2006092563 A1 | 9/2006 |
| WO | WO-2006092565 A1 | 9/2006 |
| WO | WO-2006115958 A1 | 11/2006 |
| WO | WO-2006125940 A1 | 11/2006 |
| WO | WO-2006132992 A2 | 12/2006 |
| WO | WO-2007002180 A2 | 1/2007 |
| WO | WO-2007014355 A2 | 2/2007 |
| WO | WO-2007016290 A2 | 2/2007 |
| WO | WO-2007018898 A2 | 2/2007 |
| WO | WO-2007034161 A2 | 3/2007 |
| WO | WO-2007051000 A2 | 5/2007 |
| WO | WO-2007059233 A2 | 5/2007 |
| WO | WO-2007074430 A1 | 7/2007 |
| WO | WO-2007089603 A2 | 8/2007 |
| WO | WO-2007098220 A2 | 8/2007 |
| WO | WO-2007121579 A1 | 11/2007 |
| WO | WO-2007129121 A1 | 11/2007 |
| WO | WO-2007131110 A2 | 11/2007 |
| WO | WO-2007137304 A2 | 11/2007 |
| WO | WO-2007139734 A2 | 12/2007 |
| WO | WO-2007142625 A2 | 12/2007 |
| WO | WO-2007145825 A2 | 12/2007 |
| WO | WO-2007146987 A2 | 12/2007 |
| WO | WO-2007147439 A1 | 12/2007 |
| WO | WO-2008020964 A2 | 2/2008 |
| WO | WO-2008021687 A1 | 2/2008 |
| WO | WO-2008021969 A2 | 2/2008 |
| WO | WO-2008027972 A1 | 3/2008 |
| WO | WO-2008039237 A1 | 4/2008 |
| WO | WO-2008039249 A1 | 4/2008 |
| WO | WO-2008039270 A1 | 4/2008 |
| WO | WO-2008045383 A2 | 4/2008 |
| WO | WO-2008/061566 A1 | 5/2008 |
| WO | WO-2008057281 A2 | 5/2008 |
| WO | WO-2008070763 A1 | 6/2008 |
| WO | WO-2008080148 A2 | 7/2008 |
| WO | WO-2008089404 A2 | 7/2008 |
| WO | WO-2008101080 A1 | 8/2008 |
| WO | WO-2008101228 A2 | 8/2008 |
| WO | WO-2008103797 A2 | 8/2008 |
| WO | WO-2008109123 A2 | 9/2008 |
| WO | WO-2008109125 A1 | 9/2008 |
| WO | WO-2008112912 A2 | 9/2008 |
| WO | WO-2008118728 A1 | 10/2008 |
| WO | WO-2008118928 A2 | 10/2008 |
| WO | WO-2008124748 A1 | 10/2008 |
| WO | WO-2008131357 A1 | 10/2008 |
| WO | WO-2009005969 A2 | 1/2009 |
| WO | WO-2009022614 A1 | 2/2009 |
| WO | WO-2009023851 A1 | 2/2009 |
| WO | WO-2009033057 A2 | 3/2009 |
| WO | WO-2009039506 A1 | 3/2009 |
| WO | WO-2009046394 A1 | 4/2009 |
| WO | WO-2009066105 A1 | 5/2009 |
| WO | WO-2009067649 A2 | 5/2009 |
| WO | WO-2009091497 A2 | 7/2009 |
| WO | WO-2009120944 A2 | 10/2009 |
| WO | WO-2009137761 A2 | 11/2009 |
| WO | WO-2009143092 A1 | 11/2009 |

(56) References Cited

FOREIGN PATENT DOCUMENTS

| | | |
|---|---|---|
| WO | WO-2009143331 A1 | 11/2009 |
| WO | WO-2009150650 A2 | 12/2009 |
| WO | WO-2009152307 A1 | 12/2009 |
| WO | WO-2010028332 A2 | 3/2010 |
| WO | WO-2010030434 A1 | 3/2010 |
| WO | WO-2010045425 A1 | 4/2010 |
| WO | WO-2010050771 A2 | 5/2010 |
| WO | WO-2010054404 A1 | 5/2010 |
| WO | WO-2010056714 A1 | 5/2010 |
| WO | WO-2010063795 A1 | 6/2010 |
| WO | WO-2010090940 A1 | 8/2010 |
| WO | WO-2010093333 A1 | 8/2010 |
| WO | WO-2010098871 A2 | 9/2010 |
| WO | WO-2010134913 A1 | 11/2010 |
| WO | WO-2011008672 A2 | 1/2011 |
| WO | WO-2011013103 A1 | 2/2011 |
| WO | WO-2011044343 A2 | 4/2011 |
| WO | WO-2011056458 A1 | 5/2011 |
| WO | WO-2011060311 A2 | 5/2011 |
| WO | WO-2011084969 A1 | 7/2011 |
| WO | WO-2011127137 A1 | 10/2011 |
| WO | WO-2012006306 A2 | 1/2012 |
| WO | WO-2012009431 A2 | 1/2012 |
| WO | WO-2012/013577 A1 | 2/2012 |
| WO | WO-2012021671 A1 | 2/2012 |
| WO | WO-2012040438 A1 | 3/2012 |
| WO | WO-2012044551 A1 | 4/2012 |
| WO | WO-2012044554 A1 | 4/2012 |
| WO | WO-2012044597 A1 | 4/2012 |
| WO | WO-2012044606 A2 | 4/2012 |
| WO | WO-2012044820 A1 | 4/2012 |
| WO | WO-2012044844 A2 | 4/2012 |
| WO | WO-2012044853 A1 | 4/2012 |
| WO | WO-2012044854 A1 | 4/2012 |
| WO | WO-2012058213 A2 | 5/2012 |
| WO | WO-2012068156 A2 | 5/2012 |
| WO | WO-2012109760 A1 | 8/2012 |
| WO | WO-2012127462 A1 | 9/2012 |
| WO | WO-2012135705 A1 | 10/2012 |
| WO | WO-2012143913 A2 | 10/2012 |
| WO | WO-2012148667 A2 | 11/2012 |
| WO | WO-2012148668 A2 | 11/2012 |
| WO | WO-2012148703 A2 | 11/2012 |
| WO | WO-2012160163 A1 | 11/2012 |
| WO | WO-2012166503 A1 | 12/2012 |
| WO | WO-2013009252 A2 | 1/2013 |
| WO | WO-2013009699 A2 | 1/2013 |
| WO | WO-2013023114 A1 | 2/2013 |
| WO | WO-2013036409 A1 | 3/2013 |
| WO | WO-2013043707 A2 | 3/2013 |
| WO | WO-2013043717 A1 | 3/2013 |
| WO | WO-2013043721 A2 | 3/2013 |
| WO | WO-2013062978 A2 | 5/2013 |
| WO | WO-2013116869 A1 | 8/2013 |
| WO | WO-2013148762 A2 | 10/2013 |
| WO | WO-2013151888 A1 | 10/2013 |
| WO | WO-2013167427 A1 | 11/2013 |
| WO | WO-2013188130 A1 | 12/2013 |
| WO | WO-2014/008289 A2 | 1/2014 |
| WO | WO-2014004199 A1 | 1/2014 |
| WO | WO-2014004294 A2 | 1/2014 |
| WO | WO-2014/113438 A1 | 7/2014 |
| WO | WO-2014/134034 A2 | 9/2014 |
| WO | WO-2014/172213 A2 | 10/2014 |
| WO | WO-2014158882 A2 | 10/2014 |
| WO | WO-2015/032797 A1 | 3/2015 |
| WO | WO-2015/148136 A1 | 10/2015 |
| WO | WO-2015148141 A1 | 10/2015 |
| WO | WO-2015153642 A1 | 10/2015 |

OTHER PUBLICATIONS

Disclosed Anonymously, "Motor-Driven Surgical Stapler Improvements," Research Disclosure Database No. 526041, Published: Feb. 2008.
Van Meer et al., "A Disposable Plastic Compact Wrist for Smart Minimally Invasive Surgical Tools," LAAS/CNRS (Aug. 2005).
Breedveld et al., "A New, Easily Miniaturized Sterrable Endoscope," IEEE Engineering in Medicine and Biology Magazine (Nov./Dec. 2005).
D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).
Datasheet for Panasonic TK Relays Ultra Low Profile 2 A Polarized Relay, Copyright Matsushita Electric Works, Ltd. (Known of at least as early as Aug. 17, 2010), 5 pages.
ASTM procedure D2240-00, "Standard Test Method for Rubber Property-Durometer Hardness," (Published Aug. 2000).
ASTM procedure D2240-05, "Standard Test Method for Rubber Property-Durometer Hardness," (Published Apr. 2010).
Covidien Brochure, "Endo GIA™ Reloads with Tri-Staple™ Technology," (2010), 1 page.
Covidien Brochure, "Endo GIA™ Reloads with Tri-Staple™ Technology and Endo GIA™ Ultra Universal Staplers," (2010), 2 pages.
Covidien Brochure, "Endo GIA™ Curved Tip Reload with Tri-Staple™ Technology," (2012), 2 pages.
Covidien Brochure, "Endo GIA™ Reloads with Tri-Staple™ Technology," (2010), 2 pages.
Covidien Brochure, "Endo GIA™ Ultra Universal Stapler," (2010), 2 pages.
Miyata et al., "Biomolecule-Sensitive Hydrogels," Advanced Drug Delivery Reviews, 54 (2002) pp. 79-98.
Jeong et al., "Thermosensitive Sol-Gel Reversible Hydrogels," Advanced Drug Delivery Reviews, 54 (2002) pp. 37-51.
Qiu et al., "Environment-Sensitive Hydrogels for Drug Delivery," Advanced Drug Delivery Reviews, 53 (2001) pp. 321-339.
Hoffman, "Hydrogels for Biomedical Applications," Advanced Drug Delivery Reviews, 43 (2002) pp. 3-12.
Hoffman, "Hydrogels for Biomedical Applications," Advanced Drug Delivery Reviews, 54 (2002) pp. 3-12.
Peppas, "Physiologically Responsive Hydrogels," Journal of Bioactive and Compatible Polymers, vol. 6 (Jul. 1991) pp. 241-246.
Peppas, Editor "Hydrogels in Medicine and Pharmacy," vol. I, Fundamentals, CRC Press, 1986.
Young, "Microcellular foams via phase separation," Journal of Vacuum Science & Technology A 4(3), (May/Jun. 1986).
Pitt et al., "Attachment of Hyaluronan to Metallic Surfaces," J. Biomed. Mater. Res. 68A: pp. 95-106, 2004.
Solorio et al., "Gelatin Microspheres Crosslinked with Genipin for Local Delivery of Growth Factors," J. Tissue Eng. Regen. Med. (2010), 4(7): pp. 514-523.
http://ninpgan.net/publications/51-100/89.pdf; 2004, Ning Pan, On Uniqueness of Fibrous Materials, Design & Nature II. Eds: Colins, M. and Brebbia, C. WIT Press, Boston, 493-504.
Covidien iDrive™ Ultra in Service Reference Card, "iDrive™ Ultra Powered Stapling Device," (4 pages).
Covidien "iDrive™ Ultra Powered Stapling System, A Guide for Surgeons," (6 pages).
Covidien "iDrive™ Ultra Powered Stapling System, Cleaning and Sterilization Guide," (2 pages).
Covidien Brochure "iDrive™ Ultra Powered Stapling System," (6 pages).
"Indian Standard: Automotive Vehicles—Brakes and Braking Systems (IS 11852-1:2001)", Mar. 1, 2001.
Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.
Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).

(56) References Cited

OTHER PUBLICATIONS

Covidien iDrive™ Ultra Powered Stapling System ibrochure, "The Power of iDrive™ Ultra Powered Stapling System and Tri-Staple™ Technology," (23 pages).
Patrick J. Sweeney: "RFID for Dummies", Mar. 11, 2010, pp. 365-365, XP055150775, ISBN: 978-1-11-805447-5, Retrieved from the Internet: URL: books.google.de/books?isbn=1118054474 [retrieved on Nov. 4, 2014]—book not attached.
Allegro MicroSystems, LLC, Automotive Full Bridge MOSFET Driver, A3941-DS, Rev. 5, 21 pages, http://www.allegromicro.com/~/media/Files/Datasheets/A3941-Datasheet.ashx?la=en.
Data Sheet of LM4F230H5QR, 2007.
Seils et al., Covidien Summary: Clinical Study "UCONN Biodynamics: Final Report on Results," (2 pages).
Byrne et al., "Molecular Imprinting Within Hydrogels," Advanced Drug Delivery Reviews, 54 (2002) pp. 149-161.
Fast, Versatile Blackfin Processors Handle Advanced RFID Reader Applications; Analog Dialogue: vol. 40—Sep. 2006; http://www.analog.com/library/analogDialogue/archives/40-09/rfid.pdf; Wayback Machine to Feb. 15, 2012.
Chen et al., "Elastomeric Biomaterials for Tissue Engineering," Progress in Polymer Science 38 (2013), pp. 584-671.
Matsuda, "Thermodynamics of Formation of Porous Polymeric Membrane from Solutions," Polymer Journal, vol. 23, No. 5, pp. 435-444 (1991).
Covidien Brochure, "Endo GIA™ Black Reload with Tri-Staple™ Technology," (2012), 2 pages.
"Biomedical Coatings," Fort Wayne Metals, Research Products Corporation, obtained online at www.fwmetals.com on Jun. 21, 2010 (1 page).
The Sodem Aseptic Battery Transfer Kit, Sodem Systems, 2000, 3 pages.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20., pp. 1744-1748.
Serial Communication Protocol; Michael Lemmon Feb. 1, 2009; http://www3.nd.edu/~lemmon/courses/ee224/web-manual/web-manual/lab12/node2.html; Wayback Machine to Apr. 29, 2012.
Lyon et al. "The Relationship Between Current Load and Temperature for Quasi-Steady State and Transient Conditions," SPIE—International Society for Optical Engineering. Proceedings, vol. 4020, (pp. 62-70), Mar. 30, 2000.
Anonymous: "Sense & Control Application Note Current Sensing Using Linear Hall Sensors," Feb. 3, 2009, pp. 1-18. Retrieved from the Internet: URL: http://www.infineon.com/dgdl/Current_Sensing_Rev.1.1.pdf?fileId=db3a304332d040720132d939503e5f17 [retrieved on Oct. 18, 2016].
Mouser Electronics, "LM317M 3—Terminal Adjustable Regulator with Overcurrent/Overtemperature Self Protection", Mar. 31, 2014 (Mar. 31, 2014), XP0555246104, Retrieved from the Internet: URL: http://www.mouser.com/ds/2/405/lm317m-440423.pdf, pp. 1-8.
Mouser Electronics, "LM317 3—Terminal Adjustable Regulator with Overcurrent/Overtemperature Self Protection", Sep. 30, 2016 (Sep. 30, 2016), XP0555246104, Retrieved from the Internet: URL: http://www.mouser.com/ds/2/405/lm317m-440423.pdf, pp. 1-9.
Cuper et al., "The Use of Near-Infrared Light for Safe and Effective Visualization of Subsurface Blood Vessels to Facilitate Blood Withdrawal in Children," Medical Engineering & Physics, vol. 35, No. 4, pp. 433-440 (2013).
Yan et al, Comparison of the effects of Mg-6Zn and Ti-3Al-2.5V alloys on TGF-β/TNF-α/VEGF/b-FGF in the healing of the intestinal track in vivo, Biomed. Mater. 9 (2014), 11 pages.
Pellicer et al. "On the biodegradability, mechanical behavior, and cytocompatibility of amorphous Mg72Zn23Ca5 and crystalline Mg70Zn23Ca5Pd2 alloys as temporary implant materials," J Biomed Mater Res Part A ,2013:101A:502-517.
Anonymous, Analog Devices Wiki, Chapter 11: The Current Mirror, Aug. 20, 2017, 22 pages. https://wiki.analog.com/university/courses/electronics/text/chapter-11?rev=1503222341.
Yan et al., "Comparison of the effects of Mg-6Zn and titanium on intestinal tract in vivo," J Mater Sci: Mater Med (2013), 11 pages.
Brar et al., "Investigation of the mechanical and degradation properties of Mg—Sr and Mg—Zn—Sr alloys for use as potential biodegradable implant materials," J. Mech. Behavior of Biomed. Mater. 7 (2012) pp. 87-95.
Texas Instruments: "Current Recirculation and Decay Modes," Application Report SLVA321—Mar. 2009; Retrieved from the Internet: URL:http://www.ti.com/lit/an/slva321/slva321 [retrieved on Apr. 25, 2017], 7 pages.

\* cited by examiner

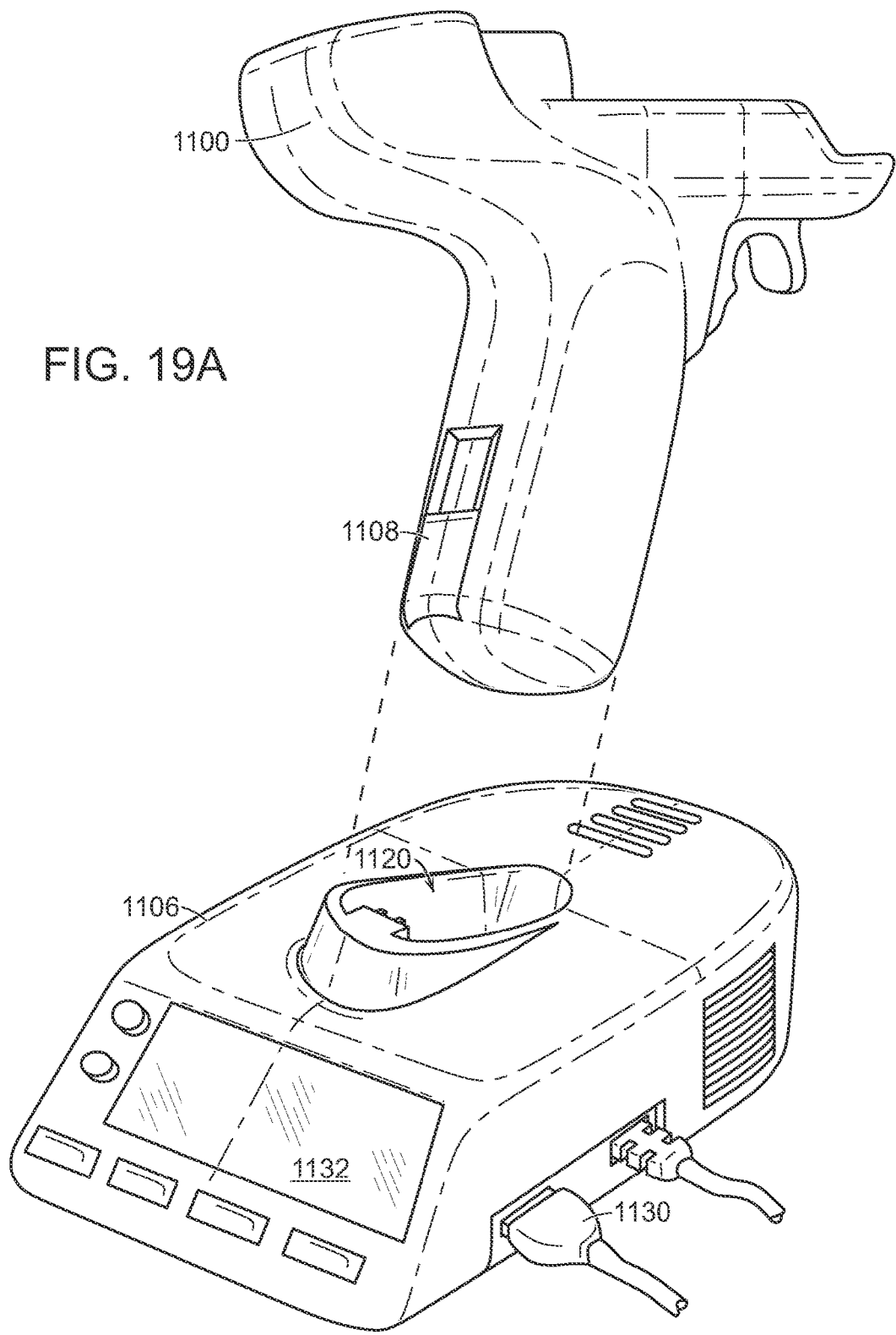

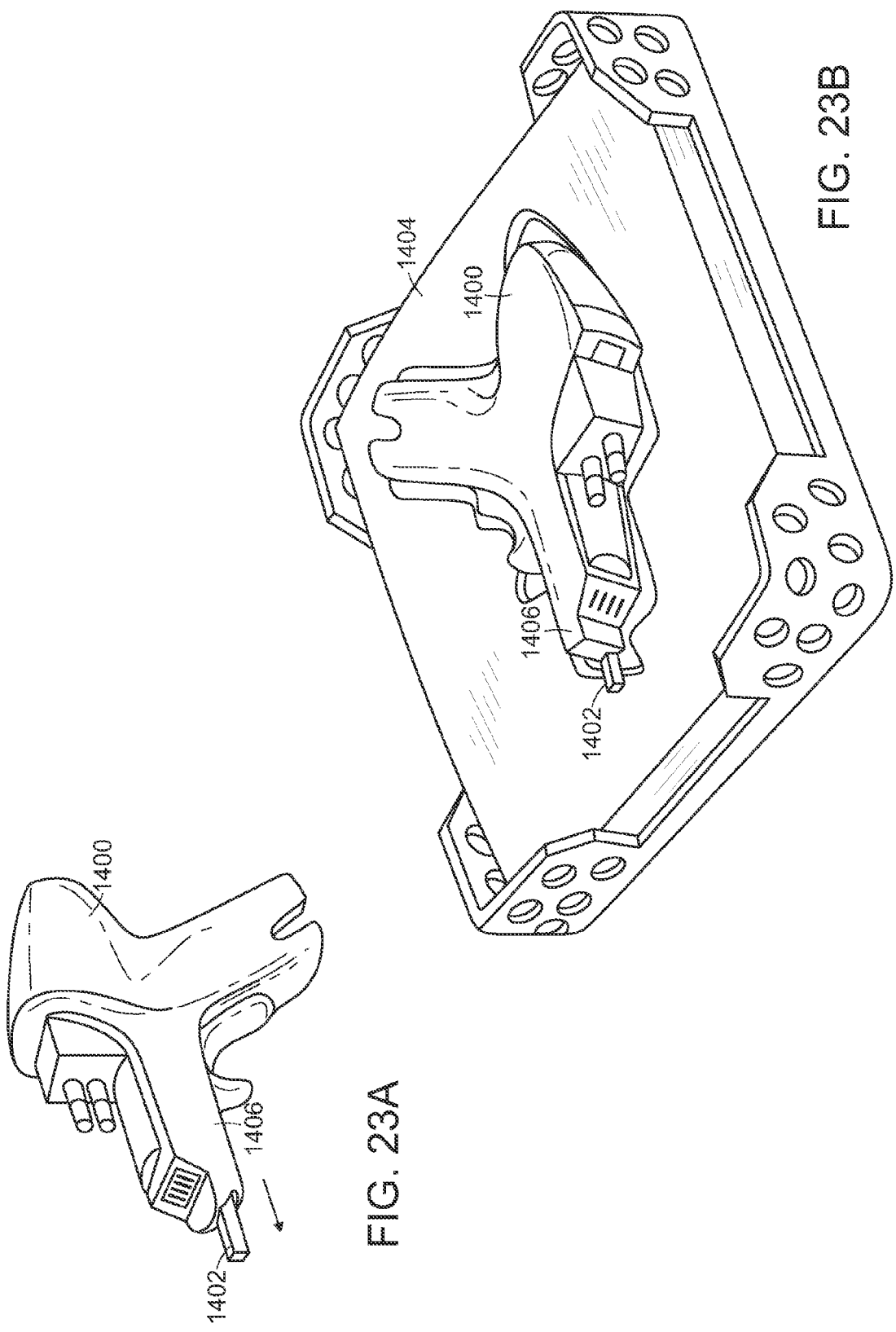

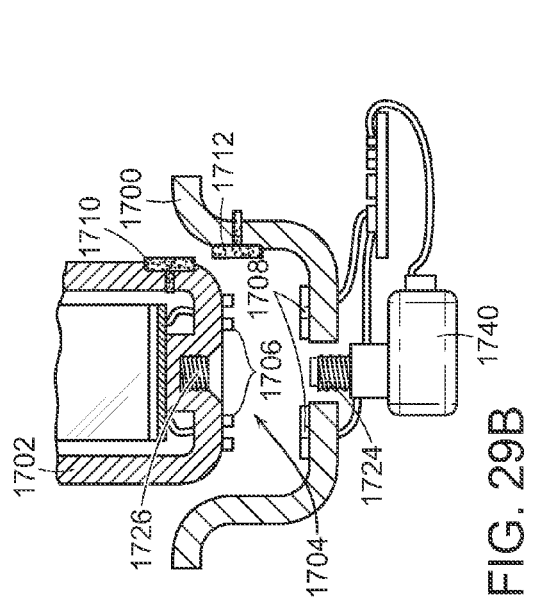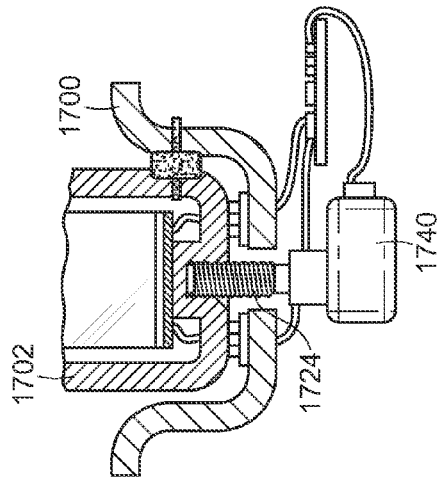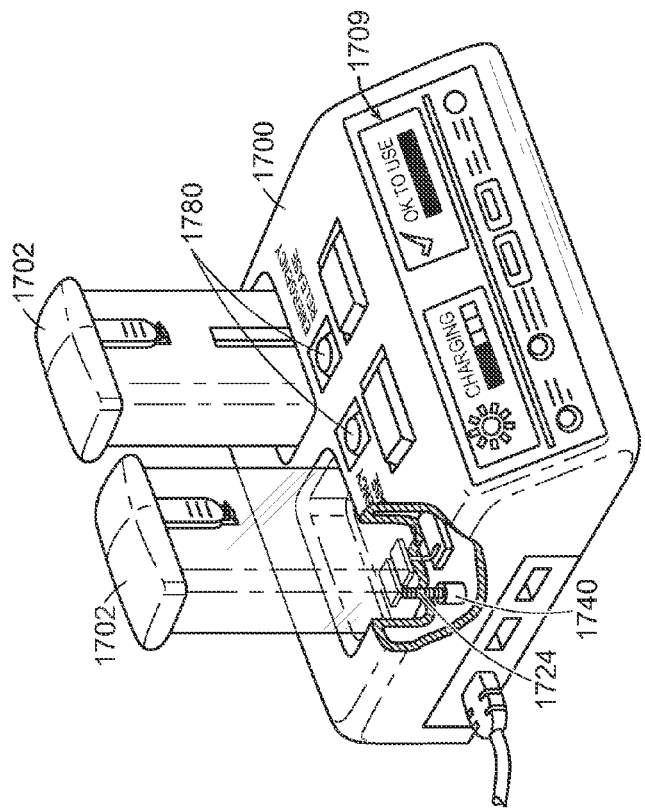
FIG. 29B
FIG. 29C
FIG. 29A

POWER ADAPTER FOR A SURGICAL INSTRUMENT

BACKGROUND

The present invention relates to surgical instruments and, in various embodiments, to surgical stapling and cutting instruments and staple cartridges for use therewith.

A stapling instrument can include a pair of cooperating elongate jaw members, wherein each jaw member can be adapted to be inserted into a patient and positioned relative to tissue that is to be stapled and/or incised. In various embodiments, one of the jaw members can support a staple cartridge with at least two laterally spaced rows of staples contained therein, and the other jaw member can support an anvil with staple-forming pockets aligned with the rows of staples in the staple cartridge. Generally, the stapling instrument can further include a pusher bar and a knife blade which are slidable relative to the jaw members to sequentially eject the staples from the staple cartridge via camming surfaces on the pusher bar and/or camming surfaces on a wedge sled that is pushed by the pusher bar. In at least one embodiment, the camming surfaces can be configured to activate a plurality of staple drivers carried by the cartridge and associated with the staples in order to push the staples against the anvil and form laterally spaced rows of deformed staples in the tissue gripped between the jaw members. In at least one embodiment, the knife blade can trail the camming surfaces and cut the tissue along a line between the staple rows. Examples of such stapling instruments are disclosed in U.S. Pat. No. 7,794,475, entitled SURGICAL STAPLES HAVING COMPRESSIBLE OR CRUSHABLE MEMBERS FOR SECURING TISSUE THEREIN AND STAPLING INSTRUMENTS FOR DEPLOYING THE SAME, the entire disclosure of which is hereby incorporated by reference herein.

The foregoing discussion is intended only to illustrate various aspects of the related art in the field of the invention at the time, and should not be taken as a disavowal of claim scope.

BRIEF DESCRIPTION OF THE DRAWINGS

Various features of the embodiments described herein, together with advantages thereof, may be understood in accordance with the following description taken in conjunction with the accompanying drawings as follows:

FIGS. 19A, 19B and 19C illustrate a charging station and a handle module, where the charging station is for charging a battery pack of the handle module;

FIG. 23A illustrates a handle module with a projecting device that, when projected, prevents insertion of the handle module into a sterilization tray;

FIG. 23B illustrates the handle module of FIG. 23A and a sterilization tray;

FIG. 29A illustrates a charging station for charging one or more removable battery packs that can be used in a handle module;

FIGS. 29B and 29C illustrate a mechanism of the charging station for securing a battery pack to the charging station;

FIG. 38A is a detail cross-sectional view of one of the shock absorbing elements of the battery assembly of FIG. 38;

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
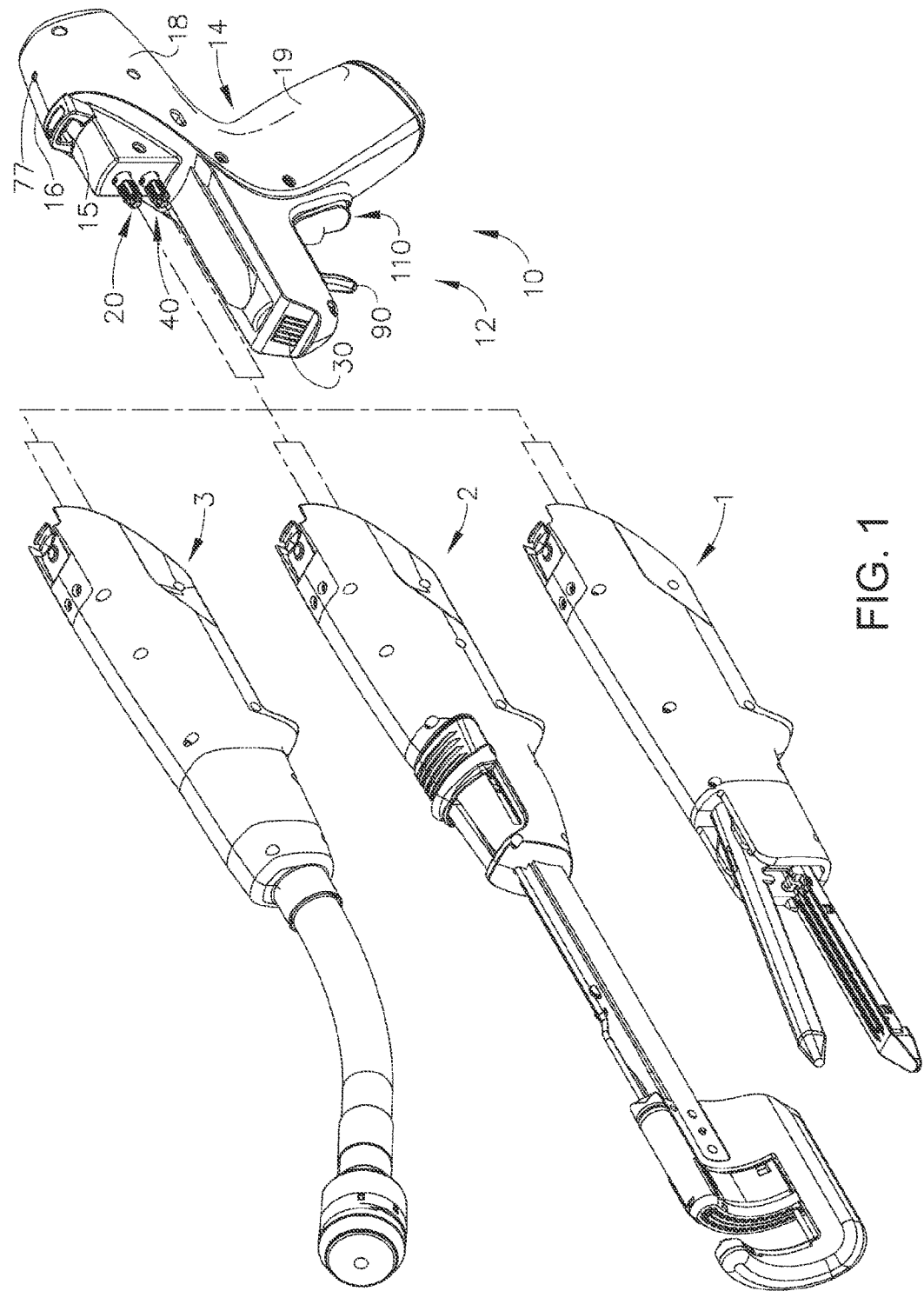
FIG. 1 is a perspective view of a modular surgical system including a motor-driven handle module and three interchangeable detachable shaft modules.
Figure 2:
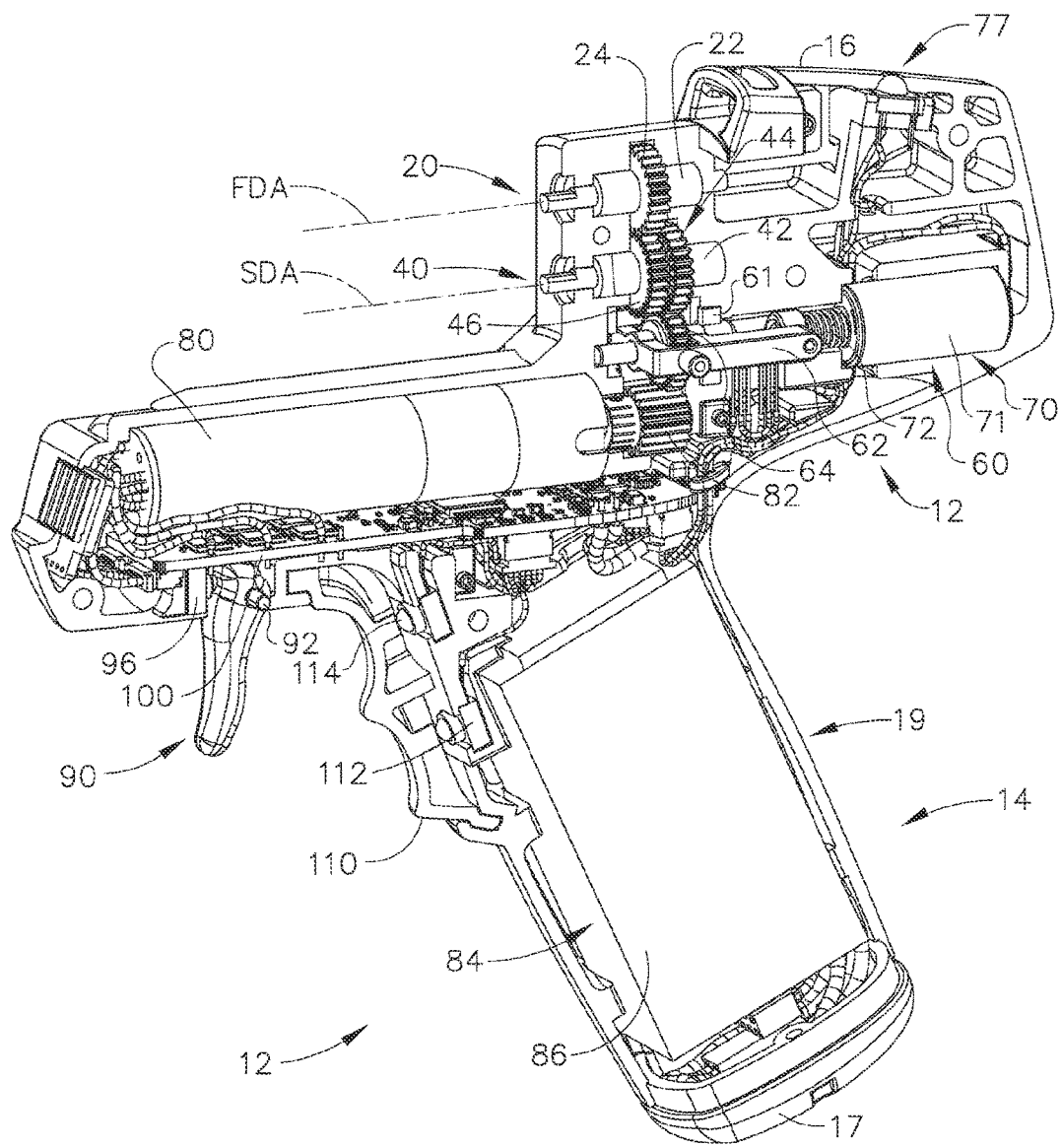
FIG. 2 is a side perspective view of the handle module of FIG. 1 with a portion of the handle housing removed for clarity.

Applicant of the present application owns the following patent applications that were filed on Feb. 27, 2015, and which are each herein incorporated by reference in their respective entireties:

U.S. patent application Ser. No. 14/633,562, entitled SURGICAL APPARATUS CONFIGURED TO TRACK AN END-OF-LIFE PARAMETER;

U.S. patent application Ser. No. 14/633,576, entitled SURGICAL INSTRUMENT SYSTEM COMPRISING AN INSPECTION STATION;

U.S. patent application Ser. No. 14/633,546, entitled SURGICAL APPARATUS CONFIGURED TO ASSESS WHETHER A PERFORMANCE PARAMETER OF THE SURGICAL APPARATUS IS WITHIN AN ACCEPTABLE PERFORMANCE BAND;

U.S. patent application Ser. No. 14/633,560, entitled SURGICAL CHARGING SYSTEM THAT CHARGES AND/OR CONDITIONS ONE OR MORE BATTERIES;

U.S. patent application Ser. No. 14/633,566, entitled CHARGING SYSTEM THAT ENABLES EMERGENCY RESOLUTIONS FOR CHARGING A BATTERY;

U.S. patent application Ser. No. 14/633,555, entitled SYSTEM FOR MONITORING WHETHER A SURGICAL INSTRUMENT NEEDS TO BE SERVICED;

U.S. patent application Ser. No. 14/633,542, entitled REINFORCED BATTERY FOR A SURGICAL INSTRUMENT;

U.S. patent application Ser. No. 14/633,526, entitled ADAPTABLE SURGICAL INSTRUMENT HANDLE; and U.S. patent application Ser. No. 14/633,541, entitled MODULAR STAPLING ASSEMBLY.

Applicant of the present application owns the following patent applications that were filed on Dec. 18, 2014 and which are each herein incorporated by reference in their respective entireties:

U.S. patent application Ser. No. 14/574,478, entitled SURGICAL INSTRUMENT SYSTEMS COMPRISING AN ARTICULATABLE END EFFECTOR AND MEANS FOR ADJUSTING THE FIRING STROKE OF A FIRING;

U.S. patent application Ser. No. 14/574,483, entitled SURGICAL INSTRUMENT ASSEMBLY COMPRISING LOCKABLE SYSTEMS;

U.S. patent application Ser. No. 14/575,139, entitled DRIVE ARRANGEMENTS FOR ARTICULATABLE SURGICAL INSTRUMENTS;

U.S. patent application Ser. No. 14/575,148, entitled LOCKING ARRANGEMENTS FOR DETACHABLE SHAFT ASSEMBLIES WITH ARTICULATABLE SURGICAL END EFFECTORS;

U.S. patent application Ser. No. 14/575,130, entitled SURGICAL INSTRUMENT WITH AN ANVIL THAT IS SELECTIVELY MOVABLE ABOUT A DISCRETE NON-MOVABLE AXIS RELATIVE TO A STAPLE CARTRIDGE;

U.S. patent application Ser. No. 14/575,143, entitled SURGICAL INSTRUMENTS WITH IMPROVED CLOSURE ARRANGEMENTS;

U.S. patent application Ser. No. 14/575,117, entitled SURGICAL INSTRUMENTS WITH ARTICULATABLE END EFFECTORS AND MOVABLE FIRING BEAM SUPPORT ARRANGEMENTS;

U.S. patent application Ser. No. 14/575,154, entitled SURGICAL INSTRUMENTS WITH ARTICULATABLE END EFFECTORS AND IMPROVED FIRING BEAM SUPPORT ARRANGEMENTS;

U.S. patent application Ser. No. 14/574,493, entitled SURGICAL INSTRUMENT ASSEMBLY COMPRISING A FLEXIBLE ARTICULATION SYSTEM; and U.S. patent application Ser. No. 14/574,500, entitled SURGICAL INSTRUMENT ASSEMBLY COMPRISING A LOCKABLE ARTICULATION SYSTEM.

Applicant of the present application owns the following patent applications that were filed on Mar. 1, 2013 and which are each herein incorporated by reference in their respective entireties:

U.S. patent application Ser. No. 13/782,295, entitled ARTICULATABLE SURGICAL INSTRUMENTS WITH CONDUCTIVE PATHWAYS FOR SIGNAL COMMUNICATION, now U.S. Patent Application Publication No. 2014/0246471;

U.S. patent application Ser. No. 13/782,323, entitled ROTARY POWERED ARTICULATION JOINTS FOR SURGICAL INSTRUMENTS, now U.S. Patent Application Publication No. 2014/0246472;

U.S. patent application Ser. No. 13/782,338, entitled THUMBWHEEL SWITCH ARRANGEMENTS FOR SURGICAL INSTRUMENTS, now U.S. Patent Application Publication No. 2014/0249557;

U.S. patent application Ser. No. 13/782,499, entitled ELECTROMECHANICAL SURGICAL DEVICE WITH SIGNAL RELAY ARRANGEMENT, now U.S. Patent Application Publication No. 2014/0246474;

U.S. patent application Ser. No. 13/782,460, entitled MULTIPLE PROCESSOR MOTOR CONTROL FOR MODULAR SURGICAL INSTRUMENTS, now U.S. Patent Application Publication No. 2014/0246478;

U.S. patent application Ser. No. 13/782,358, entitled JOYSTICK SWITCH ASSEMBLIES FOR SURGICAL INSTRUMENTS, now U.S. Patent Application Publication No. 2014/0246477;

U.S. patent application Ser. No. 13/782,481, entitled SENSOR STRAIGHTENED END EFFECTOR DURING REMOVAL THROUGH TROCAR, now U.S. Patent Application Publication No. 2014/0246479;

U.S. patent application Ser. No. 13/782,518, entitled CONTROL METHODS FOR SURGICAL INSTRUMENTS WITH REMOVABLE IMPLEMENT PORTIONS, now U.S. Patent Application Publication No. 2014/0246475;

U.S. patent application Ser. No. 13/782,375, entitled ROTARY POWERED SURGICAL INSTRUMENTS WITH MULTIPLE DEGREES OF FREEDOM, now U.S. Patent Application Publication No. 2014/0246473; and U.S. patent application Ser. No. 13/782,536, entitled SURGICAL INSTRUMENT SOFT STOP, now U.S. Patent Application Publication No. 2014/0246476.

Applicant of the present application also owns the following patent applications that were filed on Mar. 14, 2013 and which are each herein incorporated by reference in their respective entireties:

U.S. patent application Ser. No. 13/803,097, entitled ARTICULATABLE SURGICAL INSTRUMENT COMPRISING A FIRING DRIVE, now U.S. Patent Application Publication No. 2014/0263542;

U.S. patent application Ser. No. 13/803,193, entitled CONTROL ARRANGEMENTS FOR A DRIVE MEMBER OF A SURGICAL INSTRUMENT, now U.S. Patent Application Publication No. 2014/0263537;

U.S. patent application Ser. No. 13/803,053, entitled INTERCHANGEABLE SHAFT ASSEMBLIES FOR USE WITH A SURGICAL INSTRUMENT, now U.S. Patent Application Publication No. 2014/0263564;

U.S. patent application Ser. No. 13/803,086, entitled ARTICULATABLE SURGICAL INSTRUMENT COMPRISING AN ARTICULATION LOCK, now U.S. Patent Application Publication No. 2014/0263541;

U.S. patent application Ser. No. 13/803,210, entitled SENSOR ARRANGEMENTS FOR ABSOLUTE POSITIONING SYSTEM FOR SURGICAL INSTRUMENTS, now U.S. Patent Application Publication No. 2014/0263538;

U.S. patent application Ser. No. 13/803,148, entitled MULTI-FUNCTION MOTOR FOR A SURGICAL INSTRUMENT, now U.S. Patent Application Publication No. 2014/0263554;

U.S. patent application Ser. No. 13/803,066, entitled DRIVE SYSTEM LOCKOUT ARRANGEMENTS FOR MODULAR SURGICAL INSTRUMENTS, now U.S. Patent Application Publication No. 2014/0263565;

U.S. patent application Ser. No. 13/803,117, entitled ARTICULATION CONTROL SYSTEM FOR ARTICULATABLE SURGICAL INSTRUMENTS, now U.S. Patent Application Publication No. 2014/0263553;

U.S. patent application Ser. No. 13/803,130, entitled DRIVE TRAIN CONTROL ARRANGEMENTS FOR MODULAR SURGICAL INSTRUMENTS, now U.S. Patent Application Publication No. 2014/0263543; and U.S. patent application Ser. No. 13/803,159, entitled METHOD AND SYSTEM FOR OPERATING A SURGICAL INSTRUMENT, now U.S. Patent Application Publication No. 2014/0277017.

Applicant of the present application also owns the following patent application that was filed on Mar. 7, 2014 and is herein incorporated by reference in its entirety:

U.S. patent application Ser. No. 14/200,111, entitled CONTROL SYSTEMS FOR SURGICAL INSTRUMENTS, now U.S. Patent Application Publication No. 2014/0263539.

Applicant of the present application also owns the following patent applications that were filed on Mar. 26, 2014 and are each herein incorporated by reference in their respective entireties:

U.S. patent application Ser. No. 14/226,106, entitled POWER MANAGEMENT CONTROL SYSTEMS FOR SURGICAL INSTRUMENTS;

U.S. patent application Ser. No. 14/226,099, entitled STERILIZATION VERIFICATION CIRCUIT;

U.S. patent application Ser. No. 14/226,094, entitled VERIFICATION OF NUMBER OF BATTERY EXCHANGES/PROCEDURE COUNT;

U.S. patent application Ser. No. 14/226,117, entitled POWER MANAGEMENT THROUGH SLEEP OPTIONS OF SEGMENTED CIRCUIT AND WAKE UP CONTROL;

U.S. patent application Ser. No. 14/226,075, entitled MODULAR POWERED SURGICAL INSTRUMENT WITH DETACHABLE SHAFT ASSEMBLIES;

U.S. patent application Ser. No. 14/226,093, entitled FEEDBACK ALGORITHMS FOR MANUAL BAILOUT SYSTEMS FOR SURGICAL INSTRUMENTS;

U.S. patent application Ser. No. 14/226,116, entitled SURGICAL INSTRUMENT UTILIZING SENSOR ADAPTATION;

U.S. patent application Ser. No. 14/226,071, entitled SURGICAL INSTRUMENT CONTROL CIRCUIT HAVING A SAFETY PROCESSOR;

U.S. patent application Ser. No. 14/226,097, entitled SURGICAL INSTRUMENT COMPRISING INTERACTIVE SYSTEMS;

U.S. patent application Ser. No. 14/226,126, entitled INTERFACE SYSTEMS FOR USE WITH SURGICAL INSTRUMENTS;

U.S. patent application Ser. No. 14/226,133, entitled MODULAR SURGICAL INSTRUMENT SYSTEM;

U.S. patent application Ser. No. 14/226,081, entitled SYSTEMS AND METHODS FOR CONTROLLING A SEGMENTED CIRCUIT;

U.S. patent application Ser. No. 14/226,076, entitled POWER MANAGEMENT THROUGH SEGMENTED CIRCUIT AND VARIABLE VOLTAGE PROTECTION;

U.S. patent application Ser. No. 14/226,111, entitled SURGICAL STAPLING INSTRUMENT SYSTEM; and U.S. patent application Ser. No. 14/226,125, entitled SURGICAL INSTRUMENT COMPRISING A ROTATABLE SHAFT.

Applicant of the present application also owns the following patent applications that were filed on Sep. 5, 2014 and which are each herein incorporated by reference in their respective entireties:

U.S. patent application Ser. No. 14/479,103, entitled CIRCUITRY AND SENSORS FOR POWERED MEDICAL DEVICE;

U.S. patent application Ser. No. 14/479,119, entitled ADJUNCT WITH INTEGRATED SENSORS TO QUANTIFY TISSUE COMPRESSION;

U.S. patent application Ser. No. 14/478,908, entitled MONITORING DEVICE DEGRADATION BASED ON COMPONENT EVALUATION;

U.S. patent application Ser. No. 14/478,895, entitled MULTIPLE SENSORS WITH ONE SENSOR AFFECTING A SECOND SENSOR'S OUTPUT OR INTERPRETATION;

U.S. patent application Ser. No. 14/479,110, entitled USE OF POLARITY OF HALL MAGNET DETECTION TO DETECT MISLOADED CARTRIDGE;

U.S. patent application Ser. No. 14/479,098, entitled SMART CARTRIDGE WAKE UP OPERATION AND DATA RETENTION;

U.S. patent application Ser. No. 14/479,115, entitled MULTIPLE MOTOR CONTROL FOR POWERED MEDICAL DEVICE; and U.S. patent application Ser. No. 14/479,108, entitled LOCAL DISPLAY OF TISSUE PARAMETER STABILIZATION.

Applicant of the present application also owns the following patent applications that were filed on Apr. 9, 2014 and which are each herein incorporated by reference in their respective entireties:

U.S. patent application Ser. No. 14/248,590, entitled MOTOR DRIVEN SURGICAL INSTRUMENTS WITH LOCKABLE DUAL DRIVE SHAFTS, now U.S. Patent Application Publication No. 2014/0305987;

U.S. patent application Ser. No. 14/248,581, entitled SURGICAL INSTRUMENT COMPRISING A CLOSING DRIVE AND A FIRING DRIVE OPERATED FROM THE SAME ROTATABLE OUTPUT, now U.S. Patent Application Publication No. 2014/0305989;

U.S. patent application Ser. No. 14/248,595, entitled SURGICAL INSTRUMENT SHAFT INCLUDING SWITCHES FOR CONTROLLING THE OPERATION OF THE SURGICAL INSTRUMENT, now U.S. Patent Application Publication No. 2014/0305988;

U.S. patent application Ser. No. 14/248,588, entitled POWERED LINEAR SURGICAL STAPLER, now U.S. Patent Application Publication No. 2014/0309666;

U.S. patent application Ser. No. 14/248,591, entitled TRANSMISSION ARRANGEMENT FOR A SURGICAL INSTRUMENT, now U.S. Patent Application Publication No. 2014/0305991;

U.S. patent application Ser. No. 14/248,584, entitled MODULAR MOTOR DRIVEN SURGICAL INSTRU- MENTS WITH ALIGNMENT FEATURES FOR ALIGNING ROTARY DRIVE SHAFTS WITH SURGICAL END EFFECTOR SHAFTS, now U.S. Patent Application Publication No. 2014/0305994;

U.S. patent application Ser. No. 14/248,587, entitled POWERED SURGICAL STAPLER, now U.S. Patent Application Publication No. 2014/0309665;

U.S. patent application Ser. No. 14/248,586, entitled DRIVE SYSTEM DECOUPLING ARRANGEMENT FOR A SURGICAL INSTRUMENT, now U.S. Patent Application Publication No. 2014/0305990; and U.S. patent application Ser. No. 14/248,607, entitled MODULAR MOTOR DRIVEN SURGICAL INSTRUMENTS WITH STATUS INDICATION ARRANGEMENTS, now U.S. Patent Application Publication No. 2014/0305992.

Applicant of the present application also owns the following patent applications that were filed on Apr. 16, 2013 and which are each herein incorporated by reference in their respective entireties:

U.S. Provisional Patent Application Ser. No. 61/812,365, entitled SURGICAL INSTRUMENT WITH MULTIPLE FUNCTIONS PERFORMED BY A SINGLE MOTOR;

U.S. Provisional Patent Application Ser. No. 61/812,376, entitled LINEAR CUTTER WITH POWER;

U.S. Provisional Patent Application Ser. No. 61/812,382, entitled LINEAR CUTTER WITH MOTOR AND PISTOL GRIP;

U.S. Provisional Patent Application Ser. No. 61/812,385, entitled SURGICAL INSTRUMENT HANDLE WITH MULTIPLE ACTUATION MOTORS AND MOTOR CONTROL; and U.S. Provisional Patent Application Ser. No. 61/812,372, entitled SURGICAL INSTRUMENT WITH MULTIPLE FUNCTIONS PERFORMED BY A SINGLE MOTOR.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongated shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

An end effector can be configured to articulate relative to the handle and/or shaft of a surgical instrument. For example, the end effector can be pivotably and/or rotatably coupled to the shaft of the surgical instrument such that the end effector is configured to pivot relative to the shaft and the handle. In various instances, the end effector can be configured to articulate at an articulation joint located intermediate the end effector and the shaft. In other instances, the shaft can include a proximal portion, a distal portion, and an articulation joint, which can be located intermediate the proximal portion and the distal portion of the shaft, for example.

FIGS. 1-5 illustrate aspects of a modular surgical cutting and fastening instrument that, in one form, includes a motor-driven, reusable handle module 10 that may be used, and reused, in connection with one or a variety of different detachable (and typically reusable) shaft modules (DSM)s. As described in more detail below, the handle module 10 may include a housing 12 with one or more motor-driven rotary drive systems that generate and apply various control motions to corresponding drive shaft portions of a particular DSM coupled thereto. Two such rotary drive systems 20, 40 are shown in the handle module 10 of FIGS. 1 and 5. The first rotary drive system 20 may be employed, for example, to apply "closure" motions to a corresponding closure drive shaft assembly that is operably supported in the DSM and the second rotary drive system 40 may be employed, for example, to apply "firing" motions to a corresponding firing drive shaft assembly in the DSM that is coupled thereto. The various DSMs may be releasably and interchangeably connected to the housing 12. Three exemplary DSMs that could be connected to the handle module 10 in various arrangements are depicted in FIG. 1. The depicted exemplary DSMs include an open linear stapler DSM 1, a curved cutter stapler DSM 2, and a circular surgical stapler DSM 3. Other DSM types that are adapted for the drive systems 20, 40 of the handle module 10 could also be used, including an endocutter DSM, which is described in more detail in U.S. patent application Ser. No. 14/633,541, entitled MODULAR STAPLING ASSEMBLY, which was filed on Feb. 27, 2015, and is incorporated by reference in its entirety. More details about an exemplary dual-drive surgical cutting and fastening instrument are provided in U.S. patent application Ser. No. 14/248,590, entitled MOTOR DRIVEN SURGICAL INSTRUMENTS WITH LOCKABLE DUAL DRIVE SHAFTS, filed Apr. 9, 2014, hereinafter "the '590 application," which is incorporated herein by reference in its entirety.

As shown in FIGS. 1-5, the housing 12 comprises a handle 14 that is configured to be grasped, manipulated and actuated by a clinician. The handle 14 may comprise a pair of handle housing segments 16 and 18 that may be interconnected by screws, snap features, adhesive, etc. In the illustrated arrangement, the handle housing segments 16, 18 cooperate to form a pistol grip portion 19 that can be gripped and manipulated by the clinician. The handle 14 operably supports the two rotary drive systems 20, 40.

The first and second rotary drive systems 20, 40 may be powered by a motor 80 through a "shiftable" transmission assembly 60 that essentially shifts power/motion between two power trains. The first rotary drive system 20 includes a first rotary drive shaft 22 that is rotatably supported in the housing 12 of the handle 14 and defines a first drive shaft axis "FDA-FDA." A first drive gear 24 is keyed onto or otherwise non-rotatably affixed to the first rotary drive shaft 22 for rotation therewith about the first drive shaft axis FDA-FDA. Similarly, the second rotary drive system 40 includes a second rotary drive shaft 42 that is rotatably supported in the housing 12 of the handle 14 and defines a second drive shaft axis "SDA-SDA." In at least one arrangement, the second drive shaft axis SDA-SDA is offset from and parallel or substantially parallel to the first drive shaft axis FDA-FDA. As used in this context, the term "offset" means that the first and second drive shaft axes are not coaxial. The second rotary drive shaft 42 has a second drive gear 44 keyed onto or otherwise non-rotatably affixed to the second drive shaft 42 for rotation therewith about the second drive shaft axis SDA-SDA. In addition, the second drive shaft 42 has an intermediate drive gear 46 rotatably journaled thereon such that the intermediate drive gear 46 is freely rotatable on the second rotary drive shaft 42 about the second drive shaft axis SDA-SDA.

In one form, the motor 80 includes a motor output shaft that has a motor drive gear 82 attached thereto. The motor drive gear 82 is configured for intermeshing "operable" engagement with the transmission assembly 60. In at least one form, the transmission assembly 60 includes a transmission carriage 62 that is supported for axial travel between the drive gear 82 and gears 44 and 46 on the second rotary drive shaft 42. For example, the transmission carriage 62 may be slidably journaled on a support shaft 63 that is mounted within the housing 12 on a shaft mount 61 such that the line of action of the transmission carriage is perpendicular to the gear trains of the rotary drive systems. The shaft mount 61 is configured to be rigidly supported within slots or other features within the handle module 10. The transmission carriage 62 includes a carriage gear 64 that is rotatably supported on the support shaft 63 and is configured for selective meshing engagement with gears 44 and 46 while in driving engagement with drive gear 82. In the arrangement depicted in FIGS. 1-5, the transmission carriage 62 is attached operably to a shifter or a "means for shifting" 70 that is configured to shift axially the transmission carriage 62 between a "first drive position" and a "second drive position." In one form, for example, the means for shifting 70 includes a shifter solenoid 71 that is supported within the housing 12 of the handle 14. The shifter solenoid 71 may comprise a bi-stable solenoid or, for example, may comprise a dual position, spring loaded solenoid. The illustrated arrangement includes a spring 72 that biases the transmission carriage 62 in the distal direction "DD" to the first drive position wherein the carriage gear 64 is in meshing engagement with the intermediate drive gear 46 while also in meshing engagement with the drive gear 82. When in that first drive position, activation of the motor 80 will result in rotation of gears 82, 46 and 24, which will ultimately result in rotation of the first drive shaft 22.

Figure 3:
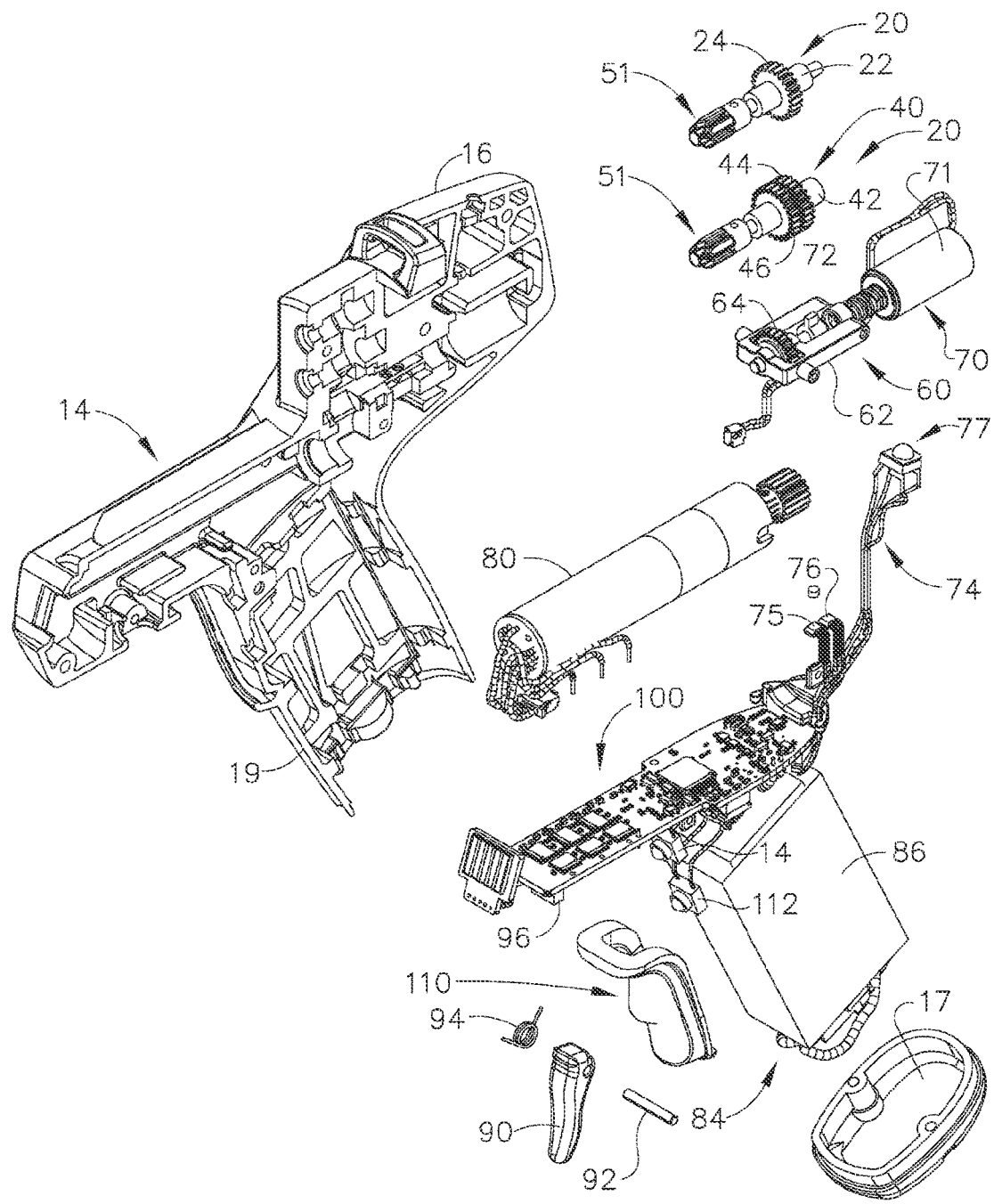
FIG. 3 is a partial exploded assembly view of the handle module of FIG. 1.
Figure 4:
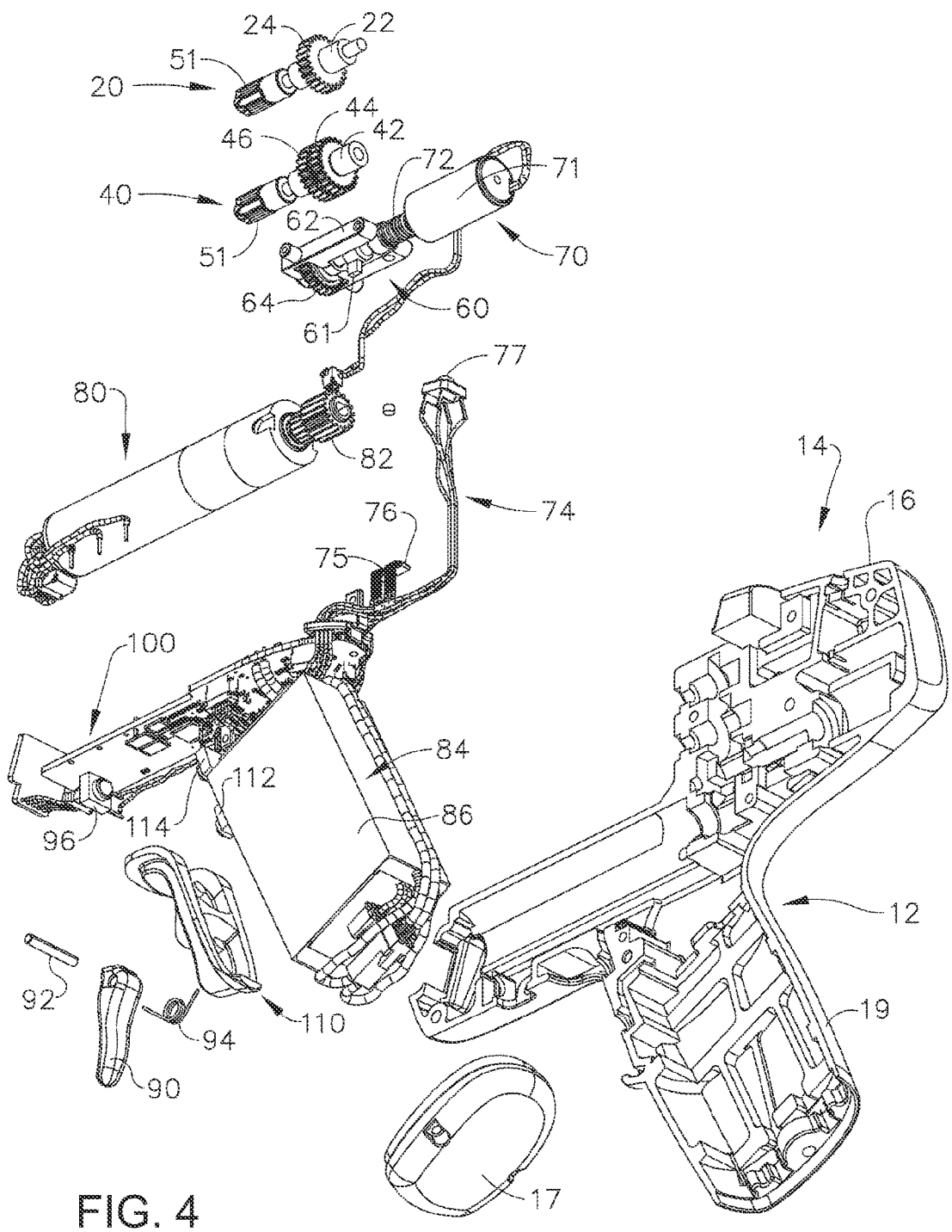
FIG. 4 is another partial exploded assembly view of the handle module of FIG. 1.
Figure 5:
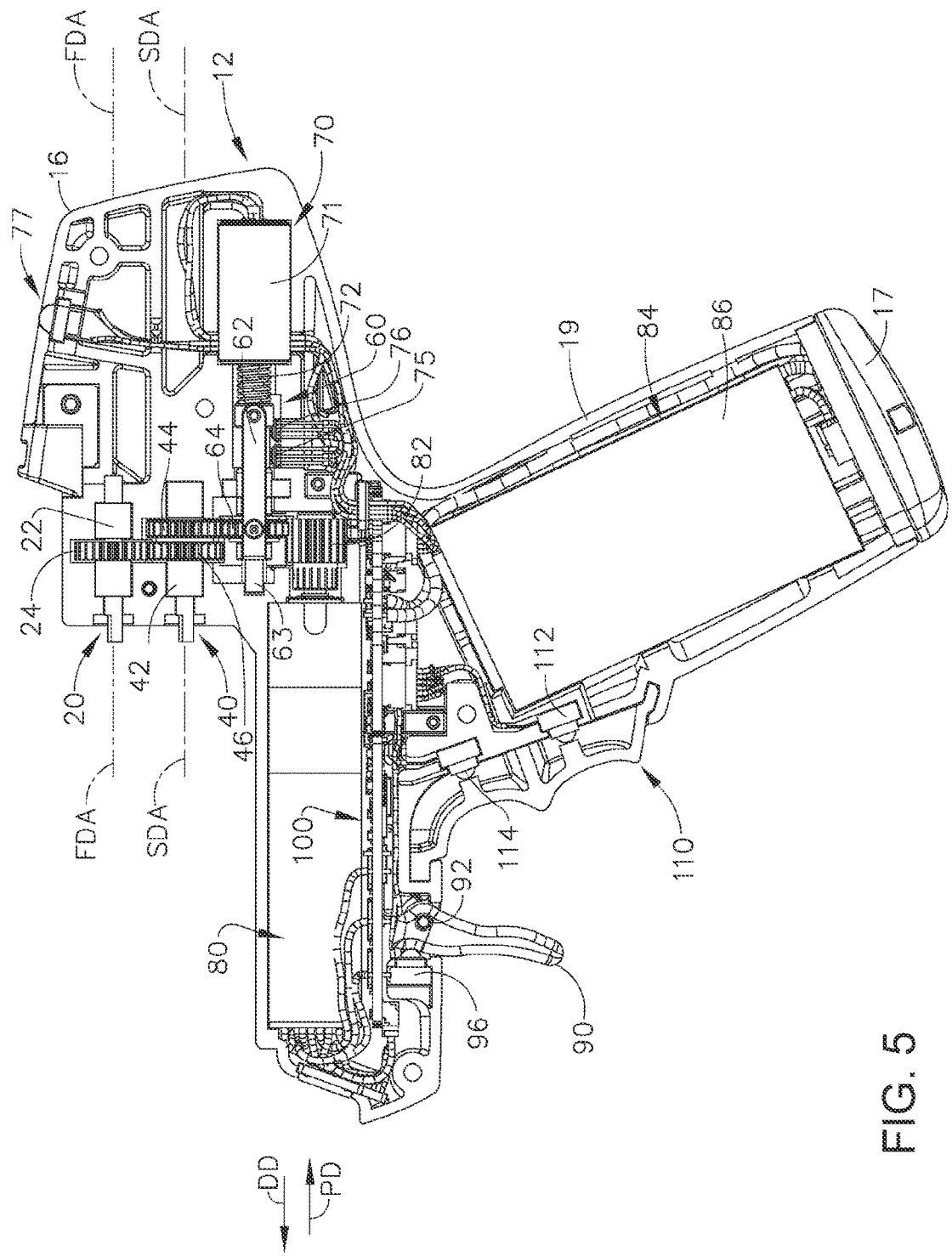
FIG. 5 is a side elevational view of the handle module of FIG. 1 with a portion of the handle housing removed.

The shifter solenoid 71 may be actuated by a firing trigger 90 that is pivotally supported on the housing 12 of handle 14 as shown in FIGS. 1-5. In the illustrated embodiment, the firing trigger 90 is pivotally supported on a firing trigger shaft 92 mounted in the handle 14. The firing trigger 90 is normally biased in an unactuated position by a firing trigger spring 94, as shown in FIG. 3. The firing trigger 90 is mounted for operable actuation of a firing switch 96 that is operably supported on a control circuit board assembly 100 housed in the housing 12 of the handle module 10. In the illustrated arrangement, actuation of the firing trigger 90 results in the actuation of the shifter solenoid 71. Actuation of the firing trigger 90 results in the shifter solenoid 71 pulling the transmission carriage 62 in the proximal direction "PD" to thereby move the carriage gear 64 into meshing engagement with the second drive gear 44. Actuation of motor 80 when the carriage gear 64 is in meshing engagement with the drive gear 82 and the second drive gear 44 will result in the rotation of the second drive shaft 42 about the second drive shaft axis "SDA." The shiftable transmission assembly 60 may also include an indicator system 74 that includes a pair of switches 75 and 76 that are operably coupled to the control board 100 as well as a transmission indicator light 77. The switches 75, 76 serve to detect the position of the transmission carriage 62, which results in the control system actuating the indicator light 77 depending upon the position of the transmission carriage 62. For example, the indicator light 77 may be energized when the transmission carriage 62 is in the first drive position. This provides the clinician with an indication that actuation of the motor 80 will result in the actuation of the first drive system 20.

The motor 80 may be a DC brushed driving motor having a maximum rotation of, approximately, 25,000 RPM, for example. In other arrangements, the motor may include a brushless motor, a cordless motor, a synchronous motor, a stepper motor, or any other suitable electric motor, including autoclavable motors. The motor 80 may be powered by a power source 84 that in one form may comprise a power pack 86 that is removably stored in the pistol grip portion 19 of the handle 14. To access the power pack 86, the clinician removes a removable cap 17 that is attached at the bottom of the pistol grip portion 19. The power pack 86 may operably support a plurality of battery cells (not shown) therein. The battery cells may each comprise, for example, a Lithium Ion ("LI") or other suitable battery type. The power pack 86 is configured for removable operable attachment to the control circuit board assembly 100 of the handle module 10, which is also operably coupled to the motor 80 and mounted within the handle 14. The power pack 86 may comprise a number of battery cells connected in series that may serve as the power source for the surgical instrument. In addition, the power source 84 may be replaceable and/or rechargeable and, in at least one instance, can include CR123 batteries, for example.

The motor 80 may be actuated by a "rocker-trigger" 110 that is pivotally mounted to the pistol grip portion 19 of the handle 14. The rocker trigger 110 is configured to actuate a first motor switch 112 that is operably coupled to the control board 100. The first motor switch 112 may comprise a pressure switch that is actuated by pivoting the rocker trigger 110 into contact therewith. Actuation of the first motor switch 112 will result in actuation of the motor 80 such that the drive gear 82 rotates in a first rotary direction. A second motor switch 114 is also attached to the circuit board 100 and mounted for selective contact by the rocker trigger 110. Actuation of the second motor switch 114 will result in actuation of the motor 80 such that the drive gear 82 is rotated in a second direction. For example, in use, a voltage polarity provided by the power source 84 can operate the electric motor 80 in a clockwise direction wherein the voltage polarity applied to the electric motor by the battery can be reversed in order to operate the electric motor 80 in a counter-clockwise direction. The handle 14 can also include a sensor that is configured to detect the directions in which the drive systems are being moved.

The housing 12 may also comprise a surgical instrument contact board 30 mounted thereto. Correspondingly, the various DSMs (e.g., DSMs 1, 2, 3) may include a mating DSM contact board (see FIGS. 34-60 of the '590 application). The DSM contact board may be positioned in the DSM such that when the DSM is operably coupled to the handle module 10, the end effector contact board is electrically coupled to a handle module contact board 30 mounted in the handle module 10. In such a manner, data and/or electric power can be transferred between the handle module 10 and the DSM via the mating contact boards.

Figure 6:
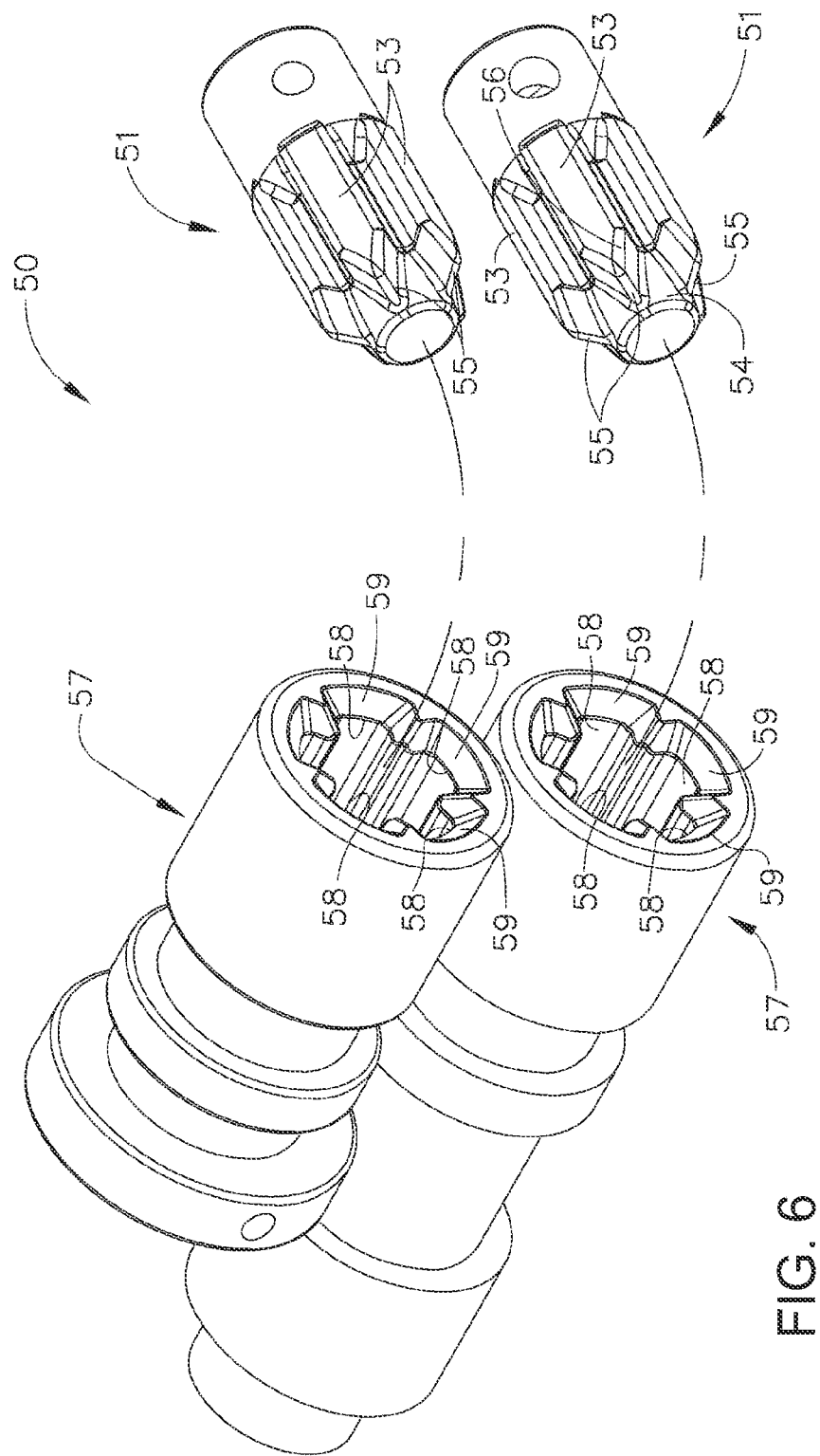
FIG. 6 is an exploded assembly view of a mechanical coupling system for operably coupling the rotary drive systems of the handle module of FIG. 1 to the drive systems of a detachable shaft module.

FIG. 6 illustrates one form of mechanical coupling system 50 that may be employed to facilitate the simultaneous removable and operable coupling of the two drive systems 20, 40 in the handle module 10 to the corresponding "driven" shafts in the DSMs. The coupling system 50 may comprise male couplers that may be attached to the drive shafts in the handle module 10 and corresponding female socket couplers that are attached to the driven shafts in the surgical DSM. Each of the male couplers 51 are configured to be drivingly received within corresponding female socket couplers 57 that may also be attached to the driven shafts within the DSM.

Arrangements for driving the drive systems 20, 40 are disclosed in the '590 application, including that the handle module 10 may include multiple motors.

Figure 7:
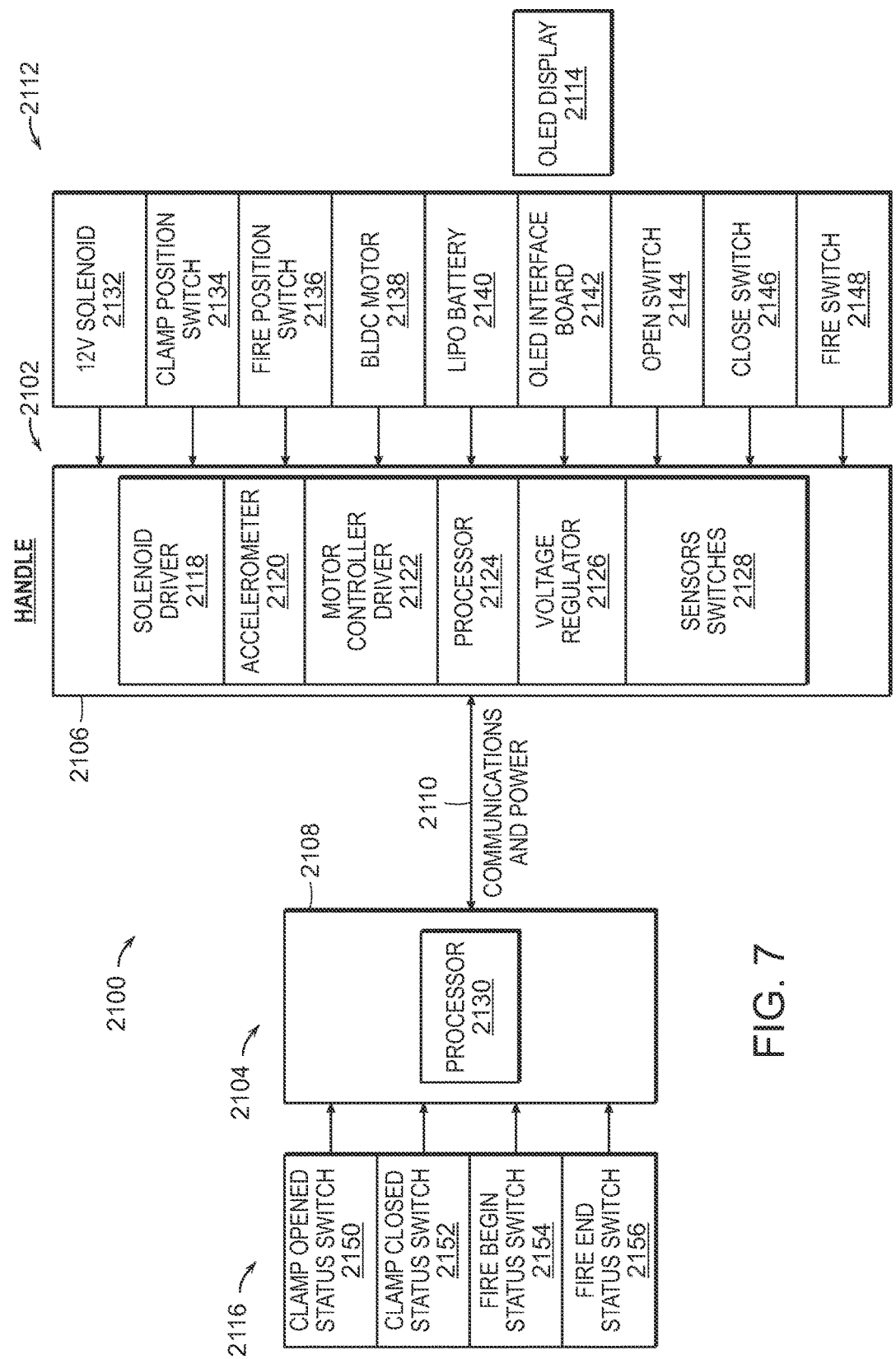
FIG. 7 is block diagram depicting electrical components of the handle module of FIG. 1 and the detachable shaft module.

FIG. 7 is a block diagram of a modular motor driven surgical instrument 2100 comprising a handle module 2102 and a DSM 2104. The handle and DSMs 2102, 2104 comprise respective electrical subsystems 2106, 2108 electrically coupled by a communications and power interface 2110. The components of the electrical subsystem 2106 of the handle portion 2102 are supported by, and can be connected to, the previously described control board 100. The communications and power interface 2110 is configured such that electrical signals and/or power can be readily exchanged between the handle portion 2102 and the shaft portion 2104.

In the illustrated example, the electrical subsystem 2106 of the handle module 2102 is coupled electrically to various electrical elements 2112 and a display 2114. In one instance, the display 2114 is an organic light emitting diode (OLED) display, although the display 2114 should not be limited in this context, and other display technologies could be used. The electrical subsystem 2108 of the DSM 2104 is electrically coupled to various electrical elements 2116 of the DSM 2104.

In one aspect, the electrical subsystem 2106 of the handle module 2102 comprises a solenoid driver 2118, an accelerometer system 2120, a motor controller/driver 2122, a handle processor 2124, a voltage regulator 2126, and is configured to receive inputs from a plurality of sensor switches 2128 that may be located either in the DSM and/or the handle. The handle processor 2124 may be a general-purpose microcontroller suitable for medical and surgical instrument applications. In one instance, the handle processor 2124 may be a TM4C123BH6ZRB microcontroller from Texas Instruments that comprises a 32-bit ARM® Cortex™-M4 80-MHz processor and on-chip memory, such as 256 KB Flash, 32 KB SRAM, internal ROM for C Series software, and 2 KB EEPROM. The electrical subsystem 2106 could also comprise one or more separate, external memory chips/circuits (not shown) connected to the handle processor 2124 via a data bus. As used herein, a "processor" or "processor circuit," such as the handle processor 2124, may be implemented as a microcontroller, microprocessor, a field programmable gate array (FPGA), or an application specific integrated circuit (ASIC), that executes program code, such as firmware and/or software, stored in associated memory to perform the various functions programmed by the program code.

In one aspect, the electrical subsystem 2106 of the handle module 2102 receives signals from the various electrical components 2112, including a solenoid 2132, a clamp position switch 2134, a fire position switch 2136, a motor 2138, a battery pack 2140, an OLED interface board 2142 (which drives the display 2114), and various switches, such as an open switch 2144 (which indicates whether the closure trigger is open), a close switch 2146 (which indicates whether the closure trigger is closed), and a fire switch 2148 (which indicated whether the fire switch is activated or not). The motor 2138 may represent motor 80 in FIGS. 2-5.

In one aspect, the electrical subsystem 2108 of the DSM 2104 comprises a shaft processor 2130. The electrical subsystem 2108 of the DSM is configured to receive signals from various switches and sensors 2116 located in the DSM that are indicative of the status of the clamp jaws and cutting element in the DSM. In particular, the electrical subsystem 2108 of the DSM may receive signals from a clamp opened status switch 2150 (which indicates whether the end effector clamp is open), a clamp closed status switch 2152 (which indicates whether the end effector clamp is closed), a fire begin status switch 2154 (which indicates whether the end effector commenced firing), and a fire end status switch 2156 (which indicates whether the end effector ended firing), so that the various switches indicate the states of the clamp and cutting element.

The accelerometer system 2120 may include a MEMS motion sensor that senses 3-axis motion of the handle module 10, such as a LIS331DLM accelerometer from STMicroelectronics. The motor controller/driver 2122 may comprise a three phase brushless DC (BLDC) controller and MOSFET driver, such as the A3930 motor controller/driver provided by Allegro, for example. In one aspect, the modular motor driven surgical instrument 2100 is equipped with a brushless DC electric motor 2138 (BLDC motor, BL motor), also known as an electronically commutated motor (ECM, EC motor). One such motor is the BLDC Motor B0610H4314 provided by Portescap. The sensor switches 2128 may include one or more unipolar integrated circuit type Hall Effect sensors. The voltage regulator 2126 regulates the power supplied to the various electrical components of the handle module 2102 and DSM 2104 from a power source (e.g., battery 2140). The battery 2140, which can represent battery pack 86 in FIGS. 1-5, may be, for example, a lithium-ion polymer (LiPo) battery, polymer lithium ion, and/or lithium polymer batteries, for example, which (abbreviated Li-poly, Li-Pol, LiPo, LIP, PLi or LiP) are rechargeable (secondary cell) batteries. The LIPO battery 2140 may comprise several (e.g., four or six) identical secondary cells in parallel (a "pack"). The OLED interface 2142 is an interface to the OLED display 2114, which comprises organic light-emitting diodes.

In one aspect, the DSM processor 2130 of the electrical subsystem 2108 of the DSM 2104 may be implemented as an ultra-low power 16-bit mixed signal MCU, such as the MSP430FR5738 Ultra-low Power MCU from Texas Instruments. It may comprise, among other things, internal RAM nonvolatile memory, a CPU, an A/D converter, a 16-channel comparator, and three enhanced serial channels capable of I2C, SPI, or UART protocols. The subsystem 2108 could also comprise one or more separate, external memory chips/circuits connected to the DSM processor 2130 via a data bus.

More details about exemplary electrical subsystem for the handle and DSMs 2102, 2104 may be found in the '590 application. In operation, the electrical subsystem 2106 of the handle module 2102 receives signals from the open switch 2144, close switch 2146, and fire switch 2148 supported on a housing of the handle module portion 2102 (e.g., housing 12). When a signal is received from the close switch 2146 the handle processor 2124 operates the motor 2138 to initiate closing the clamp arm. Once the clamp is closed, the clamp closed status switch 2152 in the end effector sends a signal to the shaft processor 2130, which communicates the status of the clamp arm to the handle processor 2124 through the communications and power interface 2110.

Once the target tissue has been clamped, the fire switch 2148 may be actuated to generate a signal, which is received by the handle processor 2124. In response, the handle processor 2124 actuates the transmission carriage to its second drive position such that actuation of the motor 2138 will result in the rotation of a second drive shaft. Once the cutting member is positioned, the fire begin status switch 2154 located in the end effector sends a signal indicative of the position of the cutting member to the DSM processor 2130, which communicates the position back to the handle processor 2124 through the communications and power interface 2110.

Actuating the first switch 2148 once again sends a signal to the handle processor 2138, which in response actuates the second drive system and the firing system in the DSM to drive the tissue cutting member and wedge sled assembly distally through the surgical staple cartridge. Once the tissue cutting member and wedge sled assembly have been driven to their distal-most positions in the surgical staple cartridge, the fire end switch 2156 sends a signal to the DSM processor 2130 which communicates the position back to the handle processor 2124 through the interface 2110. Now the fire switch 2148 may be activated to send a signal to the handle processor 2124, which operates the motor 2138 in reverse rotation to return the firing system to its starting position.

Actuating the open switch 2144 once again sends a signal to the handle processor 2124, which operates the motor 2138 to open the clamp. Once open, the clamp opened status switch 2150 located in the end effector sends a signal to the shaft processor 2130, which communicates the position of the clamp to the handle processor 2124. The clamp position switch 2134 and the fire position switch 2136 provide signals to the handle processor 2124 that indicate the respective positions of the clamp arm and the cutting member.

Figure 8:
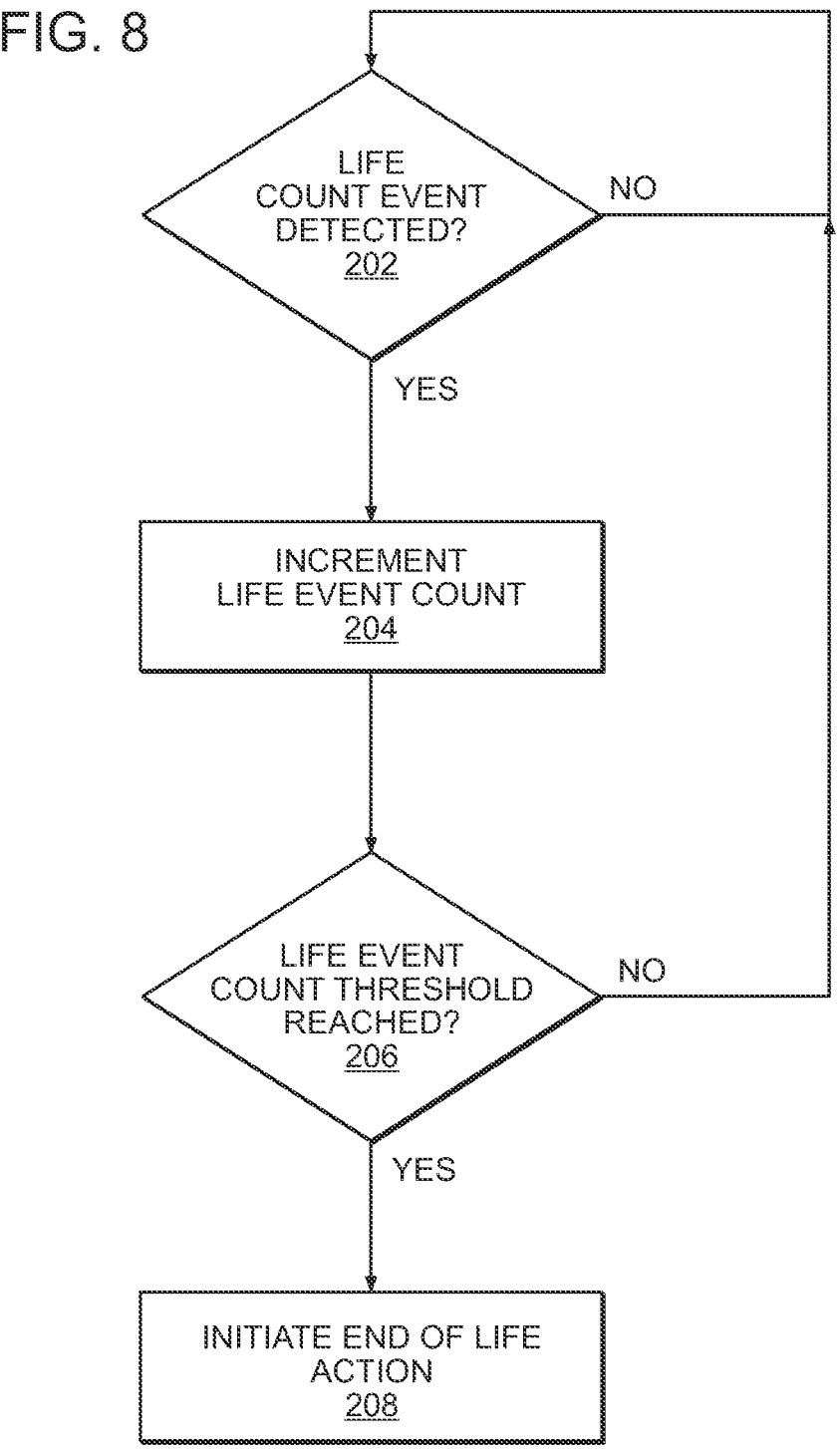
FIG. 8 is a diagram of a process flow executed by a handle processor of the handle module of FIG. 1 to determine when the handle module reaches its end of life.

FIG. 8 is a diagram of a process flow that may be executed by the handle processor 2124 in various instances by executing software and/or firmware instructions for the handle processor 2124 stored in the internal memory of the processor and/or in an external memory chip/circuit connected to the handle processor 2124. At step 202, the handle processor 2124 monitors input signals from sensors of the instrument 2100 for so-called "life events." The life events are events or actions involving the handle module 2102 and/or the DSM 2104 wherein the handle module 2102 should be retired (i.e., no longer used) once the threshold number of life events is reached. The life events could be the clamping of the end effector, the firing of the end effector, combinations of these events, and/or other events or actions involving the handle module 2102 and/or DSM 2104 that can be and are sensed by the instrument 2100. For example, the open switch 2144, the close switch 2146, and the fire switch 2148 of the handle module 2102 may be coupled to the handle processor 2124. In addition to or in lieu of the above, the clamp opened status switch 2150, the clamp closed status switch 2152, the fire begin status switch 2154, and the fire end status switch 2156 in the DSM 2104 may be coupled to the handle processor 2124 (via the interface 2110). A life event may occur and may be counted when some or all these respective switches are activated, and/or activated in a particular sequence detected by the handle processor 2124, depending on the design and application of the handle module 2102 and instrument 2100. For example, in various implementations, each detected clamp closure and each detected firing may count as a life event. Stated another way, a detected clamp closure can comprise a first life event and a detected firing can comprise a second, or different, life event. In other implementations, a sequence of a clamp closure followed by firing may count as one life event. Also, as described above, the handle processor 2124 can use inputs from the handle sensors 2144, 2146, 2148 and/or the DSM sensors 2150, 2152, 2154, 2156, for example, to detect life events.

The handle processor 2124 keeps a count of the life events. When a life event is detected, the handle processor 2124 increments the present value of the life event counter in either its internal or external memory at step 204. The counter may be a count-up counter, where the count is increased by one count (increment by +1) when a life event occurs until a pre-established threshold is met; or the counter may be a count-down counter, where the count is decreased by one count (incremented by −1) when a life event occurs until a specific end count (e.g., zero) is reached after starting at value that is different from the end count by the pre-established threshold. The pre-established life event count threshold could be set at any value desired by the manufacturer of the handle module 2102 in view of the particular sensor events that count as life events.

If the life event counter reaches the pre-established life event threshold at step 206, the handle processor 2124 may initiate one or more end-of-life actions at step 208, such as causing the display 2114 of the handle module 2102 or some other display (e.g., a mechanical counter visible to the user), for example, in communication with the handle processor 2124 to indicate that the handle module 2102 is spent (at end-of-life) and should be retired. Any suitable visual, tactile, and/or audible indication may be used. For example, the display 2114 may include an icon and/or text indicating that the end-of-life for the handle module has been reached. The display 2114 could also indicate the life event count on an on-going basis, such as by a numerical display or volume indicator (full, close to empty, etc.), for example, so that the user can monitor whether the handle module is nearing the end of its life cycle. In addition or in lieu of a constant display of the life event count, the display 2114 may have an icon and/or use text to show that the handle module is nearing the end of its life (e.g., "N uses left"). The handle processor 2124 may also initiate conditions that prevent further use of the handle module 2102 when the end-of-life count is reached, as described further below. If the end-of-life count has not been reached, the handle processor 2124 continues to monitor the switches and sensors for life count events until the end-of-life threshold is reached.

Various implementations of sensors could be used to detect certain life events. For example, the DSM that is used (e.g., DSM 1, 2 or 3) may include two drive shafts—one for driving the closure system and one for driving the firing system (each driven by one of the drive systems 20, 40 respectively), for example. Each such drive shaft may drive a carriage forward during a clamping or firing event, respectively. As such, the closure and/or firing systems may include switches that are triggered when the closure or firing carriage, as the case may be, contacts them. The switch(es) may be coupled to the handle processor 2124, and the handle processor 2124 may register a life event count when it receives a signal from the switch(es) that it has been triggered. The switches may be automatically-resettable push button switches that reset each time they are contacted—and triggered—by the carriage driven by the drive shaft.

Further to the above, the '590 application describes that the DSMs 1-3 may include a pair of lead screws for driving the closure and firing systems of various different types of DSMs. Examples of such lead screw pairs are shown in the '590 application at FIGS. 34-37 thereof for an open linear stapler, FIGS. 38-41 thereof for a curved cutter stapler, and FIGS. 42-45 thereof for a circular surgical stapler. Other DSM types that are adapted for the handle module could also be used, such as endocutters and/or right-angle staplers, for example. Since different DSMs could be used with the handle module, the handle module (e.g., the handle processor 2124) could use more sophisticated algorithms for tracking handle module usage and remaining life that depend on the number of times the various types of DSMs are used and fired. For example, in one instantiation, the handle processor 2124 could compute a progressively accumulating life event score that weighs the use by different DSMs differently (depending on how stressful they are on the handle module, for example) and compares the score to a predetermined threshold value. When the handle module's score reaches the threshold value, the handle module is retired (e.g., one or more end-of-life actions are taken). For example, the handle processor 2124 may compute the life event score based on the following relationship:

$$\text{Life Event Score} = \Sigma_{i=1}^{N} W_i \Sigma_{j=1}^{S} F_{i,j}$$

where i=1, . . . N represents the different DSM types that could be used with the handle module (e.g., endocutter, liner open, circular, curved, right-angle stapler, etc.), $W_i$ is a weighting factor for DSM type i, and $F_{i,j}$ is the number of firings for DSM type i over the j=1, . . . S procedures involving DSM type i. DSM types that impart less stress in general on the handle module could have a lower weight W than then DSM types that impart greater stress in general on the handle module. That way, in various arrangements, a handle module that is used only for high stress procedures would expire prior to a handle module that is used only for less stressful procedures, all other things being equal.

Figure 9:
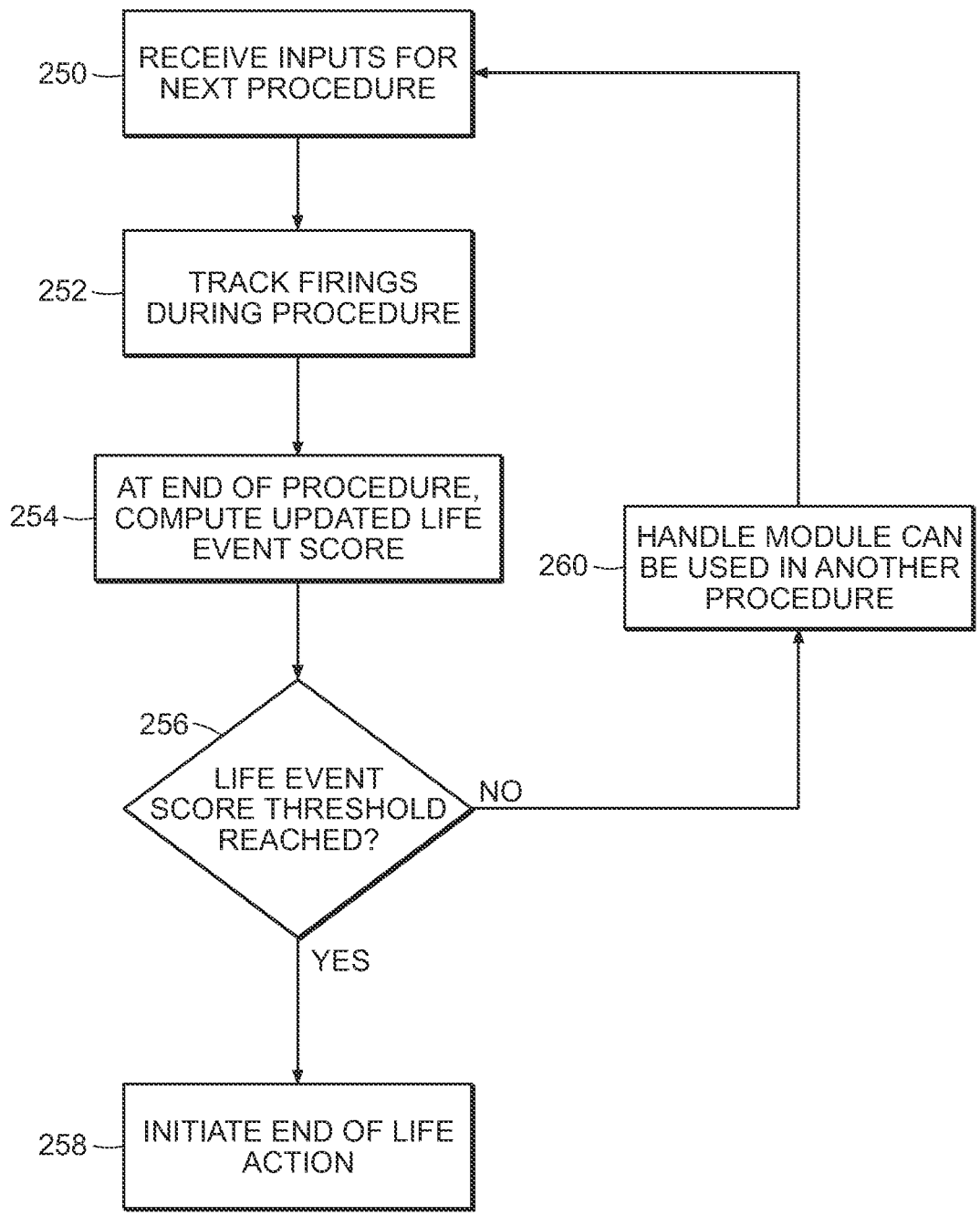
FIG. 9 is another diagram of a process flow executed by the handle processor of the handle module of FIG. 1 to determine when the handle module reaches its end of life.

FIG. 9 illustrates an exemplary process flow that the handle processor 2124 may execute to compute a life event score and/or compare the life event score to a threshold score. In such instances, the handle processor 2124 can execute firmware and/or software stored in internal and/or external memory, for example. Assuming that the threshold score of the handle module has not yet been reached, the process starts at block 250 where the handle processor 2124 receives inputs for the upcoming procedure. At least one such input can include an identification of the type of DSM that is attached to the handle module, which the handle processor can receive from the DSM processor 2130 when the DSM is connected to the handle module and/or when the handle processor 2124 and the DSM processor 2130 establish a data connection therebetween. In the process of recognizing and/or authenticating the DSM, the DSM processor 2130 sends an identifier to the handle processor 2124 that identifies the type of DSM (e.g., endocutter, circular, etc.) that is attached to the handle module. Next at step 252, the handle processor 2124 tracks how many times the handle module is fired during the surgical procedure. The handle processor 2124 may track how many times the handle module has been fired by tracking the number of times the firing trigger has been activated and/or by tracking feedback from the DSM, such as indications that the end effector cartridge has been replaced, for example.

Following the procedure and/or at any other suitable time, referring now to step 254, the handle processor 2124 may update the handle processor's life event score by adding the score for the just-completed procedure to the prior score. The score for the just-completed procedure may be based on multiplying the weighting for the DSM type used in the procedure $W_i$ and the number of firings in the procedure S. The handle processor 2124 may determine the weighting for the DSM type $W_i$ by looking up the weighting in a look-up table (stored in internal and/or external memory) based on the type identifier received from the DSM at step 250. At step 256, the handle processor compares the updated life event score for the handle module to the pre-established threshold score to determine if the handle module is at the end of its life. If the threshold has been reached, the process advances to step 258 where one or more end-of-life actions for the handle module are taken such as, for example, one or more of the end-of-life actions described herein. On the other hand, if the threshold has not yet been reached, the process can advance to step 260 so that the handle module can be used in at least one more procedure, whereupon the process of FIG. 9 is repeated.

The loading conditions experienced by the instrument can be used to track the usage of both the handle module and the DSM to assess whether one or both of the handle module and the DSM should be retired. One such instantiation can involve comparing the force actually exerted by the instrument to drive the firing member of the end effector to the force that the instrument was expected to experience, for example. Similarly, the force actually exerted to retract the firing member can be compared to the force that the instrument was expected to experience in order to assess whether the handle module and/or the DSM should be retired. The handle module can be rated to a threshold number of firings based on the force levels that the handle module is expected to experience. Similarly, the DSM can be rated to a threshold number of firings based on the force levels that the DSM is expected to experience. The handle module threshold number and the DSM threshold number can be the same or different. If the actual forces experienced by the handle module and/or the DSM meaningfully exceed the expected force levels, the handle processor and/or the DSM processor, as the case may be, can determine that the handle module and/or the DSM should be retired before reaching its expected number of firings.

Figure 10A:
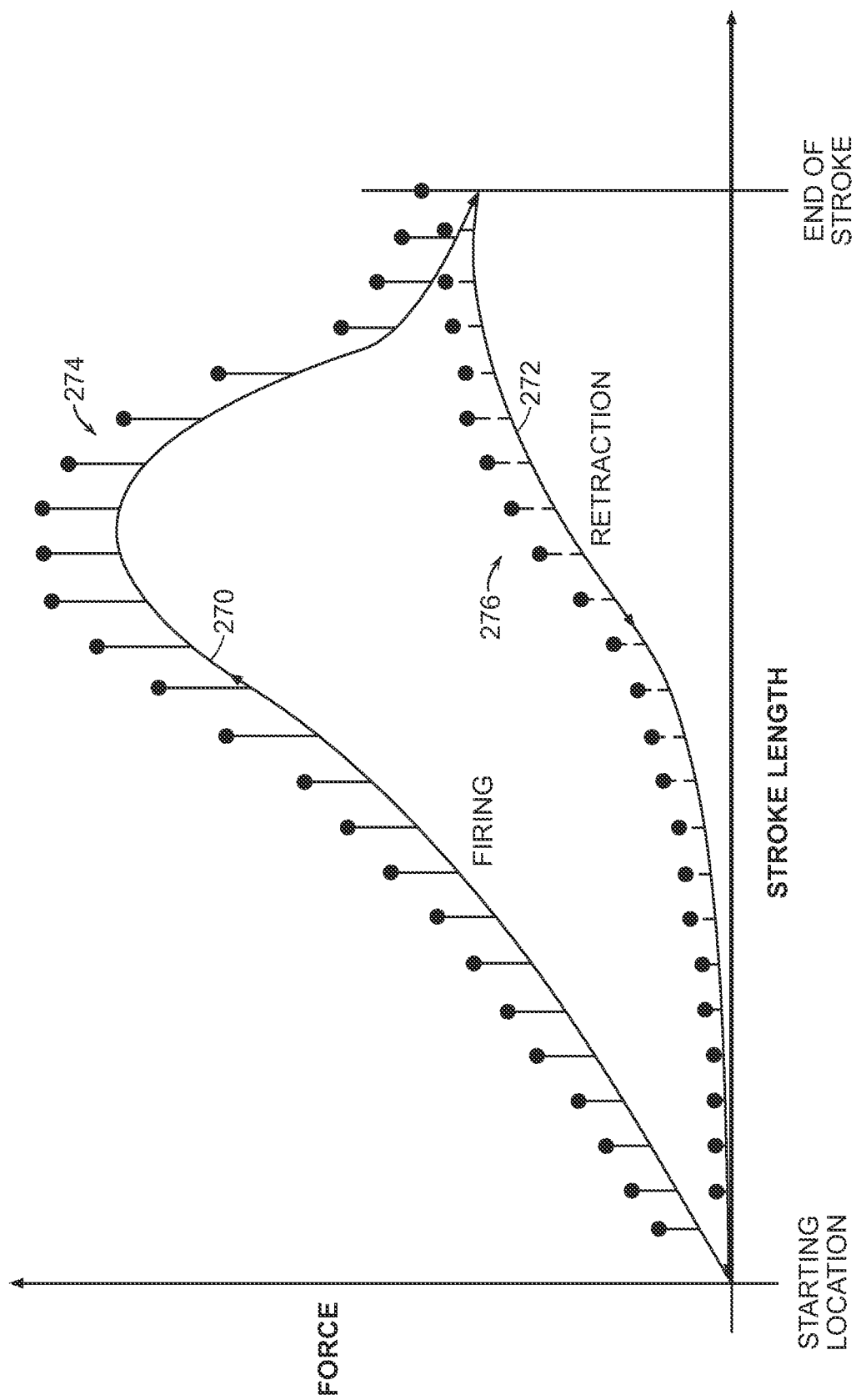
FIG. 10A is a chart showing differences between the expected firing and retraction forces to be applied by the handle module of FIG. 1 and the actual firing and retraction forces applied by the handle module as a function of the stroke of the shaft module.

In some instances, further to the above, the force exerted by a handle module and/or DSM may be constant throughout a firing stroke of the firing member; however, it is quite common for the force exerted by the handle module and/or DSM to change throughout the firing stroke. In either event, the force exerted by the handle module and/or the force expected to be exerted by the handle module can be a function of the firing member position. Similarly, the force exerted by the DSM and/or the force expected to be exerted by the DSM can be a function of the firing member position. A particular type of DSM can have an expected firing force which is correlated to the firing stroke of the DSM throughout the entire length thereof, i.e., the distance between the initial starting position of the firing member and its end-of-stroke position. The DSM can also have an expected retraction force which is correlated to the retraction stroke of the DSM throughout the entire length thereof, i.e., the distance between the end-of-stroke position of the firing member and its starting position. FIG. 10A shows an example of expected forces for one type of DSM. The upper curve 270 shows the expected firing forces as the firing member traverses the end effector from its starting position to its end-of-stroke position, and the lower curve 272 shows the expected retraction forces as the firing member is retracted back to its starting position. In this particular example, the expected firing forces are greater than the expected retraction forces.

For each firing, further to the above, the handle module and/or DSM processors can track the force exerted per unit distance increment (e.g., 1 millimeter) of stroke length. Moreover, the handle module and/or DSM processors can track the force exerted for each distance increment of stroke length and then compare the actual forces to the expected forces to see if the actual forces exerted exceeded the expected forces or not. One way to measure the force exerted by the instrument during firing and retraction is to measure the torque output of the motor(s) during the firing and retraction strokes. In at least one instance, the torque output of a motor can be determined based on the current drawn by the motor and the motor speed. In at least one such instance, the voltage applied to the motor is constant. The current can be measured with a current sensor; the motor speed can be measured with an encoder, for example. FIG. 10A shows exemplary force measurements as departures from the expected firing stroke forces and the expected retraction stroke forces. In this diagram, for the sake of simplicity in the illustration, all of the measured forces exceeded the expected force, and only the difference between the measured force and the expected force is show by the line segments 274 for the firing stroke and the by the dotted line segments 276 for the retraction stroke. The reader should appreciate that one or more measured forces could be less than their respective expected force.

Figure 10B:
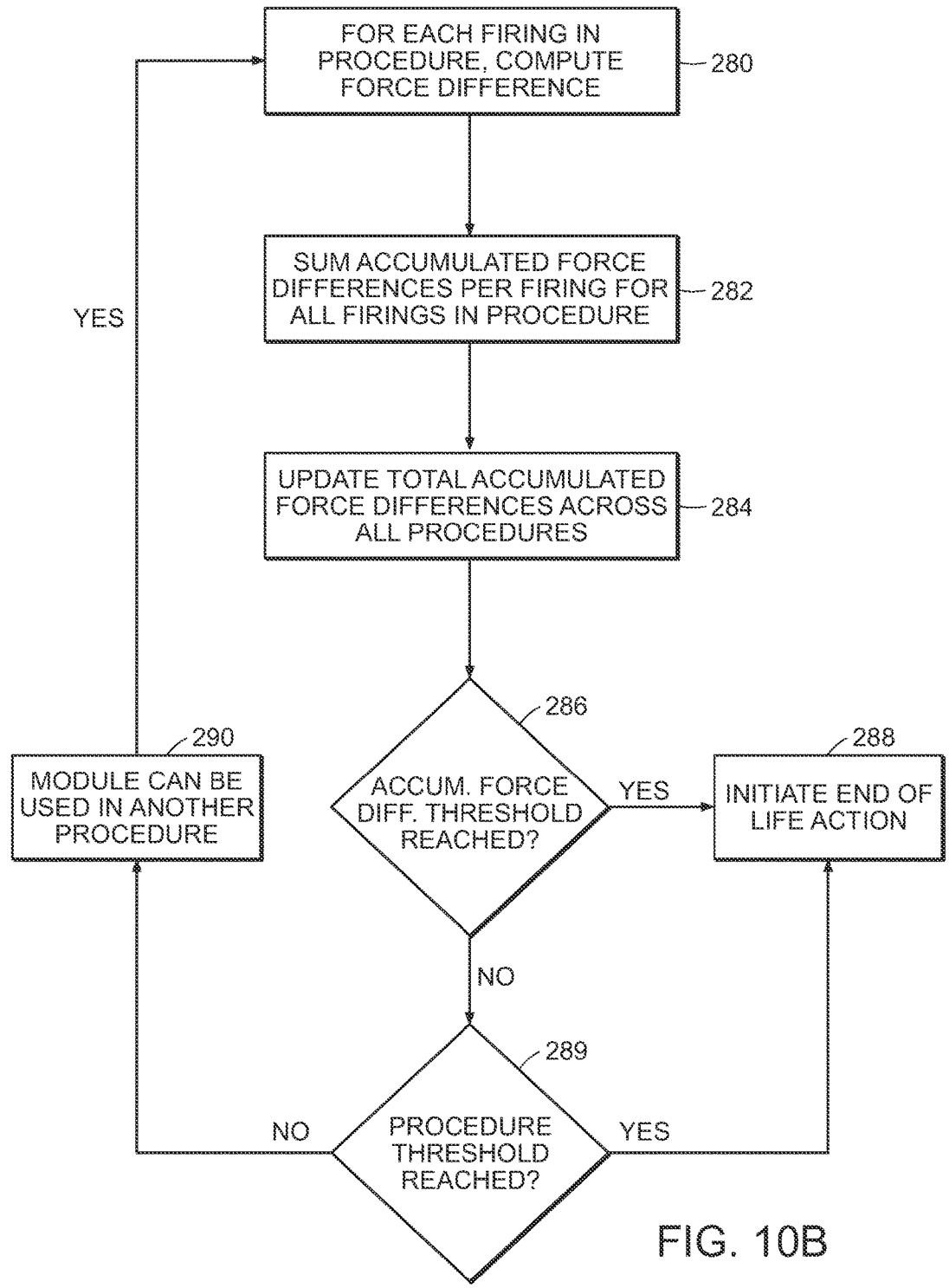
FIG. 10B is a diagram of a process flow executed by the handle processor of the handle module of FIG. 1 to determine when the handle module reaches its end of life based on the differences between the expected firing and retraction forces to be applied by the handle module of FIG. 1 and the actual firing and retraction forces applied by the handle module.

FIG. 10B is a diagram of an exemplary process flow executed by the handle module processor and/or the DSM processor by executing firmware and/or software stored in the memory of the handle module and/or DSM, as the case may be. Referring now to step 280, the processor can aggregate, i.e., accumulate, the difference between the measured force and the expected force at each unit length increment (denoted ΔL below) along the firing stroke and/or the retraction stroke of the instrument. For example, the accumulated force difference for a firing stroke and a subsequent retraction stroke could be computed based on the following relationship:

$$\text{Accumulated Force Difference} = \Sigma_{\Delta L=0}^{EOS}(F_{m,f,\Delta L} - F_{e,f,\Delta L}) + \Sigma_{\Delta L=EOS}^{0}(F_{m,r,\Delta L} - F_{e,r,\Delta L})$$

where EOS represents end-of-stroke location; $F_{m,f,\Delta L}$ and $F_{e,f,\Delta L}$ represent the measured and expected firing forces, respectively, at position ΔL; and $F_{m,r,\Delta L}$ and $F_{e,r,\Delta L}$ represent the measured and expected retraction forces respectively at position ΔL. At step 282, the processor can then accumulate the force differences by summing the accumulated force differences per firing for each of the firings that the handle module and/or DSM has experienced.

With regard to one particular embodiment, further to the above, the processor can calculate the accumulated force differences in real-time. In at least one instance, the processor can calculate the force differences after each firing and retraction cycle. In certain instances, the processor can calculate the force differences after each surgical procedure, which may include more than one firing and retraction cycle. For example, if there were seven (7) firings in a particular procedure, then the processor would sum the result from step 280 for each of the seven firings. Next, at step 284, the handle can update the total accumulated force differences for the handle module and/or the DSM, as the case may be, by adding the accumulated force differences for the recently-completed procedure to the total prior to the recently-completed procedure (or zero in the case of the module's first procedure). At step 286, the processor can then compare the updated accumulated force difference total to a threshold. If the threshold has been reached or otherwise satisfied, the process advances to step 288 where an end-of-life action for the handle module or DSM, as the case may be, is taken. Conversely, if at step 286 the processor determines that the threshold has not yet been reached, the handle module and/or DSM, as the case may be, can be used once again.

Even if the accumulated force difference threshold has not yet been reached, the handle module and/or the DSM, as the case may be, may have reached the end of its life according to a different threshold. For instance, the process of FIG. 10B can advance to step 289 after step 286 where the processor compares the total number of procedures involving the handle module and/or the DSM, as the case may be, to a procedure count threshold. In at least one example, a handle module can have a procedure count threshold of 20 procedures and a DSM can have a procedure count threshold of 10 procedures. Other examples are possible. In at least one other example, a handle module and a DSM can have the same procedure count threshold. If the procedure count threshold has been reached, the end-of-life action for the handle module and/or DSM, as the case may be, is initiated at step 288. Conversely, if the procedure count threshold has not yet been reached, the process advances to step 290 where the handle module and/or the DSM is prepared for another procedure. Any of the techniques described herein for tracking procedure counts may be used to detect the end of a procedure.

In various embodiments, the handle processor could perform the calculations for both the handle module and the DSM and then communicate the results for the DSM to the DSM processor so that the DSM processor can initiate the end-of-life actions, if required. Similarly, the DSM processor could perform the calculations for both the handle module and the DSM and then communicate the results for the handle module to the handle processor so that the handle processor can initiate the end-of-life actions, if required. In another arrangement, all of the measured forces for a procedure can be downloaded following a procedure to a remote processor, such as a processor in an inspection station or another remote computer-or-processor-based system that is connected to the handle module following a procedure for post-procedure processing, for example. Such an inspection station is disclosed and described in connection with FIGS. 12A-B, for example.

Figure 10C:
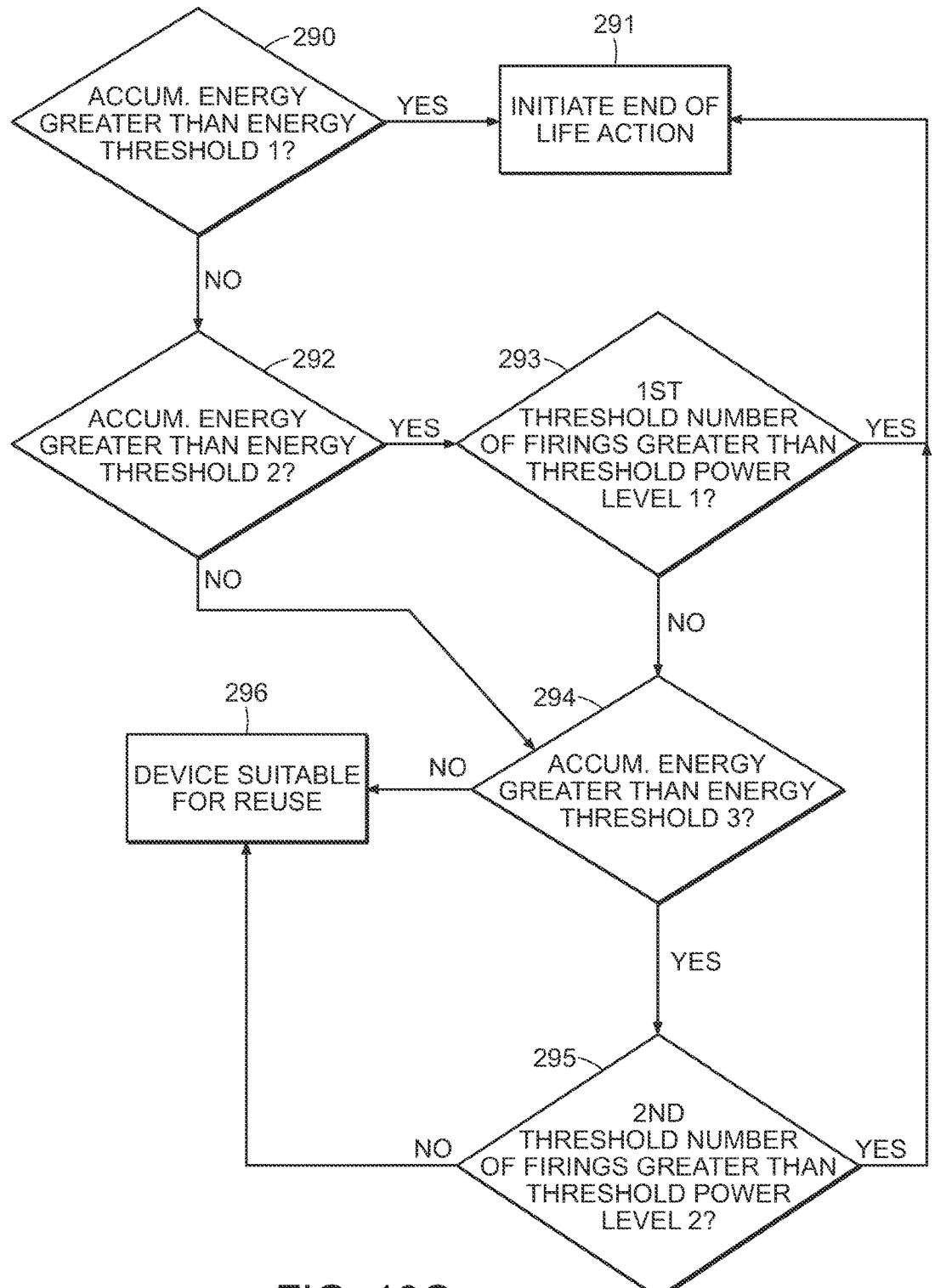
FIG. 10C is a diagram of a process flow executed by the handle processor of the handle module of FIG. 1 to determine when the handle module reaches its end of life based on the energy expended by the handle module during use, in aggregate, and the energy expended by the handle module during each use.
Figure 10D:
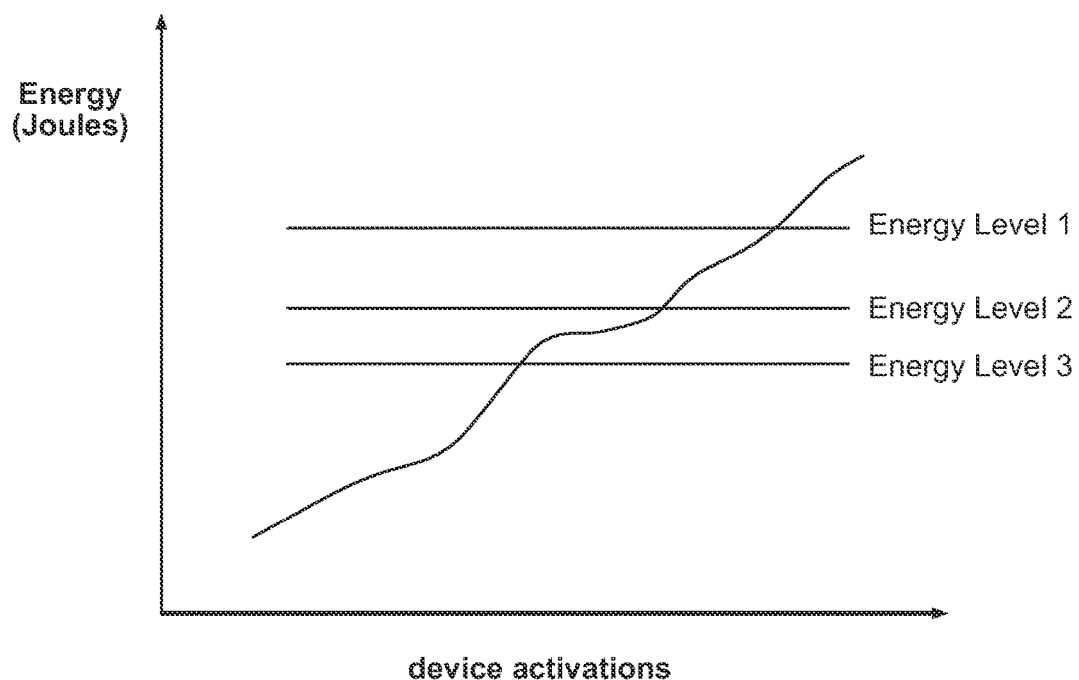
FIG. 10D is a chart showing an example of the energy expended by the handle module over a number of device activations, in aggregate.
Figure 10E:
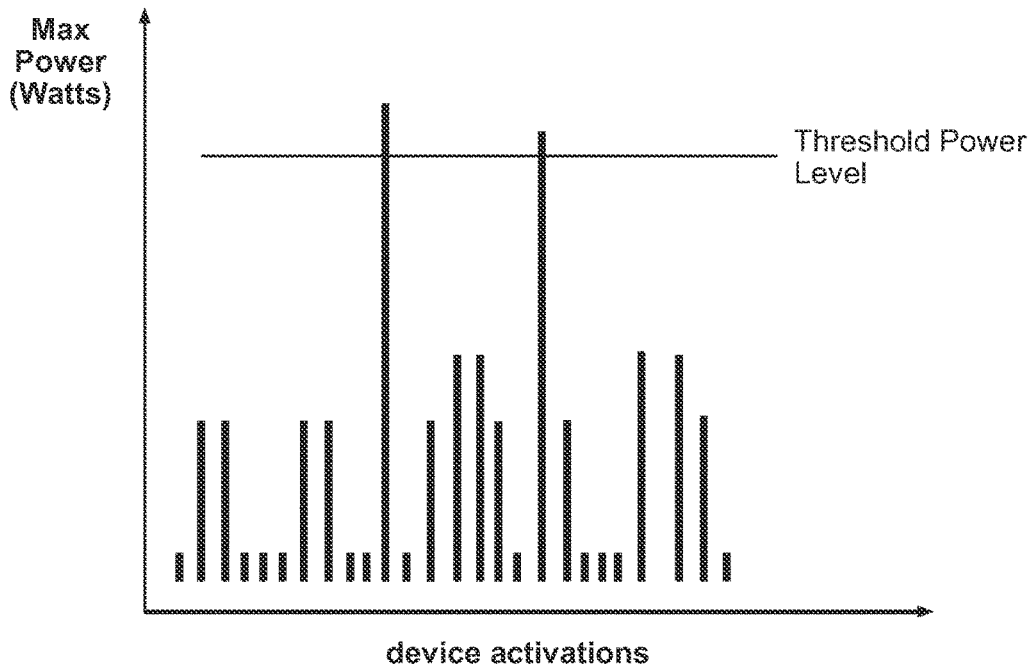
FIG. 10E is a chart showing an example of the power expended during each activation of the handle module of FIG. 1.

FIG. 10C illustrates, in conjunction with FIGS. 10D and 10E, another exemplary process flow that the handle processor could employ to monitor whether the handle module, for example, has reached its end of life. The process illustrated in FIG. 10C determines whether the handle module has reached its end of life based on the energy used by the handle module over its life, an exemplary graph of which is shown in FIG. 10D. FIG. 10D depicts the aggregate, or accumulated, energy spent by a handle module as a function of the uses, or firings, of the handle module. In addition to or in lieu of the above, the process illustrated in FIG. 10C can determine whether the handle module has reached its end of life based on the power used during each firing of the handle module, an exemplary graph of which is shown in FIG. 10E. FIG. 10E depicts the power consumed for each individual firing of the handle module. In at least one particular embodiment, the processor, in implementing the exemplary process of FIG. 10C, monitors whether the energy expended by the handle module, in the aggregate, exceeds various thresholds (see FIG. 10D) and, concomitantly, whether the handle module has had a certain number of firings above a threshold power level (see FIG. 10E). When both of these conditions have been met, in at least one instance, the handle processor can conclude that the handle module is at its end of life. In certain instances, the handle processor could utilize any number of multiple-factor tests, with thresholds for each test, to determine if a handle module is at its end of life. In at least one instance, the handle processor can determine that it has reached its end of life if any test threshold has been met or exceeded.

Following a procedure, the handle processor can execute the process of FIG. 10C by executing firmware and/or software stored in internal and/or external memory to determine whether the handle module is at its end of life. At step 290, the handle processor can compare the accumulated energy of the handle module over its life to a first threshold energy level, i.e., Energy Level 1 in FIG. 10D. Energy Level 1 can be 40 kJ, for example. The handle module may include a micro watt or power meter connected to the motor(s) of the handle module to measure and record the electrical parameters of the motor(s) so that the energy and power outputs of the motor(s) can be determined. If the first threshold energy level has been reached or exceeded, i.e., Energy Level 1, the handle processor can determine at step 291 that the handle module is at its end of life and initiate an end-of-life action, such as one or more of the end-of-life actions described herein, for example.

If the handle processor determines that first threshold energy level, i.e., Energy Level 1, has not been met at step 290, the process advances to step 292 where the handle module determines if a second, (e.g., lower) energy threshold has been met, i.e., Energy Level 2 in FIG. 10D. Energy Level 2 can be 30 kJ, for example. If the second threshold energy level has been reached or exceeded (without reaching or exceeding the first threshold energy level), the process advances to step 293 where the handle processor determines if the handle module has undergone a certain number of firings over its life that have exceeded a first power level threshold, e.g., two firings greater than 55 Watts (see FIG. 10E). If the second energy level threshold has been met or exceeded and the power level threshold has been met or exceeded the predetermined number of times, the handle processor can determine that the handle module is at its end of life. If, however, the power level threshold has not been met or exceeded the predetermined number of times, the handle processor can determine that the handle module has not yet reached its end of life even though the second energy level threshold has been met or exceeded. The dual factors of steps 292 and 293 can be another test on the handle module's life, and if the handle module fails both tests (i.e., both thresholds or conditions have been satisfied), the handle module can be determined to be at its end of life.

The handle processor can execute any number of such dual-factor tests. The example of FIG. 10C shows one additional such dual-factor test. If the dual factors of steps 292 and 293 are not both satisfied, the process can advance to step 294 where the handle module determines if a third (e.g., still lower) energy threshold, i.e., Energy Level 3, has been met. Energy Level 3 can be 25 kJ, for example. If the third threshold energy level has been reached or exceeded (without reaching or exceeding the third threshold energy level), the process advances to step 295 where the handle processor determines if the handle module has had a certain number of firings over its life (preferably greater than the number of such firings checked for at step 293) that exceeded a second power level threshold (which could be the same or different from the power level threshold at step 293), e.g., four firings greater than 55 Watts. The dual factors of steps 294 and 295 can be another test on the handle module's life, and if the handle module fails both tests (i.e., the thresholds or conditions have been satisfied), the handle module can be determined to be at its end of life. Otherwise, the handle processor can determine that the handle module is not at its end of life and can be used in a subsequent procedure.

It should be apparent that the steps of FIG. 10C can be performed in various orders while still achieving the same result. For example, steps 294 and 295 can be performed before step 290, and so on.

According to current best practices, a handle module should be sterilized before it is used to perform a surgical procedure. In various instances, the handle module is placed in a sterilization tray which is then placed in a sterilization chamber. In addition to or in lieu of the above described manners for tracking the end of life of the handle module, the number of times that the handle module is placed in a sterilization tray for sterilization could be used to track the end of life for the handle module. Stated another way, the number of times that a handle module is sterilized can serve as a proxy for the number of times that the handle module has been used. In at least one exemplary embodiment, each handle module has its own sterilization tray that keeps the sterilization count for that particular handle module. In such an arrangement, the sterilization tray may include a counter that is incremented each time the associated handle module is placed in the tray. The counter can have visual readout display that can show the number of times the handle module has been sterilized if a count-up counter is used or the number of sterilizations remaining, or permitted, when a count-down counter is used. That way the user can know when the sterilization limit is reached and, as a result, the user can retire the handle module and/or take other appropriate end-of-life measures. In order for the placement of the handle module in a sterilization tray to be used a proxy for the number of times the handle module is sterilized and, thus, a proxy for the number of times the handle module has been used, the handle module should be sterilized in one and only one sterilization tray. That way, the counter does not count placements in the tray of other handle modules. Accordingly, the handle module and sterilization tray could be provided together, as a kit for example, and they may include identifiers (e.g., numbers or icons) which show that they are to be used together. The handle module and DSM could be sterilized separately or together, for example.

Figure 11A:
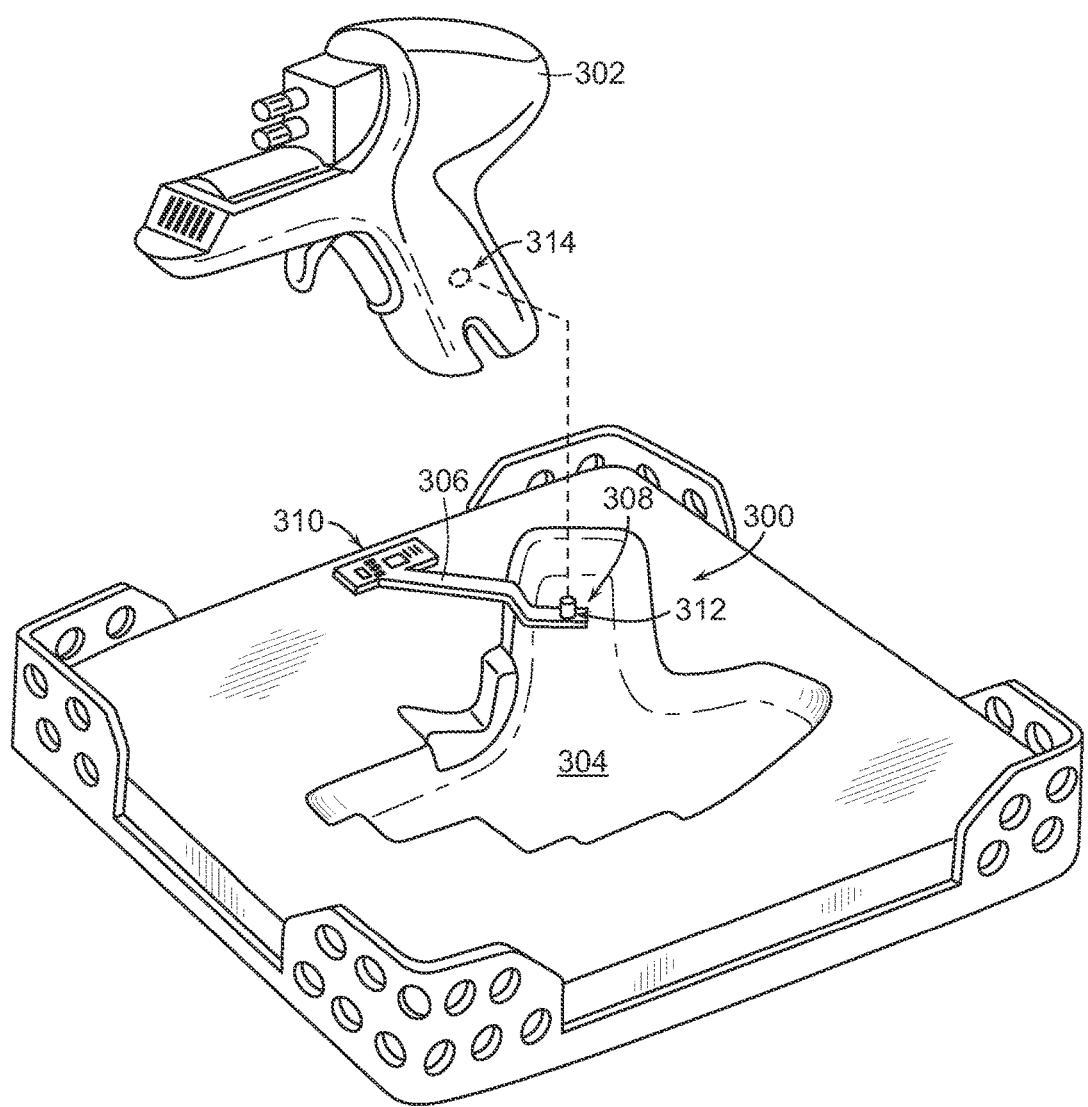
FIGS. 11A and 11B illustrate a sterilization tray in which a handle module may be inserted for sterilization.
Figure 11B:
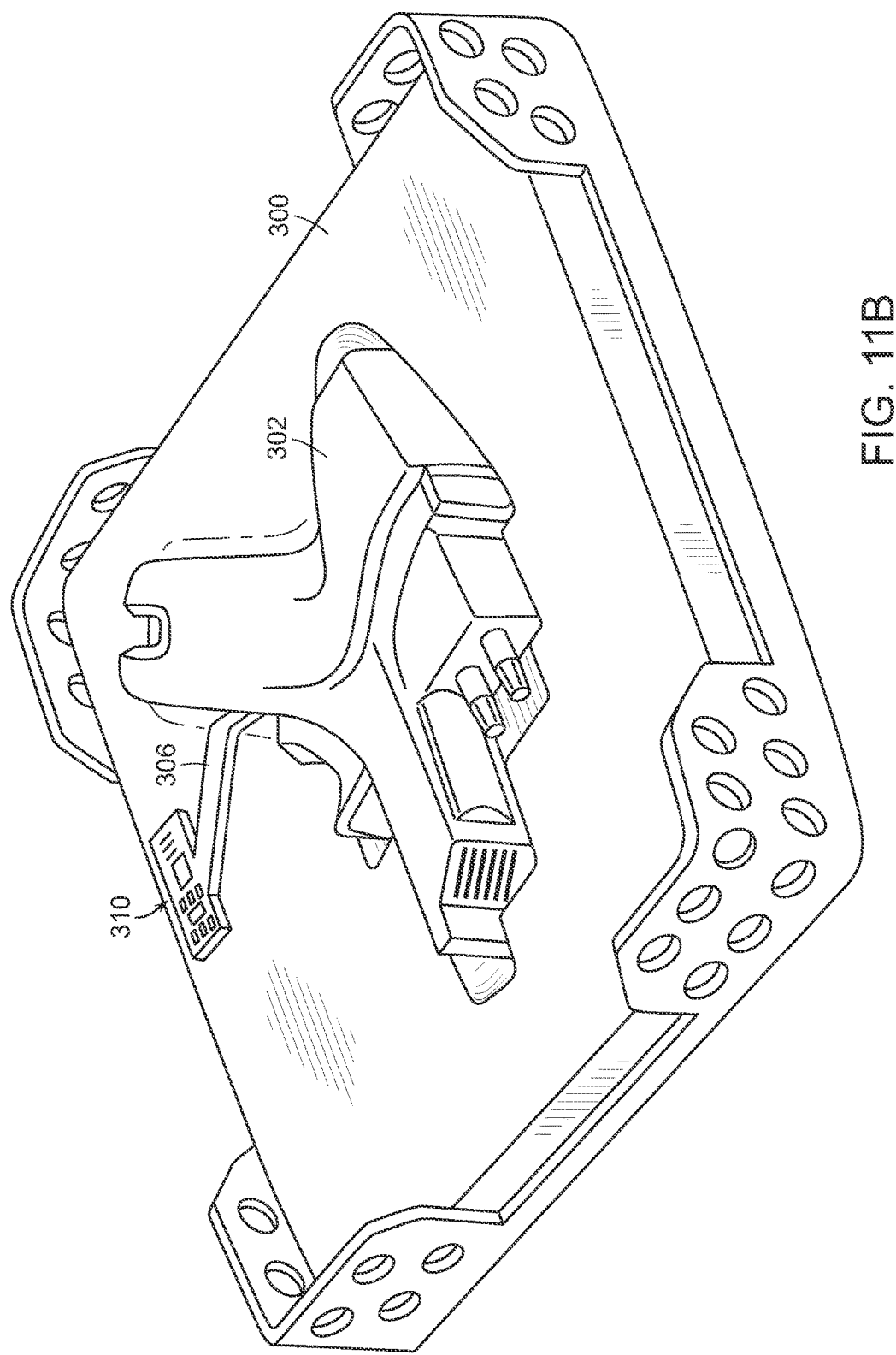

FIG. 11A depicts an exemplary sterilization tray 300 and a handle module 302 which is positionable in the sterilization tray 300. The sterilization tray 300 defines an opening, or recess, 304 whose shape matches the shape of handle module 302 to be placed therein. The recess 304 is configured to closely receive the handle module 302 such that there is little, if any, relative movement possible therebetween. The sterilization tray 300 includes a stroke counter 306 that has a lever arm 308 that extends into the opening 304. The stroke counter 306 further includes a counter visual readout 310. When the user places the handle module 302 in the opening 304, the lever arm end 308 is depressed, toggled, or stroked, which registers as a count, thereby incrementing the stoke counter 306 by one for a count-up counter (or −1 for a count-down counter) which is displayed on the readout 310. To reduce false toggles or strokes of the lever arm 306, in various arrangements, the lever arm end 308 may include a protrusion 312 configured to fit into a corresponding opening 314 defined in the handle module 302. FIG. 11B shows the handle module 302 after it is placed in the sterilization tray 300. The lever end arm 308 is not visible in FIG. 11B because it is underneath the handle module 302. The counter readout 310 remains visible to the user when the handle module 302 is positioned in the opening 304.

Figure 11C:
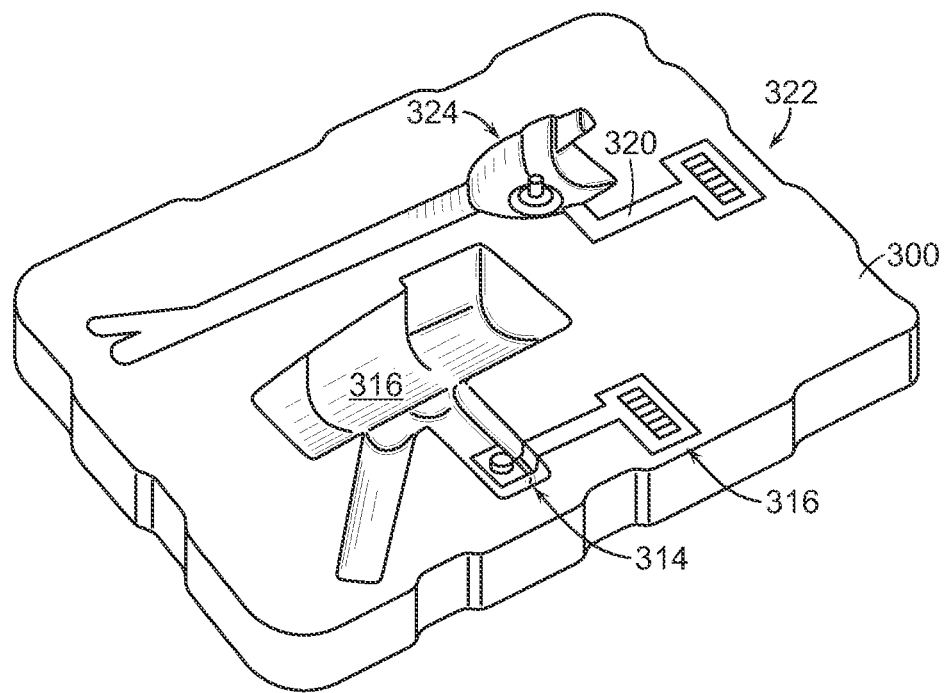
FIGS. 11C and 11D illustrate a sterilization tray in which a handle module and a detachable shaft module may be inserted for sterilization.
Figure 11D:
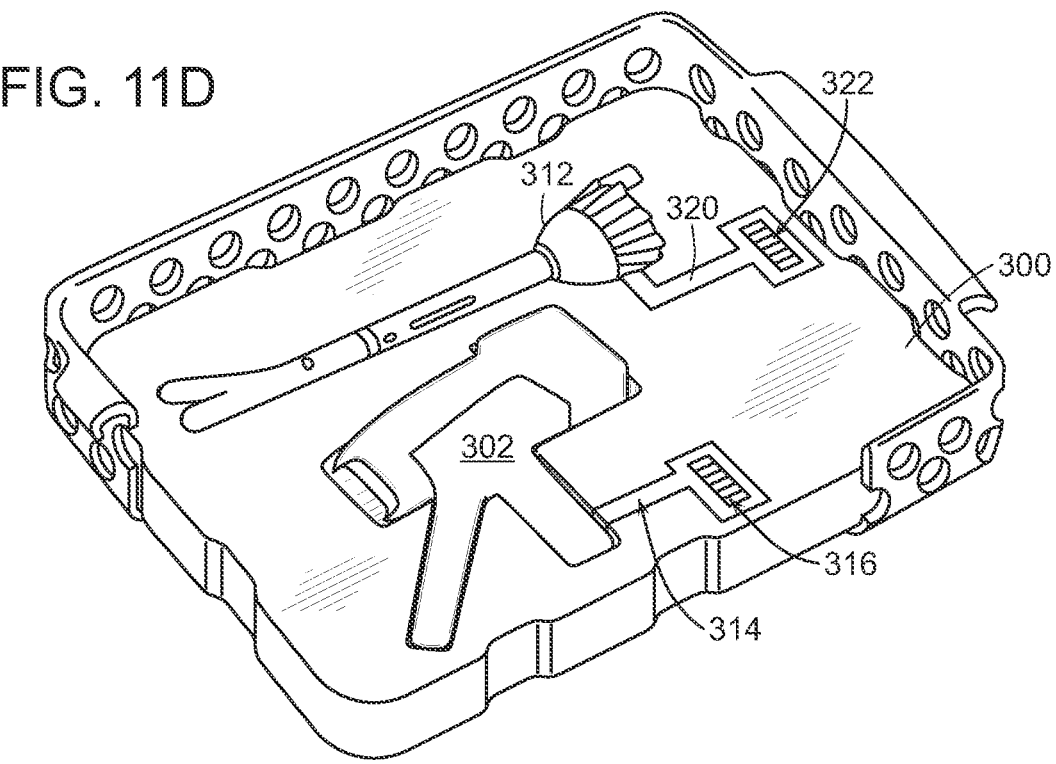

FIGS. 11C and 11D depict a variation where a handle module 302 can be placed in sterilization tray 300 with a DSM 312. Handle module 302 is similar to handle module 10 in many respects and DSM 312 represents an exemplary DSM. In such an arrangement, the sterilization tray 300 includes a handle module opening 318 for receiving the handle module 302, a handle module lever counter 314, and a handle module counter readout 316. The tray 300 also includes a DSM opening 324 for receiving the DSM 312, a DSM lever counter 320, and a DSM counter readout 322. In such an arrangement, the handle module 302 and the DSM 312 should only be sterilized in a particular sterilization tray 300 so that their respective sterilizations can be accurately tracked. The handle module counter 312 shows the number of times the handle module 302 has been sterilized in the sterilization tray 300, and/or the number of sterilizations remaining. The DSM counter 324 shows the number of times the DSM 312 has been sterilized in the sterilization tray 300, and/or the number of sterilizations remaining. The handle module 302 could be sterilized without the DSM 312, and vice versa, in which case their respective counts may not be equal.

Figure 11E:
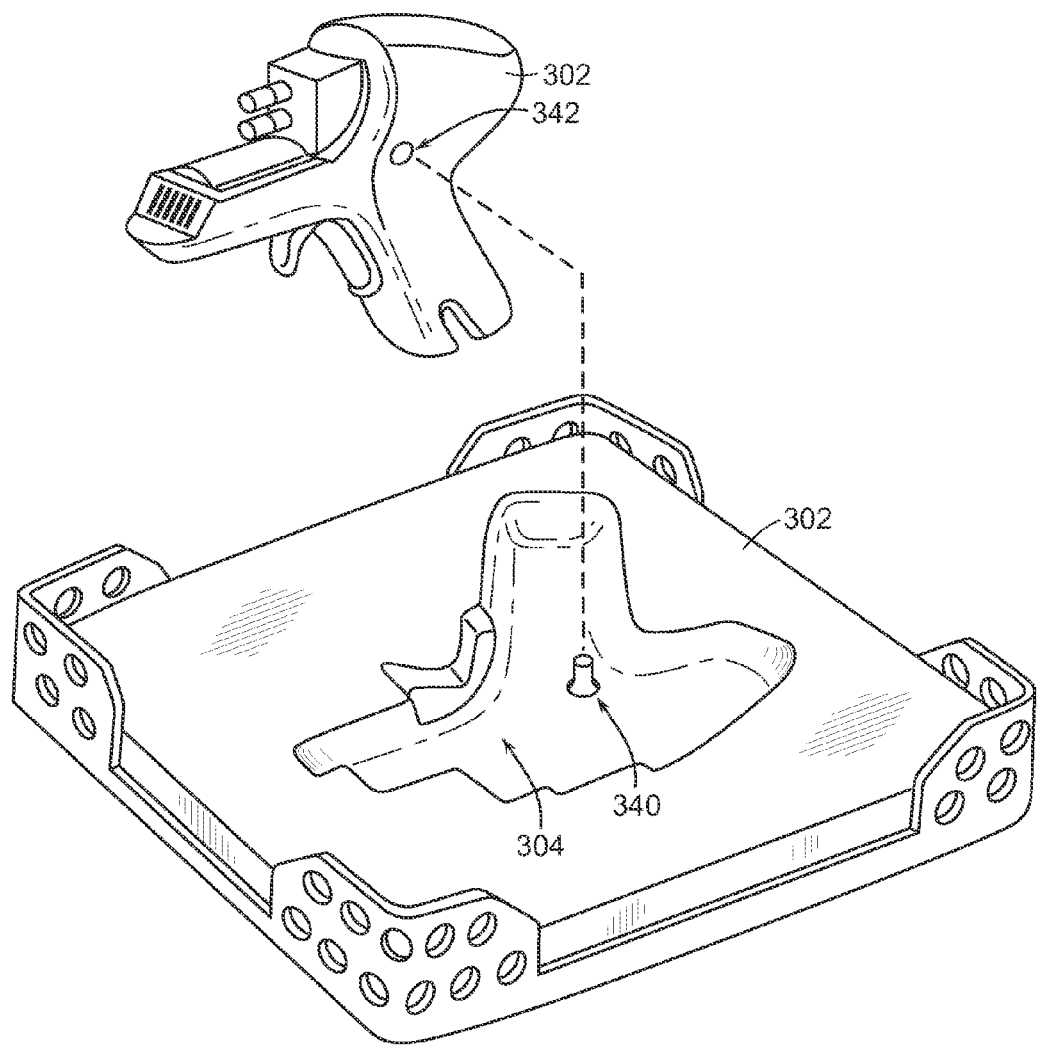
FIG. 11E illustrates another sterilization tray in which a handle module may be inserted for sterilization.
Figure 11F:
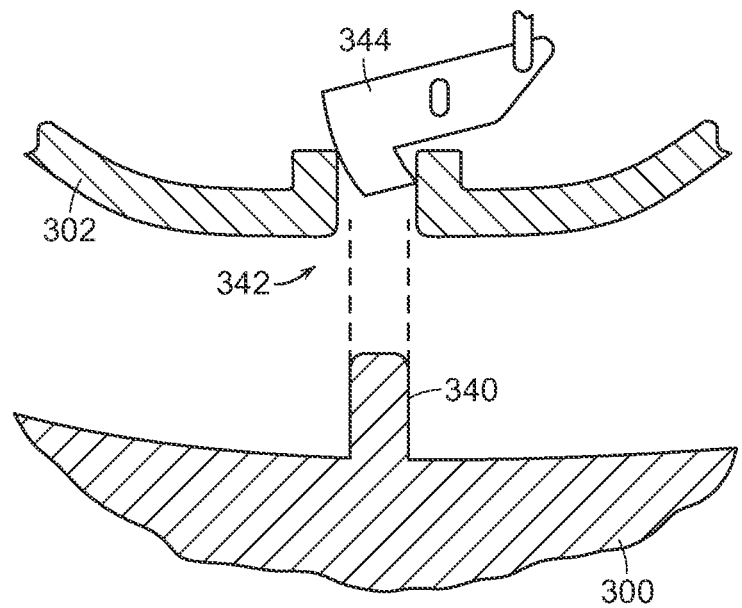
FIGS. 11F, 11G, 11H, and 11I illustrate aspects of the sterilization tray of FIG. 11E interfacing with a handle module.
Figure 11G:
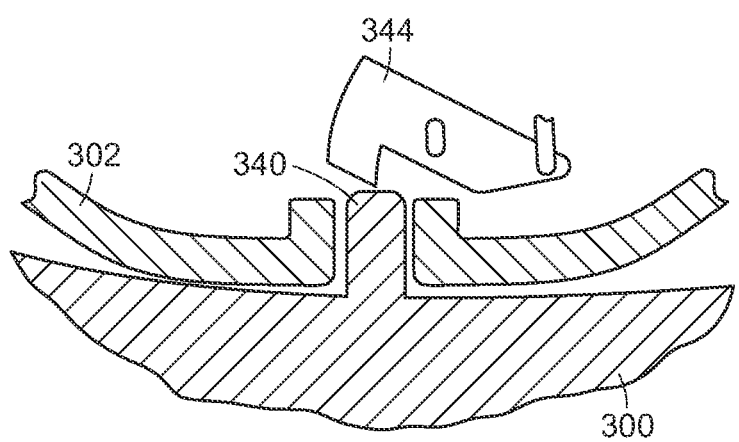
Figure 11H:
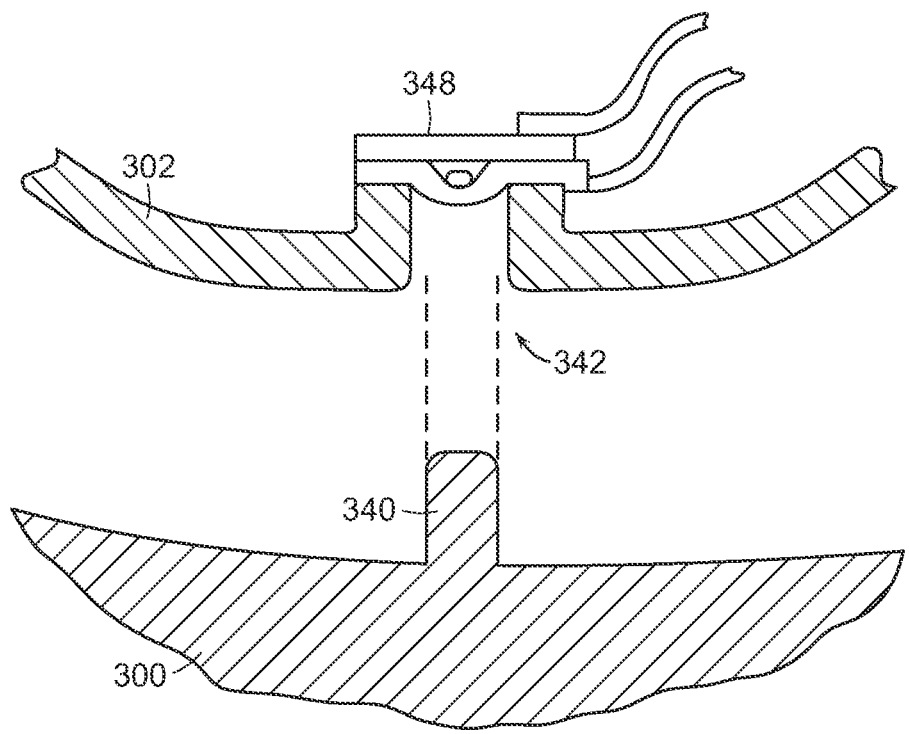
Figure 11I:
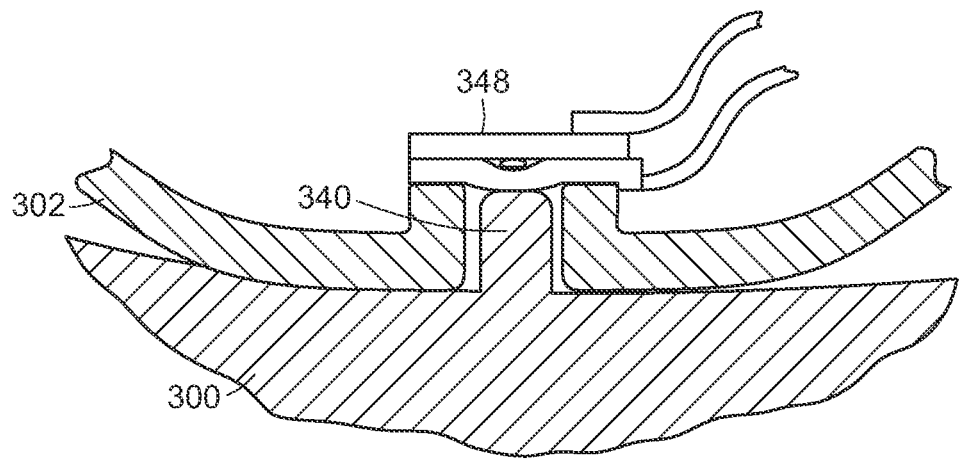

FIGS. 11E to 11I illustrate other arrangements for using a sterilization tray 300 to track uses of a handle module. In FIG. 11E, the sterilization tray 300 includes a protrusion 340 extending upwardly from the bottom of the opening 304 in the sterilization tray. The protrusion 340 is positioned to extend into a corresponding opening 342 defined in the handle module 302 when the handle module 302 is seated in the opening 304. As shown in FIG. 11F, the handle module 302 may comprise a two-position mechanical toggle switch 344 having a portion extending into the opening 342 defined by the handle 302 when the switch 344 is in a first position. When the handle module 302 is placed in the sterilization tray 300, the opening 342 is aligned with the protrusion 340 such that the protrusion 340 pushes the switch 344 to a second position, as shown in FIG. 11G. The switch 344 may be in communication with the handle processor and the handle processor may update an internal sterilization count (stored in internal and/or external processor memory of the handle module) when the switch 344 is moved from the first position (FIG. 11F) to the second position (FIG. 11G). In such an embodiment, the handle module 302 may comprise a power source as described herein to power the handle processor and to update the sterilization count during sterilization. Such a power source can comprise a secondary battery which is not removed from the handle module even if a primary battery is removed from the handle module 302. The handle processor may compare the sterilization count to a predetermined threshold (e.g., 20 sterilizations) and when the sterilization count reaches the predetermined threshold, the handle processor may implement one or more of the various end-of-life actions described herein, for example. The switch 344 may stay in the "triggered" or "activated" state until it is reset at a later time, such as after the sterilization process, for example (see FIG. 36). The switch 344 can be biased by a spring, for example, to revert back to its open position once the handle module 302 is removed from the tray 300 and the protrusion 340 is removed from the opening 342. The handle module processor could also set an internal flag to indicate that the handle module 302 was placed in the sterilization tray 300 and this flag can later be reset after the sterilization process (see FIG. 37). FIGS. 11H and 11I illustrate a similar embodiment with a contact switch 348. When the handle module 302 is placed in the sterilization tray 300, the opening 342 is aligned with the protrusion 340 such that the protrusion 340 closes the contact switch 348, as shown in FIG. 11G, when the handle module 302 is seated in the opening 304. The contact switch 348 is in communication with the handle processor to update the sterilization count of the handle module. The contact switch 348 may be biased to revert back to its open position (FIG. 11H) by a spring, for example, when the handle 302 is removed from the tray 300 and pressure being applied to the contact switch 348 by the inserted protrusion 340 is removed.

In addition to or in lieu of the above described manners for tracking the end of life of a handle module, the end of the life of a handle module could be tracked through the use of an inspection station to which the handle module can be connected. The inspection station could be used at any suitable time to evaluate whether the handle module can be used to perform a surgical procedure and/or a subsequent step in a surgical procedure. For instance, an inspection station could be used before, during, and/or after the sterilization process of a handle module and/or while preparing the handle module for reuse. The handle module could be connected to the inspection station after (i) the post-op cleanup for reusable components of the handle module following a procedure (usually involving a manual wipe down of the component or instrument); (ii) decontamination (e.g., by auto-washer) of the component or instrument; and/or (iii) cleaning and/or room drying of the component or instrument, for example. Placement of the handle module on the inspection station can be a proxy for the number of times the handle module was used, sterilized, and/or otherwise processed for reuse. A display on the inspection station (or elsewhere) may indicate to a user when a threshold number of placements of the handle module on the inspection station has been reached or is about to be reached, at which point the user can take appropriate action with respect to the handle module, such as retire it, for example. Also, the inspection station could upload data to the handle processor that prevents further usage of the handle module (e.g., disables the handle module) when the handle module has reached the end of its life.

Figure 12B:
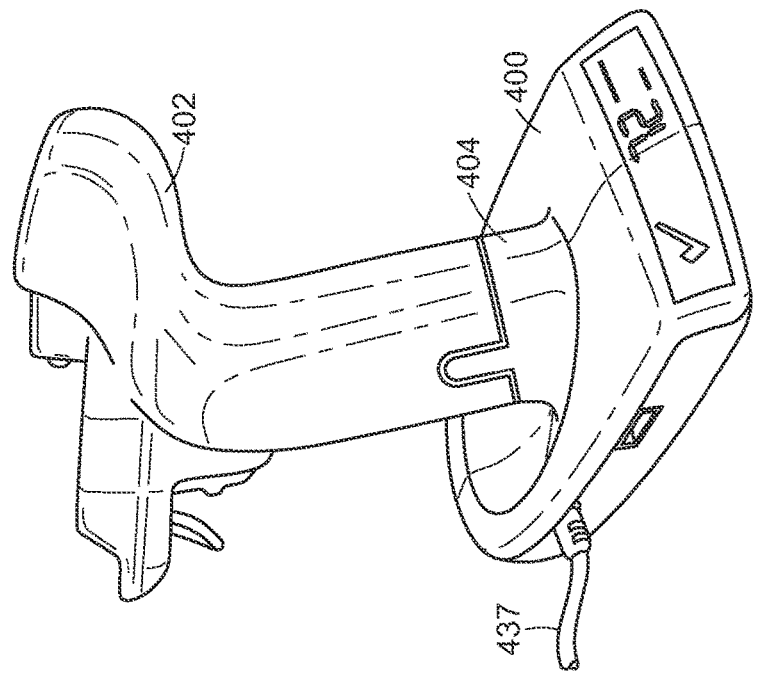
FIGS. 12A, 12B and 12E illustrate an inspection station for inspecting a handle module before, during, and/or following a surgical procedure.
Figure 12A:
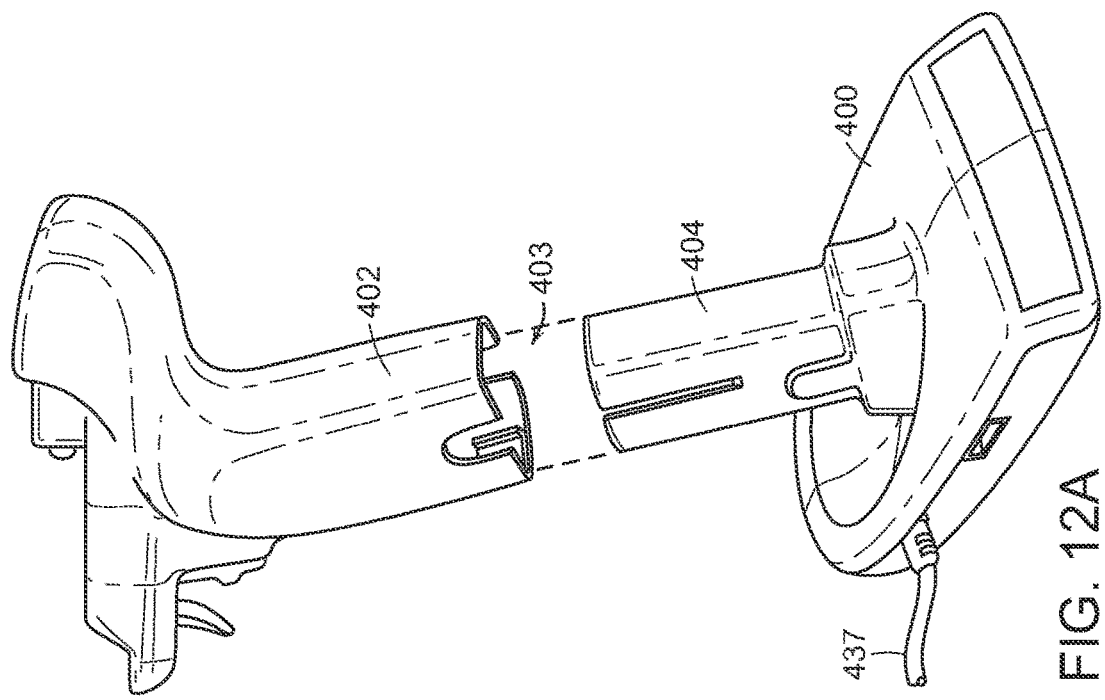

Further to the above, FIGS. 12A and 12B illustrate an exemplary inspection station 400 and handle module 402. The handle module 402 is similar to the handle module 10 in many respects. FIG. 12A shows the handle module 402 before being placed on the inspection station 400 and FIG. 12B shows the handle module 402 after being placed into position on the inspection station 400. Similar to other embodiments disclosed herein, the handle module 402 comprises a battery cavity 403 defined therein which is configured to receive a battery pack therein. See battery pack 86 in FIGS. 2-5, for example. As also disclosed elsewhere herein, the battery pack is readily insertable into and removable from the battery cavity 403. FIG. 12A also shows that the battery pack is removed from the handle module 402 thereby exposing the battery cavity 403 prior to the handle module 402 being placed on the inspection system 400. The inspection station 400 comprises an insert, or data/power adapter, 404 extending therefrom that is sized and configured to fit within the battery cavity 403 of the handle module 402. The data/power adapter 404 is placed in communication with the processor of the handle module via the power contacts configured to engage the power terminals of the battery pack and/or via one or more signal contacts positioned in the battery cavity 403, as described in greater detail further below. The handle module 402 may be positioned on the inspection station 400 by sliding the opening 403 over the data/power adapter 404.

Figure 12C:
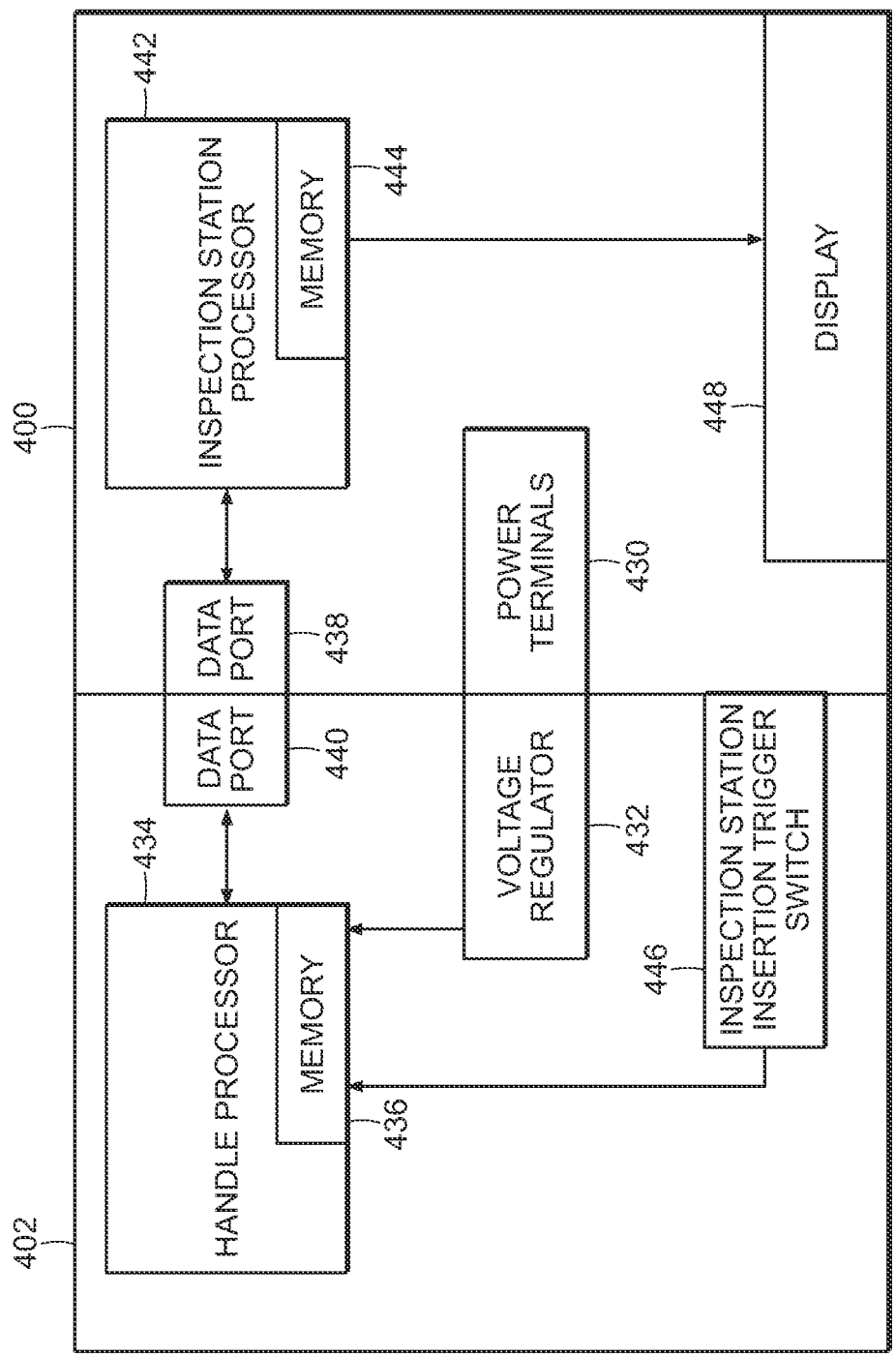
FIG. 12C is a block diagram of the inspection station and the handle module.

FIG. 12C is a block diagram illustrating certain components of the inspection station 400 and the handle module 402. The data/power adapter 404 includes power terminals 430 that provide voltage there-across to a voltage regulator 432 of the handle module 402 in the same or similar manner in which the battery pack provides voltage to the voltage regulator 432 when the battery pack is positioned in the opening 403. For instance, if a battery pack is configured to supply 6V DC to the voltage regulator 432, the insert 404 can be configured to supply 6V DC to the voltage regulator 432, for example. The voltage regulator 432 provides electrical power to the control board 100 (see FIGS. 1-6) of the handle module 402 to power the components of the control board 100, including a handle processor 434 and the associated internal and/or external memory 436, for example. The inspection station 400 may itself be powered by an AC power source through a power cord 437 utilizing appropriate AC-DC converters. The inspection station 400 includes data ports 438 which come into contact with data ports 440 of the handle module 402 when the handle module 402 is engaged with the inspection station 400 so that the handle processor 434 can be in communication with the inspection station processor 442. As the reader will appreciate, the inspection station 400 can further include internal and/or external memory 444 associated with the inspection station processor 442.

Figure 12D:
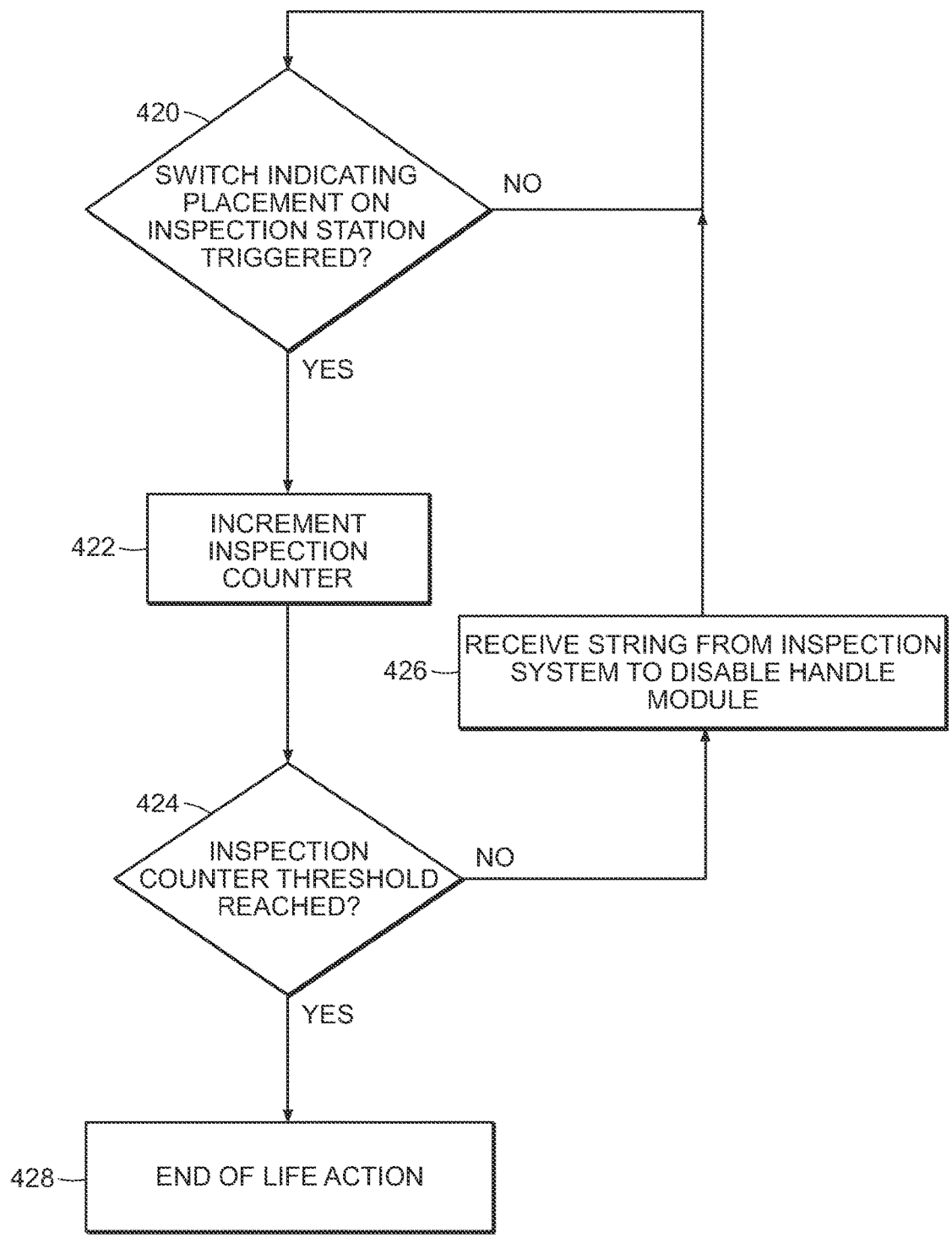
FIG. 12D is a diagram of a process flow executed by the handle processor of the handle module to determine when the handle module reaches its end of life based on a number of times the handle module is placed on the inspection station.

FIG. 12D is a diagram of a process flow that may be performed by the handle processor 434 and/or the inspection station processor 442 when executing software and/or firmware in the handle memory 436 and/or the inspection station memory 444 to track and respond to the number of times the handle module 402 is placed on the inspection station 400. In various arrangements, whenever the handle module 402 is installed on the inspection device 400 such that the insert 404 makes data and/or power connections to the control board 100 of the handle module 402, the handle processor 434 may increment an inspection counter. The inspection counter may be a count-up counter from zero to a pre-established threshold number of inspections or a count-down counter from the pre-established threshold number of inspections to zero. In at least one instance, the handle module 402 includes an inspection station insertion switch 446 (FIG. 12C) that is triggered when the data/power adapter 404 is fully and properly inserted into the opening 403. This switch 446 may be in communication with the handle processor 434 via the control board 100 and, when the switch 446 is triggered at step 420 of FIG. 12D, the handle processor 434 may increment (by +1 or −1 as the case may be, depending on the type of counter) the inspection counter at step 422. At step 424, the handle processor 434 may compare the inspection count to the predetermined threshold. If the threshold has not yet been reached, the handle processor 434 may then output at step 426 the value of the inspection counter to the inspection station processor 442 while in data communication with the inspection station 400 via the insert 404.

Figure 12E:
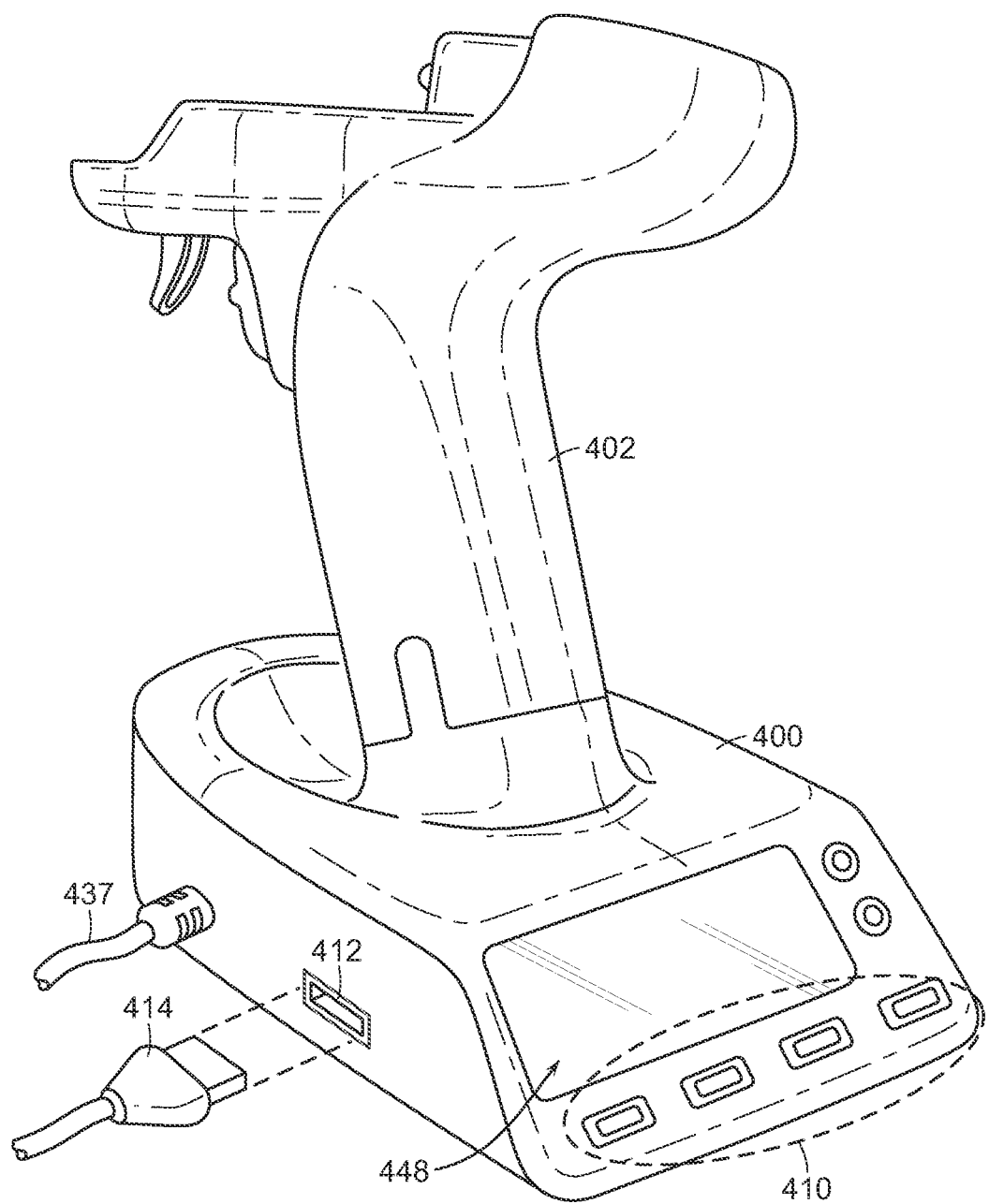

Referring to FIG. 12E, the inspection station 400 may include a visual display 448 that displays visual information related to the inspection counter, such as the number of times the handle module 402 has been placed on the inspection station 400 and/or the number (or approximate number) of times remaining that the handle module 402 should be placed on the inspection station 400 for inspection before the handle module 402 has reached its end-of-life, for example. However, if the inspection count threshold has been reached, the process may advance to step 428 where appropriate end-of-life action(s) may be taken. One such end-of-life action is that the display 448 of the inspection station 400 may visually display to the user that the handle module 402 should not be used any further. Another end-of-life action that could be employed in addition to or in lieu of the visual display is that the inspection station processor 442 sends an instruction string to the handle processor 434 that causes the handle processor 434 to disable further use of the handle module 402. For example, the instruction string could instruct the handle processor 434 to never thereafter actuate the motor of the handle module 402 or some other disabling action. For example, the instruction string may instruct the handle processor to set a flag that, when set, prevents the handle processor 434 from actuating the motor.

In various embodiments, the inspection station insertion switch 446 may be a pressure switch that is actuated when the data/power adapter 404 is fully inserted into the opening 403 and reset when the data/power adapter 404 is removed, or at least partially removed, from the opening 403. In various aspects, there could be a timer associated with the inspection station insertion switch 446 so that the inspection station counter is incremented (step 422 of FIG. 12D) only if the switch 446 is activated for at least a threshold period of time (e.g., 30 seconds, etc.). Such a timer could reduce the number of false positives, i.e., short placements of the handle module 402 on the inspection station 400 that are likely not associated with post-procedure inspection or sterilization of the handle module 402.

In another variation, the inspection station 400 includes a pressure switch with a counter whose readout is displayed to a user. The inspection station pressure switch is activated by placement of the handle module 402 on the inspection station 400. For example, the inspection station pressure switch could be at the base on the insert 404 of the inspection station 400 such that when the handle module 402 is fully slid onto the insert 404, the inspection station pressure switch is activated. Each time the inspection station pressure switch is activated, the counter could be updated (e.g., incremented by one) so that the readout shows the number of times that the handle module 402 has been installed on the inspection system 400. Such a counter could be a mechanical counter and/or an electronic counter, for example. If the limit, or threshold, is displayed on the inspection station 400, displayed on the handle module 402, and/or otherwise publicized to the user, the user can know if the limit has been reached or is being approached. In at least one instance, the limit could be printed on the inspection station 400 and/or the handle module 402, for example.

The display 448 of the inspection station 400 could also display other information obtained by the inspection station 400 and/or communicated to the inspection station 400 from the handle module 402 via the data connection therebetween. For example, the handle processor memory may store a device type identifier for the handle module (e.g., a serial number) and that device type identifier may be downloaded to the inspection station processor 442 for display on the display 448. In addition to or in lieu of the above, the display 448 may indicate a state of the handle module, such as how close the handle module is to its end-of-life and/or whether or not the handle module as been locked out, for example, based on status data received from the handle processor 434. As described herein, the display 448 could indicate the number of remaining uses (e.g., procedures) for the handle module and/or the number of procedures in which the handle module has been used. As disclosed herein, the inspection station 400 could also be used to perform post-procedure testing of the handle module 402 to ensure that the handle module 402 can be used in a subsequent procedure. This testing can include moisture testing, seal integrity testing, and/or simulated load testing, for example. The display could indicate the results of those tests (e.g., passed, failed, in progress).

In addition to or in lieu of the above, the display 448 of the inspection station 400 may indicate the status of the inspection station itself, such as whether the inspection station is (i) downloading data from the handle module, (ii) uploading data and/or software upgrades to the handle module, (iii) processing data, and/or (iv) performing testing, for example. The display 448 may indicate results from the testing and data processing, such as whether the handle module is ready to use in another procedure, whether the handle module needs servicing, whether the warranty of the handle module has expired because the handle module has reached its threshold number of uses, for example, and/or other warnings. The display 448 of the inspection station 400 may be a LED-backlit LCD display, for example, that is controlled by the inspection station processor 442. The inspection station 400 may also include control buttons 410, as shown in FIG. 12E, where a user could input data and/or configuration settings that are stored and used by the inspection station processor 442. The display 448 could also be a touch-screen where users could enter data and/or configuration settings, for example, via the touch-screen. The inspection station 400 may include an external data port 412, such as a USB, micro or mini USB, for example, for connection to a data cable 414 so that data can be uploaded from or downloaded to the inspection station 400. For example, procedure data from the handle module 402 could be downloaded to the inspection station 400 and then downloaded to a remote computer device via the data port 412. Software and/or firmware upgrades could be downloaded from a remote computer device via the data port 412 to the inspection station 400 and then uploaded to the handle module 402, for example.

Figure 13A:
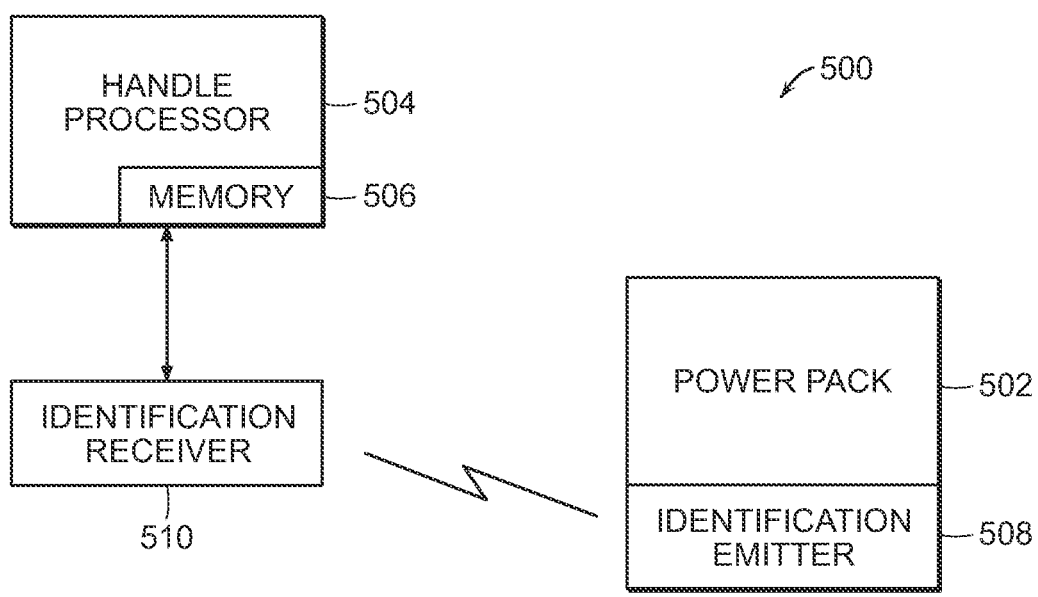
FIG. 13A is a block diagram illustrating aspects of a handle module and a removable battery pack, where the battery pack includes an identification emitter so that the handle module can identify the battery pack.
Figure 13B:
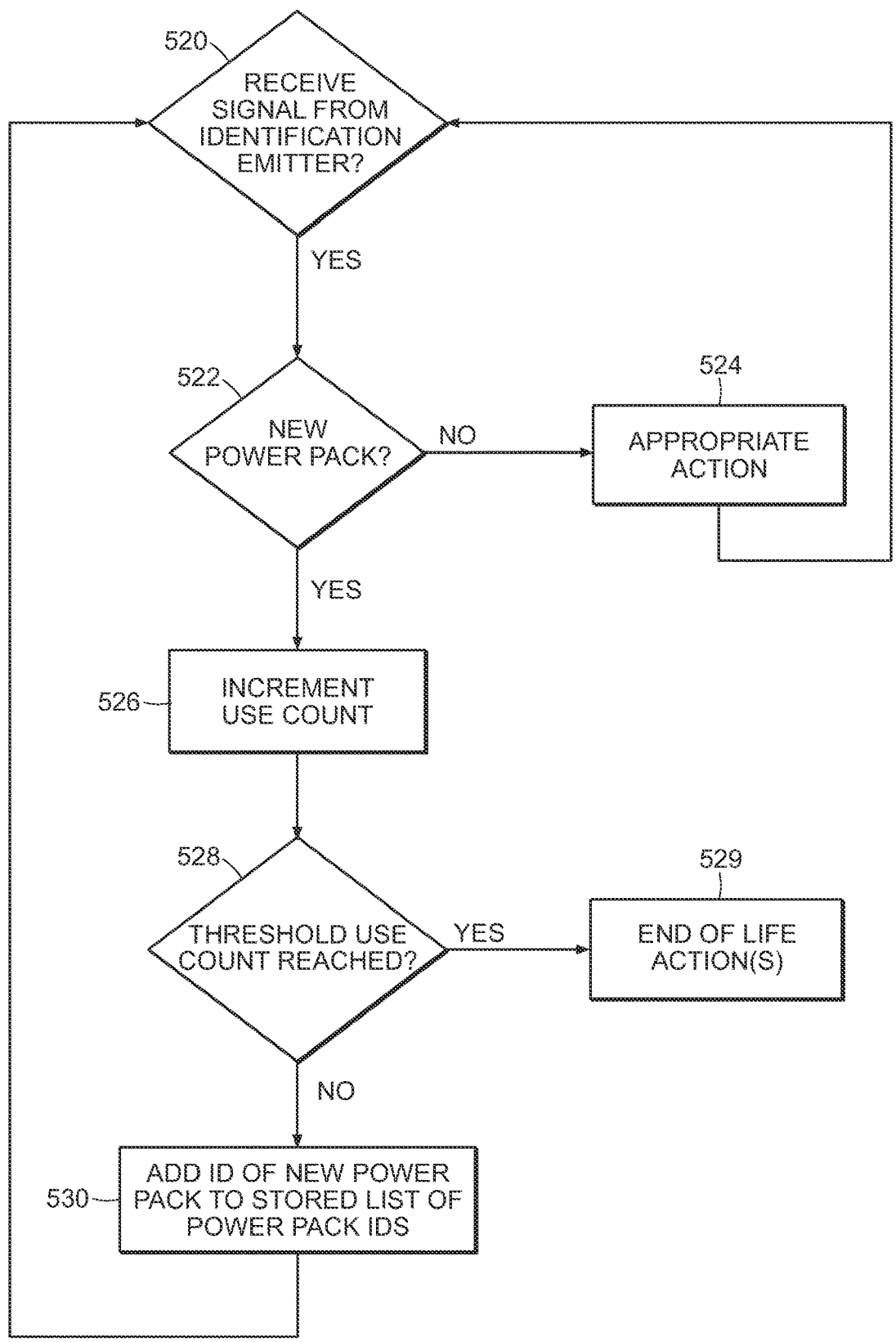
FIG. 13B illustrates a process flow executed by the handle processor of the handle module of FIG. 13A to determine when the handle module reaches its end of life based on a number of times a battery pack has been installed in the handle module.

FIGS. 13A and 13B depict an arrangement for tracking the use of a handle module by tracking the installation of power packs in the handle module. FIG. 13A is a block diagram of a handle module 500. The handle module 500 is similar to the handle module 10 in many respects. The handle module 500 includes a removable power pack 502, such as a battery, for example, and a handle processor 504. FIG. 13B illustrates a process flow that may be executed by the handle processor 504. The process can be executed from firmware and/or software in memory 506 which is associated with the processor 504. As illustrated in FIG. 13A, the power pack 502 may include an identification emitter 508, such as a RFID tag, for example, that can communicate with an identification receiver 510, such as a RFID reader, for example, in the handle module 500. The identification emitter 508 is a wireless signal emitter, for example; however, any suitable identification emitter could be used. The identification receiver 510 is a wireless signal receiver that is in communication with the handle processor 504, for example; however, any suitable identification receiver could be used. The identification emitter 508 transmits a unique ID for the power pack 502 which can be received by the identification receiver 510. The strength of the signal emitted by the identification emitter 508 can be controlled or limited such that the identification receiver 510 can only detect the signal emitted from the identification emitter 508 when the power pack 502 is very close to the identification receiver 510 (e.g., within 10 cm). In at least one instance, the identification receiver 510 can be mounted on the control board 100 (FIGS. 2-4) such that the identification receiver 510 can only detect the identification emitter 508 when the power pack 502 has been inserted in the handle module 500. In various instances, short range RFID tags and readers could be used such that the identification receiver 510 is less likely to falsely detect power packs 502 that are not installed in the handle module 500.

Referring to the process flow depicted in FIG. 13B, the identification reader 510 detects an identification emitter at step 520. At step 522, the handle processor 504 determines whether the power pack 502 is a new power pack based on its ID received by the identification receiver 510. The term "new" in this context means that a particular power pack 502 has not been used with a particular handle module 500. The handle processor 504 may perform this step by comparing the ID for the newly detected power pack 502 to a stored list of power pack IDs that were previously detected by the identification receiver 510. Such a list of previously-used power pack IDs are stored in a non-volatile memory of the handle module 500, for example. If the power pack 502 is not new, i.e., its ID is on the stored list of previously used power packs, the process advances to step 524, where appropriate and pre-established action(s) is taken. For example, the handle processor 504 can disable use of the handle module 500 until a new, i.e., previously-unrecognized, power pack is installed in the handle module 500. In at least one such instance, the handle module 500 can disable the motor 80. In addition to or in lieu of the above, the display of the handle module 500 can display to the user that the power pack is not new and request installation of a different power pack, which returns the process to step 520.

If the power pack 502 is determined to be new by the processor 504, i.e., the ID of the power pack 502 is not on the stored list of previously-used power packs, the process advances to step 526 where the handle processor 504 increments the use count for the handle module 500. As before, a count-up counter and/or a count-down counter could be used. At step 528, the handle processor 504 compares the use count to a pre-established threshold value that represents the number of times that the handle module 500 should be used with a different, unique power pack. Such a use count can serve as a proxy for the number of times the handle module 500 has been used in patient procedures. If the use count threshold has been reached at step 528, a pre-established end-of-life action(s) can be taken at step 529. For example, the handle processor 504 may disable the motor, the handle module display may display to the user that the handle module 500 has no remaining uses, and/or activate an alarm alerting the user that there are no remaining uses, for example. If the use count threshold has not been reached, the handle processor 504 adds the ID of the new power pack 502 to the stored list of previously-used power packs at step 530 so that the new power pack 502 cannot be used after its current use. In other variations, the steps illustrated in FIG. 13B could be performed in different orders. For example, the new power pack ID could be added to the stored list prior to incrementing the use count. Other techniques for tracking installation of power packs in the handle module are described below in connection with FIGS. 14E and 15A-B.

The embodiment described above in connection with FIGS. 13A and 13B can be used with rechargeable and/or non-rechargeable battery packs. That said, battery packs which are used with a handle module 500, recharged, and then reused with the same handle module 500 may cause the handle module 500 to go into a lockout mode. With regard to this particular embodiment, recharged battery packs would have to be reused with a different handle module. Along these lines, an embodiment of the handle module 500 is envisioned in which a recharged battery pack can be reused with the same handle module 500.

In at least one instance, the processor 504 can employ logic which prevents a battery pack 502 from being counted two or more times for the same use. In at least one instance, the processor 504 may not count a battery pack 502 a second time unless it has been dis-engaged from and re-engaged with the handle module 500. Even then, the processor 504 may require an elapsed time between the first engagement and the subsequent engagement before counting the subsequent engagement as a second use. Such an elapsed time could be the time that it takes to recharge the battery pack, for example.

In addition to or in lieu of the above, a handle module can track the number of times that a DSM is connected to and/or disconnected from the handle module as a proxy for the number of times that the handle module has been used. The handle module can display the updated number of uses remaining for the handle module, the estimated number of uses remaining for the handle module, such as with a volume indicator that indicates the percentage of life remaining, for example, and/or the number of times that the handle module has been used. When the use threshold limit has been reached, the handle module, via the handle processor, can take one or more end-of-life actions, such as displaying that the handle module is spent, disabling further use of the handle module by disabling the motor, for example, and/or sounding an audible alarm, for example. FIGS. 14A-G represent different arrangements for tracking the connection or disconnection of an DSM to a handle module, as discussed in greater detail further below.

Figure 14A:
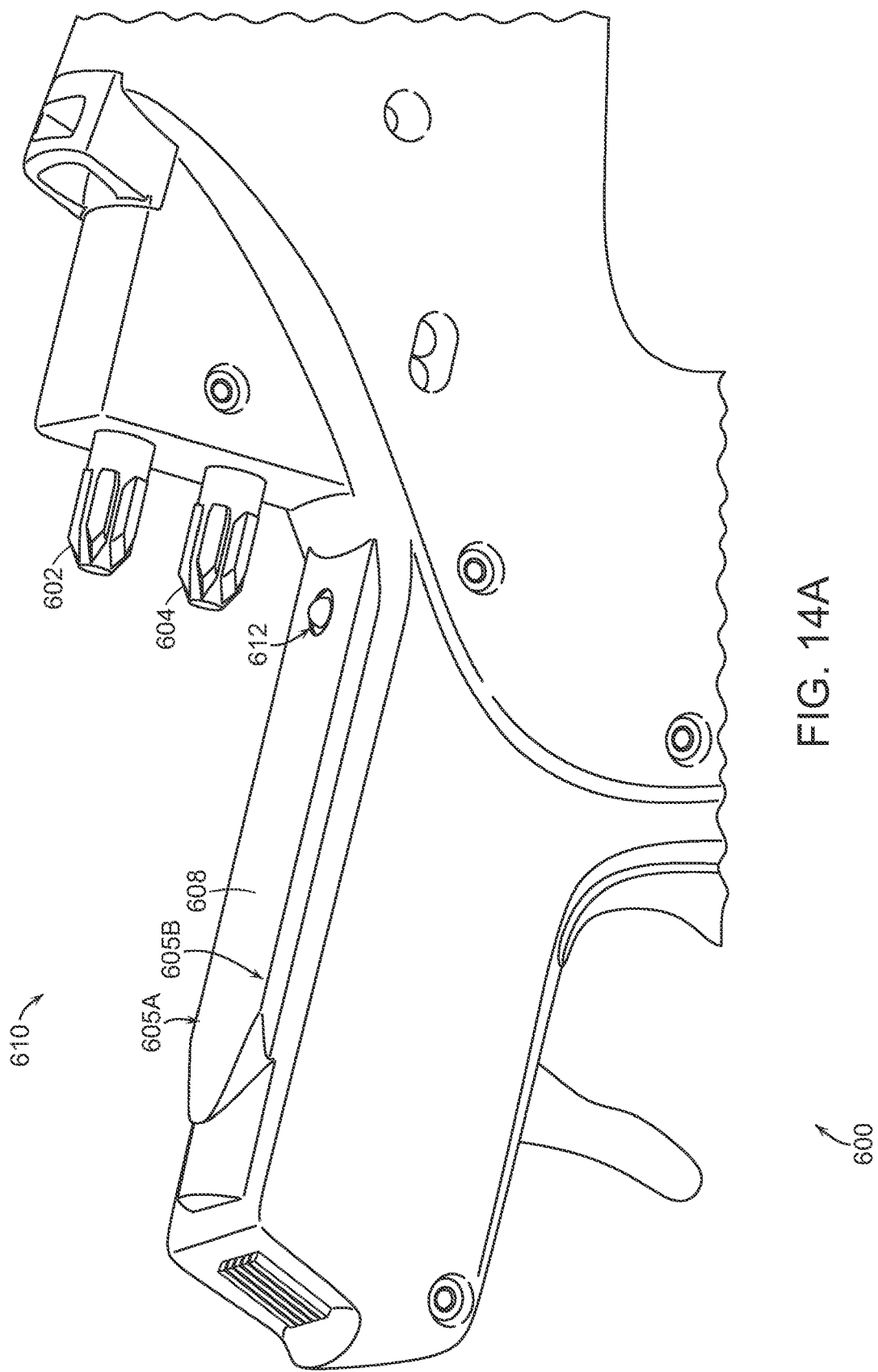
FIGS. 14A, 14B, and 14C illustrate aspects of a handle module that detects the attachment of a detachable shaft module thereto.

Turning now to FIG. 14A, a handle module 600, which is similar to the handle module 10 in many respects, comprises two rotary drive systems 602, 604. A DSM having two drive systems, discussed above, can be operably coupled to the rotary drive systems 602, 604. The DSM can have grooves that are configured to receive and slide onto bilateral edges 605A, 605B of a tongue defined in a connection area 608 on the upper portion of the handle module 600. In such an arrangement, the handle module 600 may include a depressible switch 612 on the tongue, as shown in FIG. 14A, and/or elsewhere in the connection area 608 such that, when a DSM, such as DSM 634 (FIGS. 14B and 14C), for example, is connected to the handle module 600, the depressible switch 612 is depressed. In at least one instance, the DSM may not depress the switch 612 until the DSM has been fully seated onto the handle module 600. The switch 612 may be connected to the handle processor wherein the handle processor may count the number of times the depressible switch 612 is depressed as a proxy for the number of times that a DSM has been connected to the handle module 600 and/or as a proxy for the number of times that the handle module 600 has been used. Also, the handle processor could require that the depressible switch 612 be depressed continuously for at least a certain period of time (e.g., 30 seconds) before incrementing the count to reduce instances of false positives. When a pre-established threshold number of uses, or activations of switch 612, has been reached, an end-of-life action(s) may be performed, as described herein.

Figure 14B:
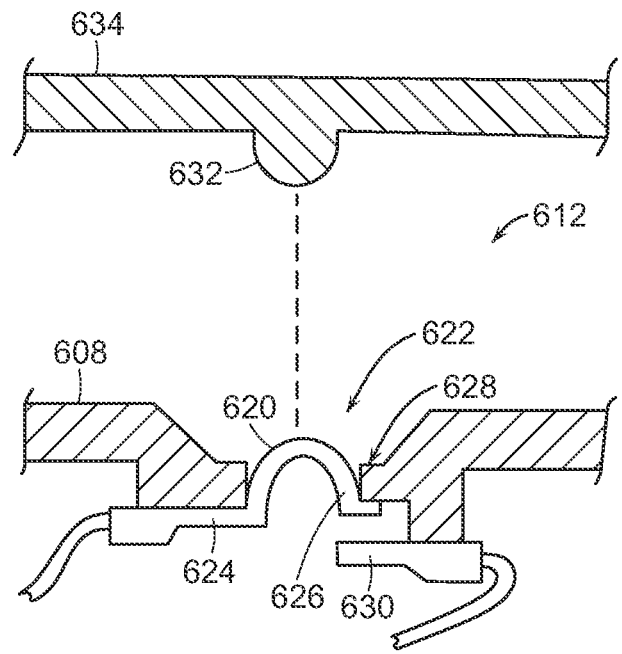
Figure 14C:
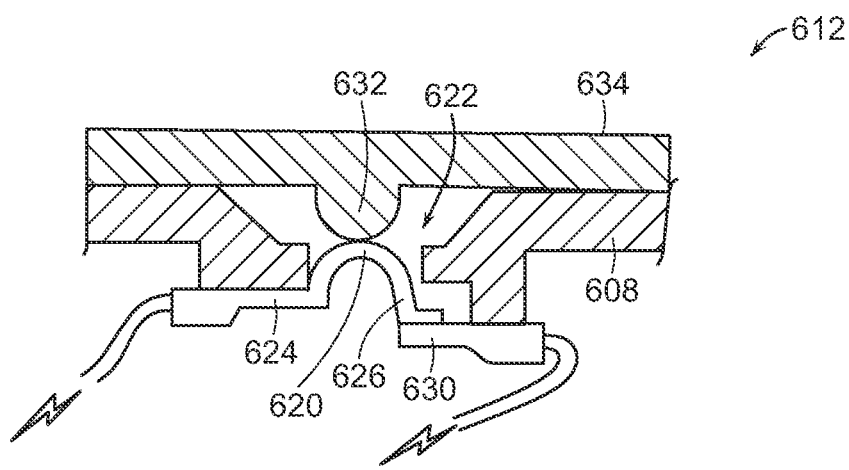

FIGS. 14B and 14C illustrate one arrangement for an electro-mechanical depressible switch 612. As shown, the depressible switch 612 includes a head 620 that extends into an opening 622 defined in the tongue and/or any other suitable DSM-mating surface of the handle module 600. The head 620 may be at the end of a spring arm 624 configured to bias the position of the head 620 upwardly into the opening 622. The spring arm 624 also includes a shoulder 626 positioned behind an extension, or edge, 628 defined in the handle module 600 that limits the upward movement of the head 620 in the opening 622 to a desired position. The depressible switch 612 also includes a contact 630. When the switch 612 is in an unactuated, or open, condition, as illustrated in FIG. 14B, the spring arm 624 is not in engaged with the contact 630; when the DSM 634 is attached to the handle module 600 and pushes the head 620 downwardly, as illustrated in FIG. 14C, the shoulder 626 of the spring arm 624 engages the contact 630 and closes the switch 612. The DSM 634 includes a projection 632 extending therefrom which is configured to contact the head 620. The switch arm 624 and the contact 630 can be comprised of electrically conductive materials which can complete a circuit in communication with the handle processor when the head 620 is depressed downwardly by the DSM 634, as discussed above.

Figure 14D:
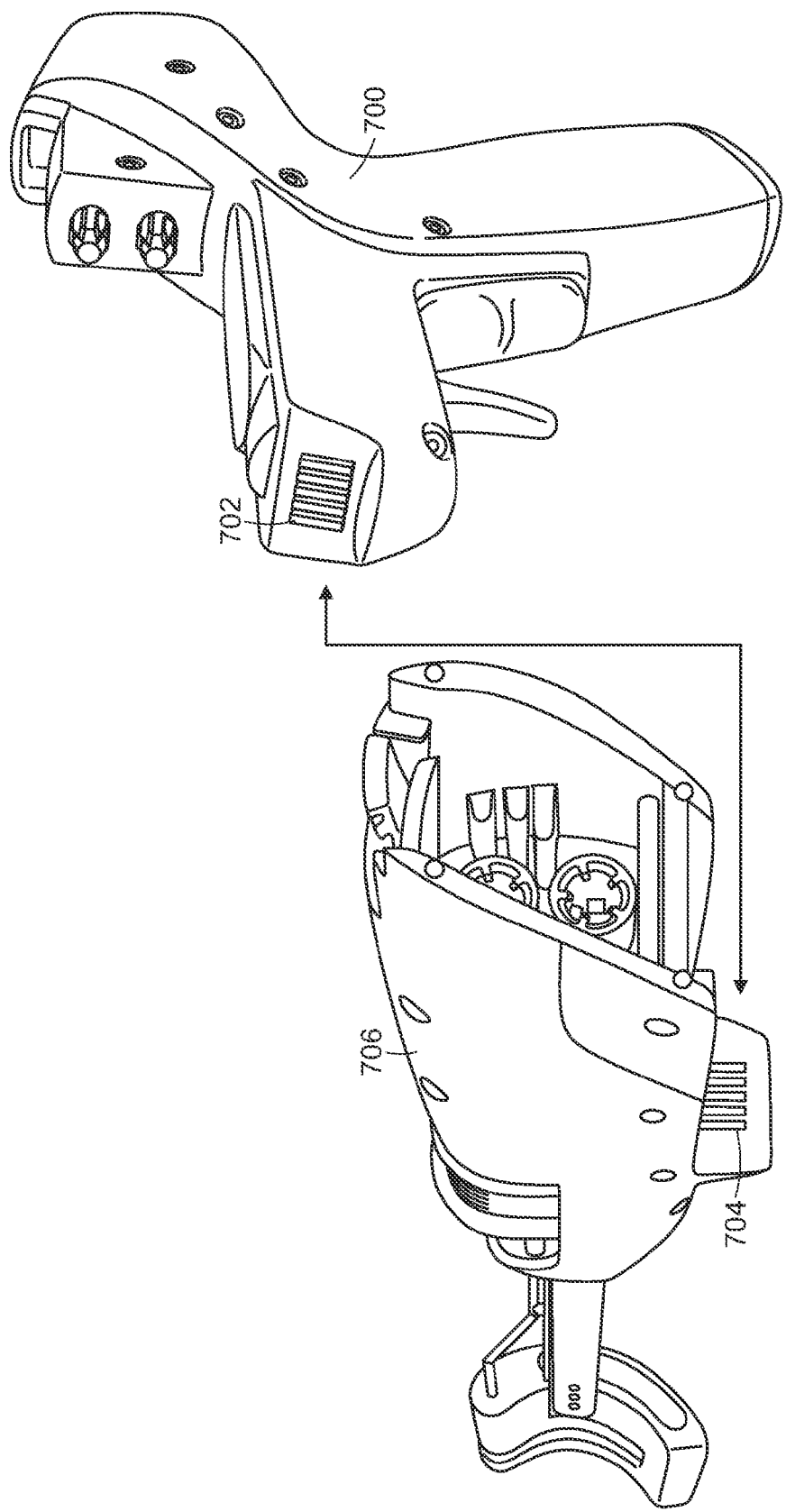
FIG. 14D illustrates a handle module and a detachable shaft module, where the handle module detects attachment of the detachable shaft module thereto.

Referring now to FIG. 14D, a handle module 700 may include an electrical contact board 702 that interfaces/mates with and makes electrical connections to a corresponding electrical contact board 704 on a DSM 706. In at least one instance, the processor of the handle module 700 may count the number of times that a DSM, such as the DSM 706, for example, is assembled to the handle module 700. The processor can increase the DSM-connection count when the contacts 704 of the DSM 706 engage the contacts 702 of the handle module 700 and make a working data connection therebetween. The mating of the contact boards 702, 704 can serve as a proxy for the number of times that a DSM has been connected to the handle module 700 and as a proxy for the number of times that the handle module 700 has been used. Similar to the above, the handle processor could require that there be a data connection between the contact boards 702, 704 continuously for at least a certain period of time (e.g., 30 seconds) before incrementing the count to reduce the instances of false positives. In another variation, the handle processor and the DSM processor may exchange data when the DSM 706 is connected to the handle module 700. In this exchange, the handle processor can receive identification information for the DSM 706 so that the handle processor can identify the DSM 706 connected to the handle module 700 (e.g., the model type for the DSM). In such an arrangement, the handle processor may increment the DSM-connection count each time that the handle processor receives identification information from a DSM that is attached thereto. In any of these variations, the handle processor compares the DSM connection count to a pre-established threshold, and if the threshold is reached, the handle processor takes an end-of-life action(s).

Figure 14E:
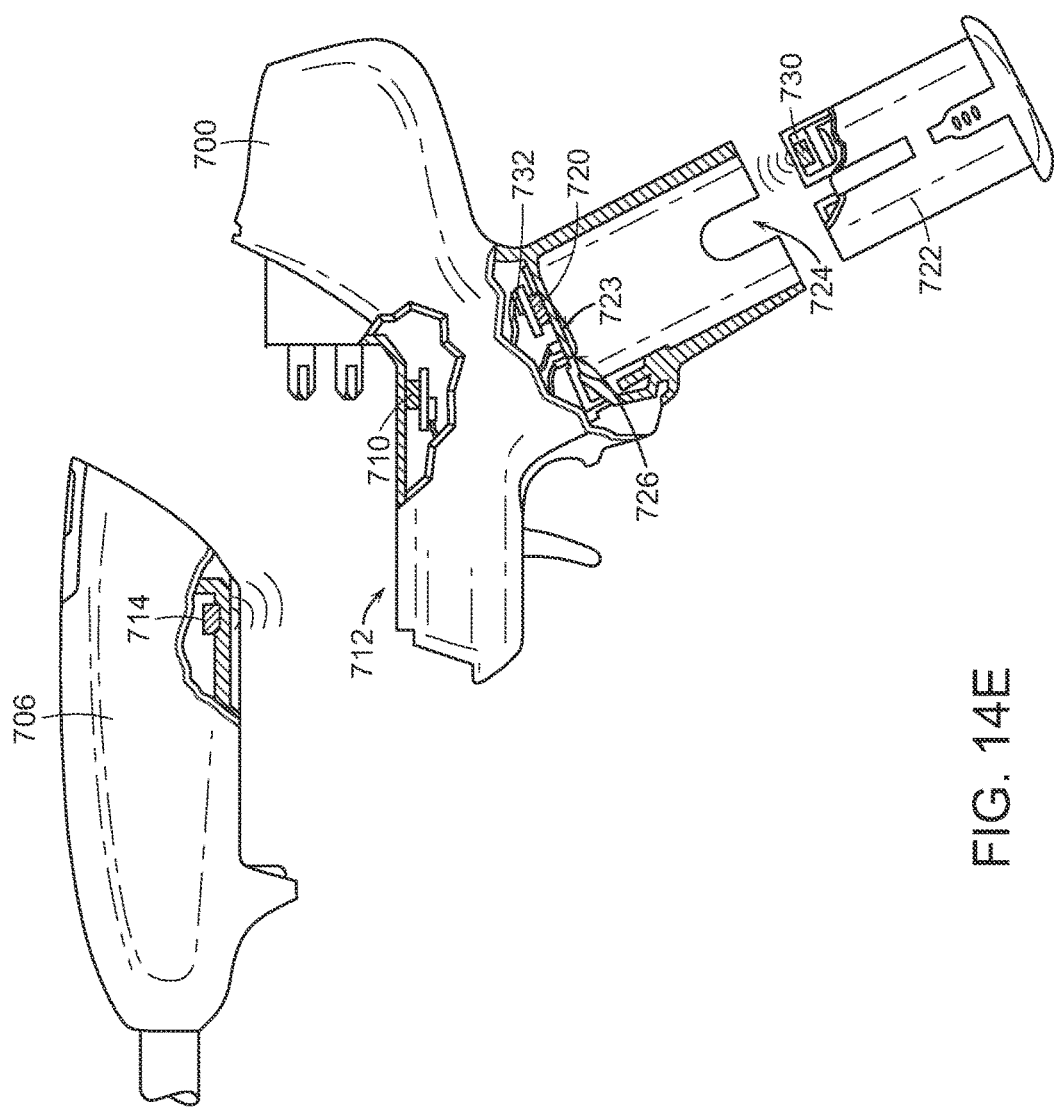
FIG. 14E illustrates the handle module of FIG. 14D, where the handle module also detects attachment of a removable battery pack.
Figure 14F:
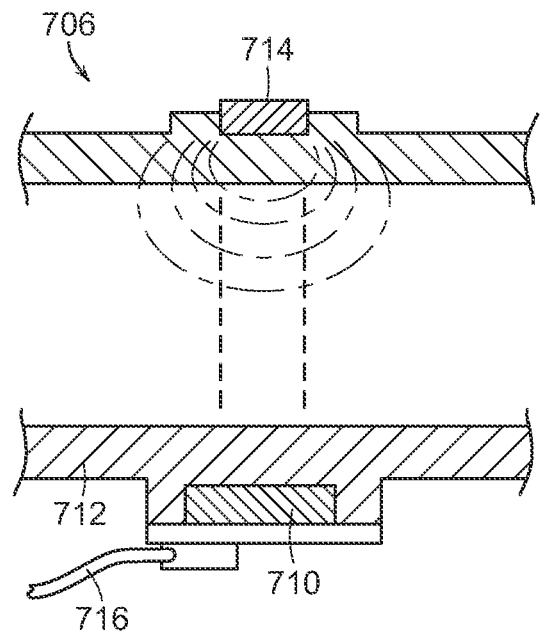
FIGS. 14F and 14G illustrate a sensor for the handle module of FIG. 14D to detect the insertion of a removable battery pack therein.
Figure 14G:
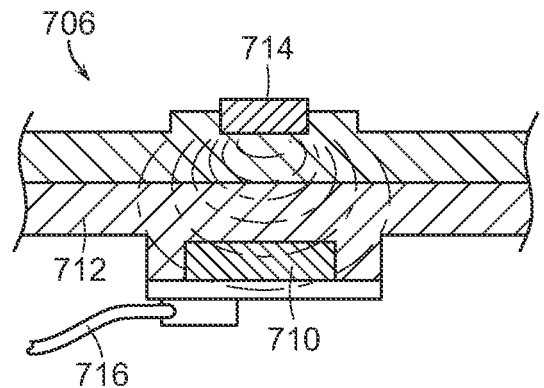

An alternative arrangement for detecting the connection of a DSM to a handle module is shown in FIGS. 14E-14G. The illustrated arrangement uses a Hall Effect sensor to detect the connection of the DSM 706 to the handle module 700. As shown in FIG. 14E, the handle module 700 may include a Hall Effector sensor 710 positioned relative to an upper surface 712 of the handle module 700 to which the DSM 706 is to be attached. Correspondingly, the DSM 706 includes a magnet 714, such as a permanent magnet, for example, that is in close proximity to the Hall Effect sensor 710 when the DSM 706 is fully and properly connected to the handle module 700, as shown in FIG. 14G. The Hall Effector sensor 710 may be in communication with the handle processor via a lead wire 716, for example. The Hall Effect sensor 710 can sense the approaching magnet 714 of the DSM 706 as the DSM 706 is installed on the handle module 700. The magnetic field generated by the magnet 714 may be constant and the handle processor can have access to data regarding the magnetic field such that the distance between the magnet 714 and the Hall Effect sensor 710 can be determined based on the output of the Hall Effect sensor 710. Once the distance between the magnet 714 and the Hall Effect sensor 710 stabilizes to a distance corresponding to the DSM 706 being fully and properly installed on the handle module 700, the handle processor can infer that the DSM 706 is fully and properly installed on the handle module 700 and update the DSM-connection count.

Similarly, referring again to FIG. 14E, the handle module 700 includes a battery cavity 724 configured to receive a battery pack 722 therein. The handle module 700 further includes a Hall Effect sensor 720 configured to detect the insertion of the removable battery pack 722 into the battery cavity 724. The battery-pack Hall Effect sensor 720 can be positioned at an upper interior surface 723 in the battery cavity 724 in the handle module 700 for the battery pack 722. As the reader will appreciate, the battery pack 722 is configured to supply power to the handle module 700 via electrical terminals 726 and it may be desirable to position the Hall Effect sensor 720 as far away as possible from the electrical terminals 726 such that any magnetic fields generated by the current flowing through the terminals 726 do not substantially disturb the ability of the Hall Effect sensor 720 to properly detect the insertion of the battery pack 722 into the handle module 700. The battery pack 722 includes a magnet 730, such as a permanent magnet, for example, that the Hall Effect sensor 720 senses as the battery pack 722 is inserted into the battery cavity 724. Similar to the DSM Hall Effect sensor 710, the battery pack Hall Effector sensor 720 is in communication with the handle processor via a lead wire 732, for example. The Hall Effect sensor 720 can sense the approaching battery pack magnet 730 as the battery pack 722 is installed into the battery cavity 724. The magnetic field generated by the magnet 730 may be constant and the handle processor can have access to data regarding the magnetic field such that the distance between the magnet 730 and the Hall Effect sensor 720 can be determined based on the output of the Hall Effect sensor 720. Once the distance between the magnet 730 and the Hall Effect sensor 720 stabilizes to a distance corresponding to the battery pack 722 being fully and properly installed in the handle module 700, the handle processor can infer that the battery pack 722 is fully and properly installed in the handle module 700 and update the battery-pack-connection count.

A handle module can track the number of times that a DSM and/or a battery pack is connected to and/or disconnected from the handle module as a proxy for the number of times that the handle module has been used. The handle module can display the updated number of uses remaining for the handle module, the estimated number of uses remaining for the handle module, such as with a volume indicator that indicates the percentage of life remaining, for example, and/or the number of times that the handle module has been used. When the use threshold limit has been reached, the handle module, via the handle processor, can take one or more end-of-life actions, such as displaying that the handle module is spent, disabling further use of the handle module by disabling the motor, for example, and/or sounding an audible alarm, for example.

Figure 15A:
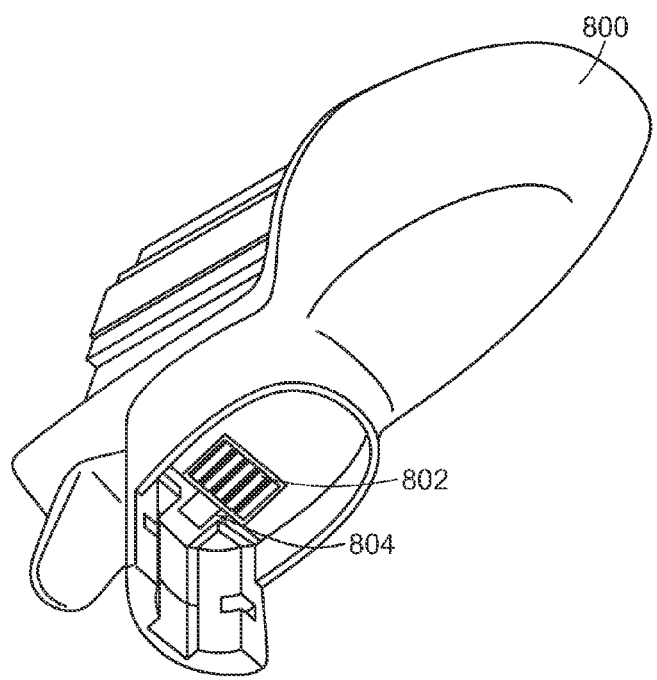
FIGS. 15A and 15B illustrate another sensor for the handle module to detect the insertion of a removable battery pack therein.
Figure 15B:
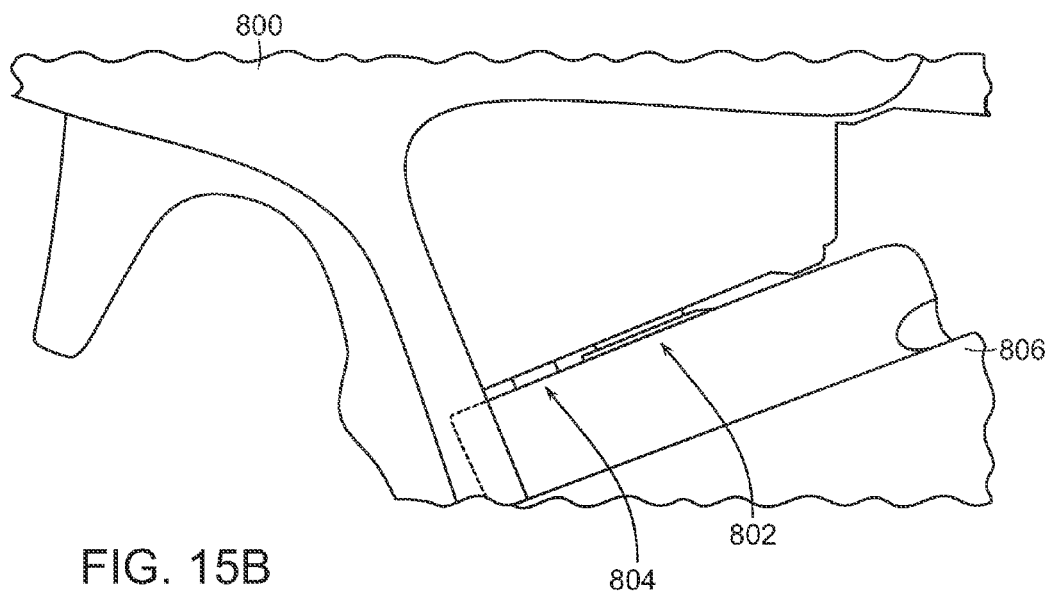

Turning now to FIGS. 15A and 15B, a handle module 800 can track the installation of power packs thereto utilizing a pressure switch that is depressed when a power pack 806, for example, is completely and properly attached to the handle module 800. The handle module 800 is similar to the handle module 10 in many respects. The handle 800 includes an electrically conductive contact pad 802 that the power pack 806 connects to in order to supply voltage to the electrical components of the handle module 800. In the illustrated arrangement, a pressure switch 804 is adjacent to the conductive contact pad 802 and it is in communication with the handle processor. When the power pack 806 is assembled to the handle module 800, referring to FIG. 15B, the housing of the power pack 806 depresses and actuates the pressure switch 804. Each time the pressure switch 804 is actuated, the handle processor can increment the power-pack-connection count until a threshold is reached, at which point an end of life action(s) can be undertaken. Similar to the above, the handle processor may require that the pressure switch 804 be actuated continuously for a period of time (e.g., 30 seconds) before incrementing the power-pack-connection count to reduce instances of false positives. In other arrangements, an electro-mechanical switch could be used, for example.

In various instances, a processor of a handle module can increment the use count each time that the handle processor is powered on. In certain instances, the processor of a handle module can automatically power down when a battery pack is disengaged from the handle module. Similarly, the processor can automatically power up when a battery pack is engaged with the handle module. In at least one such embodiment, the battery pack is the sole power source for the handle module and the disconnection of the battery pack from the handle module may immediately de-power the processor and the connection of a battery pack to the handle module may immediately re-power the processor. In certain embodiments, the handle module can include one or more capacitive elements which can store power from a battery pack when the battery pack is engaged with the handle module. When the battery pack is disconnected from the handle module, the capacitive elements can provide power to the processor for a period of time and, as a result, the processor may not power down during a battery pack change. In such instances, the processor can count a life, or use, event if a battery installation is detected by a sensor, as described above, and/or if the processor is powered on after being de-powered.

In various instances, the handle processor of the handle module 800 can track how often it receives electrical power via the conductive contact pad 802 that is used to couple the battery power pack 806 to the internal electrical components of the handle module 800. For example, the handle module 800 may comprise a micro voltage and/or current sensor (not shown) connected to the conductive contact pad 802. The voltage and/or current sensor may be in communication with the handle processor. When a threshold input voltage and/or current from the power pack 806 is detected at the contact pad 802, the handle processor can increment the battery-pack-connection count. This arrangement may be useful where the handle processor is powered at times by power sources other than the power pack, such as by supercapacitors or other sources.

Figure 16:
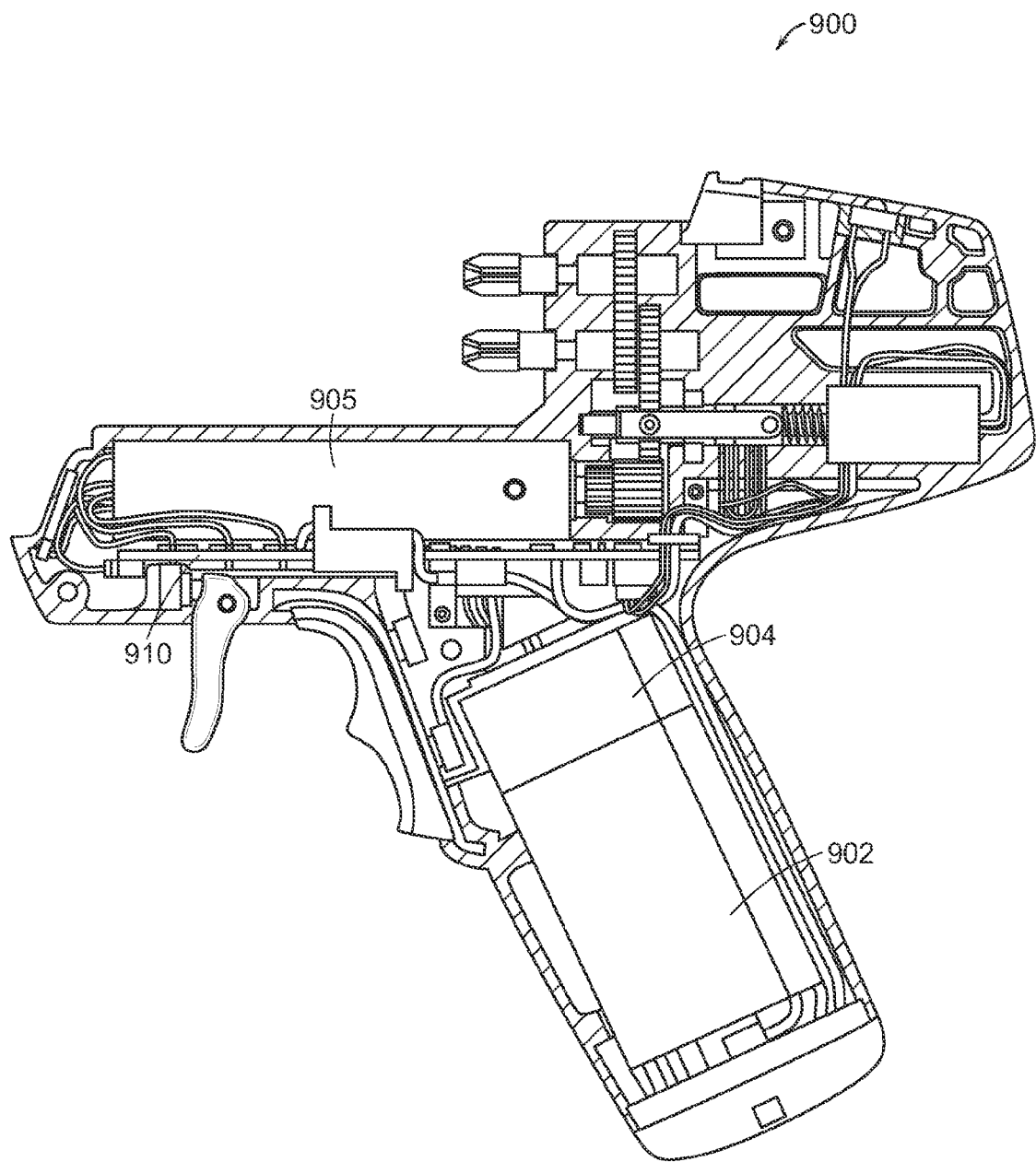
FIG. 16 illustrates a handle module with multiple power packs.

Turning now to FIG. 16, a handle module 900 comprises a plurality of power sources, including a removable battery power pack 902 and a secondary power source 904, for example. The removable battery power pack 902 is similar to the removable battery power packs described herein in many respects. The battery power pack 902 contains multiple Li ion and/or LiPo battery cells, for example. The secondary power source 904 provides a source of power to the handle module 900 even when the removable battery power pack 902 has been removed or otherwise disconnected from the handle module 900. With regard to this embodiment, the secondary power source 904 is used for low-power operations of the handle module 900, such as powering the electronic components on the control board 910 when the removable battery power pack 902 is removed from the handle module 900—and not for high-power operations, such as powering the motor(s) 905 of the handle module 900, for example. In various arrangements, the secondary power source 904 may comprise rechargeable battery cells and/or supercapacitors (a/k/a ultracapacitors) that are charged by the removable battery power pack 902 when it is installed. The secondary power source 904 can power the electronic components on the control board 910 in the absence of the primary power source 902 for as long as the secondary power source 904 possesses a sufficient charge.

Figure 17A:
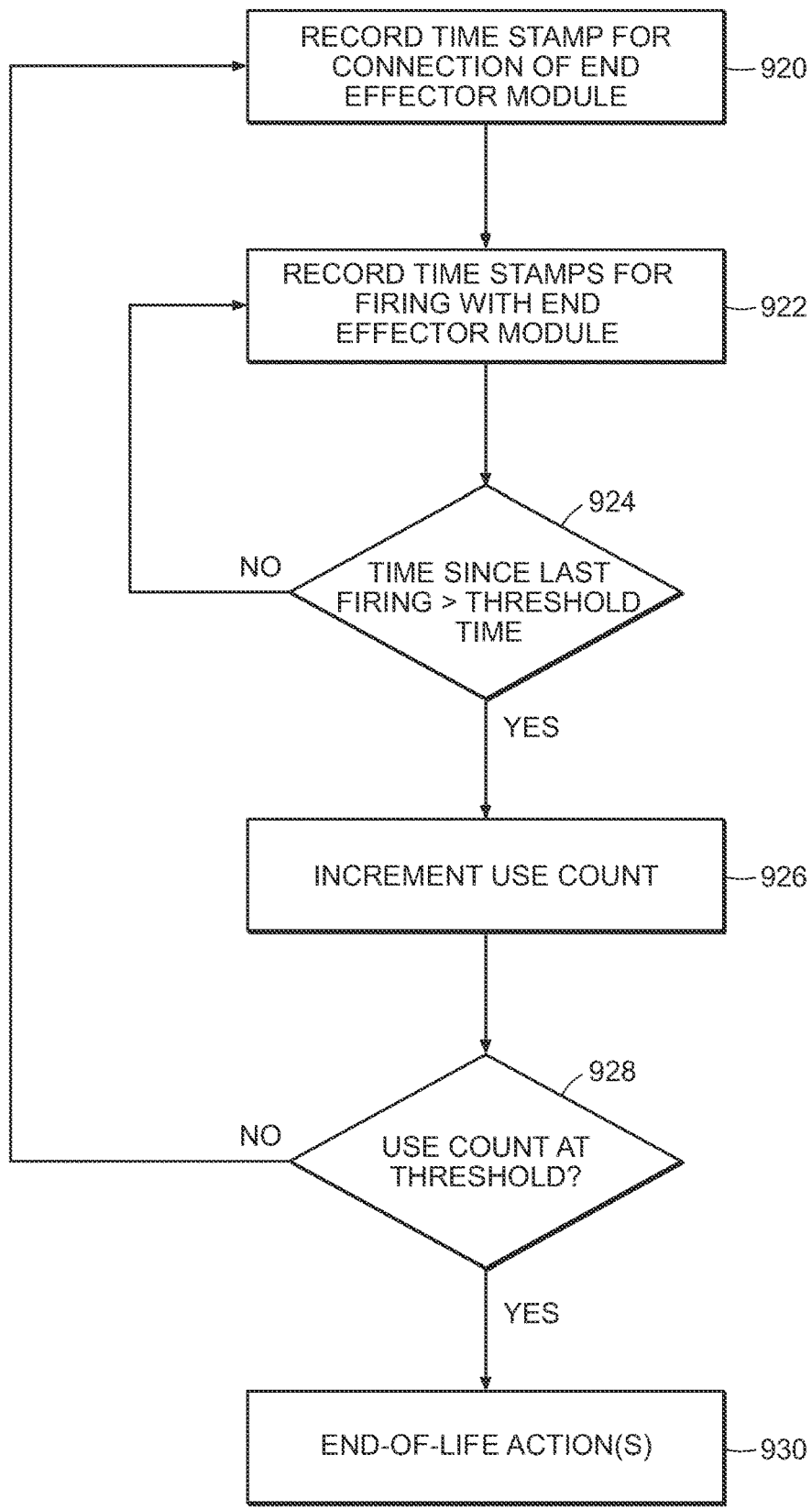
FIGS. 17A and 17B illustrate additional process flows executed by the handle processor of a handle module to determine when the handle module reaches its end of life.

The secondary power source 904 may permit the handle module 900 to track use events and/or take end-of-life actions even when the power pack 902 is not installed in the handle module 900. FIG. 17A is a flow chart of a process executable by the processor of the control board 910, such as handle processor 2124, for example. The process can be executed from software and/or firmware stored in the memory of the handle module, for example, in accordance with at least one embodiment. Prior to performing a surgical procedure, the power pack 902 is installed in the handle module 900. At step 920 of the process, the handle processor may record a time stamp for when a DSM is properly connected to the handle module 900. Once the surgical procedure begins, at step 922, the handle processor may record time stamps for each firing of the handle module 900 that occur during the surgical procedure. In addition, the handle processor can track the time which elapses between the firings. In at least one instance, the secondary power source 904 can continue to supply power to the handle processor to track the time following a firing event even if the removable power pack 902 is removed from the handle module 900. At step 924, the handle processor can determine whether the elapsed time since the last firing is greater than a threshold time period. In at least one instance, the threshold time period may be on the order of the time required to substantially process and sterilize the handle module following a procedure, for example. If the time period between firings is not greater than the threshold, it can be assumed that the procedure is ongoing and the process may return to step 922 to record the time stamp for the next firing. On the other hand, if the time period between firings is greater than the threshold, it can be assumed that the procedure has concluded, at which point, at step 926, the handle processor can increment the use count of the handle module 900. At step 928, the handle processor compares the use count to the pre-programmed threshold use count for the handle module 900. If the use count is less than the threshold, the handle module 900 can be used in another procedure and the process can return to step 920 to await connection of a DSM for the next procedure. On the other hand, if the use count threshold has been reached, the process advances to step 930, where the end-of-life action(s) for the handle module 900 can be initiated. As described above, the end-of-life action(s) can include disabling the handle module such that the handle module cannot be used in subsequent surgical procedures. In at least one instance, the motor of the handle module can be physically and/or electronically disabled. In certain instances, the end-of-life action(s) include visually indicating the end of life for the handle module on a display of the handle module and/or sounding an audible alarm, for example.

Figure 17B:
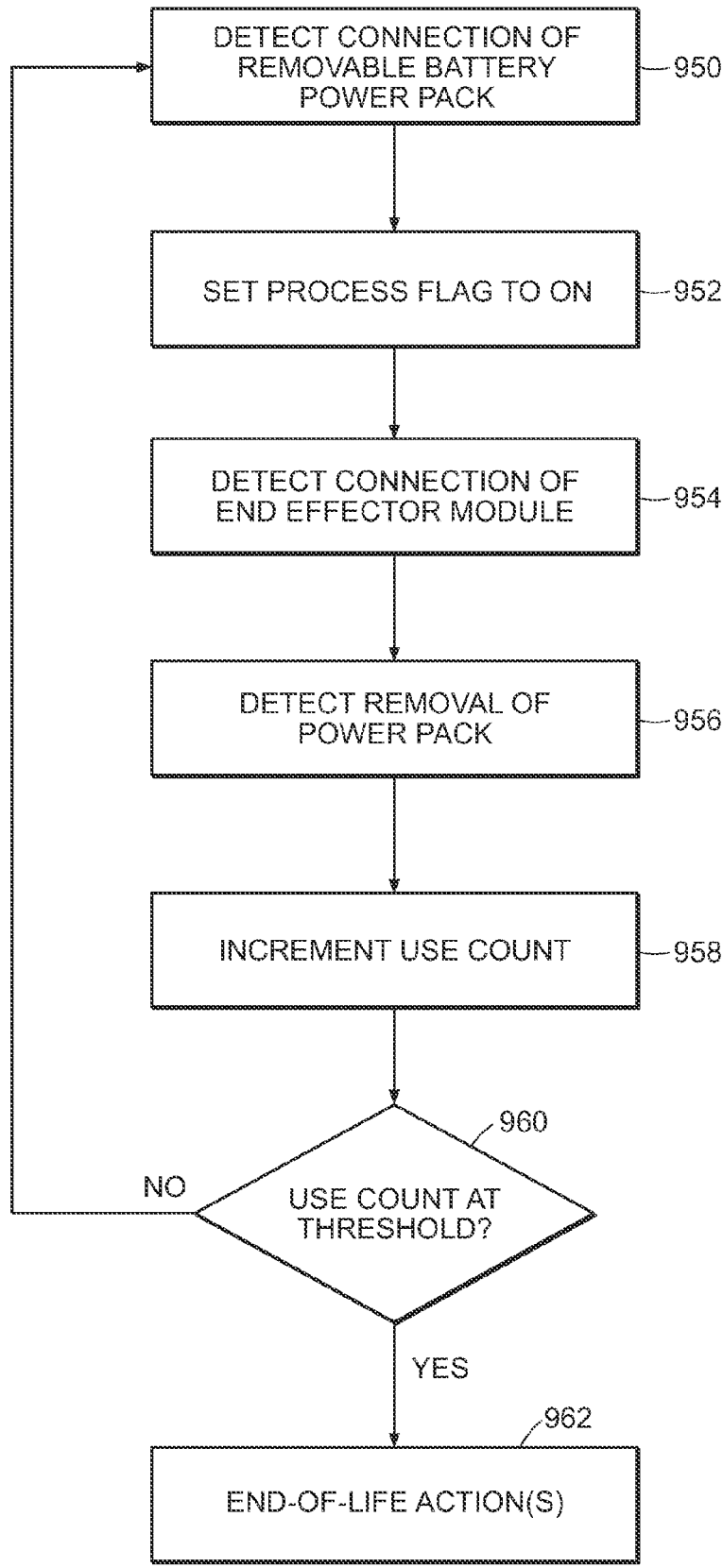

FIG. 17B is a flow chart of another exemplary process that can be executed by the handle processor and powered at times by the secondary power source 904 to track uses of the handle module. At step 950, the handle processor can detect the connection of the removable battery power pack 902 to the handle module 900. Various techniques for detecting the insertion of the battery power pack 902 are described elsewhere herein. In various instances, the insertion of the power pack 902 indicates to the handle processor that a surgical procedure involving the handle module 900 is about to commence. As a result, the handle processor can set a process flag to ON at step 952 when the handle processor detects the insertion of the power pack 902 into the handle module 900. At step 954, the handle processor can detect the complete and proper connection of a DSM to the handle module for the procedure. Various techniques for detecting the attachment of a DSM are described elsewhere herein. Once the DSM and the battery pack 902 have been properly attached, the surgical instrument can be used to complete a surgical procedure. In the event that the battery pack 902 is removed from the handle module 900, the handle processor can detect removal of the battery power pack 902 at step 956. Various techniques for detecting the removal of a power pack are disclosed elsewhere herein. In various instances, removal of the power pack is indicative of the conclusion of a surgical procedure and, as a result, the handle processor, now powered by the secondary power source 904, can increment the use count for the handle module 900 at step 958. Even if the removal of the power pack does not constitute the end of a surgical procedure, the insertion of a new battery pack and/or the re-insertion of a re-charged battery pack can be viewed as another use. Such reuse of the handle module 900 may be conditioned on a test administered at step 960 to assess whether the handle module 900 has reached the end of its useful life. If the end of the handle module's life has been reached, the handle processor can initiate an appropriate end-of-life action(s) at step 962. Various end-of-life actions are disclosed elsewhere herein. It should be appreciated that, with regard to any of the embodiments disclosed herein, an end-of-life action can be overridden by the user of the handle module. Such instances can typically arise when the use threshold count has been reached in the middle of a surgical procedure, for example.

Figure 18A:
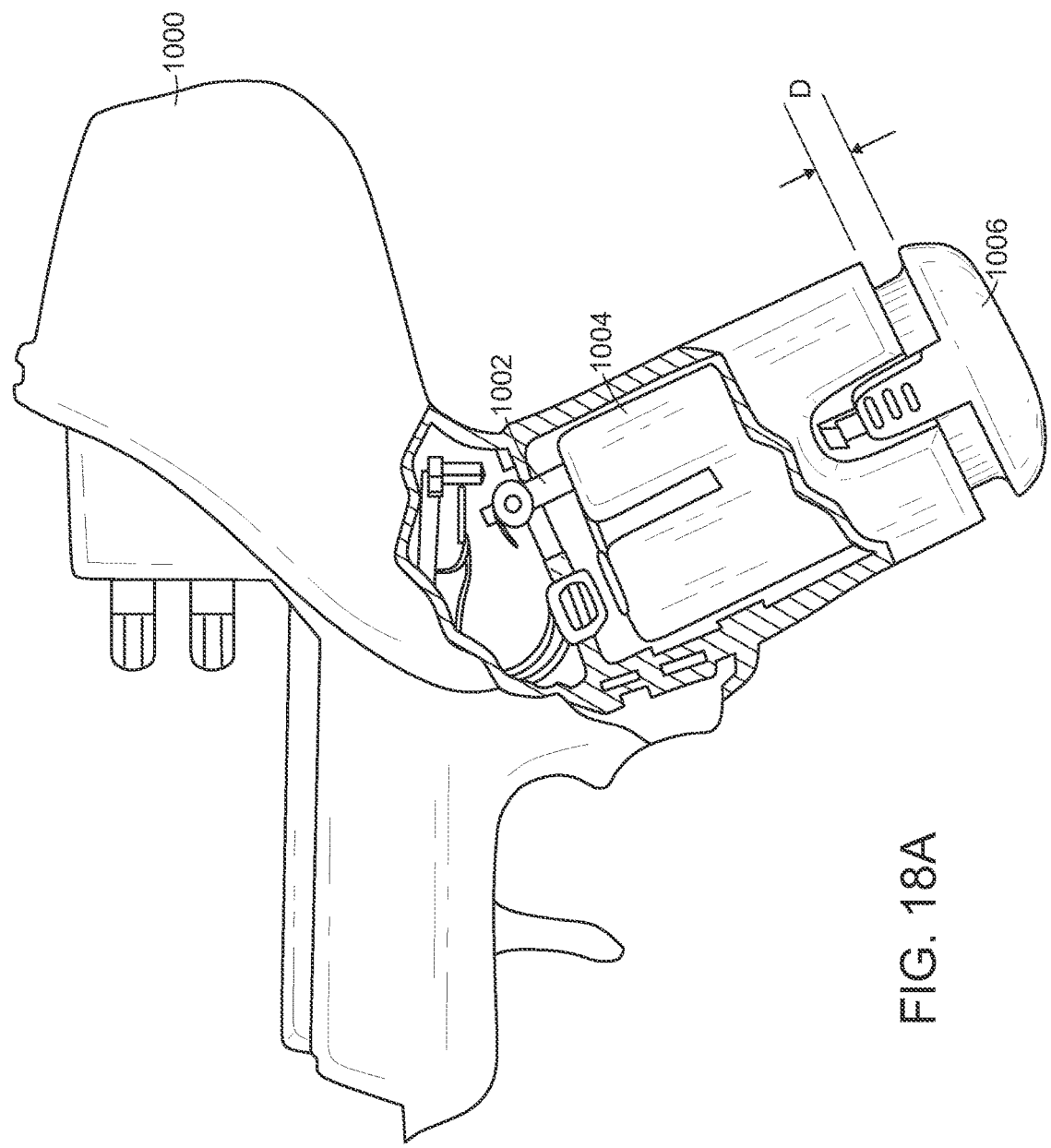
FIGS. 18A, 18B and 18C illustrate a handle module that with a mechanism that prevents the insertion of a battery pack in certain circumstances.

FIGS. 18A-18E show end-of-life actions that could be taken by a handle module that uses a removably battery power pack, for example, to prevent further use of the handle module. FIG. 18A illustrates a handle module 1000 which includes an internal spring-activated lock-out 1002. The lock-out 1002, when released by the handle module 1000, prevents the complete and proper installation of a battery power pack 1004, and/or any other suitable battery pack, into the handle module 1000. In various instances, the lock-out 1002 can be configured to completely prevent the power pack 1004 from entering the handle module 1000. In other instances, the lock-out 1002 can prevent the power pack 1004 from being inserted to a depth in which the battery contacts make electrical contact with the handle contacts, as illustrated in FIG. 18A and described in greater detail further below. Owing to the activation of the lock-out 1002, the power pack 1004 sticks out of the handle module 1000 by a distance D, as also illustrated in FIG. 18A. But for the lock-out 1002, the battery pack 1004 could be seated to a depth in which an end cap 1006 of the battery pack 1004 is flush, or at least substantially flush, with the housing of the handle module 1000.

As discussed above, the lock-out 1002 can selectively prevent the power pack 1004 from supplying power to the handle module 1000. In the non-locked-out state of the handle module 1000 illustrated in FIG. 18B, an electrical contact pad 1016 of the handle module 1000 can be in contact with a contact pad 1018 of the battery pack 1004 so that the internal electrical components of the handle module 1000 can be powered by the battery power pack 1004. In the locked-out state of the handle module 1000 illustrated in FIG. 18C, the lock-out 1002 prevents the contact pad 1018 of the battery pack 1004 from contacting the contact pad 1016 of the handle module 1000. In embodiments where the handle module 1000 does not include a secondary power source and/or a means for storing power, the handle module 1000 will be unusable in its locked-out condition. In embodiments where the handle module 1000 includes a secondary power source and/or a means for storing power, the handle module 1000 can utilize the power from these other sources to run the operating system of the handle module 1000, but not the drive systems and/or electric motors of the handle module 1000, for example.

Figure 18B:
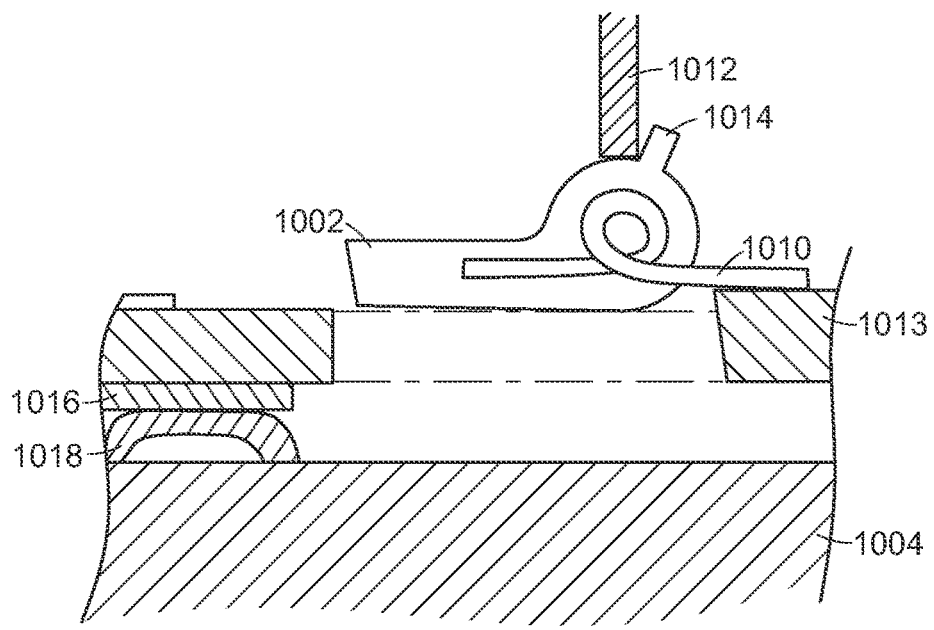
Figure 18C:
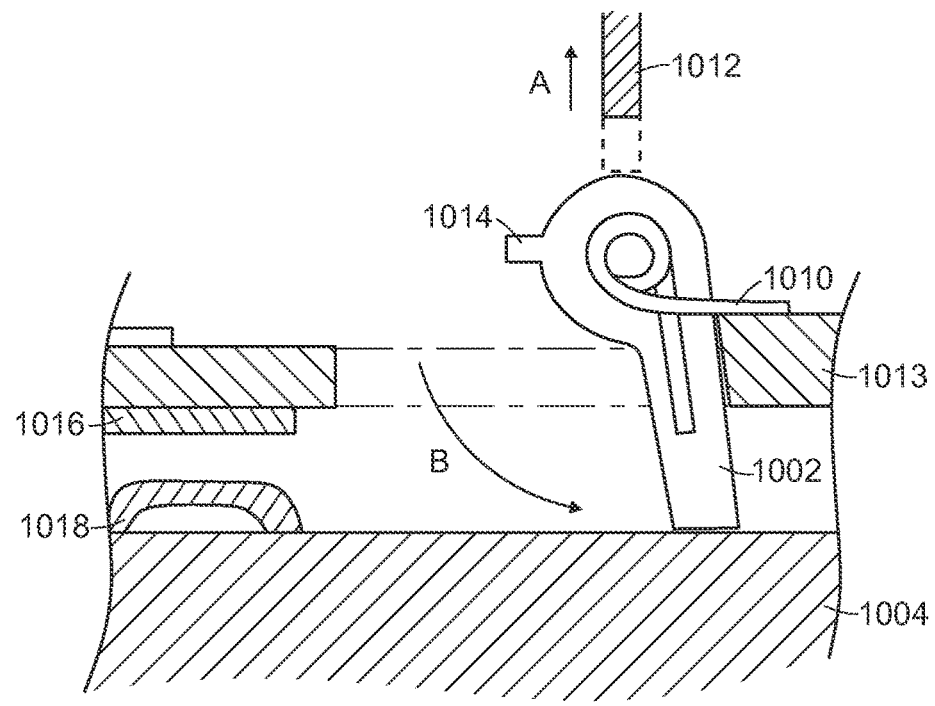

FIG. 18B illustrates the lock-out 1002 in a normal, operational state where it is not locking out the battery pack 1004 and FIG. 18C illustrates the lock-out 1002 in the locked-out state where it is locking out the battery pack 1004. The lock-out 1002 is biased to rotate from its unlocked position (FIG. 18B) to its locked-out position (FIG. 18C) by a torsion spring 1010 that is connected to the lock-out 1002. The torsion spring 1010 has a first end biased against an internal surface 1013 of the handle module 1000 and a second end mounted to the lock-out 1002. The handle module 1000 further includes a latch 1012 configured to releasably hold the lock-out 1002 in its unlocked position. The lock-out 1002 includes a lock shoulder 1014 that abuts the latch 1012 when the latch 1012 is in an extended position and, thus, holds the lock-out 1002 in its unlocked position. When the latch 1012 is retracted, as illustrated in FIG. 18C, the shoulder 1014 of the lock-out 1002 is no longer engaged with the latch 1012 and the torsion spring 1010 can bias the lock-out 1002 into its locked-out position.

When an end-of-life condition of the handle module 1000 has not yet been reached, a latch actuator of the handle module 1000 can hold the latch 1012 in the position illustrated in FIG. 18B. When an end-of-life condition is reached, however, the latch actuator may move the latch 1012 in the direction indicated by arrow A to move the latch 1012 away from the lock shoulder 1014 thereby allowing the lock-out 1002 to rotate counter-clockwise, as indicated by the arrow B in FIG. 18C, due to the bias of the spring 1010. In the locked-out state, the lock-out 1002 protrudes into the battery compartment of the handle module such that, when a battery pack 1004 is inserted in the handle module 1000, the electrical contact pad 1016 of the handle module 1000 does not contact the contact pad 1018 of the battery pack 1004, as discussed above. The latch actuator can comprise any suitable actuator, such as a solenoid, for example.

Figure 18D:
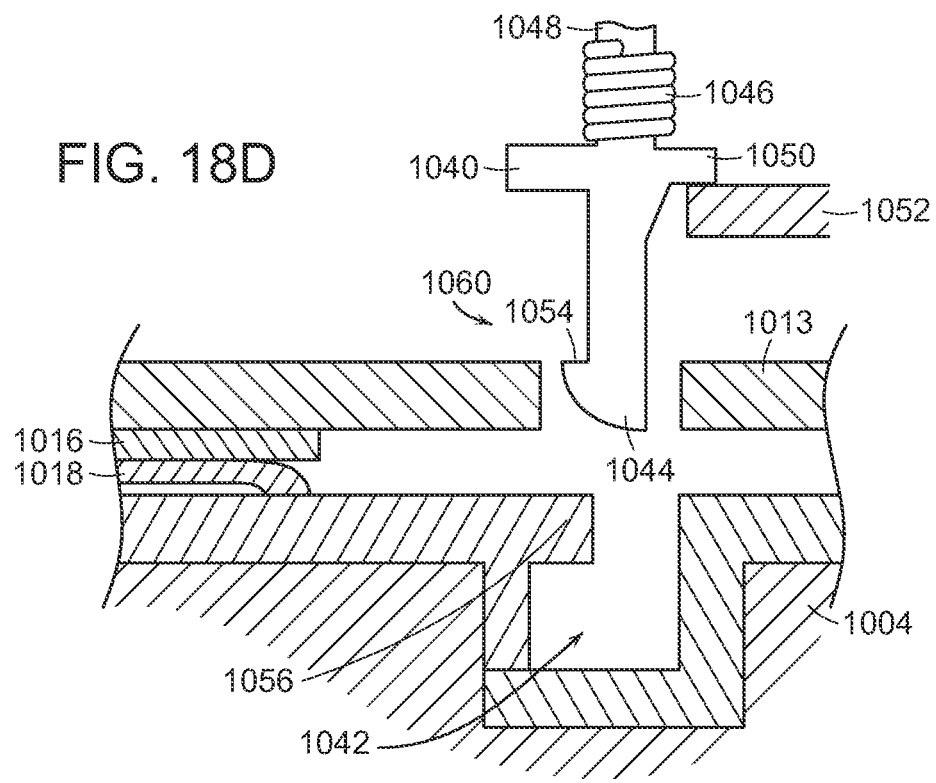
FIGS. 18D and 18E illustrate a mechanism of the handle module of FIG. 18A that prevents removal of the battery pack from the handle module in certain circumstances.
Figure 18E:
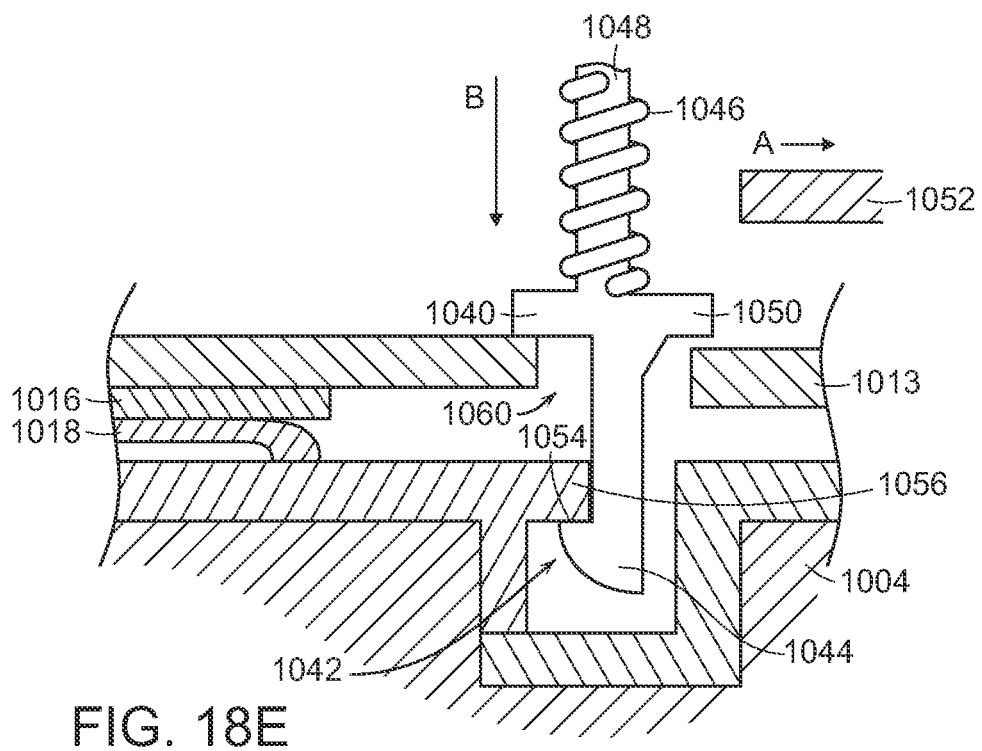

In addition to or in lieu of the above, FIGS. 18D and 18E illustrate an embodiment in which, at the determined end-of-life for the handle module, a battery pack positioned in the handle module cannot be removed from the handle module, thereby preventing the insertion of a new (or recharged) battery pack in the handle module for a subsequent procedure. FIG. 18D illustrates a battery pack 1004 in a normal, operational state where it can be removed from the handle module following a procedure and FIG. 18E illustrates a latch 1040 locking the battery pack 1004 in the handle module such that the battery pack 1004 cannot be removed from the handle module. As shown in FIGS. 18D and 18E, the battery pack 1004 may define an opening 1042 in which a latch head 1044 of the latch 1040 can be inserted to lock the battery pack 1004 in position. The latch 1040 is biased downwardly by a compression spring 1046 mounted on an upper shaft 1048 of the latch 1040. The latch 1040 also includes an upper shoulder 1050 that, in the normal operating state of the handle module, shown in FIG. 18D, abuts a second latch 1052 that is positioned to keep the spring 1046 in a compressed state and prevent the downward movement of the latch 1040. As also shown in FIGS. 18D and 18E, the latch head 1044 includes a shoulder 1054 that, when the latch 1044 is in its actuated position as shown in FIG. 18E, locks behind a mating shoulder 1056 defined by the battery pack 1004.

In operation, when the handle processor determines that the handle module has reached the end of its life (by any of the means described herein), the handle processor may actuate the second latch 1052 causing the second latch 1052 to move out of the way of the latch 1044. The second latch 1052 may be actuated by any suitable actuator, such as a solenoid, for example. In the illustrated embodiment, the second latch 1052 moves left to right away from the shoulder 1050 of the latch 1040 as indicated by the arrow A when the latch 1052 is actuated. The removal of the second latch 1052 away from the shoulder 1050 allows the spring 1046 to decompress and urge the latch 1044 downward, as indicated by the arrow B, through an opening 1060 defined in the housing 1013 of the handle module. As the latch 1040 is moved downwardly by the spring 1046, the latch head 1044 extends into the opening 1042 defined in the battery pack 1004. The latch shoulder 1054 of the latch head 1044 can slide through the opening 1042 and lock in behind the mating shoulder 1056 of the battery pack 1004. The downward movement of the latch head 1044 is limited by the handle module housing 1013 when the upper shoulder 1050 of the latch 1040 contacts the handle module housing 1013. As a result, the battery pack 1004 cannot be removed from the handle module, thereby preventing insertion of a new (or recharged) battery pack into the handle module for a subsequent procedure.

Figure 19C:
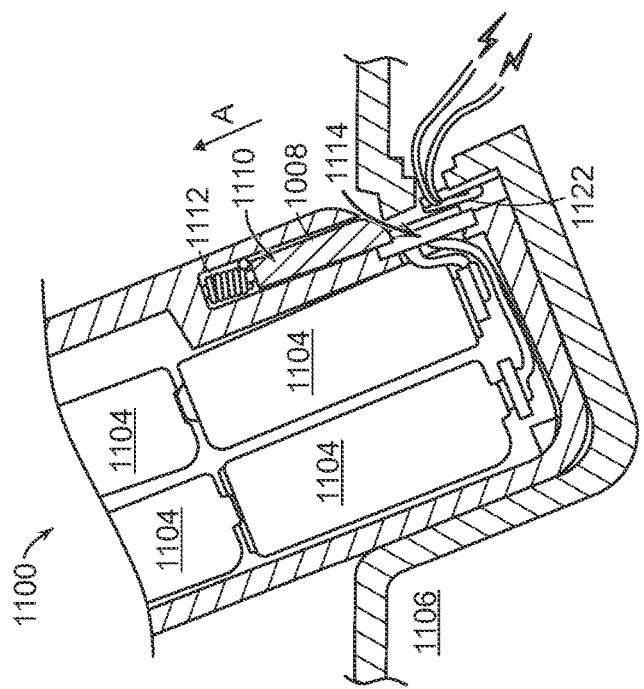
Figure 19B:
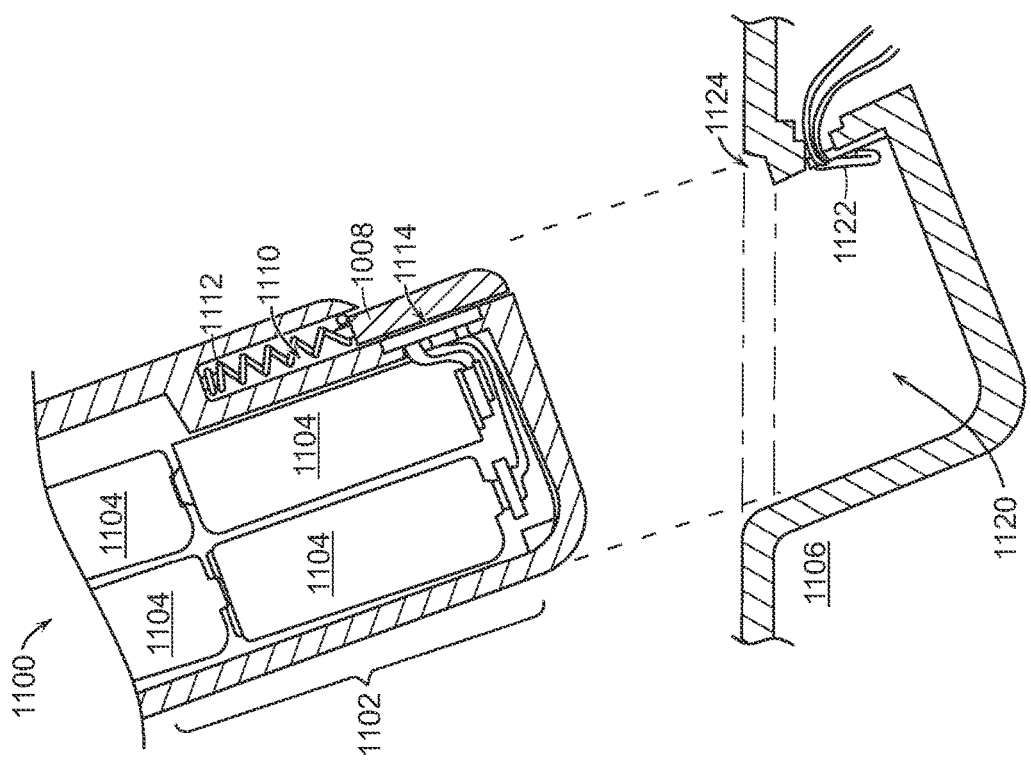

Referring now to FIGS. 19A-19C, a handle module 1100 comprises a rechargeable battery pack 1102 (with one or more rechargeable battery cells 1104) that can be recharged when the handle module 1100 is docked to a charging station 1106. The handle module 1100 further includes a slidable door 1108 that slides, generally up and down in a channel 1110 defined in the handle module 1100, between an open position (FIG. 19C) and a closed position (FIG. 19B). A compression spring 1112 is positioned in the channel 1110 which is configured to bias the slidable door 1108 downwardly into its closed position. When the door 1108 is in its closed position, the door 1108 can shield the battery charging terminals 1114, as depicted in FIG. 19B, from being damaged and/or accidentally coming into contact with a conductive surface in the surrounding environment, for example. To recharge the battery cells 1104, the handle module 1100 is placed in a receiving area 1120 defined by the charging station 1106 that includes charging terminals 1122 that mate and contact with the charging terminals 1114 of the handle module 1100 when the handle module 1100 is inserted fully and properly in the receiving area 1120, as shown in FIG. 19C. As the handle module 1100 is placed in the received area 1120, the slidable door 1108 engages a shoulder 1124 of the charging station 1106 which urges the slidable door 1108 upward, as indicated by the arrow A, compressing the spring 1112, and unshielding (or revealing) the battery pack charging terminals 1114. At such point, the charging terminals 1114 can connect to and contact the receiving station charging terminals 1122 to thereby recharge the battery cells 1104 of the battery pack 1102.

The charging station 1106 may be powered by an AC power supply via a power cord 1130. The charging station 1106 may also include a visual display 1132 that displays information about the handle module 1100. For example, the charging station 1106 may include a processor (not shown) that communicates with the handle processor when the handle module 1100 is installed in the charging station 1106. For example, the charging terminals 1114, 1122 may also include data terminals that provide a data path between the processors. The charging station processor can receive information/data from the handle processor that can be displayed on the display 1132. The displayed information can include, for example, the charge status of the battery pack 1102 (e.g., X % charged) and/or any information tracked by the handle processor, such as the life count or remaining uses of the handle module and/or the number of lifetime firings, for example.

Figure 20B:
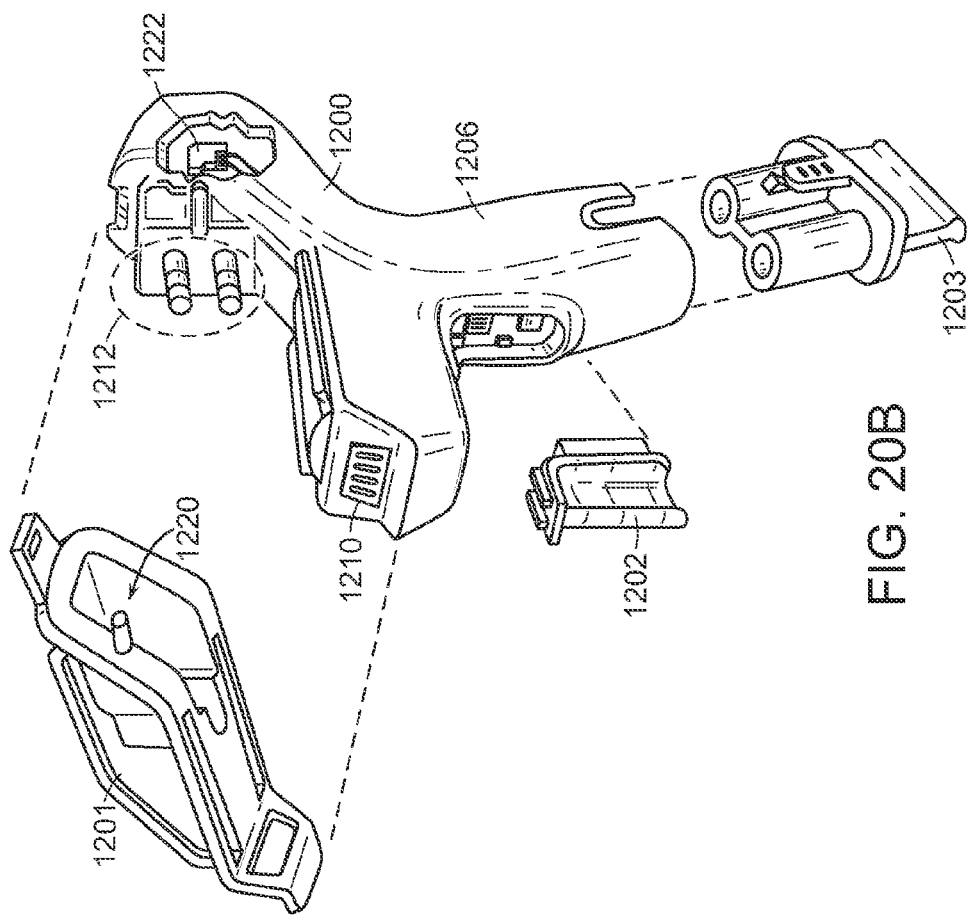
FIGS. 20A and 20B illustrate a handle module with sterilization covers for covering components of the handle module during the sterilization thereof.
Figure 20A:
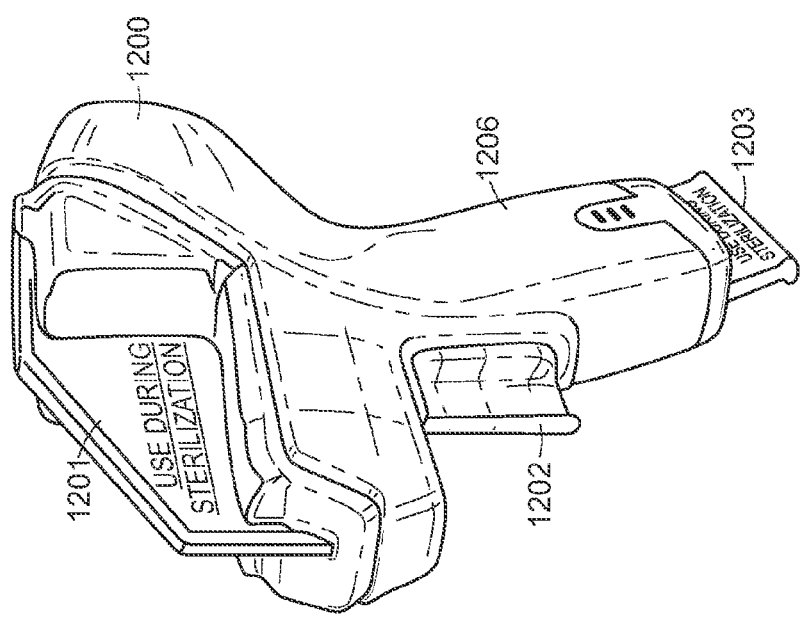

FIGS. 20A-20B show covers 1201, 1202, 1203 that can be used with a handle module 1200 during a sterilization process to protect the internal components of the handle module 1200. The handle module 1200 includes an attachment portion configured to have a DSM attached thereto. An end effector connection area cover 1201 can connect to (e.g., snap-fit) and cover where the DSM connects to the handle module 1200. The handle module 1200 also includes a removable trigger assembly which is used to actuate the drive systems of the handle module 1200. In addition to or in lieu of the above, a trigger cover 1202 can connect to (e.g., snap-fit) and cover the opening that is created when the firing trigger assembly is removed from the handle module 1200. The handle module 1200 further comprises a battery cavity configured to receive a removable power pack therein. Also in addition to or in lieu of the above, a battery pack cover 1203 can connect to and cover where the battery pack is inserted in a pistol grip portion 1206 of the handle module 1200. These covers 1201, 1202, 1203 are preferably made of a material that is resistant to the chemicals used to sterilize the handle module, such as plastic, for example. Further, the covers 1201, 1202, 1203 can cover electrical contacts of the handle module 1200 including an end effector contact board 1210, drive systems 1212, and/or the internal contacts for the battery pack (not shown), for example.

The attachment of the covers 1201, 1202, and/or 1203 to the handle module 1200 can aid in tracking the number of times that the handle module 1200 has been used and/or sterilized. Similarly, the detachment of the covers 1201, 1202, and/or 1203 from the handle module 1200 can aid in tracking the number of times that the handle 1200 has been used and/or sterilized. At least one of the covers 1201, 1202, 1203 can include means to trigger a switch on the handle module 1200 indicating that the cover has been installed. When such a switch is triggered, the handle processor can assume that a sterilization procedure is imminent and enter a sterilization operation mode which is optimized to endure a sterilization procedure. When the handle processor is in a sterilization operation mode, the handle processor can prevent the motor(s) of the handle module 1200 from being operated, de-power certain contacts and/or sensors, power-up certain contacts and/or sensors, record any data stored in transient memory to a memory chip, copy the memory of the handle module to a back-up memory, and/or create a copy the current version of the operating system software for the handle module, for example. The handle processor can also increase the use count of the handle module 1200 when one or more of the covers 1201, 1202, 1203 are attached to or detached from the handle module 1200. In the illustrated arrangement, the DSM connection area cover 1201 includes a protrusion 1220 that contacts and actuates a corresponding switch 1222 on the handle module 1200 (e.g., a depressible switch, or a contact switch, etc.) when the cover 1201 is placed on the handle module 1200. The switch 1222 may be in communication with the handle processor and, in various instances, the handle processor may update its sterilization count when actuation of the switch 1222 is detected. In other arrangements, the trigger 1220 could be on other cover pieces 1202, 1203 and/or placed in different position on the DSM connection area cover 1201. In any event, since the battery pack is ordinarily removed during sterilization, the covers 1201, 1202, 1203 are preferably used in a handle module with a secondary power source that powers the handle processor even when the battery pack is removed, as described herein. As described in other arrangements herein, the handle processor may implement one or more of the end-of-life actions described herein when the sterilization count reaches the threshold level.

Figure 20D:
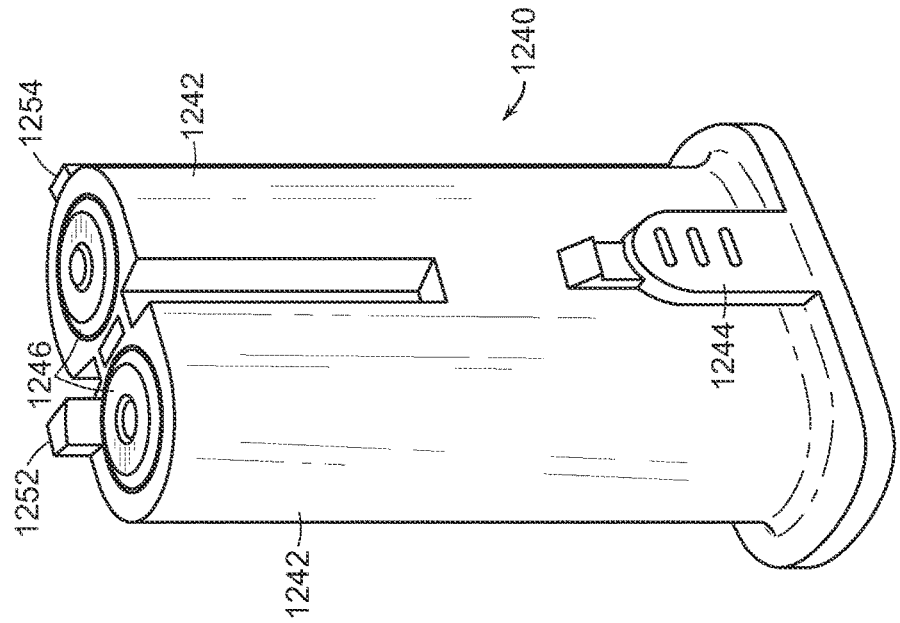
FIG. 20D illustrates a removable battery pack for the handle module of FIG. 20A.
Figure 20C:
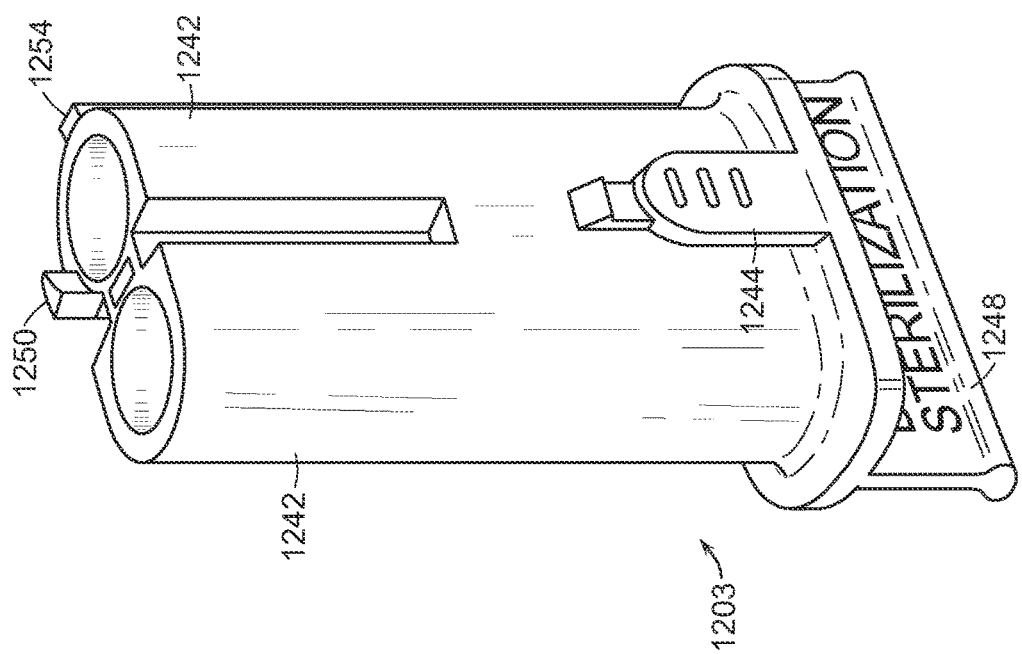
FIG. 20C illustrates a sterilization cover for a battery cavity of the handle module of FIG. 20A.

FIG. 20C shows a variation of the battery pack cover 1203 and FIG. 20D shows a battery pack 1240 that is interchangeable with the battery pack cover 1203 in FIG. 20C. Because the battery pack cover 1203 and the battery pack 1240 are both designed to fit into the battery pack opening in the pistol grip portion 1206 of the handle module 1200 in lieu of one another, the battery pack cover 1203 of FIG. 20C has a shape and configuration that is very similar to the battery pack 1240 of FIG. 20D. For example, the battery pack cover 1203 and the battery pack 1240 both include a clip 1244 for locking to the handle module 1200. Also, the battery pack cover 1203 and the battery pack 1240 both include one or more tubular vessels 1242. The battery cells 1246 may be inside the vessels 1242 in the battery pack 1240 but not for the cover 1203. The cover 1203, however, also includes a feature(s) that readily distinguishes it from the battery pack 1240. In the illustrated arrangement, the cover 1203 includes a relatively thin, long, easily-graspable tab 1248 at the bottom of the cover 1203 that can include markings indicating that it is for use in sterilization, as shown in FIG. 20C.

As also shown in FIGS. 20C and 20D, each of the cover 1203 and the battery pack 1240 may include a respective tab 1250, 1252 that are located in different relative locations. In the illustrated arrangement, the tab 1250 of the cover 1203 is on the right vessel 1242 and the tab 1252 on the battery pack 1240 is on the left vessel 1242 thereof. When inserted into the handle module 1200, the tabs 1250, 1252 may contact and actuate corresponding and respective switches in the handle module 1200 to identify the insertion of the cover 1203 or battery pack 1240, as the case may be. The switches (not shown) may be in communication with the handle processor, and the handle processor can use the actuation of the respective switches to update its use, sterilization, and/or battery-pack-connection counts, as the case may be. The actuation of the sterilization switch can place the handle module 1200 in a sterilization operation mode and the actuation of the battery switch can place the handle module in a surgical operation mode, for example. The tabs 1250, 1252 are preferably in two different locations such that the handle module 1200 may include two different switches: a battery switch which is only actuated by the battery pack 1240 and a sterilization switch which is only actuated by the sterilization cover 1203. In various arrangements, the tabs 1250, 1252 could be located at mirror opposite positions on the vessels 1242, for example. Both the cover 1203 and battery pack 1240 can include feature(s) so that they can only be inserted in one orientation, to thereby prevent the battery pack tab 1252 from actuating the sterilization cover switch and vice versa. In the illustrated arrangement, for instance, the battery pack cover 1203 and the battery pack 1240 both include a tongue 1254 on only one side thereof that can fit into a corresponding groove defined in only one side of the handle module 1200.

Figure 21A:
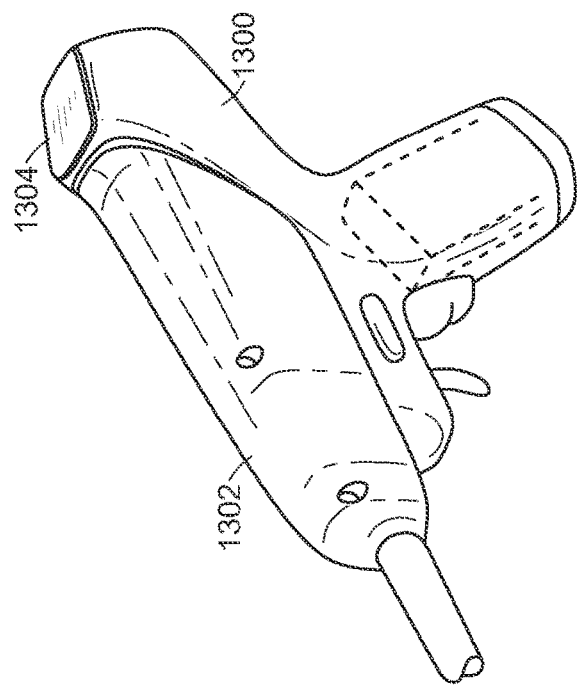
FIGS. 21A, 21B, 21C and 21D illustrate display configurations for a surgical instrument comprising a handle module and a detachable shaft module.
Figure 21B:
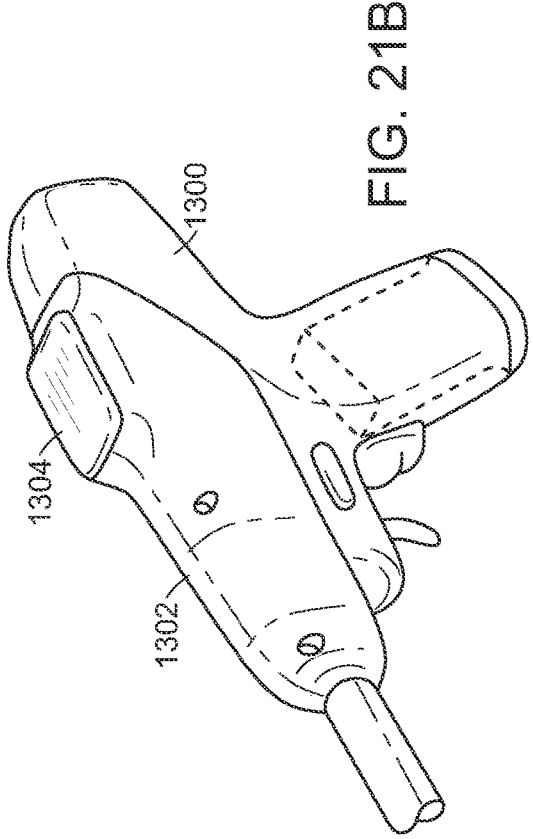
Figure 21C:
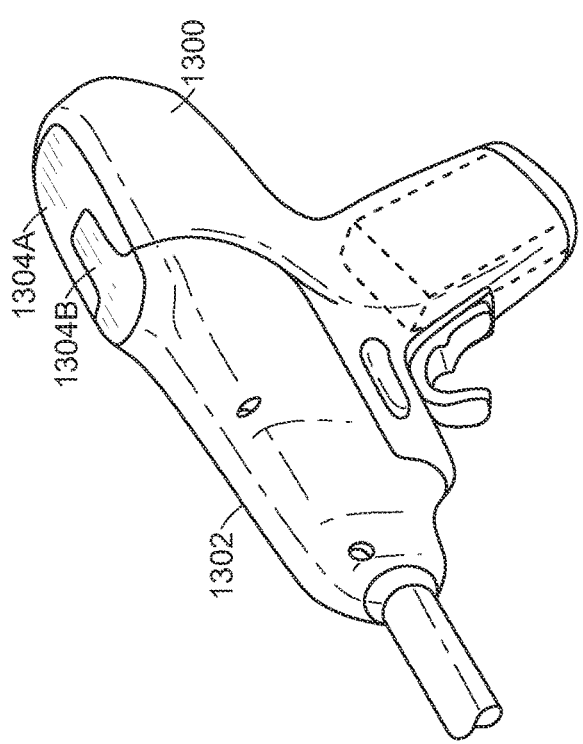

FIGS. 21A-21C show exemplary displays for a handle module 1300 and/or a DSM 1302 that may provide visual information to a user about the status of the handle module 1300 and/or DSM 1302. As shown in FIG. 21A, the display may include a display portion 1304A on the handle module 1300 and a display portion 1304B on the DSM. The display portions 1304A and 1304B can be adjacent to one another or separated from one another. In certain instances, the display portions 1304A and 1304B can be utilized to display discrete, or non-overlapping, sets of information. In various instances, the display portions 1304A and 1304B can be utilized to display co-ordinated information which may or may not be duplicative. In certain other instances, the display 1304 could be wholly on the DSM 1302 as shown in FIG. 21B or, alternatively, the display 1304 could be wholly on the handle module 1300 as shown in FIG. 21C. The display 1304 may comprise a flat panel display, such as a LED-backlit LCD flat panel display, for example, and/or any other suitable flat panel or non-flat panel display type. The display 1304 may be controlled by the handle processor and/or the DSM processor.

Figure 21D:
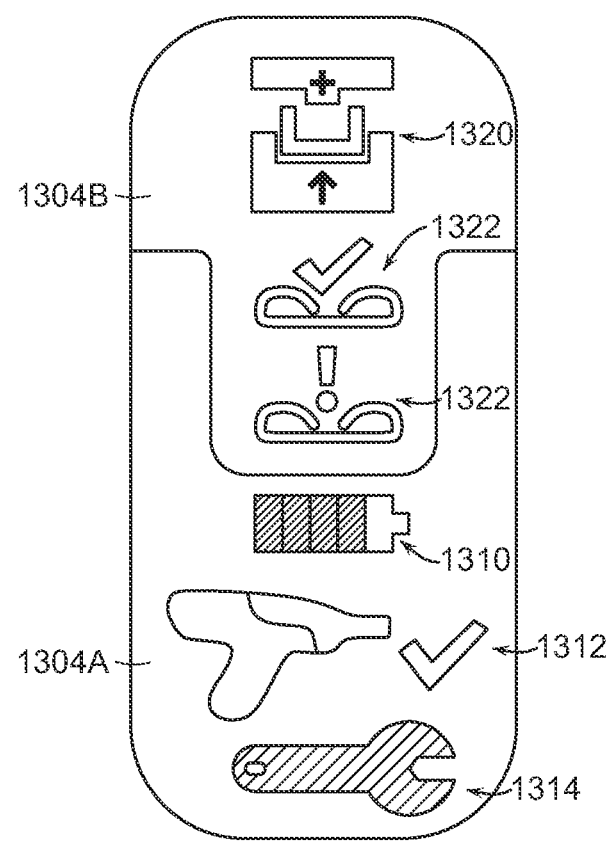

FIG. 21D shows an exemplary display configuration wherein the display comprises adjacent handle and end effector portions 1304A, 1304B. As shown in FIG. 21D, the handle portion 1304A indicators may include indicators related to the handle module, such as a battery status indicator 1310, an indicator 1312 that shows that the DSM connected to the handle module is recognized, and/or a general handle module error indicator 1314. The DSM display 1304B may include indicators related to the DSM, such as an indicator 1320 for whether the end effector jaws are closed, an indicator for whether the staples in the end effector have not yet been fired, an indicator 1322 for whether the staples have been properly fired, and/or an indicator 1324 for whether there is an error related to the staples or staple cartridge, for example. Of course, in other variations, fewer, more, and/or different icons could be used to alert the user/clinician as to the status of various components and aspects of the handle module 1300 and/or DSM 1302. For example, the display 1304 may indicate the number of firings remaining for the battery pack and/or the number of remaining uses for the handle module, for example. The display may include buttons and/or a touch screen interface where a user/clinician could input information to the handle module and/or DSM processors/memory.

Figure 22:
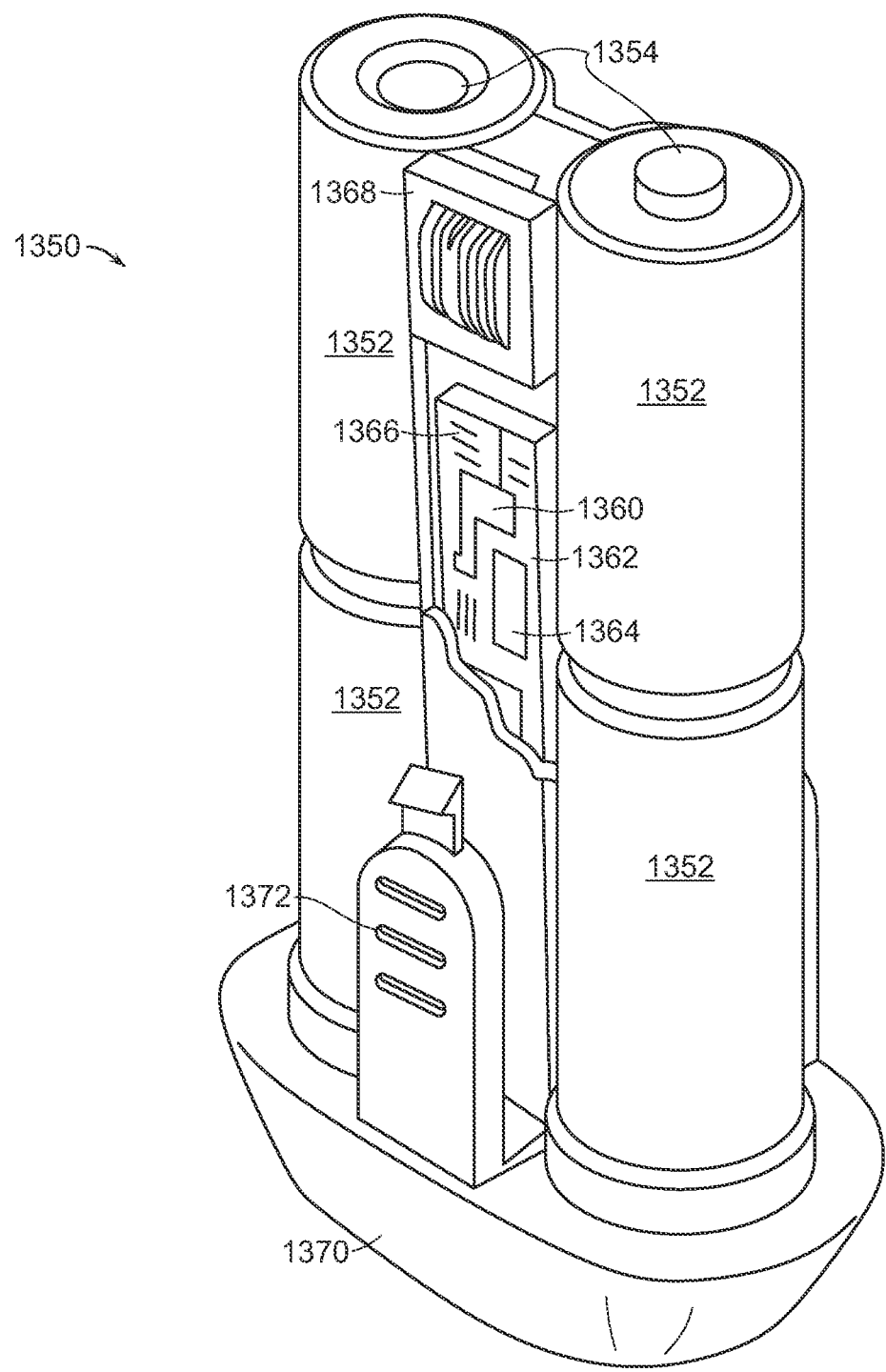
FIG. 22 illustrates a removable battery pack with an internal circuit board.

In various instances, a removable battery pack may be sterilized and recharged after a procedure so that it can be reused in a subsequent procedure in the same handle module and/or a different handle module. FIG. 22 is a diagram of a removable battery pack 1350 that can track the number of times it has been sterilized, which can be a proxy for the number of times that the battery pack 1350 has been used in surgical procedures. The battery pack 1350 may include a number of battery cells 1352 with output voltage terminals 1354. As shown in FIG. 22, the battery pack 1350 may also include a battery pack processor 1360 mounted to a battery pack circuit board 1362. The battery pack processor 1360 may include internal or external memory (such as external memory chip 1364 mounted to the circuit board 1362), and the battery pack processor 1360 can execute software/firmware stored in the memory. As such, the batter pack processor, 1360 can implement a battery management system (BMS) that manages the rechargeable battery. The BMS can protect the battery from being operated outside its safe operating area, monitor the state of the battery, calculate secondary data, report that data, control its environment, authenticate the battery, and/or balance the cells of the battery, for example.

In various arrangements, the battery pack 1350 may also include a micro moisture or humidity sensor 1366 for sensing when the battery pack 1350 is in a moist or humid environment consistent with undergoing a sterilization process, for example. The battery pack processor 1360 may be in communication with the moisture/humidity sensor 1366 such that, for each instance that the moisture/humidity sensor 1366 detects a threshold level of moisture or humidity for a threshold period of time which is consistent with a typical sterilization process, the battery processor 1360 may update its sterilization count as a proxy for the number of times the battery pack 1350 has been used. In various instances, the battery processor 1360 can be configured to not count aberrational events that might yield false positives. In any event, once the threshold sterilization count has been reached, the battery pack processor 1360 may disable use of the battery pack 1350. For example, as shown in FIG. 22, the battery pack 1350 may include a data terminal 1368 that can provide a connection to the handle processor of the handle module. When the battery pack 1350 is spent (e.g., reached the sterilization count threshold), the battery pack processor 1360 may send a signal to the handle processor that the battery pack 1350 should not be used. The handle processor may then indicate through its display that there is a problem with the battery pack 1350.

In various instances, the battery pack processor 1360 may update its use count based on data connections to a handle module. Every time the battery pack processor 1360 detects a data connection to a handle module, the battery pack processor can update its use count.

The battery pack 1350 may include a secondary power source (not shown) that is charged by the battery cells 1352 when the battery cells 1352 are charged and/or supply power to a handle module during a surgical procedure. In such an embodiment, the low-power battery pack electronic components can remain powered even when the battery pack 1350 is not installed in a handle module. Also, as shown in FIG. 22, the battery pack 1350 may include an end cap 1370 and a latch 1372 for facilitating the connection of the battery pack 1350 to the handle module.

FIGS. 23A and 23B illustrate another possible end-of-life action for a handle module. In the illustrated arrangement, a handle module 1400 includes a projecting portion 1402 that is movable between a retracted position and an extended position. Prior to the end-of-life of the handle module 1400, the projecting portion 1402 is held in its retracted position. In such a position, the projecting portion 1402 does not interfere with the handle module 1400 being positioned in the corresponding opening in its sterilization tray 1404. Once the handle processor determines that the handle module 1400 has reached its end-of-life, according to any suitable algorithm, the projecting portion 1402 is moved into its extended position. In such a position, the projecting portion 1402 interferes with the proper placement of the handle module 1400 in its corresponding opening in the sterilization tray 1404. In the illustrated arrangement, the projecting portion 1402 is at the distal end 1406 of the handle module 1400, but it could be placed anywhere that is convenient and that, when projected, inhibits placing the handle module 1400 in the corresponding opening of the sterilization tray 1404. As mentioned before in connection with FIG. 11A, the sterilization tray includes an opening whose shape corresponds to the shape of the handle module so that the handle module is closely received in the opening. In the arrangement of FIGS. 23A and 23B, the handle module 1400 fits into the opening in the sterilization tray 1404 when the projection portion 1402 is retracted (not projected), but does not fit into the opening when the projecting portion 1402 is projected outwardly from the handle module 1400 as shown in FIGS. 23A and 23B. The projecting portion 1402 may be solenoid-driven, for example. When the handle processor has determined that the end-of-life for the handle module 1400 has been reached, the coil of the solenoid is energized so that the solenoid armature is extended outwardly thereby causing the projecting portion 1402 to extend outwardly from the handle module 1400, for example. The handle module 1400 may also include a stopper, such as a spring-loaded detent, for example, that prevents the retraction of the solenoid armature and the projecting portion 1402 once they have been actuated.

Figure 24A:
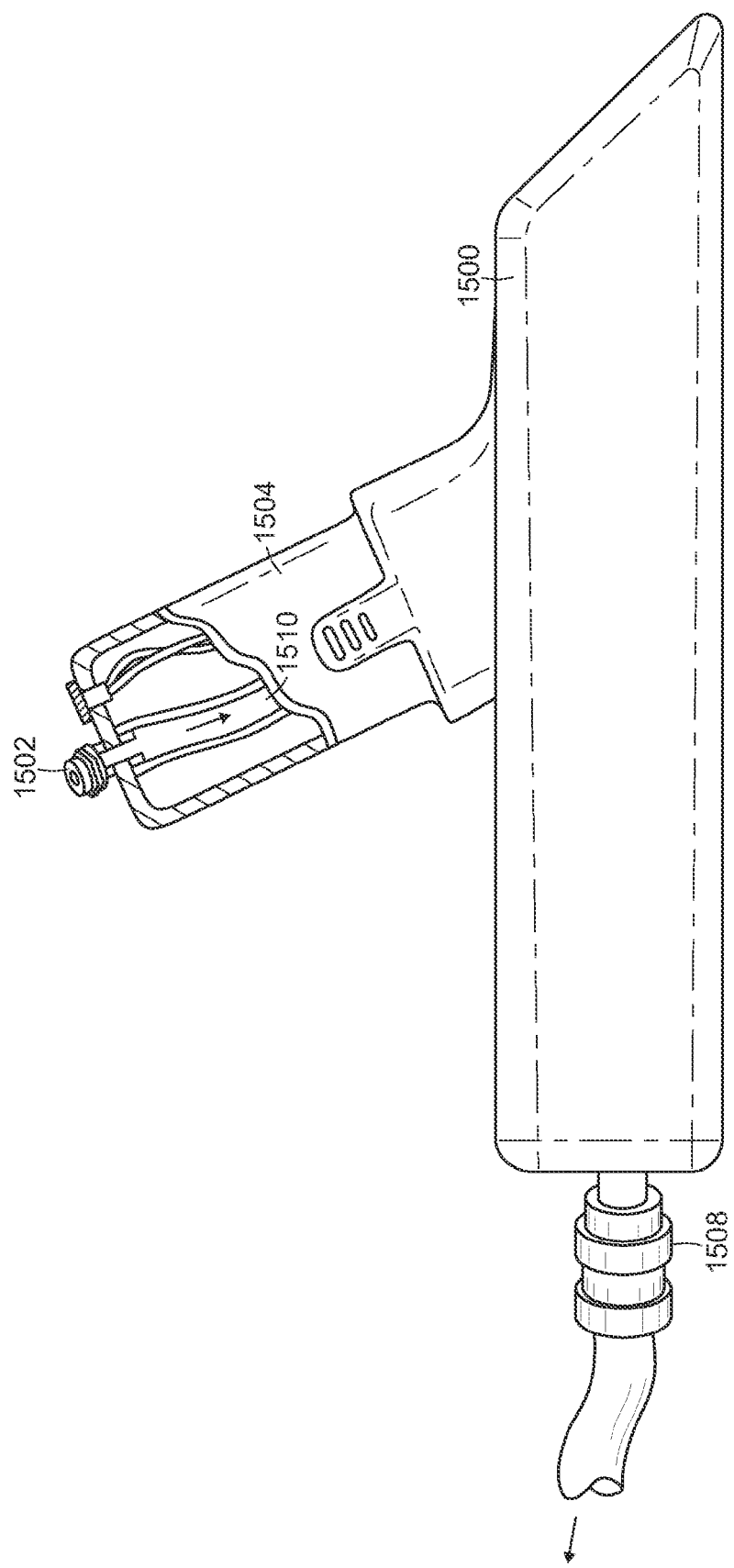
FIGS. 24A and 24B illustrate a handle module inspection station for applying vacuum pressure to a handle module.
Figure 24B:
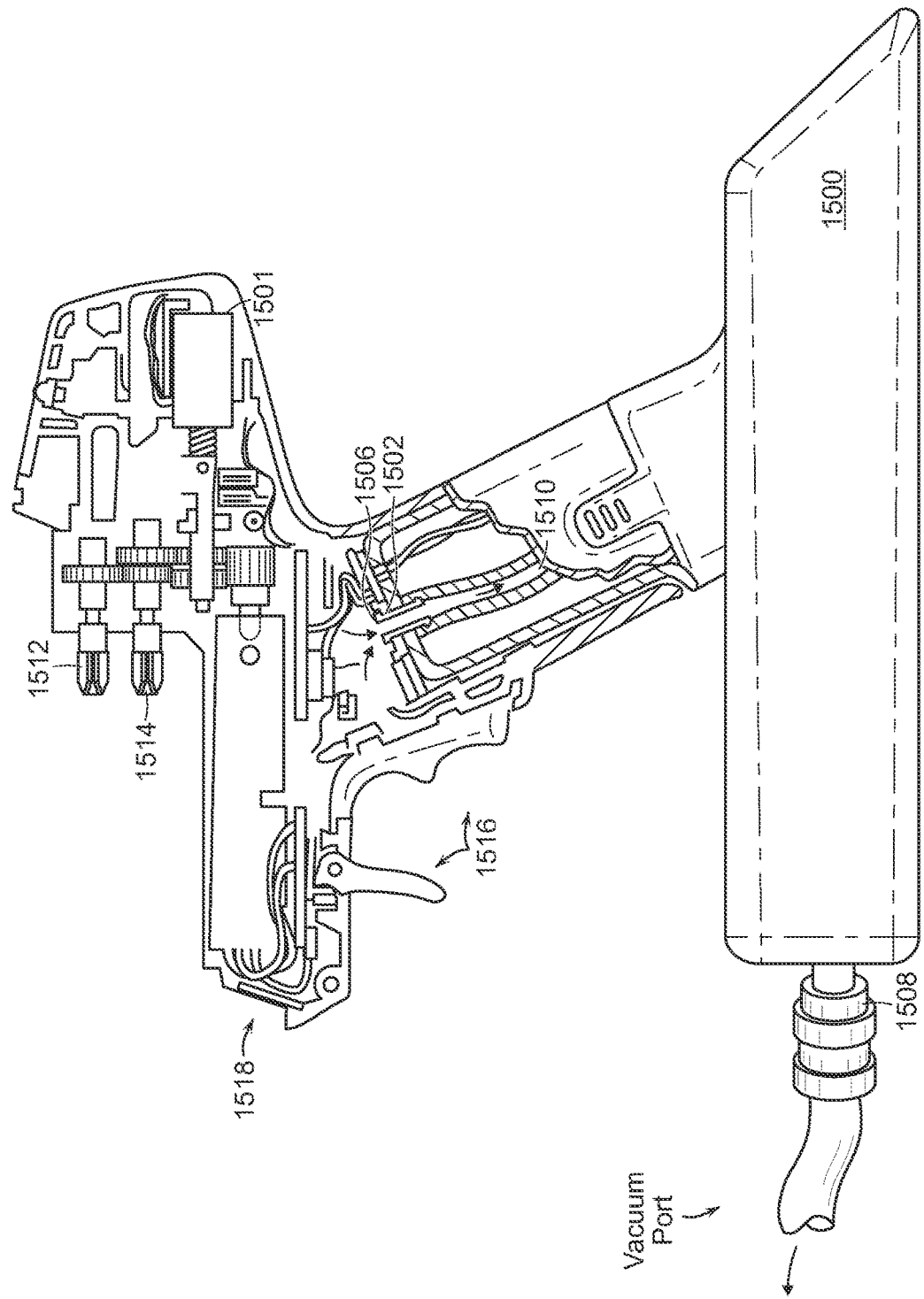

As described in connection with FIGS. 12A-E, a handle module could be connected to an inspection station before, during, and/or following a procedure. The inspection station can be used to perform tests on the handle module to determine if the handle module is in a condition suitable for another surgical procedure, or whether the handle module needs to be conditioned or repaired before it is suitable for another surgical procedure. As shown in FIGS. 24A and 24B, an inspection station 1500 includes an extension 1504 configured to be inserted into the empty battery cavity of a handle module such that the extension 1504 can be placed in communication with the handle module, similar to the embodiments described above. A handle module 1501 depicted in FIG. 24B comprises such a handle module, for example. The inspection station includes a vacuum coupling 1502 at the upper portion of the extension 1504 which can mate to a corresponding vacuum coupling 1506 in the internal portion of the handle module 1501. The inspection station 1500 may be connected to a vacuum pump via a vacuum port 1508, which is connected to the vacuum coupling 1502 of the inspection station 1500 via a tube 1510. When the vacuum pump is turned on, it may draw air from the internal portion of the handle module 1501 to dry the internal portions of the handle module 1501. The inspection station 1500 may include pressure gauges and/or air flow sensors in communication with the tube 1510 that measure how well the handle module 1501 holds the vacuum pressure. In various instances, such a vacuum test can evaluate the integrity of various seals throughout the handle module 1501, such as seals engaged with the rotary drive outputs 1512, 1514, seals engaged with the firing trigger areas 1516, and/or seals engaged with the electrical contact board 1518 that connects to the DSM, for example. If the various handle module seals are not satisfactory, and the handle module does not adequately maintain the vacuum as detected by the vacuum sensors, the inspection station 1500 can issue a warning via its display indicating that the handle module 1501 needs to be repaired.

Figure 25A:
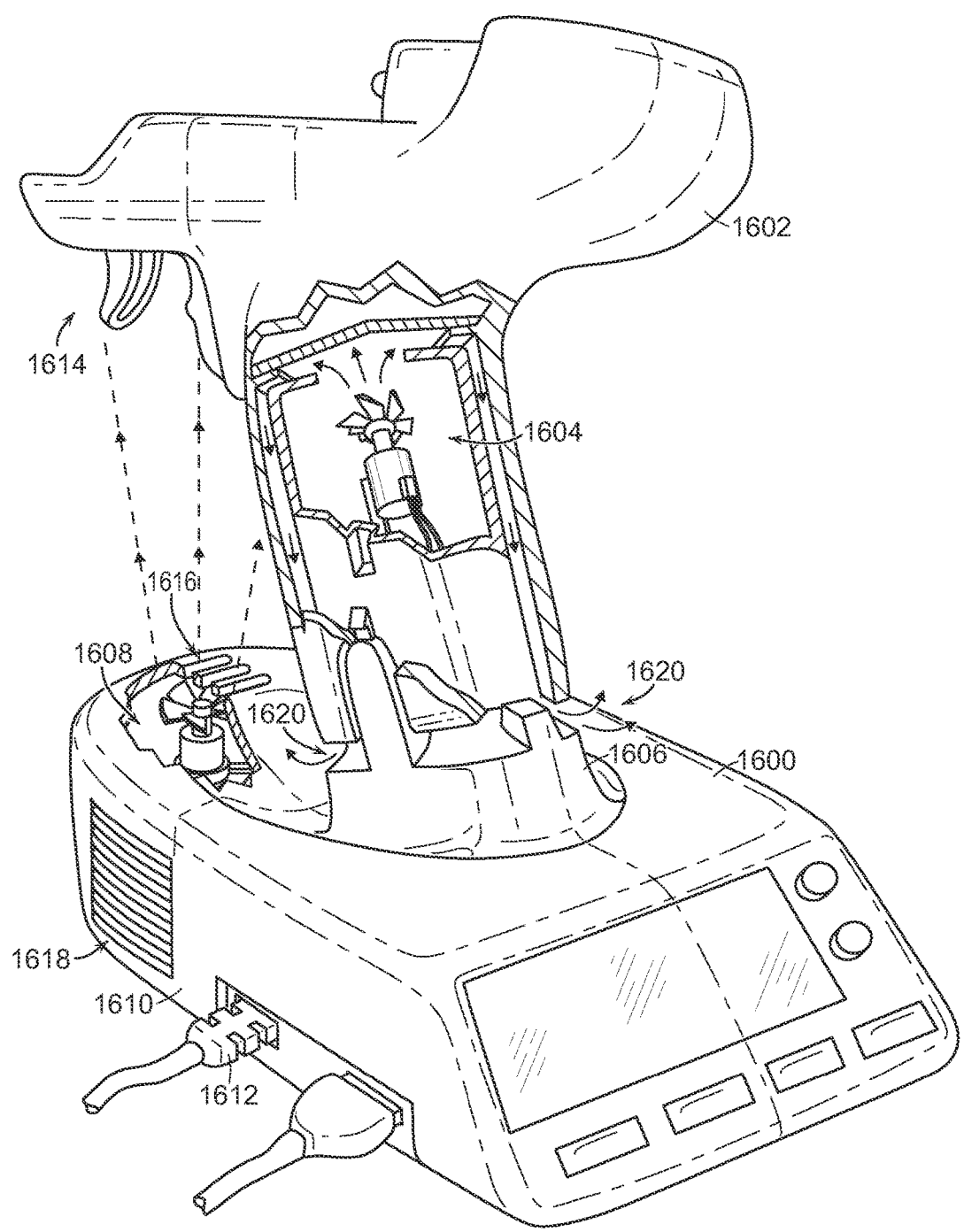
FIGS. 25A, 25B, 25C and 25D illustrate a handle module inspection station with one or more fans for drying the handle module.

In addition to or in lieu of the above, an inspection station could be adapted to dry a handle module following a surgical procedure and/or sterilization procedure as part of preparing the handle module for a subsequent procedure. FIG. 25A illustrates an inspection station 1600 that could be used to dry a handle module 1602, for example. Similar to the above, the inspection station 1600 includes a base portion 1610 and, in addition, an extension 1606 extending from the base portion 1610 that is positionable in the empty battery cavity of the handle module 1602 in order to place the handle module 1602 in communication with the inspection station 1600. The inspection station 1600 includes two fans—a first fan 1604 located at the upper end of the extension 1606—and a second fan 1608 located at the front of the base portion 1610. The fans 1604 and 1608 are electrically powered, such as by an AC power source via a power adapter 1612, for example. The first fan 1604 can be aimed at the internal components of the handle module 1602 through an opening in the battery pack cavity. The upper surface of the extension 1606 can include vent openings through which the air blown by the first fan 1604 can circulate to the handle module 1602. The second fan 1608 can be aimed at a trigger area 1614 of the handle module 1602 to dry the trigger area 1614 and the surrounding areas of the handle module 1602. The top, front surface of the base portion 1610 of the inspection station 1600 can include vent openings 1616 for the second fan 1608 so that air blown from the second fan 1608 can be circulated to the trigger area 1614. The base portion 1610 may also include an air intake for the fans 1604 and 1608, such as an air intake 1618 in the base portion 1610. The inspection station 1600 may also include exhaust vents, such as bilateral exhaust vents 1620 at the bottom of the extension 1606, to allow exhaust to escape from the inspection station 1600. The inspection station 1600 could include as many fans, air intakes, and/or air exhausts as deemed necessary.

Figure 25B:
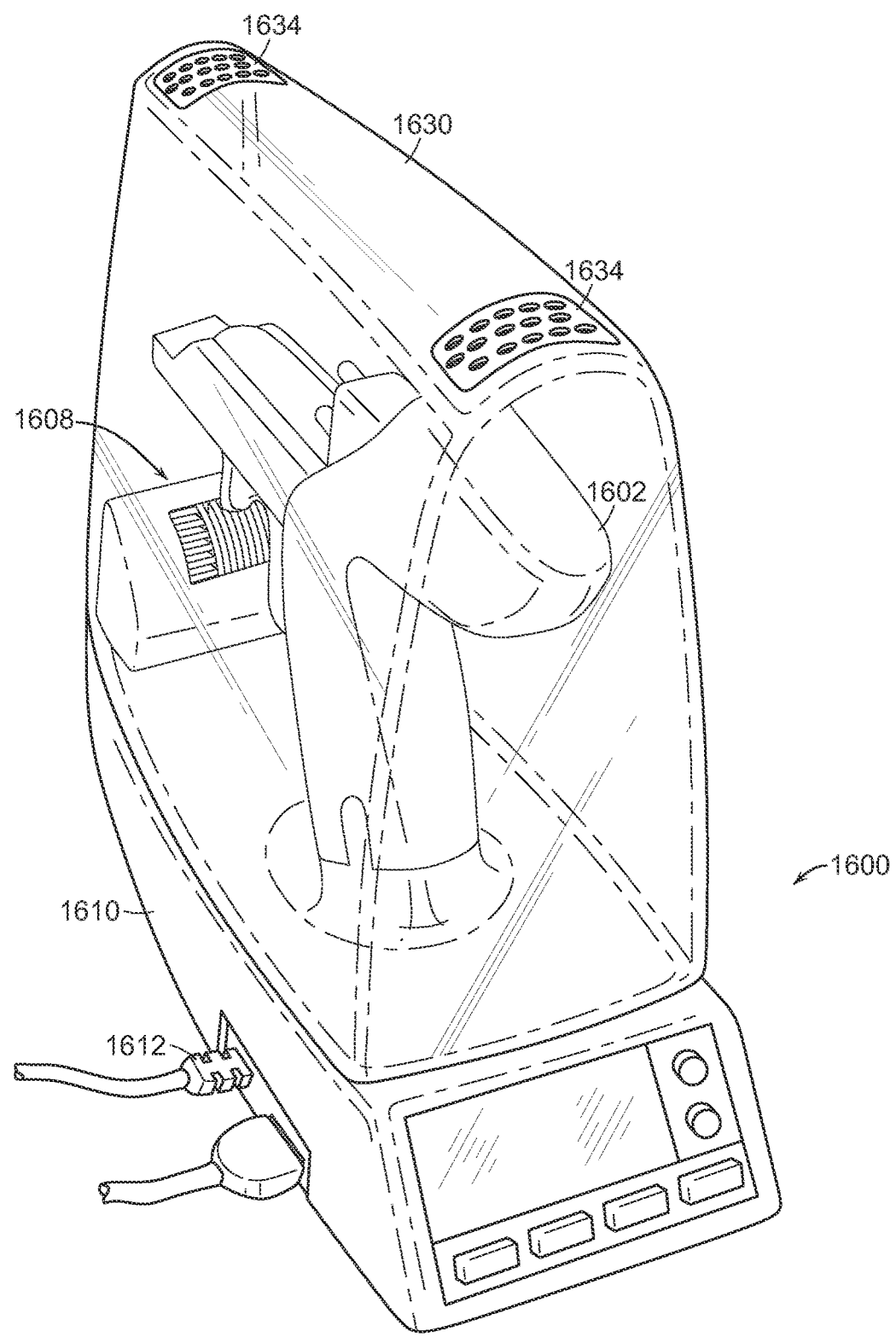
Figure 25C:
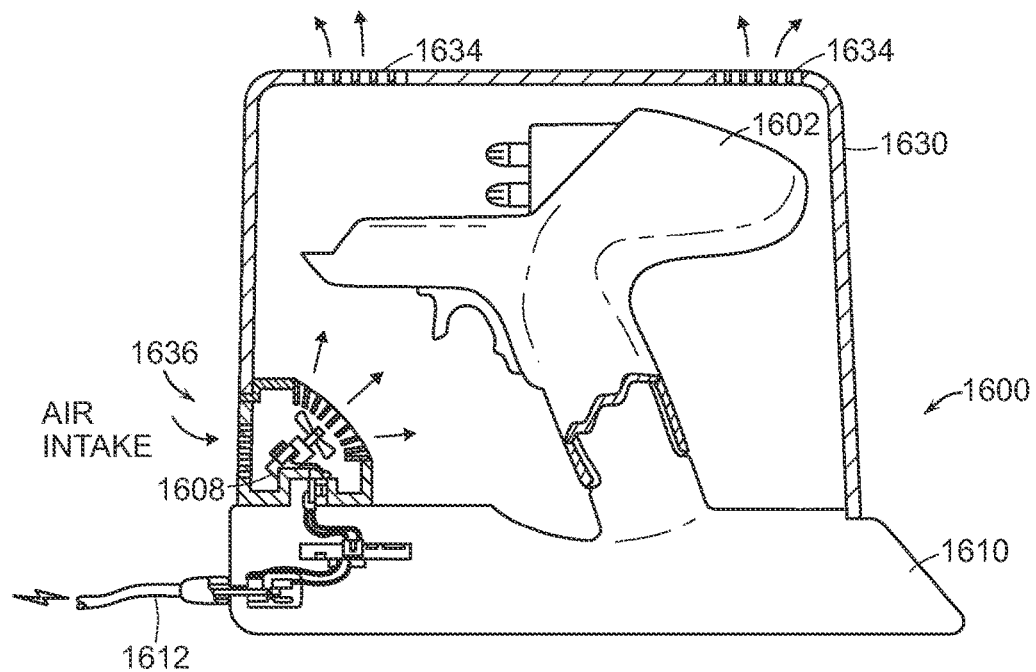
Figure 25D:
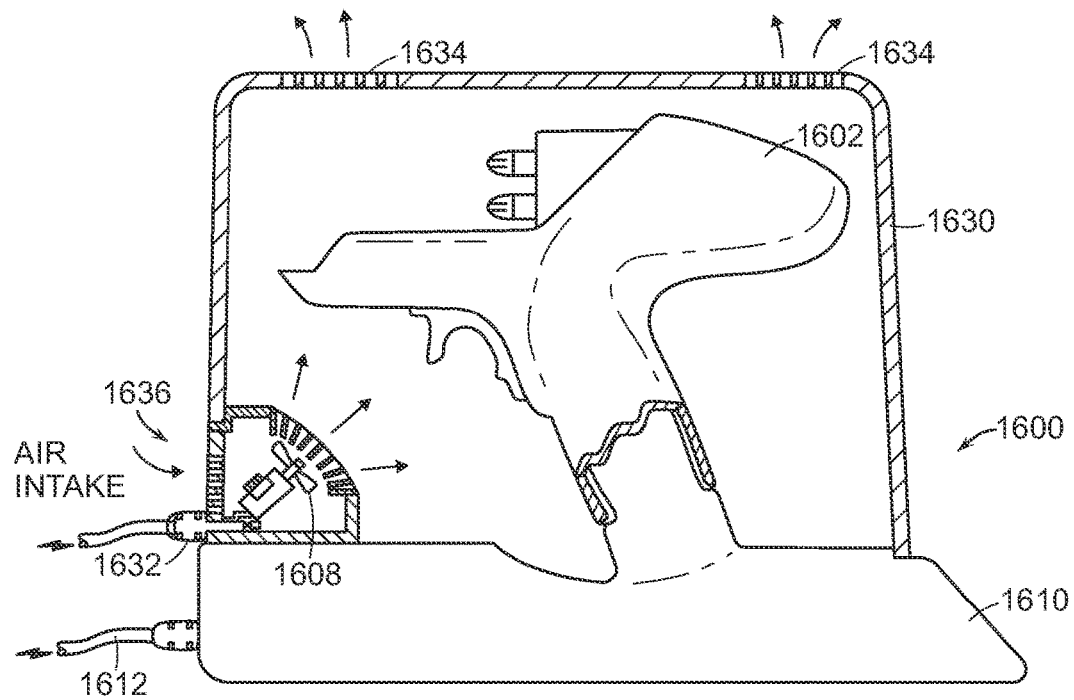

FIGS. 25B, 25C, and 25D illustrate another exemplary inspection station 1600. The base portion 1610 in FIGS. 25B, 25C, and 25D is longer front-to-back than the base station in FIG. 25A, and the lower front fan 1608 in FIGS. 25B, 25C, and 25D is raised above the base portion 1610 and angled at the trigger area 1614. The arrangement shown in FIGS. 25B, 25C, and 25D also includes a cover (or lid) 1630 that attaches to the base portion 1610 of the inspection 1600 and that covers and envelops the handle module 1602. The cover 1630 may be made of hard, translucent plastic, such as polycarbonate, for example. In one aspect, the fan 1608 may be powered by the adapter 1612 for the inspection station 1600, as shown in FIG. 25C. In another aspect, the fan 1608 may have its own power adapter 1632, separate from the power adapter 1612 for the inspection station 1600, as shown in FIG. 25D. The upper surface of the cover/lid 1630 may include one or more air exhaust vents 1634, and the cover/lid 1630 may also include air intake vents 1636 near the fan 1608.

Figure 25E:
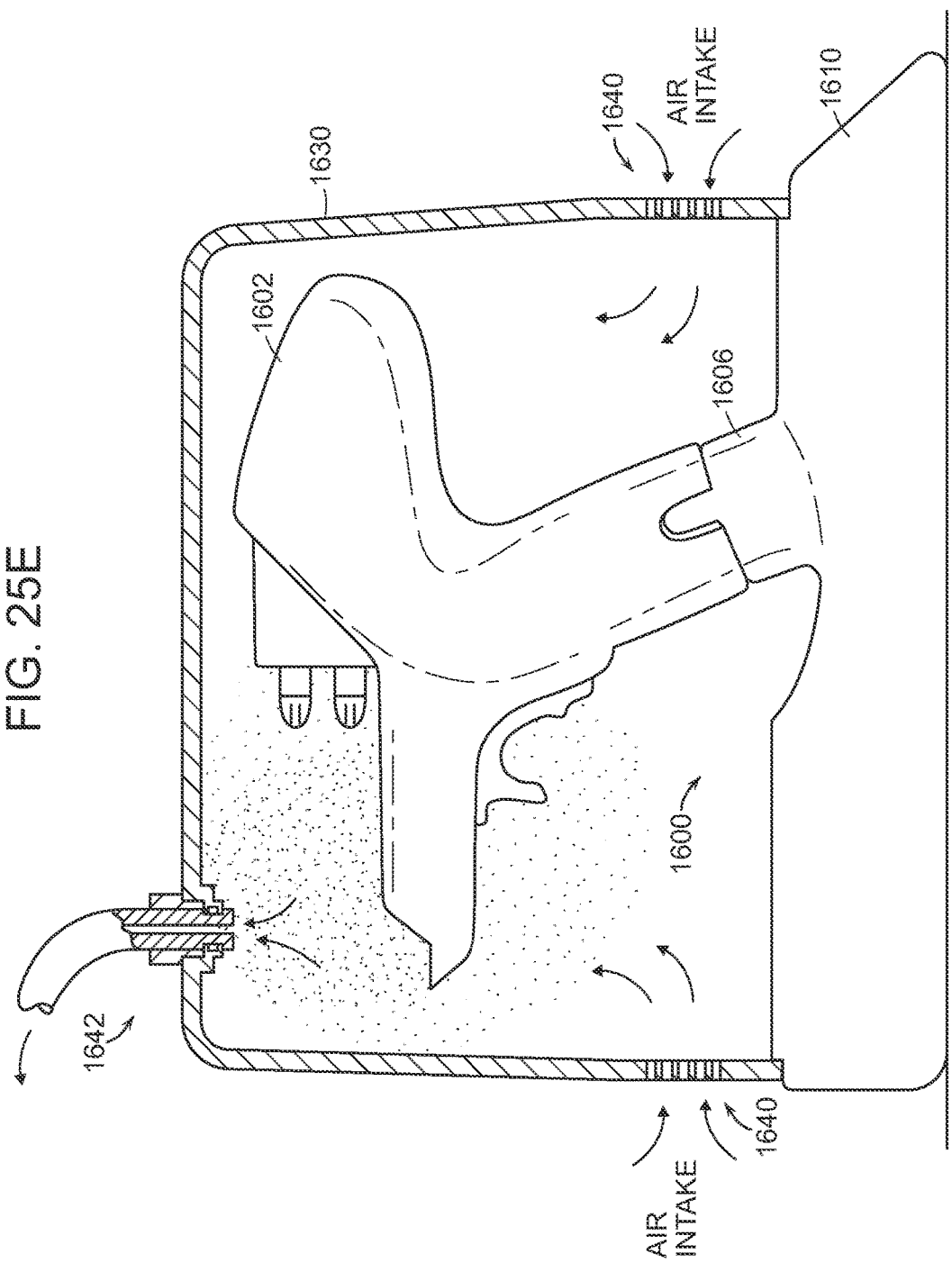
FIG. 25E illustrates an inspection station with a vacuum port to dry a handle module.

FIG. 25E illustrates another arrangement for the inspection station 1600 that uses vacuum flow to dry the handle module 1602. In such an arrangement, the cover/lid 1630 may define one or more air intakes 1640 (two of which are illustrated in FIG. 25E) and have a vacuum port 1642 configured to be placed in communication with a vacuum pump. To dry the handle module 1602, the vacuum pump is turned on to draw air from the air intakes 1640, across the handle module 1602, and into the vacuum port 1642. Preferably, the vacuum port 1642 is spaced away from the air intakes 1640 to increase the air flow across the handle module 1602. In the example of FIG. 25E, the air intakes 1640 are at the bottom of the cover/lid 1630 and the vacuum port 1642 is at the top of the cover/lid 1630; however, any suitable arrangement could be utilized.

A handle module, such as handle module 1602, for example, could also be tested by a simulated load adapter. In various instances, the handle module 1602 can be tested by a load adapter 1650 when the handle module 1602 is connected to the inspection station 1600, as shown in the examples of FIGS. 26A-26D. In other instances, a simulated load adapter can be configured to test a handle module without a complementing inspection station. In any event, the simulated load adapter 1650 may include a housing 1651 and opposing load motors 1652, 1654 positioned in the housing 1651. As described in greater detail further below, the first load motor 1652 is configured to apply a first test load to a first drive motor of the handle module 1602 and the second load motor 1654 is configured to apply a second test load to a second drive motor of the handle module 1602. The first load motor 1652 is configured to drive a first mating nut 1660 which is operably engageable with a coupler 1656 driven by the first drive motor of the handle module 1602. The second load motor 1654 is configured to drive a second mating nut 1662 which is operably engageable with a coupler 1658 driven by the second drive motor of the handle module 1602.

The simulated load adapter 1650 may comprise a motor control circuit on a circuit board with at least a processor, memory and a motor controller for controlling the load motors 1652, 1654, for example. The motor control circuit may be embodied as one integrated circuit (e.g., a SOC) or a number of discrete integrated circuits or other circuitry. The motor control circuit may control the motors 1652, 1654 to apply an opposing force, under varying load conditions, to the rotary drive systems of the handle module 1602. The power drawn by the rotary drive systems of the handle module 1602 to resist and/or overcome the opposing forces can be monitored by the inspection station 1600 to determine whether the handle module motor(s) and rotary drive systems are functioning properly. In various instances, the first motor 1652 of the simulated load adapter 1650 can be driven in one direction and the drive motor of the handle module 1602 can drive the first coupler 1656 in an opposite direction. If the drive motor of the handle module 1602 is unable to resist or overcome the simulated load applied by the first motor 1652 of the simulated load adapter 1650, then the simulated load adapter 1650 can instruct the handle module 1602 that the handle module 1602 cannot perform as required. In various instances, the second motor 1654 of the simulated load adapter 1650 can be driven in one direction and the drive motor of the handle module 1602 can drive the second coupler 1658 in an opposite direction. If the drive motor of the handle module 1602 is unable to resist or overcome the simulated load applied by the second motor 1654 of the simulated load adapter 1650, then the simulated load adapter 1650 can instruct the handle module 1602 that the handle module 1602 cannot perform as required. Such an assessment can constitute one facet of the overall assessment of whether the handle module 1602 is suitable for another procedure.

In various instances, further to the above, the simulated load adapter motor control circuit can vary the load imparted by the simulated load adapter motors 1652, 1654 on the rotary drive systems of the handle module 1600 from (relatively) low to (relatively) high in a way that simulates the load that the handle module rotary drive systems are expected to experience during a surgical procedure. In at least one instance, the motor control circuit can be programmed so that it can vary the load profiles of the motors 1652, 1654 based on the type of DSM to be used in an upcoming procedure. For example, using the user interface 1672 (e.g., the buttons 1670 and/or a touch screen of the interface 1672), the user could specify the desired simulated load conditions, such as selecting a pre-programmed simulated load condition corresponding to the different available DSMs, for example. The simulated load adapter 1650 may have a data contact terminal 1674 that mates with the data connection terminal of the handle module 1602. In such a manner, the user's load profile selection can be uploaded from the inspection station processor, to the handle module processor, and to the motor control circuit of the load simulator 1650. In real-time and/or after the simulation, the motor control circuit can download to the handle module processor and/or the inspection station processor time-stamped power readings for the power (e.g., volt-amps) supplied to the load simulator motors 1652, 1654 during the simulation. The inspection station processor and/or the handle module processor can correlate these readings to time-stamped readings for the power drawn by the handle module motor(s) to evaluate the efficacy of the handle module motor(s) and rotary drive systems.

Figure 26A:
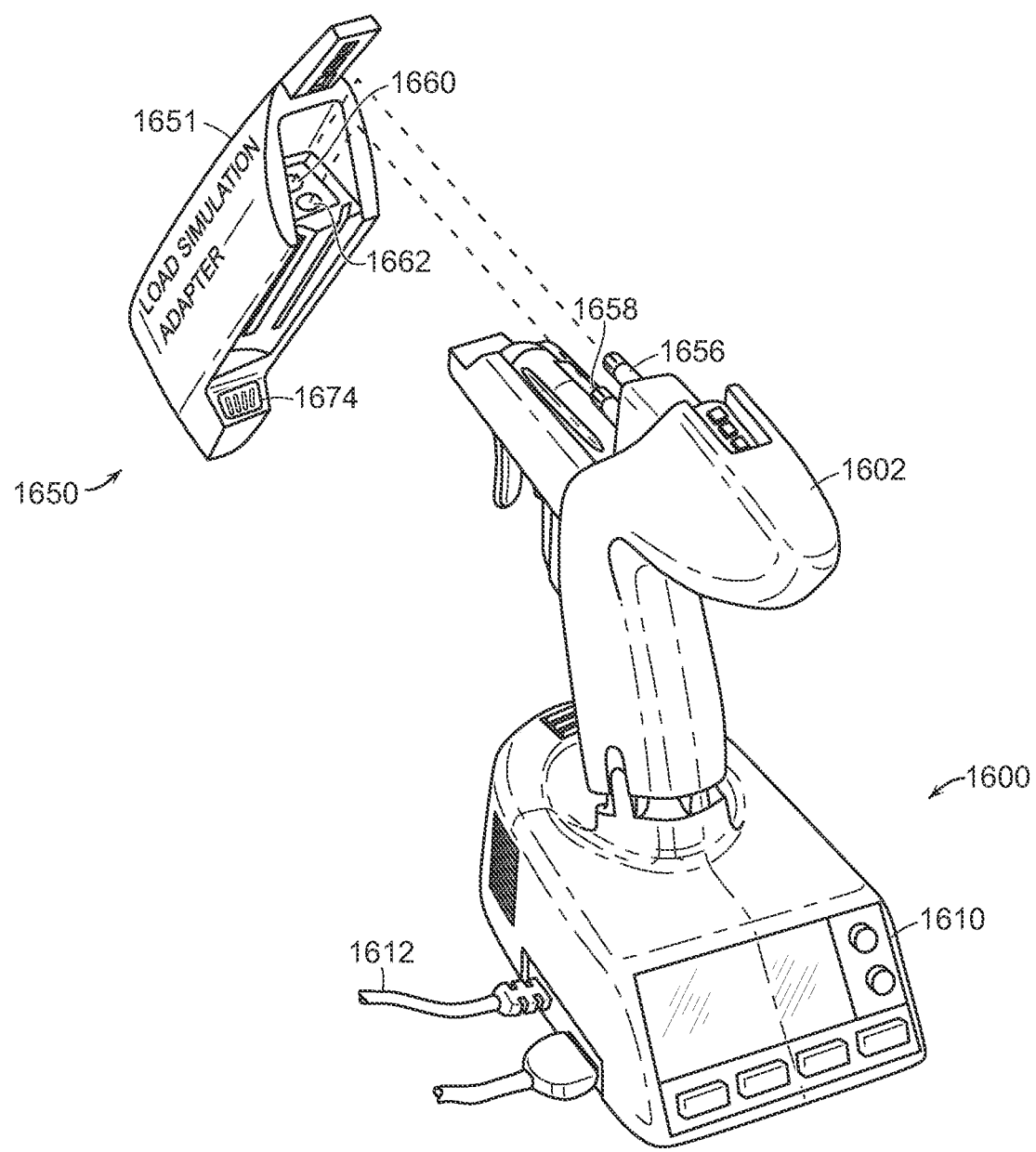
FIGS. 26A, 26B and 26C illustrate an inspection station, a handle module, and a load simulation adapter for applying a simulated load to the handle module when the handle module is connected to the inspection station.
Figure 26B:
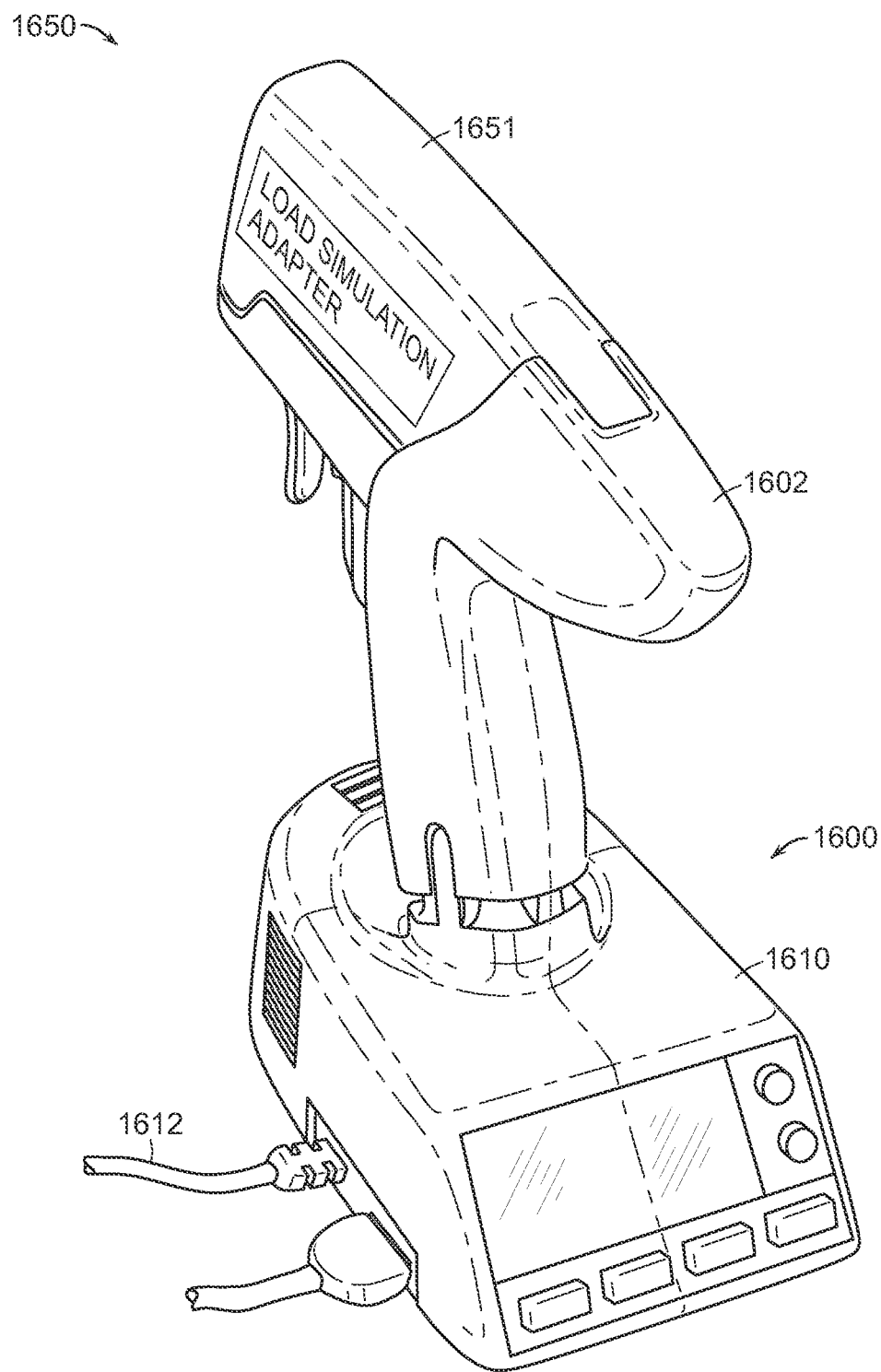
Figure 26C:
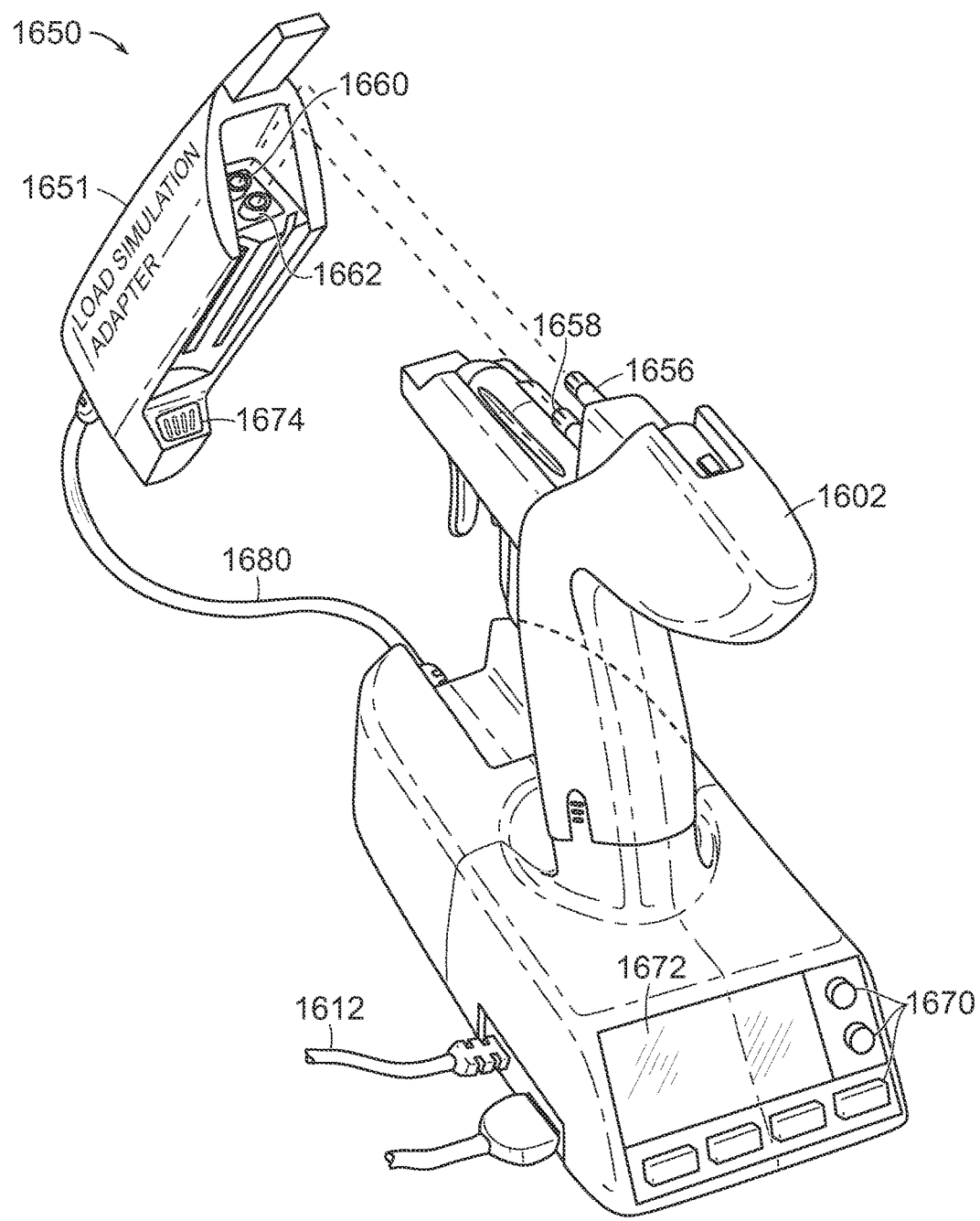
Figure 26D:
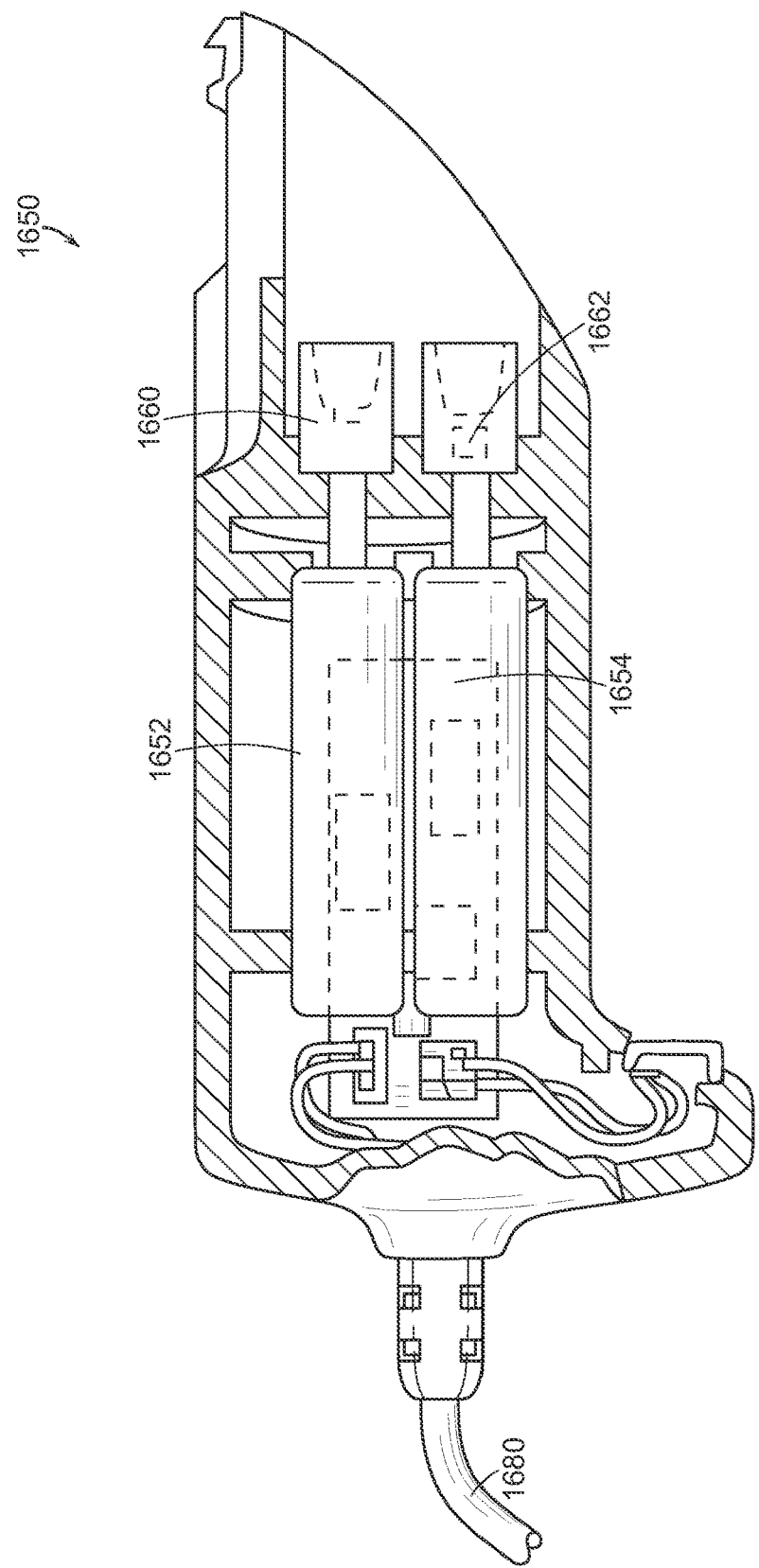
FIG. 26D is a cross-sectional view of the load simulation adapter of FIGS. 26A-26C.

The simulated load adapter 1650 may be powered by the inspection station 1600, for example. As shown in the example of FIG. 26B, electrical power from the inspection station 1600 could be supplied to the simulated load adapter 1650 via the handle module 1602 and the electrical contact board 1674. In the example of FIG. 26C, a separate power cord 1680 extending from the inspection station 1600 to the simulated load adapter 1650 can supply electrical power directly to the load simulator adapter 1650, bypassing the handle module 1602. In another arrangement, the load simulation adapter 1650 could have its own connection to an AC power source and/or its own battery power supply. In various instances, the cord 1680 can also place the load simulator 1650 in direct signal communication with the inspection station 1600.

Figure 26E:
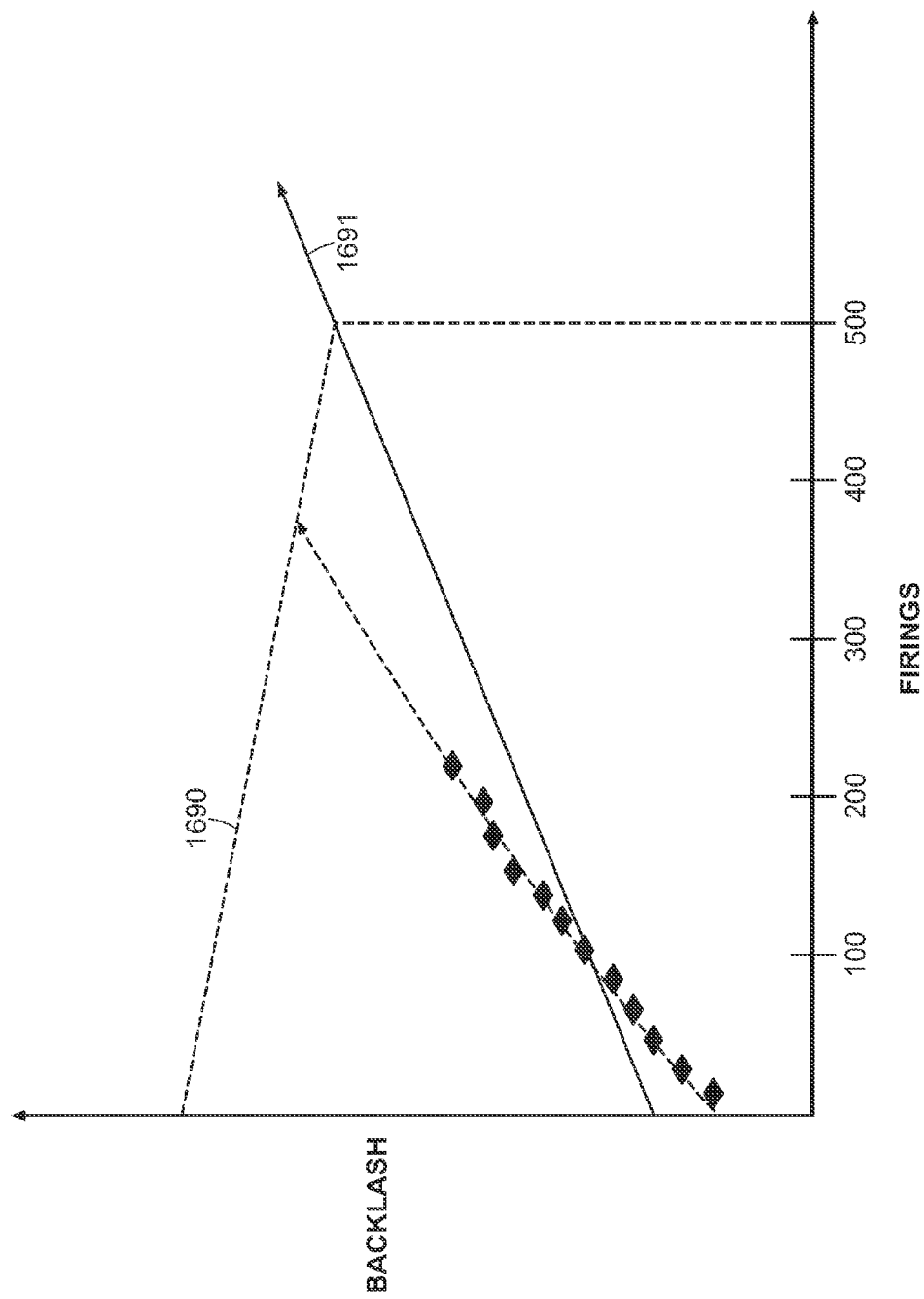
FIG. 26E is a chart illustrating a sample model of gear backlash for a handle module as a function of use.

The simulated load adapter 1650 could also be used to monitor backlash in the handle module gears that are part of the rotary drive systems. When the simulated load adapter 1650 is in a backlash detection mode, the simulated load adapter motor control circuit can cause one or both of the simulated load motors 1652, 1654 to rotate, and the processors of either the inspection system 1600 and/or the handle module 1602 can track the rotations by the corresponding rotary drive systems of the handle module 1602. The difference in rotation between the simulated load adaptor motors 1652, 1654 and the rotary drive systems of the handle module 1602 is an indication of the backlash in the respective rotary drive systems of the handle module 1602, which can diminish the life of the handle module. In other words, an increase in backlash can decrease the number of uses remaining for the handle module 1602. Accordingly, at each inspection of a handle module 1602, the inspection station 1600 and the load simulator 1650 can check the handle module's backlash and write the result to the handle module's memory. The handle module memory can store and time-stamp the backlash readings. The handle processor and/or the inspection station processor can determine a revised end-of-life threshold for the handle module, in terms of firings, for example, based on a model for the effect of backlash on the number of remaining uses. A sample model is depicted in FIG. 26E. Dashed line 1690 shows a threshold limit for backlash as a function of the number of firings of a handle module. Line 1691 depicts the expected backlash for the handle module as a function of use (e.g., firings). In this example, the backlash threshold is reached (lines 1690 and 1691 intersect) at about 500 firings. Since the backlash measurements can be tracked over time (and hence over the number of firings), the handle processor and/or the inspection processor can compare the backlash measurements, indicated by the diamonds FIG. 26E, to determine that the handle module backlash is trending to reach the threshold at less than 500 firings, in this example about 370 firings. This revised, updated firing threshold could be used in assessing the remaining life of the handle module. For example, if the handle module has been fired 220 times, and its revised end-of-life is 370 firings because of backlash, the processor could determine that the handle module has 150 firings remaining; or if 7 firings per procedure are assumed, then the handle module has 21 procedures remaining. The backlash can be tested for each rotary drive system of the handle module in this manner and the one with the least remaining life can dictate the overall remaining life of the handle module.

The above being said, if less backlash than expected is measured, then the firings needed to reach the end-of-life threshold of the handle module can be revised upwardly, or increased. In fact, the end-of-life threshold of a handle module can be increased if any parameter and/or a combination of parameters indicates that the handle module is experiencing less wear than expected, for example. Correspondingly, the end-of-life threshold of a handle module can be decreased if any parameter and/or a combination of parameters indicates that the handle module is experiencing more wear than expected, for example. Moreover, the various parameter thresholds disclosed herein can be fixed or adaptable. A threshold parameter can be adapted based on intrinsic and/or extrinsic information. For instance, the control system of a handle module can evaluate patterns or trends in parameter data and adapt a parameter threshold relative to the pattern or trend. In at least one instance, the control system can establish a baseline from sensed parameter data and establish a parameter threshold relative to that baseline. In some instances, the control system of a handle module can evaluate patterns or trends in the data obtained for a first parameter and adjust the threshold of a second parameter based on the evaluation of the first parameter data. In at least one instance, the control system can establish a baseline from sensed data of a first parameter and establish a threshold for a second parameter relative to that baseline. Moreover, many thresholds are described herein as comprising two ranges, i.e., a first range below the threshold and a second range above the threshold. The threshold itself may be part of the first range or the second range, depending on the circumstances. That said, a threshold, as used herein, may comprise three ranges, i.e., a first range below a minimum value, a second range above a maximum value, and a third range between the minimum value and the maximum value. If the sensed data for a parameter is in the first range, the control system may take a first action and, if the sensed data for the parameter is in the second range, the control system may take a second action, which may or may not be the same as the first action. If the sensed data for the parameter is in the third range, the control system may take a third action, which could include no action at all. The minimum value could be part of the first range or the third range, depending on the circumstances, and the maximum value could be part of the third range or the second range, depending on the circumstances. If data is sensed in a first range, in at least one embodiment, the control system may adapt a threshold in one direction and, if the data is sensed in a second range, the control system may adapt the threshold in the opposite direction while, if the data is sensed in a third range, the control system may not adapt the threshold, for example.

Figure 27A:
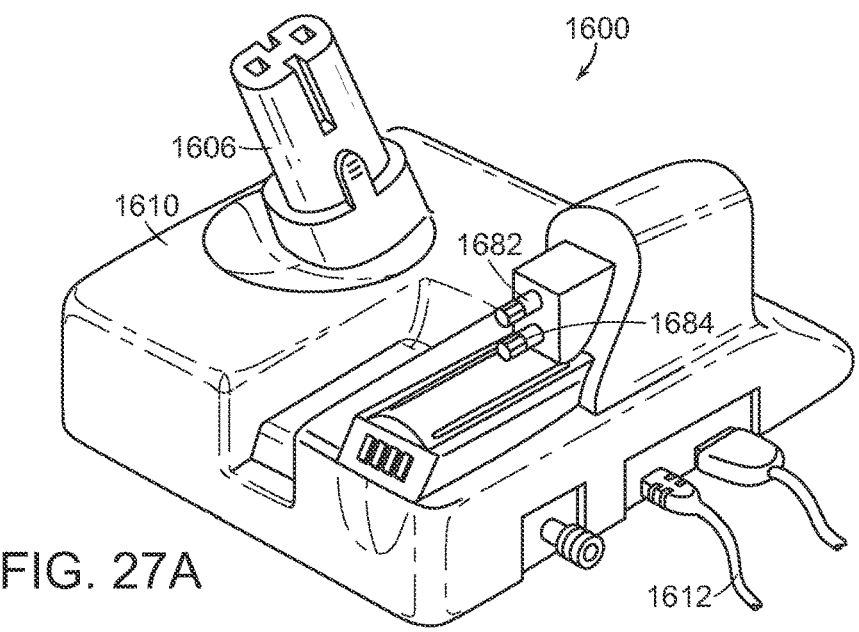
FIGS. 27A and 27B illustrate an inspection station that can accommodate both a handle module and a detachable shaft module.
Figure 27B:
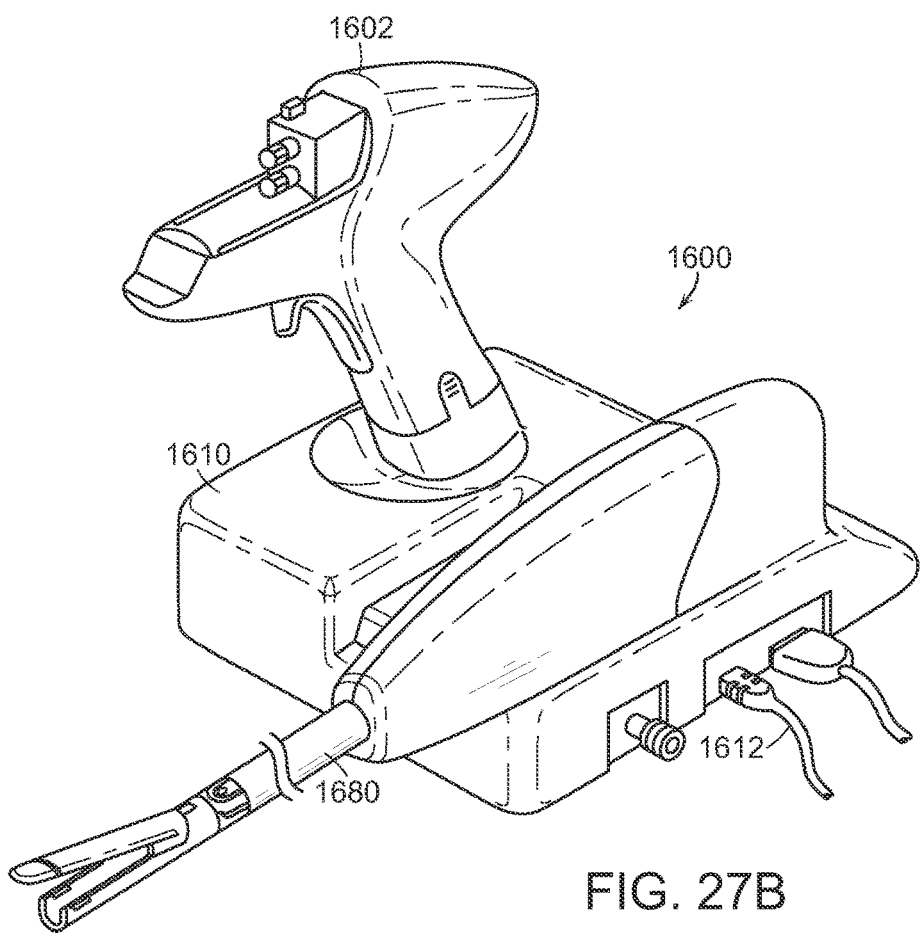

In another aspect, as shown in FIGS. 27A and 27B, the inspection station 1600 could accommodate both a handle module 1602 and one or more DSMs 1680, for example. FIG. 27A illustrates such an inspection station 1600 by itself; FIG. 27B shows the inspection station 1600 with both the handle module 1602 and a DSM 1680 connected thereto. The inspection station processor may be in communication with the handle module processor and/or the DSM processor in order to download and upload data and information. As shown in FIG. 27A, an inspection station 1600 that also supports DSMs may include rotary drives 1682, 1684, configured like the rotary drives 1656, 1658 of the handle module 1600. The inspection station 1600 may actuate the inspection station rotary drives 1682, 1684 to test the drive systems of the DSM 1680. In yet other arrangements, the DSM 1680 may have its own inspection station for performing the various tests and/or data transfers, for example.

In view of the above, an inspection station 1600 could be used to perform a number of pre-procedure and/or post-procedure instrument processing tasks for a handle module and/or a DSM, such as, for example:

Determine and display a device ID (e.g., serial number) and/or model, and the state of the device (e.g., end-of-life, locked out, etc.);

Read/download data from the memory of the handle module 1602, such as the number of firings/cycles, performance parameters, handle and/or DSM software versions;

Based on the device identification, set and upload the operation instructions and criteria for the handle module and/or DSM, which the inspection station can retrieve from memory based on the device ID;

Perform various electronic tests, such as modular connection integrity tests, memory version tests, system electronic checks, transfer rate (read/write) checks, scheduled maintenance checks, warranty expiration checks, end-of-life checks, system lockout checks, and/or internal battery life conditioning tests;

Perform various physical tests, such motor performance tests (with and/or without simulated loads as described above), seal integrity tests, etc.;

Performance testing, such as comparing actual data from a procedure (downloaded from the handle module and/or DSM memory) to expected procedure data;

Reset lockouts in the handle module where necessary;

Dry the device;

Inform users (e.g., via the display) that the device (handle module and/or DSM) is or is not suitable for continued use;

Upgrade software of the handle module and/or DSM;

Write test results to the handle module memory and/or DSM memory; and/or

Transmit handle and/or DSM performance and usage data to a remote computer system, via a USB or wireless (e.g., WiFi) connection, for example.

The inspection station memory may store software and/or firmware that the inspection station processor executes to perform these various functions.

The displays of the inspection station and/or the handle module may also make maintenance and servicing recommendations based on the various usage related data for the handle module. Based on usage data such as the number of procedures, the number of sterilizations, the number and/or intensity of firings, and/or the gear backlash, for example, the inspection station and/or handle module processors can determine whether various maintenance or servicing tasks should be undertaken or recommended with respect to the handle module and/or the DSM, and communicate those recommendations to a user via the displays of either the inspection station and/or the handle module. The maintenance and servicing recommendations could be performed and communicated to the user following a completed procedure, during a procedure, and/or at the beginning of a procedure.

Figure 28A:
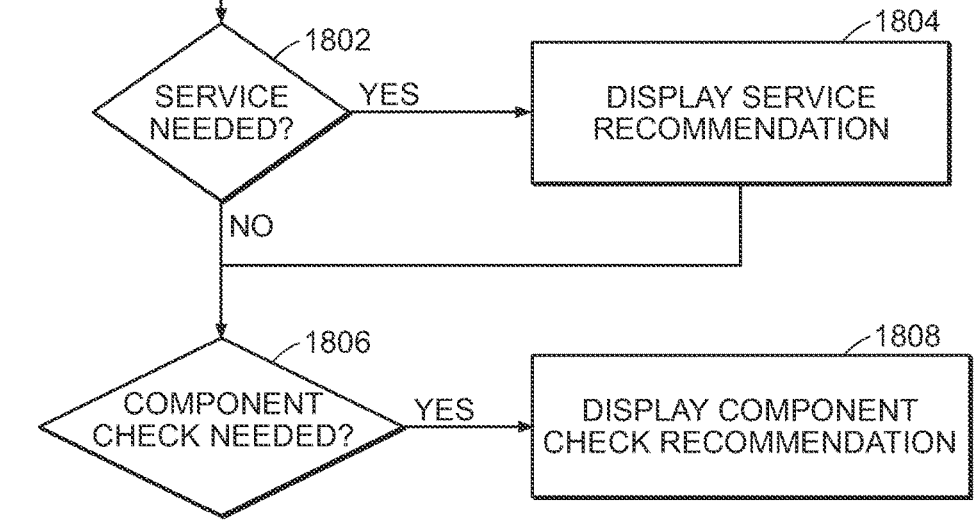
FIG. 28A illustrates a process flow executed by an inspection station processor to make service recommendations for a handle module.
Figure 28B:
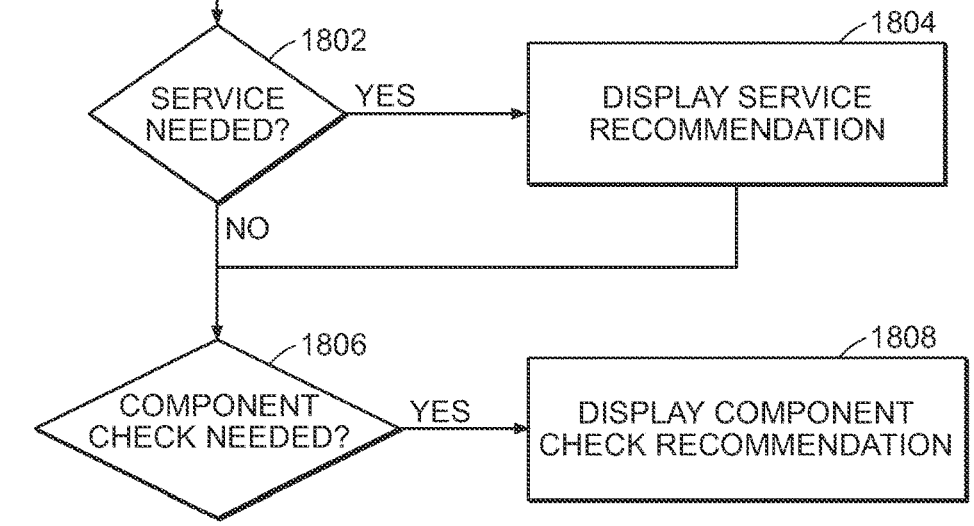
FIG. 28B illustrates a process flow executed by a handle module processor to make service recommendations for a handle module.

FIGS. 28A-28B are exemplary process flows for making maintenance and/or service recommendations that could be performed by the handle module processor and/or the inspection station processor by executing firmware and/or software in the processors' associated memory. FIG. 28A illustrates an exemplary process flow for the inspection station processor 442. At step 1800, following a procedure, the handle module is connected to the inspection station (see FIG. 19A, for example), whereupon usage and performance data from the handle module memory is downloaded to the inspection station. This data may include a count of the number of procedures for the handle module; various ways to count the number of procedures are described herein. The data may also include the number of firings by the handle module, the intensity (e.g., force) for each firing, the firing force differential between the expected firing force and the actual firing force, the (accumulated) energy spent by the handle module over the life of the handle module, and/or the gear backlash, for example.

At step 1802, based on the data, the inspection station processor determines whether service of the handle module is needed. The inspection station processor may parse the usage and performance data multiple ways as programmed to determine if service is needed, and may make one or several service recommendations at step 1804 if it is determined that service is required. The service recommendations could be as extensive as suggesting that the handle module be rebuilt, or as minor as lubricating certain parts, for example. Also, for example, one service check that the inspection station processor may perform at step 1802 is that for every $N_1$ procedures and/or every $S_1$ firings, or some combination of procedures and firings (e.g., $N_2$ procedures and $S_2$ firings), the handle module should be rebuilt. In such a case, if the inspection station processor determines that any of those thresholds has been met, at step 1804 the inspection station processor may control the inspection station display to show that the handle module should be rebuilt. Another service check that the inspection station processor may perform at step 1802 is that at every $S_3$ firings, the rotary drive systems' gears should be lubricated. Other service checks that the inspection station can perform and recommend if appropriate include: electrical integrity checks for electrical contacts of the handle module; testing of the communication system; extended diagnostics of electronics of the handle module (e.g., RAM and/or ROM integrity, processor operation, idle and operating current draw, operating temperatures of selected components, etc.); operation of indicators, displays and sensors; and/or battery issues, such as cycling, balancing and/or testing, for example. Service checks can be performed on a battery to evaluate the condition of the battery. For instance, the inspection station can assess whether the battery is nearing the end of its life, if rechargeable, or nearing a threshold for less than one firing remaining for a disposable battery, for example. Yet other services checks include firing the device (in a diagnostics mode or other mode that permits firing without a DSM or cartridge) to monitor abnormalities in a motor parameter (such as voltage or current, etc.). A damaged gear can cause a change in motor load, detectable through the monitored motor parameters, that can indicate an internal problem requiring replacement. Also, a generally higher motor load can indicate a need for cleaning or lubrication, or damage within the device.

At step 1806 the inspection station processor may determine whether any components of the handle module need to be checked. As before, the inspection station processor may parse the usage and performance data multiple ways as programmed to determine if the checking of various handle module components is needed, and may make one or several component check recommendations at step 1808 if it is determined that component checking is required. For example, if the inspection station processor determines that the gear backlash is beyond a pre-established threshold at step 1806, the inspection station processor may display a suggestion at step 1808 that the gears of the rotary drive systems should be checked. Also, if the inspection station processor determines that the accumulated energy spent by the handle module is beyond a pre-established threshold at step 1806, the inspection station processor may display a suggestion at step 1808 that the motor(s) and/or the gears of the rotary drive systems should be checked. Similarly, if the inspection station processor determines that a threshold number of firings (in the most-recently completed procedure and/or during the life of the handle module) exceed a pre-established intensity threshold (e.g., force or electric power) at step 1806, the inspection station processor may display a suggestion at step 1808 that the motor(s) and/or the gears of the rotary drive systems should be checked. The inspection station processor, via the display, could also recommend that the DSM be checked in various embodiments. For example, if the inspection station processor determines that a threshold number of firings in the most-recently completed procedure exceed a pre-established intensity threshold at step 1806, the inspection station processor may display a suggestion at step 1808 that the sharpness of the cutting instrument in the end effector should be checked, since a dull cutting instrument may necessitate greater force to execute a cutting stroke.

The handle module processor may also make service and/or component checking determinations and recommendations. FIG. 28B illustrates an exemplary process flow for the handle module processor 2124. The process of FIG. 28B is similar to that of FIG. 28A, except that, at step 1801, the handle module processor stores usage and performance data from its procedures and post-procedure processing so that it can make the determinations at step 1802 and 1806 about whether service and/or component checking is required. The recommendations and suggestions displayed at steps 1804 and 1808 may be on the handle module's display and/or, in the case when the handle module is connected to the inspection station and there is a data connection therebetween, the handle module processor may communicate the recommendations to the inspection station processor so that the inspection station display can display the recommendations, in lieu of or in addition to displaying them on the handle module display.

As shown in FIGS. 27A and 27B, a DSM 1680 could also be connected to an inspection station 1600. In such an arrangement, the DSM processor and/or the inspection station processor may make service and component checking determinations and recommendations based on usage and performance data stored in the DSM memory.

Figure 35:
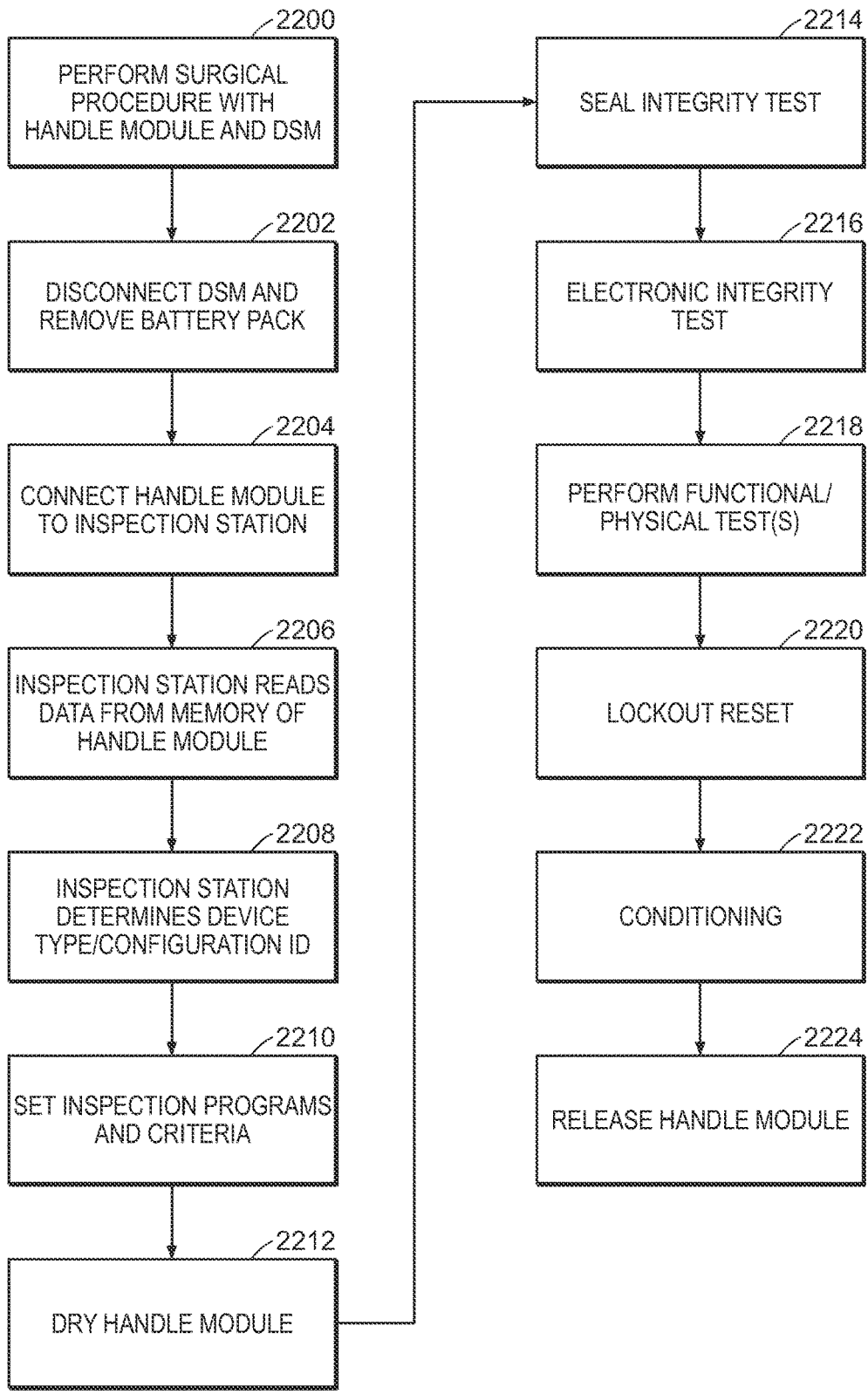
FIG. 35 is a flow chart of a process using an inspection station.

To that end, FIG. 35 is a flow chart illustrating steps that can be performed with the inspection stations described herein. At step 2200, a clinician performs a surgical procedure with the surgical instrument comprising the handle module and one of the DSMs. As described herein, the handle module memory can store usage and procedure data from throughout the procedure, such as motor energy and power levels, motor torque, and/or time stamps for actuation of various triggers, for example. Following the procedure, at step 2202, the clinician can disconnect the DSM from the handle module and remove the removable battery pack so that the handle module can be prepared for use in a subsequent procedure by, at step 2204, connecting the handle module to the inspection station as shown herein, for example. At step 2206, the inspection station can download (or read) the procedure and usage data from the memory of the handle module. The inspection station can also download the identification data for the handle module, which the inspection station processor can use to determine the handle module type and/or configuration at step 2208, which the inspection station can display on its display.

At step 2210, the inspection station can set the inspection programs and inspection criteria for the handle module based on its type and configuration. For example, the inspection station memory may store the inspection programs that should be performed for each handle module type and configuration, as well as the criteria for the inspections. Based on the handle module type and configuration ID resolved by the inspection station at step 2208, the inspection station can call and/or set the appropriate inspection programs and inspection criteria to be used for the handle module. For example, at step 2212, the inspection module can dry components of the handle module, such as described herein in conjunction with FIGS. 25A-25E, for example. Also, at step 2214 the seal integrity tests can be performed, such as described herein in conjunction with FIGS. 24A-24B, for example. At step 2216, electronic integrity tests for the handle module can be performed. These tests can include testing that electrical connections exist between the appropriate components, and for data processing components of the handle module, that the protocols and connections for transmitting data are functioning. At step 2218, functional and/or physical tests of the handle module can be performed. For example, the motor(s) and/or the rotary drive systems can be tested (e.g., driven) to make sure that they are functioning properly. At step 2220, the handle module lockouts that need to be reset following a procedure can be reset. At step 2222, further necessary conditioning for the handle module can be performed. This conditioning can include any other conditioning necessary to prepare the handle module for a subsequent surgical procedure, and/or performance of any service recommendations identified by the inspection station. At step 2224, the handle module can be released from the inspection station, whereupon it can be used in a subsequent surgical procedure (or sterilized before using in a subsequent procedure). The inspection station may "release" the handle module by indicating on the display of the inspection station that it can be removed, for example.

As shown in FIGS. 27A and 27B, a DSM could also be connected to such an inspection station following its use in a surgical procedure in order to inspect the DSM. A similar process to that illustrated in FIG. 35 can be used for the DSM connected to the inspection station to prepare the DSM for a subsequent procedure.

Various steps illustrated in FIG. 35 can be performed in different orders or simultaneously and the steps illustrated in FIG. 35 do not necessarily need to be performed in the order illustrated in FIG. 35, although they could be. For example, the electronic integrity tests (step 2216) could be performed before the seal integrity test (step 2214), etc.

Figure 36:
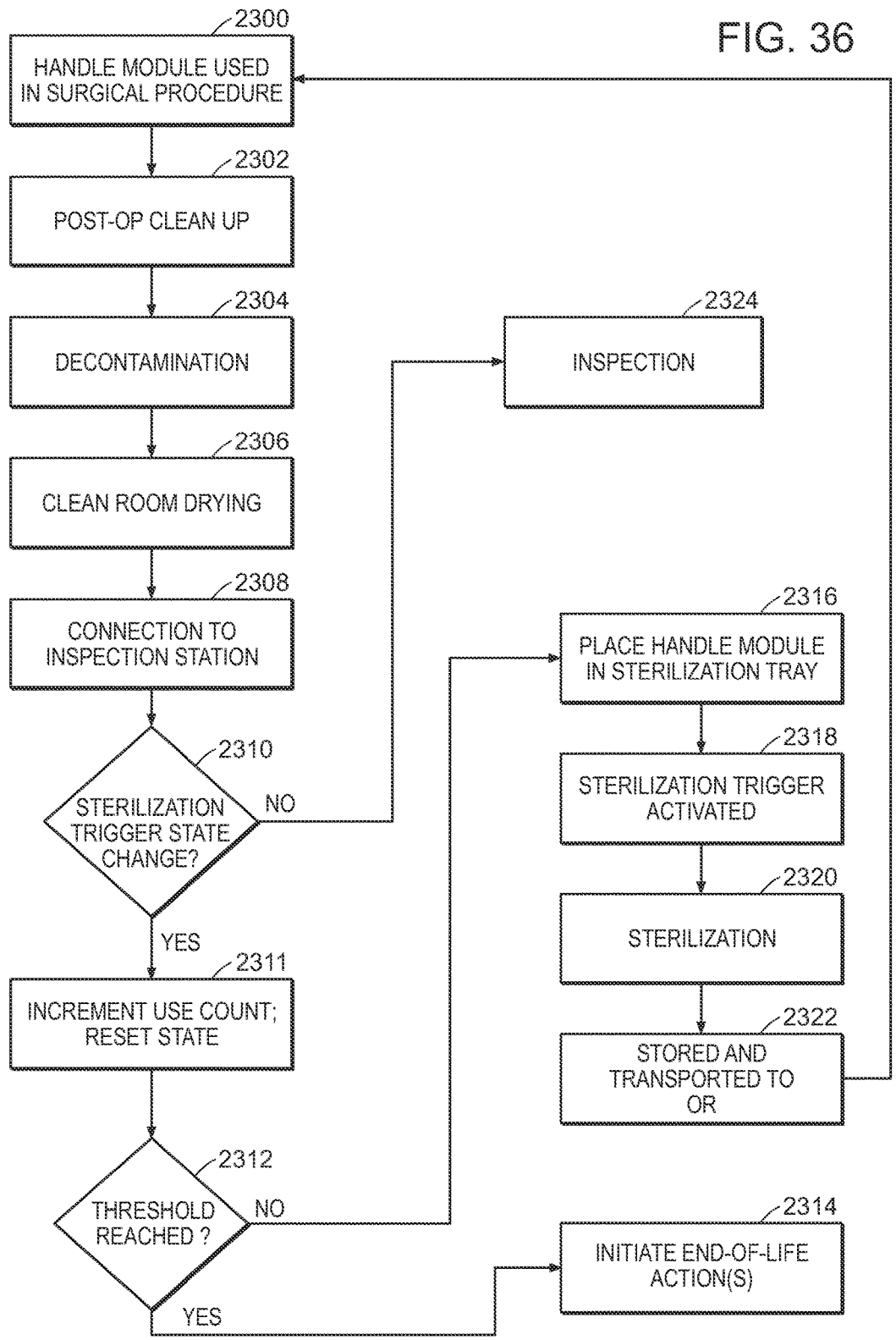
FIGS. 36 and 37 are process flow charts illustrating exemplary steps for sterilizing a handle module and tracking the number of times it is sterilized.
Figure 37:
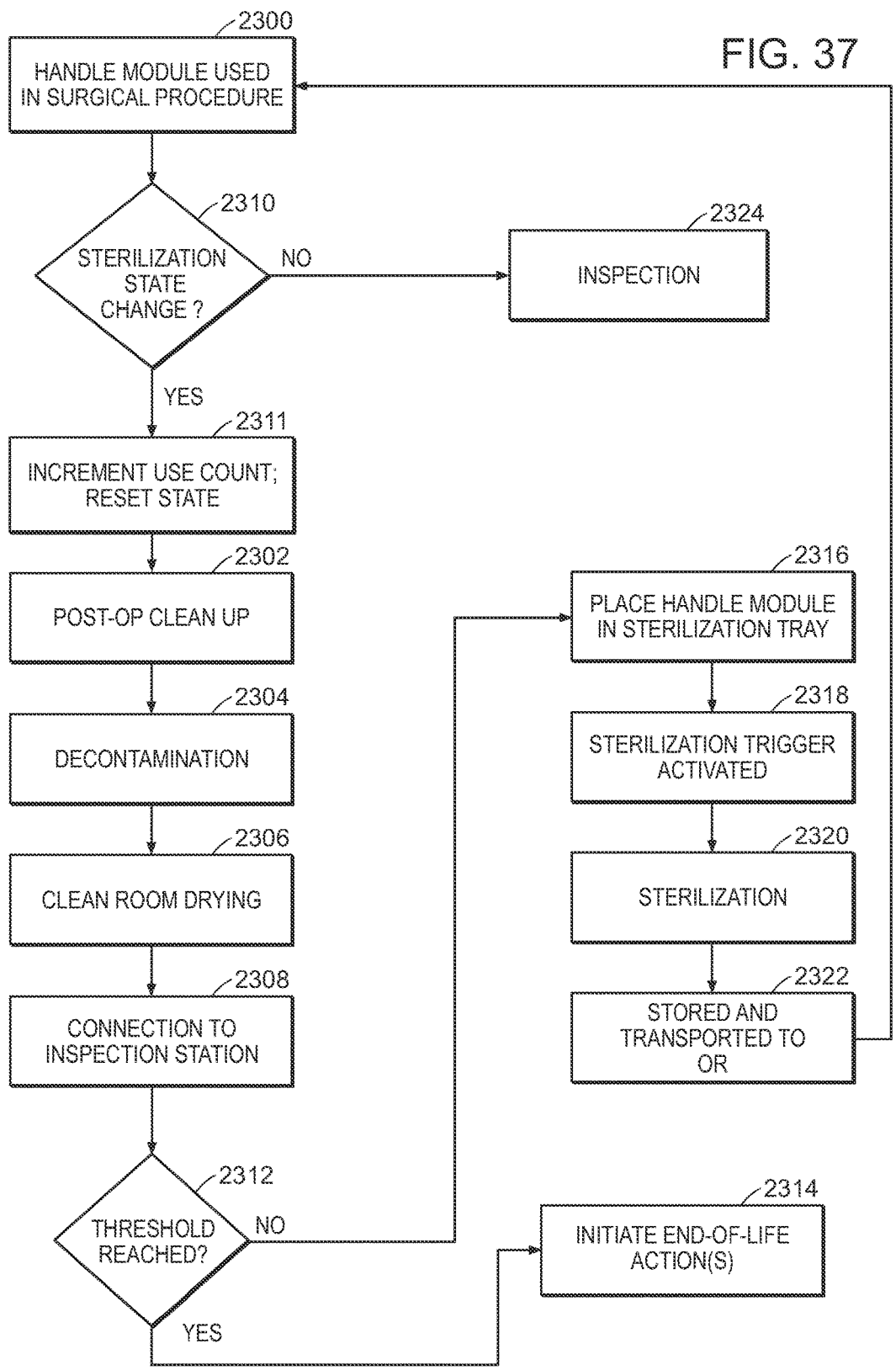

FIGS. 36 and 37 are flow charts illustrating exemplary steps involved in sterilizing a handle module and tracking the number of times it is used/sterilized. In FIG. 36, the process starts at step 2300 where the handle module (and a DSM) are used in a surgical procedure. After the procedure, at step 2302, a post-op clean-up of the handle module can be performed, which can entail a manual wipe down of the handle module, for example. Thereafter, at step 2304, the handle module can be decontaminated, such as with an auto-washer, for example. At step 2306, the handle module can be dried in a clean room, using heat and/or air, for example. At step 2308, the handle module can be connected to an inspection station, such as the inspection stations described herein in connection with FIGS. 12A-12C, 19A, 25A-25E, 26A-26C, and/or 27A-27B, for example.

At step 2310, the inspection station can query or interrogate the handle module to determine if the sterilization switch (e.g., switch 344, see FIGS. 11E-11I) was activated or otherwise in the state that indicates its prior placement in a sterilization tray, such as shown above in FIGS. 11E-11I. If the sterilization tray switch is in the triggered or actuated state, at step 2311 the sterilization count is increased and the switch state reset. Then, at step 2312, the inspection station can determine whether the threshold sterilization count for the handle module has been reached, as described herein. If the sterilization count has been reached, at step 2314, any of the herein-described end-of-life actions for the handle module can be taken.

Conversely, if the threshold has not yet been reached, the process can advance to step 2316 where the handle module is prepared for sterilization, such as by placing the handle module in its corresponding sterilization tray (see FIGS. 11E-11I, for example) and/or placing the sterilization covers on it (see FIGS. 20A-20D, for example), which in either case can activate the sterilization trigger at step 2318. The handle module can be sterilized at step 2320, whereupon it can be stored and subsequently transported to an operating room at step 2322 for use in a subsequent procedure at step 2300.

Returning to step 2310, if the sterilization trigger is not activated or its status changed, the handle module may have to be physically inspected at step 2324.

The exemplary process flow of FIG. 37 is similar to that of FIG. 36, except that following the procedure at step 2300, the handle module can be powered back on to determine if its sterilization state flag (set by handle module processor when the switch 344 is activated, see FIGS. 11E-11I) is set at step 2310. If so, at step 2311 the sterilization count can be updated and the sterilization state reset.

As mentioned above, the handle module battery pack may be removed from the handle module following a surgical procedure so that it can be used in the same or another, similarly-configured handle module in a subsequent procedure, typically after recharging. FIGS. 29A-D illustrate a charging station 1700 for recharging battery packs 1702. The battery packs 1702 are inserted into receptacles 1704 defined in the charging station 1700, shown in the side-views of FIGS. 29B and 29C, such that, when the battery packs 1702 are inserted, their respective power terminals 1706 contact corresponding charge terminals 1708 at the bottom of the receptacles 1704 to charge the respective battery packs 1702. The illustrated charging station 1700 can simultaneously charge two battery packs, although in other arrangements a charging station could have receptacles for storing and charging more or fewer battery packs.

The charging station 1700 may include a display 1709 that displays the status of the battery packs 1702 in terms of the charging process, such as currently charging or charged/ready to use, for example. For battery packs currently charging, the display may show how far along the charging process is and/or how far there is to go. Text and/or graphics may be used to indicate the charging status, such as a volume and/or other type of fractional indicator that indicates how charged the battery pack is (e.g., 40% charged, 50% charged, etc.).

Figure 29D:
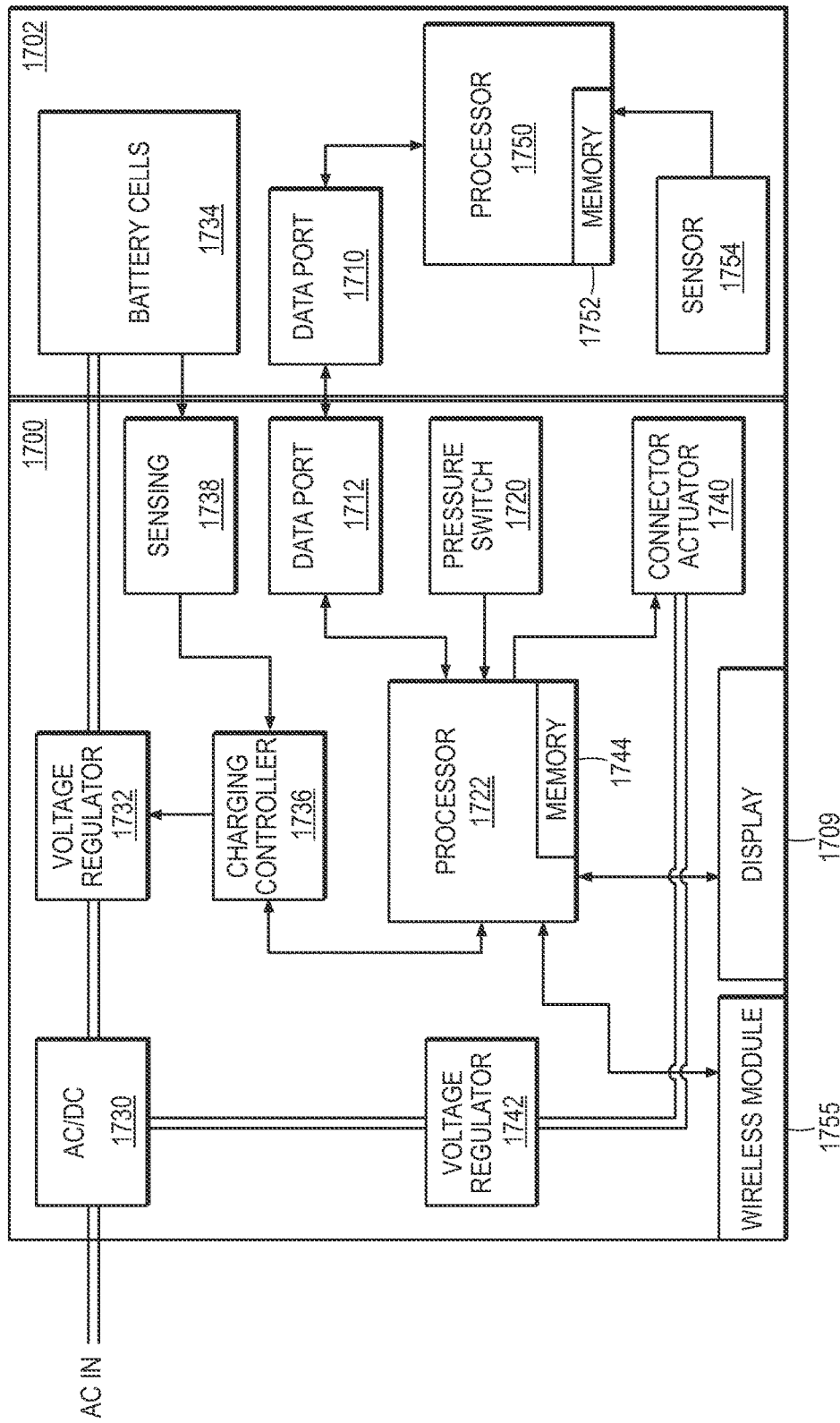
FIG. 29D is a block diagram of the charging station and a battery pack.

As shown in FIGS. 29B and 29C, the receptacle 1704 may be sized so that the end portion of the battery pack 1702 that is inserted into the receptacle fits in easily (e.g., a zero insertion force connection). The charging station 1700 may include means for detecting when the battery pack 1702 is inserted into the receptacle. For example, as shown in the block diagram of FIG. 29D, the charging station 1700 may include a pressure switch 1720, in communication with the charging station processor 1722, at the bottom of the receptacle 1704 that is actuated when the battery pack 1702 is inserted. Additionally or alternatively, the charging station processor 1722 may detect the insertion of a battery back 1702 when a charging station data terminal 1712 makes a data connection with the battery pack data terminal 1710. In any case, when the battery pack 1702 is inserted into the receptacle 1704 of the charging station 1700 for charging, the charging station 1700 may temporarily secure the battery pack 1702 to the charging station 1700 so that the battery pack 1702 cannot be removed prematurely (e.g., prior to charging and/or a complete charging). In one arrangement, as shown in FIGS. 29B and 29C, this is accomplished by a screw 1724 at the bottom of the receptacle 1704 of the charging station 1700 that automatically screws into a corresponding opening 1726 in the bottom of the battery pack 1702 that is sized and threaded for receiving the screw 1724.

FIG. 29D is a simplified block diagram of the charging station 1700 and a battery pack 1702 according to various arrangements. Assuming the charging station 1700 is powered by an AC power source, the charging station 1700 may include an AC/DC converter 1730 to convert the AC voltage into DC voltage and a voltage regulator 1732 for converting the DC voltage to the desired charging voltage and/or current for charging the battery cells 1734 of the battery pack 1702. The charging station 1700 may include a charging controller circuit 1736 for controlling the voltage regulator 1732 based on sensed parameters of the charging operation, such as current, voltage and/or temperature, which can be sensed by the sensing circuit 1738 of the charging station 1700. For example, when charging a battery pack 1702 under normal charging conditions, the charging controller circuit 1736 may control the voltage regulator 1732 to charge at a constant current until the Li-ion or LiPo battery cells 1734 reach a specified voltage per cell (Vpc). Then the charging controller circuit 1736 can hold the cells at that Vpc until the charge current drops to X % of the initial charge rate (e.g., 10%), at which point the charging process can terminate. Other charging regimens, appropriate to the battery technology, can be performed.

The pressure switch 1720 may detect the insertion of the battery pack 1702 into the receptacle 1704 of the charging station 1700 and, when activated, send a signal to the charging station processor 1722. The charging station processor 1722 may send in response a control signal to a connection actuator 1740, such as a linear actuator, that drives the screw 1724 into the battery pack screw opening 1726. The connection actuator 1740 may be powered by a second voltage regulator 1742 that can power, in addition to the connection actuator 1740, the other electronic components of the charging station 1700.

Further to the above, the battery pack 1702 may include a data terminal 1710 that, when the battery pack 1702 is inserted into the receptacle 1704, mates with a corresponding data terminal 1712 of the charging station 1700. The charging station processor 1722 may have internal or external memory 1744 that stores firmware and/or software to be executed by the charging station processor 1722. By executing the firmware and/or software, the charging station processor 1722 can (i) control the display 1709, (ii) control aspects of the battery cell charging process by communicating with the charging controller 1736, and/or (iii) exchange data with the battery pack processor 1750 via the data terminals 1710, 1712. As described herein, the battery pack electronics may also include memory 1752 that stores firmware and/or software to be executed by the battery pack processor 1750, such as a battery management system (BMS). The battery pack 1702 may also comprise sensors 1754 for sensing conditions related to the battery pack 1702, such as moisture and/or humidity, for example, as described above. The data terminal 1712 of the charging station 1700 may also supply low-level power to the battery pack processor 1750. The charging station 1700 may also include a wireless module 1755 in communication with the processor 1722 that can communicate with remote devices via wireless communication links (e.g., Wi-Fi, Bluetooth, LTE, etc.). As such, the charging station 1700 could communicate wirelessly to remote computing systems (e.g., servers, desktops, tablet computer, laptops, smartphones, etc.) the charge status and other data regarding the battery packs 1702 installed in the charging station 1700 (e.g., impending end-of-life, temperature). The charging station could also include a port for a wired connection (e.g., USB-type port) so that charge status and other data regarding the battery packs 1702 can be downloaded from the charging station 1700 to the connected device. That way, the surgical staff and/or the battery pack supplier can receive such information.

Figure 29E:
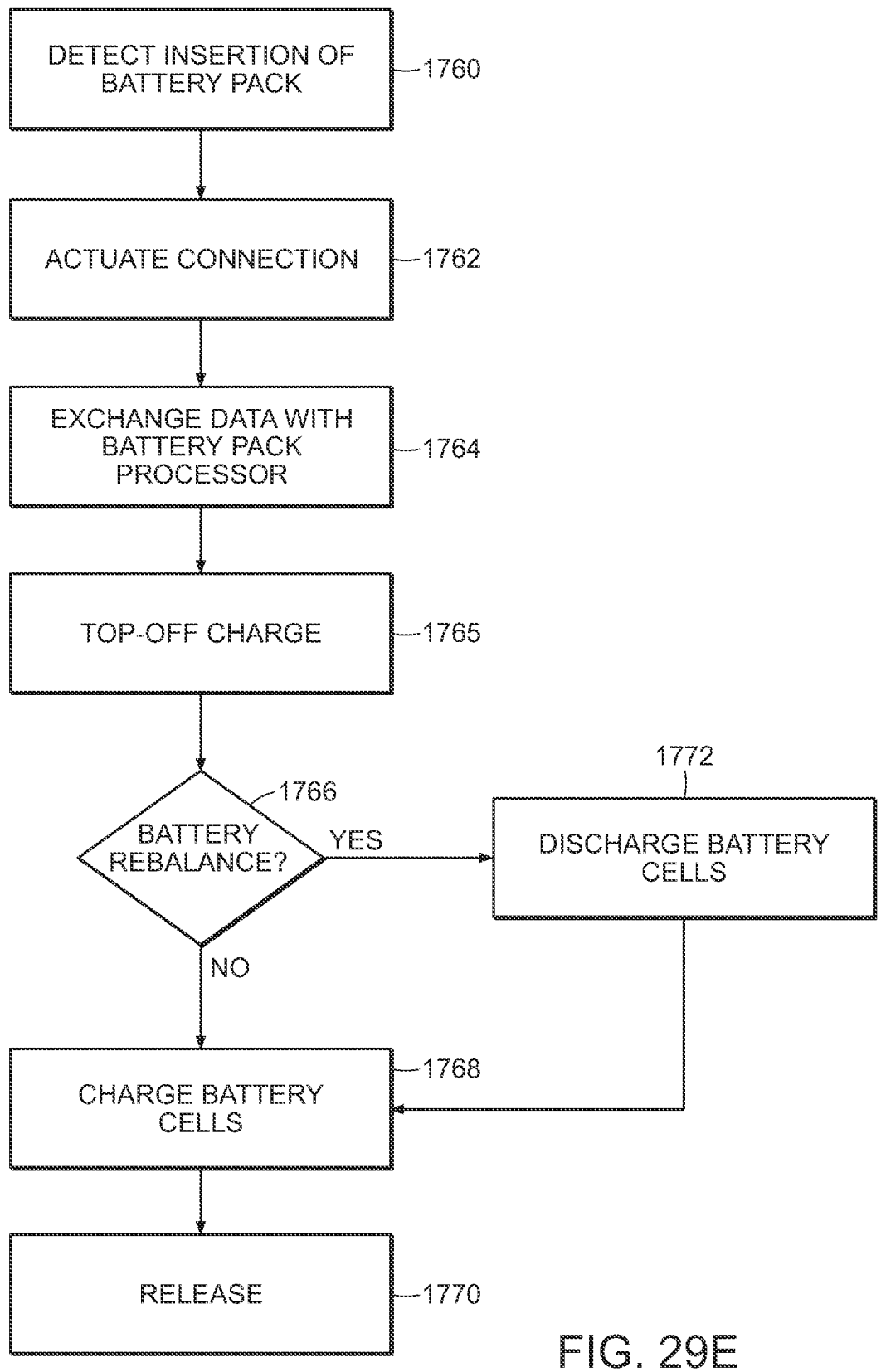
FIG. 29E illustrates a process flow executed by a handle module charging station.

In one aspect, to extend battery run time as well as battery life, for example, the battery cells comprising the battery pack 1702 may be rebalanced from time to time during the life of the battery pack 1702. FIG. 29E is a diagram of a process flow that can be performed by the charging station processor 1722 (by executing firmware/software stored in the memory 1744) to rebalance the battery cells. At step 1760, the charging station processor 1722 can detect the insertion of a battery pack 1702 into the inspection station 1700 for charging based on, for example, the signal from the pressure switch 1720 in the receptacle 1704 and/or by some other suitable means. At step 1762, the charging station processor 1722 can actuate the connection actuator 1740 to temporarily secure the battery pack 1702 to the charging station 1700 during the charging (and/or discharging) session. At step 1764, the charging station processor 1722 can exchange data with the battery pack processor 1750. Among other things, the battery pack processor 1750 can exchange a log of the times the battery pack 1702 has been charged and the times that its cells were balanced. At step 1765, the charging station 1700 can quickly top-off the charge of the battery cells in case the battery pack is needed before a complete charging or discharging cycle can be performed. The top-off charge at step 1765 could be, for example, to merely charge the battery cells at a constant current to bring them to the specified Vpc level or a fraction thereof. At step 1766, the charging station processor 1722 can determine whether the battery cells should be balanced again. In various aspects, the cells may be balanced every N times they are charged, where N is an integer greater than or equal to one, and preferably greater than one. If it is not time to rebalance the cells, the process advances to step 1768 where the battery cells are recharged and at step 1770 released for use, such as by de-actuating the connection actuator 1740 so that the battery pack 1702 can be removed from the receptacle. On the other hand, at step 1766, if it is determined that the battery cells need to be rebalanced, the process can advance to step 1772 where the cells are discharged before being charged at step 1768. The cells may be discharged at step 1772 to a suitable (low) voltage level As shown in FIG. 29A, the charging station 1700 may include an emergency release button 1780 for each battery pack charging receptacle, or just one emergency release button 1780 that releases only the battery pack 1702 that presently has the most charge (and thus most suitable for emergency use). In various aspects, the charging station processor 1722 may initiate one or many actions when the emergency release button 1780 is depressed for a particular battery pack 1702 when charging of that battery pack is in process. For example, the charging station processor 1722 can signal the connection actuator 1740 to unscrew the battery pack 1702 so that it can be removed. Also, before such mechanical release of the battery pack 1702, the charging station processor 1722 can instruct the charging controller to take action to expedite rapid charging of the battery pack 1702. For example, the charging station processor 1722 can instruct the charging controller 1736 to use a charging profile that more rapidly charges the battery cells 1734 for a brief time period, even though such rapid, short-term charging may not fully charge the battery cells to their capacity or promote longevity of the battery cells. Common charge profile stages for charging Li-ion battery cells include (i) trickle charge, (ii) constant current charge, and (iii) constant voltage charge. The charging controller circuit 1736 can switch to one of these profiles (e.g., constant current charge) in the short duration to provide the battery pack 1702 with as much additional charge as possible in the short time period. Also, the charging station processor 1722 can coordinate increasing the charging voltage available for charging the battery cells by making other power sources available for charging, such as from other receptacles and/or charge storing devices (e.g., supercapacitors or battery cells) in the charging station 1700. Data about such charging procedures can also be logged in the battery pack memory.

Figure 30A:
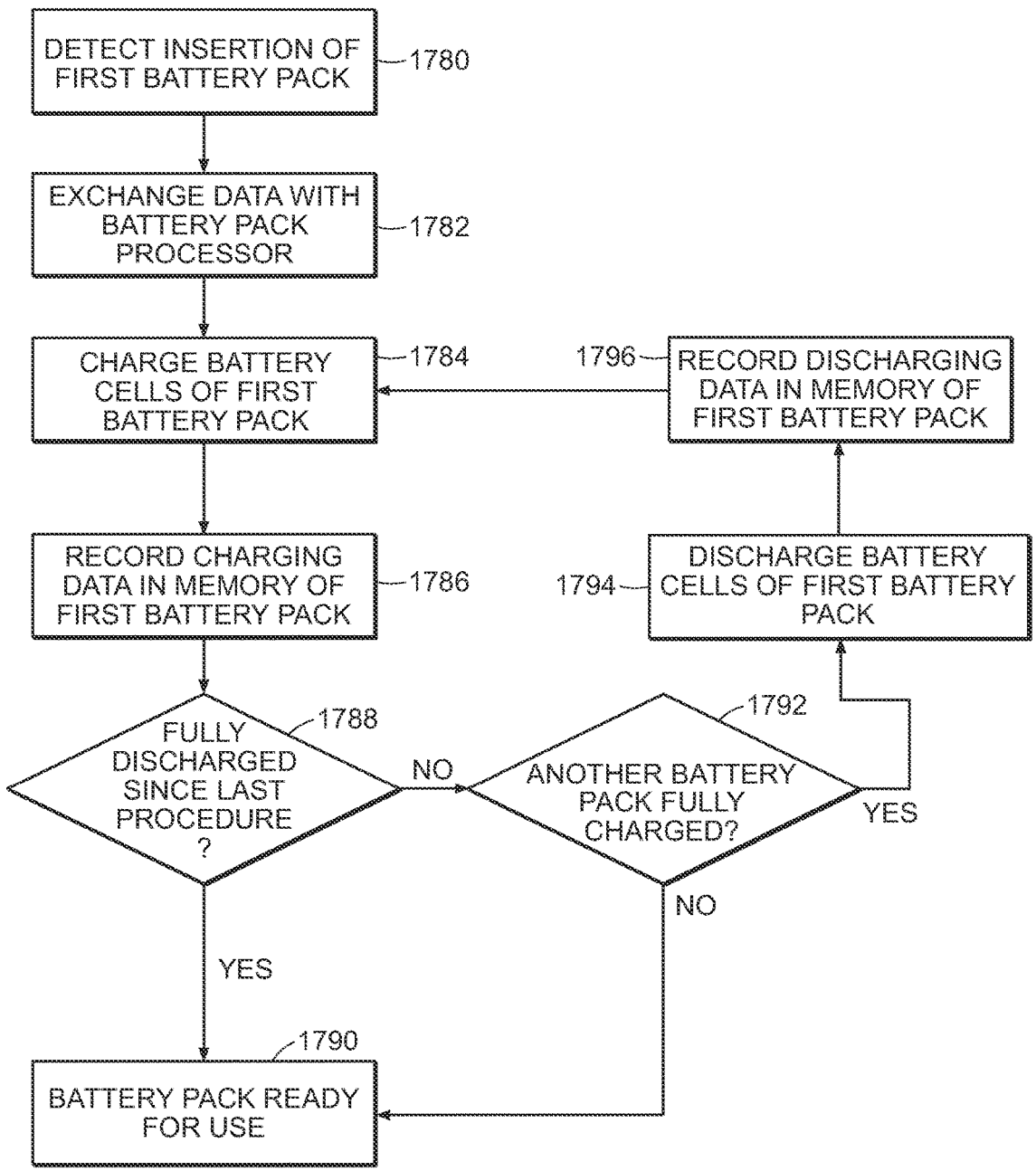
FIGS. 30A and 30B illustrate process flows executed by a handle module charging station.

FIG. 30A illustrates another exemplary charging/discharging determination process that the charging station processor 1722 may undertake, in addition to or in lieu of the process shown in FIG. 29E. The process of FIG. 30A recognizes that discharging of surgical instrument battery packs often is beneficial to their longevity, but that the battery packs should not be discharged if there is insufficient time to discharge them before they will be needed in a surgical procedure. The process of FIG. 30A starts at step 1780 where a "first" rechargeable battery pack is inserted into one of the charging receptacles 1704 of the charging station 1700. At step 1782, battery pack usage data from the first battery pack is downloaded to the charging station memory, which may include the current remaining battery capacity. Although not shown in FIG. 30A, the first battery pack could also be secured to the charging station when it is inserted (see FIGS. 29B-29C, for example). At step 1784, the charging station 1700 may immediately charge the first battery pack in case it might be needed in a currently ongoing or imminent procedure. At step 1786, data about the charging of the first battery pack at step 1784 is written to the memory of the first battery pack. This data can include, for example, time stamps for the beginning and ending of the charging step, as well as the starting and ending battery capacity.

At step 1788, the charging station processor checks the charging/discharging log for the first battery pack and, if the first battery pack was fully discharged since the last procedure, the process advances to step 1790 where the first battery pack is ready for use in a procedure. At this step, the charging station display may indicate that the first battery pack is ready for use. On the other hand, if at step 1788 it is determined that the first battery pack has not been fully discharged since its last procedure, the process may advance to step 1792 where the charging station processor can determine if there is at least one other fully charged battery pack in its charging receptacles. If so, at step 1794 the first battery pack can be fully discharged to prolong its longevity and because there is another fully charged battery pack ready for use if needed. Once the discharge of the first battery pack is complete, at step 1796 the discharging data (e.g., beginning and ending time-stamps, beginning and end capacities) can be written to the first battery pack memory so that the evaluation at step 1788 can be performed. Thereafter, the process can advance to step 1784 where the battery cells of the first battery pack are recharged, and the process repeats. If the first battery pack was discharged at step 1794 since the last procedure, from step 1788 the process will advance to step 1790 because another discharge of the battery cells is not required.

Modifications to the process of FIG. 30A can be made. For example, the initial charging step 1784 could be eliminated and/or moved between steps 1788 and 1790 and/or between steps 1792 and 1790, for example.

Figure 30B:
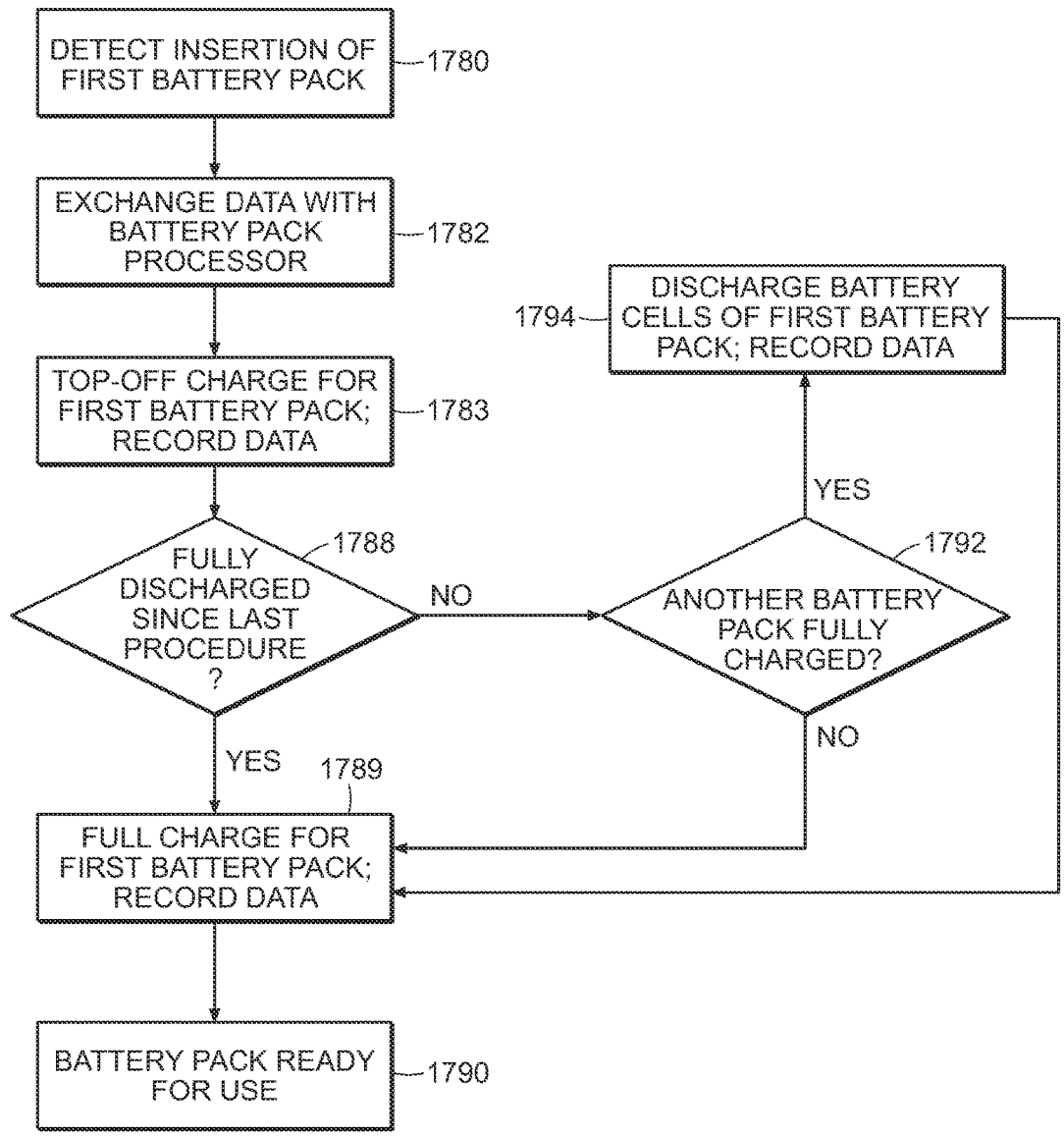

FIG. 30B illustrates another exemplary charging/discharging determination process that the charging station processor 1722 may undertake. The process of FIG. 30B is similar to that of FIG. 30A, except that at step 1783, following step 1782, the charging station 1700 can perform a quick charge top-off of the battery pack (e.g., short charge to less than full capacity) and record data about the top-off charging in the battery pack memory. Then at step 1788, as in FIG. 30A, the charging station processor can determine if the battery pack was discharged fully since the last procedure and, if so, at step 1789, then perform a full charging of the battery pack, at which point the battery pack is ready for use (block 1790). On the other hand, at step 1788, if the charging station processor determines that the battery pack was not fully discharged since the last procedure, the process can advance to step 1792 where the charging station determines if another battery pack is currently inserted in one of its receptacles 1704 is ready for use (e.g., adequately or fully charged). If not, the first battery pack can be fully charged at step 1789. However, if another battery pack is adequately or fully charged and ready for use, at step 1794 the first battery pack can be discharged (with data about the discharge being stored in the battery pack memory). After full discharge, the process can advance to step 1789 so that the first battery pack can then be charged.

In various embodiments, the charging station processor 1722 can monitor and store the times at which the various battery cells are inserted into it, as indications of when procedures are being performed by the hospital or surgical unit in which the charging station is located. The charging station processor 1722 can be programmed to determine times of the day when the hospital or surgical unit is typically performing procedures involving instruments that utilize such battery packs and when it is not. In particular, the charging station processor 1722 can determine a statistical likelihood that the hospital or surgical unit is performing a procedure involving instruments that utilize such battery packs for non-overlapping time increments that span a 24-hour period, such as one-hour increments, for example. Thus, for the full charging of the battery packs (e.g., at step 1789 of FIG. 30B), the charging station can commence such full charging steps at times when there is a low likelihood of an ongoing procedure, especially in instances where there is an already another fully charged battery pack ready for use. That is, for example, in FIG. 30B, the full charging at step 1789 following discharging at step 1792 need not immediately follow the discharging at step 1792 but could instead be scheduled for a time that there is a low likelihood of an ongoing procedure, as determined and scheduled by the charging station processor 1722. Further, the personnel at the hospital or surgical unit can input to the charging station 1700, via the user interface 1709, for example, data about when procedures are to be performed and/or the types of procedures (or the amount of charge needed for the procedures) that are to be performed. This data can be stored in the charging station memory 1744 and used by the charging station processor 1722 to determine when to charge the battery packs.

Figure 31:
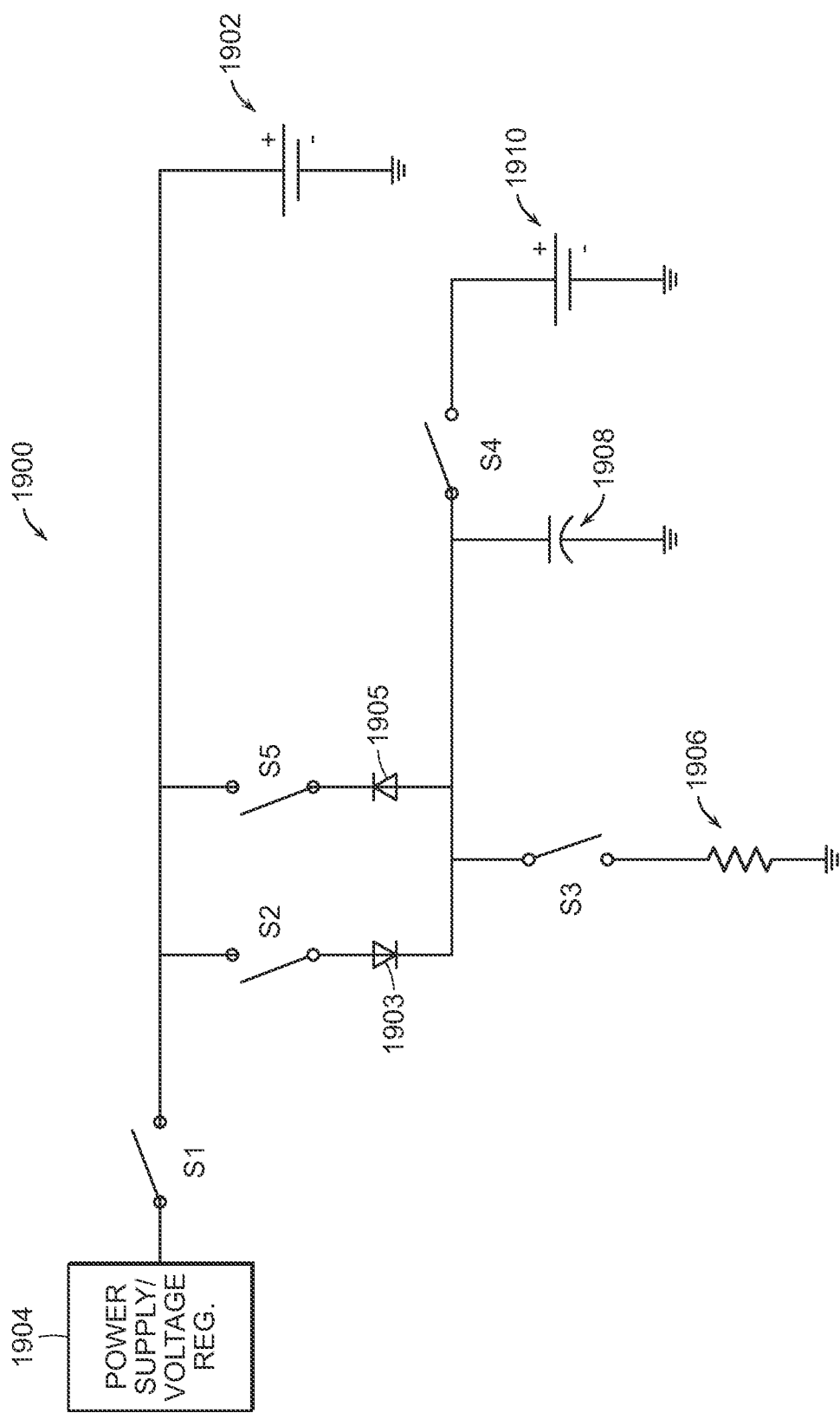
FIGS. 31 and 32 are electrical schematic diagrams of a charging station.

In a system that charges and discharges batteries, there can be a significant amount of energy wasted in dumping the power from the cell(s) under maintenance in the form of heat because typically the charge on a battery cell to be discharged is drained through a resistive load. Accordingly, the charging station may include fans and/or heat sinks to help dissipate heat. In other aspects, the charging station may use the charge on a cell to be discharged to charge another cell in the charging station or store it in another charge storing device. FIG. 31 is a simplified diagram of a circuit 1900 for discharging battery cells in such a manner. When charging the "first" battery cell 1902, the power source/voltage regulator 1904 is connected to the first battery cell 1902 by closing switch S1, with all other switches (S2, S3, S4 and S5) being open. To discharge the first battery cell 1902 through the resistor 1906, switches S2 and S3 are closed and switches S1, S4 and S5 are open. The diode 1903 controls the direction in which current flows from the first battery cell 1902. To discharge the first battery cell 1902 to the energy storage device 1908 (e.g., supercapacitor or another battery cell internal to the charging station and not ordinarily for use in a surgical instrument), switch S2 is closed and the rest of the switches S1, S3, S4 and S5 are open. The diode 1903 controls the direction in which current flows to the energy storage device 1908. To charge the first battery cell 1902 with the charge on the energy storage device 1908, switch S5 is closed and the rest of the switches S1, S2, S3, and S4 are open. The diode 1905 controls the direction in which current flows to the first battery cell 1902. To charge another battery cell 1910 with the first battery cell 1902, switches S2 and S4 are closed and switches S1, S3 and S5 are open. The switches S1, S2, S3, S4 and S5 can be controlled by the charging station processor 1722 and/or the charging controller 1736.

Figure 32:
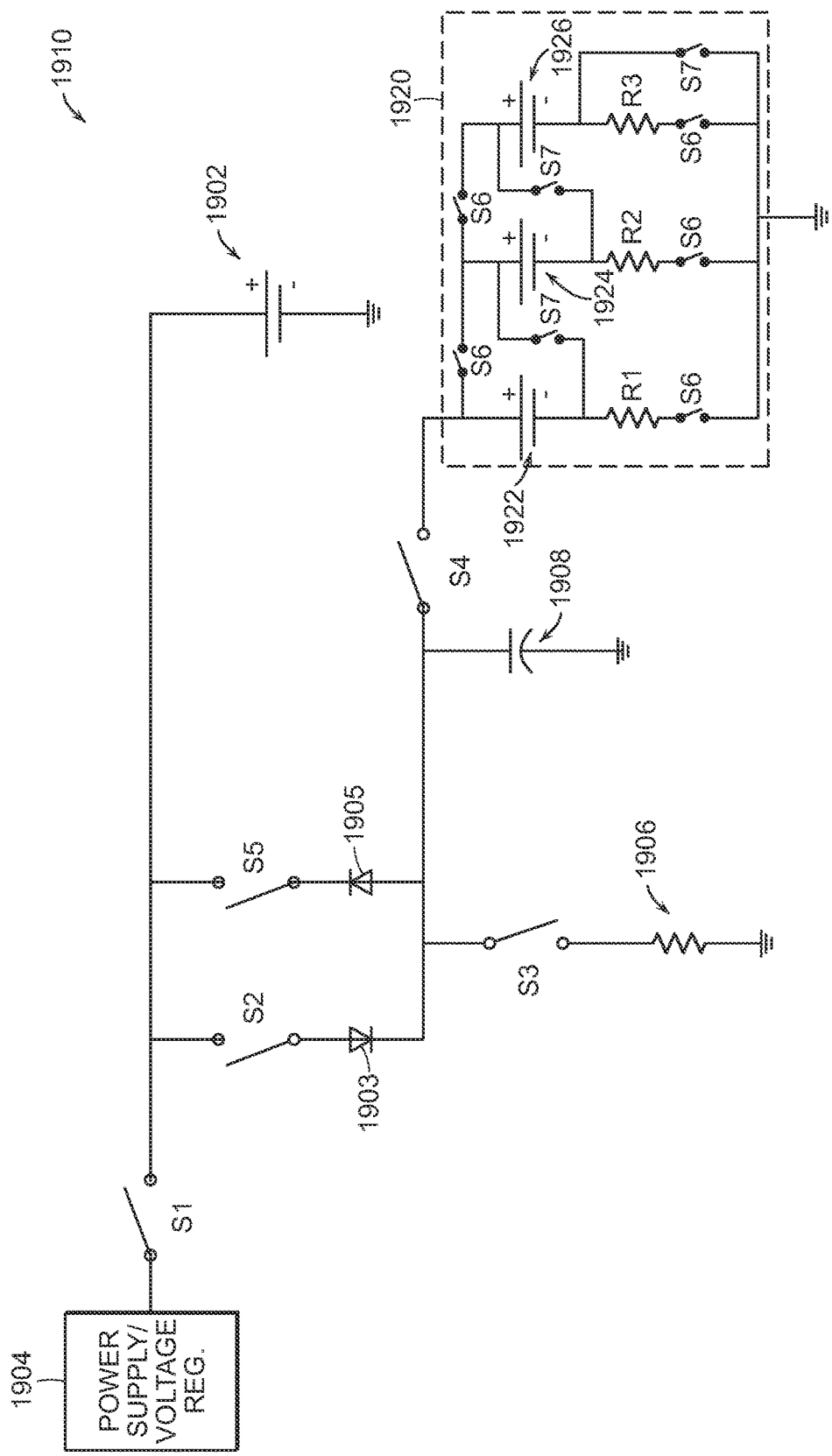

FIG. 32 shows a circuit for charging and discharging the first battery pack 1902 that is similar to that of FIG. 31, except that the configuration of FIG. 32 includes a set of battery cells 1920 that can be used to charge the first battery cell 1902. In the illustrated arrangement, the set 1920 includes three battery cells 1922, 1924, 1926, although in other arrangements the set 1920 may include more or less battery cells. The battery cells 1922, 1924, and 1926 in the set 1920 may be internal battery cells of the charging station and/or other battery packs inserted into the charging station. The cells 1922, 1924, 1926 in the set 1920 may be used, for example, to rapidly charge the first battery pack 1902, such as in a situation where a replacement battery pack is needed in an ongoing procedure. In the illustrated arrangement, the cells 1922, 1924, 1926 in the set 1920 may be connected in series or in parallel to provide increased voltage (when connected in series) or increased current (when connected in parallel). To connect the cells 1922, 1924, 1926 in series, the switches S7 are closed and the switches S6 are open. To connect the cells 1922, 1924, 1926 in parallel, the switches S6 are closed and the switches S7 are open. Each cell may have an associated resistor R1, R2, R3 respectively, for example, to provide a current source when connected in parallel.

In one aspect, referring back to FIG. 29A, if a clinician is in the midst of a procedure and needs a new battery pack to complete the procedure, the clinician (or his/her assistant) can select and remove from the charging station 1700 one of the battery packs that is fully charged and ready for use, which may be indicated on the display 1709 of the charging station 1700. If none of the battery packs 1702 is indicated as ready for use, the clinician can press the emergency release button 1780, for example, which may release the battery pack 1702 currently in the charging station 1700 that has the most charge at the moment, as determined by the charging controller 1736 and/or the charging station processor 1722, so that the partially-charged battery pack can be inserted into the handle module currently being used in the procedure. The charging station 1700 may also include visual indicators to indicate which battery pack 1702 is being released in the emergency so that it is clear which battery pack should be removed from the charging station for insertion into the surgical instrument. For charging stations 1700 that include means for securing the battery pack 1702 to the charging station 1700 during charging, such as the screw 1724 in the arrangement of FIGS. 29A-29C, activation of the emergency release button 1780 can cause the connection means to disconnect (or unsecure) the appropriate battery pack 1702, as described herein. At about the same time, the charging station 1722 can take steps to rapidly charge the selected battery pack 1702 for a short time period, preferably to give it at least enough charge to complete one or a couple of firings. As described herein, the charging station processor 1722 may, in conjunction with the charging controller circuit 1736, change the charging profile (e.g., constant current or constant voltage charge), charge the battery pack with a supercapacitor(s) 1908, and/or charge the battery pack with one or more other battery cells (which could be connected in series or in parallel, as described herein). In various arrangements, the battery pack 1702 is not released (e.g., by disconnecting the screw 1724) until the short-term charging charges the battery pack 1702 to a charge level to a threshold charge that is sufficient to complete one or a couple of firings.

Figure 33B:
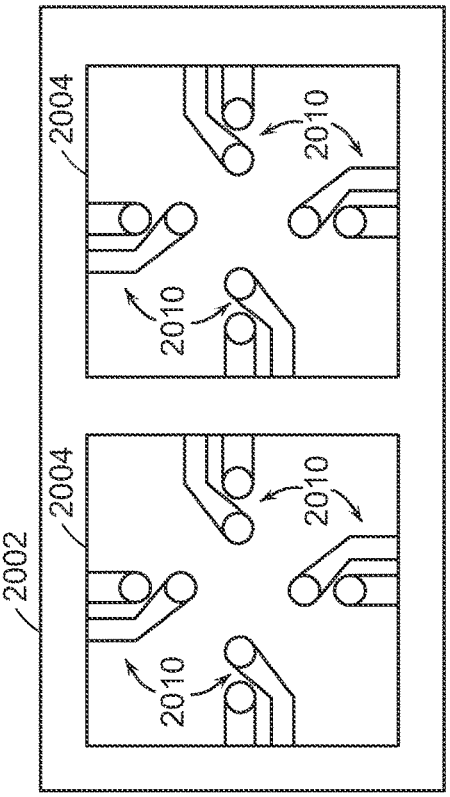
FIG. 33B is a top view of a charging station showing its contact configuration for the battery pack of FIG. 33A.
Figure 34B:
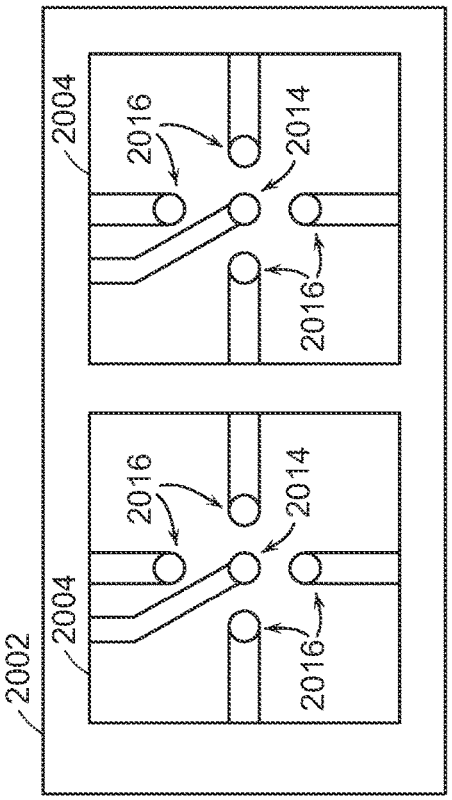
FIG. 34B is a top view of a charging station showing its contact configuration for the battery pack of FIG. 34A.
Figure 33A:
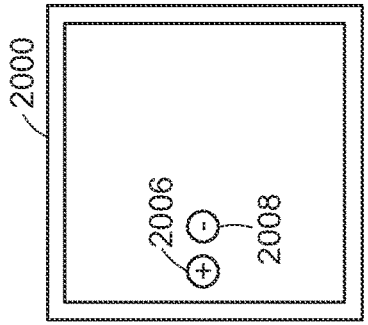
FIG. 33A is a top view of a battery pack.
Figure 34A:
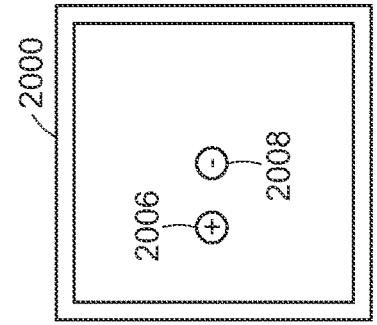
FIG. 34A is a top view of a battery pack.

In various aspects, the charging station may also be configured to ease the proper placement of the battery packs into the charging station for charging and/or to enhance the engagement between the electrical contacts between the battery pack and the charge terminals of the charging station to thereby increase the efficiency of the charging process. For example, the wells (or receptacles) in the charging station can have multiple sets of terminals so that no matter which way the battery pack is inserted into the well/receptacle, the battery pack's charging terminals contact one set of charging terminals of the charging station. FIGS. 33A and 33B illustrate top views of a battery pack 2000 and a charging station 2002, respectively, wherein the battery pack 2000 has a square cross-sectional shape and the wells/receptacles 2004 of the charging station 2002 are sized to the receive such a square-cross-sectional battery pack 2000. The illustrated charging station 2002 has two wells/receptacles 2004, but in other arrangements the charging station 2002 can have one well/receptacle or more than two wells/receptacles. As shown in FIG. 33A, the battery pack 2000 has a positive terminal 2006 and a negative terminal 2008 that the charging station terminals contact in order to charge the battery packs. In the illustrated arrangement, the terminals 2006, 2008 are not centered on the top of the battery pack 2000. Because such a battery pack 2000 could be inserted into one of square-shaped wells/receptacles 2004 in one of four configurations (each 90 degree turn, and assuming the side of the battery pack 2000 with the terminals 2006-2008 is always face-down), each well/receptacle can have four pairs of charging terminals 2010 positioned in it so that, no matter which way the battery pack 2000 is turned when it is inserted into the well/receptacle 2004, the off-center battery pack terminals 2006-2008 will make contact with one of the charging station terminal pairs 2010. Each charging station terminal pair 2010 is connected to the charging circuitry of the charging station, but only the one pair 2010 that contacts the battery pack terminals 2006-2008 will have a completed circuit so that charging current can flow to the battery pack 2000. In another arrangement, as shown in FIGS. 34A and 34B, one of the battery pack terminals could be in the center of the battery pack 2000. In the illustrated case, the negative terminal 2008 is in the center with the positive terminal 2006 to one side; however, the opposite arrangement could be utilized in another embodiment. The wells/receptacle of the charging station could correspondingly have one terminal 2014 in the center for contacting the negative terminal 2008 of the battery pack 2000, and four terminals 2016 on each side of the center terminal 2014 for contacting the positive terminal 2006 no matter which way the battery pack 2000 is inserted into the well/receptacle. For battery packs that have other geometries, there may need to be a fewer or greater number of terminal pairs in the well/receptacles (such as two pairs for a rectangular battery pack).

As discussed above, a surgical instrument can include a battery assembly capable of being attached to and/or detached from the surgical instrument. Such handling of the battery assembly can increase the chances of damaging the battery assembly. For example, the battery assembly may be inadvertently dropped while assembling the battery assembly to the surgical instrument and/or transporting the battery assembly to a charging station. Discussed in greater detail further below, the battery assembly can be configured to protect the housing, battery cells, and/or power supply circuit of the battery assembly in the event that the battery assembly is inadvertently dropped.

Figure 38:
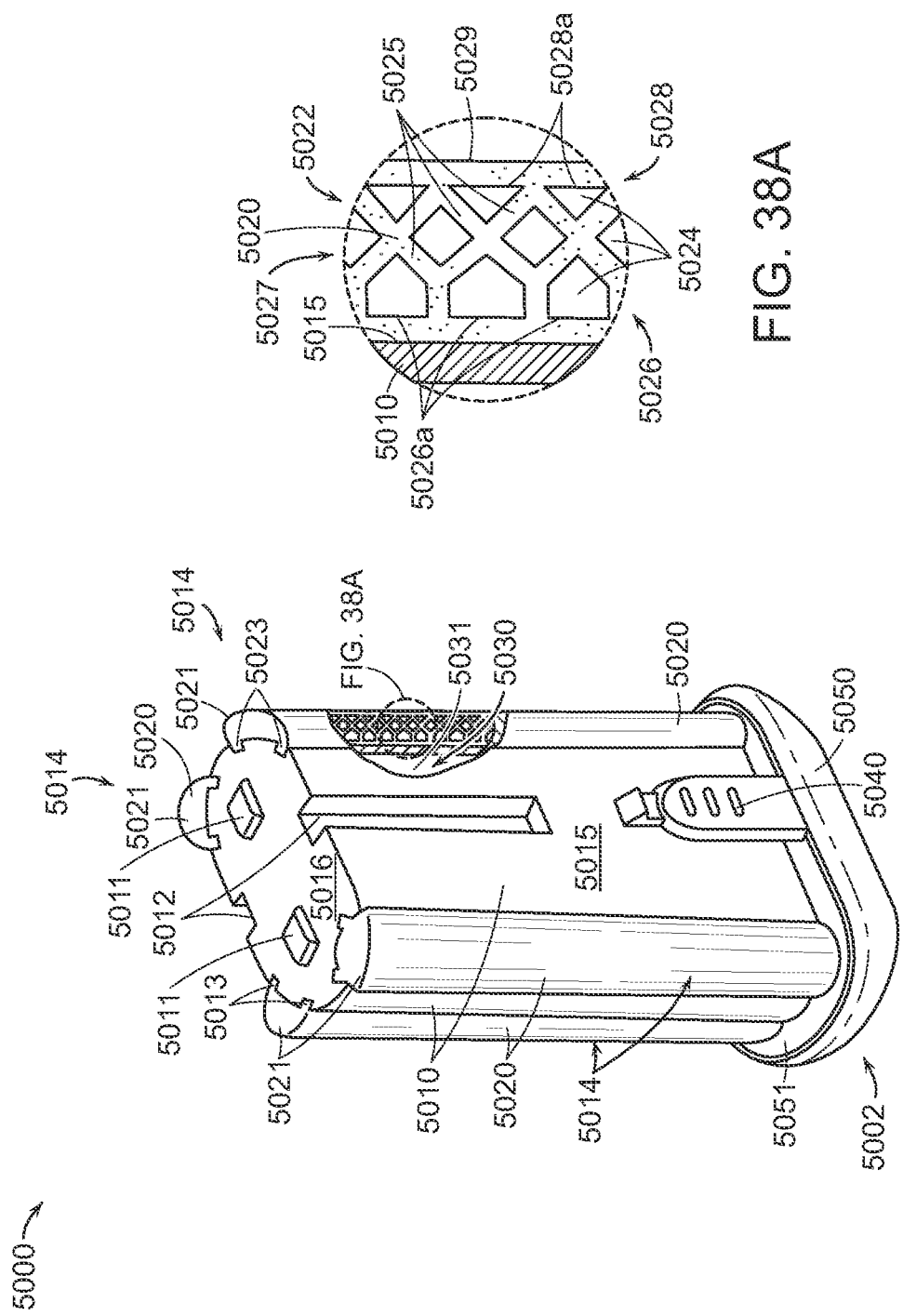
FIG. 38 is a perspective view of a battery assembly for use with a surgical instrument, wherein the battery assembly comprises a plurality of shock absorbing elements, according to at least one embodiment.

Referring now to FIG. 38, a battery assembly, such as battery assembly 5000, for example, can comprise a battery housing 5010 and a plurality of internal components 5030 including at least one battery cell 5031 and/or a power supply circuit positioned within the battery housing 5010. The at least one battery cell 5031 may comprise a lithium-ion battery, for example. The battery assembly 5000 also comprises one or more electrical contacts 5011 configured to transmit electrical energy provided by the at least one battery cell 5031 to the surgical instrument. The battery assembly 5000 further comprises one or more alignment features 5012 configured to assist a user in properly assembling the battery assembly 5000 to the surgical instrument. The alignment features 5012 comprise slots, for example, which are alignable with projections extending from the surgical instrument. The alignment features 5012 are symmetrically arranged around the perimeter of the battery housing 5010. Although not illustrated, other embodiments are envisioned in which the alignment features 5012 comprise a non-symmetrical configuration permitting the battery assembly 5000 to be attached to the surgical instrument in only one orientation. The battery assembly 5000 further comprises a lock mechanism 5040 configured to secure the battery assembly 5000 to the surgical instrument during use. When the battery assembly 5000 is attached the surgical instrument, the battery assembly 5000 can transmit electrical energy to electrical receiving contacts of the surgical instrument.

The battery housing 5010 can act as a container configured to house the internal components 5030 and/or act as a support structure configured to support various components thereon. Functioning as a container and/or a support structure, the battery housing 5010 may be rigid in order to support the internal components 5030 positioned therein. The battery housing 5010 may be comprised of a plastic material, for example. In certain instances, the inner housing 5010 is comprised of an elastomeric material, for example. Referring again to FIG. 38, the battery housing 5010 comprises a top face, a bottom face 5016, a plurality of lateral faces 5015, and a plurality of corners 5014. The bottom face 5016 can be associated with the electrical contacts 5011. The lateral faces 5015 and the corners 5014 are configured to surround the internal components 5030.

Various embodiments discussed herein relate to the protection of a battery assembly for use with a surgical instrument. Referring again to FIG. 38, the battery assembly 5000 comprises a radial and/or vertical reinforcement configured to protect the battery housing 5010, the internal components 5030, and/or the electrical contacts 5011. The radial and/or vertical reinforcement may comprise a shock absorbing layer, for example. In various instances, the shock absorbing layer may surround the battery housing 5010 in order to absorb an impact force that is applied to a lateral face 5015, the bottom face 5016, and/or a corner 5014 of the battery housing 5010. In addition to or in lieu of the above, a shock absorbing layer is housed within the battery housing 5010. Also, in addition to or in lieu of the above, the battery assembly 5000 may further comprise an outer housing for added protection. The outer housing can be configured to house the battery housing 5010 and the shock absorbing layer.

One means for protecting the battery assembly 5000 is illustrated in detail in FIG. 38A, for example, comprising a battery housing, or inner housing 5010, and a shock absorbing layer 5020. As discussed above, the housing 5010 may be comprised of a rigid material which can support the internal components 5030 of the battery assembly 5000. The shock absorbing layer 5020 may contain a lattice structure 5022 comprising a plurality of cells 5024. The cells 5024 can lower the density of the shock absorbing layer 5020. The cells 5024 can have an open cellular structure and/or a closed cellular structure. Moreover, the lattice structure 5022 can comprise one or more lattice layers. For instance, the lattice structure 5022 can include a first, or inner, lattice layer and a second, or outer, lattice layer.

The lattice structure 5022 further comprises a plurality of struts 5025 designed to deflect and/or buckle under pressure. If the battery assembly 5000 is dropped, an impact force is absorbed through the compression of the cells 5024 and the buckling and/or deflection of the struts 5025. Therefore, the shock absorbing layer 5020 can absorb shock and/or vibrational energy rather than relying on the battery housing 5010 to absorb the energy which could, in some circumstances, result in the damaging of the internal components 5030 of the battery assembly 5000. In various instances, the shock absorbing layer 5020 may comprise a foam-like structure and/or an elastomeric material, for example.

In various instances, referring again to FIG. 38, the cells 5024 are arranged in rows, for example, having an inner row of cells 5026, an intermediate row of cells 5027, and an outer row of cells 5028. Each cell of the inner row of cells 5026 can comprise a planar wall 5026a. The cells 5026 are oriented such that the planar walls 5026a of the cells 5026 are at least substantially parallel with a lateral face 5015 of the battery housing 5010. Each cell of the outer row of cells 5028 can comprise a planar wall 5028a. The cells 5028 are oriented such that planar walls 5028a of the cells 5028 are at least substantially parallel with an outer surface 5029 of the shock absorbing layer 5020. Orienting the planar walls 5026a, 5028a of each cell of the inner row 5026 and the outer row 5028 in such a manner can create a more shock resistant shock absorbing layer 5020. The shock absorbing layer 5020 may comprise corner portions positioned near the corners 5014 of the battery housing 5010 that can absorb an impact force directed to a corner 5014 of the battery housing 5010. The corner portions 5020 are not connected to one another; however, embodiments are envisioned in which the corner portions 5020 could be connected to one another.

In various instances, the battery assembly 5000 comprises a plurality of shock absorbing elements 5020. The shock absorbing elements 5020 are positioned to protect the corners 5014 of the battery assembly 5000. In various instances, an impact force may be more concentrated at the corners 5014 which can increase the risk of damaging the battery housing 5010 and/or the internal components 5030. The shock absorbing elements 5020 comprise end portions 5021 which extend beyond a bottom face 5016 of the battery housing 5010 in order to prevent damage to the electrical contacts 5011, for example, and to further protect the battery assembly 5000. If the battery assembly 5000 is dropped in an orientation such that the bottom face 5016 is at least substantially parallel with the ground, one or more of the end portions 5021 can absorb the impact force and dissipate the impact energy.

It may be preferred that a battery assembly be useable after experiencing an impact force, such as when the battery assembly 5000 is inadvertently dropped. In such instances, the shock absorbing elements 5020 are configured to allow the battery assembly 5000 to retain the ability to be properly fitted into the battery receiving portion of the surgical instrument and still transmit electrical energy to the electrical receiving contacts of the surgical instrument even though the battery assembly 5000 has been dropped. The shock absorbing elements 5020 may comprise crumple zones configured to deform when an impact force is applied. In at least one instance, a crumple zone may not permanently deform, or at least substantially permanently deform, if the impact force is below a crumple force threshold. In such instances, the crumple zone may permanently deform only if the impact force meets or exceeds the crumple force threshold. The crumple zones may limit the direction of the deformation of the shock absorbing elements 5020 toward the center of the battery assembly 5000. This inward deformation can preserve the ability of the battery assembly 5000 to fit into the battery receiving portion of the surgical instrument by preventing outward deformation that would cause the battery assembly 5000 to acquire a shape that would not fit into the battery receiving portion of the surgical instrument.

In various instances, the shock absorbing elements 5020 may experience an excessive amount of deformation requiring replacement of the shock absorbing elements 5020. In the event that the shock absorbing elements 5020 need to be replaced, the battery assembly 5000 can be configured so that the user of the surgical instrument can remove the damaged shock absorbing elements from the battery assembly 5000 and then attach useable shock absorbing elements thereto. Discussed in greater detail below, it may be preferred that the shock absorbing elements 5020 can be replaced in a timely fashion. Minimizing the amount of time required to replace the shock absorbing elements 5020 can be important when introducing another task to a surgical operation.

Assembling the shock absorbing elements 5020 to the battery assembly 5000 may be necessary when the shock absorbing elements 5020 need to be replaced. In various instances, the shock absorbing elements 5020 comprise one or more protrusions 5023 configured to slide and/or wedge into corresponding slots 5013 in the battery housing 5010. The slots 5013 are configured to receive the protrusions 5023 of new and/or useable shock absorbing elements in the event that the shock absorbing elements 5020 need to be replaced. In various instances, the protrusions 5023 and the slots 5013 can comprise a press-fit therebetween which can permit the protrusions 5023 to be slid within the slots 5013 along the corners of the housing 5010. In at least one instance, the protrusions 5023 and the slots 5013 can comprise a wedge-fit therebetween. In various instances, the shock absorbing elements 5020 may be attached to the battery housing 5010 in a snap-fit fashion. In at least one instance, the battery housing 5010 may comprise apertures configured to receive the protrusions 5023 in a snap fit-fashion. In certain instances, the protrusions 5023 can enter into the slots 5013 radially in a snap-fit manner. In addition to or in lieu of the above, the shock absorbing elements 5020 may be attached to the housing 5010 utilizing an adhesive, for example.

In various instances, the battery assembly 5000 further comprises a shock absorbing cap 5050. The shock absorbing cap 5050 is positioned at an outer end 5002 of the battery assembly 5000. The shock absorbing cap comprises a shoulder 5051 configured to contact the surgical instrument when the battery assembly 5000 is fully seated in the surgical instrument. The shoulder 5051 can act as a stop, for example, and can define the fully seated position of the battery assembly 5000. In various instances, the shoulder 5051 is configured to abut the shock absorbing elements 5020. If the battery assembly 5000 is attached to the surgical instrument, the shock absorbing cap 5050 can protect the battery assembly 5000 and/or the surgical instrument if the surgical instrument is dropped in an orientation such that the top face is at least substantially parallel with ground upon impact. On the other hand, if the battery assembly 5000 is not attached to the surgical instrument the shock absorbing cap 5050 can still protect the battery assembly 5000 if the battery assembly 5000 is dropped in an orientation such that the top face is at least substantially parallel to the ground.

Figure 39:
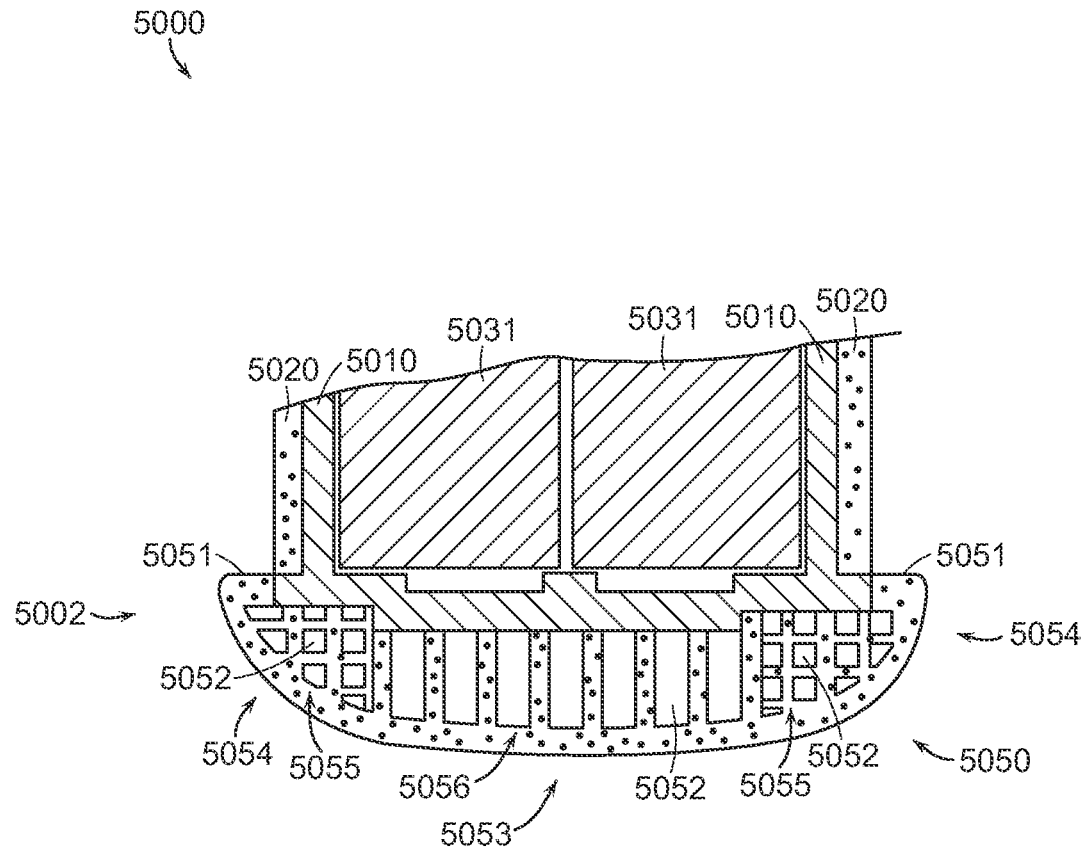
FIG. 39 is a partial cross-sectional view of the battery assembly of FIG. 38.

A partial, cross-sectional view of the battery assembly 5000 is illustrated in FIG. 39. The shock absorbing cap 5050 comprises a lattice structure, or cellular structure, comprising a plurality of cells 5052. The shock absorbing cap 5050 can comprise a material similar to that of the shock absorbing layer 5020. A denser lattice arrangement 5055 is used near outer edges 5054 of the battery assembly 5000 which can dissipate a more concentrated impact force. The shock absorbing cap 5050 comprises a center portion 5053 comprising a columnar lattice arrangement 5056 configured to absorb an impact energy generated by an impact force applied to the center portion 5053. In various instances, the column lattice arrangement 5056 is configured to dissipate a broadly-applied impact force.

In various instances, the shock absorbing cap 5050 may comprise crumple zones configured to deform when an impact force is applied. The shock absorbing cap 5050 can be designed to use the crumple zones to prevent the battery assembly 5000 from bouncing on the floor, for example, in the event the battery assembly 5000 is dropped.

The shock absorbing cap 5050 may be readily replaceable. In the event that the shock absorbing cap 5050 experiences an excessive amount of deformation requiring replacement of the shock absorbing cap 5050, the battery assembly 5000 can be configured so that the user of the surgical instrument can remove the damaged shock absorbing cap from the battery assembly 5000 and attach a useable shock absorbing cap.

In various instances, the shock absorbing elements 5020 can be tethered by intermediate portions. The intermediate portions can be configured to protect the lateral faces 5015 and/or the alignment features 5012 of the battery housing 5010. It can be appreciated that if an impact force is applied over the surface area of a lateral face 5015 of the battery housing 5010, the stress generated by the impact force would be less than that if the same impact force were to be applied to a corner 5014 of the battery housing 5010 which has a smaller surface area. Stated another way, the more surface area over which an impact force is distributed, the lower the stress and the stress concentration will be. Therefore, it may not be necessary that the intermediate portions between the shock absorbing elements 5020 be comprised of a composition which is as substantial as the shock absorbing elements 5020. In at least one instance, as a result, the intermediate portions may comprise a thinner composition than the shock absorbing elements 5020; however, various embodiments are envisioned in which the intermediate portions comprise the same and/or a thicker composition than the shock absorbing elements 5020.

Each of the shock absorbing elements 5020 of the battery assembly 5000 comprise a similar construction; however, other embodiments are envisioned in which one or more of the shock absorbing elements 5020 may be different than the others. In at least one such instance, at least one of the shock absorbing elements 5020 can comprise an additional weight, such as a metal weight, for example, positioned therein which can cause the battery assembly 5000 to fall and land in a specific orientation. Such an effect could also be achieved by placing one or more weights in the battery housing 5010, for example.

Figures 40, 40A:
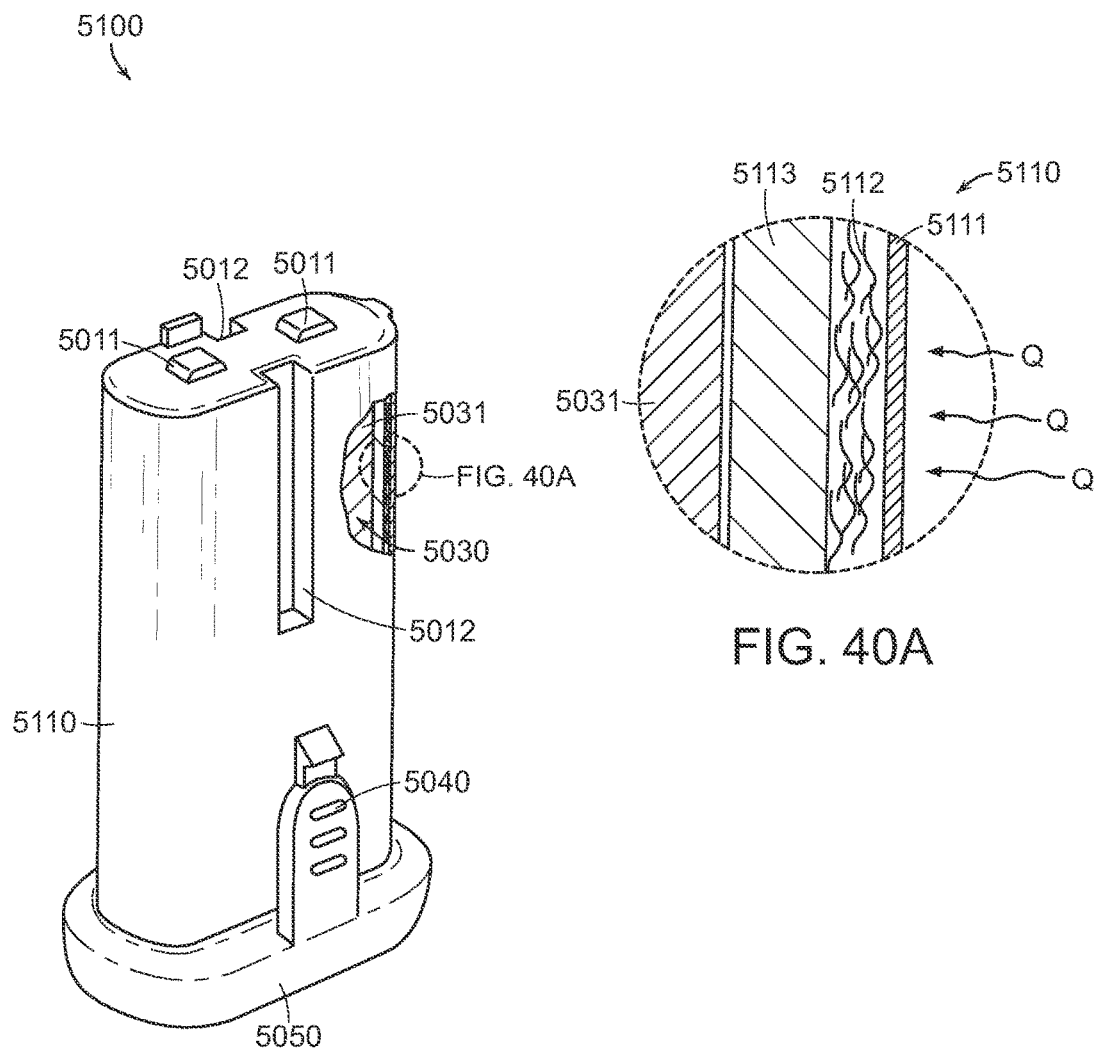
FIG. 40 is a perspective view of a battery assembly for use with a surgical instrument comprising a battery housing configured to protect one or more battery cells of the battery assembly.
FIG. 40A is a detail cross-sectional view of the battery assembly of FIG. 40.
Figure 41:
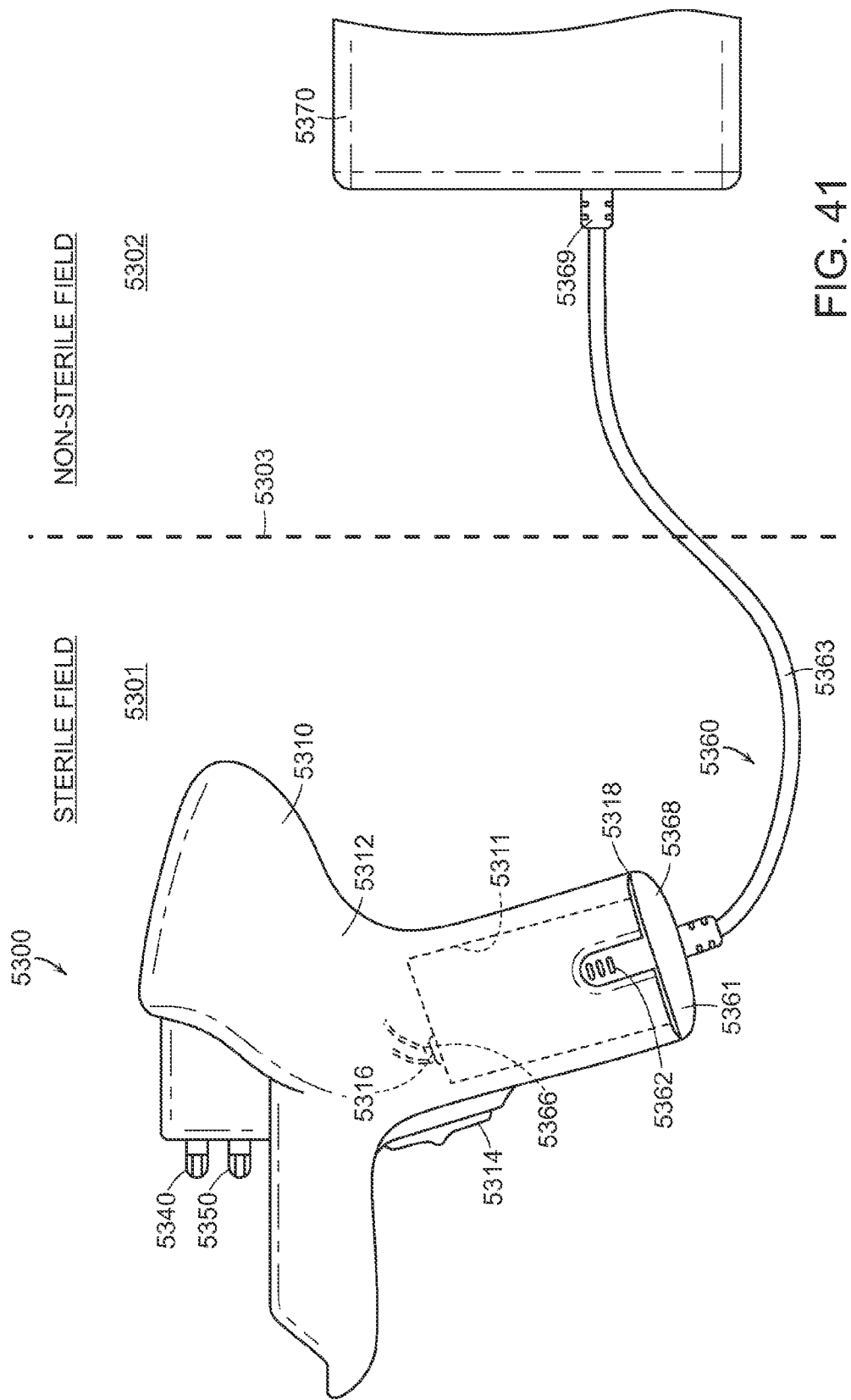
FIG. 41 illustrates a handle of a surgical instrument system including a power adapter extending from the handle to a power source in accordance with at least one embodiment.

A battery assembly 5100, which is similar to the battery assembly 5000 in many respects, is depicted in FIG. 40. The battery assembly 5100 can comprise means for protecting the internal components 5030 of the battery assembly 5100 from damage as a result of impact shock and/or heat. Various means for protecting the battery assembly 5100 from impact shock are discussed above. Heat, which is represented by Q in FIG. 40A, can pass through the battery housing 5110 and can be absorbed by the battery cells 5031 positioned in the battery housing 5110, for example.

It should be appreciated that heat flows from a higher temperature environment to a lower temperature environment. Under typical sterilization conditions, the battery assembly 5100 is exposed to a high temperature and, as a result, heat flows from a sterilization chamber into the battery assembly 5100. In some circumstances, however, the battery assembly 5100 may be improperly sterilized and may be exposed to an excessive temperature. If at least one of the battery cells 5031 absorbs and/or retains a damaging amount of heat Q, the battery cells 5031 may experience a thermal runaway event and fail.

Referring now to FIG. 40A, the battery housing 5110 comprises a heat reflective shell, or shield, 5111, a shock absorbing layer 5112, and a heat sink layer 5113. The reflective shell 5111 is configured to reflect and/or block the transfer of heat Q generated by improper sterilization, for example. In various instances, the reflective shell 5111 may be comprised of a material with a low thermal conductivity, such as a polymer and/or ceramic material, for example. A material having a low thermal conductivity usually has a low thermal expansion rate. A material having a low thermal conductivity can also perform well as an insulating layer. In any event, the reflective shell 5111 can comprise a reflective outer surface which can reflect heat away from the battery assembly 5100. The reflective outer surface can be comprised of a polished metal, such as polished aluminum, for example.

Further to the above, the heat sink layer 5113 is configured to absorb heat that passes through the reflective shell 5111. The heat sink layer 5113 can also be configured to absorb heat generated by the battery cells 5031 when the battery cells 5031 are being re-charged, for example. In some instances, the battery cells 5031 may generate an atypical amount of heat due to the overcharging and/or overuse thereof. In various instances, the heat sink layer 5113 can be comprised of a material having a high thermal conductivity such as a metal, for example. Any suitable material having a high thermal conductivity can be used to absorb heat generated by the at least one battery cell 5031. Moreover, a material having a high thermal conductivity often has a high thermal expansion rate.

Further to the above, the battery cells 5031 can expand as they are being charged. The expanding battery cells 5031 can push the heat sink layer 5113 outwardly. Moreover, the heat sink layer 5113 can rapidly expand outwardly due to its high thermal expansion rate. Such outward movement of the battery cells 5031 and the heat sink layer 5113 can push the shock absorbing layer 5112 toward the reflective shell 5111 and apply pressure to the reflective shell 5111. Such pressure can generate stress within the reflective shell 5111, the heat sink layer 5113, and the battery cells 5031, especially in embodiments where the reflective shell 5111 is comprised of a material which has a lower thermal expansion rate than the heat sink layer 5113. In such instances, the heat sink layer 5113 may expand more than the reflective shell 5111 thereby creating additional stress in the reflective shell 5111, the heat sink layer 5113, and the battery cells 5031.

The shock absorbing layer 5112 is configured to permit expansion of the battery cells 5031 while preventing damage to the battery housing 5110. Acting as a degree of freedom for the battery housing 5110, the shock absorbing layer 5112 may expand and/or contract in order to manage the expansion and/or contraction of the battery cells 5031 by allowing the heat sink layer 5113 and the at least one battery cell 5031 to expand and/or contract due to the transfer of heat while maintaining the supportive ability of the battery assembly 5100. In various instances, the expansion and contraction of the shock absorbing layer 5112 can prevent damage to the battery housing 5110. The shock absorbing layer 5112 can absorb thermal shocks as well as impact shocks Turning now to FIGS. 41 and 42, a surgical instrument system 5300 includes a handle 5310 which is usable with a shaft assembly selected from a plurality of shaft assemblies. Further to the above, one or more of such shaft assemblies can include a staple cartridge, for example. The handle 5310 comprises a housing 5312, a first rotatable drive output 5340, and a second rotatable drive output 5350. The handle 5310 further includes a first actuator 5314 for operating the first rotatable drive output 5340 and a second actuator 5315 for operating the second rotatable drive output 5350. The handle housing 5312 comprises a battery cavity 5311 configured to receive a battery therein. The battery can be any suitable battery, such as a lithium ion battery, for example. In various instances, the battery is insertable into and removable from the battery cavity 5311. In many instances, such a battery can provide power to the handle 5310 to operate the surgical instrument system 5300 without the complement of an additional and/or tethered power source, for instance. Such a design can be advantageous for many reasons. For instance, when the surgical instrument system 5300 is untethered to a power source, the entirety of the surgical instrument system 5300 can be present in a sterile field of the operating suite. Such batteries, however, can only supply a finite amount of power. In many circumstances, the finite amount of power that the battery can supply is sufficient to operate the surgical instrument system 5300. On the other hand, some circumstances can arise in which the battery cannot supply the surgical instrument system 5300 with the requisite power.

Referring again to FIG. 41, the battery positioned in the battery cavity 5311 of the handle 5310 can be removed and replaced with a power supply adapter 5360, for example. The power supply adapter 5360 comprises a distal plug 5361 positionable in the battery cavity 5311. The distal plug 5361 comprises a plurality of electrical contacts 5366 which are engageable with corresponding electrical contacts 5316 in the handle 5310. In various instances, the battery and the distal plug 5361 can engage the same electrical contacts 5316, depending on which one is positioned in the battery cavity 5311. In such instances, the handle 5310 can be supplied with power from one set of electrical contacts 5316 regardless of whether the battery or the power supply adapter 5360 is engaged with the handle 5310. In other instances, the battery engages a first set of electrical contacts 5316 and the distal plug 5361 engages a different set of electrical contacts 5316. In such instances, a microprocessor of the handle 5310 can be configured to identify whether the battery or the power supply adapter 5360 is coupled to the handle 5310.

The distal plug 5361 of the power supply adapter 5360 can comprise any suitable shape so long as the distal plug 5361 is positionable in the battery cavity 5311. In various instances, the distal plug 5361 can comprise the same geometry as the battery, for example. In certain instances, the housing of the distal plug 5361 is analogous or sufficiently similar to the housing of the battery. In any event, the distal plug 5361 can be configured such that there is little, if any, relative movement between the distal plug 5361 and the battery cavity 5311 once the distal plug 5361 has been fully seated in the battery cavity 5311. In at least one instance, the distal plug 5361 comprises a stop 5368 configured to contact a stop datum 5318 defined on the handle housing 5312. When the stop plug stop 5368 contacts the handle stop datum 5318, the plug 5361 may be fully seated in the battery cavity 5311. The handle 5310 and/or the plug 5361 can comprise a lock configured to hold the plug 5361 in its fully seated position. For instance, the plug 5361 comprises at least one lock 5362 configured to releasably engage the housing 5312.

The power supply adapter 5360 further comprises a cord 5363 extending from the plug 5361. The cord 5363 electrically couples the plug 5361 with a power source, such as power source 5370, for example. The power source 5370 can comprise any suitable power source such as a signal generator that receives power from a 110V, 60 Hz power source and/or a battery, for example. The cord 5363 comprises any suitable number of conductors and insulators to communicate electrical power from the power source 5370 to the plug 5361. In at least one instance, the cord 5363 comprises a supply conductor, a return conductor, and a ground conductor, for example, which are electrically insulated from one another by an insulator jacket. Each conductor of the cord 5363 can comprise a proximal terminal contained within a proximal plug 5369, for example. In various instances, the proximal plug 5369 can be releasably attached to the power source 5370. In certain other instances, the proximal plug may not be readily detached from the power source 5370.

In various instances, the power source 5370 can comprise a direct current (DC) power source, for example. In such instances, the battery and the power supply adapter 5360 can both supply DC power to the handle 5310, depending on which one is electrically coupled to the handle 5310. The power supply adapter 5360 and the power source 5370 can co-operatively supply electrical power to the handle 5310 which is equal to and/or in excess of the electrical power that the battery can supply to the handle 5310. In at least one instance, a surgeon using the handle 5310 as part of the surgical instrument system 5300 may determine that the handle 5310 is underpowered, remove the battery from the handle 5310, and couple the power supply adapter 5360 to the handle 5310. The power source 5370 can then be operated to supply sufficient power to the handle 5310 via the power supply adaptor 5360 to operate the surgical instrument system in the desired manner. In various instances, the power source 5370 can supply a larger voltage to the handle 5310, for example.

In certain instances, the power source 5370 can comprise an alternating current (AC) power source. In at least one such instance, the power supply adapter 5360 can include an alternating current to direct current (AC/DC) power converter configured to convert the AC power supplied by the power source 5370 to DC power. In such instances, the battery and the power supply adapter 5360 can both supply DC power to the handle 5310, depending on which one is electrically coupled to the handle 5310. The AC/DC power converter can include a transformer, a full-wave bridge rectifier, and/or a filter capacitor, for example; however, any suitable AC/DC power converter could be utilized. The AC/DC power converter is positioned in the plug 5361; however, the AC/DC power converter can be positioned within the power supply adapter 5360 in any suitable location, such as the cable 5363, for example.

In various instances, the handle 5310 includes a AC/DC power converter in addition to or in lieu of the AC/DC power converter of the power supply adapter 5360. Such an embodiment could implement the dual sets of battery contacts 5316 discussed above. In at least one such embodiment, a battery power supply circuit can comprise, one, a first circuit segment including the first set of contacts 5316 which are engaged by the battery and, two, a second circuit segment in parallel to the first circuit segment which includes the second set of contacts 5316 that are engaged by the power supply adapter 5360. The second circuit segment includes an AC/DC power converter configured to convert the AC power supplied by the power source 5370 to DC power while the first circuit segment does not include an AC/DC power converter as the battery is already configured to supply DC power.

Referring again to FIG. 41, the handle 5310 may be in a sterile operating field 5301 and the power supply 5370 may be in a non-sterile field 5302. In such instances, the power supply adapter 5360 can extend between the sterile field 5301 and the non-sterile field 5302. The sterile field 5301 and the non-sterile field are separated by a boundary 5303. The boundary 5303 may comprise a physical boundary, such as a wall, for example, or a virtual boundary intermediate a sterile operating table and a non-sterile back table, for example.

Figure 42:
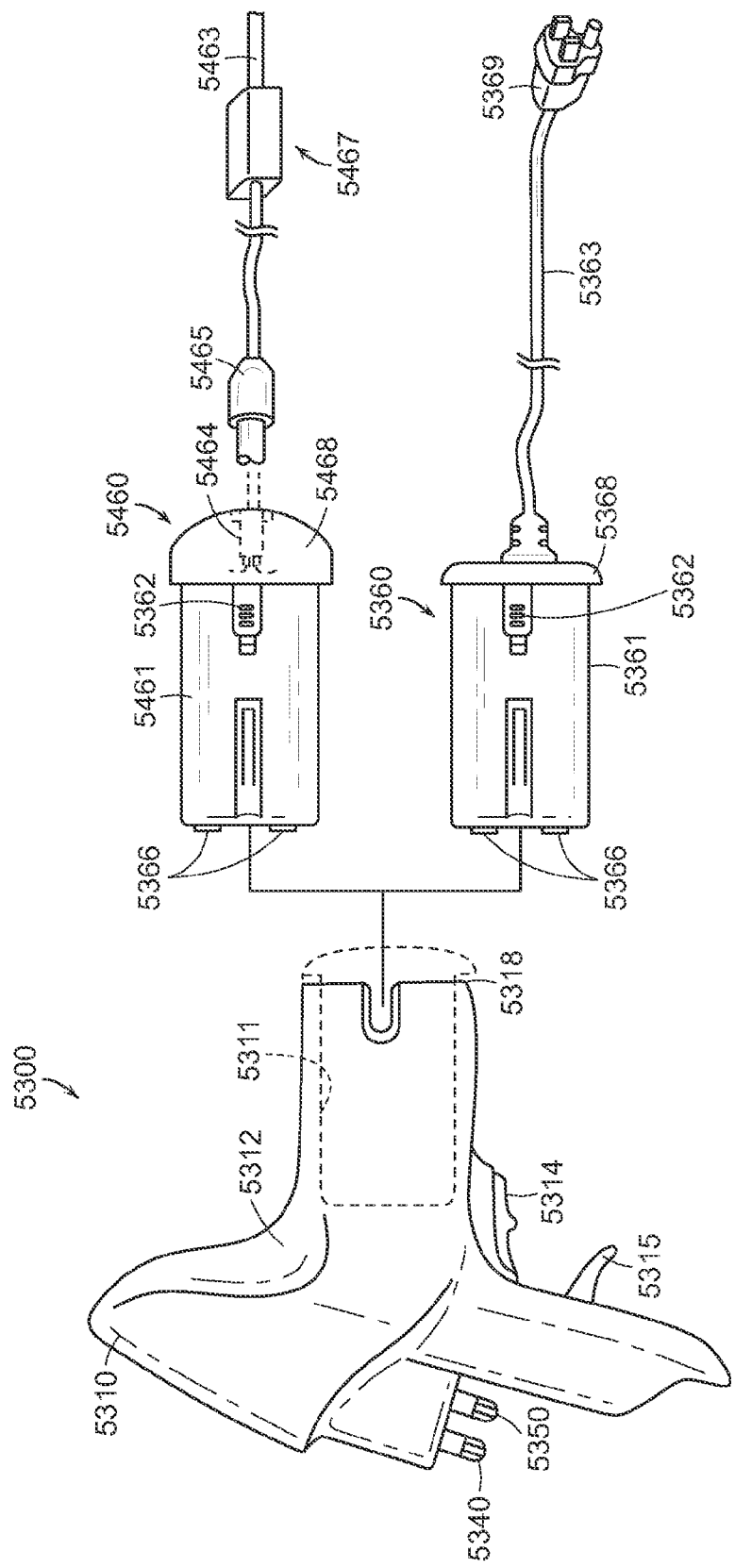
FIG. 42 illustrates the handle of FIG. 41 which is selectively usable with the power adapter of FIG. 41 or a power adapter system including a removable battery and a detachable power cord in accordance with at least one embodiment

In order to use the power supply adapter 5360, the battery positioned in the battery cavity 5311 must be removed in order to install the plug 5361 of the power supply adapter 5360 into the battery cavity 5311. Alternative embodiments are envisioned in which the battery can remain in the battery cavity 5311 when a power supply adapter is operably coupled with the handle 5310. Turning now to FIG. 42, a battery 5461 is positionable in the battery cavity 5311. The battery 5461 is readily removable from the battery cavity 5311 when the lock 5362 is deactivated; however, embodiments are envisioned in which the battery 5461 is not readily removable from the battery cavity 5311. Similar to the plug 5361, the battery 5461 can be sized and configured such that the battery 5461 is closely received in the battery cavity 5311 in order to limit relative movement between the battery 5461 and the battery cavity 5311 when the battery 5461 is fully seated in the battery cavity 5311. Also similar to the plug 5361, the battery 5461 comprises an end stop 5468 configured to contact the stop datum 5318 of the handle 5310.

The battery 5461 comprises one or more lithium ion battery cells, for example, positioned therein. Similar to the above, the battery 5461 can supply sufficient power to the handle 5310 to operate the surgical instrument system in various instances. In the event that the battery cells of the battery 5461 lack the necessary power to operate the surgical instrument system, a power supply adapter 5460 can be coupled to the battery 5461. The power supply adapter 5460 is similar to the power supply adapter 5360 in many respects. Similar to the above, the power supply adapter 5460 comprises a cord 5463 including a proximal end 5369 which can be connected to a power source, such as power source 5370, for example. The battery 5461 includes an electrical connector 5464 defined therein which is configured to receive a distal connector 5465 of the cord 5463 to electrically couple the power source 5370 to the battery 5461.

Figure 43:
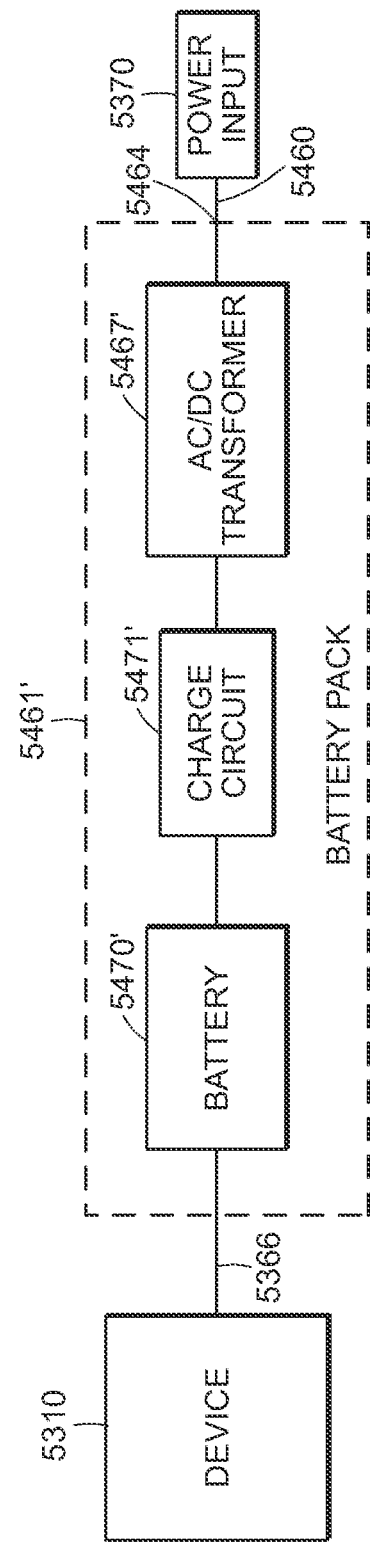
FIG. 43 is a schematic representation of a power adapter in accordance with at least one embodiment.

In at least one instance, further to the above, the power supply adapter 5460 can be placed in series with the cells of the battery 5461 when the adapter connector 5465 is inserted into the battery connector 5464. In such instances, the battery 5461 and the power source 5370 can both supply power to the handle 5310. FIG. 43 depicts such an embodiment. As disclosed in FIG. 43, a battery 5461' comprises a power supply circuit including one or more battery cells 5470' which are configured to supply DC power to the handle 5310. When the power supply adapter 5460 is electrically coupled to the battery 5461', the power source 5370 can, one, re-charge the battery cells 5470' via re-charging circuit 5471' and/or, two, supplement the power that the battery cells 5470' are supplying to the handle 5310. In the instances where the power source 5370 comprises an AC power source, the battery 5461' can comprise an AC/DC transformer 5467' which is configured to convert the AC power supplied by the power source 5370 to DC power before the power is supplied to the charge circuit 5471' and/or the battery cells 5470'. The power supply circuit in the battery comprises the battery connector 5464, the AC/DC transformer 5467', the charge circuit 5471', the battery cells 5470', and the battery terminals 5366 which are in series with one another; however, any suitable arrangement for the power supply circuit can be utilized.

Figure 44:
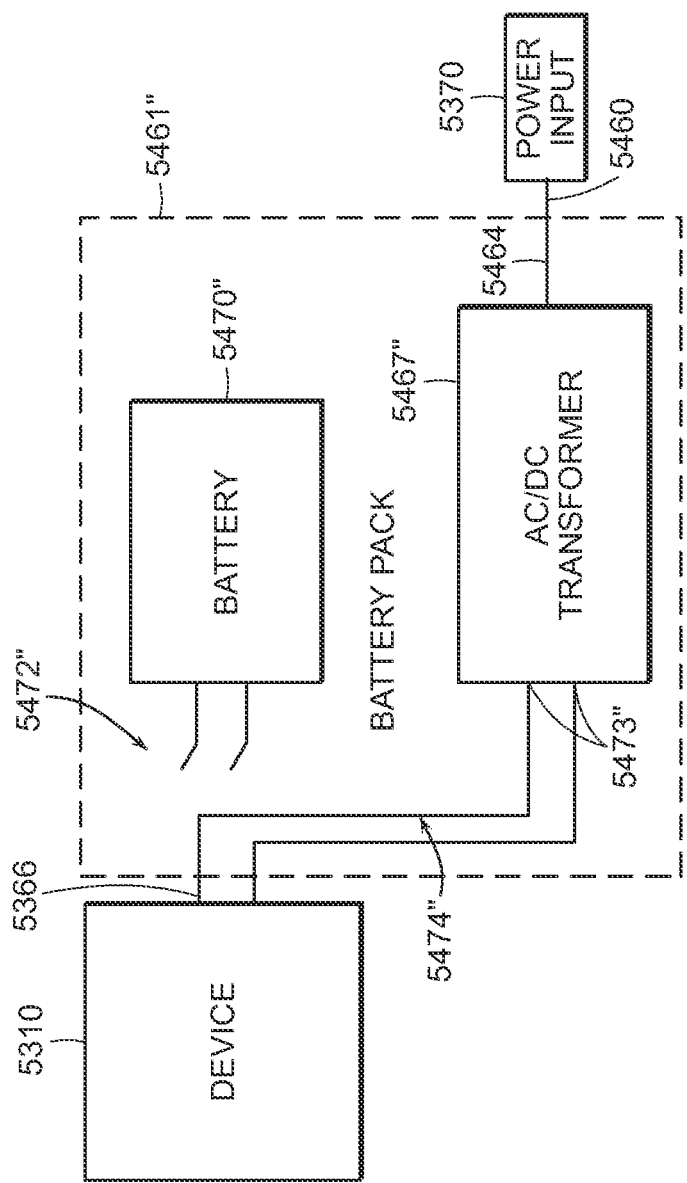
FIG. 44 is a schematic representation of a power adapter in accordance with at least one embodiment.

In other instances, the insertion of the adapter connector 5465 into the battery connector 5464 can electrically couple the power source 5370 with the handle 5310 and, concurrently, electrically decouple the battery cells of the battery 5461 from the handle 5310. FIG. 44 depicts such an embodiment. As disclosed in FIG. 44, a battery 5461" comprises a power supply circuit including one or more battery cells 5470" which are configured to supply DC power to the handle 5310. The battery cells 5470" are in electrical communication with the battery contacts 5366 via a first circuit segment 5472" and a battery switch 5474" when the adapter connector 5465 is not positioned in the battery connector 5464. In such instances, the battery switch 5474" is in a first switch state. The insertion of the adapter connector 5465 into the battery connector 5464 places the switch 5474" in a second switch state, as illustrated in FIG. 44, in which the battery cells 5470" are no longer able to supply electrical power to the contacts 5366. Additionally, the power supply adapter 5460 and the battery connector 5464 are in electrical communication with the battery contacts 5366 via a second circuit segment 5473" and the battery switch 5474" when the switch 5474" is in its second switch state. In the instances where the power source 5370 comprises an AC power source, the second circuit segment 5473" of the battery 5461" can comprise an AC/DC transformer 5467" which is configured to convert the AC power supplied by the power source 5370 to DC power.

As discussed above, referring again to FIG. 44, the battery switch 5474" can be operated to selectively place the first parallel circuit segment 5472" including the battery cells 5470" in electrical communication with the battery contacts 5366 when the switch 5474" is in its first switch state and, alternatively, the second parallel circuit segment 5473" including the battery connector 5464 and the AC/DC transformer 5467" in electrical communication with the battery contacts 5366 when the switch 5474" is in its second switch state. The battery switch 5474" can comprise a mechanical switch, an electromechanical switch, and/or an electronic switch, as described in greater detail further below.

A mechanical battery switch 5474" can comprise a sliding busbar which is pushed between a first position associated with a first switch state of the switch 5474" and a second position associated with a second switch state of the switch 5474", for example. In the first position of the sliding busbar, the busbar couples the first circuit segment 5472" with the battery contacts 5366 but does not couple the second circuit segment 5473" with the battery contacts 5366. In the second position of the sliding busbar, the busbar couples the second circuit segment 5473" with the battery contacts 5366 but does not couple the first circuit segment 5472" with the battery contacts 5366. The battery 5461 can further comprise a biasing member, such as a spring, for example, configured to bias the busbar into its first position and, thus, bias the battery switch 5474" into its first switch state. Further to the above, the adapter connector 5465 can contact the busbar of the switch 5474" when the adapter connector 5465 is inserted into the battery connector 5464 and push the busbar from its first position into its second position and place the switch 5474" into its second switch state. When the adapter connector 5465 is removed from the battery connector 5464, the biasing member can return the busbar to its first position and electrically re-couple the battery cells 5470" with the battery contacts 5366. In certain alternative embodiments, the insertion of the adapter connector 5465 into the battery connector 5464 may permanently decouple the battery cells 5470" from the battery contacts 5466. In at least one such embodiment, the battery 5461" can comprise a lock configured to hold the busbar in its second position once the busbar is pushed into its second position by the adapter connector 5465. Such an embodiment can provide a permanent lockout to prevent the battery 5461" from being used again to supply power from the battery cells 5470" as it may be undesirable and/or unreliable to reuse and/or recharge a battery that was unable to provide the handle 5310 with sufficient power.

An electromechanical switch 5474" can comprise a relay, for example. The relay can be biased into a first relay state when the adapter connector 5465 is not positioned in the battery connector 5464. The relay can be switched into a second relay state when the adapter connector 5465 is electrically coupled to the battery connector 5464. The relay can comprise an electromagnet, which can include a wire coil and an armature, for example, that is activated when the contacts of the adapter connector 5465 interface with the battery connector 5464. In at least one instance, the power supply adapter 5460 can comprise a relay control circuit in addition to the power circuits which can provide the coil of the relay with a sufficient voltage to move the armature of the relay between its first switch state and its second switch state. In various instances, the switch 5474" can comprise a latching relay, for example. In at least one instance, the switch 5474" can comprise a contactor, for example, which can be electronically controlled by a microprocessor and a control circuit, for example.

Certain electronic switches may not have any moving components, such as a solid-state relay, for example. A solid-state relay can utilize a thyristor, TRIAC and/or any other solid-state switching device, for example. A solid-state relay can be activated by a control signal from the power source 5370, for example, to switch the load being supplied to the battery contacts 5366 from the battery cells 5470" to the power source 5370. In at least one instance, the solid-state relay can comprise a contactor solid-state relay, for example. In various instances, an electronic switch can comprise a microprocessor and a sensor in signal communication with the microprocessor which detects whether power is being supplied to a contact of the battery connector 5464, for example. In at least one instance, the sensor can be configured to inductively detect a field that is generated when voltage is applied to the contacts of the battery connector 5464. In certain instances, the microprocessor can be responsive to a control signal received from the power supply 5370, for example, to switch a relay between a first relay state and a second relay state to control whether the first parallel circuit segment 5472" or the second parallel circuit segment 5473", respectively, is in electrical communication with the battery contacts 5366.

Further to the above, the power supply adapter 5460 can include an AC/DC power converter. The power supply adapter 5460 includes an AC/DC power transformer 5467 in the cord 5463; however, an AC/DC power transformer may be placed in any suitable location in the power supply adapter 5460.

In various instances, a power adapter supply system can include a battery, such as the battery 5361, 5461, 5461', and/or 5461", for example, and a power supply adapter, such as the power supply adapter 5360 and/or 5460, for example.

Figure 45:
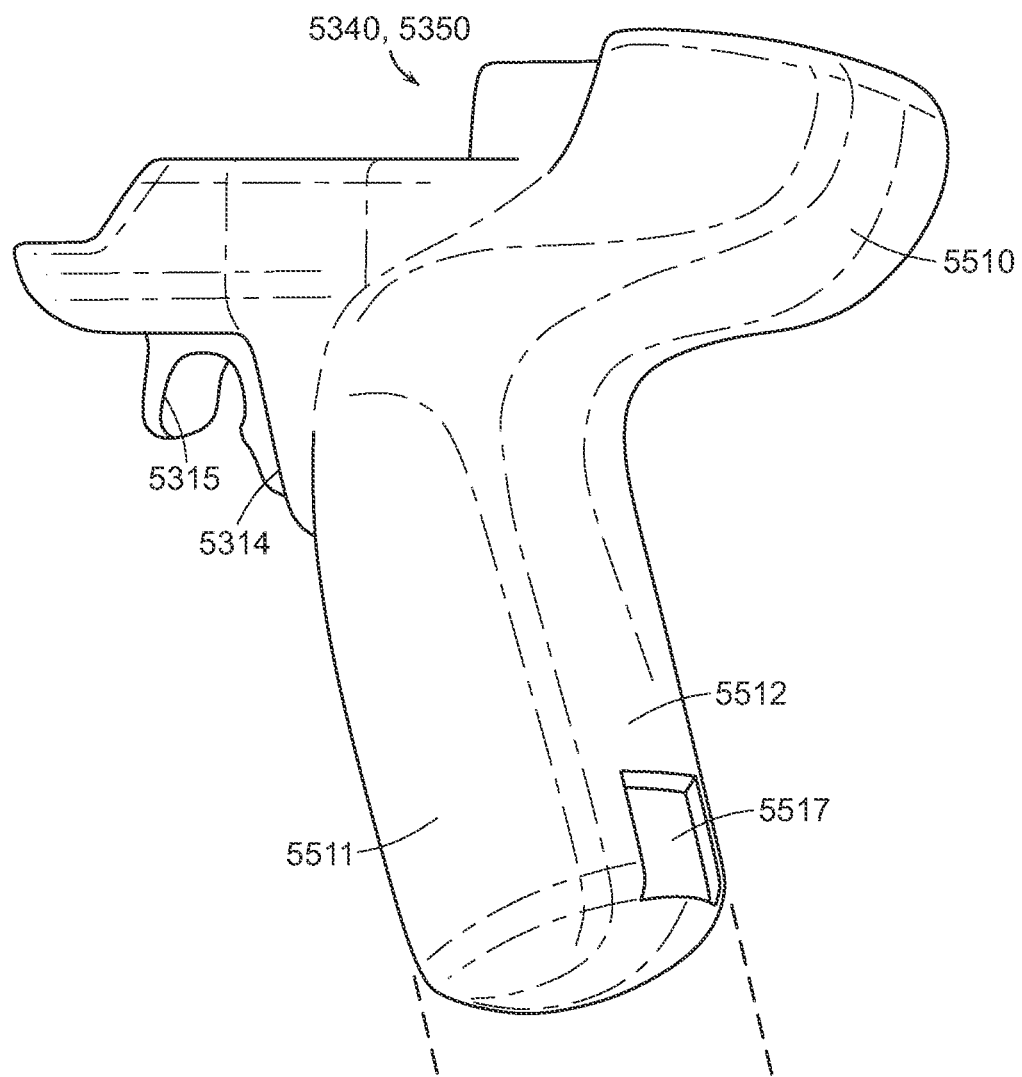
FIG. 45 is a perspective view of a handle of a surgical instrument system including a battery.
Figure 46:
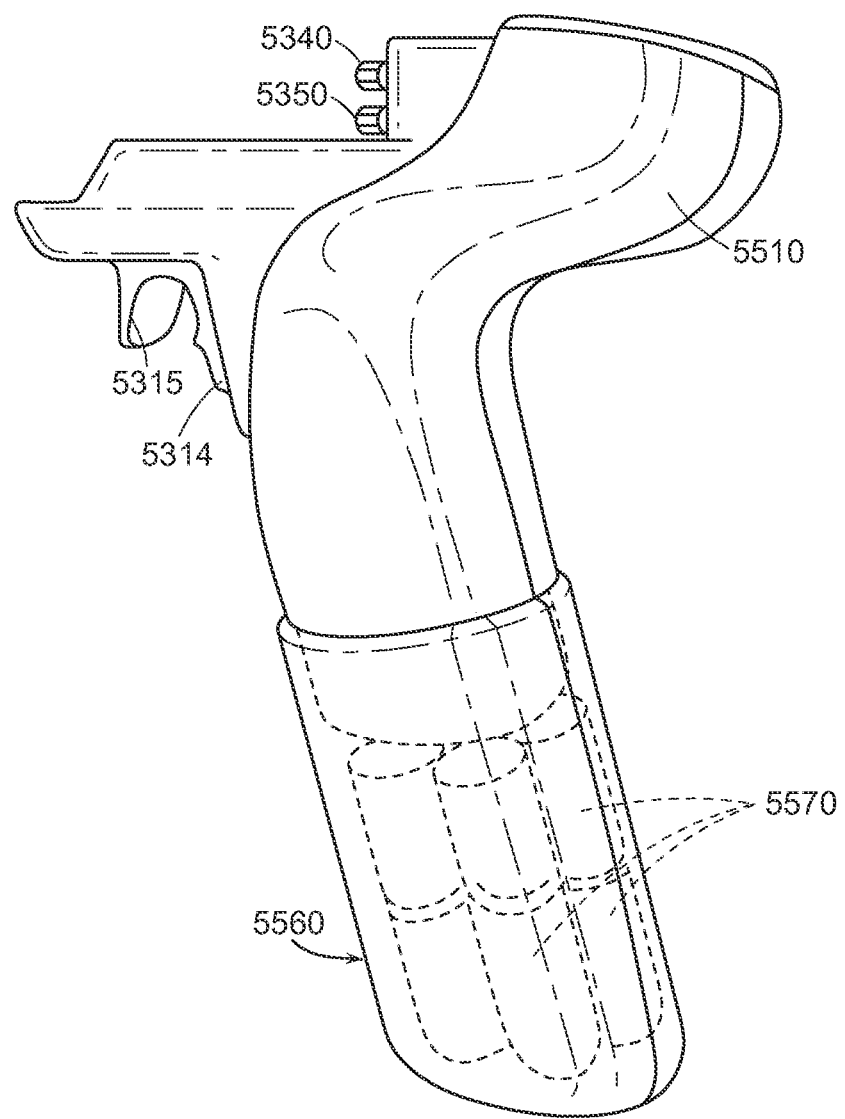
FIG. 46 is a perspective view of a second battery attached to the handle of FIG. 45.
Figure 47:
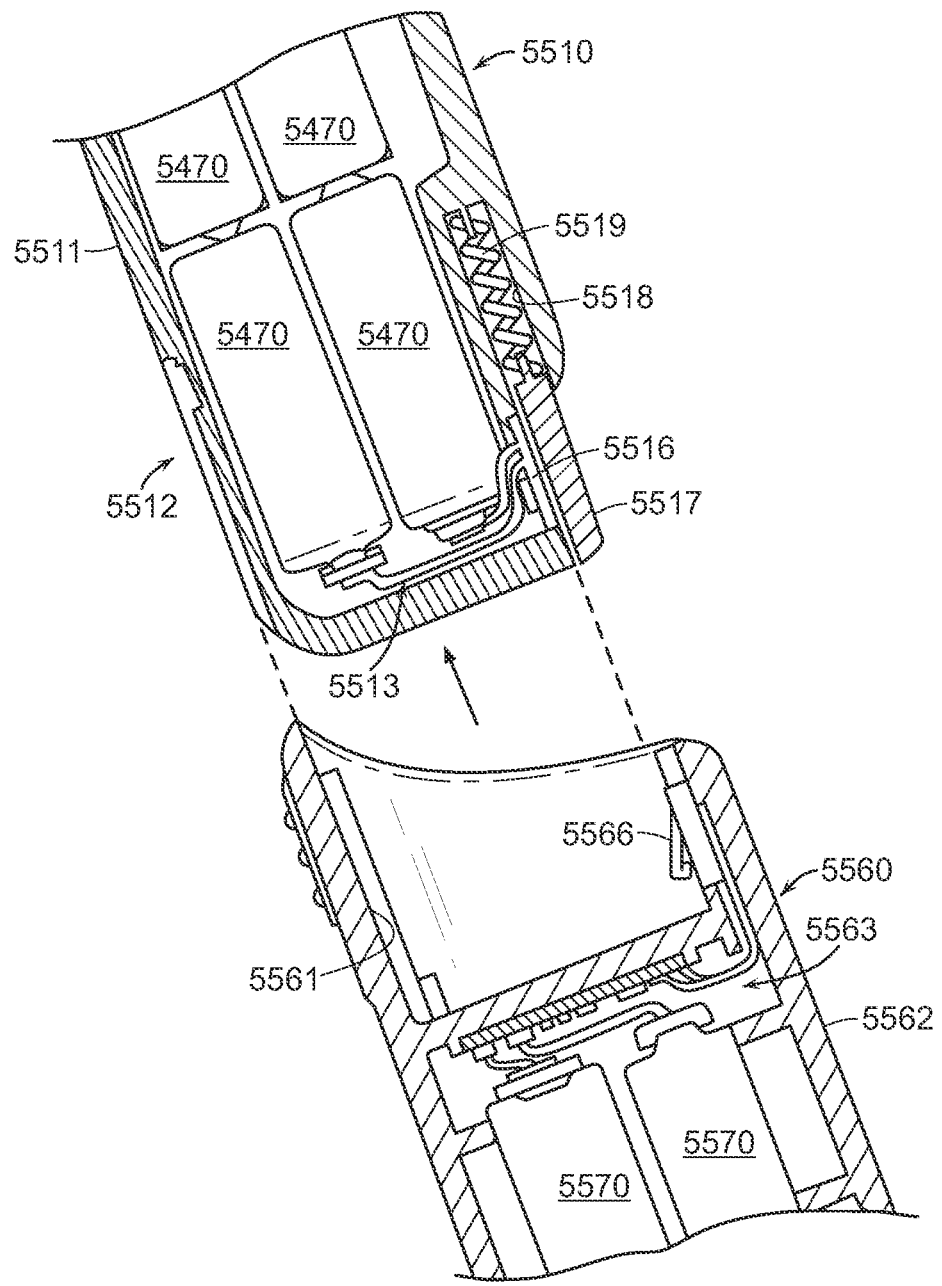
FIG. 47 is a cross-sectional view of the handle and the battery of FIG. 45 and the second battery of FIG. 46.

Turning now to FIGS. 45-47, a handle 5510 of a surgical instrument system comprises a gripping portion, or pistol grip, 5511 and a housing 5512. The handle 5510 further comprises one or more battery cells, such as battery cells 5470, for example, positioned in the gripping portion 5511. In many instances, the battery cells 5470 can provide enough power to the handle 5510 to operate the surgical instrument system. In other instances, the battery cells 5470 may not be able to provide enough power to the handle 5510. In such instances, as described in greater detail further below, a supplemental battery, such as supplemental battery 5560, for example, can be attached to the handle 5510 to provide power to the handle 5510.

Further to the above, referring primarily to FIG. 47, the battery cells 5470 are arranged in series as part of a battery power supply circuit 5513. The battery power supply circuit 5513 is in electrical communication with an electrical connector 5516 defined in the housing 5512. The electrical connector 5516 can comprise any suitable number of electrical contacts. In at least one instance, the electrical connector 5516 comprises two electrical contacts, for example. The electrical connector 5516 is positioned at the end of the gripping portion 5511; however, the electrical connector 5516 can be positioned at any suitable location on the handle 5510.

The handle 5510 further comprises a connector cover 5517. The connector cover 5517 is movable between a first position in which it covers the electrical connector 5516 and a second position in which the electrical connector 5516 is exposed. The housing 5512 comprises a slot 5518 defined therein configured to slidably receive and support the connector cover 5517. The handle 5510 further comprises a biasing member, such as spring 5519, for example, positioned in the slot 5518 intermediate the housing 5512 and the connector cover 5517. The spring 5519 is configured to bias the connector cover 5517 into its first position to cover the electrical connector 5516.

As discussed above, the supplemental battery 5560 is attachable to the handle 5510. The supplemental battery 5560 comprises a housing 5562 and one or more battery cells, such as battery cells 5570, for example, positioned therein. The battery cells 5570 are arranged in series as part of a supplemental battery supply circuit 5563. The supplemental battery supply circuit 5563 is in electrical communication with an electrical connector 5566 defined in the battery housing 5562. The electrical connector 5566 comprises the same number of electrical contacts as the electrical connector 5516 and are configured to form mating pairs with the electrical contacts of the electrical connector 5516.

The housing 5562 of the supplemental battery 5560 further comprises a cavity, or receptacle, 5561 defined therein which is configured to receive the gripping portion 5511 of the handle 5510. The cavity 5561 is configured to closely receive the gripping portion 5511 such that there is little to no relative movement between the supplemental battery 5560 and the handle 5510 when the supplemental battery 5560 is fully assembled thereto. As the supplemental battery 5560 is being assembled to the handle 5510, the housing 5562 contacts the connector cover 5517 and pushes the connector cover 5517 into its second position to expose the electrical connector 5516. Once the contacts of the electrical connector 5516 have been at least partially exposed, the contacts of the electrical connector 5566 can engage the contacts of the electrical connector 5516. At such point, the supplemental battery supply circuit 5563 has been electrically coupled to the battery power supply circuit 5513.

The electrical connectors 5516 and 5566 can be positioned and arranged such that they do not engage one another until the supplemental battery 5560 has been fully seated onto the gripping portion 5511. In other embodiments, the electrical connectors 5516 and 5566 can be positioned and arranged such that they engage one another prior to the supplemental battery 5560 being fully seated onto the gripping portion 5511. In either event, the housing 5512 of the handle 5510 and/or the housing 5562 of the supplemental battery 5560 can comprise a lock configured to hold the supplemental battery 5560 to the housing 5510. The lock is releasable to allow the supplemental battery 5560 to be readily removed from the handle 5510; however, embodiments are envisioned in which the lock does not permit the supplemental battery 5560 to be readily released from the handle 5510.

As discussed above, the supplemental battery supply circuit 5563 is electrically coupled to the battery power supply circuit 5513 when the supplemental battery 5560 is assembled to the handle 5510. In various instances, the supplemental battery cells 5570 are placed in series with the handle battery cells 5470 and can increase the power available to the handle 5510. Such embodiments can be useful when the handle battery cells 5470 have become drained from use, for example. In other instances, the supplemental battery cells 5570 of the supplemental battery 5560 are placed in parallel with the battery cells 5470 of the handle 5510. In at least one such instance, the handle battery cells 5470 can be electrically decoupled from the handle 5510 when the supplemental battery cells 5570 are electrically coupled with the handle 5510. Such embodiments can be useful when a short has occurred in the handle battery cells 5470. Various embodiments of the handle 5510 can include a switch which can allow the user to selectively place the supplemental battery cells 5570 in series with or in parallel with the handle battery cells 5470.

EXAMPLES

Example 1

A surgical apparatus comprising a handle module comprising an attachment portion, wherein a detachable shaft module is attachable to the attachment portion for collectively performing a surgical procedure, and wherein the handle module comprises a rotary drive system for driving the detachable shaft module, an electric motor coupled to the rotary drive system for powering the rotary drive system, and one or more sensors. The handle module further comprises a handle module processor circuit in communication with the one or more sensors and the electric motor, wherein the handle module processor circuit is programmed to control the electric motor, track an end-of-life parameter for the handle module based on input from the one or more sensors, and maintain a count of the end-of-life parameter.

Example 2

The surgical apparatus of Example 1, further comprising means, in communication with the handle module processor circuit, for taking an end-of-life action when the handle module processor circuit determines that the count for the end-of-life parameter reaches a threshold value.

Example 3

The surgical apparatus of Example 2, wherein the means for taking the end-of-life action comprises a display that displays to a user of the surgical apparatus information indicative of the end-of-life parameter reaching the threshold valve.

Example 4

The surgical apparatus of Example 3, wherein the display displays the count.

Example 5

The surgical apparatus of Examples 3 or 4, wherein the display displays an indicator that indicates a remaining number of uses for the handle module before the threshold value is reached.

Example 6

The surgical apparatus of Examples 2, 3, 4, or 5, wherein the means for taking the end-of-life action comprises means for disabling the handle module for a subsequent surgical procedure.

Example 7

The surgical apparatus of Example 6, wherein the means for disabling the handle module comprises means for disabling the operation of the electric motor.

Example 8

The surgical apparatus of Examples 6 or 7, wherein the means for disabling the handle module comprise means for preventing installation of a charged battery pack in the handle module.

Example 9

The surgical apparatus of Examples 2, 3, 4, 5, 6, 7, or 8, wherein the end-of-life parameter is selected from the group consisting of a number of firings by the handle module, a number of surgical procedures involving the handle module, a number of attachments of a detachable shaft module to the handle module, a number of sterilizations of the handle module, and a number of attachments of removable battery packs to the handle module, wherein the removable battery packs are for supplying electric power to the handle module during a surgical procedure.

Example 10

The surgical apparatus of Examples 2, 3, 4, 5, 6, 7, 8, or 9, wherein the end-of-life parameter is computed according to a function whose inputs include the number of firings by the handle module and the number of surgical procedures involving the handle module.

Example 11

The surgical apparatus of Example 10, wherein the function computes the end-of-life parameter by using different weighting coefficients for different detachable shaft modules.

Example 12

The surgical apparatus of Examples 2, 3, 4, 5, 6, 7, 8, 9, 10, or 11, wherein the detachable shaft module comprises an end effector with a firing member that, when fired, traverses a stroke length, and wherein the end-of-life parameter comprises a usage parameter for the handle module indicative of differences between the force that is expected to be exerted by the handle module and the force actually exerted by the handle module over the stroke length of the firing member.

Example 13

The surgical apparatus of Examples 2, 3, 4, 5, 6, 7, 8, 9, 10, 11, or 12, wherein the end-of-life parameter comprises the number of times the handle module has been sterilized.

Example 14

The surgical apparatus of Examples 2, 3, 4, 5, 6, 7, 8, 9, 10, 11, 12, or 13, wherein the handle module includes a sterilization sensor that is in communication with the handle module processor circuit that is actuated when a protective sterilization cover is attached to the handle module.

Example 15

The surgical apparatus of Example 14, wherein the sterilization sensor comprises a switch that is actuated when the protective sterilization cover is attached to the handle module.

Example 16

The surgical apparatus of Examples 2, 3, 4, 5, 6, 7, 8, 9, 10, 11, 12, 13, 14 or 15, further comprising an inspection station, wherein the handle module is connectable to the inspection station for inspection of the handle module following the surgical procedure, wherein the inspection station comprises an inspection station processor circuit that communicates with the handle module processor circuit via a data connection when the handle module is connected to the inspection station, and an inspection station display in communication with the inspection station processor circuit, wherein the inspection station display displays information about the handle module when the handle module is connected to the inspection station.

Example 17

A surgical apparatus comprising a handle module that is attachable to a detachable shaft module for collectively performing a surgical procedure, wherein the handle module comprises a rotary drive system which is activatable to drive the detachable shaft module, an electric motor coupled to the rotary drive system for powering the rotary drive system, and means for tracking a count of an end-of-life parameter for the handle module based on the number of times in which the rotary drive system is activated.

Example 18

The surgical apparatus of Example 17, wherein the means for tracking the count of the end-of-life parameter comprises a processor circuit and memory, wherein the memory stores program code that is executed by the processor to track the count of the end-of-life parameter for the handle module.

Example 19

The surgical apparatus of Examples 17 or 18, wherein the handle module is powered by a removable battery pack, and wherein the means for tracking the count of the end-of-life parameter for the handle module is further based on a number of times a removable battery pack is connected to the handle module.

Example 20

The surgical apparatus of Examples 17, 18, or 19, further comprising a sterilization tray for holding the handle module during a sterilization procedure, wherein the means for tracking the count of the end-of-life parameter for the handle module comprises a counter on the sterilization tray that increments the count when the handle module is placed in the sterilization tray.

Example 21

An apparatus, comprising a handle module that is attachable to a detachable shaft module for collectively performing a surgical procedure, wherein the handle module comprises a rotary drive system for driving the detachable shaft module, an electric motor coupled to the rotary drive system for powering the rotary drive system, and a handle module processor circuit in communication with the electric motor. The apparatus further comprises an inspection station for connection to the handle module when the handle module is not being used in a surgical procedure, wherein the inspection station comprises an inspection station processor circuit that communicates with the handle module processor circuit via a data connection when the handle module is connected to the inspection station, and an inspection station display in communication with the inspection station processor circuit, wherein the inspection station display displays information about handle module connected to the inspection station.

Example 22

The apparatus of Example 21, wherein the inspection station comprises an electric power source for supplying electric power to the handle module when the handle module is connected to the inspection station.

Example 23

The apparatus of Examples 21 or 22, wherein the inspection station is configured to perform one or more tests on the handle module to determine the suitability of the handle module for use in a subsequent surgical procedure.

Example 24

The apparatus of Example 23, wherein the one or more tests comprises a seal integrity test of the handle module.

Example 25

The apparatus of Examples 23 or 24, wherein the one or more tests comprises a gear backlash test for the rotary drive system of the handle module.

Example 26

The apparatus of Examples 21, 22, 23, 24, or 25, wherein the inspection station is configured to perform a conditioning action to condition the handle module for use in a subsequent surgical procedure.

Example 27

The apparatus of Example 26, wherein the conditioning action comprises drying components of the handle module.

Example 28

The apparatus of Examples 21, 22, 23, 24, 25, 26, or 27, wherein the inspection station comprises one or more fans for blowing air on the components of the handle module.

Example 29

The apparatus of Examples 21, 22, 23, 24, 25, 26, 27, or 28, wherein the inspection station comprises a vacuum port for drying the components of the handle module with vacuum pressure air flow.

Example 30

The apparatus of Examples 21, 22, 23, 24, 25, 26, 27, 28, or 29, wherein the inspection station further comprises a load simulation adapter connectable to the rotary drive system of the handle module.

Example 31

The apparatus of Example 30, wherein the load simulation adapter comprises a motor for supplying a simulated load to the rotary drive system of the handle module.

Example 32

The apparatus of Examples 21, 22, 23, 24, 25, 26, 27, 28, 29, 30, or 31 wherein the inspection station is further connected to the detachable shaft module.

Example 33

A surgical process comprising performing, by a clinician, a surgical procedure on a patient with a surgical instrument that comprises a handle module connected to a detachable shaft module, wherein the handle module includes a memory that stores data about the handle module and the surgical procedure, while the handle module is connected to the inspection station, downloading to a memory of the inspection station data about the surgical procedure stored in the memory of the handle module, and while the handle module is connected to the inspection station, visually displaying on a display of the inspection of station information about the handle module.

Example 34

The surgical process of Example 33, further comprising following the surgical procedure and prior to connecting the handle module to an inspection station, removing a removable battery pack from the handle module, wherein the removable battery pack powered the handle module during the surgical procedure, and while the handle module is connected to the inspection station, electrically powering the handle module with electric power from the inspection station.

Example 35

The surgical process of Examples 33 or 34, while the handle module is connected to the inspection station, performing one or more tests on the handle module to determine the suitability of the handle module for use in a subsequent surgical procedure.

Example 36

The surgical process of Example 35, wherein the one or more tests comprises a seal integrity test of the handle module.

Example 37

The surgical process of Examples 35 or 36, wherein the one or more tests comprises a gear backlash test.

Example 38

The surgical process of Examples 34, 35, 36, or 37, while the handle module is connected to the inspection station, performing a conditioning action to condition the handle module for use in a subsequent surgical procedure.

Example 39

The surgical process of Example 38, wherein the conditioning action comprises drying components of the handle module.

Example 40

A surgical apparatus comprising a handle module that is attachable to a detachable shaft module for collectively performing a surgical procedure, wherein the handle module comprises a rotary drive system for driving the detachable shaft module, an electric motor coupled to the rotary drive system for powering the rotary drive system, one or more sensors for sensing data about the electric motor, and a handle module processor circuit in communication with the one or more sensors, wherein the handle module processor circuit is programmed to monitor a performance parameter of the handle module based on input from the one or more sensors, and wherein the handle module processor circuit monitors the performance parameter of the handle module by monitoring whether the performance parameter is outside an acceptable performance band.

Example 41

The surgical apparatus of Example 40, wherein the processor circuit monitors the performance parameter of the handle module by monitoring whether the performance parameter is below or above the acceptable performance band.

Example 42

The surgical apparatus of Examples 40 or 41, wherein the handle module further comprises means for taking remedial action when the handle module processor circuit determines that the performance parameter is outside the acceptable performance band.

Example 43

The surgical apparatus of Examples 40, 41, or 42, wherein the performance parameter comprises a performance parameter of the electric motor.

Example 44

The surgical apparatus of Example 43, wherein the performance parameter of the electric motor comprises the energy consumed by the electric motor over the life of the handle module.

Example 45

The surgical apparatus of Examples 43 or 44, wherein the performance parameter of the electric motor comprises the power consumed by the electric motor for each firing of the handle module.

Example 46

The surgical apparatus of Examples 43, 44, or 45, wherein the performance parameter of the electric motor comprises the energy consumed by the electric motor over the life of the handle module and the power consumed by the electric motor for each firing of the handle module.

Example 47

The surgical apparatus of Example 46, wherein the handle module processor circuit is programmed to determine that remedial action should be taken when at least one of the following conditions is met the energy consumed by the electric motor over the life of the handle module exceeds a first energy threshold value, and the energy consumed by the electric motor over the life of the handle module exceeds a second energy threshold value, which is lower than the first energy threshold value, and the handle module has had a threshold number of device firings above a threshold power level.

Example 48

The surgical apparatus of Examples 43, 44, 45, 46, or 47 wherein the performance parameter comprises output torque of the electric motor.

Example 49

The surgical apparatus of Examples 40, 41, 42, 43, 44, 45, 46, 47, or 48 wherein the performance parameter comprises a performance parameter of the rotary drive system.

Example 50

The surgical apparatus of Example 49 wherein the performance parameter of the rotary drive system comprises gear backlash.

Example 51

The surgical apparatus of Examples 42, 43, 44, 45, 46, 47, 48, 49 or 50, wherein the means for taking remedial action comprises a display for displaying a condition of the handle module.

Example 52

The surgical apparatus of Examples 42, 43, 44, 45, 46, 47, 48, 49, 50, or 51 wherein the means for taking remedial action comprises means for disabling the handle module.

Example 53

The surgical apparatus of Example 52, wherein the means for disabling the handle module comprises means for preventing the insertion of a charged, removable battery pack into the handle module to power the handle module during a surgical procedure.

Example 54

The surgical apparatus of Example 53, wherein the means for preventing the insertion of a charged, removable battery pack comprises a spring-loaded mechanical lock-out.

Example 55

The surgical apparatus of Examples 53 or 54, wherein the means for preventing the insertion of a charged, removable battery pack comprises a latch that, when actuated, prevents the removal of a discharged, removable battery pack from the handle module.

Example 56

A surgical apparatus, comprising a detachable shaft module and a handle module connected to the detachable shaft module for collectively performing a surgical procedure, wherein the handle module comprises a rotary drive system for driving the detachable shaft module, an electric motor coupled to the rotary drive system for powering the rotary drive system, means for monitoring a performance parameter of at least one of the electric motor and the rotary drive system, and means for taking a remedial action upon a determination that the performance parameter is outside an acceptable performance band.

Example 57

The surgical apparatus of Example 56, wherein the performance parameter comprises the energy consumed by the electric motor over the life of the handle module.

Example 58

The surgical apparatus of Examples 56 or 57, wherein the performance parameter comprises the power consumed by the electric motor for each firing of the handle module.

Example 59

The surgical apparatus of Examples 56, 57, or 58, wherein the performance parameter comprises the output torque of the electric motor.

Example 60

The surgical apparatus of Examples 56, 57, 58, or 59, wherein the means for taking remedial action comprises means for disabling the handle module.

Example 61

The surgical apparatus of Example 60, wherein the means for disabling the handle module comprises means for disabling the electric motor.

Example 62

The surgical apparatus of Examples 60 or 61, wherein the means for disabling the handle module comprises means for preventing the insertion of a charged, removable battery pack into the handle module to power the handle module during a surgical procedure.

Example 63

A combination, comprising a handle module that is attachable to a detachable shaft module for collectively performing a surgical procedure, a removable, rechargeable battery pack connectable to the handle module for providing electric power to the handle module during a surgical procedure, wherein the battery pack comprises a memory for storing charging data and discharging data for the battery pack, and a charging station for at least one of charging and discharging the battery pack when the battery pack is removed from the handle module and inserted into the charging station, wherein the charging station is for at least one of charging and discharging the battery pack based on the charging data and discharging data stored in the memory of the battery pack.

Example 64

The combination of Example 63, wherein the battery pack comprises a plurality of battery cells, the charging station comprises a charging station processor circuit that determines when the battery cells should be rebalanced based on the charging data and discharging data stored in the battery pack memory and based on rebalancing criteria, and the charging station rebalances the battery cells of the battery pack when the charging station processor circuit determines that the battery cells should be rebalanced.

Example 65

The combination of Example 64, wherein the charging station processor circuit is programmed to determine that the battery cells should be rebalanced after N charges of the battery pack without rebalancing, where N is an integer greater than zero.

Example 66

The combination of Examples 64 or 65, wherein prior to rebalancing the battery cells, the charging station is configured to top off a charge of the battery cells.

Example 67

The combination of Examples 63, 64, 65, or 66, wherein the charging station comprises a charging station processor circuit that determines whether the battery pack should be discharged based on the charging and discharging data stored in the battery pack memory and based on discharging criteria, and wherein the charging station discharges the battery pack when the charging station processor circuit determines that the battery pack should be discharged.

Example 68

The combination of Example 67, wherein the discharging criteria comprise whether a second battery pack installed in the charging station is fully charged and ready for use in the handle module.

Example 69

The combination of Examples 63, 64, 65, 66, 67, or 68, wherein the charging station is programmed to charge the battery pack at a time of day based on surgical procedure schedule data for an organizational user of the charging station, and wherein the surgical procedure schedule data is stored in a memory of the charging station.

Example 70

The combination of Example 69, wherein the surgical procedure schedule data comprises a statistical likelihood that the organizational user is performing a surgical procedure with the handle module at the time of day.

Example 71

The combination of Examples 63, 64, 65, 66, 67, 68, 69, or 70, wherein the charging station comprises means for automatically securing the battery pack to the charging station when the battery pack is not ready for use in the handle module for a surgical procedure.

Example 72

The combination of Example 71, wherein the means for automatically securing the battery pack to the charging station comprises a screw that, when actuated by insertion of the battery pack into the charging station, screws into the battery pack.

Example 73

The combination of Examples 71 or 72, wherein the means for automatically securing the battery pack to the charging station further comprises a linear actuator for actuating the screw.

Example 74

The combination of Examples 63, 64, 65, 66, 67, 68, 69, 70, 71, 72, or 73, wherein the charging station comprises a display for displaying charge status information about the battery pack.

Example 75

The combination of Examples 63, 64, 65, 66, 67, 68, 69, 70, 71, 72, 73, or 74, wherein the charging station comprises means for rapidly charging the first battery pack when a rapid charge user input for the battery pack is received by the charging station.

Example 76

The combination of Example 75, wherein the charging station comprises means for automatically securing the battery pack to the charging station when the battery pack is not ready for use in the handle module for a surgical procedure.

Example 77

A surgical process comprising performing, by a clinician, a surgical procedure on a patient with a surgical instrument that comprises a handle module connected to a detachable shaft module, wherein the handle module is powered during the surgical procedure by a removable, rechargeable battery pack, and wherein the battery pack comprises a memory for storing charging data and discharging data for the battery pack, removing the battery pack from the handle module after it has been used during the surgical procedure, following the removing step, placing the battery pack in a charging station to recharge the battery pack, following the placement step, downloading by the charging station the charging and discharging data from the memory of the battery pack, and following the downloading step, at least one of charging and discharging, by the charging station, the battery pack based on the charging data and discharging data stored in the memory of the battery pack.

Example 78

The surgical process of Example 77, wherein the battery pack comprises a plurality of battery cells, and wherein the process further comprises: following the downloading step, determining, by the charging station, whether the battery cells should be rebalanced based on the charging data and discharging data stored in the battery pack memory and based on rebalancing criteria, and upon determining that rebalancing of the battery cells of the battery pack should be performed, rebalancing the battery cells by the charging station.

Example 79

The surgical process of Examples 77 or 78, following the downloading step, rapidly charging the battery pack in response to receipt of a rapid charge user input.

Example 80

The surgical process of Examples 77, 78, or 79, following the placement step, automatically securing the battery pack to the charging station when the battery pack is not ready for use in the handle module for a surgical procedure.

Example 81

A combination, comprising a handle module that is attachable to a detachable shaft module for collectively performing a surgical procedure, a removable, rechargeable battery pack connectable to the handle module for providing electric power to the handle module during a surgical procedure, and a charging station for charging the battery pack when the battery pack is removed from the handle module and inserted into the charging station, wherein the charging station comprises circuitry for rapidly charging the battery pack when a rapid charge user input for the battery pack is received by the charging station.

Example 82

The combination of Example 81, wherein the charging station comprises a display for displaying the charge status of the battery pack.

Example 83

The combination of Examples 81 or 82, wherein the charging station comprises a user interface through which a user inputs the rapid charge user input to the charging station.

Example 84

The combination of Example 83, wherein the user interface comprises a button on the charging station which is actuatable to provide the charging station with the rapid charge user input.

Example 85

The combination of Examples 81, 82, 83 or 84, wherein the circuitry for rapidly charging the battery pack comprises circuitry for changing a charging profile for the battery pack.

Example 86

The combination of Examples 81, 82, 83, 84, or 85, wherein the circuitry for changing the charging profile for the battery pack comprises a voltage regulator connected to the battery pack, and a charging controller circuit connected to the voltage regulator.

Example 87

The combination of Examples 81, 82, 83, 84, 85, or 86 wherein the circuitry for rapidly charging the battery pack comprises a charge-storing device of the charging station, and wherein charge stored on the charge-storing device is used to charge the battery pack.

Example 88

The combination of Example 87, wherein the charge-storing device comprises a supercapacitor.

Example 89

The combination of Example 88, wherein the charging station further comprises circuitry for discharging the first battery pack to the supercapacitor.

Example 90

The combination of Examples 87, 88, or 89, wherein the charge-storing device comprises one or more battery cells internal to the charging station.

Example 91

The combination of Examples 87, 88, or 89, wherein the charge-storing device comprises a plurality of battery cells internal to the charging station, and wherein the circuitry for rapidly charging the battery pack comprises circuitry for charging the battery pack with the plurality of battery cells.

Example 92

The combination of Example 91, wherein the plurality of battery cells are connected in series.

Example 93

The combination of Examples 91 or 92, wherein the plurality of battery cells are connected as parallel current sources.

Example 94

The combination of Examples 81, 82, 83, 84, 85, 86, 87, 88, 89, 90, 91, 92, or 93, wherein the charging station further comprises circuitry for discharging the first battery pack to the internal plurality of battery cells.

Example 95

The combination of Examples 81, 82, 83, 84, 85, 86, 87, 88, 89, 90, 91, 92, 93, or 94, wherein the battery pack comprises a first battery pack, wherein the charging station comprises a first charging receptacle for receiving the first battery pack to charge the first battery pack, and a second charging receptacle for receiving a second battery pack to charge the second battery pack, and wherein the circuitry for rapidly charging the first battery pack comprises circuitry for charging the first battery pack with charge stored on the second battery pack.

Example 96

The combination of Example 95, wherein the charging station further comprises circuitry for discharging the first battery pack to the second battery pack.

Example 97

The combination of Examples 95 or 96, wherein the charging station comprises a display for displaying the charge status of the first battery pack and the second battery pack.

Example 98

The combination of Examples 81, 82, 83, 84, 85, 86, 87, 88, 89, 90, 91, 92, 93, 94, 95, 96, or 97, wherein the charging station comprises means for automatically securing the battery pack to the charging station when the battery pack is not ready for use in the handle module for a surgical procedure.

Example 99

A surgical instrument system comprising a handle module for performing a surgical procedure, a removable, rechargeable battery pack connectable to the handle module for providing electric power to the handle module during the surgical procedure, and a charging station for charging the battery pack, wherein the charging station comprises circuitry for charging the handle module under two operating conditions: a first operating condition in which the battery pack is charged from a primary power source, and a second operating condition in which the battery pack is charged from the primary power source and a secondary power source in order to rapidly charge the battery pack in case the battery pack is urgently needed in the surgical procedure.

Example 100

The surgical instrument system of Example 99, wherein the secondary power source comprises a second removable, rechargeable battery pack connectable to the handle module.

Example 101

An apparatus comprising a handle module that is attachable to a detachable shaft module for collectively performing a surgical procedure, wherein the handle module comprises a handle module memory circuit for storing handle module usage data for the handle module, and an inspection station for connection to the handle module when the handle module is not being used in a surgical procedure, wherein the inspection station comprises an inspection station processor circuit for determining one or more service recommendations for the handle module based on the handle module usage data stored in the memory of the handle module and based on service recommendation criteria.

Example 102

The apparatus of Example 101, wherein the inspection station further comprises a display that is in communication with the inspection station processor circuit, and wherein the display is for displaying information about the one or more service recommendations.

Example 103

The apparatus of Examples 101 or 102, wherein the service recommendation criteria are stored in an inspection station memory of the inspection station, and wherein the inspection station processor circuit is in communication with the inspection station memory.

Example 104

The apparatus of Examples 101, 102, or 103, wherein the handle module comprises a handle module processor circuit in communication with the handle module memory circuit, and wherein the handle module processor circuit is in communication with the inspection station processor circuit when the handle module is connected to the inspection station such that usage data from the handle module memory is downloadable to the inspection station.

Example 105

The apparatus of Examples 101, 102, 103, or 104, wherein the handle module usage data comprises data selected from the group consisting of data regarding a number of surgical procedures involving the handle module, data regarding a number of device firings by the handle module, data regarding the power expended during the device firings of the handle module, data regarding the forces experienced during the device firings of the handle module, data regarding energy consumed by an electric motor of the handle module over the life of the handle module, and data regarding gear backlash for a rotary drive system of the handle module.

Example 106

The apparatus of Examples 101, 102, 103, 104, or 105 wherein the one or more service recommendations comprise a recommendation that the handle module be rebuilt.

Example 107

The apparatus of Examples 101, 102, 103, 104, 105, or 106, wherein the one or more service recommendations comprise a recommendation that one or more components of the handle module be lubricated.

Example 108

The apparatus of Examples 101, 102, 103, 104, 105, 106, or 107 wherein the one or more service recommendations comprise a recommendation that one or more components of the handle module be inspected.

Example 109

An apparatus comprising a handle module that is attachable to a detachable shaft module for collectively performing a surgical procedure, wherein the handle module comprises a handle module memory circuit for storing handle module usage data for the handle module, and a handle module processor circuit for determining one or more service recommendations for the handle module based on the handle module usage data stored in the memory of the handle module and based on service recommendation criteria.

Example 110

The apparatus of Example 109, wherein the handle module further comprises a display that is in communication with the handle module processor circuit, and wherein the display is for displaying information about the one or more service recommendations.

Example 111

The apparatus of Examples 109 or 110, wherein the handle module usage data comprises data selected from the group consisting of data regarding a number of surgical procedures involving the handle module, data regarding a number of device firings by the handle module, data regarding the power expended during the device firings of the handle module, data regarding the forces experienced during the device firings of the handle module, data regarding energy consumed by an electric motor of the handle module over the life of the handle module, and data regarding gear backlash for a rotary drive system of the handle module.

Example 112

The apparatus of Examples 109, 110, or 111, wherein the one or more service recommendations comprise a recommendation that the handle module be rebuilt.

Example 113

The apparatus of Examples 109, 110, 111, or 112, wherein the one or more service recommendations comprise a recommendation that the handle module be rebuilt.

Example 114

The apparatus of Examples 109, 110, 111, 112, or 113, wherein the one or more service recommendations comprise a recommendation that one or more components of the handle module be lubricated.

Example 115

The apparatus of Examples 109, 110, 111, 112, 113, or 114, wherein the one or more service recommendations comprise a recommendation that one or more components of the handle module be inspected.

Example 116

A surgical instrument system comprising a handle including a battery cavity and a direct current electrical motor, a battery removably positionable in the battery cavity, wherein the battery is configured to supply direct current electrical power to the direct current electrical motor, and a power adapter including a plug removably positionable in the battery cavity in lieu of the battery and a cord extending from the plug, wherein the cord is configured to transmit power to the plug from a power source. The surgical instrument system further comprises an alternating current to direct current power converter configured to convert alternating current electrical power supplied from the power source to direct current electrical power.

Example 117

The surgical instrument system of Example 116, wherein the alternating current to direct current power converter is positioned in the plug.

Example 118

The surgical instrument system of Examples 116 or 117, wherein the battery comprises a battery housing, wherein the plug comprises a plug housing, and wherein the battery housing is analogous to the plug housing.

Example 119

The surgical instrument system of Examples 116, 117, or 118, wherein the handle comprises a set of handle electrical contacts in the battery cavity, wherein the battery comprises a set of battery electrical contacts configured to engage the handle electrical contacts when the battery is positioned in the battery cavity, and wherein the plug comprises a set of plug electrical contacts configured to engage the handle electrical contacts when the plug is positioned in the battery cavity.

Example 120

The surgical instrument system of Examples 116, 117, 118, or 119, wherein the handle comprises a first set of handle electrical contacts and a second set of handle electrical contacts in the battery cavity, wherein the battery comprises a set of battery electrical contacts configured to engage the first set of handle electrical contacts when the battery is positioned in the battery cavity, and wherein the plug comprises a set of plug electrical contacts configured to engage the second set of handle electrical contacts when the plug is positioned in the battery cavity.

Example 121

The surgical instrument system of Examples 116, 117, 118, 119, or 120, wherein the alternating current to direct current power converter is positioned in the handle and is in electrical communication with the second set of handle electrical contacts.

Example 122

The surgical instrument system of Examples 116, 117, 118, 119, 120, or 121, further comprising a plurality of shaft assemblies, wherein each shaft assembly is selectively engageable with the handle.

Example 123

The surgical instrument system of Example 122, wherein at least one of the shaft assemblies comprises a stapling cartridge.

Example 124

A surgical instrument system comprising a handle including a battery cavity and a direct current electrical motor, a power adapter including a battery positioned in the battery cavity, wherein the battery comprises at least one battery cell, an electrical connector, and a cord engageable with the electrical connector, wherein the cord is configured to transmit power from a power source. The surgical instrument system further comprises an alternating current to direct current power converter configured to convert alternating current electrical power supplied from the power source to direct current electrical power and supply direct current electrical power to the direct current electrical motor.

Example 125

The surgical instrument system of Example 124, further comprising a battery circuit, wherein the at least one battery cell, the alternating current to direct current power converter, and the electrical connector are arranged in series in the battery circuit such that the at least one battery cell and the power source can supply power to the direct current electric motor when the cord is engaged with the electrical connector.

Example 126

The surgical instrument system of Example 124, further comprising a first battery circuit segment, wherein the first battery circuit segment includes the at least one battery cell, a second battery circuit segment, wherein the second battery circuit segment includes the alternating current to direct current power converter, and a switch positioned in the battery, wherein the switch is switchable between a first switch state in which the at least one battery cell can supply electrical power to the direct current electrical motor and the power supply cannot supply electrical power to the direct current electrical motor, and a second switch state in which the at least one battery cell cannot supply electrical power to the direct current electrical motor and the power supply can supply electrical power to the direct current electrical motor.

Example 127

The surgical instrument system of Example 126, wherein the switch is biased into the first switch state.

Example 128

The surgical instrument system of Examples 126 or 127, wherein the insertion of the cord into the battery electrical connector switches the switch from the first switch state into the second switch state.

Example 129

The surgical instrument system of Example 128, further comprising a biasing member configured to return the switch into the first switch state.

Example 130

The surgical instrument system of Examples 126, 127, or 128, wherein the switch is incapable of being returned to the first switch state after being placed in the second switch state.

Example 131

The surgical instrument system of Examples 124, 125, 126, 127, 128, 129, or 130, further comprising a plurality of shaft assemblies, wherein each shaft assembly is selectively engageable with the handle.

Example 132

The surgical instrument system of Example 131, wherein at least one of the shaft assemblies comprises a stapling cartridge.

Example 133

A surgical instrument system comprising a handle including a handle housing, a handle battery cell positioned in the handle housing, a handle electrical circuit, wherein the handle battery cell is configured to supply power to the handle electrical circuit, and a handle electrical connector in communication with the handle electrical circuit. The surgical instrument system further comprises a supplemental battery selectively engageable with the handle, wherein the supplemental battery comprises a battery housing engageable with the handle housing, a battery electrical circuit, a supplemental battery cell positioned in the battery housing, wherein the supplemental battery cell is configured to supply power to the battery electrical circuit, and a battery electrical connector in communication with the battery electrical circuit, wherein the battery electrical connector is engageable with the handle electrical connector when the supplemental battery is engaged with the handle to place the battery electrical circuit in communication with the handle electrical circuit.

Example 134

The surgical instrument system of Example 133, wherein the handle housing comprises a gripping portion, and wherein the battery housing comprises a receptacle configured to receive the gripping portion.

Example 135

The surgical instrument system of Examples 133 or 134, wherein the handle further comprises a connector cover movable between a first position in which the connector cover inhibits accidental contact with the handle electrical connector and a second position in which the connector cover permits the battery electrical connector to engage the handle electrical connector.

Example 136

The surgical instrument system of Example 135, wherein the battery housing is configured to move the connector cover between the first position and the second position when the supplemental battery is engaged with the handle.

Example 137

The surgical instrument system of Examples 133, 134, 135, or 136, further comprising a plurality of shaft assemblies, wherein each shaft assembly is selectively engageable with the handle.

Example 138

The surgical instrument system of Example 137, wherein at least one of the shaft assemblies comprises a stapling cartridge.

Example 139

A surgical instrument comprising a housing, a motor, and a battery assembly attachable to the housing of the surgical instrument, the battery assembly comprising a battery cell configured to provide electrical energy to the motor and a battery housing comprising a support housing configured to support the battery cell, and a shock absorbing element configured to absorb shock provided by an impact force, wherein the shock absorbing element is configured to crumple when an impact force is applied to the shock absorbing element.

Example 140

The surgical instrument of Example 139, wherein the shock absorbing element is replaceable.

Example 141

The surgical instrument of Examples 139 or 140, wherein the shock absorbing element comprises attachment means configured to permit the shock absorbing element to be attached to the battery assembly in a snap-fit fashion.

Example 142

The surgical instrument of Example 141, wherein the attachment means comprises an adhesive.

Example 143

The surgical instrument of Examples 141 or 142, wherein the battery housing further comprises an aperture, and wherein the attachment means comprises a protrusion configured to be received by the aperture in the battery housing in a wedge-fit fashion.

Example 144

The surgical instrument of Examples 139, 140, 141, 142, or 143, wherein the shock absorbing element comprises a lattice structure.

Example 145

The surgical instrument of Examples 139, 140, 141, 142, 143, or 144 wherein, when the shock absorbing element crumples, the shock absorbing element deforms in an inward direction which still permits the attachment of the battery assembly to the housing of the surgical instrument after the shock absorbing element has been impacted.

Example 146

The surgical instrument of Examples 139, 140, 141, 142, 143, 144, or 145, wherein the shock absorbing element crumples when the impact force is greater than a threshold force.

Example 147

The surgical instrument of Examples 139, 140, 141, 142, 143, 144, 145, or 146 wherein the battery assembly further comprises a plurality of corners, wherein the battery housing further comprises a plurality of the shock absorbing elements, and wherein the plurality of shock absorbing elements are positioned at each corner.

Example 148

The surgical instrument of Example 147, wherein the battery housing comprises an electrical contact configured to transmit electrical energy from the battery cell to the motor and a bottom face associated with the electrical contact, wherein each shock absorbing element comprises an end portion extending beyond the bottom face of the battery housing to protect the electrical contact.

Example 149

The surgical instrument of Examples 148 or 149, wherein each shock absorbing element comprises a bottom end and a top end, and wherein the battery assembly further comprises a shock absorbing cap positioned at the top ends of the shock absorbing elements.

Example 150

A battery assembly for use with a surgical instrument, the battery assembly comprising a battery cell, an electrical contact configured to transmit electrical energy provided by the battery cell to the surgical instrument when the battery assembly is attached to the surgical instrument, a first housing configured to support the battery cell, a second housing configured to house the first housing, and a shock absorbing layer positioned between the first housing and the second housing, wherein the shock absorbing layer comprises a lattice structure.

Example 151

The battery assembly of Example 150, wherein the shock absorbing layer comprises a foam-like material.

Example 152

The battery assembly of Examples 150 or 151, wherein the lattice structure comprises a plurality of cells, the plurality of cells comprising an inner cell comprising an inner planar wall, wherein the inner planar wall is oriented at least substantially parallel the first housing and an outer cell comprising an outer planar wall, wherein the outer planar wall is oriented at least substantially parallel the second housing.

Example 153

The battery assembly of Examples 150, 151, or 152, wherein the battery assembly further comprises a shock absorbing cap, the shock absorbing cap comprising an outer lattice and an inner lattice, wherein the outer lattice is more dense than the inner lattice.

Example 154

The battery assembly of Examples 150, 151, 152, or 153, wherein the shock absorbing layer comprises a plurality of dampening elements.

Example 155

A battery assembly for use with a surgical instrument, the battery assembly comprising a battery cell configured to provide power to the surgical instrument and a housing comprising a heat reflecting shell, a heat sink layer, and a compressible layer positioned between the heat sink layer and the heat reflecting shell, wherein the compressible layer is configured to flex in response to expansion of the battery cell.

Example 156

The battery assembly of Example 155, wherein the compressible layer is further configured to dissipate impact energy absorbed by the heat reflecting shell.

Example 157

The battery assembly of Examples 155 or 156, wherein the compressible layer comprises a lattice structure.

Example 158

The battery assembly of Example 157, wherein the lattice structure is a closed lattice structure defined by the heat reflecting shell and the heat sink layer.

Example 159

The battery assembly of Examples 155, 156, 157, or 158, wherein the heat reflecting shell comprises a first thermal expansion coefficient, wherein the heat sink layer comprises a second thermal expansion coefficient, and wherein the first thermal expansion coefficient is less than the second thermal expansion coefficient.

The entire disclosures of the following documents are hereby incorporated by reference herein in their respective entireties:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES; now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009; now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Patent Application Publication No. 2012/0298719;

U.S. patent application Ser. No. 13/524,049, entitled ARTICULATABLE SURGICAL INSTRUMENT COMPRISING A FIRING DRIVE, filed on Jun. 15, 2012; now U.S. Patent Application Publication No. 2013/0334278;

U.S. patent application Ser. No. 13/800,025, entitled STAPLE CARTRIDGE TISSUE THICKNESS SENSOR SYSTEM, filed on Mar. 13, 2013;

U.S. patent application Ser. No. 13/800,067, entitled STAPLE CARTRIDGE TISSUE THICKNESS SENSOR SYSTEM, filed on Mar. 13, 2013;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040.

Although the various embodiments of the devices have been described herein in connection with certain disclosed embodiments, many modifications and variations to those embodiments may be implemented. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

While this invention has been described as having exemplary designs, the present invention may be further modified within the spirit and scope of the disclosure. This application is therefore intended to cover any variations, uses, or adaptations of the invention using its general principles.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical instrument system, comprising:
   a handle, comprising:
      a pistol grip;
      a handle housing;
      a handle battery cell positioned in said handle housing;
      a handle electrical circuit, wherein said handle battery cell is configured to supply power to said handle electrical circuit; and
      a handle electrical connector in communication with said handle electrical circuit; and
   a supplemental battery selectively engageable with said handle, wherein said supplemental battery comprises:
      a battery housing engageable with said handle housing;
      a battery electrical circuit;
      a supplemental battery cell positioned in said battery housing, wherein said supplemental battery cell is configured to supply power to said battery electrical circuit;
      a battery electrical connector in communication with said battery electrical circuit, wherein said battery electrical connector is engageable with said handle electrical connector when said supplemental battery is engaged with said handle to place said battery electrical circuit in communication with said handle electrical circuit; and
      a receptacle defined in said battery housing, wherein said pistol grip of said handle is configured to be received within said receptacle to attach said supplemental battery to said handle,
   wherein said handle further comprises a connector cover configured to selectively cover said handle electrical connector, wherein said connector cover is movable by said battery housing when said pistol grip is received within said receptacle between a first position in which said connector cover inhibits accidental contact with said handle electrical connector and a second position in which said connector cover permits said battery electrical connector to engage said handle electrical connector, and wherein said connector cover is biased into said first position by a spring member.

2. The surgical instrument system of claim 1, further comprising a plurality of shaft assemblies, wherein each said shaft assembly is selectively engageable with said handle.

3. The surgical instrument system of claim 2, wherein at least one of said shaft assemblies comprises a stapling cartridge.

4. The surgical instrument system of claim 1, wherein said handle housing comprises a handle-grip portion which defines a grip axis, and wherein said supplemental battery is configured to be selectively engageable with said handle along said grip axis.

5. The surgical instrument system of claim 1, wherein the engagement of said supplemental battery and said handle places said handle battery cell and said supplemental battery cell in series with each other.

6. A surgical instrument assembly, comprising:
   a primary surgical instrument housing portion, comprising:
      a handle-grip portion defining a grip axis;
      a first battery cell positioned within said primary surgical instrument housing portion;
      a first electrical circuit, wherein said first battery cell is configured to supply power to said first electrical circuit; and
      a first electrical connector in communication with said first electrical circuit; and
   a supplemental battery configured to be attached to said primary surgical instrument housing portion to supply supplemental power to said primary surgical instrument housing portion, wherein said supplemental battery comprises a supplemental battery housing portion, and wherein said supplemental battery housing portion comprises:
      a second battery cell positioned within said supplemental battery housing portion;
      a second electrical circuit, wherein said second battery cell is configured to supply power to said second electrical circuit;
      a second electrical connector in communication with said second electrical circuit, wherein said first electrical connector and said second electrical connector are configured to be electrically coupled with each other when said supplemental battery is attached to said primary surgical instrument housing portion to place said first electrical circuit in communication with said second electrical circuit; and
      a receptacle defined in said supplemental battery housing portion, wherein said handle-grip portion of said primary surgical instrument housing portion is configured to be received within said receptacle to attach said supplemental battery to said primary surgical instrument housing portion,
   wherein said primary surgical instrument housing portion further comprises a connector cover configured to selectively cover said first electrical connector, wherein said connector cover is movable by said supplemental battery housing portion when said handle-grip portion is received within said receptacle between a first position in which said connector cover inhibits accidental contact with said first electrical connector and a second position in which said connector cover permits said second electrical connector to engage said first electrical connector, and wherein said connector cover is biased into said first position by a spring member.

7. The surgical instrument assembly of claim 6, wherein said supplemental battery is configured to be attached to said primary surgical instrument housing portion along said grip axis.

8. The surgical instrument assembly of claim 6, wherein the attachment of said supplemental battery and said primary surgical instrument housing portion places said first battery cell and said second battery cell in series with each other.

9. The surgical instrument assembly of claim 6, further comprising a plurality of shaft assemblies, wherein each said shaft assembly is selectively engageable with said primary surgical instrument housing portion.

10. The surgical instrument assembly of claim 9, wherein at least one of said shaft assemblies comprises a staple cartridge.

11. A surgical instrument system, comprising:
    a handle assembly comprising a primary battery assembly, wherein said primary battery assembly comprises:

a handle-grip portion;
a primary battery circuit comprising first supplemental electrical contacts; and
a primary battery source configured to supply power to said primary battery circuit; and
a supplemental battery assembly attachable to said handle assembly, wherein said supplemental battery assembly comprises:
a supplemental battery circuit comprising second supplemental electrical contacts;
a supplemental battery source configured to supply power to said supplemental battery circuit, wherein said first supplemental electrical contacts are engageable with said second supplemental electrical contacts when said supplemental battery assembly is assembled to said handle assembly to place said supplemental battery circuit in communication with said primary battery circuit; and
a receptacle defined in said supplemental battery assembly, wherein said handle-grip portion of said primary battery assembly is configured to be received within said receptacle to attach said supplemental battery assembly to said handle assembly,
wherein said handle assembly further comprises a contact cover configured to selectively cover said first supplemental electrical contacts, wherein said contact cover is movable by said supplemental battery assembly when said handle-grip portion is received within said receptacle between a first position in which said contact cover inhibits accidental contact between said first supplemental electrical contacts and a second position in which said contact cover permits said second supplemental electrical contacts to engage said first supplemental electrical contacts, and wherein said contact cover is biased into said first position by a spring member.

12. The surgical instrument system of claim 11, further comprising a plurality of shaft assemblies, wherein each said shaft assembly is selectively engageable with said handle assembly.

13. The surgical instrument system of claim 12, wherein at least one of said shaft assemblies comprises a staple cartridge.

14. The surgical instrument system of claim 11, wherein said handle-grip portion defines a grip axis, and wherein said supplemental battery assembly is configured to be attached to said handle assembly along said grip axis.

15. The surgical instrument system of claim 11, wherein the engagement of said first supplemental electrical contacts and said second supplemental electrical contacts places said primary battery source and said supplemental battery source in series with each other.

* * * * *